US011242337B2

(12) United States Patent
Dragoli et al.

(10) Patent No.: US 11,242,337 B2
(45) Date of Patent: Feb. 8, 2022

(54) COMPOUNDS USEFUL FOR TREATING GASTROINTESTINAL TRACT DISORDERS

(71) Applicant: Ardelyx, Inc., Fremont, CA (US)

(72) Inventors: Dean Dragoli, Fremont, CA (US);
Irina Dotsenko, Fremont, CA (US);
Jason Lewis, Fremont, CA (US)

(73) Assignee: ARDELYX, INC., Fremont, CA (US)

( * ) Notice: Subject to any disclaimer, the term of this patent is extended or adjusted under 35 U.S.C. 154(b) by 0 days.

(21) Appl. No.: 16/476,836

(22) PCT Filed: Jan. 9, 2018

(86) PCT No.: PCT/US2018/013020
§ 371 (c)(1),
(2) Date: Jul. 9, 2019

(87) PCT Pub. No.: WO2018/129552
PCT Pub. Date: Jul. 12, 2018

(65) Prior Publication Data
US 2019/0359599 A1     Nov. 28, 2019

Related U.S. Application Data

(60) Provisional application No. 62/541,097, filed on Aug. 4, 2017, provisional application No. 62/444,335, filed on Jan. 9, 2017.

(51) Int. Cl.
| | |
|---|---|
| *C07D 403/14* | (2006.01) |
| *A61K 47/55* | (2017.01) |
| *A61P 1/10* | (2006.01) |
| *A61P 9/12* | (2006.01) |
| *A61P 1/00* | (2006.01) |
| *A61P 9/04* | (2006.01) |
| *A61P 29/00* | (2006.01) |
| *A61P 3/12* | (2006.01) |
| *C07D 241/04* | (2006.01) |
| *C07D 401/12* | (2006.01) |
| *C07D 401/14* | (2006.01) |
| *C07D 403/12* | (2006.01) |
| *C07D 487/08* | (2006.01) |

(52) U.S. Cl.
CPC ............ *C07D 403/14* (2013.01); *A61K 47/55* (2017.08); *A61P 1/00* (2018.01); *A61P 1/10* (2018.01); *A61P 3/12* (2018.01); *A61P 9/04* (2018.01); *A61P 9/12* (2018.01); *A61P 29/00* (2018.01); *C07D 241/04* (2013.01); *C07D 401/12* (2013.01); *C07D 401/14* (2013.01); *C07D 403/12* (2013.01); *C07D 487/08* (2013.01)

(58) Field of Classification Search
CPC ..... C07D 403/14; C07D 401/12; A61K 47/55
See application file for complete search history.

(56) References Cited

U.S. PATENT DOCUMENTS

| | | |
|---|---|---|
| 3,926,891 A | 12/1975 | Gross et al. |
| 3,935,099 A | 1/1976 | Weaver et al. |
| 3,997,484 A | 12/1976 | Weaver et al. |
| 4,076,663 A | 2/1978 | Masuda et al. |
| 4,090,013 A | 5/1978 | Ganslaw et al. |
| 4,093,776 A | 6/1978 | Aoki et al. |
| 4,190,562 A | 2/1980 | Westerman |
| 4,286,082 A | 8/1981 | Tsubakimoto et al. |
| 4,340,706 A | 7/1982 | Obayashi et al. |
| 4,446,261 A | 5/1984 | Yamasaki et al. |
| 4,459,396 A | 7/1984 | Yamasaki et al. |
| 4,470,975 A | 9/1984 | Berger et al. |
| 4,683,274 A | 7/1987 | Nakamura |
| 4,708,997 A | 11/1987 | Stanley et al. |
| 4,766,004 A | 8/1988 | Moskowitz |
| 4,806,532 A | 2/1989 | Dousa |
| 4,857,610 A | 8/1989 | Chmelir et al. |
| 4,985,518 A | 1/1991 | Alexander et al. |
| 4,999,200 A | 3/1991 | Casillan |
| 5,126,150 A | 6/1992 | Piatt et al. |
| 5,130,474 A | 7/1992 | Makovec et al. |

(Continued)

FOREIGN PATENT DOCUMENTS

| | | |
|---|---|---|
| EP | 505322 B1 | 9/1992 |
| EP | 507672 B1 | 10/1992 |

(Continued)

OTHER PUBLICATIONS

Achinger, et al., "Left Ventricular Hypertrophy: Is Hyperphosphatemia among Dialysis Patients a Risk Factor?", J Am Soc Nephrol 17 (12 Suppl 3), S255-S261 (2006).

Ahmad, S , et al., "Aminoimidazoles as bioisosteres of acylguanidines: novel, potent, selective and orally bioavailable nhibitors of the sodium hydrogen exchanger isoform-1", Bioorganic & Med Chem Lett 14 (1), 177-180 (2004).

Ahmed , et al., "A propensity-matched study of the effects of chronic diuretic therapy on mortality and hospitalization in older adults with heart failure", Int J Cardiol 125(2), 246-253 (2008).

Akbar, A , et al., "Review article: visceral hypersensitivity in irritable bowel syndrome: molecular mechanisms and therapeutic agents", Aliment Pharmaco Ther 30, 423-435 (2009).

Altun, B , et al., "Salt and Blood Pressure: Time to Challenge", Cardiology 105(1), 9-16 (2006).

(Continued)

*Primary Examiner* — D Margaret M Seaman
(74) *Attorney, Agent, or Firm* — Viksnins Harris Padys Malen LLP

(57) ABSTRACT

The present disclosure is directed to compounds and methods for the treatment of disorders associated with fluid retention or salt overload, such as heart failure (in particular, congestive heart failure), chronic kidney disease, end-stage renal disease, liver disease, and peroxisome proliferator-activated receptor (PPAR) gamma agonist-induced fluid retention. The present disclosure is also directed to compounds and methods for the treatment of hypertension. The present disclosure is also directed to compounds and methods for the treatment of gastrointestinal tract disorders, including the treatment or reduction of pain associated with gastrointestinal tract disorders.

20 Claims, 2 Drawing Sheets

(56) References Cited

U.S. PATENT DOCUMENTS

| | | |
|---|---|---|
| 5,140,102 A | 8/1992 | Currie |
| 5,145,906 A | 9/1992 | Chambers et al. |
| 5,273,983 A | 12/1993 | Christinaki et al. |
| 5,364,842 A | 11/1994 | Justice et al. |
| 5,445,831 A | 8/1995 | Leis et al. |
| 5,489,670 A | 2/1996 | Currie et al. |
| 5,510,353 A | 4/1996 | Giger et al. |
| 5,587,454 A | 12/1996 | Justice et al. |
| 5,629,377 A | 5/1997 | Burgert et al. |
| 5,650,222 A | 7/1997 | Desmarais et al. |
| 5,763,499 A | 6/1998 | Desmarais |
| 5,795,864 A | 8/1998 | Amstutz et al. |
| 5,824,645 A | 10/1998 | Justice et al. |
| 5,824,691 A | 10/1998 | Kuno et al. |
| 5,859,186 A | 1/1999 | Justice et al. |
| 5,866,610 A | 2/1999 | Lang et al. |
| 5,891,849 A | 4/1999 | Amstutz et al. |
| 5,900,436 A | 5/1999 | Ramakrishna et al. |
| 5,969,097 A | 10/1999 | Wiegand et al. |
| 5,994,305 A | 11/1999 | Justice et al. |
| 6,005,010 A | 12/1999 | Schwark et al. |
| 6,054,429 A | 4/2000 | Bowersox et al. |
| 6,087,091 A | 7/2000 | Justice et al. |
| 6,107,356 A | 8/2000 | Desmarais |
| 6,136,786 A | 10/2000 | Justice et al. |
| 6,166,002 A | 12/2000 | Weichert et al. |
| 6,277,862 B1 | 8/2001 | Giardina et al. |
| 6,287,609 B1 | 9/2001 | Marlett et al. |
| 6,319,518 B1 | 11/2001 | Lee et al. |
| 6,333,354 B1 | 12/2001 | Schudt |
| 6,355,823 B1 | 3/2002 | Peerce |
| 6,399,824 B1 | 6/2002 | Hofmeister et al. |
| 6,413,494 B1 | 7/2002 | Lee et al. |
| 6,414,016 B1 | 7/2002 | Ueno |
| 6,451,781 B1 | 9/2002 | Kleemann et al. |
| 6,504,057 B2 | 1/2003 | Schwark et al. |
| 6,624,150 B2 | 9/2003 | Yerxa et al. |
| 6,703,405 B2 | 3/2004 | Hofmeister et al. |
| 6,734,188 B1 | 5/2004 | Rhodes et al. |
| 6,736,705 B2 | 5/2004 | Benning et al. |
| 6,737,423 B2 | 5/2004 | Heinelt et al. |
| 6,787,528 B2 | 9/2004 | Peerce |
| 6,887,870 B1 | 5/2005 | Ahmad et al. |
| 6,908,609 B2 | 6/2005 | Simon et al. |
| 6,911,453 B2 | 6/2005 | Hofmeister et al. |
| 7,014,862 B2 | 3/2006 | Myatt et al. |
| 7,026,303 B2 | 4/2006 | Cimiluca et al. |
| 7,041,786 B2 | 5/2006 | Shailubhai et al. |
| 7,109,184 B2 | 9/2006 | Jozefiak et al. |
| 7,119,120 B2 | 10/2006 | Jozefiak et al. |
| 7,241,775 B2 | 7/2007 | Hofmeister et al. |
| 7,309,690 B2 | 12/2007 | Dardenne et al. |
| 7,326,705 B2 | 2/2008 | Ahmad et al. |
| 7,666,898 B2 | 2/2010 | Chang et al. |
| 7,772,262 B2 | 8/2010 | Kleemann |
| 7,790,742 B2 | 9/2010 | Lang et al. |
| 8,134,015 B2 | 3/2012 | Eto et al. |
| 9,408,840 B2 | 8/2016 | Bell et al. |
| 10,272,079 B2 | 4/2019 | Carreras et al. |
| 10,376,481 B2 * | 8/2019 | Bell .................. A61K 31/18 |
| 2001/0006972 A1 | 7/2001 | Williams |
| 2003/0109417 A1 | 6/2003 | Nimmo et al. |
| 2003/0171580 A1 | 9/2003 | Hofmeister et al. |
| 2003/0216449 A1 | 11/2003 | Weinstock et al. |
| 2004/0039001 A1 | 2/2004 | Gericke et al. |
| 2004/0044211 A1 | 3/2004 | Hofmeister et al. |
| 2004/0113396 A1 | 6/2004 | Tsai |
| 2004/0224965 A1 | 11/2004 | Gericke et al. |
| 2005/0009863 A1 | 1/2005 | Hofmeister et al. |
| 2005/0020612 A1 | 1/2005 | Gericke |
| 2005/0054705 A1 | 3/2005 | Heinelt et al. |
| 2005/0113396 A1 | 5/2005 | Gericke et al. |
| 2005/0176746 A1 | 8/2005 | Weber et al. |
| 2005/0244367 A1 | 11/2005 | Hui et al. |
| 2007/0135383 A1 | 6/2007 | Chang et al. |
| 2007/0135385 A1 | 6/2007 | Chang et al. |
| 2007/0225323 A1 | 9/2007 | Lang et al. |
| 2007/0270414 A1 | 11/2007 | Kleemann |
| 2008/0058328 A1 | 3/2008 | Heinelt et al. |
| 2008/0194621 A1 | 8/2008 | Lang |
| 2008/0227685 A1 | 9/2008 | Currie et al. |
| 2008/0234317 A1 | 9/2008 | Kleemann et al. |
| 2012/0040025 A9 | 2/2012 | Currie et al. |
| 2012/0263670 A1 | 10/2012 | Charmot et al. |
| 2013/0274285 A1 | 10/2013 | Bell et al. |
| 2015/0336892 A1* | 11/2015 | Leadbetter .......... C07D 207/09 514/316 |
| 2017/0340623 A1 | 11/2017 | Charmot et al. |
| 2019/0275028 A1 | 9/2019 | Carreras et al. |

FOREIGN PATENT DOCUMENTS

| | | |
|---|---|---|
| EP | 625162 B1 | 11/1994 |
| EP | 0744397 A2 | 11/1996 |
| EP | 835126 B1 | 4/1998 |
| EP | 873753 A1 | 10/1998 |
| EP | 1321142 A1 | 6/2003 |
| EP | 1336409 A1 | 8/2003 |
| EP | 0876347 B1 | 3/2005 |
| EP | 1485391 B1 | 8/2006 |
| EP | 1465638 B1 | 5/2007 |
| EP | 1196396 B1 | 3/2008 |
| JP | 2007131532 A | 5/2007 |
| WO | 1993013128 | 7/1993 |
| WO | 1994026709 | 11/1994 |
| WO | 1995028418 | 10/1995 |
| WO | 1997001351 | 1/1997 |
| WO | 1997019927 | 6/1997 |
| WO | 1997021680 | 6/1997 |
| WO | 1997024113 | 7/1997 |
| WO | 1998011090 | 3/1998 |
| WO | 2001005398 | 1/2001 |
| WO | 2001017954 | 3/2001 |
| WO | 2001019849 | 3/2001 |
| WO | 2001021582 | 3/2001 |
| WO | 2001052844 | 7/2001 |
| WO | 2001064212 | 9/2001 |
| WO | 2001072742 | 10/2001 |
| WO | 2001082924 | 11/2001 |
| WO | 2001087294 | 11/2001 |
| WO | 2002020496 | 3/2002 |
| WO | 2002024637 | 3/2002 |
| WO | 2002028353 | 4/2002 |
| WO | 2002094187 | 11/2002 |
| WO | 2000048134 | 6/2003 |
| WO | 2003048129 | 6/2003 |
| WO | 2003048134 | 6/2003 |
| WO | 2003051866 | 6/2003 |
| WO | 2003053432 | 7/2003 |
| WO | 2003055490 | 7/2003 |
| WO | 2003057225 | 7/2003 |
| WO | 2003080630 | 10/2003 |
| WO | 2004085382 | 10/2004 |
| WO | 2004085404 | 10/2004 |
| WO | 2004085448 | 10/2004 |
| WO | 2006001931 | 1/2006 |
| WO | 2006032372 | 3/2006 |
| WO | 2008002971 | 1/2008 |
| WO | 2008106429 | 9/2008 |
| WO | 2008137318 | 11/2008 |
| WO | 2010025856 | 3/2010 |
| WO | 2010078449 | 7/2010 |
| WO | 2012006473 | 1/2012 |
| WO | 2012006475 | 1/2012 |
| WO | 2012006477 | 1/2012 |
| WO | 2012054110 | 4/2012 |
| WO | 2014029983 | 2/2014 |

(56) References Cited

FOREIGN PATENT DOCUMENTS

| WO | 2014029984 | 2/2014 |
|---|---|---|
| WO | 2014169094 | 10/2014 |

OTHER PUBLICATIONS

Barreto, F., et al., "Pharmacotherapy of chronic kidney disease and mineral bone disorder", Exp Op Pharmacother 12, 2627-2640 (2011).
Basit, A, "Advances in Colonic Drug Delivery", Drugs 65(14), 1991-2007 (2005).
Beubler, E, et al., "5-HT receptor antagonists and heat-stable *Escherichia coli* enterotoxin-induced effects in the rat", Eur J Pharm 219, 445 (1992).
Bleakman, D, et al., "Hypertonic fluid absorption from rabbit descending colon in vitro", Am J Physiol 258(3), Pt 1, G377-G390 (1990).
Bouras, E, et al., "Prucalopride accelerates gastrointestinal and colonic transit in patients with constipation without a rectal evacuation disorder", Gastroenterology 120, 354-360 (2001).
Brandt, et al., "An Evidence-Based Approach to the Management of Chronic Constipation in North America", Am J Gastroenterol 100 (Suppl 1), S1-S21 (2005).
Bueno, et al., "Serotonergic and non-serotonergic targets in the pharmacotherapy of visceral hypersensitivity", Neurogastroenterol Motility 19 (Suppl 1), 89-119 (2007).
Bundgard, H, "Design of Prodrugs: Bioreversible derivatives for various functional groups and chemical entites", Design of Prodrugs, Elsevier, Amsterdam, 7-24 (1985).
Burton, D, et al., "Colonic Transit Scintigraphy Labeled Activated Charcoal Compared with Ion Exchange Pellets", J Nucl Med 38,1807-1810 (1997).
Camilleri, M, et al., "Effect of renzapride on transit in constipation-predominant irritable bowel syndrome", Clin Gastroenterol Hepatol 2, 895-904 (2004).
Camilleri, M, et al., "Towards a relatively inexpensive, noninvasive, accurate test for colonic motility disorders", Gastroenterology 103, 36-42 (1992).
Campbell, C, et al., "Characterisation of SB-221420-A, a neuronal Ca and Na channel antagonist in experimental models of stroke", European Journal of Pharmacology 401(3), 419-428 (2000).
Campbell, R, et al., "Type 2 diabetes: Where we are today: An overview of disease burden, current treatments, and treatment strategies", Journal of American Pharmacists Assoc 49(5), S3-S9 (2009).
Chang, et al., "Current gut-directed therapies for irritable bowel syndrome", Curr Treat Options Gastroenterol 9(4), 314-323 (2006).
Chen, J, et al., "Synthesis and characterization of superporous hydrogel composites", Journal of Controlled Release 65, 73-82 (2000).
Cheng, et al., "Macroporous poly(N-isopropylacrylamide) hydrogels with fast response rates and improved protein release properties", Journal of Biomedical Materials Research—Part A, 67(1), 96-103 (2003).
Chiba, S, et al., "A Pd(II)-Catalyzed Ring-Expansion Reaction of Cyclic 2-Azidoalcohol Derivatives: Synthesis of Azaheterocycles", J Am Chem Soc 131 (36), 12886-12887 (2009).
Choi, N, "Kidney and Phosphate Metabolism", Electrolyte & Blood Pressure 6, 77-85 (2008).
Chou, et al., "Obstructive Sleep Apnea: a stand-along risk for chronic kidney diseases", Nephrol Dial Transplant 26 (7), 2244-2250 (2011).
Chourasia, M, et al., "Pharmaceutical Approaches to Colon Targeted Drug Delivery Systems", J Pharm Sci 6 (1), 33-66 (2003).
Chourasia, M, et al., "Polysaccharides for Colon Targeted Drug Delivery", Drug Deliv 11 (2), 129-148 (2004).
Coulie, B, et al., "Recombinant human neurotrophic factors accelerate colonic transit and relieve constipation in humans". Gastroenterology 119, 41-50 (2000).
Cremonini, F, et al., "Performance characteristics of scintigraphic transit measurements for studies of experimental therapies", Aliment Pharmacol Ther 16, 1781-1790 (2002).
Cruz, et al., "Incidence and Predictors of Development of Acute Renal Failure Related to Treatment of Congestive Heart Failure with ACE Inhibitors", Nephron Clin Pract 105 (2), c77-c83 (2007).
Davenport, A, et al., "Blood Pressure Control and Symptomatic Intradialytic Hypotension in Diabetic Haemodialysis Patients: A Cross-Sectional Survey", Nephron Clin Pract 109 (2), c65-c71 (2008).
Di Marco, et al., "High phosphate directly affects endothelial function by downregulating annexin II", Kidney International 83, 213-222 (2013).
Eherer, A, et al., "Effect of psyllium, calcium polycarbophil, and wheat bran on secretory diarrhea induced by phenolphthalein". Gastroenterology 104 (4), 1007-1012 (1993).
Ertl, P, et al., "Fast calculation of molecular polar surface area as a sum of fragment-based contributions and its application to the prediction of drug transport properties", J Med Chem 43(20), 3714-3717 (2000).
Eutamen, "Guanylate cyclase C-mediated antinociceptive effects of linaclotide in rodent models of visceral pain", Neurogastroenterol Motil 22(3), 312 (2010).
Fischer, M, et al., "The gel-forming polysaccharide of psyllium husk (Plantago ovata Forsk)", Carbohydrate Research 339, 2009-2012 (2004).
Geibel, J, "Secretion and Absorption By Colonic Crypts", Annu Rev Physiol 67, 471-490 (2005).
Gershon, et al., "The Serotonin Signaling System: From Basic Understanding To Drug Development for Functional GI Disorders", Gastroenterology 132 (1), 397-414 (2007).
Giachelli, "The emerging role of phosphate in vascular calcification", Kidney Int 75, 890-897 (2009).
Giral, H, et al., "NHE3 Regulatory Factor 1 (NHERF1) Modulates Intestinal Sodium-dependent Phosphate Transporter (NaPi-2b) Expression in Apical Microvilli", Journal of Biological Chemistry 287(42), 35047-35056 (2012).
Griffin, et al., "Multivalent Drug Design. Synthesis and In Vitro Analysis of an Array of Vancomycin Dimers", J Am Chem Soc 125, 6517-6531 (2003).
Guerin, et al., "Impact of Aortic Stiffness Attenuation on Survival of Patients in End-Stage Renal Failure", Circulation 103, 987-992 (2001).
Hammerle, et al., "Updates on treatment of irritable bowel syndrome", World J Gastroenterol 14 (17), 2639-2649 (2008).
Horkay, F, "Effect of cross-links on the swelling equation of state: polyacrylamide hydrogels", Macromolecules 22, 2007-2009 (1989).
Jacobsen, E, et al., "Highly enantioselective epoxidation catalysts derived from 1,2-diaminocyclohexane", J Am Chem Soc 113, 7063-7064 (1991).
Jain, A, et al., "Perspectives of Biodegradable Natural Polysaccharides for Site-Specific Drug Delivery to the Colon", J Pharm Sci 10 (1), 86-128 (2007).
Jain, S, et al., "Target-specific drug release to the colon", Expert Opin Drug Deliv 5 (5), 483-498 (2008).
Johanson, et al., "Chronic constipation: a survey of the patient perspective", Aliment Pharmacol Ther 25 (5), 599-608 (2007).
Kashani, et al., "Fluid retention in cirrhosis: pathophysiology and management", QJM 101 (2), 71-85 (2008).
Katopodis, K, "Inorganic Phosphorus Homeostasis during the First Hour of Dialysis", Renal Failure 33, 562-567 (2011).
Kiela, P, et al., "Apical NA+/H+ exchangers in the mammalian gastrointestinal tract", J Physiol Pharmacol 57(Supp 7), 51-79 (2006).
Ueda, H, et al., "Kyotorphin (tyrosine-arginine) synthetase in rat brain synaptosomes", J Biol Chem 262, 8165 (1987).
Van, et al., "Dietary phosphate restriction ameliorates endothelial dysfunction in adenine-induced kidney disease rats", J Clin Biochem Nutr 51, 27-32 (2012).
Van Den Mooter, G, et al., "Colon Drug Delivery", Expert Opin Drug Deliv (1), 111-125 (2006).
Vigne, et al., "The Amiloride-sensitive Na+/H' Exchange System in SkeleMtalu scle Cells in Cultur", J Biol Chem 57, 9394 (1982).

(56) References Cited

OTHER PUBLICATIONS

Wahba, I, et al., "Obesity and Obesity-Initiated Metabolic Syndrome: Mechanistic Links to Chronic Kidney Disease", Clinical Journal of American Society of Nephrology 2, 550-562 (2007).
Weinman, E, et al., "Fibroblast Growth Factor-23-mediated Inhibition of Renal Phosphate Transport in Mice Requires Sodium-Hydrogen Exchanger Regulatory Factor-1 (NHERF-1) and Synergizes with Parathyroid Hormone", Journal of Biological Chemistry 286 (43), 37216-37221 (2011).
Weinman, E, et al., "The role of NHERF-1 in the regulation of renal proximal tubule sodium-hydrogen exchanger 3 and sodium-dependent phosphate cotransporter 2a", J Physiol 567.1, 27-32 (2005).
Wenzl, et al., "Determinants of decreased fecal consistency in patients with diarrhea", Gastroenterology 108 (6), 1729-1738 (1995).
Wiley, et al., "Peptidomimetics derived from natural products", Medical Research Reviews 13 (3), 327-384 (1993).
Yang, T, et al., "Renal and Vascular Mechanisms of Thiazolidinedoine-Induced Fluid Retention", PPAR Reserach, article ID 943614, 8 pages (2008).
Zachos, et al., "Molecular Physiology of Intestinal N+/H+ Exchange", Annu Rev Physiol 67, 411-443 (2005).
Zammit, P, et al., "Effects on fluid and Na+ flux of varying luminal hydraulic resistance in rat colon in vivo", J Physiol 477 (Pt 3), 539-548 (1994).
Kirkpantur, et al., "Serum fibroblast growth factor-23 (FGF-23) levels are independently associated with left ventricular mass and myocardial performance index in maintenance haemodialysis patients", Nephrol Dial Transplant 26, 1346-1354 (2011).
Kumar, P, et al., "Colon Targeted Drug Delivery Systems—An Overview", Curr Drug Deliv 5 (3), 186-198 (2008).
Kunzelmann, et al., "Electrolyte Transport in the Mammalian Colon: Mechanisms and Implications for Disease", Physiol Rev 82 (1), 245-289 (2002).
Ledoussal, C, et al., "Renal salt wasting in mice lacking NHE3 Na+/H+ exchanger but not in mice lacking NHE2", Am J Physiol Renal Physiol 281, F718-F727 (2001).
Lewis, et al., "Stool form scale as a useful guide to intestinal transit time", Scand J Gastroenterol 32, 920-924 (1997).
Li, X, "Biodegradable Polymeric Prodrugs of Antihypertensive Agents", Department of Pharmaceutics Dissertation, 1-241 (1991).
Li, et al., "Lysophosphatidic acid inhibits cholera toxin-induced secretory diarrhea through CHTR-dependent protein interactions", J Exp Med 202, 975-986 (2005).
Linz, et al., "Antihypertensive and Laxative Effects by Pharmacological Inhibition of Sodium-Proton-Exchanger Subtype 3-Mediated Sodium Absorption in the Gut", Hypertension 60, 1560-1567 (2012).
Lipinski, "Drug-like properties and the causes of poor solubility and poor permeability", J Pharm & Toxicol Methods 44, 235-249 (2000).
Lipinski, et al., "Experimental and computational approaches to estimate solubility and permeability in drug discovery and development settings", Advanced Drug Delivery Reviews 46, 3-26 (2001).
Lopes, A, et al., "Phosphate Binder Use and Mortality Among Hemodialysis Patients in the DOPPS: Evaluation of Possible Confounding By Nutritional Status", Am J Kidney Dis 60(1), 90-101 (2012).
Lopez, et al., "Calcimimetic R-568 decreases extraosseous calcifications in uremic rats treated with calcitriol", J Am Soc Nephrol 17, 795-804 (2006).
Luks, et al., "Chronic Kidney Disease at High Altitude", J Am Soc Nephrol 19, 2262-2271 (2008).
Mahon, M, et al., "Na+/H+ Exchanger-Regulatory Factor 1 Mediates Inhibition of Phosphate Transport by Parathyroid Hormone and Second Messengers by Acting at Multiple Sites in Opossum Kidney Cells", Molecular Endocrinology 17(11), 2355-2364 (2003).
Mammen, et al., "Effective Inhibitors of Hemagglutination by Influenza Virus Synthesized from Polymers Having Active Ester Groups. Insight into Mechanism of Inhibition", Journal of Medicinal Chemistry 38, 4179-4190 (1995).
Marlett, J, et al., "The active fraction of psyllium seed husk", Proceedings of Nutrition Society 62, 207-209 (2003).
Masereel, B, et al., "An overview of inhibitors of Na+/H+ exchanger", European J of Med Chem 38, 547-554 (2003).
McKie, A, et al., "Mechanical aspects of rabbit fecal dehydration", Am J Physiol 258 (3), Pt 1, G391-G394 (1990).
McPhee, W, "Poly(N-isopropylacrylamide) Latices Prepared with Sodium Dodecyl Sulfate", Journal of Colloid and Interface Science 156, 24-30 (1993).
Medline Plus, entry for Chronic Kidney Disease, retrived from www.nlm.nih.gov/medlineplus/ency/article/000471.htm, on Aug. 6, 2015, 1-8.
Medline Plus, entry for End-stage Kidney Diseases, retrieved from www.nlm.nih.gov/medlineplus/ency/article/000500.htm, Aug. 6, 2015, 1-6.
Medline Plus, for Irritable Bowel Syndrome, retrieved from medlineplus/irritablebowelsyndrome.html>on Aug. 6, 2015, 1-6.
Merck Manual, "Hyperphosphatemia", www.merckmanuals.com/professional/endocrine-and-metabolic-disorders/electrolyte-disorders/hyperphosphatemia, 4 pages (Last full review/revision Mar. 2018).
Miyamoto, K, et al., "Sodium-dependent phosphate cotransporters: Lessons from gene knockout and mutation studies", J Pharm Sci 100, 3719-3730 (2011).
Mohrmann, et al., "Sodium-dependent transport of Pi by an established intestinal epithelial cell line (CaCo-2)", Am J Phys 250 (3), G323-G330 (1986).
Molony, D, et al., "Derangements in Phosphate Metabolism in Chronic Kidney Diseases/Endstage Renal Disease Therapeutic Considerations", Adv Chron Kidney Disease 18(2), 120-131 (2011).
Musso, D, et al., "Indanylidenes. 2. Design and Synthesis of (E)-2-(4-Chloro-6-fluoro-1-indanylidene)-N-methylacetamide, a Potent Antiinflammatory and Analgesic Agent without Centrally Acting Muscle Relaxant Activity", J Med Chem 46 (3), 409-416 (2003).
Neves, et al., "Adverse effects of hyperphosphatemia on myocardial hypertrophy, renal function, and bone in rats with renal failure", Kidney Int 66, 2237-2244 (2004).
Ogden, C, et al., "Prevalence of Overweight and Obesity in the United States, 1999-2004", JAMA 295, 1549-1555 (2006).
Oh, K, et al., "Swelling behavior of submicron gel particles", Journal of Applied Polymer Science 69, 109-114 (1998).
Ohnishi, et al., "Dietary and genetic evidence for phosphate toxicity accelerating mammalian aging", FASEB J 24, 362-371 (2010).
Pappagallo, "Incidence, Prevalence, and Management of Opioid Bowel Dysfunction", Am J Surg 182 (5A Suppl), 11S-18S (2001).
Paradiso, et al., "Na+-H+ exchange in gastric glands as measured with a cytoplasmic-trapped, fluorescent pH indicator", PNAS USA 81(23), 7436-7440 (1984).
Patent Cooperation Treaty, International Searching Authority, Search Report and Written Opinion for PCT/US2018/013020, 10 pages, Apr. 17, 2018.
Patil, S, et al., "Mucoadhesive Microspheres: A Promising Tool in Drug Delivery", Curr Drug Deliv 5(4), 312-318 (2008).
Pelton, R, et al., "Temperature-sensitive aqueous microgels", Advanceds in Colloid and Interface Science 8, 1-33 (2000).
Posserud, I, et al., "Altered Rectal Perception in Irritable Bowel Syndrome Is Associated With Symptom Severity", Gastroenterolgy 133, 1113-1123 (2007).
Prather, C, et al., "Tegaserod accelerates orocecal transit in patients with constipation-predominant irritable bowel syndrome", Gastroenterology 118, 463-468 (2000).
Rao, et al., "Evaluation of gastrointestinal transit in clinical practice: position paper of the American and European Neurogastroenterology and Motility Societies", Neurogastroenterol Motil 2, 8-23 (2011).
Sarkar, et al., "Interdialytic weight gain: implications in hemodialysis patients", Semin Dial 19, 429-433 (2006).
Schocken, D, et al., "A Scientific Statement From the American Heart Association Councils on Epidemiology and Prevention, Clinical Cardiology, Cardiovascular Nursing, and High Blood Pressure Research; Quality of Care and Outcomes Research Interdisciplinary Working Group; . . . ", Circulation 117 (19), 2544-2565 (2008).

(56) References Cited

OTHER PUBLICATIONS

Selvaraj, et al., "Tool development for Prediction of pIC50 values from the IC50 values-A pIC50 value calculator", Current Trends in Biotechnology and Pharmacy 5, 1104-1109 (2011).
Shareef, M, et al., "Colonic drug delivery: an updated review", AAPS Pharm Sci (2), E17 (2003).
Shuto, et al., "Dietary Phosphorus Acutely Impairs Endothelial Function", J Am Soc Nephrol 20 (7), 1504-1512 (2009).
Silva, A, "Advances in Prodrug Design", Mini-Reviews in Medicinal Chemistry 5, 893-914 (2005).
Sinha, V, et al., "Colonic Drug Delivery: Prodrug Approach", Pharm Res 18 (5), 557-564 (2001).
Spencer, A, et al., "Intestinal Inhibition of the Na+/H+ Exchanger 3 Prevents Cardiorenal Damage in Rats and Inhibits Na+ Uptake in Humans", Science Translational Medicine 6(227), 227ra36, 10 pages, (2014).
Spherix Global Insights Report, "RealWorld Dynamix—Exploring the Patient Journey", Dialysis Market, 2018, CKD, Non-dialysis Market 2017 (Slides 1-5).
STN Medline, AN 2011625687, 1 page (2011).
Townsend, R, et al., "Metabolic Syndrome, Components, and Cardiovascular Disease Prevalence in Chronic Kidney Disease: Findings from the Chronic Renal Insufficiency Cohort (CRIC) Study", American Journal of Nephrology 33, 477-484 (2011).

\* cited by examiner

COMPOUNDS USEFUL FOR TREATING GASTROINTESTINAL TRACT DISORDERS

This application claims priority to and benefit of U.S. provisional patent application No. 62/444,335, filed 9 Jan. 2017, and U.S. provisional patent application No. 62/541,097, filed Aug. 4, 2017, which are herein incorporated by reference in their entireties.

FIELD OF INVENTION

The present disclosure is directed to indanes derivatives that are substantially active in the gastrointestinal tract to inhibit NHE-mediated antiport of sodium ions and hydrogen ions, and the use of such compounds in the treatment of disorders associated with fluid retention or salt overload and in the treatment of gastrointestinal tract disorders, including the treatment or reduction of pain associated with a gastrointestinal tract disorder.

BACKGROUND OF THE INVENTION

Disorders Associated with Fluid Retention and Salt Overload

According to the American Heart Association, more than 5 million Americans have suffered from heart failure, and an estimated 550,000 cases of congestive heart failure (CHF) occur each year (Schocken, D. D. et al., *Prevention of heart failure: a scientific statement from the American Heart Association Councils on Epidemiology and Prevention, Clinical Cardiology, Cardiovascular Nursing, and High Blood Pressure Research*; Quality of Care and Outcomes Research Interdisciplinary Working Group; and Functional Genomics and Translational Biology Interdisciplinary Working Group: Circulation, v. 117, no. 19, p. 2544-2565 (2008)). The clinical syndrome of congestive heart failure occurs when cardiac dysfunction prevents adequate perfusion of peripheral tissues. The most common form of heart failure leading to CHF is systolic heart failure, caused by contractile failure of the myocardium. A main cause of CHF is due to ischemic coronary artery disease, with or without infarction. Long standing hypertension, particularly when it is poorly controlled, may lead to CHF.

In patients with CHF, neurohumoral compensatory mechanisms (i.e., the sympathetic nervous system and the renin-angiotensin system) are activated in an effort to maintain normal circulation. The renin-angiotensin system is activated in response to decreased cardiac output, causing increased levels of plasma renin, angiotensin II, and aldosterone. As blood volume increases in the heart, cardiac output increases proportionally, to a point where the heart is unable to dilate further. In the failing heart, contractility is reduced, so the heart operates at higher volumes and higher filling pressures to maintain output. Filling pressures may eventually increase to a level that causes transudation of fluid into the lungs and congestive symptoms (e.g., edema, shortness of breath). All of these symptoms are related to fluid volume and salt retention, and this chronic fluid and salt overload further contribute to disease progression.

Compliance with the medication regimen and with dietary sodium restrictions is a critical component of self-management for patients with heart failure and may lengthen life, reduce hospitalizations and improve quality of life. Physicians often recommend keeping salt intake below 2.3 g per day and no more than 2 g per day for people with heart failure. Most people eat considerably more than this, so it is likely that a person with congestive heart failure will need to find ways to reduce dietary salt.

A number of drug therapies currently exist for patients suffering from CHF. For example, diuretics may be used or administered to relieve congestion by decreasing volume and, consequently, filling pressures to below those that cause pulmonary edema. By counteracting the volume increase, diuretics reduce cardiac output; however, fatigue and dizziness may replace CHF symptoms. Among the classes or types of diuretics currently being used is thiazides. Thiazides inhibit NaCl transport in the kidney, thereby preventing reabsorption of Na in the cortical diluting segment at the ending portion of the loop of Henle and the proximal portion of the distal convoluted tubule. However, these drugs are not effective when the glomerular filtration rate (GFR) is less than 30 ml/min. Additionally, thiazides, as well as other diuretics, may cause hypokalemia. Also among the classes or types of diuretics currently being used is loop diuretics (e.g., furosemide). These are the most potent diuretics and are particularly effective in treating pulmonary edema. Loop diuretics inhibit the NaKCl transport system, thus preventing reabsorption of Na in the loop of Henle.

Patients that have persistent edema despite receiving high doses of diuretics may be or become diuretic-resistant. Diuretic resistance may be caused by poor availability of the drug. In patients with renal failure, which has a high occurrence in the CHF population, endogenous acids compete with loop diuretics such as furosemide for the organic acid secretory pathway in the tubular lumen of the nephron. Higher doses, or continuous infusion, are therefore needed to achieve entrance of an adequate amount of drug into the nephron. However, recent meta-analysis has raised awareness about the long-term risk of chronic use of diuretics in the treatment of CHF. For instance, in a recent study (Ahmed et al., *Int J Cardiol*, 2008 Apr. 10; 125(2): 246-253) it was shown that chronic diuretic use was associated with significantly increased mortality and hospitalization in ambulatory older adults with heart failure receiving angiotensin converting enzyme inhibitor and diuretics.

Angiotensin-converting enzyme ("ACE") inhibitors are an example of another drug therapy that may be used to treat congestive heart failure. ACE inhibitors cause vasodilatation by blocking the renin-angiotensin-aldosterone system. Abnormally low cardiac output may cause the renal system to respond by releasing renin, which then converts angiotensinogen into angiotensin I. ACE converts angiotensin I into angiotensin II. Angiotensin II stimulates the thirst centers in the hypothalamus and causes vasoconstriction, thus increasing blood pressure and venous return. Angiotensin II also causes aldosterone to be released, causing reabsorption of Na and concomitant passive reabsorption of fluid, which in turn causes the blood volume to increase. ACE inhibitors block this compensatory system and improve cardiac performance by decreasing systemic and pulmonary vascular resistance. ACE inhibitors have shown survival benefit and conventionally have been a treatment of choice for CHF. However, since ACE inhibitors lower aldosterone, the K-secreting hormone, one of the side-effects of their use is hyperkalemia. In addition, ACE inhibitors have been show to lead to acute renal failure in certain categories of CHF patients. (See. e.g., C. S. Cruz et al., "Incidence and Predictors of Development of Acute Renal Failure Related to the Treatment of Congestive Heart Failure with ACE Inhibitors, Nephron Clin. Pract., v. 105, no. 2, pp. c77-c83 (2007)).

Patients with end stage renal disease ("ESRD"), i.e., stage 5 chronic kidney failure, must undergo hemodialysis three times per week. The quasi-absence of renal function and ability to eliminate salt and fluid results in large fluctuations in body weight as fluid and salt build up in the body (sodium/volume overload). The fluid overload is characterized as interdialytic weight gain. High fluid overload is also worsened by heart dysfunction, specifically CHF. Dialysis is used to remove uremic toxins and also adjust salt and fluid homeostasis. However, symptomatic intradialytic hypotension (SIH) may occur when patients are over-dialyzed. SIH is exhibited in about 15% to 25% of the ESRD population (Davenport, A., C. Cox, and R. Thuraisingham, *Blood pressure control and symptomatic intradialytic hypotension in diabetic haemodialysis patients: a cross-sectional survey*; Nephron Clin. Pract., v. 109, no. 2, p. c65-c71 (2008)). Like in hypertensive and CHF patients, dietary restrictions of salt and fluid are highly recommended but poorly followed because of the poor palatability of low-salt food The cause of primary or "essential" hypertension is elusive. However, several observations point to the kidney as a primary factor. The strongest data for excess salt intake and elevated blood pressure come from INTERSALT, a cross-sectional study of greater than 10,000 participants. For individuals, a significant, positive, independent linear relation between 24-hour sodium excretion and systolic blood pressure was found. Higher individual 24-hour urinary sodium excretions were found to be associated with higher systolic/diastolic blood pressure on average, by 6-3/3-0 mm Hg. Primary hypertension is a typical example of a complex, multifactorial, and polygenic trait. All these monogenic hypertensive syndromes are virtually confined to mutated genes involving gain of function of various components of the renin-angiotensin-aldosterone system, resulting in excessive renal sodium retention. In a broad sense, these syndromes are characterized by increased renal sodium reabsorption arising through either primary defects in sodium transport systems or stimulation of mineralocorticoid receptor activity (Altun, B., and M. Arici, 2006, *Salt and blood pressure: time to challenge*; Cardiology, v. 105, no. 1, p. 9-16 (2006)). A much larger number of controlled studies have been performed on hypertensive subjects during the last three decades to determine whether sodium reduction will reduce established high blood pressure. Meta-analyses of these studies have clearly shown a large decrease in blood pressure in hypertensive subjects.

In end stage liver disease (ESLD), accumulation of fluid as ascites, edema or pleural effusion due to cirrhosis is common and results from a derangement in the extracellular fluid volume regulatory mechanisms. Fluid retention is the most frequent complication of ESLD and occurs in about 50% of patients within 10 years of the diagnosis of cirrhosis. This complication significantly impairs the quality of life of cirrhotic patients and is also associated with poor prognosis. The one-year and five-year survival rate is 85% and 56%, respectively (Kashani et al., *Fluid retention in cirrhosis: pathophysiology and management*; QJM, v. 101, no, 2, p. 71-85 (2008)). The most acceptable theories postulate that the initial event in ascites formation in the cirrhotic patient is sinusoidal hypertension. Portal hypertension due to an increase in sinusoidal pressure activates vasodilatory mechanisms. In advanced stages of cirrhosis, arteriolar vasodilation causes underlining of systemic arterial vascular space. This event, through a decrease in effective blood volume, leads to a drop in arterial pressure. Consequently, baroreceptor-mediated activation of renin-angiotensin aldosterone system, sympathetic nervous system and non-osmotic release of antidiuretic hormone occur to restore the normal blood homeostasis. These events cause further retention of renal sodium and fluid. Splanchnic vasodilation increases splanchnic lymph production, exceeding the lymph transportation system capacity, and leads to lymph leakage into the peritoneal cavity Persistent renal sodium and fluid retention, alongside increased splanchnic vascular permeability in addition to lymph leakage into the peritoneal cavity, play a major role in a sustained ascites formation.

Thiazolidinediones (TZD's), such as rosiglitazone, are peroxisome proliferator-activated receptor (PPAR) gamma agonist agents used for the treatment of type-2 diabetes and are widely prescribed. Unfortunately, fluid retention has emerged as the most common and serious side-effect of TZD's and has become the most frequent cause of discontinuation of therapy. The incidence of TZD-induced fluid retention ranges from 7% in monotherapy and to as high as 15% when combined with insulin (Yan, T., Soodvilai, S., *PPAR Research* volume 2008, article ID 943614). The mechanisms for such side-effects are not fully understood but may be related in Na and fluid re-absorption in the kidney. However TZD-induced fluid retention is resistant to loop diuretics or thiazide diuretics, and combination of peroxisome proliferator-activated receptor (PPAR) alpha with PPAR gamma agonists, which were proposed to reduce such fluid overload, are associated with major adverse cardiovascular events.

In view of the foregoing, it is recognized that salt and fluid accumulation contribute to the morbidity and mortality of many diseases, including heart failure (in particular, congestive heart failure), chronic kidney disease, end-stage renal disease, liver disease and the like. It is also accepted that salt and fluid accumulation are risk factors for hypertension. Accordingly, there is a clear need for a medicament that, when administered to a patient in need, would result in a reduction in sodium retention, fluid retention, or both. Such a medicament would also not involve or otherwise impair renal mechanisms of fluid/Na homeostasis.

One option to consider for treating excessive fluid overload is to induce diarrhea. Diarrhea may be triggered by several agents including, for example, laxatives such as sorbitol, polyethyleneglycol, bisacodyl and phenolphthaleine. Sorbitol and polyethyleneglycol triggers osmotic diarrhea with low levels of secreted electrolytes thus, their utility in removing sodium salt from the GI tract is limited. The mechanism of action of phenolphthalein is not clearly established, but is thought to be caused by inhibition of the Na/K ATPase and the Cl/HCO$_3$ anion exchanger and stimulation of electrogenic anion secretion (see, e.g., Eherer, A. J., C. A. Santa Ana, J. Porter, and J. S. Fordtran, 1993, Gastroenterology, v. 104, no. 4, p. 1007-1012). However, some laxatives, such as phenolphthalein, are not viable options for the chronic treatment of fluid overload, due to the potential risk of carcinogenicity in humans. Furthermore, laxatives may not be used chronically, as they have been shown to be an irritant and cause mucosal damage. Accordingly, it should also be recognized that the induction of chronic diarrhea as part of an effort to control salt and fluid overload would be an undesired treatment modality for most patients. Any medicament utilizing the GI tract for this purpose would therefore need to control diarrhea in order to be of practical benefit.

One approach for the treatment of mild diarrhea is the administration of a fluid-absorbing polymer, such as the natural plant fiber psyllium. Polymeric materials, and more specifically hydrogel polymers, may also be used for the removal of fluid from the gastrointestinal (GI) tract. The use of such polymers is described in, for example, U.S. Pat. Nos. 4,470,975 and 6,908,609, the entire contents of which are incorporated herein by reference for all relevant and consistent purposes. However, for such polymers to effectively remove significant quantities of fluid, they must desirably resist the static and osmotic pressure range existing in the GI tract. Many mammals, including humans, make a soft feces with a water content of about 70%, and do so by transporting fluid against the high hydraulic resistance imposed by the fecal mass. Several studies show that the pressure required to dehydrate feces from about 80% to about 60% is between about 500 kPa and about 1000 kPa (i.e., about 5 to about 10 atm). (See, e.g., McKie, A. T., W. Powrie, and R. J. Naftalin, 1990, Am J Physiol, v. 258, no. 3 Pt 1, p. G391-G394; Bleakman, D., and R. J. Naftalin, 1990, Am J Physiol, v. 258, no. 3 Pt 1, p. G377-G390; Zammit, P. S., M. Mendizabal, and R. J. Naftalin, 1994, J Physiol, v. 477 (Pt 3), p. 539-548.). However, the static pressure measured intraluminally is usually between about 6 kPa and about 15 kPa. The rather high pressure needed to dehydrate feces is essentially due to an osmotic process and not a mechanical process produced by muscular forces. The osmotic pressure arises from the active transport of salt across the colonic mucosa that ultimately produces a hypertonic fluid absorption. The osmotic gradient produced drives fluid from the lumen to the serosal side of the mucosa. Fluid-absorbing polymers, such as those described in for example U.S. Pat. Nos. 4,470,975 and 6,908,609, may not be able to sustain such pressure. Such polymers may collapse in a normal colon where the salt absorption process is intact, hence removing a modest quantity of fluid and thereby salt.

Synthetic polymers that bind sodium have also been described. For example, ion-exchange polymeric resins, such as Dowex-type cation exchange resins, have been known since about the 1950's. However, with the exception of Kayexalate™ (or Kionex™), which is a polystyrene sulfonate salt approved for the treatment of hyperkalemia, cation exchange resins have very limited use as drugs, due at least in part to their limited capacity and poor cation binding selectivity. Additionally, during the ion-exchange process, the resins may release a stochiometric amount of exogenous cations (e.g., H, K, Ca), which may in turn potentially cause acidosis (H), hyperkalemia (K) or contribute to vascular calcification (Ca). Such resins may also cause constipation.

Gastrointestinal Tract Disorders

Constipation is characterized by infrequent and difficult passage of stool and becomes chronic when a patient suffers specified symptoms for over 12 non-consecutive weeks within a 12-month period. Chronic constipation is idiopathic if it is not caused by other diseases or by use of medications. An evidence-based approach to the management of chronic constipation in North America (Brandt et al., 2005, Am. J. Gastroenterol. 100(Suppl.1):S5-S21) revealed that prevalence is approximately 15% of the general population. Constipation is reported more commonly in women, the elderly, non-whites, and individuals from lower socioeconomic groups.

Irritable bowel syndrome (IBS) is a common GI disorder associated with alterations in motility, secretion and visceral sensation. A range of clinical symptoms characterizes this disorder, including stool frequency and form, abdominal pain and bloating. The recognition of clinical symptoms of IBS are yet to be defined, but it is now common to refer to diarrhea-predominant IBS (D-IBS) and constipation-predominant IBS (C-IBS), wherein D-IBS is defined as continuous passage of loose or watery stools and C-IBS as a group of functional disorders which present as difficult, infrequent or seemingly incomplete defecation. The pathophysiology of IBS is not fully understood, and a number of mechanisms have been suggested. Visceral hypersensitivity is often considered to play a major etiologic role and has been proposed to be a biological marker even useful to discriminate IBS from other causes of abdominal pain. In a recent clinical study (Posserud I. et al, *Gastroenterology*, 2007; 133:1113-1123) IBS patients were submitted to a visceral sensitivity test (Balloon distention) and compared with healthy subjects. It revealed that 61% of the IBS patients had an altered visceral perception as measured by pain and discomfort threshold. Other reviews have documented the role of visceral hypersensitivity in abdominal pain symptomatic of various gastrointestinal tract disorders (Akbar, A, et al, *Aliment Pharmaco. Ther.*, 2009, 30, 423-435; Bueno et al., *Neurogastroenterol Motility* (2007) 19 (suppl.1), 89-119). Colonic and rectal distention have been widely used as a tool to assess visceral sensitivity in animal and human studies. The type of stress used to induce visceral sensitivity varies upon the models (see for instance Eutamen, H *Neurogastroenterol Motil.* 2009 Aug. 25. [Epub ahead of print]), however stress such as Partial restraint stress (PRS) is a relatively mild, non-ulcerogenic model that is considered more representative of the IBS setting.

Constipation is commonly found in the geriatric population, particularly patients with osteoporosis who have to take calcium supplements. Calcium supplements have shown to be beneficial in ostoporotic patients to restore bone density but compliance is poor because of calcium-induced constipation effects.

Opioid-induced constipation (OIC) (also referred to as opioid-induced bowel dysfunction or opioid bowel dysfuntion (OBD)) is a common adverse effect associated with opioid therapy. OIC is commonly described as constipation; however, it is a constellation of adverse gastrointestinal (GI) effects, which also includes abdominal cramping, bloating, and gastroesophageal reflux. Patients with cancer may have disease-related constipation, which is usually worsened by opioid therapy. However, OIC is not limited to cancer patients. A recent survey of patients taking opioid therapy for pain of non-cancer origin found that approximately 40% of patients experienced constipation related to opioid therapy (<3 complete bowel movements per week) compared with 7.6% in a control group. Of subjects who required laxative therapy, only 46% of opioid-treated patients (control subjects, 84%) reported achieving the desired treatment results>50% of the time (Pappagallo, 2001, Am. J. Surg. 182(54 Suppl.):11S-18S).

Some patients suffering from chronic idiopathic constipation can be successfully treated with lifestyle modification, dietary changes and increased fluid and fiber intake, and these treatments are generally tried first. For patients who fail to respond to these approaches, physicians typically recommend laxatives, most of which are available over-the-counter. Use of laxatives provided over-the-counter is judged inefficient by about half of the patients (Johanson and Kralstein, 2007, Aliment. Pharmacol. Ther. 25(5):599-608). Other therapeutic options currently prescribed or in clinical development for the treatment of IBS and chronic constipation including OIC are described in, for example: Chang et al., 2006, Curr. Teat. Options Gastroenterol. 9(4):314-323; Gershon and Tack, 2007, Gastroenterology 132(1):397-414; and, Hammerle and Surawicz, 2008, World J. Gastroenterol. 14(17):2639-2649. Such treatments include but are not limited to serotonin receptor ligands, chloride channel activators, opioid receptor antagonists, guanylate-cyclase receptor agonists and nucleotide P2Y(2) receptor agonists. Many of these treatment options are inadequate, as they may be habit forming, ineffective in some patients, may cause long term adverse effects, or otherwise are less than optimal.

Na+/H+ Exchanger (NHE) Inhibitors

A major function of the GI tract is to maintain water/Na homeostasis by absorbing virtually all water and Na to which the GI tract is exposed. The epithelial layer covering the apical surface of the mammalian colon is a typical electrolyte-transporting epithelium, which is able to move large quantities of salt and water in both directions across the mucosa. For example, each day the GI tract processes about 9 liters of fluid and about 800 meq of Na. (See, e.g., Zachos et al., *Molecular physiology of intestinal Na+/H+ exchange*; Annu. Rev. Physiol., v. 67, p. 411-443 (2005).) Only about 1.5 liters of this fluid and about 150 meq of this sodium originates from ingestion; rather, the majority of the fluid (e.g., about 7.5 liters) and sodium (about 650 meq) is secreted via the GI organs as part of digestion. The GI tract therefore represents a viable target for modulating systemic sodium and fluid levels.

Many reviews have been published on the physiology and secretory and/or absorption mechanisms of the GI tract (see, e.g., Kunzelmann et al., *Electrolyte transport in the mamma/inn colon: mechanisms and implications for disease*; Physiol. Rev., v. 82, no. 1, p. 245-289 (2002); Geibel, J. P.; *Secretion and absorption by colonic crypts*; Annu. Rev. Physiol, v. 67, p. 471-490 (2005); Zachos et al., supra; Kiela, P. R. et al., *Apical NA+/H+ exchangers in the mammalian gastrointestinal tract*; J. Physiol. Pharmacol., v. 57 Suppl. 7, p. 51-79 (2006)). The two main mechanisms of Na absorption are electroneutral and electrogenic transport. Electroneutral transport is essentially due to the Na+/H+ antiport NHE (e.g., NHE-3) and is responsible for the bulk of Na absorption. Electrogenic transport is provided by the epithelium sodium channel ("ENaC"). Electroneutral transport is located primarily in the ileal segment and proximal colon and electrogenic transport is located in the distal colon.

Plasma membrane NHEs contribute to maintenance of intracellular pH and volume, transcellular absorption of NaCl and NaHCO$_3$, and fluid balance carried out by epithelial cells, especially in the kidney, intestine, gallbladder, and salivary glands, as well as regulation of systemic pH. There exists a body of literature devoted to the role and clinical intervention on systemic NHEs to treat disorders related to ischemia and reperfusion for cardioprotection or renal protection. Nine isoforms of NHEs have been identified (Kiela, P. R., et al.; *Apical NA+/H+ exchangers in the mammalian gastrointestinal tract*; J. Physiol, Pharmacol., v. 57 Suppl 7, p. 51-79 (2006)), of which NHE-2, NHE-3 and NHE-8 are expressed on the apical side of the GI tract, with NHE-3 providing a larger contribution to transport. Another, yet to be identified, Cl-dependant NHE has been identified in the crypt of rat cells. In addition, much research has been devoted to identifying inhibitors of NHEs. The primary targets of such research have been NHE-1 and NHE-3. Small molecule NHE inhibitors are, for example, described in: U.S. Pat. Nos. 5,866,610; 6,399,824; 6,911,453; 6,703,405; 6,005,010; 6,736,705; 6,887,870; 6,737,423; 7,326,705; 5,824,691 (WO 94/026709); U.S. Pat. No. 6,399,824 (WO 02/024637); U.S. Pat. Pub. Nos, 2004/0039001 (WO 02/020496); 2005/0020612 (WO 03/055490); 2004/0113396 (WO 03/051866); 2005/0020612; 2005/0054705; 2008/0194621; 2007/0225323; 2004/0039001; 2004/0224965; 2005/0113396; 2007/0135383; 2007/0135385; 2005/0244367; 2007/0270414; International Publication Nos. WO 01/072742; WO 01/021582 (CA2387529), WO 97/024113 (CA02241531) and European Pat. No. IEP0744397 (CA2177007); all of which are incorporated herein by reference in their entirety for all relevant and consistent purposes.

However, such research failed to develop or recognize the value or importance of NHE inhibitors that are not absorbed (i.e., not systemic) and target the gastrointestinal tract, as disclosed recently in WO 2010/078449. Such inhibitors can be utilized in the treatment of disorders associated with fluid retention and salt overload and in the treatment of GI tract disorders, including the treatment or reduction of pain associated with a gastrointestinal tract disorder. Such inhibitors are particular advantageous because they can be delivered with reduced fear of systemic on-target or off-target effects (e.g., little or no risk of renal involvement or other systemic effects.

Accordingly, while progress has been made in the foregoing fields, there remains a need in the art for novel compounds for use in the disorders associated with fluid retention and salt overload and in the treatment of gastrointestinal tract disorders, including the treatment or reduction of pain associated with a gastrointestinal tract disorder. The present invention fulfills this need and provides further related advantages.

SUMMARY OF THE INVENTION

In brief, the present invention is directed to compounds that are substantially active in gastrointestinal tract to inhibit NHE-mediated antiport of sodium ions and hydrogen ions, and the use of such compounds in the treatment of disorders associated with fluid retention and salt overload and in the treatment of gastrointestinal tract disorders, including the treatment or reduction of pain associated with a gastrointestinal tract disorder.

A compound of formula I:

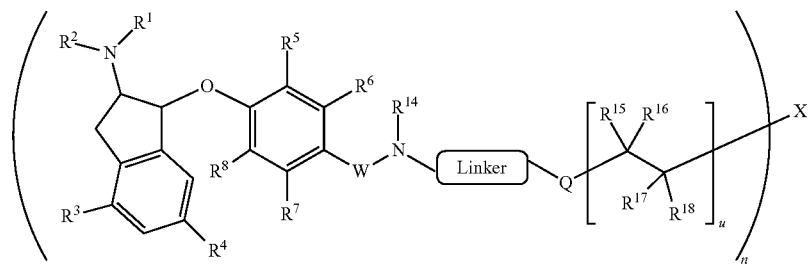

or a pharmaceutically acceptable salt, prodrug, solvate, hydrate, isomer, or tautomer thereof, wherein:

Linker is —$R^{13}$—$(CHR^{13})_p$—$[Y—(CH_2)_r]_s$—$Z$—$R^{13}$—$(CH_2)_t$—$Z$—;

X is a bond, H, N, O, $CR^{11}R^{12}$, $CR^{11}$, C, —NHC(O)NH—, —$(CHR^{13})_p$— or $C_3$-$C_6$cyclolakyl;

W is independently, at each occurrence, $S(O)_2$, C(O), or —$(CH_2)_m$—;

Z is independently, at each occurrence, a bond, C(O), or —C(O)NH—;

Y is independently, at each occurrence, O, S, NH, N($C_1$-$C_3$alkyl), or —C(O)NH—;

Q is a bond, NH, —C(O)NH—, —NHC(O)NH—, —NHC(O)N(CH_3)—, or —NHC(O)NH—$(CHR^{13})$;

m is an integer from 1 to 2;

n is an integer from 1 to 4;

r and p are independently, at each occurrence, integers from 0 to 8;

s is an integer from 0 to 4;

t is an integer from 0 to 4;

u is an integer from 0 to 2;

$R^1$ and $R^2$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, wherein each alkyl, alkenyl, cycloalkenyl, alkynyl, cycloalkyl, heterocyclyl, aryl, or heteroaryl is optionally substituted with one or more halogen, OH, CN, —$NO_2$, oxo, —$SR^9$, —$OR^9$, —$NHR^9$, —$NR^9R^{10}$, —$S(O)_2N(R^9)_2$, —$S(O)_2R^9$, —$C(O)R^9$, —$C(O)OR^9$, —$C(O)NR^9R^{10}$, —$NR^9S(O)_2R^{10}$, —$S(O)R^9$, —$S(O)NR^9R^{10}$, —$NR^8S(O)R^9$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl; or $R^1$ and $R^2$ together with the nitrogen to which they are attached can form a heterocyclyl or heteroaryl containing 1-5 heteroatoms selected from the group consisting of N, S, P and O, wherein the heterocyclyl or heteroaryl group is optionally substituted with one or more halogen, OH, CN, —$NO_2$, oxo, —$SR^9$, —$OR^9$, —$NHR^9$, —$NR^9R^{10}$, —$S(O)_2N(R^9)_2$, —$S(O)_2R^9$, —$C(O)R^9$, —$C(O)OR^9$, —$C(O)NR^9R^{10}$, —$NR^9S(O)_2R^{10}$, —$S(O)R^9$, —$S(O)NR^9R^{10}$, —$NR^9S(O)R^{10}$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl;

$R^3$ and $R^4$ are independently halogen, OH, CN, $C_1$-$C_6$alkyl, $C_1$-$C_6$alkoxy, $C_1$-$C_6$haloalkyl, $C_1$-$C_6$haloalkoxy, or —$C(O)NR^9R^{10}$;

$R^5$, $R^6$, $R^7$, and $R^8$ are independently H, halogen, OH, CN, —$NO_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —$SR^9$, —$OR^9$, —$NHR^9$, —$NR^9R^{10}$, —$S(O)_2N(R^9)_2$—, —$S(O)_2R^9$, —$C(O)R^9$, —$C(O)OR^9$, —$NR^9S(O)_2R^{10}$, —$S(O)NR^9R^{10}$, —$NR^8S(O)R^9$;

$R^9$ and $R^{10}$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, or heteroaryl containing 1-5 heteroatoms selected from the group consisting of N, S, P and O $R^{11}$ and $R^{12}$ are independently H, $C_1$-$C_6$alkyl, OH, $NH_2$, CN, or $NO_2$;

$R^{13}$ is independently, at each occurrence, a bond, H, $C_1$-$C_6$alkyl, $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R^{19}$;

$R^{14}$ is independently, at each occurrence, H, $C_1$-$C_6$alkyl, or $C_1$-$C_6$haloalkyl; or $R^6$ and $R^{14}$ together with the atoms to which they are attached may combine to form, independently, at each occurrence, 5- to-6 membered heterocyclyl wherein each $C_3$-$C_8$cycloalkyl, or heterocyclyl is optionally substituted with one or more $R^{19}$, or $R^{13}$ and $R^{14}$ together with the atoms to which they are attached may combine to form independently, at each occurrence, $C_3$-$C_8$cycloalkyl, heterocyclyl, aryl, or heteroaryl containing 1-5 heteroatoms selected from the group consisting of N, S, P and O, wherein each heterocyclyl or heteroaryl is optionally substituted with one or more $R^{19}$;

$R^{15}$, $R^{16}$, $R^{17}$, and $R^{18}$ are independently, at each occurrence, H, OH, $NH_2$, or $C_1$-$C_3$ alkyl, wherein the alkyl is optionally substituted with one or more $R^{19}$; and $R^{19}$ are independently, at each occurrence, H, OH, $NH_2$, oxo, $C_1$-$C_6$alkyl, $C_1$-$C_6$Hhaloalkyl, $C_1$-$C_6$alkoxy;

provided that:

(1) when X is H, n is 1;

(2) when X is a bond, O, or $CR^{11}R^{12}$; n is 2;

(3) when n is 3, X is $CR^{11}$ or N;

(4) when n is 4 X is C;

(5) only one of Q or X is —NHC(O)NH— at the time, (6) $R^1$ and $R^2$ together with the nitrogen to which they are attached, cannot form a pyrrolidinyl;

(7) when $R^1$ and $R^2$ are methyl, $R^3$ and $R^4$ are halogen, and $R^5$ and $R^8$ are H, Linker is not

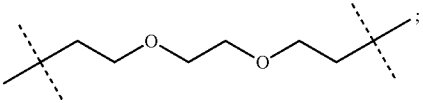

(8) when $R^1$ and $R^2$ together with the nitrogen to which they are attached form a piperidinyl, $R^3$ and $R^4$ are halogen, and $R^5$ and $R^8$ are H, Linker is not

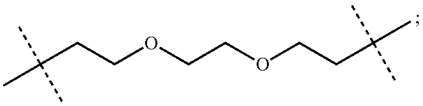

and (9) when $R^1$ and $R^2$, together with the nitrogen to which they are attached, form 3-aminopiperidin-1-yl, $R^3$ and $R^4$ are halogen, and $R^5$, $R^6$, $R^7$, and $R^8$ are H, Linker is not

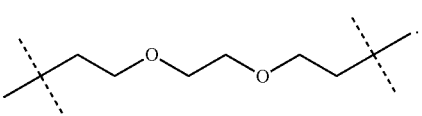

In another aspect pharmaceutical compositions are provided comprising a compound as set forth above, or a stereoisomer, pharmaceutically acceptable salt or prodrug thereof, and a pharmaceutically acceptable carrier, diluent or excipient. The pharmaceutical composition can be effective for treating a disease or disorder associated with fluid retention or salt overload. The pharmaceutical compositions can comprise the compounds of the present invention for use in treating diseases described herein. The compositions can contain at least one compound of the invention and a pharmaceutically acceptable carrier.

Another aspect of the invention relates a method for inhibiting NHE-mediated antiport of sodium and hydrogen ions. The method comprises administering to a mammal in need thereof a pharmaceutically effective amount of a compound or pharmaceutical composition described herein.

In another aspect, a method for treating a disorder associated with fluid retention or salt overload is provided. The method comprises administering to a mammal in need thereof a pharmaceutically effective amount of a compound or pharmaceutical composition as set forth above.

The present invention further provides compounds that can inhibit NHE-mediated antiport of sodium and hydrogen ions. The efficacy-safely profile of the compounds of the current invention can be improved relative to other known NHE-3 inhibitors. Additionally, the present technology also has the advantage of being able to be used for a number of different types of diseases, including, but not limited to, heart failure (such as congestive heart failure), chronic kidney disease, end-stage renal disease, hypertension, essential hypertension, primary hypertension, salt-sensitive hypertension, liver disease, and peroxisome proliferator-activated receptor (PPAR) gamma agonist-induced fluid retention is provided, gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, Parkinson's disease, multiple sclerosis, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, allergy—atopy, food allergy, infections (respiratory), acute inflammation e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type 1 diabetes, Celiac's Secondary PTH, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestitinal bacterial overgrowth, and chronic alcoholism, secondary hyperparathyroidism (PTH), celiac disease, hyperphosphatemia and the like. Additional features and advantages of the present technology will be apparent to one of skill in the art upon reading the Detailed Description of the Invention, below.

DETAILED DESCRIPTION OF THE INVENTION

Figure 1:
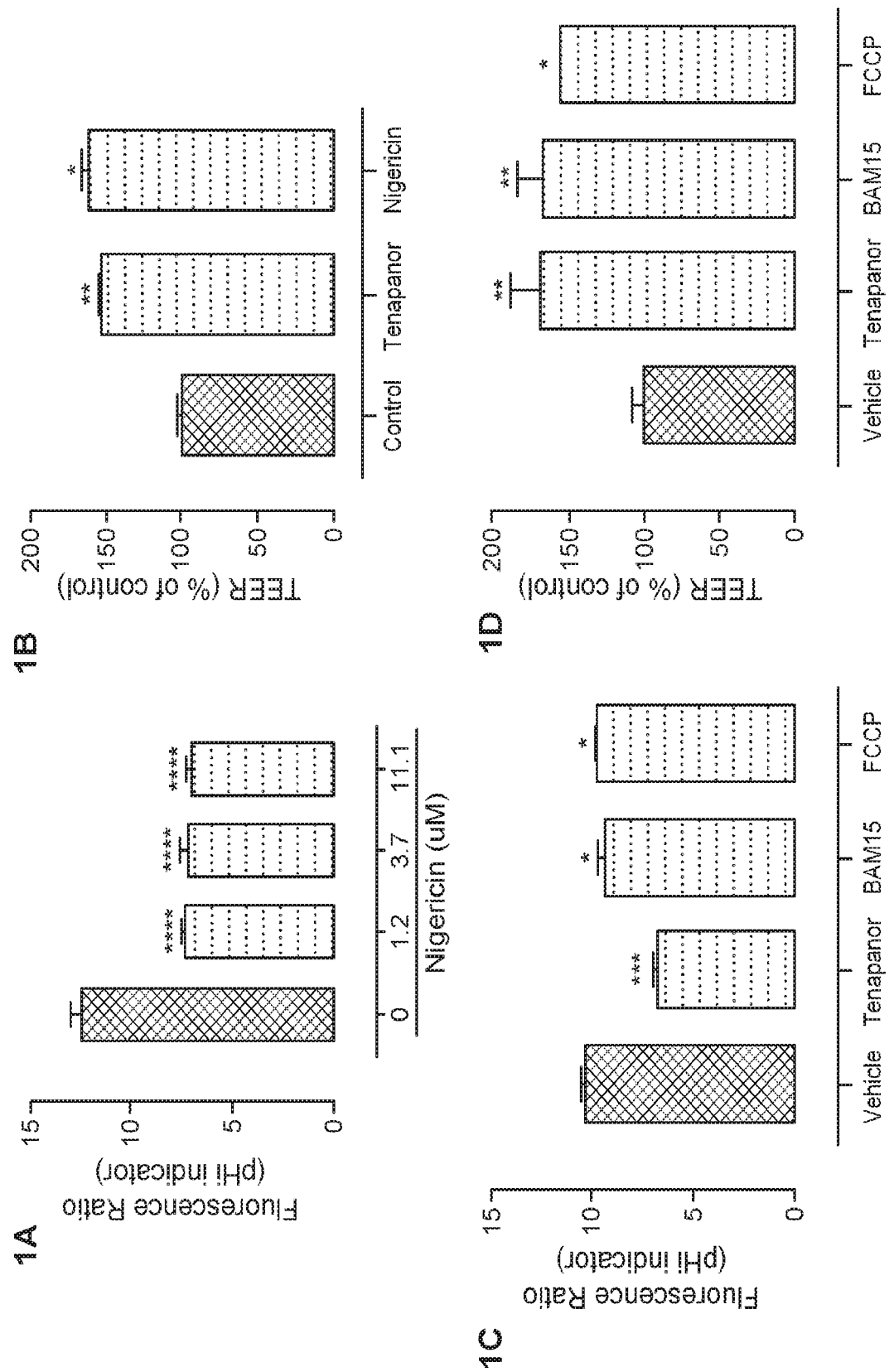
FIGS. 1A-1D: Depicts NHE3-independent changes in intracellular pH (pHi) modulate trans-epithelial electrical resistance in intestinal ileum monolayer cultures. Changes in pHi and trans-epithelial electrical resistance (TEER) with (A, B) nigericin and (C, D) BAM15 (3 μM) and FCCP (3 μM) compared with the known NHE3 inhibitor tenapanor and vehicle (DMSO) control in monolayer cultures. *P<0.05, P<0.01, *P<0.001, ****P<0.0001 vs DMSO.

A first aspect of the present invention relates to compounds of Formula:

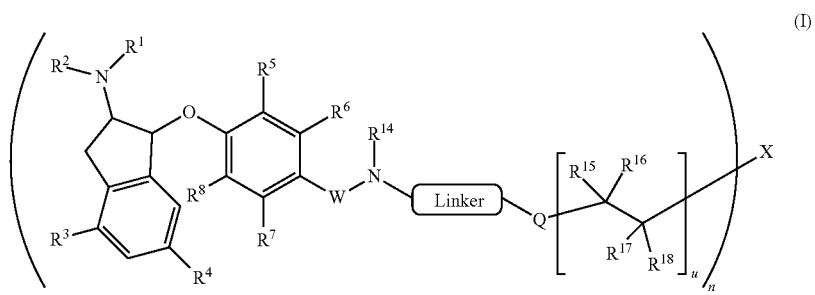

(I)

pharmaceutically acceptable salt, prodrug, solvate, hydrate, isomer, or tautomer thereof, wherein: $R^1$, $R^2$, $R^3$, $R^4$, $R^5$, $R^6$, $R^7$, $R^8$, $R^{15}$, $R^{16}$, $R^{17}$, $R^{18}$, n, u, X, and Linker are described as herein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions:

Unless the context requires otherwise, throughout the present specification and claims, the word "comprise" and variations thereof, such as, "comprises" and "comprising"

are to be construed in an open, inclusive sense, that is as "including, but not limited to".

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ radical.

"Cyano" refers to the —CN radical.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroatyl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diatylamines, N-oxides, imides, and enamines; a silicon atom in groups such as trialkylsilyl groups, dialkylarsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)N R$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O) R$_g$, —C(=O)NR$_g$R$_h$, —CH$_2$SO$_2$R$_g$, —CH$_2$SO$_2$NR$_g$R$_h$, —(CH$_2$CH$_2$O)$_{2-10}$R$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroatyl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bonded to a halogen atom, a hydroxyl group, or any other substituent described herein. Thus the term "optionally substituted" means that a given chemical moiety has the potential to contain other functional groups, but does not necessarily have any further functional groups.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), one to eight carbon atoms ($C_1$-$C_8$ alkyl) or one to six carbon atoms ($C_1$-$C_6$ and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propanyl, n-butynyl, iso-butynyl, pentynyl, or hexynyl. An alkynyl group can be unsubstituted or substituted.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2] octanyl, or bicyclo[2.2.2]octenyl. A $C_3$-$C_8$cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, phosphorous, nitrogen, or sulfur and wherein there is not delocalized π electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, oxepinyl, diazepinyl, tropanyl, and homotropanyl. A heteroycyclyl or heterocycloalkyl ring can also be fused or bridged, e.g., can be a bicyclic ring.

As used herein, the term "halo" or "halogen" means a fluoro, chloro, bromo, or iodo group.

The term "carbonyl" refers to a functional group composing a carbon atom double-bonded to an oxygen atom. It can be abbreviated herein as "oxo", as C(O), or as C=O.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —$OC_2$-$C_6$alkenyl, —$OC_2$-$C_6$alkynyl, —$C2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1□²-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying, functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxy ethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylainine, diethylamine, triethylainine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine. N ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R) or (S) or, as (D) or (L) for amino acids. The present invention is meant to include all such possible isomers, as well as their racemic and optically pure forms. Optically active (+) and (−), (R) and (S), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

In accordance with the present disclosure, the compounds described herein are designed to be substantially active or localized in the gastrointestinal lumen of a human or animal subject. The term "gastrointestinal lumen" is used interchangeably herein with the term "lumen," to refer to the space or cavity within a gastrointestinal tract (GI tract, which can also be referred to as the gut), delimited by the apical membrane of GI epithelial cells of the subject. In some embodiments, the compounds are not absorbed through the layer of epithelial cells of the GI tract (also known as the GI epithelium). "Gastrointestinal mucosa" refers to the layer(s) of cells separating the gastrointestinal lumen from the rest of the body and includes gastric and intestinal mucosa, such as the mucosa of the small intestine. A "gastrointestinal epithelial cell" or a "gut epithelial cell" as used herein refers to any epithelial cell on the surface of the gastrointestinal mucosa that faces the lumen of the gastrointestinal tract, including, for example, an epithelial cell of the stomach, an intestinal epithelial cell, a colonic epithelial cell, and the like.

A "subject" is a human, but can also be an animal in need of treatment with a compound of the disclosure, e.g., companion animals (e.g., dogs, cats, and the like), farm animals (e.g., cows, pigs, horses and the like) and laboratory animals (e.g., rats, mice, guinea pigs and the like).

"Substantially systemically non-bioavailable" and/or "substantially impermeable" as used herein (as well as variations thereof) generally refer to situations in which a statistically significant amount, and in some embodiments essentially all of the compound of the present disclosure (which includes the NHE-inhibitor small molecule), remains in the gastrointestinal lumen. For example, in accordance with one or more embodiments of the present disclosure, at least about 70%, about 80%, about 90%, about 95%, about 98%, about 99%, or even about 99.5%, of the compound remains in the gastrointestinal lumen. In such cases, localization to the gastrointestinal lumen refers to reducing net movement across a gastrointestinal layer of epithelial cells, for example, by way of both transcellular and paracellular transport, as well as by active and/or passive transport. The compound in such embodiments is hindered from net permeation of a layer of gastrointestinal epithelial cells in transcellular transport, for example, through an apical membrane of an epithelial cell of the small intestine. The compound in these embodiments is also hindered from net permeation through the "tight junctions" in paracellular transport between gastrointestinal epithelial cells lining the lumen.

In this regard it is to be noted that, in one particular embodiment, the compound is essentially not absorbed at all by the GI tract or gastrointestinal lumen. As used herein, the terms "substantially impermeable" or "substantially systemically non-bioavailable" refers to embodiments wherein no detectable amount of absorption or permeation or systemic exposure of the compound is detected, using means generally known in the art.

In this regard it is to be further noted, however, that in alternative embodiments "substantially impermeable" or "substantially systemically non-bioavailable" provides or allows for some limited absorption in the GI tract, and more particularly the gut epithelium, to occur (e.g., some detectable amount of absorption, such as for example at least about 0.1%, 0.5%, 1% or more and less than about 30%, 20%, 10%, 5%, etc., the range of absorption being for example between about 1% and 30%, or 5% and 20%, etc.; stated another way, "substantially impermeable" or "substantially systemically non-bioavailable" refers to compounds that exhibit some detectable permeability to an epithelium layer of cells in the GI tract of less than about 20% of the administered compound (e.g., less than about 15%, about 10%, or even about 5%, and for example greater than about 0.5%, or 1%), but then are cleared by the liver hepatic extraction) and/or the kidney (i.e., renal excretion).

In accordance with the present disclosure, and as further detailed herein below, it has been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of various disorders that may be associated with or caused by fluid retention and/or salt overload, and/or disorders such as heart failure (in particular, congestive heart failure), chronic kidney disease, end-stage renal disease, liver disease, and/or peroxisome proliferator-activated receptor (PPAR) gamma agonist-induced fluid retention. More specifically, it has been found that the inhibition of the NHE-mediated antiport of sodium ions and hydrogen ions in the GI tract increases the fecal excretion of sodium, effectively reducing systemic levels of sodium and fluid. This, in turn, improves the clinical status of a patient suffering from, for example, CHF, ESRD/CKD and/or liver disease. It has further been found that such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE-inhibiting compound.

Additionally, and also as further detailed herein below, it has further been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of hypertension, that may be associated with or caused by fluid retention and/or salt overload. More specifically, it has been found that the inhibition of the NHE-mediated antiport of sodium ions and hydrogen ions in the GI tract increases the fecal excretion of sodium, effectively reducing systemic levels of sodium and fluid. This, in turn, improves the clinical status of a patient suffering from hypertension. Such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE-inhibiting compound.

Additionally, and also as further detailed herein below, it has further been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of various gastrointestinal tract disorders, including the treatment or reduction of pain associated with gastrointestinal tract disorders, and more particularly to the restoration of appropriate fluid secretion in the gut and the improvement of pathological conditions encountered in constipation states. Applicants have further recognized that by blocking sodium ion re-absorption, the compounds of the present disclosure restore fluid homeostasis in the GI tract, particularly in situations wherein fluid secretion/absorption is altered in such a way that it results in a high degree of feces dehydration, low gut motility, and/or a slow transit-time producing constipation states and GI discomfort generally. It has further been found that such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE-inhibiting compound.

Due to the presence of NHEs in other organs or tissues in the body, the method of the present disclosure employs the use of compounds and compositions that are desirably highly selective or localized, thus acting substantially in the gastrointestinal tract without exposure to other tissues or organs. In this way, any systemic effects can be minimized (whether they are on-target or off-target). Accordingly, it is to be noted that, as used herein, and as further detailed elsewhere herein, "substantially active in the gastrointestinal tract" generally refers to compounds that are substantially systemically non-bioavailable and/or substantially impermeable to the layer of epithelial cells, and more specifically epithelium of the GI tract. It is to be further noted that, as used herein, and as further detailed elsewhere herein, "substantially impermeable" more particularly encompasses compounds that are impermeable to the layer of epithelial cells, and more specifically the gastrointestinal epithelium (or epithelial layer). "Gastrointestinal epithelium" refers to the membranous tissue covering the internal surface of the gastrointestinal tract. Accordingly, by being substantially impermeable, a compound has very limited ability to be transferred across the gastrointestinal epithelium, and thus contact other internal organs (e.g., the brain, heart, liver, etc.). The typical mechanism by which a compound can be transferred across the gastrointestinal epithelium is by either transcellular transit (a substance travels through the cell, mediated by either passive or active transport passing through both the apical and basolateral membranes) and/or by paracellular transit, where a substance travels between cells of an epithelium, usually through highly restrictive structures known as "tight junctions".

Without wishing to be bound to any particular theory, it is believed that the NHE-inhibiting compounds (e.g., NIH-3, -2 and/or -8 inhibitors) of the present disclosure are believed to act via a distinct and unique mechanism, to decrease paracellular permeability of the intestine. NHE3 is expressed at high levels on the apical surface of the gastrointestinal tract and couples luminal Na absorption to the secretion of intracellular protons. Inhibition of NHE3, by the NHE-inhibiting compounds (e.g., NIH-3, -2 and/or -8 inhibitors) of the present disclosure; results in accumulation of intracellular protons. The intracellular proton retention accompanying NHE3 inhibition modulates the tight junction between cells to decrease paracellular permeability which can be measured by an increase in transepithelial electrical resistance. Since increased paracellular and/or transcellular permeability of the intestine is observed in many diseases including, but not limited to a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, multiple sclerosis-induced constipation, parkinson's disease-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel disease, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type I diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestinal bactreial overgrowth, and chronic alcoholism, and the like it is anticipated that NHE inhibition could provide therapeutic benefit in these diseases by decreasing paracellular and/or transcellular permeability in the intestine Thus in some embodiments, the present disclosure provides methods of decreasing paracellular permeability of the intestine. In some embodiments, the method of decreasing paracellular permeability of the intestine comprises administration of an NHE3 inhibitor. In some embodiments, the inhibition of NHE3 results in an accumulation of intracellular protons. In some embodiments, the decrease in paracellular permeability is due to an increase in intracellular protons independent of and without NHE3 inhibition. In other words, an increase in intracellular protons without NHE3 inhibition results in a decrease in paracelllar permeability. Thus methods of decreasing paracellular permeability comprising increasing intracellular protons is provided. In some embodiments, methods of treating diseases associated with paracellular permeability are provided comprising administering an agent that increases intracellular protons at tight junctions thereby decreasing paracellular permeability and thus treating the disease. Non limiting examples of such diseases include, Crohn's disease, ulcerative colitis and related diseases referred to as inflammatory bowel syndrome, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestinal bactreial overgrowth, and chronic alcoholism, and the like.

In some embodiments, the present disclosure provides methods of modulating transcellular permeability of the intestine. In some embodiments, the method of modulating transcellular permeability of the intestine comprises administration of an NHE3 inhibitor. In some embodiments, the inhibition of NHE3 results in a substance travelling through the cell, mediated by either passive or active transport passing through both the apical and basolateral membranes. Thus methods of modulating transcellular permeability comprising mediating either passive or active transport of a substance passing through both the apical and basolateral membranes is provided. In some embodiments, methods of treating diseases associated with transcellular permeability are provided comprising administering an agent that mediates either passive or active transport of a substance passing through both the apical and basolateral membranes of a cell, thereby modulating transcellular permeability and thus treating the disease. Non limiting examples of such diseases include a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, multiple sclerosis-induced constipation, parkinson's disease-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction.

The compounds of the present disclosure may therefore not be absorbed, and are thus essentially not systemically bioavailable at all (e.g., impermeable to the gastrointestinal epithelium at all), or they show no detectable concentration of the compound in serum. Alternatively, the compounds may: (i) exhibit some detectable permeability to the layer of epithelial cells, and more particularly the epithelium of the GI tract, of less than about 20% of the administered compound (e.g., less than about 15%, about 10%, or even about 5%, and for example greater than about 0.5%, or 1%), but then are rapidly cleared in the liver (i.e., hepatic extraction) via first-pass metabolism; and/or (ii) exhibit some detectable permeability to the layer of epithelial cells, and more particularly the epithelium of the GI tract, of less than about 20% of the administered compound (e.g., less than about 15%, about 10%, or even about 5%, and for example greater than about 0.5%, or 1%), but then are rapidly cleared in the kidney (i.e., renal excretion).

Compounds may also be cleared from circulation unchanged into the bile by biliary excretion. The compounds of the present disclosure may therefore not exhibit detectable concentrations in the bile. Alternatively, the compounds may exhibit some detectable concentration in the bile and more particularly the epithelium of the binary tract and gallbladder of 10 nM, less than 1 μM, less than 0.1 μM, less than 0.01 μM or less than about 0.001 μM.

In this regard it is to be still further noted that, as used herein, "substantially systemically non-bioavailable" generally refers to the inability to detect a compound in the systemic circulation of an animal or human following an oral dose of the compound. For a compound to be bioavailable, it must be transferred across the gastrointestinal epithelium (that is, substantially permeable as defined above), be transported via the portal circulation to the liver, avoid substantial metabolism in the liver, and then be transferred into systemic circulation.

Without being held to any particular theory, the NHE-inhibiting compounds (e.g., NHE-3, -2 and/or -8 inhibitors) of the present disclosure are believed to act via a distinct and unique mechanism, causing the retention of fluid and ions in the GI tract (and stimulating fecal excretion) rather than stimulating increased secretion of said fluid and ions. For example, lubiprostone (Amitiza® Sucampo/Takeda) is a bicyclic fatty acid prostaglandin E1 analog that activates the Type 2 Chloride Channel (ClC-2) and increases chloride-rich fluid secretion from the serosal to the mucosal side of the GI tract (see, e.g., Pharmacological Reviews for Amitiza®, NDA package). Linaclotide (MD-1100 acetate, Microbia/Forest Labs) is a 14 amino acid peptide analogue of an endogenous hormone, guanylin, and indirectly activates the Cystic Fibrosis Transmembrane Conductance Regulator (CFTR) thereby inducing fluid and electrolyte secretion into the GI (see, e.g., Li et al., J. Exp. Med., vol. 202 (2005), pp. 975-986). The substantially impermeable NHE-inhibiting compounds of the present disclosure act to inhibit the reuptake of salt and fluid rather than promote secretion. Since the GI tract processes about 9 liters of fluid and about 800 meq of Na each day, it is anticipated that NHE inhibition could permit the removal of substantial quantities of systemic fluid and sodium to resorb edema and resolve CHF symptoms.

I. Substantially Impermeable or Substantially Systemically Non-Bioavailable NHE-Inhibiting Compounds In one aspect, the compounds of the present disclosure are generally represented by Formula (I):

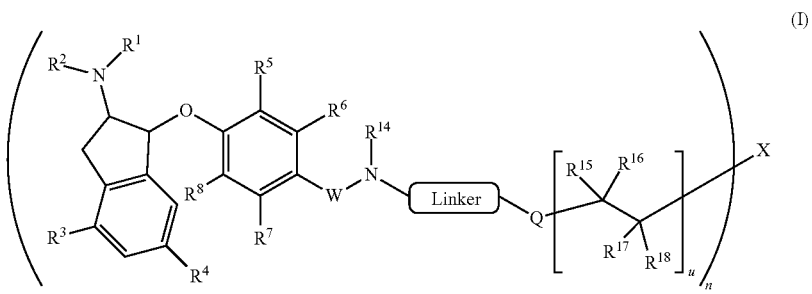

(I)

and pharmaceutically acceptable salts, prodrugs, solvates, hydrates, isomers, and tautomers thereof, wherein:

Linker is —$(CHR^{13})_p$—[Y—$(CH_2)_r$]$_s$—Z—$R^{13}$—$(CH_2)_t$—Z—;

W is independently, at each occurrence, $S(O)_2$, C(O), or —$(CH_2)_m$—;

Z is independently, at each occurrence, a bond, C(O), or —C(O)NH—;

Y is independently, at each occurrence, O, S, NH, N($C_1$-$C_3$alkyl), or —C(O)NH—;

Q is a bond, NH, —C(O)NH—, —NHC(O)NH—, —NHC(O)N($CH_3$)—, or —NHC(O)NH—$(CHR^{13})$; m is an integer from 1 to 2; n is an integer from 1 to 4;

r and p are independently, at each occurrence, integers from 0 to 8;

s is an integer from 0 to 4;

t is an integer from 0 to 4;

u is an integer from 0 to 2;

$R^1$ and $R^2$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, wherein each alkyl, alkenyl, cycloalkenyl, alkynyl, cycloalkyl, heterocyclyl, aryl, or heteroaryl is optionally substituted with one or more halogen, OH, CN, —$NO_2$, oxo, —$SR^9$, —$OR^9$, —$NHR^9$, —$NR^9R^{10}$, —$S(O)_2N(R^9)_2$, —$S(O)_2R^9$, —$C(O)R^9$, —$C(O)OR^9$, —$C(O)NR^9R^{10}$, —$NR^9S(O)_2R^{10}$, —$S(O)R^9$, —$S(O)NR^9R^{10}$, —$NR^8S(O)$ R$^9$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, heterocycle, aryl, or heteroaryl; or R$^1$ and R$^2$ together with the nitrogen to which they are attached can form a heterocylyl or heteroaryl containing 1-5 heteroatoms selected from the group consisting of N, S, P and O, wherein the heterocyclyl or heteroaryl group is optionally substituted with one or more halogen, OH, CN, —NO$_2$, oxo, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —C(O)NR$^9$R$^{10}$, —NR$^9$S(O)$_2$R$^{10}$, —S(O)R$^9$, —S(O)NR$^9$R$^{10}$, —NR$^9$S(O)R$^{10}$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, heterocycle, aryl, or heteroaryl;

R$^3$ and R$^4$ are independently halogen, OH, CN, C$_1$-C$_6$alkyl, C$_1$-C$_6$alkoxy, C$_1$-C$_6$haloalkyl, C$_1$-C$_6$haloalkoxy, or —C(O)NR$^9$R$^{10}$, R$^5$, R$^6$, R$^7$, and R$^8$ are independently H, halogen, OH, CN, —NO$_2$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$R$^{10}$, —S(O)R$^9$, —S(O)NR$^9$R$^{10}$, —NR$^8$S(O)R$^9$;

R$^9$ and R$^{10}$ are independently H, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, or heteroaryl containing 1-5 heteroatoms selected from the group consisting of N, S, P and O X is a bond, H, N, O, CR$^{11}$R$^{12}$, CR$^{11}$, C, —NHC(O)NH—, or C$_3$-C$_6$cyclolakyl;

R$^{11}$ and R$^{12}$ are independently H, C$_1$-C$_6$alkyl, OH, NH$_2$, CN, or NO$_2$;

R$^{13}$ is independently, at each occurrence, a bond, H, C$_1$-C$_6$alkyl, C$_4$-C$_8$cycloalkenyl, C$_3$-C$_8$cycloalkyl, heterocyclyl, aryl, or heteroaryl, wherein each cycloalkenyl, cycloalkyl, heterocyclyl, aryl, or heteroaryl is optionally substituted with one or more R$^{19}$;

R$^{14}$ is independently, at each occurrence, H, C$_1$-C$_6$alkyl, or C$_1$-C$_6$haloalkyl; or R$^6$ and R$^{14}$ together with the atoms to which they are attached may combine to form, independently, at each occurrence, 5- to 6-membered heterocyclyl, wherein each C$_3$-C$_8$cycloalkyl, or heterocyclyl is optionally substituted with one r more R$^{19}$; or R$^{13}$ and R$^{14}$ together with the atoms to which they are attached may combine to form independently, at each occurrence, C$_3$-C$_8$cycloalkyl, heterocyclyl, aryl, or heteroaryl containing 1-5 heteroatoms selected from the group consisting of N, S, P and O, wherein each heterocyclyl or heteroaryl is optionally substituted with one or more R$^{19}$;

R$^{15}$, R$^{16}$, R$^{17}$, and R$^{18}$ are independently, at each occurrence, H, OH, NH$_2$, or C$_1$-C$_3$ alkyl, wherein the alkyl is optionally substituted with one or more R$^{19}$; and R$^{19}$ are independently, at each occurrence, H, OH, NH$_2$, oxo, C$_1$-C$_6$alkyl, C$_1$-C$_6$Hhaloalkyl, C$_1$-C$_6$alkoxy provided that:

(1) when X is H, n is 1;
(2) when X is a bond, O, or CR$^{11}$R$^{12}$, n is 2;
(3) when n is 3, X is CR$^{11}$ or N;
(4) when n is 4 X is C;
(5) only one of Q or X is —NHC(O)NH— at the time,
(6) R$^1$ and R$^2$ together with the nitrogen to which they are attached, cannot form a pyrrolidinyl;
(7) when R$^1$ and R$^2$ are methyl, R$^3$ and R$^4$ are halogen, and R$^5$ and R$^8$ are H, Linker is not

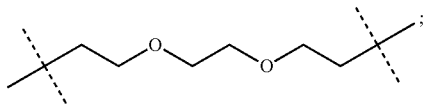

(8) when R$^1$ and R$^2$ together with the nitrogen to which they are attached form a piperidinyl, R$^3$ and R$^4$ are halogen, and R$^5$ and R$^8$ are H, Linker is not

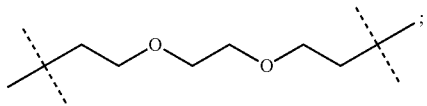

or (9) when R$^1$ and R$^2$, together with the nitrogen to which they are attached, form 3-aminopiperidin-1-yl, R$^3$ and R$^4$ are halogen, and R$^5$, R$^6$, R$^7$, and R$^8$ are H, Linker is not

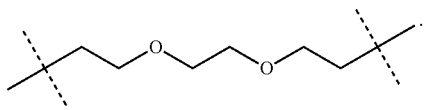

In an embodiment the NHE-inhibiting compounds of Formula (I) possess overall physicochemical properties that render them substantially impermeable or substantially systemically non-bioavailable.

In an embodiment, the compound of the invention has a structure according to formula I'

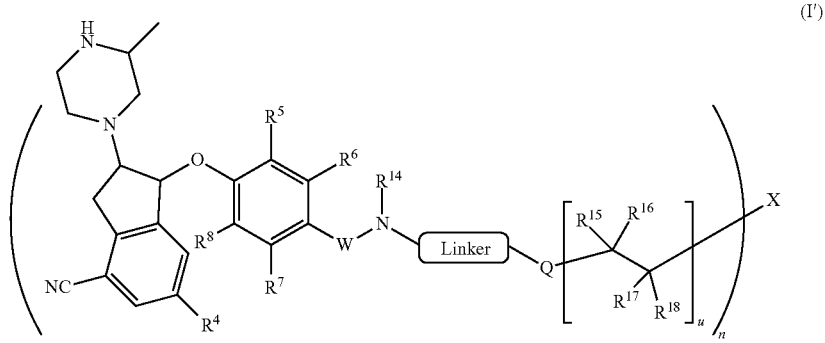

(I')

or a pharmaceutically acceptable salt thereof, wherein:

Linker is —R$^{13}$—(CHR$^{13}$)$_p$—[Y—(CH$_2$)$_r$]$_s$—Z—R$^{13}$—(CH$_2$)$_t$—Z—;

X is a bond, H, N, O, CR$^{11}$R$^{12}$, CR$^{11}$, C, —NHC(O)NH—, —(CHR$^{13}$)$_p$— or C$_3$-C$_6$cyclolakyl;

W is independently, at each occurrence, S(O)$_2$, C(O), or —(CH$_2$)$_m$—;

Z is independently, at each occurrence, a bond, C(O), or —C(O)NH—;

Y is independently, at each occurrence, O, S, NH, N(C$_1$-C$_3$alkyl), or —C(O)NH—;

Q is a bond, NH, —C(O)NH—, —NHC(O)NH—, —NHC(O)N(CH$_3$)—, or —NHC(O)NH—(CHR$^{13}$);

m is an integer from 1 to 2;

n is an integer from 1 to 4;

r and p are independently, at each occurrence, integers from 0 to 8;

s is an integer from 0 to 4;

t is an integer from 0 to 4;

u is an integer from 0 to 2;

R$^1$ and R$^2$ are independently H, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl containing 1-5 heteroatoms selected from the group consisting of N, S, P and O, wherein each alkyl, alkenyl, cycloalkenyl, alkynyl, cycloalkyl, heterocyclyl, aryl, or heteroaryl is optionally substituted with one or more halogen, OH, CN, —NO$_2$, oxo, —SR$^9$, —OR$^9$, —NHR$^9$, —NR$^9$R$^{10}$, —S(O)$_2$N(R$^9$)$_2$, —S(O)$_2$R$^9$, —C(O)R$^9$, —C(O)OR$^9$, —C(O)NR$^9$R$^{10}$, —NR$^9$S(O)$_2$R$^{10}$, —S(O)R$^9$, —S(O)NR$^9$R$^{10}$, —NR$^8$S(O)R$^9$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, heterocycle, aryl, or heteroaryl; or R$^1$ and R$^2$ together with the nitrogen to which they are attached can form a heterocyclyl or heteroaryl containing 1-5 heteroatoms selected from the group consisting of N, S, P and O, wherein the heterocyclyl or heteroaryl group is optionally substituted with one or more halogen, OH, CN, —NO$_2$, oxo, —SR$^9$, —OR$^9$, —NHR$^9$, —NR$^9$R$^{10}$, —S(O)$_2$N(R$^9$)$_2$, —S(O)$_2$R$^9$, —C(O)R$^9$, —C(O)OR$^9$, —C(O)NR$^9$R$^{10}$, —NR$^9$S(O)$_2$R$^{10}$, —S(O)R$^9$, —S(O)NR$^9$R$^{10}$, —NR$^9$S(O)R$^{10}$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, heterocycle, aryl, or heteroaryl;

R$^3$ and R$^4$ are independently halogen, OH, CN, C$_1$-C$_6$alkoxy, C$_1$-C$_6$alkoxy, C$_1$-C$_6$haloalkyl, C$_1$-C$_6$haloalkoxy, or —C(O)NR$^9$R$^{10}$;

R$^5$, R$^6$, R$^7$, and R$^8$ are independently H, halogen, OH, CN, —NO$_2$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl containing 1-5 heteroatoms selected from the group consisting of N, S, P and O, —SR$^9$, —OR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$R$^{10}$, —S(O)R$^9$, —S(O)NR$^9$R$^{10}$, —NR$^8$S(O)R$^9$;

R$^9$ and R$^{10}$ are independently H, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, or heteroaryl containing 1-5 heteroatoms selected from the group consisting of N, S, P and O R$^{11}$ and R$^{12}$ are independently H, OH, NH$_2$, CN, or NO$_2$;

R$^{13}$ is independently, at each occurrence, a bond, H, C$_1$-C$_6$alkyl, C$_4$-C$_8$cycloalkenyl, C$_3$-C$_8$cycloalkyl, heterocyclyl, aryl, or heteroaryl, wherein each cycloalkenyl, cycloalkyl, heterocyclyl, aryl, or heteroaryl is optionally substituted with one or more R$^{19}$;

R$^{14}$ is independently, at each occurrence, H, C$_1$-C$_6$alkyl, or C$_1$-C$_6$haloalkyl; or R$^6$ and R$^{14}$ together with the atoms to which they are attached may combine to form, independently, at each occurrence, 5- to-6 membered heterocyclyl, wherein each C$_3$-C$_8$ cycloalkyl, or heterocyclyl is optionally substituted with one or more R$^{19}$; or R$^{13}$ and R$^{14}$ together with the atoms to which they are attached may combine to form independently, at each occurrence, C$_3$-C$_8$ cycloalkyl, heterocyclyl, aryl, or heteroaryl containing 1-5 heteroatoms selected from the group consisting of N, S, P and O, wherein each heterocyclyl or heteroaryl is optionally substituted with one or more R$^{19}$;

R$^{15}$, R$^{16}$, R$^{17}$, and R$^{18}$ are independently, at each occurrence, H, OH, NH$_2$, or C$_1$-C$_3$ alkyl, wherein the alkyl is optionally substituted with one or more R$^{19}$; and R$^{19}$ are independently, at each occurrence, H, OH, NH$_2$, oxo, C$_1$-C$_6$alkyl, C$_1$-C$_6$Hhaloalkyl, C$_1$-C$_6$alkoxy.

It is to be noted that, in the many structures illustrated herein, all of the various linkages or bonds will not be shown in every instance. However, this should not be viewed in a limiting sense. Rather, it is to be understood that the NHE-inhibiting molecule is bound or interconnected in some way (e.g., by a bond or Linker) such that the resulting NHE-inhibiting compound is suitable for use (i.e., substantially impermeable or substantially systemically non-bioavailable in the GI tract).

In yet other embodiments, the polyvalent NHE-inhibiting compound may be in oligomeric or polymeric form. It is to be noted that the repeat unit in each Formula (I) generally encompasses repeating units of various polymeric embodiments, including linear, branched and dendritic structures, which may optionally be produced by methods referred to herein. In each polymeric, or more general polyvalent, embodiment, it is to be noted that each repeat unit may be the same or different, and may or may not be linked through the "X" moiety by a Linker, which in turn may be the same or different when present. In this regard it is to be noted that as used herein, "polyvalent" refers to a molecule that has multiple (e.g., 2, 4, 6, 8, 10 or more) NHE-inhibiting molecule.

In one embodiment of the invention, the Linker is -heterocyclyl-(CHR$^{13}$)$_p$—[Y—(CH$_2$)$_r$]$_s$—. In another embodiment of the invention, the Linker may be represented by, but not limited to,

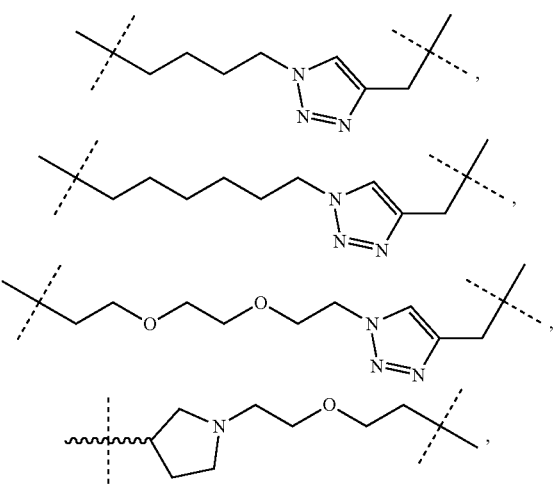

-continued

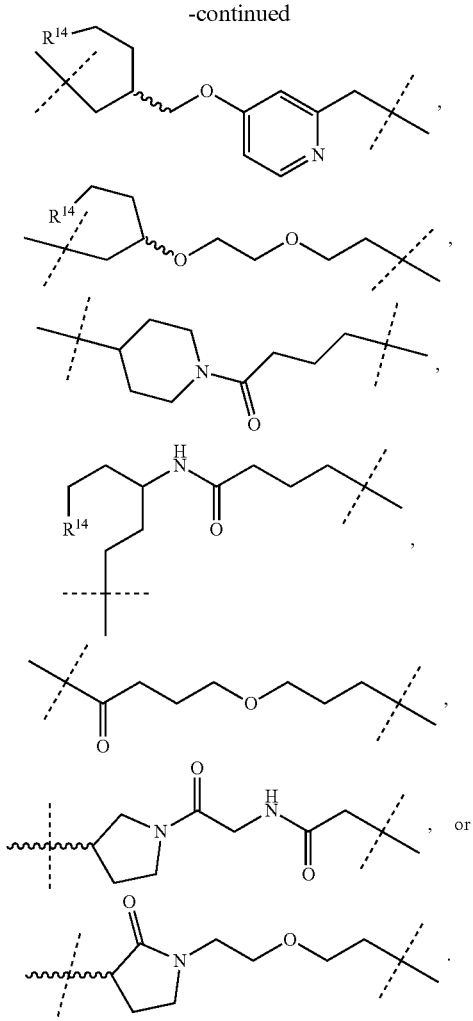

In another embodiment, the Linker may represented, without limitation, by

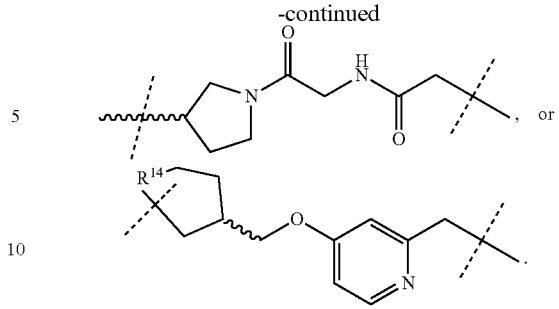

In some embodiments, of the invention, $R^1$ and $R^2$ are $C_1$-$C_6$alkyl. In some embodiments, $R^1$ and $R^2$ are methyl.

Yet in other embodiments of the compounds of Formula I, $R^1$ and $R^2$ together with the nitrogen to which they are attached may form a heterocyclyl or heteroaryl containing 1-5 heteroatoms selected from the group consisting of N, S, P and O. In some embodiments of the compounds of Formula I, the heterocyclyl or heteroaryl formed by $R^1$ and $R^2$ together with the nitrogen to which they are attached is optionally substituted with one or more H, halogen, —$NR^9R^{10}$, or $C_1$-$C_6$alkyl.

In other embodiments of the compounds of Formula I, $R^1$ and $R^2$ together with the nitrogen to which they are attached can form a heterocycle. In some embodiments of the compounds of Formula I, the heterocycle formed by $R^1$ and $R^2$ together with the nitrogen to which they are attached is optionally substituted with one or more oxo. In other embodiments of the compounds of Formula I, $R^1$ and $R^2$ together with the nitrogen to which they are attached may also form a piperidine or piperazine. In further embodiments of the compounds of Formula I, the piperidine or piperazine is optionally substituted with one or more oxo, halogen, —$NR^9R^{10}$, or $C_1$-$C_6$alkyl. In a particular embodiment, the piperazine is substituted with methyl.

In some embodiments of the compounds of Formula I, $R^9$ and $R^{10}$ are $C_1$-$C_6$alkyl. In other embodiments, $R^9$ and $R^{10}$ are methyl. In some embodiments of the compounds of Formula I, $R^3$ is halogen, CN, $C_1$-$C_6$alkyl, $C_1$-$C_6$alkoxy, $C_1$-$C_6$haloalkyl, or $C_1$-$C_6$haloalkoxy. In some embodiments of the compounds of Formula I, $R^3$ is halogen, CN, or $C_1$-$C_6$alkyl. In an embodiment, $R^3$ is CN. In some embodiments, $R^3$ is F, Cl, CN, or methyl.

In some embodiments of the compounds of Formula I, $R^4$ is halogen or $C_1$-$C_6$alkyl. In some embodiments of the compounds of Formula I, $R^4$ is F, Cl, or methyl. In an embodiment, $R^3$ is CN and $R^4$ is Cl.

In other embodiments of the compounds of Formula I, $R^5$ is H, halogen, $C_1$-$C_6$alkyl, or $OR^9$. In yet other embodiments, $R^5$ is H, F, or methyl.

In another embodiment of the invention, $R^6$, $R^7$, and $R^8$ are H, halogen, or C1-C6alkyl. In another embodiment, $R^6$, $R^7$, and $R^8$ are all H. It has be observed that compounds of the invention incorporating a halogen or alkyl substituent at $R^6$ while $R^5$, $R^7$ and $R^8$ are each H exhibit less interaction with cytochrome enzymes. Accordingly, in an embodiment, $R^5$, $R^7$ and $R^8$ are each H and $R^6$ is halogen or $C_{1-6}$alkyl. In an embodiment, $R^5$, $R^7$ and $R^8$ are each H and $R^6$ is F. In an embodiment, $R^5$, $R^7$ and $R^8$ are each H and $R^6$ is Me.

In another embodiment of the compounds of Formula I, Q is —NHC(O)NH—. In a particular embodiment, Q is —NHC(O)NH— and the Linker is -heterocyclyl-$(CHR^{13})_p$—$[Y$—$(CH_2)_r]_s$—. In a particular embodiment, Q is —NHC(O)NH—, the Linker is -heterocyclyl-$(CHR^{13})_p$—

[Y—(CH$_2$)$_r$]$_s$— and u is 0. In a particular embodiment, Q is —NHC(O)NH—, the Linker is -heterocyclyl-(CHR$^{13}$)$_p$—[Y—(CH$_2$)$_r$]$_s$—, u is 0 and n is 2. In a particular embodiment, Q is —NHC(O)NH—, the Linker is -heterocyclyl-(CHR$^{13}$)$_p$—[Y—(CH$_2$)$_r$]$_s$—, u is 0, n is 2 and X is —(CHR$^{13}$)$_p$— or C$_3$-C$_6$cyclolakyl. In another embodiment, Q is a bond.

In one embodiment of the compounds of Formula I, R$^{15}$, R$^{16}$, R$^{17}$, and R$^{18}$ are all H. In one embodiment of the compounds of Formula I, R$^{15}$ and R$^{17}$ are H. In one embodiment of the compounds of Formula I, R$^{16}$ and R$^{18}$ are OH. In yet another embodiment of the compounds of Formula I, R$^{15}$ and R$^{17}$ are H and R$^{16}$ and R$^{18}$ are OH.

In one embodiment of the compounds of Formula I, Y is O, r is 2, and s is 1. In another embodiment, Y is O, r is 2, and s is 2. In some embodiments, s is 0. In some embodiments, Z is C(O).

In some embodiments of the compounds of Formula I, R$^{13}$ is H, C$_1$-C$_6$ alkyl, heterocyclyl or heteroaryl. In some embodiments of the compounds of Formula I, the heterocyclyl or heteroaryl of R$^{13}$ is optionally substituted with one or more R$^{19}$. In some embodiments, R$^{13}$ is heterocyclyl optionally substituted with one or more R$^{19}$. In some embodiments, R$^{19}$ is oxo. In some embodiments of the compounds of Formula I, n is 2. In other embodiments of the compounds of Formula I, n is 3 or 4.

In one embodiment of the invention, the compounds of Formula I have the Formula Ia or Ia':

In one embodiment of the invention, the compounds of Formula I have the Formula Ib or Ib':

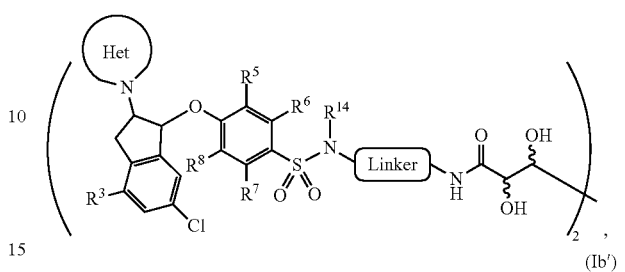

(Ib)

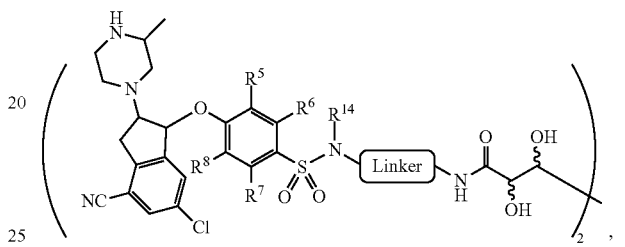

(Ib')

wherein the ring Het represents R$^1$ and R$^2$ together with the nitrogen to which they are attached can form a heterocyclyl (Ia)

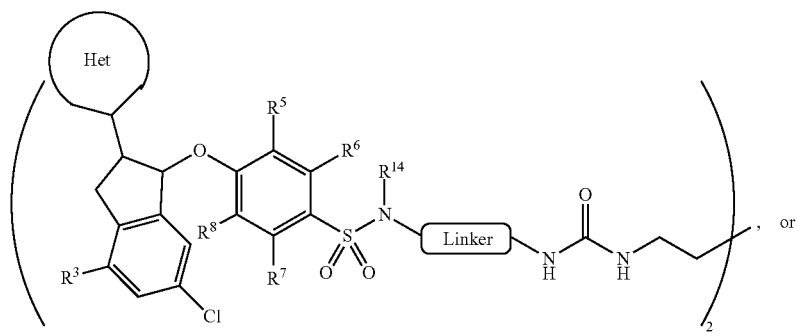

, or (Ia')

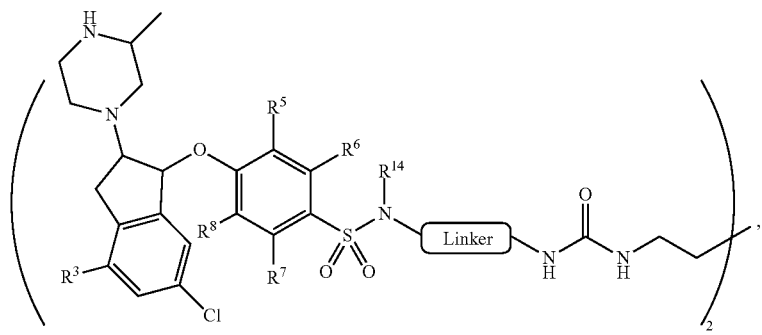

, or heteroaryl containing 1-5 heteroatoms selected from the group consisting of N, S, P and O, wherein the heterocyclyl or heteroaryl group is optionally substituted with one or more halogen, OH, CN, —NO$_2$, oxo, —SR$^9$, —OR$^9$, —NHR$^9$, —NR$^9$R$^{10}$, —S(O)$_2$N(R$^9$)$_2$, —S(O)$_2$R$^9$, —C(O)R$^9$, —C(O)OR$^9$, —C(O)NR$^9$R$^{10}$, —NR$^9$S(O)$_2$R$^{10}$, —S(O)R$^9$, —S(O)NR$^9$R$^{10}$, —NR$^9$S(O)R$^{10}$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, heterocycle, aryl, or heteroaryl, In one embodiment of the invention, the compounds of Formula I have the Formula Ic or Ic':

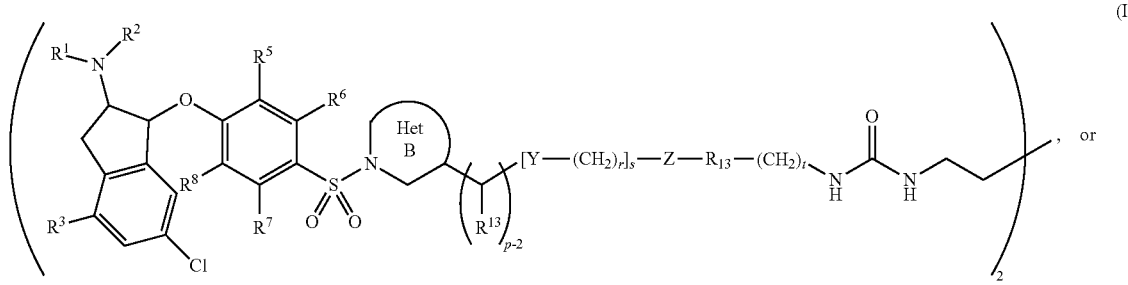

(Ic)

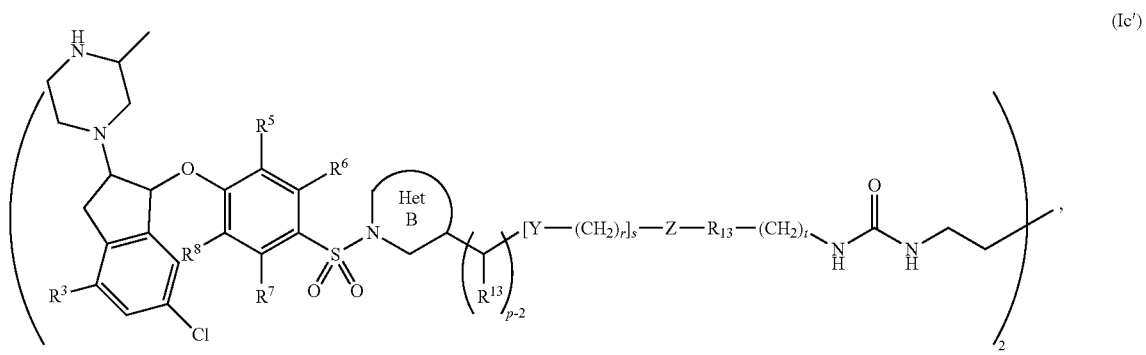

(Ic')

wherein Het B represents a C$_3$-C$_8$ cycloalkyl, heterocyclyl, aryl, or heteroaryl containing 1-5 heteroatoms selected from the group consisting of N, S, P and O, wherein each heterocyclyl or heteroaryl is optionally substituted with one or more R$^{19}$.

In one embodiment of the invention, the compounds of Formula I have the Formula Id or Id':

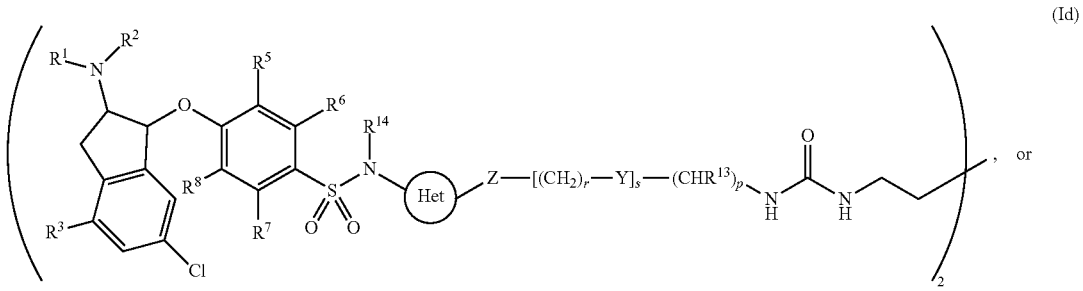

(Id)

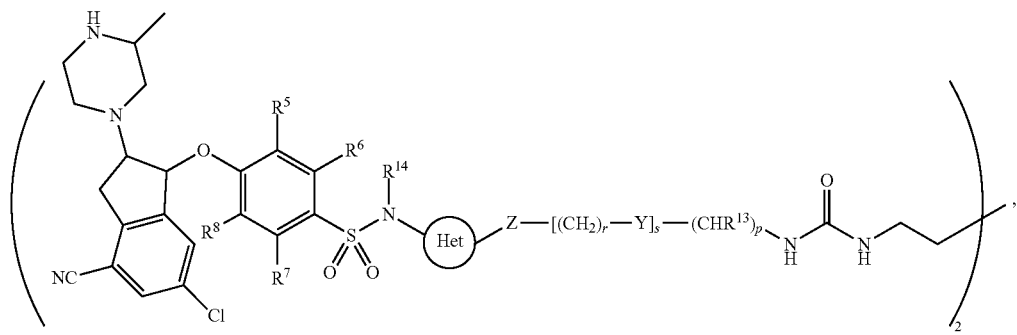

(Id')

wherein Het is $R^{13}$ which represents $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R^{19}$.

In one embodiment of the invention, the compounds of Formula I have the Formula Ie or Ie':

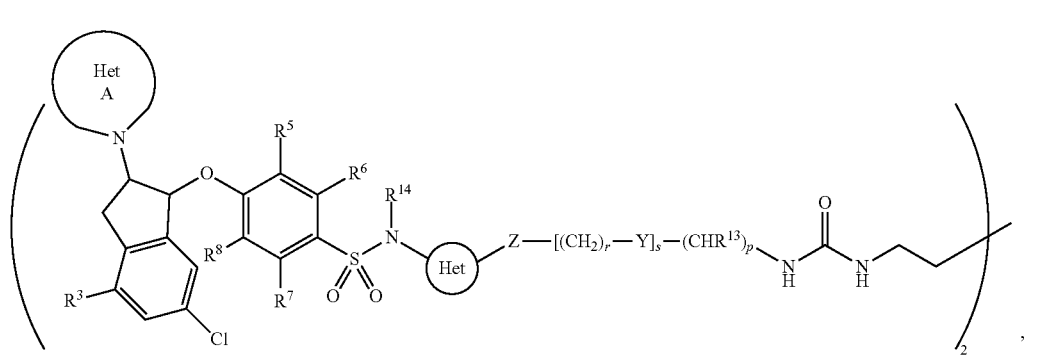

(Ie)

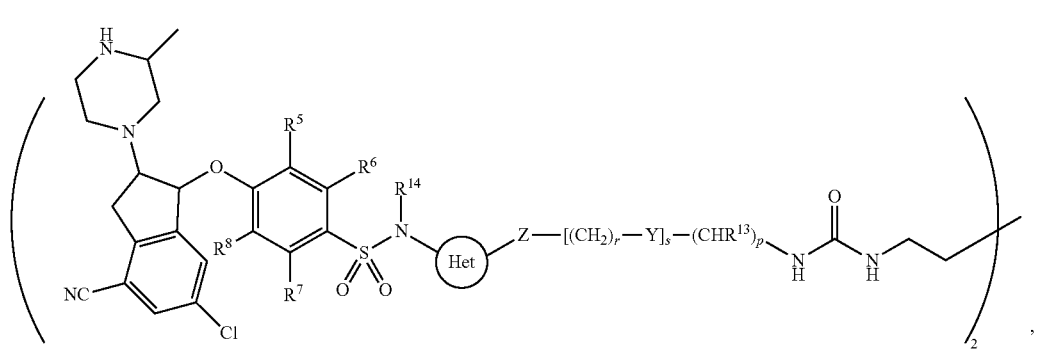

(Ie')

wherein the ring Het A represents $R^1$ and $R^2$ together with the nitrogen to which they are attached can form a heterocyclyl or heteroaryl containing 1-5 heteroatoms selected from the group consisting of N, S, P and O, wherein the heterocyclyl or heteroaryl group is optionally substituted with one or more halogen, OH, CN, —$NO_2$, oxo, —$SR^9$, —$OR^9$, —$NHR^9$, —$NR^9R^{10}$, —$S(O)_2N(R^9)_2$, —$S(O)_2R^9$, —$C(O)R^9$, —$C(O)OR^9$, —$C(O)NR^9R^{10}$, —$NR^9S(O)_2R^{10}$, —$S(O)R^9$, —$S(O)NR^9R^{10}$, —$NR^9S(O)R^{10}$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl; and Het is $R^{13}$ which represents $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R^{19}$.

In one embodiment of the invention, the compounds of Formula I have the Formula If or If':
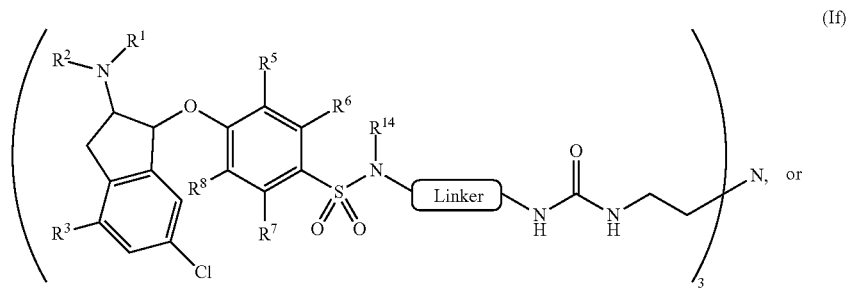
(If)
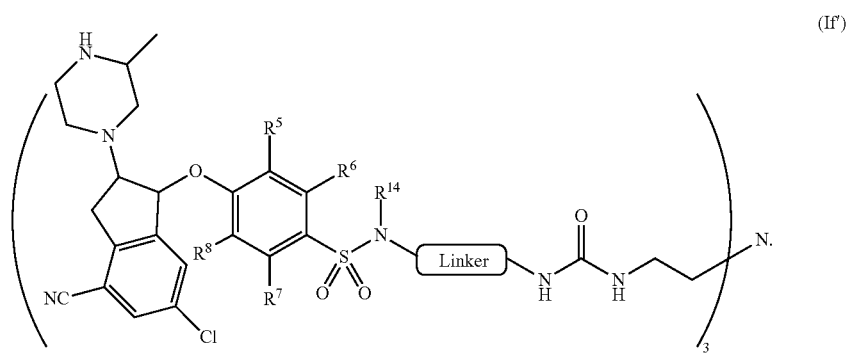
(If')
In one embodiment of the invention, the compounds of Formula I have the Formula Ig or Ig':
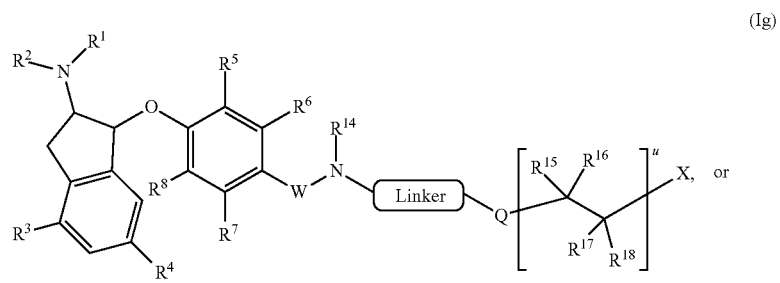
(Ig)
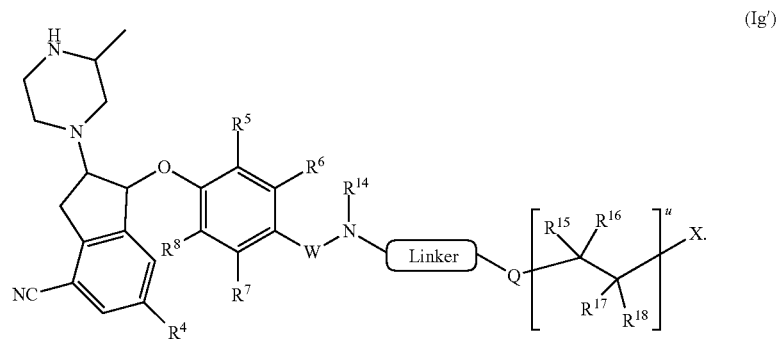
(Ig')

In one embodiment of the invention, the compounds of Formula I have the Formula Ih or Ih':
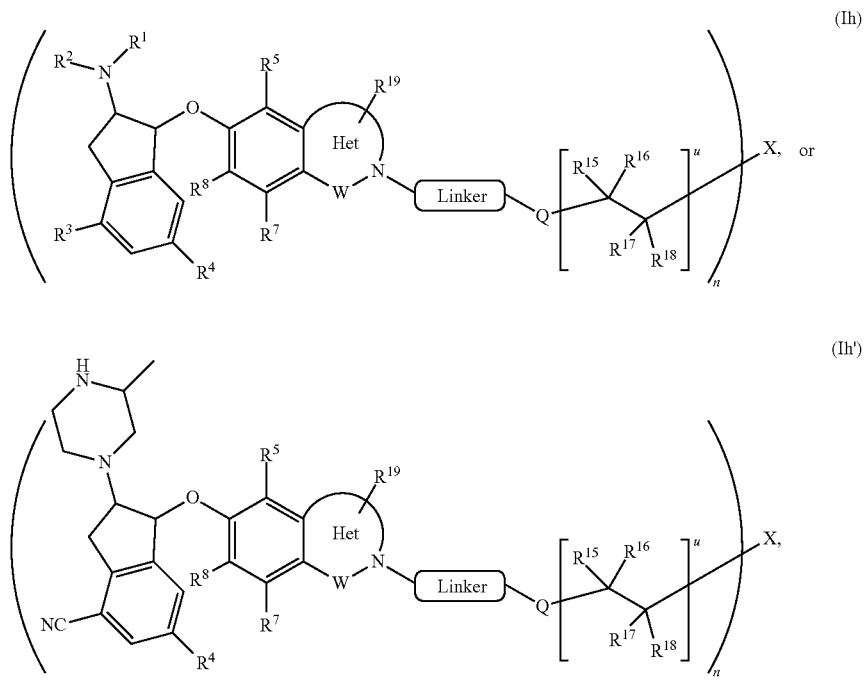
wherein:
Het represents $R^6$ and $R^{14}$ together with the atoms to which they are attached forming, independently, at each occurrence, a 5- to 6- membered heterocyclyl.
In one embodiment of the invention, the compounds of Formula I have the Formula Ii or Ii':
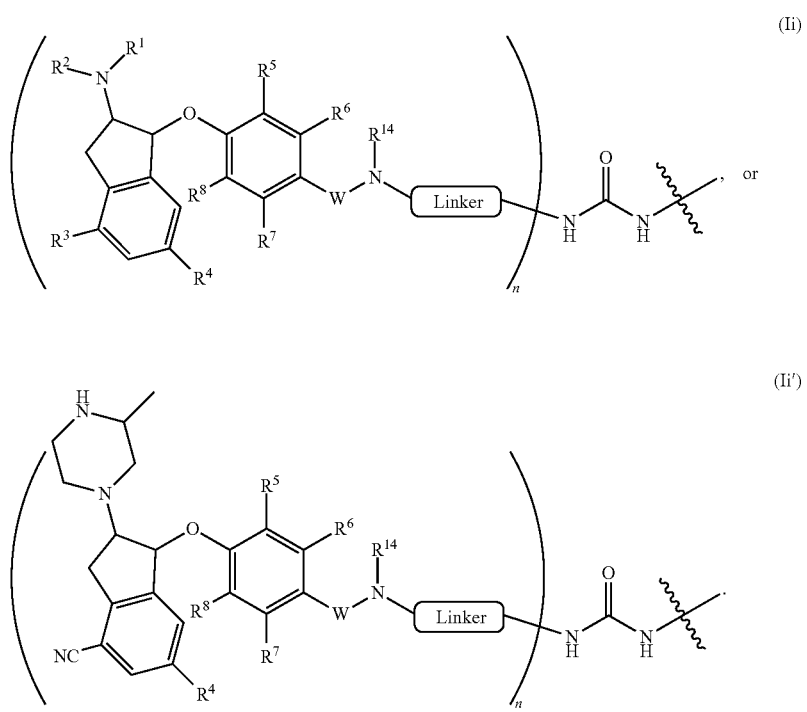

In other embodiments, compounds of Formula I include, but are not limited to,

1-[2-(2-[2-[(4-[[[(1S,1S)-2-[(3R)-3-Aminopiperidin-1-yl]-4,6-dichloro-2,3-dihydro-1H-inden-1-yl]oxy]-3-methylbenzene)sulfonamido]ethoxy]ethoxy)ethyl]-3-[4-([[2-(2-[2-[(4-[[[(1S,2S)-2-[(3R)-3-aminopiperidin-1-yl]-4,6-dichloro-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[[(1S,2S)-2-[(3R)-3-Aminopiperidin-1-yl]-4,6-dichloro-2,3-dihydro-1H-inden-1-yl]oxy]-3-fluorobenzene)sulfonamido]ethoxy]ethoxy)ethyl]-1-[4-([[2-(2-[2-[(4-[[[(1S,2S)-2-[(3R)-3-aminopiperidin-1-yl]-4,6-dichloro-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[[(1S,2S)-2-[(3R)-3-Aminopiperidin-1-yl]-6-Chloro-4-methyl-2,3-dihydro-1H-inden-1-yl]oxy]benzene)sulfonamido]ethoxy]ethoxy)ethyl]-1-[4-([[2-(2-[2-[(4-[[[(1S,2S)-2-[(3R)-3-aminopiperidin-1-yl]-6-chloro-4-methyl-2,3-dihydro-1H-inden-1-yl]oxy]benzene)sulfonamido]ethoxy]ethoxy)ethyl]carbamoyl]amino)butyl]urea;

3-[2-(2-[2-[(4-[[[(1S,2S)-2-[(3R)-3-Aminopiperidin-1-yl]-6-chloro-4-cyano-2,3-dihydro-1H-inden-1-yl]oxy]benzene)sulfonamido]ethoxy]ethoxy)ethyl]-1-[4-([[2-(2-[2-[(4-[[[(1S,2S)-2-[(3R)-3-aminopiperidin-1-yl]-6-chloro-4-cyano-2,3-dihydro-1H-inden-1-yl]oxy]benzene)sulfonamido]ethoxy]ethoxy)ethyl]carbamoyl]amino)butyl]urea;

3-[2-(2-[2-[(4-[[[(1S,2S)-2-[(3R)-3-Aminopiperidin-1-yl]-6-chloro-4-methoxy-2,3-dihydro-1H-inden-1-yl]oxy]benzene)sulfonamido]ethoxy]ethoxy)ethyl]-1-[4-([[2-(2-[2-[(4-[[[(1S,2S)-2-[(3R)-3-aminopiperidin-1-yl]-6-chloro-4-methoxy-2,3-dihydro-1H-inden-1-yl]oxy]benzene)sulfonamido]ethoxy]ethoxy)ethyl]carbamoyl]amino)butyl]urea;

1-[2-(2-[2-[(4-[[[(1S,2S)-2-[(3R)-3-Aminopiperidin-1-yl]-6-chloro-4-fluoro-2,3-dihydro-1H-inden-1-yl]oxy]-3-methylbenzene)sulfonamido]ethoxy]ethoxy)ethyl]-3-[4-([[2-(2-[2-[(4-[[[(1S,2S)-2-[(3R)-3-aminopiperidin-1-yl]-6-chloro-4-fluoro-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[[(1S,2S)-2-[(3R)-3-Aminopiperidin-1-yl]-6-chloro-4-methyl-2,3-dihydro-1H-inden-1-yl]oxy]-3-methylbenzene)sulfonamido]ethoxy]ethoxy)ethyl]-1-[4-([[2-(2-[2-[(4-[[[(1S,2S)-2-[(3R)-3-aminopiperidin-1-yl]-6-chloro-4-methyl-2,3-dihydro-1H-inden-1-yl]oxy]-3-methylbenzene)sulfonamido]ethoxy]ethoxy)ethyl]carbamoyl]amino)butyl] urea;

3-[2-(2-[2-[(4-[[[(1S,2S)-2-[(3R)-3-Aminopiperidin-1-yl]-6-chloro-4-cyano-2,3-dihydro-1H-inden-1-yl]oxy]-3-methylbenzene)sulfonamido]ethoxy]ethoxy)ethyl]-1-[4-([[2-(2-[2-[(4-[[[(1S,2S)-2-[(3R)-3-aminopiperidin-1-yl]-6-chloro-4-cyano-2,3-dihydro-1H-inden-1-yl]oxy]-3-methylbenzene) sulfonamido]ethoxy]ethoxy)ethyl]carbamoyl]amino)butyl]urea;

3-[2-(2-[2-[(4-[[[(1S,2S)-2-[(3R)-3-Aminopiperidin-1-yl]-6-chloro-4-methoxy-2,3-dihydro-1H-inden-1-yl]oxy]-3-methylbenzene)sulfonamido]ethoxy]ethoxy)ethyl]-1-[4-([[2-(2-[2-[(4-[[[(1S,2S)-2-[(3R)-3-aminopiperidin-1-yl]-6-chloro-4-methoxy-2,3-dihydro-1H-inden-1-yl]oxy]-3-methylbenzene)sulfonamido]ethoxy]ethoxy)ethyl]carbamoyl]amino)butyl]urea;

3-[2-(2-[2-([4-[[[(1S,2S)-2-[(3R)-3-Aminopiperidin-1-yl]-6-chloro-4-methyl-2,3-dihydro-1H-inden-1-yl]oxy]-3-fluoro benzene)sulfonamido]ethoxy]ethoxy)ethyl]-1-[4-([[2-(2-[2-[(4-[[[(1S,2S)-2-[(3R)-3-aminopiperidin-1-yl]-6-chloro-4-methyl-2,3-dihydro-1H-inden-1-yl]oxy]-3-fluorobenzene)sulfonamido]ethoxy]ethoxy)ethyl] carbamoyl]amino)butyl]urea;

3-[2-(2-[2-[(4-[[[(1S,2S)-6-Chloro-2-(dimethylamino)-4-methyl-2,3-dihydro-1H-inden-1-yl]oxy]benzene)sulfonamido]ethoxy]ethoxy)ethyl]-1-[4-([[2-(2-[2-[(4-[[[(1S,2S)-6-chloro-2-(dimethylamino)-4-methyl-2,3-dihydro-1H-inden-1-yl]oxy]benzene)sulfonamido]ethoxy]ethoxy)ethyl]carbamoyl]amino)butyl]urea;

3-[2-(2-[2-[(4-[[[(1S,2S)-6-Chloro-4-cyano-2-(dimethylamino)-2,3-dihydro-1H-inden-1-yl]oxy]benzene)sulfonamido]ethoxy]ethoxy)ethyl]-1-[4-([[2-(2-[2-[(4-[[[(1S,2S)-6-chloro-4-cyano-2-(dimethylamino)-2,3-dihydro-1H-inden-1-yl]oxy]benzene)sulfonamido]ethoxy]ethoxy)ethyl]carbamoyl]amino)butyl]urea;

3-[2-(2-[2-[(4-[[[(1S,2S)-6-Chloro-2-(dimethylamino)-4-(trifluoromethyl)-2,3-dihydro-1H-inden-1-yl]oxy]benzene)sulfonamido]ethoxy]ethoxy)ethyl]-1-[4-([[2-(2-[2-[(4-[[[(1S,2S)-6-chloro-2-(dimethylamino)-4-(trifluoromethyl)-2,3-dihydro-1H-inden-1-yl]oxy]benzene)sulfonamido]ethoxy]ethoxy)ethyl]carbamoyl]amino)butyl]urea;

1-[2-(2-[2-[(4-[[[(1S,2S)-6-Chloro-2-(dimethylamino)-4-(trifluoromethoxy)-2,3-dihydro-1H-inden-1-yl]oxy]benzene)sulfonamido]ethoxy]ethoxy)ethyl]-3-[4-([[2-(2-[2-[(4-[[[(1S,2S)-6-chloro-2-(dimethylamino)-4-(trifluoromethoxy)-2,3-dihydro-1H-inden-1-yl]oxy]benzene)sulfonamido]ethoxy]ethoxy)ethyl]carbamoyl]amino)butyl]urea;

3-[2-(2-[2-[(4-[[[(1S,2S)-6-Chloro-2-(dimethylamino)-4-methoxy-2,3-dihydro-1H-inden-1-yl]oxy]benzene)sulfonamido]ethoxy]ethoxy)ethyl]-1-[4-([[2-(2-[2-[(4-[[[(1S,2S)-6-chloro-2-(dimethylamino)-4-methoxy-2,3-dihydro-1H-inden-1-yl]oxy]benzene)sulfonamido]ethoxy]ethoxy)ethyl]carbamoyl]amino)butyl]urea;

3-[2-(2-[2-[(4-[[[(1S,2S)-6-Chloro-2-(dimethylamino)-4-fluoro-2,3-dihydro-1H-inden-1-yl]oxy]-3-methylbenzene)sulfonamido]ethoxy]ethoxy)ethyl]-1-[4-([[2-(2-[2-[(4-[[[(1S,2S)-6-chloro-2-(dimethylamino)-4-fluoro-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[[(1S,2S)-6-Chloro-2-(dimethylamino)-4-methyl-2,3-dihydro-1H-inden-1-yl]oxy]-3-methylbenzene)sulfonamido]ethoxy]ethoxy)ethyl]-1-[4-([[2-(2-[2-[(4-[[[(1S,2S)-6-chloro-2-(dimethylamino)-4-methyl-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[[(1S,2S)-6-Chloro-4-cyano-2-(dimethylamino)-2,3-dihydro-1H-inden-1-yl]oxy]-3-methylbenzene)sulfonamido]ethoxy]ethoxy)ethyl]-1-[4-([[2-(2-[2-[(4-[[[(1S,2S)-6-chloro-4-cyano-2-(dimethylamino)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[[(1S,2S)-6-Chloro-2-(dimethylamino)-4-(trifluoromethyl)-2,3-dihydro-1H-inden-1H-yl]oxy]-3-methylbenzene)sulfonamido]ethoxy]ethoxy)ethyl]-1-[4-([[2-(2-[2-[(4-[[[(1S,2S)-6-chloro-2-(dimethylamino)-4-(trifluoromethyl)-2,3-dihydro-1H-inden-1-yl]oxy]-3-methylbenzene)sulfonamido]ethoxy]ethoxy)ethyl]carbamoyl]amino)butyl]urea;

1-[2-(2-[2-[(4-[[[(1S,2S)-6-Chloro-2-(dimethylamino)-4-(trifluoromethoxy)-2,3-dihydro-1H-inden-1-yl]oxy]-3- methylbenzene)sulfonamido]ethoxy]ethoxy)ethyl]-3-[4-([[2-(2-[2-[(4-[[(1S,2S)-6-chloro-2-(dimethylamino)-4-(trifluoromethoxy)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methoxy-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-methoxy-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-4,6-Dichloro-2-(dimethylamino)-2,3-dihydro-1H-inden-1-yl]oxy]-3-methylbenzene)sulfonamido]ethoxy]ethoxy)ethyl]-1-[4-[[2-(2-[2-[(4-[[(1S,2S)-4,6-dichloro-2-(dimethylamino)-2,3-dihydro-1H-inden-1-yl]oxy]-3-methyl benzene)sulfonamido]ethoxy]ethoxy)ethyl]carbamoyl]amino)butyl]urea dihydrochloride;

3-[2-(2-[2-[(4-[[(1S,2S)-4,6-Dichloro-2-(dimethylamino)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-2-(dimethylamino)-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-2-(dimethylamino)-4-methyl-2,3-dihydro-1H-inden-1-yl]oxy]-3-fluorobenzene)sulfonamido] ethoxy]ethoxy)ethyl]carbamoyl]amino)butyl]urea;

3-[2-(2-[2-([4-[[(1S,2S)-4,6-Dichloro-2-[(3R)-3-(dimethylamino)piperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-4,6-Dichloro-2-[(3R)-3-(dimethylamino)piperidin-1-yl]-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-4,6-Dichloro-2-[(3R)-3-(dimethylamino)piperidin-1-yl]-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-4,6-Dichloro-2-(piperazin-1-yl)-2,3-dihydro-1H-inden-1-yl]oxy]benzene)sulfonamido]ethoxy]ethoxy)ethyl]-1-[4-([[2-(2-[2-[4-[[(1S,2S)-4,6-dichloro-2-(piperazin-1-yl)-2,3-dihydro-1H-inden-1-yl]oxy]benzene)sulfonamido]ethoxy]ethoxy)ethyl]carbamoyl]amino)butyl]urea;

3-[2-(2-[2-[4-[[(1S,2S)-4,6-Dichloro-2-(piperazin-1-yl)-2,3-dihydro-1H-inden-1-yl]oxy]-3-methylbenzene)sulfonamido]ethoxy]ethoxy)ethyl]-1-[4-[[2-(2-[2-[(4-[[(1S,2S)-4,6-dichloro-2-(piperazin-1-yl)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-4,6-Dichloro-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-methyl-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-4-methyl-2-piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-methyl-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]-3-fluorobenzene)sulfonamido]ethoxy]ethoxy)ethyl]-1-[4-([[2-(2-[2-[4-[[(1S,2S)-6-chloro-4-cyano-2-(dimethylamino)-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-fluorobenzene)sulfonamido]ethoxy]ethoxy)ethyl]carbamoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-methylbenzene)sulfonamido]ethoxy]ethoxy)ethyl]carbamoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea;

3-[2-(2-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino) butyl]urea;

3-[2-(2-[[(3R)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3R)-1-[(4-[[(1S,2S)-4,6-dichloro-2-(dimethylamino)-2,3-dihydro-1H-inden-1-yl]oxy]-3-methylbenzene) sulfonyl]pyrrolidin-3-yl]methoxy] ethoxy)ethyl]carbamoyl] amino)butyl]urea;

3-[2-(2-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3S)-1-[4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy] ethoxy)ethyl]carbamoyl]amino)butyl]urea;

3-[2-(2-[[(3R)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3R)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino)butyl]urea;

3-[(4-[[(3S)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-[(4-[[(3R)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3R)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-[(4-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-[(4-[[(3R)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3R)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-(2-[2-[(3S)-3-[(4-[[(1S,2S)-4,6-Dichloro-2-(dimethylamino)-2,3-dihydro-1H-inden-1-yl]oxy]-3-methylbenzene) sulfonamido]pyrrolidin-1-yl]ethoxy]ethyl)-1-(4-[[(2-[2-[(3S)-3-[(4-[[(1S,2S)-4,6-dichloro-2-(dimethylamino)-2,3-dihydro-1H-inden-1-yl]oxy]-3-methylbenzene)sulfonamido]pyrrolidin-1-yl]ethoxy]ethyl) carbamoyl]amino]butyl) urea;

3-(2-[2-[(3R)-3-[(4-[[(1S,2S)-4,6-Dichloro-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3R)-3-[(4-[[(1S,2S)-4,6-dichloro-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl) urea;

3-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido] pyrrolidin-1-yl]ethoxy] ethyl)carbamoyl]amino]butyl) urea;

3-(2-[2-[(3R)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl-ethoxy]ethyl)-1-(4-[[(2-[2-[(3R)-3-[(4-[[(1S,2S)-6-chloro-4-cyano-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl) urea;

1-([1-[2-(2-[2-[(4-[[(1S,2S)-2-[(3R)-3-Aminopiperidin-1-yl]-4,6-dichloro-2,3-dihydro-1H-inden-1-yl]oxy]benzene) sulfonamido]ethoxy]ethoxy)ethyl]-1H-1,2,3-triazol-4-yl]methyl)-3-(4-[[([1-[2-(2-[2-[(4-[[(1S,2S)-2-[(3R)-3-aminopiperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)carbamoyl]amino] butyl)urea;

(2R,3S,4R,5S)—N¹,N⁶-Bis([1-[2-(2-[2-[4-[[(1S,2S)-2-[(3R)-3-aminopiperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)-2,3,4,5-tetrahydroxyhexanediamide;

3-[(1-[4-[(4-[[(1S,2S)-2-[(3R)-3-Aminopiperidin-1-yl]-4,6-dichloro-2,3-dihydro-1H-inden-1-yl]oxy]benzene)sulfonamido]butyl]-1H-1,2,3-triazol-4-yl)methyl]-1-[4-([[(1-[4-[(4-[[(1S,2S)-2-[(3R)-3-aminopiperidin-1-yl]-4,6-dichloro-2,3-dihydro-1H-inden-1-yl]oxy]benzene)sulfonamido]butyl]-1H-1,2,3-triazol-4-yl)methyl]carbamoyl]amino)butyl]urea;

3-[(1-[6-[(4-[[(1S,2S)-2-[(3R)-3-Aminopiperidin-1-yl]-4,6-dichloro-2,3-dihydro-1H-inden-1-yl]oxy]benzene)sulfonamido]hexyl]-1H-1,2,3-triazol-4-yl)methyl]-1-[4-([[(1-[6-[(4-[[(1S,2S)-2-[(3R)-3-aminopiperidin-1-yl]-4,6-dichloro-2,3-dihydro-1H-inden-1-yl]oxy]benzene) sulfonamido]hexyl]-1H-1,2,3-triazol-4-yl)methyl]carbamoyl]amino)butyl]urea;

(4R,4aS,8S,8aR)—N⁴,N⁸-Bis([1-(4-[4-((1S,2S)-2-[(3R)-3-aminopiperidin-1-yl]-4,6-dichloro-2,3-dihydro-1H-inden-1-yloxy)phenyl sulfonamide]butyl)-1H-1,2,3-triazol-4-yl]methyl)-2,2,6,6-tetramethyl-tetrahydro-[1,3]dioxino[5,4-d][1,3]dioxine-4,8-dicarboxamide;

(4R,4aS,8S,8aR)—N¹,N⁸-Bis([1-(6-[4-((1S,2S)-2-[(3R)-3-amino piperidin-1-yl]-4,6-dichloro-2,3-dihydro-1H-inden-1-yloxy)phenylsulfonamido]hexyl)-1H-1,2,3-triazol-4-yl]methyl)-2,2,6,6-tetramethyl-tetrahydro-[1,3]dioxino[5,4-d][1,3]dioxine-4,8-dicarboxamide;

3-[8-[(4-[[(1S,2S)-2-[(3R)-3-Aminopiperidin-1-yl]-4,6-dichloro-2,3-dihydro-1H-inden-1-yl]oxy]benzene)sulfonamido]octyl]-1-[4-[([8-[(4-[[(1S,2S)-2-{[(3R)-3-aminopiperidin-1-yl]-4,6-dichloro-2,3-dihydro-1H-inden-1-yl]oxy]benzene) sulfonamido]octyl]carbamoyl)amino]butyl]urea;

3-[8-[(4-[[(1S,2S)-2-[(3R)-3-Aminopiperidin-1-yl]-4,6-dichloro-2,3-dihydro-1H-inden-1-yl]oxy]-3-methylbenzene) sulfonamido]octyl]-1-[4-[([8-[(4-[[(1S,2S)-2-[(3R)-3-aminopiperidin-1-yl]-4,6-dichloro-2,3-dihydro-1H-inden-1-yl]oxy]-3-methylbenzene)sulfonamido]octyl]carbamoyl)amino]butyl]urea;

3-[8-[(4-[[(1S,2S)-4,6-Dichloro-2-(dimethylamino)-2,3-dihydro-1H-inden-1-yl]oxy]benzene)sulfonamido]octyl]-1-[4-[([8-[(4-[[(1S,2S)-4,6-dichloro-2-(dimethylamino)-2,3-dihydro-1H-inden-1-yl]oxy]benzene)sulfonamido]octyl]carbamoyl)amino]butyl]urea;

3-[8-[(4-[[(1S,2S)-4,6-Dichloro-2-(dimethylamino)-2,3-dihydro-1H-inden-1-yl]oxy]-3-methylbenzene)sulfonamido]octyl]-1-[4-[([8-[(4-[[(1S,2S)-4,6-dichloro-2-(dimethylamino)-2,3-dihydro-1H-inden-1-yl]oxy]-3-methylbenzene) sulfonamido]octyl]carbamoyl)amino]butyl]urea;

3-[2-(2-[2-[(4-[[(1S,2S)-4,6-Dichloro-2-[(2R)-2-methylpiperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(2R)-2-methylpiperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-4,6-Dichloro-2-[(2S)-2-methylpiperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(2S)-2-methylpiperidin-1-yl]-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[2-Azabicyclo[2.2.1]heptan-2-yl]-4,6-dichloro-2,3-dihydro-1H-inden-1-yl]oxy]benzene)sulfonamido]ethoxy]ethoxy)ethyl]-1-[4-([[2-(2-[2-[(4-[[(1S,2S)-2-[2-azabicyclo[2.2.1]heptan-2-yl]-4,6-dichloro-2,3-dihydro-1H-inden-1-yl]oxy]benzene) sulfonamido]ethoxy]ethoxy)ethyl]carbamoyl]amino)butyl]urea;

1-[2-(2-[2-[(4-[[(1S,2S)-2-[2-Azabicyclo[2.2.2]octan-2-yl]-4,6-dichloro-2,3-dihydro-1H-inden-1-yl]oxy]benzene) sulfonamido]ethoxy]ethoxy)ethyl]-3-[4-([[2-(2-[2-[(4-[[(1S,2S)-2-[2-azabicyclo[2.2.2]octan-2-yl]-4,6-dichloro-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-2-[8-azabicyclo[3.2.1]octan-8-yl]-4,6-dichloro-2,3-dihydro-1H-inden-1-yl]oxy]benzene) sulfonamido]ethoxy]ethoxy)ethyl]-1-[4-([[2-(2-[2-[(4-[[(1S,2S)-2-[8-azabicyclo[3.2.1]octan-8-yl]-4,6-dichloro-2,3-dihydro-1H-inden-1-yl]oxy]benzene)sulfonamido]ethoxy]ethoxy)ethyl]carbamoyl]amino)butyl]urea;

1-[2-(2-[2-[(4-[[(1S,2S)-2-[9-Azabicyclo[3.3.1]nonan-9-yl]-4,6-dichloro-2,3-dihydro-1H-inden-1-yl]oxy]benzene)sulfonamido]ethoxy]ethoxy)ethyl]-3-[4-([[2-(2-[2-[(4-[[(1S,2S)-2-[9-azabicyclo[3.3.1]nonan-9-yl]-4,6-dichloro-2,3-dihydro-1H-inden-1-yl]oxy]benzene) sulfonamido]ethoxy]ethoxy)ethyl]carbamoyl]amino)butyl]urea;

3-[2-(2-[2-[(4-[[(1S,2S)-4,6-Dichloro-2-(4-methylpiperazin-1-yl)-2,3-dihydro-1H-inden-1-yl]oxy]benzene) sulfonamido]ethoxy]ethoxy)ethyl]-1-[4-([[2-(2-[2-[(4-[[(1S,2S)-4,6-dichloro-2-(4-methylpiperazin-1-yl)-2,3-dihydro-1H-inden-1-yl]oxy]benzene)sulfonamido] ethoxy]ethoxy)ethyl]carbamoyl]amino)butyl]urea;

3-[2-(2-[2-[(4-[[(1S,2S)-4,6-Dichloro-2-(4-methylpiperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-(4-methylpiperazin-1-yl)-2,3-dihydro-1H-inden-1-yl]oxy]-3-methylbenzene) sulfonamido]ethoxy]ethoxy)ethyl]carbamoyl]amino) butyl]urea;

3-[2-(2-[2-[(4-[[(1S,2S)-2-(4-Acetylpiperazin-1-yl)-4,6-dichloro-2,3-dihydro-1H-inden-1-yl]oxy]benzene)sulfonamido]ethoxy]ethoxy)ethyl]-1-[4-([[2-(2-[2-[(4-[[(1S,2S)-2-(4-acetylpiperazin-1-yl)-4,6-dichloro-2,3-dihydro-1H-inden-1-yl]oxy]benzene)sulfonamido]ethoxy]ethoxy) ethyl]carbamoyl]amino)butyl]urea;

3-[2-(2-[2-[(4-[[(1S,2S)-2-(4-Acetylpiperazin-1-yl)-4,6-dichloro-2,3-dihydro-1H-inden-1-yl]oxy]-3-methylbenzene)sulfonamido]ethoxy]ethoxy)ethyl]-1-[4-([[2-(2-[2-[(4-[[(1S,2S)-2-(4-acetylpiperazin-1-yl)-4,6-dichloro-2,3-dihydro-1H-inden-1-yl]oxy]-3-methylbenzene) sulfonamido]ethoxy]ethoxy)ethyl]carbamoyl]amino) butyl]urea;

4-[(1S,2S)-4,6-dichloro-1-[4-[(2-[2-[2-([[4-([[2-(2-[2-[(4-[[(1S,2S)-4,6-dichloro-2-[4-(dimethylcarbamoyl)piperazin-1-yl]-2,3-dihydro-1H-inden-1-yl]oxy]benzene) sulfonamido]ethoxy]ethoxy)ethyl]carbamoyl]amino) butyl]carbamoyl]amino)ethoxy]ethoxy]ethyl]sulfamoyl] phenoxy]-2,3-dihydro-1H-inden-2-yl]-N,N-dimethylpiperazine-1-carboxamide;

4-[(1S,2S)-4,6-dichloro-1-[4-[(2-[2-[2-([[4-([[2-(2-[2-[4-[[(1S,2S)-4,6-dichloro-2-[4-(dimethylcarbamoyl)piperazin-1-yl]-2,3-dihydro-1H-inden-1-yl]oxy]-3-methylbenzene)sulfonamido]ethoxy]ethoxy)ethyl]carbamoyl] amino)butyl]carbamoyl]amino)ethoxy]ethoxy]ethyl) sulfamoyl]-2-methylphenoxy]-2,3-dihydro-1H-inden-2-yl]-N,N-dimethylpiperazine-1-carboxamide;

3-[2-(2-[2-[(4-[[(1S,2S)-4,6-Dichloro-2-[(3R)-3-[methyl (propan-2-yl)amino]piperidin-1-yl]-2,3-dihydro-1H-inden-1-yl]oxy]benzene) sulfonamido]ethoxy]ethoxy) ethyl]-1-[4-([[2-(2-[2-[(4-[[(1S,2S)-4,6-dichloro-2-[(3R)-3-[methyl(propan-2-yl)amino]piperidin-1-yl]-2,3-dihydro-1H-inden-1-yl]oxy]benzene)sulfonamido] ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-3,5-dimethylbenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-3,5-dimethylbenzene)sulfonamido]ethoxy]ethoxy)ethyl] carbamoyl]amino)butyl]urea; hydrochloride;

1-[2-(2-[2-[(3-[[(1S,2S)-4,6-dichloro-2-(dimethylamino)-2,3-dihydro-1H-inden-1-yl]oxy]-2,4-dimethylbenzene) sulfonamido]ethoxy]ethoxy ethyl]-3-[4-([[2-(2-[2-[(4-[[(1S,2S)-4,6-dichloro-2-(dimethylamino)-2,3-dihydro-1H-Inden-1-yl]oxy]-3,5-dimethylbenzene)sulfonamido] ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-2,5-dimethylbenzene) sulfonamido]ethoxy]ethoxy)ethyl]-1-[4-([[2-

(2-[2-[(4-[[(1S,2S)-2-[(3R)-3-aminopiperidin-1-yl]-4,6-dichloro-2,3-dihydro-1H-inden-1-yl]oxy]-2,5-dimethylbenzene)sulfonamido]ethoxy]ethoxy)ethyl]carbamoyl]amino)butyl]urea;

3-[2-(2-[2-[(4-[[(chloro-2-(dimethylamino)-2,3-dihydro-1H-inden-1-yl]oxy]-2,5-dimethylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-2,5-dimethylbenzene)sulfonamido]ethoxy]ethoxy)ethyl]carbamoyl]amino)butyl]urea;

1-[2-(2-[2-([4-[[(1S,2S)-2-[(3R)-3-Aminopiperidin-1-yl]-4,6-dichloro-2,3-dihydro-1H-inden-1-yl]oxy]-3-fluoro-5-methylbenzene)sulfonamido]ethoxy]ethoxy)ethyl]-3-[4-([[2-(2-[2-[(4-[[(1S,2S)-2-[(3R)-3-aminopiperidin-1-yl]-4,6-chloro-2,3-dihydro-1H-inden-1-yl]oxy]-3-fluoro-5-methylbenzene)sulfonamido]ethoxy]ethoxy)ethyl]carbamoyl]amino)butyl]urea; hydrochloride;

1-[2-(2-[2-[(4-[[(1S,2S)-4,6-Dichloro-2-(dimethylamino)-2,3-dihydro-1H-inden-1-yl]oxy]-3-fluoro-5-methylbenzene)sulfonamido]ethoxy]ethoxy)ethyl]-3-[4-([[2-(2-[2-[(4-[[(1S,2S)-4,6-dichloro-2-(dimethylamino)-2,3-dihydro-1H-inden-1-yl]oxy]-3-fluoro-5-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-3,5-difluorobenzene) sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-3,5-difluorobenzene)sulfonamido]ethoxy]ethoxy)ethyl]carbamoyl]amino)butyl]urea;

4-([[(1S,2S)-4,6-dichloro-2-(dimethylamino)-2,3-dihydro-1H-inden-1-yl]oxy)-N-[26-([[(1S,2S)-4,6-dichloro-2-(dimethylamino)-2,3-dihydro-1H-inden-1-yl]oxy)-3,5-difluorophenyl]sulfonamido)-10,17-dioxo-3,6,21,24-tetraoxa-9,11,16,18-tetraazahexacosyl]-3,5-difluorobenzenesulfonamide:

3-[2-(2-[2-[(4-[[(1S,2S)-2-[(3R)-3-Aminopiperidin-1-yl]-4,6-dichloro-2,3-dihydro-1H-inden-1-yl]oxy]-5-fluoro-2-methylbenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-5-fluoro-2-methylbenzene)sulfonamido]ethoxy]ethoxy)ethyl]carbamoyl]amino)butyl]urea;

3-[2-(2-[2-[(4-[[(1S,2S)-4,6-Dichloro-2-(dimethylamino)-2,3-dihydro-1H-inden-1-yl]oxy]-5-fluoro-2-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-5-fluoro-2-methylbenzene)sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-2-fluoro-5-methylbenzene)sulfonamido]ethoxy]ethoxy)ethyl]-1-[4-([[2-(2-[2-[(4-[[(1S,2S)-2-[(3R)-3-aminopiperidin-1-yl]4,6-dichloro-2,3-dihydro-1H-inden-1-yl]oxy]-2-fluoro-5-methylbenzene)sulfonamido]ethoxy]ethoxy)ethyl]carbamoyl]amino)butyl]urea;

3-[2-(2-[2-[(4-[[(1S,2S)-4,6-Dichloro-2-(dimethylamino)-2,3-dihydro-1H-inden-1-yl]oxy]-2-fluoro-5-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-2-fluoro-5-methylbenzene)sulfonamido]ethoxy]ethoxy)ethyl]carbamoyl]amino)butyl]urea;

1-(2-[2-[(3S)-3-[(4-[[(1S,2S)-4,6-Dichloro-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3S)-3-[(4-[[(1S,2S)-4,6-dichloro-2-(dimethylamino)-2,3-dihydro-1H-inden-1-yl]oxy]-3-methylbenzene)sulfonamido]-2-oxopyrrolidin-1-yl]ethoxy]ethyl)carbamoyl]amino]butyl)urea;

1-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)carbamoyl]amino]butyl)urea;

3-[2-(2-[[(3R)-1-[(4-[[(1S,2S)-2-[(3R)-3-Aminopiperidin-1-yl]-4,6-dichloro-2,3-dihydro-1H-inden-1-yl]oxy]benzene)sulfonyl]pyrrolidin-3-yl]oxy]ethoxy)ethyl]-1-[4-([[2-(2-[[(3R)-1-[(4-[[(1S,2S)-2-[(3R)-3-aminopiperidin-1-yl]-4,6-dichloro-2,3-dihydro-1H-inden-1-yl]oxy]benzene)sulfonyl]pyrrolidin-3-yl]oxy]ethoxy)ethyl]carbamoyl]amino)butyl]urea;

3-[2-(2-[[(3S)-1-[(4-[[(1S,2S)-2-[(3R)-3-Aminopiperidin-1-yl]-4,6-dichloro-2,3-dihydro-1H-inden-1-yl]oxy]benzene)sulfonyl]pyrrolidin-3-yl]oxy]ethoxy)ethyl]-1-[4-([[2-(2-[[(3S)-1-[(4-[[(1S,2S)-2-[(3R)-3-aminopiperidin-1-yl]-4,6-dichloro-2,3-dihydro-1H-inden-1-yl]oxy]benzene)sulfonyl]pyrrolidin-3-yl]oxy]ethoxy)ethyl]carbamoyl]amino)butyl]urea;

3-[2-[2-([1-[(4-[[(1S,2S)-2-[(3R)-3-Aminopiperidin-1-yl]-4,6-dichloro-2,3-dihydro-1H-inden-1-yl]oxy]benzene)sulfonyl]piperidin-4-yl]oxy)ethoxy]ethyl]-1-[4-[([2-[2-([1-[(4-[[(1S,2S)-2-[(3R)-3-aminopiperidin-1-yl]-4,6-dichloro-2,3-dihydro-1H-inden-1-yl]oxy]benzene)sulfonyl]piperidin-4-yl]oxy)ethoxy]ethyl]carbamoyl)amino]butyl]urea;

1-(2-[2-[(2S)-2-[(4-[[(1S,2S)-2-[(3R)-3-Aminopiperidin-1-yl]-4,6-dichloro-2,3-dihydro-1H-inden-1-yl]oxy]benzene)sulfonamido]propoxy]ethoxy]ethyl)-3-(4-[[(2-[2-[(2S)-2-[(4-[[(1S,2S)-2-[(3R)-3-aminopiperidin-1-yl]-4,6-dichloro-2,3-dihydro-1H-inden-1-yl]oxy]benzene)sulfonamido]propoxy]ethoxy]ethyl)carbamoyl]amino]butyl)urea; hydrochloride;

3-(2-[2-[(2R)-2-[(4-[[(1S,2S)-2-[(3R)-3-Aminopiperidin-1-yl]-4,6-dichloro-2,3-dihydro-1H-inden-1-yl]oxy]benzene)sulfonamido]propoxy]ethoxy]ethyl)-1-(4-[[(2-[2-[(2R)-2-[(4-[[(1S,2S)-2-[(3R)-3-aminopiperidin-1-yl]-4,6-dichloro-2,3-dihydro-1H-inden-1-yl]oxy]benzene)sulfonamido]propoxy]ethoxy]ethyl)carbamoyl]amino]butyl)urea;

3-(2-[2-[(2S)-2-[(4-[[(1S,2S)-2-[(3R)-3-Aminopiperidin-1-yl]-4,6-dichloro-2,3-dihydro-1H-inden-1-yl]oxy]benzene)sulfonamido]-3-methylbutoxy]ethoxy]ethyl)-1-(4-[[(2-[2-[(2S)-2-[(4-[[(1S,2S)-2-[(3R)-3-aminopiperidin-1-yl]-4,6-dichloro-2,3-dihydro-1H-inden-1-yl]oxy]benzene) sulfonamido]-3-methylbutoxy]ethoxy]ethyl)carbamoyl]amino]butyl)urea dihydrochloride;

3-(2-[2-[(2R)-2-[(4-[[(1S,2S)-2-[(3R)-3-Aminopiperidin-1-yl]-4,6-dichloro-2,3-dihydro-1H-inden-1-yl]oxy]benzene)sulfonamido]-3-methylbutoxy]ethoxy]ethyl)-1-(4-[[(2-[2-[(2R)-2-[(4-[[(1S,2S)-2-[(3R)-3-aminopiperidin-1-yl]-4,6-dichloro-2,3-dihydro-1H-inden-1-yl]oxy]benzene)sulfonamido]-3-methylbutoxy]ethoxy]ethyl)carbamoyl]amino]butyl)urea;

1-[2-(2-[2-[(4-[[(1S,2S)-2-[(3R)-3-Aminoperidin-1-yl]-4,6-dichloro-2,3-dihydro-1H-inden-1-yl]oxy]benzene)sulfonamido]-2-methylpropoxy]ethoxy)ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]benzene)

sulfonamido]-2-methylpropoxy]ethoxy)ethyl]carbamoyl] amino)butyl]urea; hydrochloride;

1-[2-(2-[2-[(4-[[(1S,2S)-2-[(3R)-3-Aminopiperidin-1-yl]-4,6-dichloro-2,3-dihydro-1H-inden-1-yl]oxy]-2-methoxybenzene)sulfonamido]ethoxy]ethoxy)ethyl]-3-[4-([[2-(2-[2-(4-[[(1S,2S)-2-[(3R)-3-aminopiperidin-1-yl]-4,6-dichloro-2,3-dihydro-1H-inden-1-yl]oxy]-2-methoxybenzene)sulfonamido]ethoxy]ethoxy)ethyl] carbamoyl]amino)butyl]urea;

3-[2-(2-[2-[(4-[[(1S,2S)-2-[(3R)-3-Aminopiperidin-1-yl]-4,6-dichloro-2,3-dihydro-1H-inden-1-yl]oxy]-2-methylbenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-2-methylbenzene)sulfonamido]ethoxy]ethoxy)ethyl] carbamoyl]amino)butyl]urea;

1-[2-(2-[2-([4-[[(1S,2S)-2-[(3R)-3-Aminopiperidin-1-yl]-4,6-dichloro-2,3-dihydro-1H-inden-1-yl]oxy]-2-fluorobenzene)sulfonamido]ethoxy]ethoxy)ethyl]-3-[4-([[2-(2-[2-[4-[[(1S,2S)-2-[(3R)-3-aminopiperidin-1-yl]-4,6-dichloro-2,3-dihydro-1H-inden-1-yl]oxy]-2-fluorobenzene)sulfonamido]ethoxy]ethoxy)ethyl] carbamoyl]amino)butyl]urea;

4-([(1S,2S)-2-[(R)-3-Aminopiperidin-1-yl]-4,6-dichloro-2,3-dihydro-1H-inden-1-yl]oxy)-N-[26-([4-([(1S,2S)-2-[(R)-3-aminopiperidin-1-yl]-4,6-dichloro-2,3-dihydro-1H-inden-1-yl]oxy)-2-chlorophenyl]sulfonamido)-10,17-dioxo-3,6,21,24-tetraoxa-9,11,16,18-tetraazahexacosyl]-2-chlorobenzenesulfonamide;

4-([(1S,2S)-4,6-Dichloro-2-(piperazin-1-yl)-2,3-dihydro-1H-inden-1-yl]oxy)-N—[(R)-1-(20-[(R)-3-([4-([(1S,2S)-4,6-dichloro-2-(piperazin-1-yl)-2,3-dihydro-1H-inden-1-yl]oxy)-3-fluorophenyl]sulfonamido)pyrrolidin-1-yl]-7,14-dioxo-3,18-dioxa-6,8,13,15-tetraazaicosyl)pyrrolidin-3-yl]-3-fluorobenzenesulfonamide; tetra(trifluoroacetate);

4-([(1S,2S)-4,6-Dichloro-2-(piperazin-1-yl)-2,3-dihydro-1H-inden-1-yl]oxy)-N—[(S)-1-(20-[(S)-3-([4-([(1S,2S)-4,6-dichloro-2-(piperazin-1-yl)-2,3-dihydro-1H-inden-1-yl]oxy)-3-fluorophenyl]sulfonamido)pyrrolidin-1-yl]-7,14-dioxo-3,18-dioxa-6,8,13,15-tetraazaicosyl)pyrrolidin-3-yl]-3-fluorobenzenesulfonamide, tetra(trifluoroacetate);

4-([(1S2S)-6-Chloro-4-cyano-2-(piperazin-1-yl)-2,3-dihydro-1H-inden-1-yl]oxy)-N—[(S)-1-(20-[(S)-3-([4-([(1S,2S)-6-chloro-4-cyano-2-(piperazin-1-yl)-2,3-dihydro-1H-inden-1-yl]oxy)phenyl]sulfonamido) pyrrolidin-1-yl]-7,14-dioxo-3,18-dioxa-6,8,13,15-tetraazaicosyl)pyrrolidin-3-yl]benzenesulfonamide; tetra(trifluoroacetate);

4-([(1S,2S)-6-Chloro-4-cyano-2-(piperazin-1-yl)-2,3-dihydro-1H-inden-1-yl]oxy)-N—[(R)-1-(20-[(R)-3-([4-([(1S,2S)-6-chloro-4-cyano-2-(piperazin-1-yl)-2,3-dihydro-1H-inden-1-yl]oxy)phenyl]sulfonamido) pyrrolidin-1-yl]-7,14-dioxo-3,18-dioxa-6,8,13,15-tetraazaicosyl)pyrrolidin-3-yl]benzenesulfonamide; tetra(trifluoroacetate);

4-([(1S,2S)-6-Chloro-4-cyano-2-(piperazin-1-yl)-2,3-dihydro-1H-inden-1-yl]oxy)-N—[(R)-1-(20-[(R)-3-[4-([(1S,2S)-6-chloro-4-cyano-2-(piperazin-1-yl)-2,3-dihydro-1H-inden-1-yl]oxy)-3-fluorophenyl)sulfonamide)pyrrolidin-1-yl]-7,14-dioxo-3,18-dioxa-6,8,13,15-tetraazaicosyl)pyrrolidin-3-yl]-3-fluorobenzenesulfonamide; tetra(trifluoroacetate);

4-([(1S,2S)-6-Chloro-4-cyano-2-(piperazin-1-yl)-2,3-dihydro-1H-inden-1-yl]oxy)-N—[(S)-1-(20-[(S)-3-([4-([(1S,2S)-6-chloro-4-cyano-2-(piperazin-1-yl)-2,3-dihydro-1H-inden-1-yl]oxy)-3-fluorophenyl)sulfonamide)pyrrolidin-1-yl]-7,14-dioxo-3,18-dioxa-6,8,13,15-tetraazaicosyl)pyrrolidin-3-yl]-3-fluorobenzenesulfonamide; tetra(trifluoroacetate);

4-([(1S,2S)-4,6-Dichloro-2-(dimethylamino)-2,3-dihydro-1H-inden-1-yl]oxy)-N—[(S)-1-(20-[(S)-3-([4-([(1S,2S)-4,6-dichloro-2-(dimethylamino)-2,3-dihydro-1H-inden-1-yl]oxy)-3-fluorophenyl]sulfonamido)pyrrolidin-1-yl]-7,14-dioxo-3,18-dioxa-6,8,13,15-tetraazaicosyl) pyrrolidin-3-yl]-3-fluorobenzenesulfonamide; tetra (trifluoroacetate);

4-([(1S,2S)-4,6-Dichloro-2-(dimethylamino)-2,3-dihydro-1H-inden-1-yl]oxy)-N—[(R)-1-(20-[(R)-3-([4-([(1S,2S)-4,6-dichloro-2-(dimethylamino)-2,3-dihydro-1H-inden-1-yl]oxy)-3-fluorophenyl]sulfonamido)pyrrolidin-1-yl]-7,14-dioxo-3,18-dioxa-6,8,13,15-tetraazaicosyl) pyrrolidin-3-yl]-3-fluorobenzenesulfonamide; tetra (trifluoroacetate);

4-([(1S,2S)-6-Chloro-2-[(R)-3-(dimethylamino)piperidin-1-yl]-4-methyl-2,3-dihydro-1H-inden-1-yl]oxy)-N—[(R)-1-(20-[(R)-3-([4-([(1S,2S)-6-chloro-2-[(R)-3-(dimethylamino)piperidin-1-yl]-4-methyl-2,3-dihydro-1H-inden-1-yl]oxy)-3-methylphenyl]sulfonamido)pyrrolidin-1-yl]-7,14-dioxo-3,18-dioxa-6,8,13,15-tetraazaicosyl)pyrrolidin-3-yl]-3-methylbenzenesulfonamide; tetra (trifluoroacetate);

4-([(1S,2S)-6-Chloro-2-[(R)-3-(dimethylamino)piperidin-1-yl]-4-methyl-2,3-dihydro-1H-inden-1-yl]oxy)-N—[(S)-1-(20-[(S)-3-([4-([(1S,2S)-6-chloro-2-[(R)-3-(dimethylamino)piperidin-1-yl]-4-methyl-2,3-dihydro-1H-inden-1-yl]oxy)-3-methylphenyl]sulfonamido)pyrrolidin-1-yl]-7,14-dioxo-3,18-dioxa-6,8,13,15-tetraazaicosyl)pyrrolidin-3-yl]-3-methylbenzenesulfonamide; tetra (trifluoroacetate);

4-([(1S,2S)-6-Chloro-4-cyano-2-(piperazin-1-yl)-2,3-dihydro-1H-inden-1-yl]oxy)-N-[1-(18-[4-([(1S,2S)-6-chloro-4-cyano-2-(piperazin-1-yl)-2,3-dihydro-1H-inden-1-yl]oxy)phenyl]sulfonamido)piperidin-1-yl]-6,13,18-trioxo-5,7,12,14-tetraazaoctadecanoyl)piperidin-4-yl] benzenesulfonamide;

4-([(1S,2S)-6-Chloro-4-cyano-2-(piperazin-1-yl)-2,3-dihydro-1H-inden-1-yl]oxy)-N—[(S)-1-(14-[(S)-3-[4-([(1S,2S)-6-chloro-4-cyano-2-(piperazin-1-yl)-2,3-dihydro-1H-inden-1-yl]oxy)phenyl]sulfonamido) pyrrolidin-1-yl]-4,11,14-trioxo-3,5,10,12-tetraazatetradecanoyl)pyrrolidin-3-yl] benzenesulfonamide;

4-([(1S,2S)-6-Chloro-4-cyano-2-(piperazin-1-yl)-2,3-dihydro-1H-inden-1-yl]oxy)-N—[(S)-1-[(2S,13S)-14-[(S)-3-([4-([(1S,2S)-6-chloro-4-cyano-2-(piperazin-1-yl)-2,3-dihydro-1H-inden-1-yl]oxy)phenyl]sulfonamido) pyrrolidin-1-yl]-2,13-dimethyl-4,11,14-trioxo-3,5,10,12-tetraazatetradecanoyl]pyrrolidin-3-yl] benzenesulfonamide;

$N^1,N^{14}$-bis(2-[(S)-3-([4-([(1S,2S)-6-chloro-4-cyano-2-(piperazin-1-yl)-2,3-dihydro-1H-inden-1-yl]oxy)phenyl] sulfonamido)pyrrolidin-1-yl]-2-oxoethyl)-4,11-dioxo-3,5,10,12-tetraazatetradecanediamide;

$N^1,N^{14}$-bis(2)-[(R)-3-([4-([(1S,2S)-6-chloro-4-cyano-2-(piperazin-1-yl)-2,3-dihydro-1H-inden-1-yl]oxy)phenyl] sulfonamido)pyrrolidin-1-yl]-2-oxoethyl)-4,11-dioxo-3,5,10,12-tetraazatetradecanediamide;

$N^1,N^{18}$-Bis(1-([4-([(1S,2S)-6-chloro-4-cyano-2-(piperazin-1-yl)-2,3-dihydro-1H-inden-1-yl]oxy)phenyl]sulfonyl)piperidin-4-yl)-6,13-dioxo-5,7,12,14-tetraazaoctadecanediamide;

4-([(1S,2S)-6-Chloro-4-cyano-2-[(R)-3-(dimethylamino)piperidin-1-yl]-2,3-dihydro-1H-inden-1-yl]oxy)-N-[26-([4-([(1S,2S)-6-chloro-4-cyano-2-[(R)-3-(dimethylamino)piperidin-1-yl]-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

4-([(1S,2S)-6-Chloro-4-cyano-2-[(S)-3-dimethylamino)piperidin-1-yl]-2,3-dihydro-1H-inden-1-yl]oxy)-N-[26-([4-([1S,2S)-6-chloro-4-cyano-2-[(S)-3-dimethylamino)piperidin-1-yl]-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

4-([1S,2S)-6-chloro-4-cyano-2-(piperazin-1-yl)-2,3-dihydro-1H-inden-1-yl]oxy)-N-[1-(20-[4-([4-([(1S,2S)-6-chloro-4-cyano-2-(piperazin-1-yl)-2,3-dihydro-1H-inden-1-yl]oxy)phenyl]sulfonamide]piperidin-1-yl)-7,14-dioxo-3,18-dioxa-6,8,13,15-tetraazaicosyl]piperidin-4-yl)benzenesulfonamide;

$N^1,N^{18}$-Bis([4-([(1S,2S)-6-chloro-4-cyano-2-(piperazin-1-yl)-2,3-dihydro-1H-inden-1-yl]oxy)phenyl]sulfonyl)-6,13-dioxo-5,7,12,14-tetraazaoctadecanediamide;

N-([4-([(1S,2S)-6-chloro-4-cyano-2-(piperazin-1-yl)-2,3-dihydro-1H-inden-1-yl]oxy)phenyl]sulfonyl)-1-[16-[([4-(1S,2S)-6-chloro-4-cyano-2-(piperazin-1-yl)-2,3-dihydro-1H-inden-1-yl]oxy)phenyl]sulfonyl)carbamoyl]piperidin-1-yl)-5,12-dioxo-4,6,11,13-tetraazahexadecyl]piperidine-4-carboxamide;

4-([(1S,2S)-6-chloro-4-cyano-2-(1,4-diazepan-1-yl)-2,3-dihydro-1H-inden-1-]oxy)-N—(S)-1-(20-[(S)-3-([4-([(1S,2S)-6-chloro-4-cyano-2-(1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-(1,4-diazepan-1-yl)-2,3-dihydro-1H-inden-1-yl]oxy)-N—[(R)-1-(20-[(R)-3-([4-([(1S,2S)-6-chloro-4-cyano-2-(1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-(4-methyl-1,4-diazepan-1-yl)-2,3-dihydro-1H-inden-1-yl]oxy)-N—[(S)-1-(20-[(S)-3-([4-([(1S,2S)-6-chloro-4-cyano-2-(4-methyl-1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-(4-methyl-1,4-diazepan-1-yl)-2,3-dihydro-1H-inden-1-yl]oxy)-N—[(R)-1-(20-[(R)-3-([4-([(1S,2S)-6-chloro-4-cyano-2-(4-methyl-1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-2-[(1S,4S)-2,5-diazabicyclo[2.2.1]heptan-2-yl]-6-chloro-4-cyano-2,3-dihydro-1H-inden-1-yl]oxy)-N—[(S)-1-(20-[(S)-3-([4-([(1S,2S)-2-[(1S,4S)-2,5-diazabicyclo[2.2.1]heptan-2-yl]-6-chloro-4-cyano-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-2-[(1S,4S)-2,5-diazabicyclo[2.2.1]heptan-2-yl]-6-chloro-4-cyano-2,3-dihydro-1H-inden-1-yl]oxy)-N—[(R)-1-(20-[(R)-3-([4-([(1S,2S)-2-[(1S,4S)-2,5-diazabicyclo[2.2.1]heptan-2-yl]-6-chloro-4-cyano-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(R)-3-methylpiperazin-1-yl]-2,3-dihydro-1H-inden-1-yl]oxy)-N—[(S)-1-(20-[(S)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(R)-3-methylpiperazin-1-yl]-2,3-dihydro-1H-inden-1-yl]oxy)-N—[(R)-1-(20-[(R)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(S)-3-methylpiperazin-1-yl]-2,3-dihydro-1H-inden-1-yl]oxy)-N—[(S)-1-(20-[(S)-3-([4-([(1S,2S)-6-chloro-4-cyano-2-[(S)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(S)-3-methylpiperazin-1-yl]-2,3-dihydro-1H-inden-1-yl]oxy)-N—[(R)-1-(20-[(R)-3-([4-([(1S,2S)-6-chloro-4-cyano-2-[(S)-3-methylpiperazin-1-yl]-2,3-dihydro-1H-inden-1H-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(3S,5S)-3,5-dimethylpiperazin-1-yl]-2,3-dihydro-1H-inden-1-yl]oxy)-N—[(S)-1-(20-[(S)-3-([4-([(1S,2S)-6-chloro-4-cyano-2-[(3S,5R)-3,5-dimethylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-[(3S,5R)-3,5-dimethylpiperazin-1-yl]-2,3-dihydro-1H-inden-1-yl]oxy)-N—[(R)-1-(20-[(R)-3-([4-([(1S,2S)-6-chloro-4-cyano-2-[(3S,5R)-3,5-dimethylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([(1S,2S)-6-chloro-4-cyano-2-(piperazin-1-yl)-2,3-dihydro-1H-inden-1-yl]oxy)-N—[(S)-1-(20-[(S)-3-([4-([(1S,2S)-6-chloro-4-cyano-2-(piperazin-1-yl)-2,3-dihydro-1H-inden-1-yl]oxy)phenyl]sulfonamido)-2-oxopiperidin-1-yl]-7,14-dioxo-3,18-dioxa-6,8,13,15-tetraazaicosyl)-2-oxopiperidin-3-yl]benzenesulfonamide;

4-([(1S,2S)-6-Chloro-4-cyano-2-(piperazin-1-yl)-2,3-dihydro-1H-inden-1-yl]oxy)-N-[2-(2-[2-(3-[(1r,4r)-4-(3-[2-(2-[2-([4-([(1S,2S)-6-chloro-4-cyano-2-(piperazin-1-yl)-2,3-dihydro-1H-inden-1-yl]oxy)phenyl]sulfonamido)ethoxy]ethoxy)ethyl]ureido)cyclohexyl]ureido)ethoxy]ethoxy) ethyl]benzenesulfonamide, 4-([(1S,2S)-6-Chloro-4-cyano-2-(piperazin-1-yl)-2,3-dihydro-1H-inden-1-yl]oxy)-N—[(R)-1-(18-[(R)-3-([4-([(1S,2S)-6-chloro-4-cyano-2-(piperazin-1-yl)-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide;

4-([(1S,2S)-6-Chloro-4-cyano-2-(piperazin-1-yl)-2,3-dihydro-1H-inden-1-yl]oxy)benzenesulfonamide;

N-(2-[2-(2-Aminoethoxy)ethoxy]ethyl)-4-([(1S,2S)-6-chloro-4-cyano-2-(piperazin-1-yl)-2,3-dihydro-1H-inden-1-yl]oxy)benzenesulfonamide;

N-[1-(4-Aminobutanoyl)piperidin-4-yl]-4-([(1S,2S)-6-chloro-4-cyano-2-(piperazin-1-yl)-2,3-dihydro-1H-inden-1-yl]oxy)benzenesulfonamide;

4-([[(1S,2S)-6-Chloro-4-cyano-2-(piperazin-1-yl)-2,3-dihydro-1H-inden-1-yl]oxy)-N-(3-oxo-7,10-dioxa-2,4-diazadodecan-12-yl)benzenesulfonamide;

4-([1S,2S)-6-Chloro-4-cyano-2-(piperazin-1-yl)-2,3-dihydro-1H-inden-1-yl]oxy)-N-(1-[4-(3-methylureido)butanoyl]piperidin-4-yl)benzenesulfonamide;

4-([[(1S,2S)-6-Chloro-4-cyano-2-(piperazin-1-yl)-2,3-dihydro-1H-inden-1-yl]oxy)-N-[(2S,3R,4S,5R)-1,3,4,5,6-pentahydroxyhexan-2-yl]benzenesulfonamide;

4-([4-([[(1S,2S)-6-Chloro-4-cyano-2-(piperazin-1-yl)-2,3-dihydro-1H-inden-1-yl]oxy)phenyl]sulfonamido)-N-[(2S,3R,4S,5R)-1,3,4,5,6-pentahydroxyhexan-2-yl]piperidine-1-carboxamide;

4-(3-[4-([4-([[(1S,2S)-6-Chloro-4-cyano-2-(piperazin-1-yl)-2,3-dihydro-1H-inden-1-yl]oxy)phenyl]sulfonamido)-4-oxobutyl]ureido)-N-[4-([[(1S,2S)-6-chloro-4-cyano-2-(piperazin-1-yl)-2,3-dihydro-1H-inden-1-yl]oxy)phenyl]sulfonyl)butanamide;

4-([[(1S,2S)-6-Chloro-4-cyano-2-(piperazin-1-yl)-2,3-dihydro-1H-inden-1-yl]oxy)-N-[1-(4-[3-(4-[4-([[(1S,2S)-6-chloro-4-cyano-2-(piperazin-1-yl)-2,3-dihydro-1H-inden-1-yl]oxy)phenyl]sulfonamido)piperidin-1-yl]-4-oxobutyl)ureido]butanoyl)piperidin-4-yl]benzenesulfonamide;

4-([[(1S,2S)-6-Chloro-4-cyano-2-(piperazin-1-yl)-2,3-dihydro-1H-inden-1-yl]oxy)-N-[19-([4-([[(1S,2S)-6-chloro-4-cyano-2-(piperazin-1-yl)-2,3-dihydro-1H-inden-1-yl]oxy)phenyl]sulfonamido)-10-oxo-3,6,14,17-tetraoxa-9,11-diazanonadecyl]benzenesulfonamide;

4-([[(1S,2S)-6-Chloro-4-amido-2-(piperazin-1-yl)-2,3-dihydro-1H-inden-1-yl]oxy)-N-[26-([4-([[(1S,2S)-6-chloro-4-amido-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

4-([[(1S,2S)-4-Cyano-6-methyl-2-(piperazin-1-yl)-2,3-dihydro-1H-inden-1-yl]oxy)-N-[26-([4-([[(1S,2S)-4-cyano-6-methyl-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

1,1'-(Butane-1,4-diyl)bis[3-(4-[6-([[(1S,2S)-6-chloro-4-cyano-2-(piperazin-1-yl)-2,3-dihydro-1H-inden-1-yl]oxy)-3,4-dihydroisoquinolin-2(1H)-yl]-4-oxobutyl)urea];

1,1'-(Butane-1,4-diyl)bis[3-(4-[7-([[(1S,2S)-6-chloro-4-cyano-2-(piperazin-1-yl)-2,3-dihydro-1H-inden-1-yl]oxy)-3,4-dihydroisoquinolin-2(1H)-yl]-4-oxobutyl)urea];

N,N'-(6,14-Dioxo-10-oxa-5,7,13,15-tetraazanonadecane-1,19-diyl)bis[6-([[(1S,2S)-6-chloro-4-cyano-2-(piperazin-1-yl)-2,3-dihydro-1H-inden-1-yl]oxy)-3,4-dihydroisoquinoline-2(1H)-carboxamide];

N,N'-(6,14-Dioxo-10-oxa-5,7,13,15-tetraazanonadecane-1,19-diyl)bis[7-([[(1S,2S)-6-chloro-4-cyano-2-(piperazin-1-yl)-2,3-dihydro-1H-inden-1-yl]oxy)-3,4-dihydroisoquinoline-2(1H)-carboxamide];

4-([[(1S,2S)-6-Chloro-4-cyano-2-[(R)-3-methylpiperazin-1-yl]-2,3-dihydro-1H-inden-1-yl]oxy)-N—[(S)-1-(18-[(S)-3-([4-([[(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide;

4-([[(1S,2S)-6-Chloro-4-cyano-2-[(R)-3-methylpiperazin-1-yl]-2,3-dihydro-1H-inden-1-yl]oxy)-N—[(R)-1-(18-[(R)-3-([4-([[(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide;

4-([[(1S,2S)-6-Chloro-4-cyano-2-[(R)-3-methylpiperazin-1-yl]-2,3-dihydro-1H-inden-1-yl]oxy)-N-[1-(18-[4-([[(1S,2S)-6-chloro-4-cyano-2-[(R)-3-methylpiperazin-1-yl]-2,3-dihydro-1H-inden-1-yl]oxy)phenyl]sulfonamido)piperidin-1-yl]-6,13,18-trioxo-5,7,12,14-tetraazaoctadecanoyl)piperidin-4-yl]benzenesulfonamide;

$N^1,N^{14}$-Bis(2-[(S)-3-([4-([[(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide;

4-([[(1S,2S)-6-Chloro-4-cyano-2-[(R)-3-methylpiperazin-1-yl]-2,3-dihydro-1H-inden-1-yl]oxy)-N-[1-(20-[4-([[(1S,2S)-6-chloro-4-cyano-2-[(R)-3-methylpiperazin-1-yl]-2,3-dihydro-1H-inden-1-yl]oxy)phenyl]sulfonamido)piperidin-1-yl]-7,14-dioxo-3,18-dioxa-6,8,13,15-tetraazaicosyl)piperidin-4-yl]benzenesulfonamide;

4-([[(1S,2S)-4,6-Dichloro-2-[(R)-3-methylpiperazin-1-yl]-2,3-dihydro-1H-inden-1-yl]oxy)-N—[(S)-1-(20-[(S)-3-([4-([[(1S,2,3)-4,6-dichloro-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

$N^1,N^{14}$-Bis(2-[(S)-3-([4-([[(1S,2S)-4,6-dichloro-2-[(R)-3-methylpiperazin-1-yl]-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide;

1,1'-(Butane-1,4-diyl)bis(3-[2-(2-[6-([[(1S,2S)-6-chloro-4-cyano-2-(piperazin-1-yl)-2,3-dihydro-1H-inden-1-yl]oxy)-1-oxoisoindolin-2-yl]ethoxy)ethyl]urea); and 1,1'-(Butane-1,4-diyl)bis(3-[2-(2-[5-([[(1S,2S)-6-chloro-4-cyano-2-(piperazin-1-yl)-2,3-dihydro-1H-inden-1-yl]oxy)-1-oxoisoindolin-2-yl]ethoxy)ethyl]urea).

(1S,2S)-1-(4-{[(3S)-1-[2-(2-{[(4-{[(2-{2-[(3S)-3-(4-{[(1S,2S)-4-carboxy-6-chloro-2-   [(3R)-3-methylpiperazin-1-yl]-2,3-dihydro-1H-inden-1-yl]oxy}benzenesulfonamido)-1-hydroxy-1$\lambda^4$-pyrrolidin-1-yl]ethoxy}ethyl)carbamoyl]amino}butyl)carbamoyl]amino}ethoxy)ethyl]-1-hydroxy-1$\lambda^4$-pyrrolidin-3-yl]sulfamoyl}phenoxy)-6-chloro-2-[(3R)-3-methylpiperazin-1-yl]-2,3-dihydro-1H-indene-4-carboxylic acid;

3-(2-{2-[(3S)-3-(4-{[(1S,2S)-6-chloro-4-cyano-2-[(3R)-3-methylpiperazin-1-yl]-2,3-dihydro-1H-inden-1-yl]oxy}(2,3,5,6-$^2H_4$)benzenesulfonamido)pyrrolidin-1-yl]ethoxy}ethyl)-1-(4-{[2-{2-[(3S)-3-(4-{[(1S,2 S)-6-chloro-4-cyano-2-[(3R)-3-methylpiperazin-1-yl]-2,3-dihydro-1H-inden-1-yl]oxy}(2,3,5,6-$^2H_4$)benzenesulfonamido)pyrrolidin-1-yl]ethoxy}-ethyl)carbamoyl]amino}(1,1,2,2,3,3,4,4-$^2H_8$)butyl)urea;

3-(2-{2-[2-(4-{[(1S,2S)-4-cyano-6-methyl-2-[(3R)-3-methylpiperazin-1-yl]-2,3-dihydro-1H-inden-1-yl]oxy}benzenesulfonamido)ethoxy]ethoxy}ethyl)-1-(4-{[(2-{2-[2-(4-{[(1S,2S)-4-cyano-6-methyl-2-[(3R)-3-methylpiperazin-1-yl]-2,3-dihydro-1H-inden-1-yl]oxy}benzenesulfonamido)ethoxy]ethoxy}ethyl)carbamoyl]amino}butyl)urea;

3-(2-{2-[(3S)-3-(4-{[(1S,2S)-4,6-dichloro-2-[(3R)-3-methylpiperazin-1-yl]-2,3-dihydro-1H-inden-1-yl]oxy}benzenesulfonamido)pyrrolidin-1-yl]ethoxy}ethyl)-1-(4-{[(2-{2-[(3S)-3-(4-{[(1S,2S)-4,6-dichloro-2-[(3R)-3-methylpiperazin-1-yl]-2,3-dihydro-1H-inden-1-yl]oxy}benzenesulfonamido)pyrrolidin-1-yl]ethoxy}ethyl)carbamoyl]amino}butyl)urea;

N-{2-[(3S)-3-(4-{[(1S,2S)-4,6-dichloro-2-[(3R)-3-methylpiperazin-1-yl]-2,3-dihydro-1H-inden-1-yl]oxy}benzenesulfonamido)pyrrolidin-1-yl]-2-oxoethyl}-2-({[({2-[(3S)-3-(4-{[(1S,2S)-4,6-dichloro-2-[(3R)-3-methylpiperazin-1-yl]-2,3-dihydro-1H-inden-1-yl]oxy}benzenesulfonamido)pyrrolidin-1-yl]-2-oxoethyl}carbamoyl)methyl]carbamoyl}amino)butyl]carbamoyl}amino)acetamide;

3-(2-{2-[2-(4-{[(1S,2S)-6-chloro-4-cyano-2-(piperazin-1-yl)-2,3-dihydro-1H-inden-1-yl]oxy}benzenesulfonamido)ethoxy]ethoxy}ethyl)-1-[(1s,4s)-4-{[(2-{2-[2-(4-{[(1S,2S)-6-chloro-4-cyano-2-(piperazin-1-yl)-2,3-dihydro-1H-inden-1-yl]oxy}benzenesulfonamido)ethoxy]ethoxy}ethyl)carbamoyl]amino}cyclohexyl]urea;

1,3-bis(2-{2-[2(4-{[(1S,2S)-6-chloro-4-cyano-2-(piperazin-1-yl)-2,3-dihydro-1H-inden-1-yl]oxy}benzenesulfonamido)ethoxy]ethoxy}ethyl)urea;

4-([(1S,2S)-6-Chloro-4-cyano-2-(piperazin-1-yl)-2,3-dihydro-1H-inden-1-yl]oxy)-N-[19-([4-([(1S,2S)-6-chloro-4-cyano-2-(piperazin-1-yl)-2,3-dihydro-1H-inden-1-yl]oxy)phenyl]sulfonamido)-10-oxo-3,6,14,17-tetraoxa-9,11-diazanonadecyl]benzenesulfonamide;

3-(2-{2-[2-(4-{[(1S,2S)-6-chloro-4-cyano-2-(piperazin-1-yl)-2,3-dihydro-1H-inden-1-yl]oxy}benzenesulfonamido)ethoxy]ethoxy}ethyl)-1-[(1r,4r)-4-{[(2-{2-[2-(4-{[(1S,2S)-6-chloro-4-cyano-2-(piperazin-1-yl)-2,3-dihydro-1H-inden-1-yl]oxy}benzenesulfonamido)ethoxy]ethoxy}ethyl)carbamoyl]amino}cyclohexyl]urea;

3-(2-{2-[(3S)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]ethoxy}ethyl)-1-(4-{[(2-{2-[(3S)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]ethoxy}ethyl)carbamoyl]amino}(1,1,2,2,3,3,4,4-$^2$H$_8$)butyl)urea;

3-{4-[(3S)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]-4-oxobutyl}-1-{4-[({4-[(3S)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]-4-oxobutyl}carbamoyl)amino]butyl}urea;

3-{4-[4-(4-{[(1S,2S)-6-chloro-4-cyano-2-[(3R)-3-methylpiperazin-1-yl]-2,3-dihydro-1H-inden-1-yl]oxy}benzenesulfonamido)piperidin-1-yl]-4-oxobutyl}-1-{4-[({4-[4-(4-{[(1S,2S)-6-chloro-4-cyano-2-[(3R)-3-methylpiperazin-1-yl]-2,3-dihydro-1H-inden-1-yl]oxy}benzenesulfonamido)piperidin-1-yl]-4-oxobutyl}carbamoyl)amino]butyl}urea;

N-{2-[(3R)-3-(4-{[(1S,2S)-6-chloro-4-cyano-2-(piperazin-1-yl)-2,3-dihydro-1H-inden-1-yl]oxy}benzenesulfonamido)pyrrolidin-1-yl]-2-oxoethyl}-2-({[4-({[({2-[(3R)-3-(4-{[(1S,2S)-6-chloro-4-cyano-2-(piperazin-1-yl)-2,3-dihydro-1H-inden-1-yl]oxy}benzenesulfonamido)pyrrolidin-1-yl]-2-oxoethyl}carbamoyl)methyl]carbamoyl}amino)butyl]carbamoyl}amino)acetamide;

3-(2-{2-[4-(4-{[(1S,2S)-6-chloro-4-cyano-2-[(3R)-3-methylpiperazin-1-yl]-2,3-dihydro-1H-inden-1-yl]oxy}benzenesulfonamido)piperidin-1-yl]ethoxy}ethyl)-1-(4-{[(2-{2-[4-(4-{[(1S,2S)-6-chloro-4-cyano-2-[(3R)-3-methylpiperazin-1-yl]-2,3-dihydro-1H-inden-1-yl]oxy}benzenesulfonamido)piperidin-1-yl]ethoxy}ethyl)carbamoyl]amino}butyl)urea;

3-{2-[(3S)-3-(4-{[(1S,2S)-6-chloro-4-cyano-2-(piperazin-1-yl)-2,3-dihydro-1H-inden-1-yl]oxy}benzenesulfonamido)pyrrolidin-1-yl]-2-oxoethyl}-1-{4-[({2-[(3S)-3-(4-{[(1S,2S)-6-chloro-4-cyano-2-(piperazin-1-yl)-2,3-dihydro-1H-inden-1-yl]oxy}benzenesulfonamido)pyrrolidin-1-yl]-2-oxoethyl}carbamoyl)amino]butyl}urea; and (3S)—N-(4-{[(1S,2S)-6-chloro-4-cyano-2-(piperazin-1-yl)-2,3-dihydro-1H-inden-1-yl]oxy}benzenesulfonyl)-1-[2-(2-{[(4-{[(2-{2-[(3S)-3-[(4-{[(1S,2S)-6-chloro-4-cyano-2-(piperazin-1-yl)-2,3-dihydro-1H-inden-1-yl]oxy}benzenesulfonyl)carbamoyl]pyrrolidin-1-yl]ethoxy}ethyl)carbamoyl]amino}butyl)carbamoyl]amino}ethoxy)ethyl]pyrrolidine-3-carboxamide.

In other embodiments, W is $S(O)_2$, $C(O)$, or $—(CH_2)_m—$. In other embodiments. W is $S(O)_2$. In other embodiments, W is $C(O)$. In other embodiments, W is $—(CH_2)_2—$. In other embodiments, W is $—(CH_2)—$.

In some embodiments, Y is O, S, NH, $N(C_1-C_3alkyl)$, or $—C(O)NH—$. In some embodiments, Y is O. In some embodiments, Y is S. In some embodiments, Y is NH. In some embodiments, Y is $N(C_1-C_3alkyl)$. In some embodiments, Y is $—C(O)NH—$. In some embodiments, Y is O, S, NH, or $N(C_1-C_3alkyl)$. In some embodiments, Y is O, S, or NH. In some embodiments, Y is O or S.

In some embodiments, Q is a bond, NH, $—C(O)NH—$, $—NHC(O)NH—$, $—NHC(O)N(CH_3)—$, or $—NHC(O)NH—(CHR^{13})$. In some embodiments, Q is a bond, NH, $—C(O)NH—$, $—NHC(O)NH—$, or $—NHC(O)N(CH_3)—$. In some embodiments, Q is a bond, NH, $—C(O)NH—$, or $—NHC(O)NH—$. In some embodiments, Q is a bond, NH, or $—C(O)NH—$. In some embodiments, Q is a bond or NH. In some embodiments, Q is a bond. In some embodiments, Q is $—NHC(O)NH—$. In some embodiments, Q is $—C(O)NH—$. In some embodiments, Q is $—NHC(O)NH—$. In some embodiments, Q is $—NHC(O)N(CH_3)—$. In some embodiments, Q is $—NHC(O)NH—(CHR^{13})$.

In some embodiments, $R^1$ and $R^2$ are independently H, $C_1-C_6alkyl$, $C_2-C_6alkenyl$, $C_1-C_8cycloalkenyl$, $C_2-C_6alkynyl$, $C_3-C_8cycloalkyl$, heterocyclyl, aryl, or heteroaryl. In some embodiments, $R^1$ and $R^2$ are independently H, $C_1-C_6alkyl$, $C_2-C_6alkenyl$, $C_4-C_8cycloalkenyl$, $C_2-C_6alkynyl$, $C_3-C_8cycloalkyl$, heterocyclyl, or aryl. In some embodiments, $R^1$ and $R^2$ are independently H, $C_1-C_6alkyl$, $C_2-C_6alkenyl$, $C_4-C_8cycloalkenyl$, $C_2-C_6alkynyl$, $C_3-C_8cycloalkyl$, or heterocyclyl. In some embodiments, $R^1$ and $R^2$ are independently H, $C_1-C_6alkyl$, $C_2-C_6alkenyl$, $C_4-C_8cycloalkenyl$, $C_2-C_6alkynyl$, $C_3-C_8cycloalkyl$, heterocyclyl, aryl, or heteroaryl. In some embodiments, $R^1$ and $R^2$ are independently H, $C_1-C_6alkyl$, $C_2-C_6alkenyl$, $C_4-C_8cycloalkenyl$, $C_2-C_6alkynyl$, or $C_3-C_8cycloalkyl$. In some embodiments, $R^1$ and $R^2$ are independently H, $C_1-C_6alkyl$, $C_2-C_8alkenyl$, $C_4-C_8cycloalkenyl$, or $C_2-C_6alkynyl$. In some embodiments, $R^1$ and $R^2$ are independently H, $C_1-C_6alkyl$, $C_2-C_6alkenyl$, or $C_4-C_8cycloalkenyl$. In some embodiments, $R^1$ and $R^2$ are independently H, $C_1-C_6alkyl$, or $C_2-C_6alkenyl$. In some embodiments, $R^1$ and $R^2$ are independently H or $C_1-C_6alkyl$. In some embodiments, $R^1$ and $R^2$ are independently H, $C_1-C_6alkyl$, $C_2-C_6alkenyl$, $C_1-C_8cycloalkenyl$, $C_2-C_6alkynyl$, $C_3-C_8cycloalkyl$, heterocyclyl, aryl, or heteroaryl wherein each alkyl, alkenyl, cycloalkenyl, alkynyl, cycloalkyl, heterocyclyl, aryl, or heteroaryl is optionally substituted with one or more halogen, OH, CN, $—NO_2$, oxo, $—SR^9$, $—OR^9$, $—NHR^9$, $—NR^9R^{10}$, $—S(O)_2N(R^9)_2—$, $—S(O)_2R^9$, $—C(O)R^9$, $—C(O)OR^9$, $—C(O)NR^9R^{10}$, $—NR^9S(O)_2R^{10}$, $—S(O)R^9$, $—S(O)NR^9R^{10}$, $—NR^8S(O)$ $R^9$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl.

In another embodiment, $R^3$ is halogen, OH, CN, $C_1$-$C_6$alkyl, $C_1$-$C_6$alkoxy, $C_1$-$C_6$haloalkyl, $C_1$-$C_6$haloalkoxy, or —C(O)NR$^9$R$^{10}$. In one embodiment, $R^3$ is halogen, OH, CN, $C_1$-$C_6$alkyl, $C_1$-$C_6$alkoxy, $C_1$-$C_6$haloalkyl, or $C_1$-$C_6$haloalkoxy. In one embodiment, $R^3$ is halogen, OH, CN, $C_1$-$C_6$alkyl, $C_1$-$C_6$alkoxy, or $C_1$-$C_6$haloalkyl. In one embodiment, $R^3$ is halogen, OH, CN, $C_1$-$C_6$alkyl, or $C_1$-$C_6$alkoxy. In one embodiment, $R^3$ is halogen, OH, CN, or $C_1$-$C_6$alkyl. $R^3$ is halogen, OH, or CN. In one embodiment, $R^3$ is halogen or OH. In one embodiment, $R^3$ is halogen. $R^3$ is OH. In one embodiment, $R^3$ is CN. In one embodiment, $R^3$ is $C_1$-$C_6$alkyl. In one embodiment, $R^3$ is $C_1$-$C_6$alkoxy. In one embodiment, $R^3$ is $C_1$-$C_6$haloalkyl. In one embodiment, $R^3$ is $C_1$-$C_6$haloalkoxy. In one embodiment, $R^3$ is —C(O)NR$^9$R$^{10}$.

In another embodiment, $R^4$ is halogen, OH, CN, $C_1$-$C_6$alkyl, $C_1$-$C_6$alkoxy, $C_1$-$C_6$haloalkyl, $C_1$-$C_6$haloalkoxy, or —C(O)NR$^9$R$^{10}$. In one embodiment, $R^4$ is halogen, OH, CN, $C_1$-$C_6$alkyl, $C_1$-$C_6$alkoxy, $C_1$-$C_6$haloalkyl, or $C_1$-$C_6$haloalkoxy. In one embodiment, $R^4$ is halogen, OH, CN, $C_1$-$C_6$alkyl, $C_1$-$C_6$alkoxy, or $C_1$-$C_6$haloalkyl. In one embodiment, $R^4$ is halogen, OH, CN, $C_1$-$C_6$alkyl, or $C_1$-$C_6$alkoxy. In one embodiment, $R^4$ is halogen, OH, CN, or $C_1$-$C_6$alkyl. $R^3$ is halogen, OH, or CN. In one embodiment, $R^4$ is halogen or OH. In one embodiment, $R^4$ is halogen. $R^3$ is OH. In one embodiment, $R^4$ is CN. In one embodiment, $R^4$ is $C_1$-$C_6$alkyl. In one embodiment. $R^4$ is $C_1$-$C_6$alkoxy. In one embodiment, $R^4$ is $C_1$-$C_6$haloalkyl. In one embodiment, $R^4$ is $C_1$-$C_6$haloalkoxy. In one embodiment, $R^4$ is —C(O)NR$^9$R$^{10}$.

In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —S(O)$_2$N(R$^9$)$_2$—, —S(O)$_2$R$^9$, —C(O)R$^9$, —C(O)OR$^9$, —NR$^9$S(O)$_2$R$^{10}$, —S(O)R$^9$, —S(O)NR$^9$R$^{10}$, —NR$^8$S(O)R$^9$. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$R$^{10}$, —S(O)NR$^9$R$^{10}$. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$. In one embodiment, $R^{10}$, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_1$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_1$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl containing 1-5 heteroatoms selected from the group consisting of N, S, P and O. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, or aryl. In one embodiment, $R^5$, $R^6$, $R^7$, and $R^8$ are independently H, halogen, OH, CN, —NO$_2$, $C_1$-$C_6$alkyl $C_2$-$C_6$alkenyl, $C_4$-$C_8$cycloalkenyl, $C_2$-$C_6$alkynyl, $C_3$-$C_8$cycloalkyl, or heterocyclyl. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, or $C_3$-$C_8$cycloalkyl. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, or $C_2$-$C_6$alkynyl. In one embodiment, $R^5$, $R^6$, $R^7$, and $R^8$ are independently H, halogen, OH, CN, —NO$_2$, $C_1$-$C_6$alkyl, $C_2$-$C_6$alkenyl, or $C_4$-$C_8$cycloalkenyl. In one embodiment, $R^5$, $R^6$, $R^7$, and $R^8$ are independently H, halogen, OH, CN, —NO$_2$, $C_1$-$C_6$alkyl, or $C_2$-$C_6$alkenyl. In one embodiment, $R^5$, $R^6$, $R^7$, and $R^8$ are independently H, halogen, OH, CN, —NO$_2$, or $C_1$-$C_6$alkyl. In one embodiment, $R^5$, $R^6$, $R^7$, and $R^8$ are independently H, halogen, OH, CN, or —NO$_2$. In one embodiment, $R^5$, $R^6$, $R^7$, and $R^8$ are independently H, halogen, OH, or CN. In one embodiment, $R^5$, $R^6$, $R^7$, and $R^8$ are independently H, halogen, or OH. In one embodiment, $R^5$, $R^6$, $R^7$, and $R^8$ are independently H or halogen.

In one embodiment, $R^{15}$, $R^{16}$, $R^{17}$, and $R^{18}$ are independently, at each occurrence, H, OH, NH$_2$, or $C_1$-$C_3$ alkyl. In a further embodiment, $R^{15}$, $R^{16}$, $R^{17}$, and $R^{18}$ are independently, at each occurrence, H, OH, or NH$_2$. In a further embodiment, $R^{15}$, $R^{16}$, $R^{17}$, and $R^{18}$ are independently, at each occurrence, H or OH. In a further embodiment, $R^{16}$, $R^{17}$, and $R^{18}$ are independently, at each occurrence, H, OH, $NH_2$, or $C_1$-$C_3$ alkyl, wherein the alkyl is optionally substituted with one or more $R^{19}$.

In one embodiment, X is a bond, H, N, O, $CR^{11}R^{12}$, $CR^{11}$, C, —NHC(O)NH—, or $C_3$-$C_6$cycloalkyl. In one embodiment, X is a bond, H, N, O, $CR^{11}R^{12}$, $CR^{11}$, C, or —NHC(O)NH—. In one embodiment, X is a bond, H, N, O, $CR^{11}R^{12}$, $CR^{11}$, or C. In one embodiment, X is a bond, H, N, O, $CR^{11}R^{12}$, or $CR^{11}$. In one embodiment, X is a bond, H, N, O, or $CR^{11}R^{12}$. In one embodiment, X is a bond, H, N, or O. X is a bond, H, or N. In one embodiment, X is a bond or H. In one embodiment, X is a bond. In another embodiment X is H and n is 1. In another embodiment, X is N when n is 3. In another embodiment, X is O and n is 2. In another embodiment, X is $CR^{11}R^{12}$ and n is 2. In another embodiment, X is $CR^{11}$ and n is 3. In another embodiment, X is C and n is 4. In another embodiment, X is —NHC(O)NH—. In another embodiment, X is $C_3$-$C_6$cycloalkyl.

In some embodiments, $R^{14}$ is H, $C_1$-$C_6$alkyl, or $C_1$-$C_6$haloalkyl. In some embodiments, $R^{14}$ is H or $C_1$-$C_6$alkyl. In some embodiments, $R^{14}$ is H. In some embodiments, $R^{14}$ is $C_1$-$C_6$alkyl. In some embodiments, $R^{14}$ is $C_1$-$C_6$haloalkyl.

In yet other embodiments, $R^6$ and $R^{14}$ together with the atoms to which they are attached may combine to form, a 5- to-6 membered heterocyclyl. In other embodiments, $R^6$ and $R^{14}$ together with the atoms to which they are attached may combine to form, independently, at each occurrence, 5- to-6 membered heterocyclyl, wherein the heterocyclyl is optionally substituted with one or more $R^{19}$.

In other embodiments, $R^{13}$ and $R^{14}$ together with the atoms to which they are attached may combine to form independently, at each occurrence, $C_3$-$C_8$cycloalkyl, heterocyclyl, aryl, or heteroatyl. In other embodiments, $R^{13}$ and $R^{14}$ together with the atoms to which they are attached may combine to form independently, at each occurrence, $C_3$-$C_8$cycloalkyl, heterocyclyl, or aryl. In some embodiments, $R^{13}$ and $R^{14}$ together with the atoms to which they are attached may combine to form independently, at each occurrence, $C_3$-$C_8$cycloalkyl or heterocyclyl. In some embodiments, $R^{13}$ and $R^{14}$ together with the atoms to which they are attached may combine to form independently, at each occurrence, $C_3$-$C_8$cycloalkyl. In some embodiments, $R^{13}$ and $R^{14}$ together with the atoms to which they are attached may combine to form independently, at each occurrence, heterocyclyl. In some embodiments, $R^{13}$ and $R^{14}$ together with the atoms to which they are attached may combine to form independently, at each occurrence, aryl. In some embodiments, $R^{13}$ and $R^{14}$ together with the atoms to which they are attached may combine to form independently, at each occurrence, heteroaryl.

In other embodiments, $R^{13}$ and $R^{14}$ together with the atoms to which they are attached may combine to form independently, at each occurrence, $C_3$-$C_8$ cycloalkyl, heterocyclyl, aryl, or heteroaryl, wherein each heterocyclyl or heteroaryl is optionally substituted with one or more $R^{19}$. In other embodiments, $R^{13}$ and $R^{14}$ together with the atoms to which they are attached may combine to form independently, at each occurrence, $C_3$-$C_8$ cycloalkyl, heterocyclyl, or aryl, wherein each heterocyclyl is optionally substituted with one or more $R^{19}$. In some embodiments, $R^{13}$ and $R^{14}$ together with the atoms to which they are attached may combine to form independently, at each occurrence, $C_3$-$C_8$ cycloalkyl or heterocyclyl, wherein each heterocyclyl is optionally substituted with one or more $R^{19}$. In some embodiments, $R^{13}$ and $R^{14}$ together with the atoms to which they are attached may combine to form independently, at each occurrence, $C_3$-$C_8$ cycloalkyl. In some embodiments, $R^{13}$ and $R^{14}$ together with the atoms to which they are attached may combine to form independently, at each occurrence, heterocyclyl, wherein each heterocyclyl is optionally substituted with one or more $R^{19}$. In some embodiments, $R^{13}$ and $R^{14}$ together with the atoms to which they are attached may combine to form independently, at each occurrence, aryl. In some embodiments, $R^{13}$ and $R^{14}$ together with the atoms to which they are attached may combine to form independently, at each occurrence, heteroaryl, wherein each heteroaryl is optionally substituted with one or more $R^{19}$.

In some embodiments, u is 0, 1, or 2. In some embodiments, u is 0 or 1. In some embodiments, u is 0. In some embodiments, u is 1. In some embodiments, u is 2.

In some embodiments, n is 1, 2, 3, or 4. In some embodiments, n is 1, 2, or 3. In some embodiments, n is 1 or 2. In some embodiments, n is 1. In some embodiments, n is 2. In some embodiments, n is 3. In some embodiments, n is 4.

In some embodiments, s is 0, 1, 2, 3, or 4. In some embodiments, s is 0, 1, 2, or 3. In some embodiments, s is 0, 1, or 2. In some embodiments, s is 0 or 1. In some embodiments, s is 0. In some embodiments, s is 1. In some embodiments, s is 2. In some embodiments, s is 3. In some embodiments, s is 4.

In some embodiments, r is 0, 1, 2, 3, 4, 5, 7, or 8. In some embodiments, r is 0, 1, 2, 3, 4, 5, 6, or 7. In some embodiments, r is 0, 1, 2, 3, 4, 5, or 6. In some embodiments, r is 0, 1, 2, 3, 4, or 5. In some embodiments, r is 0, 1, 2, 3, or 4. In some embodiments, r is 0, 1, 2, or 3. In some embodiments, r is 0, 1, or 2. In some embodiments, r is 0 or 1. In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8.

In some embodiments, p is 0, 1, 2, 3, 4, 5, 6, 7, or 8. In some embodiments, p is 0, 1, 2, 3, 4, 5, 6, or 7. In some embodiments, p is 0, 1, 2, 3, 4, 5, or 6. In some embodiments, p is 0, 1, 2, 3, 4, or 5. In some embodiments, p is 0, 1, 2, 3, or 4. In some embodiments, p is 0, 1, 2, or 3. In some embodiments, p is 0, 1, or 2. In some embodiments, p is 0 or 1. In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8.

In designing and making the substantially impermeable or substantially systemically non-bioavailable NHE-inhibiting compounds of the present invention that may be utilized for the treatments detailed in the instant disclosure.

Another aspect, compounds of the present invention with extended hydrocarbon functionalities may collapse upon themselves in an intramolecular fashion, causing an increased enthalpic barrier for interaction with the desired biological target. Accordingly, when designing "X" and Linkers moieties, these are designed to be resistant to hydrophobic collapse. For example, conformational constraints such as rigid monocyclic, bicyclic or polycyclic rings can be installed in a "X" and Linker moiety to increase the rigidity of the structure. Unsaturated bonds, such as alkenes and alkynes, may also or alternatively be installed. Such modifications may ensure the NHE-inhibiting compound is accessible for productive binding with its target. Furthermore, the hydrophilicity of the Linkers may be improved by adding hydrogen bond donor or acceptor motifs, or ionic motifs such as amines that are protonated in the GI, or acids that are deprotonated. Such modifications will increase the hydrophilicity of the "X" and Linker moieties and help prevent hydrophobic collapse. Furthermore, such modifications will also contribute to the impermeability of the resulting compounds by increasing tPSA.

One skilled in the art may also consider a variety of functional groups that will allow the facile and specific attachment of the rest of the molecule of the compounds of Formula I to the "X" moiety and/or Linker. These functional groups can include electrophiles, which can react with nucleophilic groups, and/or nucleophiles, which can react with electrophilic "X" and Linker moieties. NHE-inhibiting compounds of Formula I may also be similarly derivatized with, for example, boronic acid groups. The NHE-inhibiting compounds of Formula I may also contain olefins via olefin metathesis chemistry, or alkynes or azides which can then react with appropriate other "X" and Linker via [2+3] cycloaddition.

It is to be noted that one skilled in the art can envision a number of "X" and Linker moieties that may be functionalized with an appropriate electrophile or nucleophile. Shown below are a series of such compounds selected based on several design considerations, including solubility, steric effects, and their ability to confer, or be consistent with, favorable structure-activity relationships. In this regard it is to be further noted, however, that the structures provided below, and above, are for illustration purposes only, and therefore should not be viewed in a limiting sense.

Exemplary electrophilic and nucleophilic Linker moieties include, but are not limited to, the Linker moieties illustrated in the Examples and the following:

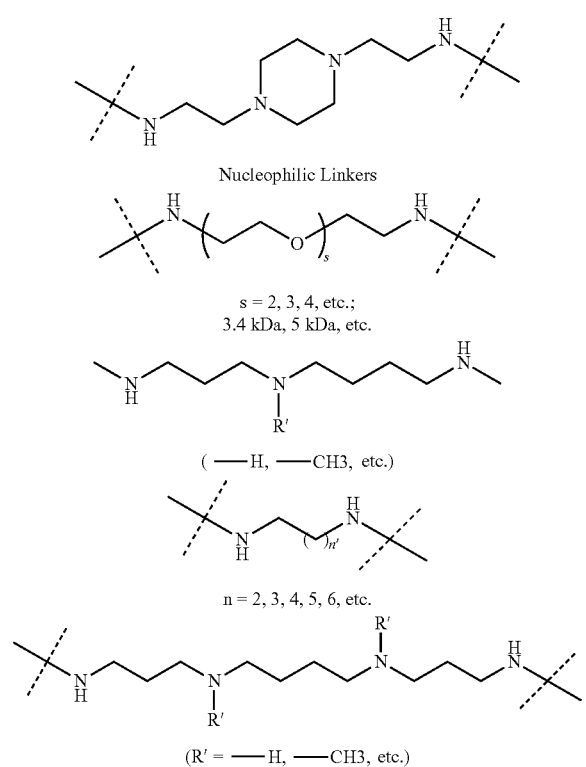

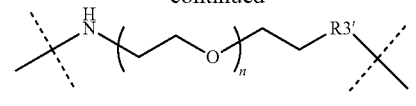

n = 2, 3, 4, etc.;
R3' = —CO—, —O—, —S—, —C═CH$_2$, —C≡C—, etc
3.4 kDA, 5 kDa, etc.

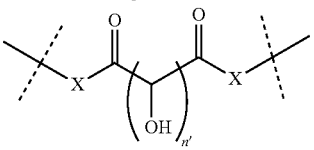

n' = 0, 1, 2, 3, 4, etc
X = —O—, —NH—, etc

Electrophilic Linkers

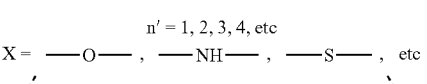

n' = 1, 2, 3, 4, etc
X = —O—, —NH—, —S—, etc

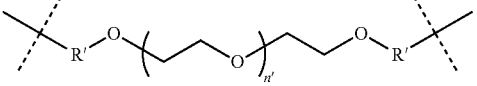

n' = 2, 3, 4, etc.;
3.4 kDa, 5 kDa, etc.
R' = tosyl, mesyl, etc

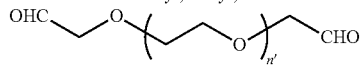

n' = 2, 3, 4, etc.;
3.4 kDa, 5 kDa, etc.

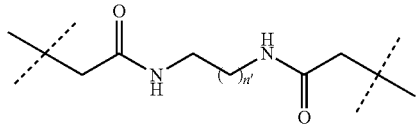

n' = 2, 3, 4, 5, 6, etc.

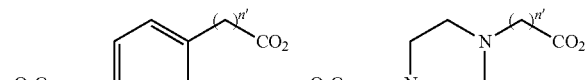

n' = 1, 2, 3, etc.      n' = 1, 2, 3, etc.

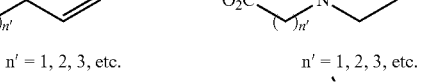

n' = 2, 3, 4, etc.;
3.4 kDa, 5 kDa, etc.

The linking moiety, Linker, in each of the described embodiments can also be a chemical bond or other moiety, for example that can be hydrophilic and/or hydrophobic. In one embodiment, the linking moiety can be a polymer moiety grafted onto a polymer backbone, for example, using living free radical polymerization approaches known in the art.

In another embodiment, "X" moieties illustrated in the compounds of Formula I may also include, but are not limited to, ether moieties, ester moieties, sulfide moieties, disulfide moieties, amine moieties, aryl moieties, alkoxyl moieties, etc., such as, for example, the following:

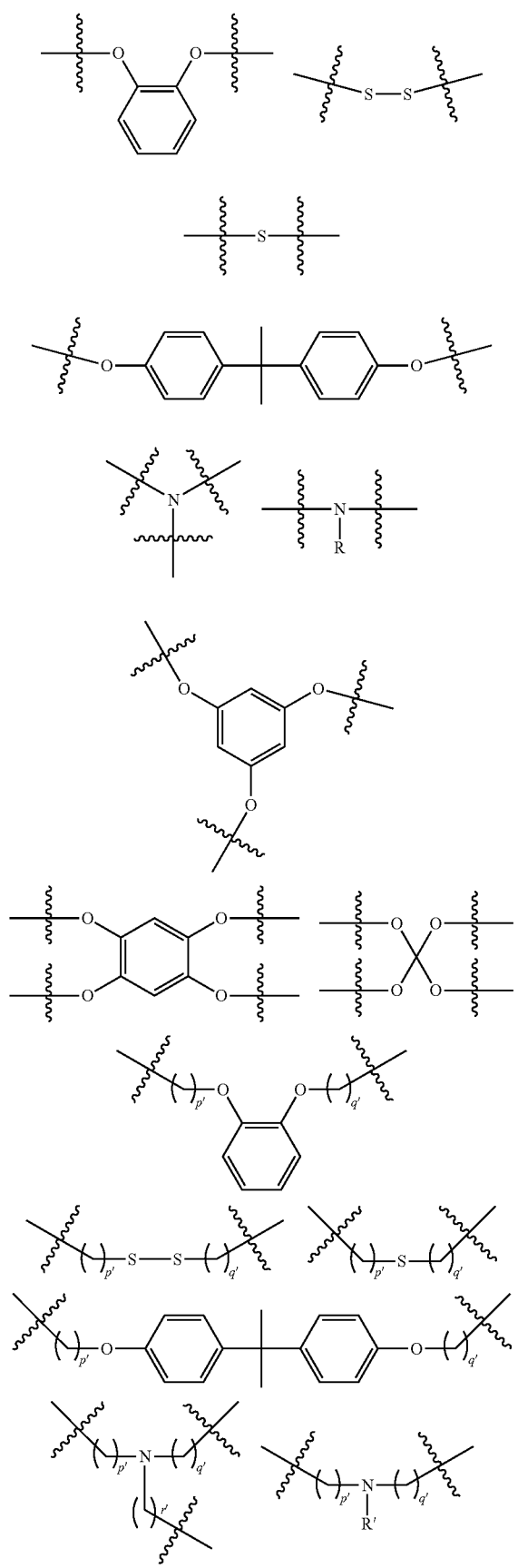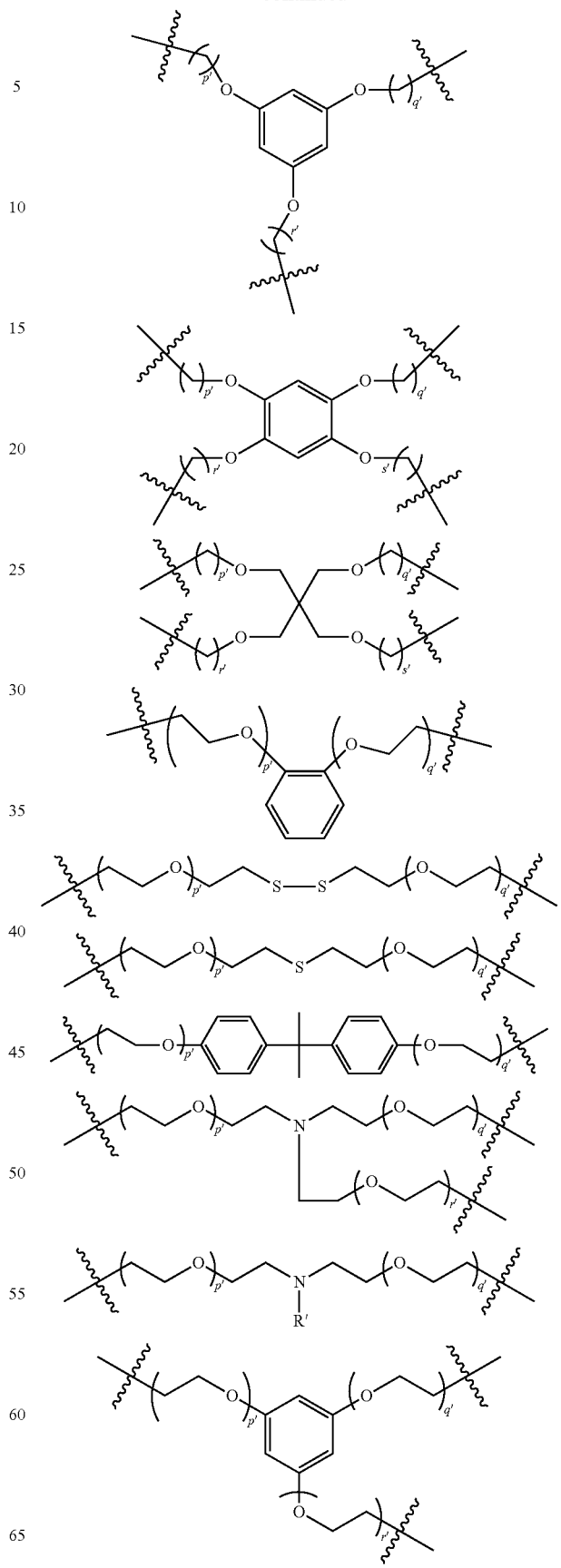

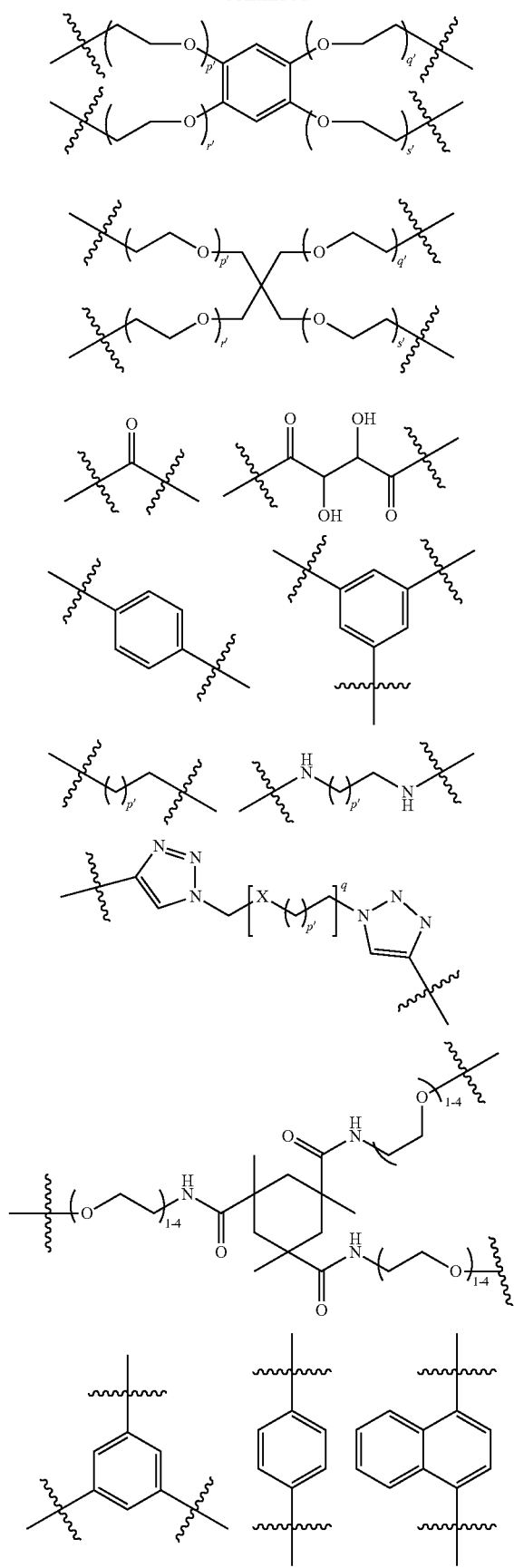
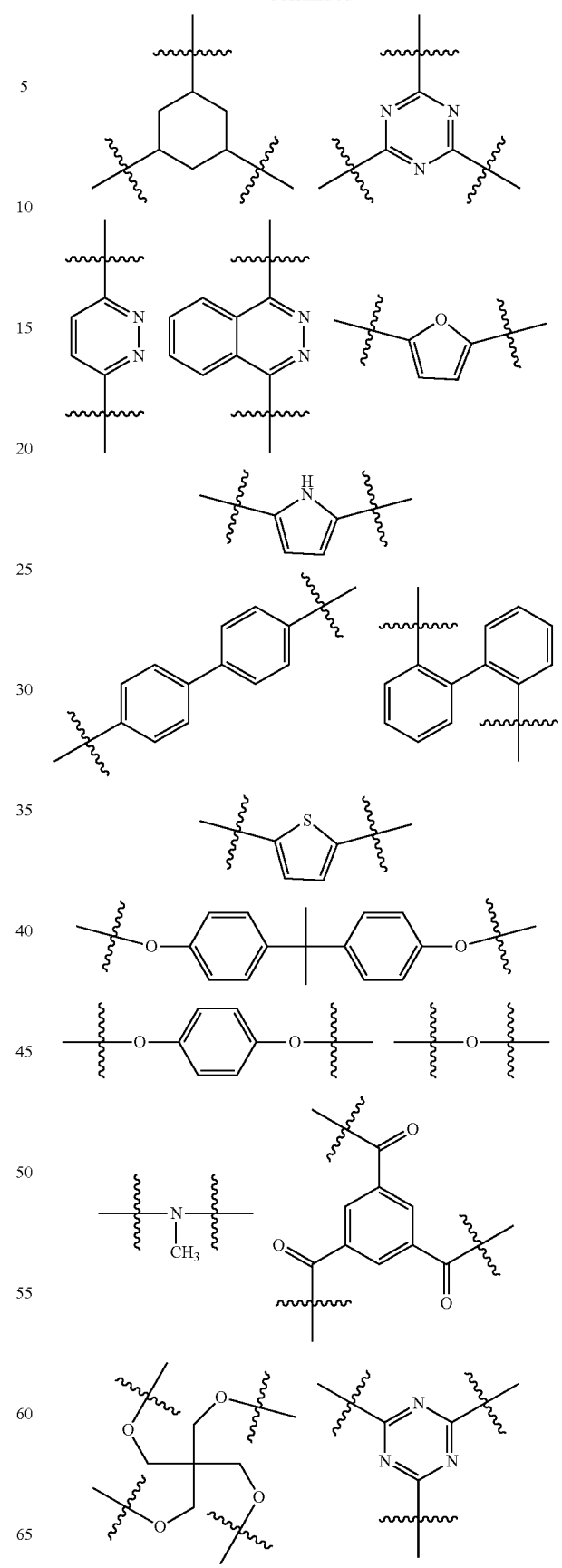

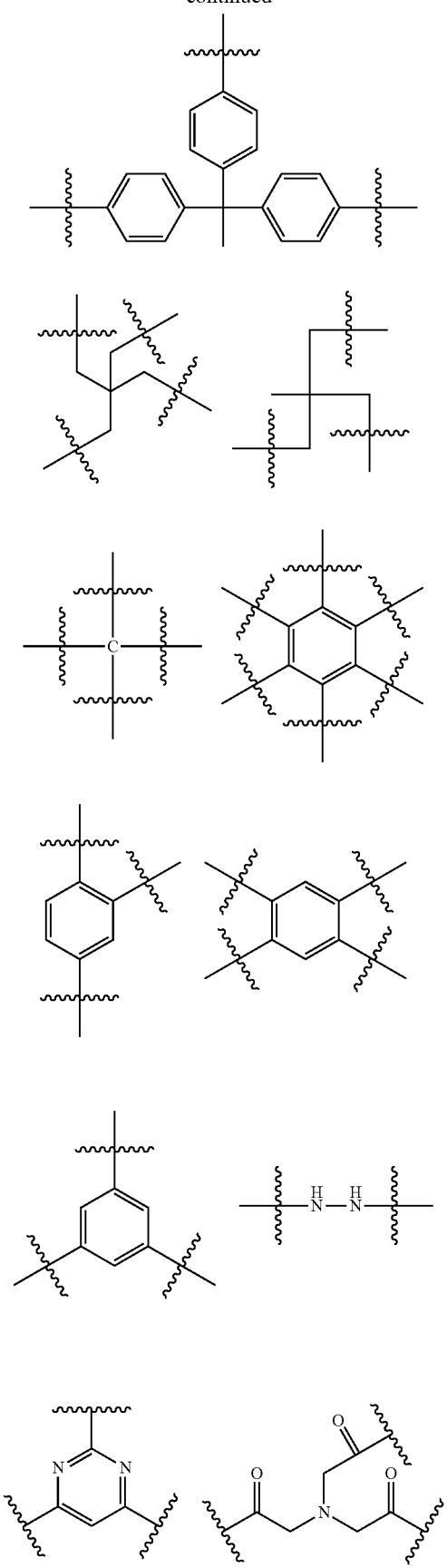

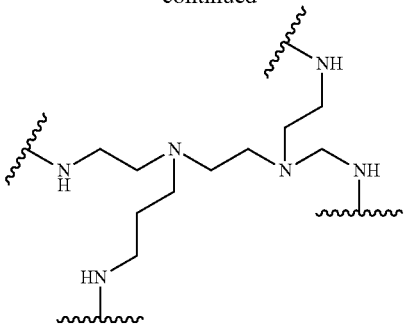

wherein the broken bonds (i.e., those having a wavy bond, ⸾, through them) are points of connection to the rest of the molecule of Formula I when n>1, where said points of connection can be made using chemistries and functional groups known to the art of medicinal chemistry; and further wherein each p', q', r' and s' is an independently selected integer ranging from about 0 to about 48, from about 0 to about 36, or from about 0 to about 24, or from about 0 to about 16. In some instances, each p, q, r and s can be an independently selected integer ranging from about 0 to 12. Additionally, R' can be a substituent moiety generally selected from halide, hydroxyl, amine, thiol, ether, carbonyl, carboxyl, ester, amide, carbocyclic, heterocyclic, and moieties comprising combinations thereof.

In another approach, the "X" moiety of formula I may be a dendrimer, defined as a repeatedly branched molecule (see, e.g., J. M. J. Fréchet, D. A. Tomalia, *Dendrimers and Other Dendritic Polymers*, John Wiley &, Sons, Ltd. NY, N.Y., 2001) and schematically represented below:

In another approach, the "X" moiety of formula I may be a dendrimer, defined as a repeatedly branched molecule (see, e.g., J. M. J. Fréchet, D. A. Tomalia, Dendrimers and Other Dendritic Polymers, John Wiley & Sons, Ltd. NY, NY, 2001).

In this approach, the rest of the NHE-inhibiting molecule is attached through Linker to one, several or optionally all termini located at the periphery of the dendrimer. In another approach, a dendrimer building block named dendron, and illustrated above, is used as "X" moiety, wherein the rest of NHE-inhibiting molecule is attached to one, several or optionally all termini located at the periphery of the dendron. The number of generations herein is typically between about 0 and about 6, and between about 0 and about 3. (Generation is defined in, for example. J. M. J. Fréchet, D. A. Tomalia, *Dendrimers and Other Dendritic Polymers*, John Wiley & Sons, Ltd. NY, N.Y.) Dendrimer and/or dendron structures are well known in the art and include, for example, those shown in or illustrated by: (i) J. M. J. Fréchet, D. A. Tomalia, *Dendrimers and Other Dendritic Polymers*, John Wiley & Sons, Ltd. NY, N.Y.; (ii) George R. Newkome, Charles N. Moorefield and Fritz Vogtle, *Dendrimers and Dendrons: Concepts, Syntheses, Applications*, VCH Verlagsgesellschaft Mbh; and, (iii) Boas, U., Christensen, J. B., Heegaard, P. M. H., *Dendrimers in Medicine and Biotechnology: New Molecular Tools*, Springer, 2006.

In yet another approach, the "X" moiety may be a polymer moiety or an oligomer moiety. The polymer or oligomer may, in each case, be independently considered and comprise repeat units consisting of a repeat moiety selected from alkyl (e.g., —$CH_2$—), substituted alkyl (e.g., —CHR—, wherein, for example, R is hydroxy), alkenyl, substituted alkenyl, alkynyl, substituted alkynyl, phenyl, aryl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, as well as moieties comprising combinations thereof. In still another approach, the "X" moiety comprises repeat units resulting from the polymerization of ethylenic monomers (e.g., such as those ethylenic monomers listed elsewhere herein below).

Preferred polymers for polymeric moieties useful in constructing substantially impermeable or substantially systemically non-bioavailable NHE-inhibiting compounds that are multivalent, for use in the treatment various treatment methods disclosed herein, can be prepared by any suitable technique, such as by free radical polymerization, condensation polymerization, addition polymerization, ring-opening polymerization, and/or can be derived from naturally occurring polymers, such as saccharide polymers. Further, in some embodiments, any of these polymer moieties may be functionalized.

Examples of polysaccharides useful in preparation of such compounds include but are not limited to materials from vegetable or animal origin, including cellulose materials, hemicellulose, alkyl cellulose, hydroxyalkyl cellulose, carboxymethylcellulose, sulfoethylcellulose, starch, xylan, amylopectins, chondroitin, hyarulonate, heparin, guar, xanthan, mannan, galactomannan, chitin, and/or chitosan. More preferred, in at least some instances, are polymer moieties that do not degrade, or that do not degrade significantly, under the physiological conditions of the GI tract (such as, for example, carboxymethylcellulose, chitosan, and sulfoethylcellulose).

When free radical polymerization is used, the polymer moiety can be prepared from various classes of monomers including, for example, acrylic, methacrylic, styrenic, vinylic, and dienic, whose typical examples are given thereafter: styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, and combinations thereof. Functionalized versions of these monomers may also be used and any of these monomers may be used with other monomers as comonomers. For example, specific monomers or comonomers that may be used in this disclosure include methyl methacrylate, ethyl methacrylate, propyl methacrylate (all isomers), butyl methacrylate (all isomers), 2-ethythexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylactylamide, N,N-dimethylacrylamide, N-tert-butylmethacrylamide, N—N-butylmethacrylamide, N-methylolmethacrylamide, N-ethylolmethacrylamide, N-tert-butylacrylamide, N—N-butylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamine α-methylstyrene (all isomers), p-vinylbenzene sulfonic acid, p-vinylbenzene sulfonic sodium salt, alkoxy and alkyl silane functional monomers, maleic anhydride, N-phenylmaleimide, N-butylmaleimide, butadiene, isoprene, chloroprene, ethylene, vinyl acetate, vinylformamide, allylamine, vinylpyridines (all isomers), fluorinated acrylate, methacrylates, and combinations thereof. Main chain heteroatom polymer moieties can also be used, including polyethyleneimine and polyethers such as polyethylene oxide and polypropylene oxide, as well as copolymers thereof.

In one particular embodiment, the polymer to which the NHE-inhibiting molecule is attached, or otherwise a part of, is a polyol (e.g., a polymer having a repeat unit of, for example, a hydroxyl-substituted alkyl, such as —CH(OH)—), Polyols, such as mono- and disaccharides, with or without reducing or reducible end groups thereon, may be good candidates, for example, for installing additional functionality that could render the compound substantially impermeable.

In one particular embodiment, the NHE-inhibiting molecule is attached at one or both ends of the polymer chain. More specifically, in yet another alternative approach to the polyvalent embodiment of the present disclosure, a. macromolecule (e.g., a. polymer or oligomer) having the generic following exemplary structures

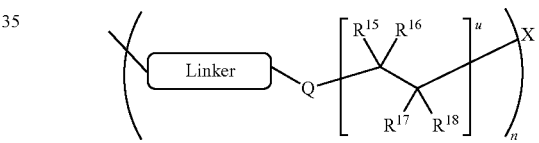

which may be exemplified, designed, and/or constructed as described for the moieties:

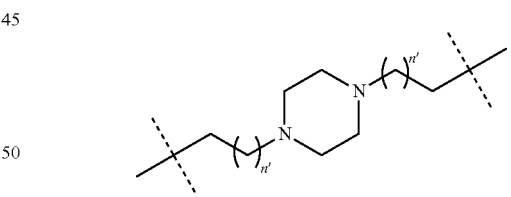

$n' = 1, 2, 3\text{-}10$, or more

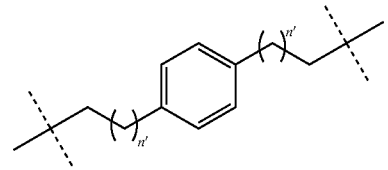

$n' = 0, 1, 2, 3\text{-}10$, or more

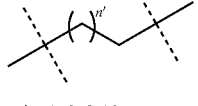

$n' = 1, 2, 3\text{-}10$, or more

-continued

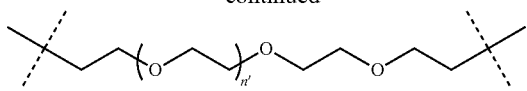

n' = 0, 1, 2, 3-10, or more

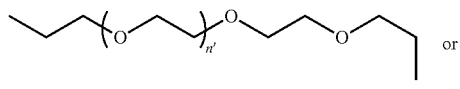

n' = 0, 1, 2, 3-10, or

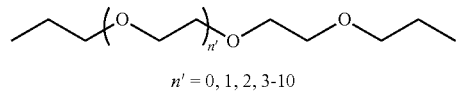

n' = 0, 1, 2, 3-10

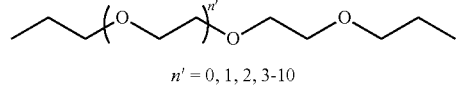

n' = 0, 1, 2, 3-10

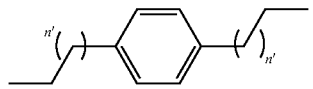

n' = 0, 1, 2, 3-10, or more

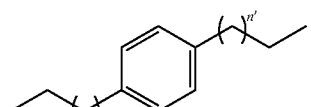

n' = 0, 1, 2, 3-10, or more

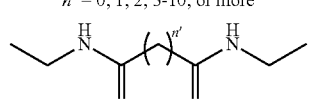

n' = 0, 1, 2, 3-10

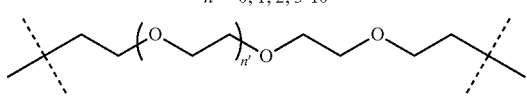

n' = 0, 1, 2, 3, 4-10

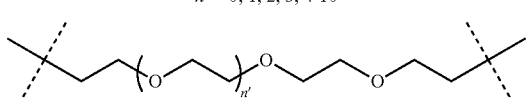

n' = 0, 1, 2, 3, 4-10

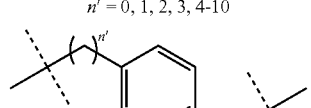

n' = 0, 1, 2, 3, 4-10

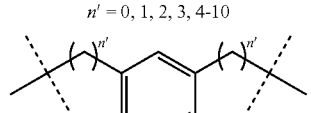

n' = 0, 1, 2, 3, 4-10

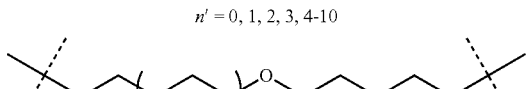

n' = 0, 1, 2, 3, 4-10

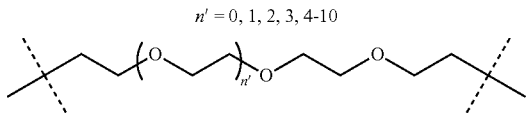

n' = 0, 1, 2, 3, 4-10

-continued

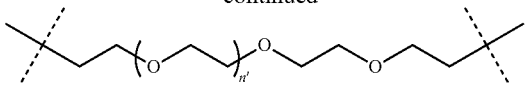

n' = 0, 1, 2, 3, 4-10

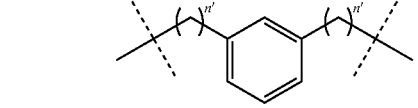

n' = 0, 1, 2, 3, 4-10

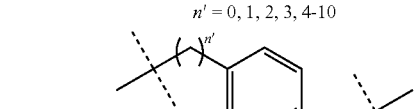

n' = 0, 1, 2, 3, 4-10

It is understood that any embodiment of the compounds of the present invention, as set forth above, and any specific substituent set forth herein in such compounds, as set forth above, may be independently combined with other embodiments and/or substituents of such compounds to form embodiments of the inventions not specifically set forth above. In addition, in the event that a list of substituents is listed for any particular substituent in a particular embodiment and/or claim, it is understood that each individual substituent may be deleted from the particular embodiment and/or claim and that the remaining list of substituents will be considered to be within the scope of the invention. Furthermore, it is understood that in the present description, combinations of substituents and/or variables of the depicted formulae are permissible only if such contributions result in stable compounds.

B. Permeability

In this regard it is to be noted that, in various embodiments, the ability of a compound to be substantially systemically non-bioavailable is based on the compound charge, size, and/or other physicochemical parameters (e.g., polar surface area, number of hydrogen bond donors and/or acceptors therein, number of freely rotatable bonds, etc.). More specifically, it is to be noted that the absorption character of a compound can be selected by applying principles of pharmacodynamics, for example, by applying Lipinski's rule, also known as "the rule of five." Although not a rule, but rather a set of guidelines, Lipinski shows that small molecule drugs with (i) a molecular weight, (ii) a number of hydrogen bond donors, (iii) a number of hydrogen bond acceptors, and/or (iv) a water/octanol partition coefficient (Moriguchi Log P), greater than a certain threshold value, generally do not show significant systemic concentration (i.e., are generally not absorbed to any significant degree). (See, e.g., Lipinski et al., *Advanced Drug Delivery Reviews*, 46, 2001 3-26, incorporated herein by reference.) Accordingly, substantially systemically non-bioavailable compounds (e.g., substantially systemically non-bioavailable compounds) can be designed to have molecular structures exceeding one or more of Lipinski's threshold values. (See also Lipinski et al., *Experimental and Computational Approaches to Estimate Solubility and Permeability in Drug Discovery and Development Settings*, Adv. Drug Delivery Reviews, 46:3-26 (2001); and Lipinski, *Drug-like Properties and the Causes of Poor Solubility and Poor Permeability*, J. Pharm. & Toxicol. Methods, 44:235-249 (2000), incorporated herein by reference.) In some embodiments, for example, a substantially impermeable or substantially systemically non-bioavailable NHE-inhibiting compound of the present disclosure can be constructed to feature one or more of the following characteristics: (i) a MW greater than about 500 Da, about 1000 Da, about 2500 Da, about 5000 Da, about 10,000 Da or more (in the non-salt form of the compound); (ii) a total number of NH and/or OH and/or other potential hydrogen bond donors greater than about 5, about 10, about 15 or more; (iii) a total number of O atoms and/or N atoms and/or other potential hydrogen bond acceptors greater than about 5, about 10, about 15 or more; and/or (iv) a Moriguchi partition coefficient greater than about $10^5$ (i.e., Log P greater than about 5, about 6, about 7, etc.), or alternatively less than about 10 (i.e., a Log P of less than 1, or even 0).

In addition to the parameters noted above, the molecular polar surface area (i.e., "PSA"), which may be characterized as the surface belonging to polar atoms, is a descriptor that has also been shown to correlate well with passive transport through membranes and, therefore, allows prediction of transport properties of drugs. It has been successfully applied for the prediction of intestinal absorption and Caco2 cell monolayer penetration. (For Caco2 cell monolayer penetration test details, see for example the description of the Caco2 Model provided in Example 31 of U.S. Pat. No. 6,737,423, the entire contents of which are incorporated herein by reference for all relevant and consistent purposes, and the text of Example 31 in particular, which may be applied for example to the evaluation or testing of the compounds of the present disclosure.) PSA is expressed in $Å^2$ (squared angstroms) and is computed from a three-dimensional molecular representation. A fast calculation method is now available (see, e.g., Ertl et al., *Journal of Medicinal Chemistry*, 2000, 43, 3714-3717, the entire contents of which are incorporated herein by reference for all relevant and consistent purposes) using a desktop computer and commercially available chemical graphic tools packages, such as ChemDraw. The term "topological PSA" (tPSA) has been coined for this fast-calculation method. tPSA is well correlated with human absorption data with common drugs (see, e.g., Table 1, below):

TABLE 1

| name | % FA[a] | TPSA[b] |
| --- | --- | --- |
| metoprolol | 102 | 50.7 |
| nordiazepam | 99 | 41.5 |
| diazepam | 97 | 32.7 |
| ozprenolol | 97 | 50.7 |
| phenazone | 97 | 26.9 |
| oxazepam | 97 | 61.7 |
| alprenolol | 96 | 41.9 |
| practolol | 95 | 70.6 |
| pindolol | 92 | 57.3 |
| ciprofloxacin | 69 | 74.6 |
| metolazone | 64 | 92.5 |
| tranexamic acid | 55 | 63.3 |
| atenolol | 54 | 84.6 |
| sulpiride | 36 | 101.7 |
| mannitol | 26 | 121.4 |
| foscarnet | 17 | 94.8 |
| sulfasalazine | 12 | 141.3 |
| olsalazine | 2.3 | 139.8 |
| lactulose | 0.6 | 197.4 |
| raffinose | 0.3 | 268.7 |

(from Ertl et al., *J. Med. Chem*, 2000, 43:3714-3717). Accordingly, in some preferred embodiments, the compounds of the present disclosure may be constructed to exhibit a tPSA value greater than about 100 $Å^2$, about 120 $Å^2$, about 130 $Å^2$, or about 140 $Å^2$, and in some instances about 150 $Å^2$, about 200 $Å^2$, about 250 $Å^2$, about 270 $Å^2$, about 300 $Å^2$, about 400 $Å^2$, or even about 500 $Å^2$, such that the compounds are substantially impermeable or substantially systemically non-bioavailable (as defined elsewhere herein).

Because there are exceptions to Lipinski's "rule," or the tPSA model, the permeability properties of the compounds of the present disclosure may be screened experimentally. The permeability coefficient can be determined by methods known to those of skill in the art, including for example by Caco-2 cell permeability assay and/or using an artificial membrane as a model of a gastrointestinal epithelial cell. (As previously noted above, see for example U.S. Pat. No. 6,737,423, Example 31 for a description of the Caco-2 Model, which is incorporated herein by reference). A synthetic membrane impregnated with, for example, lecithin and/or dodecane to mimic the net permeability characteristics of a gastrointestinal mucosa, may be utilized as a model of a gastrointestinal mucosa. The membrane can be used to separate a compartment containing the compound of the present disclosure from a compartment where the rate of permeation will be monitored. Also, parallel artificial membrane permeability assays (PAMPA) can be performed. Such in vitro measurements can reasonably indicate actual permeability in vivo. (See, for example, Wohnsland et al., *J. Med. Chem.* 2001, 44:923-930; Schmidt et al., Millipore Corp. Application Note, 2002, no AN1725EN00, and no AN1728EN00, incorporated herein by reference.)

Accordingly, in some embodiments, the compounds utilized in the methods of the present disclosure may have a permeability coefficient, $P_{app}$, of less than about $100 \times 10^{-6}$ cm/s, or less than about $10 \times 10^{-6}$ cm/s, or less than about $1 \times 10^{-6}$/s, or less than about $0.1 \times 10^{-6}$ cm/s, when measured using means known in the art (such as for example the permeability experiment described in Wohnsland et al., *J. Med. Chem,* 2001, 44, 923-930, the contents of which is incorporated herein by reference).

As previously noted, in accordance with the present disclosure, a NHE-inhibiting compound is modified as described above to hinder the net absorption through a layer of gut epithelial cells, rendering the resulting compound substantially systemically non-bioavailable, in various embodiments, the compounds of the present disclosure are substantially impermeable or substantially systemically non-bioavailable. More specifically, the NHE-inhibiting can be a dimer, multimer or polymer moiety, such that the resulting compound is substantially impermeable or substantially systemically non-bioavailable. The dimer, multimer or polymer may be of a molecular weight greater than about 500 Daltons (Da), about 1000 Da, about 2500 Da, about 5000 Da, about 10,000 Da or more, and in particular may have a molecular weight in the range of about 1000 Daltons (Da) to about 500,000 Da, or in the range of about 5000 to about 200,000 Da, and may have a molecular weight that is sufficiently high to essentially preclude any net absorption through a layer of gut epithelial cells of the compound.

C. Persistent Inhibitory Effect

In other embodiments, the substantially impermeable or substantially systemically non-bioavailable NHE-inhibiting compounds utilized in the treatment methods of the present disclosure may additionally exhibit a persistent inhibitor effect. This effect manifests itself when the inhibitory action of a compound at a certain concentration in equilibrium with the epithelial cell (e.g., at or above its inhibitory concentration, IC) does not revert to baseline (i.e., sodium transport without inhibitor) after the compound is depleted by simple washing of the luminal content.

This effect can be interpreted as a result of the tight binding of the NHE-inhibiting compounds to the NHE protein at the intestinal apical side of the gut epithelial cell. The binding can be considered as quasi-irreversible to the extent that, after the compound has been contacted with the gut epithelial cell and subsequently washed off said gut epithelial cell, the flux of sodium transport is still significantly lower than in the control without the compound. This persistent inhibitory effect has the clear advantage of maintaining drug activity within the GI tract even though the residence time of the active in the upper GI tract is short, and when no entero-biliary recycling process is effective to replenish the compound concentration near its site of action.

Such a persistent inhibitory effect has an obvious advantage in terms of patient compliance, but also in limiting drug exposure within the GI tract.

The persistence effect can be determined using in vitro methods; in one instance, cell lines expressing NHE transporters are split in different vials and treated with a NHE-inhibiting compound and sodium solution to measure the rate of sodium uptake. The cells in one set of vials are washed for different periods of time to remove the inhibitor, and sodium uptake measurement is repeated after the washing. Compounds that maintain their inhibitory effect after multiple/lengthy washing steps (compared to the inhibitory effect measured in the vials where washing does not occur) are persistent inhibitors. Persistence effect can also be characterized ex vivo by using the everted sac technique, whereby transport of Na is monitored using an excised segment of GI perfused with a solution containing the inhibitor and shortly after flushing the bathing solution with a buffer solution free from inhibitor. A persistence effect can also be characterized in vivo by observing the time needed for sodium balance to return to normal when the inhibitor treatment is discontinued. The limit of the method resides in the fact that apical cells (and therefore apical NHE transporters) are sloughed off after a period of 3 to 4 days, the typical turnover time of gut epithelial cells. A persistence effect can be achieved by increasing the residence time of the active compound at the apical surface of the gut epithelial cells; this can be obtained by designing NHE antiport inhibitors with several NHE-inhibiting molecule or oligomer (wherein "several" as used herein typically means at least about 2, about 4, about 6 or more). Examples of such structures in the context of analogs of the antibiotic vancomycin are given in Griffin, et al., *J. Am. Chem. Soc.,* 2003, 125, 6517-6531. Alternatively the compound comprises groups that contribute to increase the affinity towards the gut epithelial cell so as to increase the time of contact with the gut epithelial cell surface. Such groups are referred to as being "mucoadhesive." More specifically, the "X" and Linker moieties can be substituted by such mucoadhesive groups, such as polyacrylates, partially deacetylated chitosan or polyalkylene glycol. (See also Patil, S. B. et al., *Curr. Drug. Deliv.,* 2008, October 5(4), pp. 312-8.)

Compounds of the invention incorporating a cyano group at the 4-position of the indane ring system of formula I unexpectedly exhibited superior persistent inhibition of NHE3 in the cell-based assay described in example 181 herein in comparison to compounds incorporating other groups at said positions 4 and 6. For example, compounds incorporating 4-cyano and 6-chloro groups demonstrated superior persistent inhibition compared to the analogous compound having a 4,6-dichloro substituted indane ring system. See following table. The following pairs of compounds differ only in the 4-position substituent (either chloro (X—Cl) or cyano (X—CN)):

(A-Cl) 3-(2-{2-[(3S)-3-(4-{[(1S,2S)-4,6-dichloro-2-[(3R)-3-methylpiperazin-1-yl]-2,3-dihydro-1H-inden-1-yl]oxy}benzenesulfonamido)pyrrolidin-1-yl]ethoxy}ethyl)-1-(4-{[(2-{2-[(3S)-3-(4-{[(1S,2S)-4,6-dichloro-2-[(3R)-3-methylpiperazin-1-yl]-2,3-dihydro-1H-inden-1-yl]oxy}benzenesulfonamido)pyrrolidin-1-yl]ethoxy}ethyl)carbamoyl]amino}butyl)urea; and (A-CN) 3-(2-{2-[(3R)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]ethoxy}ethyl)-1-(4-{[(2-{2-[(3R)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]ethoxy}ethyl)carbamoyl]amino}butyl)urea.

(B-Cl) N-{2-[(3S)-3-(4-{[(1S,2S)-4,6-dichloro-2-[(3R)-3-methylpiperazin-1-yl]-2,3-dihydro-1H-inden-1-yl]oxy}benzenesulfonamido)pyrrolidin-1-yl]-2-oxoethyl}-2-({[4-({[({2-[(3S)-3-(4-{[(1S,2S)-4,6-dichloro-2-[(3R)-3-methylpiperazin-1-yl]-2,3-dihydro-1H-inden-1H-yl]oxy}benzenesulfonamido)pyrrolidin-1-yl]-2-oxoethyl}carbamoyl)methyl]carbamoyl}amino)butyl]carbamoyl}amino)acetamide; and (B-CN) N-{2-[(3S)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]-2-oxoethyl}-2-({[4-({[({2-[(3S)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]-2-oxoethyl}carbamoyl)methyl]carbamoyl}amino)butyl]carbamoyl}amino)acetamide.

(C-Cl) 3-(2-{2-[(3S)-3-(4-{[(1S,2S)-4,6-dichloro-2-(piperazin-1-yl)-2,3-dihydro-1H-inden-1-yl]oxy}-3-fluorobenzenesulfonamido)pyrrolidin-1-yl]ethoxy}ethyl)-1-(4-{[(2-{2-[(3S)-3-(4-{[(1S,2S)-4,6-dichloro-2-(piperazin-1-yl)-2,3-dihydro-1H-inden-1-yl]oxy}-3-fluorobenzenesulfonamido)pyrrolidin-1-yl]ethoxy}ethyl)carbamoyl]amino}butyl)urea; and (C-CN) 3-(2-{2-[2-(4-{[(1S,2S)-6-chloro-4-cyano-2-[(3R)-3-(dimethylamino)piperidin-1-yl]-2,3-dihydro-1H-inden-1-yl]oxy}benzenesulfonamido)ethoxy]ethoxy}ethyl)-1-(4-{[(2-{2-[2-(4-{[(1S,2S)-6-chloro-4-cyano-2-[(3R)-3-(dimethylamino)piperidin-1-yl]-2,3-dihydro-1H-inden-1-yl]oxy}benzenesulfonamido)ethoxy]ethoxy}ethyl)carbamoyl]amino}butyl)urea.

(C-Cl) 3-(2-{2-[(3S)-3-(4-{[(1S,2S)-4,6-dichloro-2-(piperazin-1-yl)-2,3-dihydro-1H-inden-1-yl]oxy}-3-fluorobenzenesulfonamido)pyrrolidin-1-yl]ethoxy}ethyl)-1-(4-{[(2-{2-[(3S)-3-(4-{[(1S,2S)-4,6-dichloro-2-(piperazin-1-yl)-2,3-dihydro-1H-inden-1-yl]oxy}-3-fluorobenzenesulfonamido)pyrrolidin-1-yl]ethoxy}ethyl)carbamoyl]amino}butyl)urea; and (C-CN) 3-(2-{2-[(3 S)-3-(4-{[(1S,2S)-6-chloro-4-cyano-2-(piperazin-1-yl)-2,3-dihydro-1H-inden-1-yl]oxy}-3-fluorobenzenesulfonamido)pyrrolidin-1-yl]ethoxy}ethyl)-1-(4-{[(2-{2-[(3S)-3-(4-{[(1S,2S)-6-chloro-4-cyano-2-(piperazin-1-yl)-2,3-dihydro-1H-inden-1-yl]oxy}-3-fluorobenzenesulfonamido)pyrrolidin-1-yl]ethoxy}ethyl)carbamoyl]amino}butyl)urea.

(D-Cl) 3-(2-{2-[2-(4-{[(1S,2S)-4,6-dichloro-2-(piperazin-1-yl)-2,3-dihydro-1H-inden-1-yl]oxy}-3-fluorobenzenesulfonamido)ethoxy]ethoxy}ethyl)-1-(4-{[(2-{2-[2-(4-{[(1S,2S)-4,6-dichloro-2-(piperazin-1-yl)-2,3-dihydro-1H-1-inden-1-yl]oxy}-3-fluorobenzenesulfonamido)ethoxy]ethoxy}ethyl)carbamoyl]amino}butyl)urea; and (D-CN) 3-(2-{2-[2-(4-{[(1S,2S)-6-chloro-4-cyano-2-(piperazin-1-yl)-2,3-dihydro-1H-inden-1-yl]oxy}-3-fluorobenzenesulfonamido)ethoxy]ethoxy}ethyl)-1-(4-{[(2-{2-

[2-(4-{[(1S,2S)-6-chloro-4-cyano-2-(piperazin-1-yl)-2,3-dihydro-1H-inden-1-yl]oxy}-3-fluorobenzenesulfonamido)ethoxy]ethoxy}ethyl)carbamoyl]amino}butyl)urea.

(E-Cl) 3-(2-{2-[2-(4-{[(1S,2S)-4,6-dichloro-2-[(3R)-3-(dimethylamino)piperidin-1-yl]-2,3-dihydro-1H-inden-1-yl]oxy}benzenesulfonamido)ethoxy]ethoxy}ethyl)-1-(4-{[(2-{2-[2-(4-{[(1S,2S)-4,6-dichloro-2-[(3R)-3-(dimethylamino)piperidin-1-yl]-2,3-dihydro-1H-inden-1-yl]oxy}benzenesulfonamido)ethoxy]ethoxy}ethyl)carbamoyl]amino}butyl)urea; and (E-CN) 3-(2-{2-[2-(4-{[(1S,2S)-6-chloro-4-cyano-2-[(3R)-3-(dimethylamino)piperidin-1-yl]-2,3-dihydro-1H-inden-1-yl]oxy}benzenesulfonamido)ethoxy]ethoxy}ethyl)-1-(4-{[(2-{2-[2-(4-{[(1S,2S)-6-chloro-4-cyano-2-[(3R)-3-(dimethylamino)piperidin-1-yl]-2,3-dihydro-1H-inden-1-yl]oxy}benzenesulfonamido)ethoxy]ethoxy}ethyl)carbamoyl]amino}butyl)urea.

(F-Cl) 3-(2-{2-[2-(4-{[(1S,2S)-4,6-dichloro-2-(piperazin-1-yl)-2,3-dihydro-1H-inden-1-yl]oxy}-3-methylbenzenesulfonamido)ethoxy]ethoxy}ethyl)-1-(4-{[(2-{2-[2-(4-{[(1S,2S)-4,6-dichloro-2-(piperazin-1-yl)-2,3-dihydro-1H-inden-1-yl]oxy}-3-methylbenzenesulfonamido)ethoxy]ethoxy}ethyl)carbamoyl]amino}butyl)urea; and (F-CN) 3-(2-{2-[2-(4-{[(1S,2S)-6-chloro-4-cyano-2-(piperazin-1-yl)-2,3-dihydro-1H-inden-1-yl]oxy}-3-methylbenzenesulfonamido)ethoxy]ethoxy}ethyl)-1-(4-{[(2-{2-[2-(4-{[(1S,2S)-6-chloro-4-cyano-2-(piperazin-1-yl)-2,3-dihydro-1H-inden-1-yl]oxy}-3-methylbenzenesulfonamido)ethoxy]ethoxy}ethyl)carbamoyl]amino}butyl)urea.

(G-Cl) 3-(2-{2-[2-(4-{[(1S,2S)-4,6-dichloro-2-(piperazin-1-yl)-2,3-dihydro-1H-inden-1-yl]oxy}benzenesulfonamido)ethoxy]ethoxy}ethyl)-1-(4-{[(2-{2-[2-(4-{[(1S,2S)-4,6-dichloro-2-(piperazin-1-yl)-2,3-dihydro-1H-inden-1-yl]oxy}benzenesulfonamido)ethoxy]ethoxy}ethyl)carbamoyl]amino}butyl)urea; and (G-CN) 3-(2-{2-[2-(4-{[(1S,2S)-6-chloro-4-cyano-2-(piperazin-1-yl)-2,3-dihydro-1H-inden-1-yl]oxy}benzenesulfonamido)ethoxy]ethoxy}ethyl)-1-(4-{[(2-{2-[2-(4-{[(1S,2S)-6-chloro-4-cyano-2-(piperazin-1-yl)-2,3-dihydro-1H-inden-1-yl]oxy}benzenesulfonamido)ethoxy]ethoxy}ethyl)carbamoyl]amino}butyl)urea.

| Compound | pIC50 (persistent) | Standard Deviation | n | Percent Inhibition |
|---|---|---|---|---|
| A-Cl | 8.6 | 0.2 | 3 | 101 |
| A-CN | 9.2 | 0.1 | 2 | 101 |
| B-Cl | 9.2 | 0 | 2 | 102 |
| B-CN | 9.9 | 0.1 | 6 | 110 |
| C-Cl | 8.4 | 0.1 | 2 | 90 |
| C-CN | 9.3 | 0.3 | 3 | 106 |
| D-Cl | 8.4 | 0.1 | 2 | — |
| D-CN | 9.3 | 0.1 | 2 | 74 |
| E-Cl | 8.3 | 0.3 | 5 | 99 |
| E-CN | 8.9 | 0.8 | 4 | 36 |
| F-Cl | 7.7 | 0.2 | 5 | 104 |
| F-CN | 8.6 | 0.1 | 2 | 88 |
| G-Cl | 8.2 | 0.1 | 2 | 82 |
| G-CN | 9.0 | 0.2 | 2 | — |

Accordingly, in an embodiment of the invention there is provided a compound having a structure according to any one of formula (I') and (Ia') through (Ii').

D. GI Enzyme Resistance

Because the compounds utilized in the treatment methods of the present disclosure are substantially systemically non-bioavailable, and/or exhibit a persistent inhibitory effect, it is also desirable that, during their prolonged residence time in the gut, these compounds sustain the hydrolytic conditions prevailing in the upper GI tract. In such embodiments, compounds of the present disclosure are resistant to enzymatic metabolism. For example, administered compounds are resistant to the activity of P450 enzymes, glucurosyl transferases, sulfotransferases, glutathione S-transferases, and the like, in the intestinal mucosa, as well as gastric (e.g., gastric lipase, and pepsine), pancreatic (e.g., trypsin, triglyceride pancreatic lipase, phospholipase A2, endonucleases, nucleotidases, and alpha-amylase), and brush-border enzymes (e.g., alkaline phosphatase, glycosidases, and proteases) generally known in the art.

The compounds that are utilized in methods of the present disclosure are also resistant to metabolism by the bacterial flora of the gut; that is, the compounds are not substrates for enzymes produced by bacterial flora. In addition, the compounds administered in accordance with the methods of the present disclosure may be substantially inactive towards the gastrointestinal flora, and do not disrupt bacterial growth or survival. As a result, in various embodiments herein, the minimal inhibitory concentration (or "MIC") against GI flora is desirably greater than about 15 µg/ml, about 30 µg/ml, about 60 µg/ml, about 120 µg/ml, or even about 240 µg/ml, the MIC in various embodiments being for example between about 16 and about 32 µg/ml, or between about 64 and about 128 µg/ml, or greater than about 256 µg/ml.

To one skilled in the art of medicinal chemistry, metabolic stability can be achieved in a number of ways. Functionality susceptible to P450-mediated oxidation can be protected by, for example, blocking the point of metabolism with a halogen or other functional group. Alternatively, electron withdrawing groups can be added to a conjugated system to generally provide protection to oxidation by reducing the electrophilicity of the compound. Proteolytic stability can be achieved by avoiding secondary amide bonds, or by incorporating changes in stereochemistry or other modifications that prevent the drug from otherwise being recognized as a substrate by the metabolizing enzyme.

E. Sodium and/or Fluid Output

It is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof, may act to increase the patient's daily fecal output of sodium by at least about 20, about 30 mmol, about 40 mmol, about 50 mmol, about 60 mmol, about 70 mmol, about 80 mmol, about 90 mmol, about 100 mmol, about 125 mmol, about 150 mmol or more, the increase being for example within the range of from about 20 to about 150 mmol/day, or from about 25 to about 100 mmol/day, or from about 30 to about 60 mmol/day Additionally, or alternatively, it is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patent in need thereof, may act to increase the patient's daily fluid output by at least about 100 ml, about 200 ml, about 300 ml, about 400 about 500 ml, about 600 ml, about 700 ml, about 800 ml, about 900 ml, about 1000 ml or more, the increase being for example within the range of from about 100 to about 1000 ml/day, or from about 150 to about 750 ml/day, or from about 200 to about 500 ml/day assuming isotonic fluid).

F. $C_{max}$ and $IC_{50}$

It is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof at a dose resulting in at least a 10% increase in fecal water content, has a $C_{max}$ that is less than the $IC_{50}$ for NHE-3, more specifically, less than about 10× (10 times) the $IC_{50}$, and, more specifically still, less than about 100× (100 times) the $IC_{50}$.

Additionally, or alternatively, it is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof, may have a $C_{max}$ of less than about 10 ng/ml, about 7.5 ng/ml, about 5 ng/ml, about 2.5 ng/ml, about 1 ng/ml, or about 0.5 ng/ml, the $C_{max}$ being for example within the range of about 1 ng/ml to about 10 ng/ml, or about 2.5 ng/ml to about 7.5 ng/ml.

Additionally, or alternatively, it is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof, may have a $IC_{50}$ of less than about 10 µM, about 7.5 µM, about 5 µM, about 2.5 µM, about 1 µM, or about 0.5 µM, the $IC_{50}$ being for example within the range of about 1 µM to about 10 µM, or about 2.5 µM to about 7.5 µM.

Additionally, or alternatively, it is also to be noted that, in various embodiments of the present disclosure, one or more of the NHE-inhibiting compounds detailed herein, when administered to a patient in need thereof, may have a ratio of $IC_{50}:C_{max}$, wherein $IC_{50}$ and $C_{max}$ are expressed in terms of the same units, of at least about 10, about 50, about 100, about 250, about 500, about 750, or about 1000.

Additionally, or alternatively, it is also to be noted that, in various embodiments of the present disclosure, wherein one or more of the NHE-inhibiting compounds as detailed herein is orally administered to a patent in need thereof, within the therapeutic range or concentration, the maximum compound concentration detected in the serum, defined as $C_{max}$, is lower than the NHE inhibitory concentration $IC_{50}$ of said compound. As previously noted, as used herein, $IC_{50}$ is defined as the quantitative measure indicating the concentration of the compound required to inhibit 50% of the NHE-mediated Na/H antiport activity in a cell based assay.

III. Pharmaceutical Compositions and Methods of Treatment

A. Compositions and Methods

1. Fluid Retention and/or Salt Overload Disorders

Another aspect of the invention is directed to method for inhibiting NHE-mediated antiport of sodium and hydrogen ions. The method comprises administering to a mammal in need thereof a pharmaceutically effective amount of a compound or pharmaceutical composition of Formula I. In one embodiment, the method comprises administering to a mammal in need thereof a pharmaceutically effective amount of a compound Ia, Ib, Ic, Id, Ie, If, Ig, Ih, or Ii or a combination thereof.

Another aspect of the invention is directed to method for treating a disorder associated with fluid retention or salt overload. The method comprises administering to a mammal in need thereof a pharmaceutically effective amount of a compound or pharmaceutical composition of Formula I. In one embodiment, the method of treating a disorder associated with fluid retention or salt overload comprises administering to a mammal in need thereof a pharmaceutically effective amount of a compound Ia, Ib, Ic, Id, Ie, If, Ig, Ih, or Ii or a combination thereof.

In one embodiment, a method for treating a disorder selected from the group consisting of heart failure (such as congestive heart failure), chronic kidney disease, end-stage renal disease, liver disease, and peroxisome proliferator-activated receptor (PPAR) gamma agonist-induced fluid retention is provided, the method comprising administering to a mammal in need thereof a pharmaceutically effective amount of a compound or pharmaceutical composition as set forth above. In another embodiment, the disorder is, but not limited to, a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, non-alcoholic fatty acid liver disease, Steatosis, primary sclerosing cholangitis, primacy biliary cholangitis, portal hypertension, autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, chronic alcoholism, and the like.

In another embodiment, a method for treating hypertension is provided, the method comprising administering to a mammal in need thereof a pharmaceutically effective amount of a compound or pharmaceutical composition as set forth above.

In further embodiments, the method comprises administering a pharmaceutically effective amount of the compound to the mammal in order to increase the mammal's daily fecal output of sodium and/or fluid. In further embodiments, the method comprises administering a pharmaceutically effective amount of the compound to the mammal in order to increase the mammal's daily fecal output of sodium by at least about 30 mmol, and/or fluid by at least about 200 ml. In further embodiments, the mammal's fecal output of sodium and/or fluid is increased without introducing another type of cation in a stoichiometric or near stoichiometric fashion via an ion exchange process. In further embodiments, the method further comprises administering to the mammal a fluid-absorbing polymer to absorb fecal fluid resulting from the use of the compound that is substantially active in the gastrointestinal tract to inhibit NHE-mediated antiport of sodium ions and hydrogen ions therein.

In further embodiments, the compound or composition is administered to treat hypertension. In further embodiments, the compound or composition is administered to treat hypertension associated with dietary salt intake. In further embodiments, administration of the compound or composition allows the mammal to intake a more palatable diet. In further embodiments, the compound or composition is administered to treat fluid overload. In further embodiments, the fluid overload is associated with congestive heart failure. In further embodiments, the fluid overload is associated with end stage renal disease. In further embodiments, the fluid overload is associated with peroxisome proliferator-activated receptor (PPAR) gamma agonist therapy. In further embodiments, the compound or composition is administered to treat sodium overload. In further embodiments, the compound or composition is administered to reduce interdialytic weight gain in ESRD patients. In further embodiments, the compound or composition is administered to treat edema. In further embodiments, the edema is caused by chemotherapy, pre-menstrual fluid overload or preeclampsia.

In further embodiments, the compound or composition is administered to treat gastric ulcers. In further embodiments, the compound or composition is administered to treat infectious diarrhea. In further embodiments, the compound or composition is administered to treat cancer (colorectal). In further embodiments, the compound or composition is administered to treat "leaky gut syndrome". In further embodiments, the compound or composition is administered to treat cystic fibrosis gastrointestinal disease. In further embodiments, the compound or composition is administered to treat multi-organ failure. In further embodiments, the compound or composition is administered to treat microscopic colitis. In further embodiments, the compound or composition is administered to treat necrotizing enterocolitis. In further embodiments, the compound or composition is administered to treat atopy. In further embodiments, the compound or composition is administered to treat food allergy. In further embodiments, the compound or composition is administered to treat respiratory infections. In further embodiments, the compound or composition is administered to treat acute inflammation (e.g., sepsis, systemic inflammatory response syndrome). In further embodiments, the compound or composition is administered to treat chronic inflammation (e.g., arthritis). In further embodiments, the compound or composition is administered to treat obesity-induced metabolic diseases (e.g., nonalcoholic steatohepatitis, Type I diabetes, Type II diabetes, cardiovascular disease). In further embodiments, the compound or composition is administered to treat kidney disease. In further embodiments, the compound or composition is administered to treat diabetic kidney disease. In further embodiments, the compound or composition is administered to treat cirrhosis. In further embodiments, the compound or composition is administered to treat steatohepatitis. In further embodiments, the compound or composition is administered to treat nonalcoholic fatty acid liver disease. In further embodiments, the compound or composition is administered to treat steatosis. In further embodiments, the compound or composition is administered to treat primary sclerosing cholangitis. In further embodiments, the compound or composition is administered to treat primary biliary cholangitis. In further embodiments, the compound or composition is administered to treat portal hypertension. In further embodiments, the compound or composition is administered to treat autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), or Raynaud's syndrome). In further embodiments, the compound or composition is administered to treat Schizophrenia. In further embodiments, the compound or composition is administered to treat autism spectrum disorders. In further embodiments, the compound or composition is administered to treat hepatic encephlopathy. In further embodiments, the compound or composition is administered to treat chronic alcoholism.

In further embodiments, the compound or composition is administered orally, by rectal suppository, or enema.

In further embodiments, the method comprises administering a pharmaceutically effective amount of the compound or composition in combination with one or more additional pharmaceutically active compounds or agents. In further embodiments, the one or more additional pharmaceutically active compounds or agents is selected from the group consisting of a diuretic, cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent, lipid-lowering agent, and peroxisome proliferator-activated receptor (PPAR) gamma agonist agent. In further embodiments, the diuretic is selected from the group consisting of a high ceiling loop diuretic, a benzothiadiazide diuretic, a potassium sparing diuretic, and an osmotic diuretic. In further embodiments, the pharmaceutically effective amount of the compound or composition, and the one or more additional pharmaceutically active compounds or agents, are administered as part of a single pharmaceutical preparation. In further embodiments, the pharmaceutically effective amount of the compound or composition, and the one or more additional pharmaceutically active compounds or agents, are administered as individual pharmaceutical preparations. In further embodiments, the individual pharmaceutical preparation is administered sequentially. In further embodiments, the individual pharmaceutical preparation is administered simultaneously.

In another embodiment, a method for treating a gastrointestinal tract disorder is provided, the method comprising administering to a mammal in need thereof a pharmaceutically effective amount of a compound or pharmaceutical composition as set forth above.

In further embodiments, the gastrointestinal tract disorder is a gastrointestinal motility disorder. In further embodiments, the gastrointestinal tract disorder is irritable bowel syndrome. In further embodiments, the gastrointestinal tract disorder is chronic constipation. In further embodiments, the gastrointestinal tract disorder is chronic idiopathic constipation. In further embodiments, the gastrointestinal tract disorder is chronic constipation occurring in cystic fibrosis patients. In further embodiments, the gastrointestinal tract disorder is opioid-induced constipation. In further embodiments, the gastrointestinal tract disorder is a functional gastrointestinal tract disorder. In further embodiments, the gastrointestinal tract disorder is selected from the group consisting of chronic intestinal pseudo-obstruction and colonic pseudo-obstruction. In further embodiments, the gastrointestinal tract disorder is Crohn's disease. In further embodiments, the gastrointestinal tract disorder is ulcerative colitis. In further embodiments, the gastrointestinal tract disorder is a disease referred to as inflammatory bowel disease. In further embodiments, the gastrointestinal tract disorder is associated with chronic kidney disease (stage 4 or 5). In further embodiments, the gastrointestinal tract disorder is constipation induced by calcium supplement. In further embodiments, the gastrointestinal tract disorder is constipation, and the constipation to be treated is associated with the use of a therapeutic agent. In further embodiments, the gastrointestinal tract disorder is constipation, and the constipation to be treated is associated with a neuropathic disorder. In further embodiments, the gastrointestinal tract disorder is constipation, and the constipation to be treated is post-surgical constipation (postoperative ileus). In further embodiments, the gastrointestinal tract disorder is constipation, and the constipation to be treated is idiopathic (functional constipation or slow transit constipation). In further embodiments, the gastrointestinal tract disorder is constipation, and the constipation to be treated is associated with neuropathic, metabolic or an endocrine disorder (e.g., diabetes mellitus, renal failure, hypothyroidism, hyperthyroidism, hypocalcaemia, Multiple Sclerosis, Parkinson's disease, spinal cord lesions, neurofibromatosis, autonomic neuropathy, Chagas disease, Hirschsprung's disease or cystic fibrosis, and the like). In further embodiments, the gastrointestinal tract disorder is constipation, and the constipation to be treated is due the use of drugs selected from analgesics e.g., opioids), antihypertensives, anticonvulsants, antidepressants, antispasmodics and antipsychotics.

In other embodiments, the gastrointestinal tract disorder is associated with gastric ulcers, infectious diarrhea, cancer (colorectal), "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (e.g., arthritis), obesity-induced metabolic diseases (e.g., nonalcoholic steatohepatitis, Type I diabetes, Type II diabetes, cardiovascular disease kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune (e,g., Type I diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), or Raynaud's syndrome), Schizophrenia, autism spectrum disorders, hepatic encephalopathy, small intestitinal bacterial overgrowth, or chronic alcoholism.

In another embodiment, a method for treating irritable bowel syndrome is provided, the method comprising administering to a mammal in need thereof a pharmaceutically effective amount of a compound or pharmaceutical composition as set forth above.

In further embodiments of the above embodiments, the compound or composition is administered to treat or reduce pain associated with a gastrointestinal tract disorder. In further embodiments, the compound or composition is administered to treat or reduce visceral hypersensitivity associated with a gastrointestinal tract disorder. In further embodiments, the compound or composition is administered to treat or reduce inflammation of the gastrointestinal tract. In further embodiments, the compound or composition is administered to reduce gastrointestinal transit time.

Compounds of the invention inhibit Transient Receptor Potential Cation channel subfamily C, member 6 (TRPC6). Accordingly, compounds of the invention are useful for treating diseases, disorders and conditions mediated with abherent TRPC6 activity, for example, cardiac hypertrophy kidney diseases, in particular, glomerular diseases.

In further embodiments, the compound or composition is administered either orally or by rectal suppository.

In further embodiments, the method comprises administering a pharmaceutically effective amount of the compound or composition, in combination with one or more additional pharmaceutically active compounds or agents. In further embodiments, the one or more additional pharmaceutically active agents or compounds are an analgesic peptide or agent. In further embodiments, the one or more additional pharmaceutically active agents or compounds are selected from the group consisting of a laxative agent selected from a bulk-producing agent (e.g. psyllium husk (Metamucil)), methylcellulose (Citrucel), polycarbophil, dietary fiber, apples, stool softeners/surfactant (e.g., docusate, Colace, Diocto), a hydrating or osmotic agent (e.g., dibasic sodium phosphate, magnesium citrate, magnesium hydroxide (Milk of magnesia), magnesium sulfate (which is Epsom salt), monobasic sodium phosphate, sodium biphosphate), and a hyperosmotic agent (e.g., glycerin suppositories, sorbitol, lactulose, and polyethylene glycol (PEG)). In further embodiments, the pharmaceutically effective amount of the compound or composition, and the one or more additional pharmaceutically active compounds or agents, are administered as part of a single pharmaceutical preparation. In further embodiments, the pharmaceutically effective amount of the compound or composition, and the one or more additional pharmaceutically active compounds or agents, are administered as individual pharmaceutical preparations. In further embodiments, the individual pharmaceutical preparation is administered sequentially. In further embodiments, the individual pharmaceutical preparation is administered simultaneously.

Another aspect of the invention is directed to pharmaceutical compositions comprising a compound of Formula I and a pharmaceutically acceptable carrier. In one embodiment, the pharmaceutical composition comprise a compound of Formula Ia, Ib, Ic, Id, Ie, If, Ig, Ih, or Ii and a pharmaceutically acceptable carrier. In another embodiment, the pharmaceutical composition described herein may be used to inhibit NHE-mediated antiport of sodium and hydrogen ions. In another embodiment, the pharmaceutical composition described herein may be used to treat disorders associated with fluid retention or salt overload A pharmaceutical composition or preparation that may be used in accordance with the present disclosure for the treatment of various disorders associated with fluid retention and/or salt overload in the gastrointestinal tract (e.g., hypertension, heart failure (in particular, congestive heart failure), chronic kidney disease, end-stage renal disease, liver disease and/or peroxisome proliferator-activated receptor (PPAR) gamma agonist-induced fluid retention) comprises, in general, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In some particular embodiments, the NHE-inhibiting compound, including any pharmaceutical composition comprising the compound, is administered with a fluid-absorbing polymer (as more fully described below).

Subjects "in need of treatment" with a compound of the present disclosure, or subjects "in need of NHE inhibition"

include subjects with diseases and/or conditions that can be treated with substantially impermeable or substantially systemically non-bioavailable NHE-inhibiting compounds, with or without a fluid-absorbing polymer, to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment may be suffering from hypertension; from salt-sensitive hypertension which may result from dietary salt intake; from a risk of a cardiovascular disorder (e.g., myocardial infarction, congestive heart failure and the like) resulting from hypertension; from heart, failure (e.g., congestive heart failure) resulting in fluid or salt overload; from chronic kidney disease resulting in fluid or salt overload, from end stage renal disease resulting in fluid or salt overload; from liver disease resulting in fluid or salt overload; from peroxisome proliferator-activated receptor (PPAR) gamma agonist-induced fluid retention; or from edema resulting from congestive heart failure or end stage renal disease. In various embodiments, a subject in need of treatment typically shows signs of hypervolemia resulting from salt and fluid retention that are common features of congestive heart failure, renal failure or liver alopeccia. Fluid retention and salt retention manifest themselves by the occurrence of shortness of breath, edema, ascites or interdialytic weight gain. Other examples of subjects that would benefit from the treatment are those suffering from congestive heart failure and hypertensive patients and, particularly, those who are resistant to treatment with diuretics, i.e., patients for whom very few therapeutic options are available. A subject "in need of treatment" also includes a subject with hypertension, salt-sensitive blood pressure and subjects with systolic/diastolic blood pressure greater than about 130-139/85-89 mm Hg.

Administration of NHE-inhibiting compounds, with or without administration of fluid-absorbing polymers, may be beneficial for patients put on "non-added salt" dietary regimen (i.e., 60-100 mmol of Na per day), to liberalize their diet while keeping a neutral or slightly negative sodium balance (i.e., the overall uptake of salt would be equal of less than the secreted salt). In that context, "liberalize their diet" means that patients treated may add salt to their meals to make the meals more palatable, or/and diversify their diet with salt-containing foods, thus maintaining a good nutritional status while improving their quality of life.

The treatment methods described herein may also help patients with edema associated with chemotherapy, premenstrual fluid overload and preeclampsia (pregnancy-induced hypertension).

Accordingly, it is to be noted that the present disclosure is further directed to methods of treatment involving the administration of the compound of the present disclosure, or a pharmaceutical composition comprising such a compound. Such methods may include, for example, a method for treating hypertension, the method comprising administering to the patient a substantially impermeable or substantially systemically non-bioavailable NHE-inhibiting compound, or a pharmaceutical composition comprising it. The method may be for reducing fluid overload associated with heart failure (in particular, congestive heart failure), the method comprising administering to the patient a substantially impermeable or substantially systemically non-bioavailable NHE-inhibiting compound or pharmaceutical composition comprising it. The method may be for reducing fluid overload associated with end stage renal disease, the method comprising administering to the patient a substantially impermeable or substantially systemically non-bioavailable NHE-inhibiting compound or composition comprising it. The method may be for reducing fluid overload associated with peroxisome proliferator-activated receptor (PPAR) gamma agonist therapy, the method comprising administering to the patient a substantially impermeable or substantially systemically non-bioavailable NHE-inhibiting compound or composition comprising it. Additionally, or alternatively, the method may be for decreasing the activity of an intestinal NHE transporter in a patient, the method comprising: administering to the patient a substantially impermeable or substantially systemically non-bioavailable NHE-inhibiting compound, or a composition comprising it.

In another embodiment, the disease to be treated, includes, but is not limited to, heart failure (such as congestive heart failure), chronic kidney disease, end-stage renal disease, liver disease, and peroxisome proliferator-activated receptor (PPAR) gamma agonist-induced fluid retention is provided, gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestitinal bacterial overgrowth, and chronic alcoholism, and the like.

2. Gastrointestinal Tract Disorders

Another aspect of the invention is directed to method for treating a disorder associated with gastrointestinal tract. The method comprises administering to a mammal in need thereof a pharmaceutically effective amount of a compound or pharmaceutical composition of Formula I. In one embodiment, the method of treating a disorder associated with gastrointestinal tract comprises administering to a mammal in need thereof a pharmaceutically effective amount of a compound Ia, Ib, Ic, Id, Ie, If, Ig, Ih, or Ii or a combination thereof.

A pharmaceutical composition or preparation that may be used in accordance with the present disclosure for the treatment of various gastrointestinal tract disorders, including the treatment or reduction of pain associated with gastrointestinal tract disorders, comprises, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In some particular embodiments, the NHE-inhibiting compound, including any pharmaceutical composition comprising the compound, is administered with a fluid-absorbing polymer (as more fully described below).

Subjects "in need of treatment" with a compound of the present disclosure, or subjects "in need of NHE inhibition" include subjects with diseases and/or conditions that can be treated with substantially impermeable or substantially systemically non-bioavailable NHE-inhibiting compounds, with or without a fluid-absorbing polymer, to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment is suffering from a gastrointestinal tract disorder, the patient is suffering from a disorder selected from the group consisting of: a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, atopy, food allergy, infections (respiratory), acute inflammation (e.g., sepsis, systemic inflammatory response syndrome), chronic inflammation (e.g., arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type I diabetes, ankylosing spondylitis, lupus, alopecia areata, rheumatoid arthritis, polymyalgia, rheumatica fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic enchlopathy, small intestitinal bacterial overgrowth, and chronic alcoholism, and the like.

In various preferred embodiments, the constipation to be treated is: associated with the use of a therapeutic agent; associated with a neuropathic disorder; post-surgical constipation (postoperative ileus); associated with a gastrointestinal tract disorder; idiopathic (functional constipation or slow transit constipation); associated with neuropathic, metabolic or endocrine disorder (e.g., diabetes mellitus, renal failure, hypothyroidism, hyperthyroidism, hypocalcaemia, Multiple Sclerosis, Parkinson's disease, spinal cord lesions, neurofibromatosis, autonomic neuropathy, Chagas disease, Hirschsprung's disease or cystic fibrosis, and the like). Constipation may also be the result of surgery (post-operative ileus) or due the use of drugs such as analgesics (e.g., opioids), antihypertensives, anticonvulsants, antidepressants, antispasmodics and antipsychotics.

In yet other embodiments, the constipation is associated with gastric ulcers, infectious diarrhea, cancer (colorectal), "leaky gut syndrome", cystic fibrosis gastrointestinal disease, multi-organ failure, microscopic colitis, necrotizing enterocolitis, atopy, food allergy, infections respiratory), acute inflammation (e.g., sepsis, systemic inflammatory response syndrome), chronic inflammation (e.g., arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type I diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestitinal bacterial overgrowth, and chronic alcoholism, and the like.

Accordingly, it is to be noted that the present disclosure is further directed to methods of treatment involving the administration of the compound of the present disclosure, or a pharmaceutical composition comprising such a compound. Such methods may include, for example, a method for increasing gastrointestinal motility in a patient, the method comprising administering to the patient a substantially non-permeable or substantially non-bioavailable NHE-inhibiting compound, or a pharmaceutical composition comprising it. Additionally, or alternatively, the method may be for decreasing the activity of an intestinal NHE transporter in a patient, the method comprising administering to the patient a substantially non-permeable or substantially non-bioavailable NHE-inhibiting compound, or a pharmaceutical composition comprising it. Additionally, or alternatively, the method may be for treating a gastrointestinal tract disorder, a gastrointestinal motility disorder, irritable bowel syndrome, chronic calcium-induced constipation in osteoporotic patients, chronic constipation occurring in cystic fibrosis patients, chronic constipation occurring in chronic kidney disease patients, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, colonic pseudo-obstruction, Crohn's disease, ulcerative colitis, inflammatory bowel disease, the method comprising administering an antagonist of the intestinal NHE, and more specifically, a substantially non-permeable or substantially non-bioavailable NHE-inhibiting compound, or a pharmaceutical composition comprising it, either orally or by rectal suppository. Additionally, or alternatively, the method may be for treating or reducing pain, including visceral pain, pain associated with a gastrointestinal tract disorder or pain associated with some other disorder, the method comprising administering to a patient a substantially non-permeable or substantially non-bioavailable NHE-inhibiting compound, or a pharmaceutical composition comprising it. Additionally, or alternatively, the method may be for treating inflammation, including inflammation of the gastrointestinal tract, e.g., inflammation associated with a gastrointestinal tract disorder or infection or some other disorder, the method comprising administering to a patient a substantially non-permeable or substantially non-bioavailable NHE-inhibiting compound, or a pharmaceutical composition comprising it.

3. Metabolic Disorders

A pharmaceutical composition or preparation that may be used in accordance with the present disclosure for the treatment of various metabolic disorders including the treatment or reduction of type II diabetes mellitus (T2DM), metabolic syndrome, and/or symptoms associated with such disorders comprises, in general, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In another embodiment, the pharmaceutical composition can be used to treat other metabolic diseases such as nonalcoholic steatohepatitis, diabetes Type I and II, and cardiovascular diseases.

Obesity is becoming a worldwide epidemic. In the United States, approximately ⅔rds of the population is either overweight (body mass index [BMI] 25 to 29.9) or obese (BMI≥30) (Ogden, C L et al, "Prevalence of overweight and obesity in the united states, 1999-2004" JAMA 2006, 295, 1549-1555). Obesity is a major risk factor for the development of diabetes and related complications, including cardiovascular disease and chronic kidney disease (CKD). The prevalence of T2DM has increased alarmingly in the United States. The American Diabetes Associated (ADA) estimates that more than 23 million U.S. adults aged 20 years or older have diabetes, with T2DM accounting for approximately 95% of these cases. The World Health Organization (WHO) has put the number of persons with diabetes worldwide at approximately 170 million (Campbell, R. K. "Type 2 diabetes: where we are today: an overview of disease burden, current treatments, and treatment strategies" Journal of the American Pharmacists Association 2009, 49(5), S3-S9).

Obesity is also a major risk factor for the development of metabolic syndrome, and subsequently the development of CKD. Metabolic syndrome, previously known as Syndrome X, the plurimetabolic syndrome, the dysmetabolic syndrome, and other names, consists of a clustering of metabolic abnormalities including abdominal obesity, hypertriglyceridemia, low levels of high-density lipoprotein (HDL) cholesterol, elevated blood pressure (BP), and elevations in fasting glucose or diabetes (Townsend, R. R. et al "Metabolic Syndrome, Components, and Cardiovascular Disease Prevalence in Chronic Kidney Disease: Findings from the Chronic Renal Insufficiency Cohort (CRIC) Study" American Journal of Nephrology 2011, 33, 477-484). Metabolic syndrome is common in patients with CKD and an important risk factor for the development and progression of CKD.

Hemodynamic factors appear to play a significant role in obesity-induced renal dysfunction. Hypertension, which is closely linked to obesity, appears to be a major cause of renal dysfunction in obese patients (Wahba, I. M. et al "Obesity and obesity-initiated metabolic syndrome: mechanistic links to chronic kidney disease" Clinical Journal of the American Society of Nephrology 2007, 2, 550-562). Studies in animals and in humans have shown that obesity is associated with elevated glomerular filtration rate (GFR) and increased renal blood flow. This likely occurs because of afferent arteriolar dilation as a result of proximal salt reabsorption, coupled with efferent renal arteriolar vasoconstriction as a result of elevated angiotensin II levels. These effects may contribute to hyperfiltration, glomerulomegaly, and later focal glomerulosclerosis. Even though GFR is increased in obesity, urinary sodium excretion in response to a saline load is often delayed, and individuals exhibit an abnormal pressure natriuresis, indicating avid proximal tubular sodium reabsorption. In addition, increased fat distribution can cause increased intra-abdominal pressure, leading to renal vein compression, thus raising renal venous pressure and diminishing renal perfusion. In creased fat, through a variety of mechanisms, can cause elevated renal interstitial fluid hydrostatic fluid and may stimulate renal sodium retention the thereby contribute to hypertension (Wahba_2007).

In view of the above, there exists a need in the art for agents that can divert sodium and fluid from a subject via mechanisms that either avoid the kidney, or do not depend upon normal kidney function. A subject with metabolic disease, including T2DM, metabolic syndrome, and the like, is a human, but can also be an animal in need of treatment with a compound of the disclosure, e.g., companion animals (e.g., dogs, cats, and the like), farm animals (e.g., cows, pigs, horses and the like) and laboratory animals (e.g., rats, mice, guinea pigs and the like).

The compounds utilized in the treatment methods of the present disclosure, as well as the pharmaceutical compositions comprising them, may accordingly be administered alone, or as part of a combination therapy or regimen that includes the administration or use of other therapeutic compounds related to the treatment of metabolic disorders such as T2DM and metabolic syndrome. In some particular embodiments, the NHE-inhibiting compound, including any pharmaceutical composition comprising the compound, is administered with a fluid absorbing polymer.

3. Urinary Protein Excretion

Figure 2:
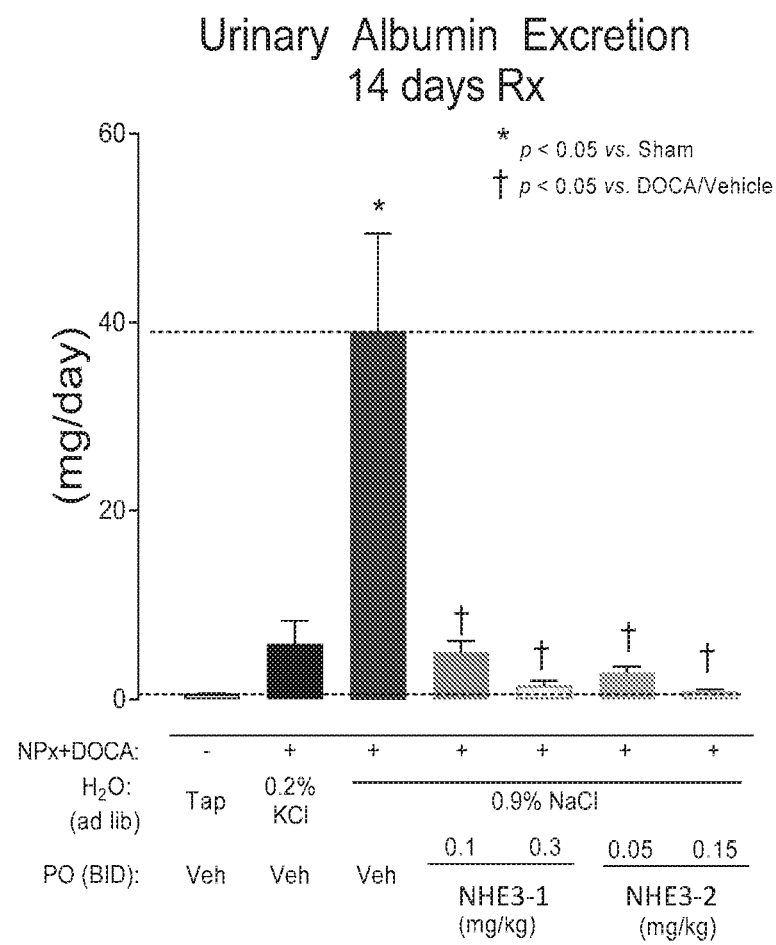
FIG. 2: Depicts dose-dependent reduction in urinary albumin excretion.

The compounds described herein have been shown to reduce urinary protein (e.g. albumin) excretion in a dose-dependent manner. FIG. 2 illustrates the effects of two NHE3 inhibitors, NHE3-1 and NHE3-2, a compound of the present disclosure, on urinary albumin excretion in rats. Accordingly, another aspect of the invention is directed to method for lowering urinary protein excretion in a mammal and disorders associated with elevated urinary protein excretion. The method comprises administering to a mammal in need thereof a pharmaceutically effective amount of a compound or pharmaceutical composition of Formula I. In one embodiment, the method of treating a disorder associated with elevated urinary protein excretion comprises administering to a mammal in need thereof a pharmaceutically effective amount of a compound Ia, Ib, Ic, Id, Ie, If, Ig, Ih, or Ii or a combination thereof. In one embodiment, the protein is albumin.

B. Combination Therapies

1. Fluid Retention and/or Salt Overload Disorders

As previously noted, the compounds described herein can be used alone or in combination with other agents. For example, the compounds can be administered together with a diuretic (i.e., High Cedilla Loop Diuretics, Benzothiadiazide Diuretics, Potassium Sparing Diuretics, Osmotic Diuretics), cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent, lipid-lowering agent, peroxisome proliferator-activated receptor (PPAR) gamma agonist agent or compound or with a fluid-absorbing polymer as more fully described below. The agent can be covalently attached to a compound described herein or it can be a separate agent that is administered together with or sequentially with a compound described herein in a combination therapy.

Combination therapy can be achieved by administering two or more agents, e.g., a substantially non-permeable or substantially systemically non-bioavailable NHE-inhibiting compound described herein and a diuretic, cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y Y-Y-X, X-X-Y-Y, etc.

The compounds described herein can be used in combination therapy with a diuretic. Among the useful diuretic agents are, for example: High Ceiling Loop Diuretics [Furosemide (Lasix), Ethacrynic Acid (Edecrin), Bumetanide (Bumex)], Benzothiadiazide Diuretics [Hydrochlorothiazide (Hydrodiuril), Chlorothiazide (Diuril), Clorthalidone (Hygroton), Benzthiazide (Aguapres), Bendroflumethiazide (Naturetin), Methyclothiazide (Aquatensen), Polythiazide (Renese), Indapamide (Lozol), Cyclothiazide (Anhydron), Hydroflumethiazide (Diucardin), Metolazone (Diulo), Quinethazone (Hydromox), Trichlormethiazide (Naqua)], Potassium Sparing Diuretics [Spironolactone (Aldactone), Triamterene (Dyrenium), Amiloride (Midamor)], and Osmotic Diuretics [Mannitol (Osmitrol)]. Diuretic agents in the various classes are known and described in the literature.

Cardiac glycosides (cardenolides) or other digitalis preparations can be administered with the compounds of the disclosure in co-therapy. Among the useful cardiac glycosides are, for example: Digitoxin (Crystodigin), Digoxin (Lanoxin) or Deslanoside (Cedilanid-D). Cardiac glycosides in the various classes are described in the literature.

Angiotensin Converting Enzyme Inhibitors (ACE inhibitors) can be administered with the compounds of the disclosure in co-therapy. Among the useful ACE inhibitors are, for example: Captopril (Capoten), Enalapril (Vasotec), Lisinopril (Prinivil). ACE inhibitors in the various classes are described in the literature.

Angiotensin-2 Receptor Antagonists (also referred to as $AT_1$-antagonists or angiotensin receptor blockers, or ARB's) can be administered with the compounds of the disclosure in co-therapy. Among the useful Angiotensin-2 Receptor Antagonists are, for example: Candesartan (Atacand), Eprosartan (Teveten), Irbesartan (Avapro), Losartan (Cozaar), Telmisartan (Micardis), Valsartan (Diovan). Angiotensin-2 Receptor Antagonists in the various classes are described in the literature.

Calcium channel blockers such as Amlodipine (Norvasc, Lotrel), Bepridil (Vascor), Diltiazem (Cardizem, Tiazac), Felodipine (Plendil), Nifedipine (Adalat, Procardia), Nimodipine (Nimotop), Nisoldipine (Sular), Verapamil (Calan, Isoptin, Verelan) and related compounds described in, for example, EP 625162B1, U.S. Pat. Nos. 5,364,842, 5,587,454, 5,824,645, 5,859,186, 5,994,305, 6,087,091, 6,136,786, WO 93/13128 A1, EP 1336409 A1, EP 835126 A1, EP 835126 B1, U.S. Pat. Nos. 5,795,864, 5,891,849, 6,054,429, WO 97/01351 A1, the entire contents of which are incorporated herein by reference for all relevant and consistent purposes, can be used with the compounds of the disclosure.

Beta blockers can be administered with the compounds of the disclosure in co-therapy. Among the useful beta blockers are, for example: Acebutolol (Sectral), Atenolol (Tenorinin), Betaxolol (Kerlone), Bisoprolol/hydrochlorothiazide (Ziac), Bisoprolol (Zebeta), Carteolol (Cartrol), Metoprolol (Lopressor, Toprol XL), Nadolol (Corgard), Propranolol (Inderal), Sotalol (Betapace), Timolol (Blocadren). Beta blockers in the various classes are described in the literature.

PPAR gamma agonists such as thiazolidinediones (also called glitazones) can be administered with the compounds of the disclosure in co-therapy. Among the useful PPAR agonists are, for example: rosiglitazone (Avandia), pioglitazone (Actos) and rivoglitazone.

Aldosterone antagonists can be administered with the compounds of the disclosure in co-therapy. Among the useful Aldosterone antagonists are, for example: eplerenone, spironolactone, and canrenone.

Renin inhibitor can be administered with the compounds of the disclosure in co-therapy. Among the useful Renin inhibitors is, for example: aliskiren.

Alpha blockers can be administered with the compounds of the disclosure in co-therapy. Among the useful Alpha blockers are, for example: Doxazosin mesylate (Cardura), Prazosin hydrochloride (Minipress). Prazosin and polythiazide (Minizide), Terazosin hydrochloride (Hytrin). Alpha blockers in the various classes are described in the literature.

Central alpha agonists can be administered with the compounds of the disclosure in co-therapy. Among the useful Central alpha agonists are, for example: Clonidine hydrochloride (Catapres), Clonidine hydrochloride and chlorthalidone (Clorpres, Combipres), Guanabenz Acetate (Wytensin), Guanfacine hydrochloride (Tenex), Methyldopa (Aldomet), Methyldopa and chlorothiazide (Aldochlor), Methyldopa and hydrochlorothiazide (Aldoril). Central alpha agonists in the various classes are described in the literature.

Vasodilators can be administered with the compounds of the disclosure in co-therapy. Among the useful vasodilators are, for example: Isosorbide dinitrate (Isordil), Nesiritide (Natrecor), Hydralazine (Apresoline), Nitrates/nitroglycerin, Minoxidil (Loniten). Vasodilators in the various classes are described in the literature.

Blood thinners can be administered with the compounds of the disclosure in co-therapy. Among the useful blood thinners are, for example: Warfarin (Coumadin) and Heparin. Blood thinners in the various classes are described in the literature.

Anti-platelet agents can be administered with the compounds of the disclosure in co-therapy. Among the useful anti-platelet agents are, for example: Cyclooxygenase inhibitors (Aspirin), Adenosine diphosphate (ADP) receptor inhibitors [Clopidogrel (Plavix), Ticlopidine (Ticlid)], Phosphodiesterase inhibitors [Cilostazol (Pletal)], Glycoprotein IIB/IIIA inhibitors [Abciximab (ReoPro), Eptifibatide (Integrilin). Tirofiban (Aggrastat), Defibrotide], Adenosine reuptake inhibitors [Dipyridamole (Persantine)]. Anti-platelet agents in the various classes are described in the literature.

Lipid-lowering agents can be administered with the compounds of the disclosure in co-therapy. Among the useful lipid-lowering agents are, for example: Statins (HMG CoA reductase inhibitors), [Atorvastatin (Lipitor), Fluvastatin (Lescol), Lovastatin (Mevacor, Altoprev), Pravastatin (Pravachol), Rosuvastatin Calcium (Crestar), Simvastatin (Zocor)], Selective cholesterol absorption inhibitors [ezetimibe (Zetia)], Resins (bile acid sequestrant or bile acid-binding drugs) [Cholestyramine (Questran, Questran Light, Prevalite, Locholest, Locholest Light), Colestipol (Colestid), Colesevelam Hcl (WelChol)], Fibrates (Fibric acid derivatives) [Gemfibrozil (Lopid), Fenofibrate (Antara, Lofibra, Tricor, and Triglide), Clofibrate (Atromid-S)], Niacin (Nicotinic acid). Lipid-lowering agents in the various classes are described in the literature.

The compounds of the disclosure can be used in combination with peptides or peptide analogs that activate the Guanylate Cyclase-receptor in the intestine and results in elevation of the intracellular second messenger, or cyclic guanosine monophosphate (cGMP), with increased chloride and bicarbonate secretion into the intestinal lumen and concomitant fluid secretion. Example of such peptides are Linaclotide (MD-1100 Acetate), endogenous hormones guanylin and uroguanylin and enteric bacterial peptides of the heat stable enterotoxin family (ST peptides) and those described in U.S. Pat. Nos. 5,140,102, 5,489,670, 5,969,097, WO 2006/001931A2, WO 2008/002971A2, WO 2008/106429A2, US 2008/0227685A1 and U.S. Pat. No. 7,041,786, the entire contents of which are incorporated herein by reference for all relevant and consistent purposes.

The compounds of the disclosure can be used in combination with type-2 chloride channel agonists, such as Amitiza (Lubiprostone) and other related compounds described in U.S. Pat. No. 6,414,016, the entire contents of which are incorporated herein by reference for all relevant and consistent purposes.

The compounds described herein can be used in combination therapy with agents used for the treatment of obesity, T2DM, metabolic syndrome and the like. Among the useful agents include: insulin; insulin secretagogues, such as sulphonylureas, glucose-lowering effectors, such as metformin; activators of the peroxisome proliferator-activated receptor γ (PPARγ), such as the thiazolidinediones; incretin-based agents including dipeptidyl peptidase-4 inhibitors such as sitagliptin, and synthetic incretin mimetics such as liraglutide and exenatide; alpha-glucosidase inhibitors, such as acarbose; glinides, such as repaglinide and nateglinide, and the like.

The compounds of the disclosure can be used in combination with P2Y2 receptor agonists, such as those described in EP 1196396B1 and U.S. Pat. No. 6,624,150, the entire contents of which are incorporated herein by reference for all relevant and consistent purposes.

Other agents include natriuretic peptides such as nesiritide, a recombinant form of brain-natriuretic peptide (BNP) and an atrial-natriuretic peptide (ANP). Vasopressin receptor antagonists such as tolvaptan and conivaptan may be co-administered as well as phosphate binders such as renagel, renleva, phoslo and fosrenol. Other agents include phosphate transport inhibitors (as described in U.S. Pat. Nos. 4,806,532; 6,355,823; 6,787,528; 7,119,120; 7,109,184; U.S. Pat, Pub. No. 2007/021509; 2006/0280719; 2006/0217426; International Pat. Pubs. WO 2001/005398, WO 2001/087294, WO 2001/082924, WO 2002/028353, WO 2003/048134, WO 2003/057225, WO2003/080630, WO 2004/085448, WO 2004/085382; European Pat. Nos. 1465638 and 1485391; and JP Patent No. 2007131532, or phosphate transport antagonists such as Nicotinamide.

2. Gastrointestinal Tract Disorders

As previously noted, the compounds described herein can be used alone or in combination with other agents. For example, the compounds can be administered together with an analgesic peptide or compound. The analgesic peptide or compound can be covalently attached to a compound described herein or it can be a separate agent that is administered together with or sequentially with a compound described herein in a combination therapy.

Combination therapy can be achieved by administering two or more agents, e.g., a substantially non-permeable or substantially non-bioavailable NHE-inhibiting compound described herein and an analgesic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The compounds described herein can be used in combination therapy with an analgesic agent, e.g., an analgesic compound or an analgesic peptide. The analgesic agent can optionally be covalently attached to a. compound described herein. Among the useful analgesic agents are, for example: Ca channel blockers, 5HT3 agonists (e.g., MCK-733), 5HT4 agonists (e.g., tegaserod, prucalopride), and 5HT1 receptor antagonists, opioid receptor agonists (loperamide, fedotozine, and fentanyl), NK1 receptor antagonists, CCK receptor agonists (e.g., loxiglumide), NK1 receptor antagonists, NK3 receptor antagonists, norepinephrine-serotonin reuptake inhibitors (NSR1), vanilloid and cannabanoid receptor agonists, and sialorphin. Analgesics agents in the various classes are described in the literature.

Opioid receptor antagonists and agonists can be administered with the compounds of the disclosure in co-therapy or linked to the compound of the disclosure, e.g., by a covalent bond. For example, opioid receptor antagonists such as naloxone, naltrexone, methyl nalozone, nalmefene, cypridime, beta funaltrexamine, naloxonazine, naltrindole, and nor-binaltorphimine are thought to be useful in the treatment of opioid-induced constipaption (OIC). It can be useful to formulate opioid antagonists of this type in a delayed or sustained release formulation, such that initial release of the antagonist is in the mid to distal small intestine and/or ascending colon. Such antagonists are described in U.S. Pat. No. 6,734,188 (WO 01/32180 A2), the entire contents of which are incorporated herein by reference for all relevant and consistent purposes. Enkephalin pentapeptide (HOE825; Tyr-D-Lys-Gly-Phe-L-homoserine) is an agonist of the µ- and γ-opioid receptors and is thought to be useful for increasing intestinal motility (Eur. J. Pharm. 219:445, 1992), and this peptide can be used in conjunction with the compounds of the disclosure. Also useful is trimebutine which is thought to bind to mu/delta/kappa opioid receptors and activate release of motilin and modulate the release of gastrin, vasoactive intestinal peptide, gastrin and glucagons. K-opioid receptor agonists such as fedotozine, ketocyclazocine, and compounds described in US 2005/0176746 (WO 03/097051 A2), the entire contents of which are incorporated herein by reference for all relevant and consistent purposes, can be used with or linked to the compounds of the disclosure. In addition, µ-opioid receptor agonists, such as morphine, diphenyloxylate, frakefamide (H-Tyr-D-Ala-Phe(F)-Phe-NH$_2$; disclosed in WO 01/019849 A1, the entire contents of which are incorporated herein by reference for all relevant and consistent purposes) and loperamide can be used.

Tyr-Arg (kyotorphin) is a dipeptide that acts by stimulating the release of met-enkephalins to elicit an analgesic effect (J. Biol. Chem. 262:8165, 1987). Kyotorphin can be used with or linked to the compounds of the disclosure. CCK receptor agonists such as caerulein from amphibians and other species are useful analgesic agents that can be used with or linked to the compounds of the disclosure.

Conotoxin peptides represent a large class of analgesic peptides that act at voltage gated Ca channels, NMDA receptors or nicotinic receptors. These peptides can be used with or linked to the compounds of the disclosure.

Peptide analogs of thymulin (U.S. Pat. No. 7,309,690 or FR 2830451, the entire contents of which are incorporated herein by reference for all relevant and consistent purposes) can have analgesic activity and can be used with or linked to the compounds of the disclosure.

CCK (CCKa or CCKb) receptor antagonists, including loxiglumide and dexloxiglumide (the R-isomer of loxiglumide) (U.S. Pat. No. 5,130,474 or WO 88/05774, the entire contents of which are incorporated herein by reference for all relevant and consistent purposes) can have analgesic activity and can be used with or linked to the compounds of the disclosure.

Other useful analgesic agents include 5-HT4 agonists such as tegaserod/zelnorm and lirexapride. Such agonists are described in: EP1321142 A1, WO 03/053432A1, EP 505322 A1, EP 505322 B1, EP 507672 A1, EP 507672 B1, U.S. Pat. Nos. 5,510,353 and 5,273,983, the entire contents of which are incorporated herein by reference for all relevant and consistent purposes.

Calcium channel blockers such as ziconotide and related compounds described in, for example, EP 625162B1, U.S. Pat. Nos. 5,364,842, 5,587,454, 5,824,645, 5,859,186, 5,994,305, 6,087,091, 6,136,786, WO 93/1312.8 A1, EP 1336409 A1, EP 835126 A1, EP 835126 B1, U.S. Pat. Nos. 5,795,864, 5,891,849, 6,054,429, WO 97/01351 A1, the entire contents of which are incorporated herein by reference for all relevant and consistent purposes, can be used with or linked to the compounds of the disclosure.

Various antagonists of the NK-1, NK-2, and NK-3 receptors (for a review see Giardina et al. 2003 Drugs 6:758) can be can be used with or linked to the compounds of the disclosure.

NK1 receptor antagonists such as: aprepitant (Merck & Co Inc), vofopitant, ezlopitant (Pfizer, Inc.), R-673 (Hoffmann-La Roche Ltd), SR-14033 and related compounds described in, for example, EP 873753 A1, U.S. 20010006972 A1, U.S. 20030109417 A1, WO 01/52844 A1, the entire contents of which are incorporated herein by reference for all relevant and consistent purposes, can be used with or linked to the compounds of the disclosure.

NK-2 receptor antagonists such as nepadutant (Menarini Ricerche SpA), saredutant (Sanofi-Synthelabo), SR-144190 (Sanofi-Synthelabo) and UK-290795 (Pfizer Inc) can be used with or linked to the compounds of the disclosure.

NK3 receptor antagonists such as osanetant (Sanofi-Synthelabo), talnetant and related compounds described in, for example, WO 02/094187 A2, EP 876347 A1, WO 97/21680 A1, U.S. Pat. No. 6,277,862, WO 98/11090, WO 95/28418, WO 97/19927, and Boden et al. (J Med. Chem. 39:1664-75, 1996) the entire contents of which are incorporated herein by reference for all relevant and consistent purposes, can be used with or linked to the compounds of the disclosure.

Norepinephrine-serotonin reuptake inhibitors such as milnacipran and related compounds described in WO 03/077897 A1, the entire contents of which are incorporated herein by reference for all relevant and consistent purposes, can be used with or linked to the compounds of the disclosure.

Vanilloid receptor antagonists such as arvanil and related compounds described in WO 01/64212 A1, the entire contents of which are incorporated herein by reference for all relevant and consistent purposes, can be used with or linked to the compounds of the disclosure.

The compounds can be used in combination therapy with a phosphodiesterase inhibitor (examples of such inhibitors can be found in U.S. Pat. No. 6,333,354, the entire contents of which are incorporated herein by reference for all relevant and consistent purposes).

The compounds can be used alone or in combination therapy to treat disorders associated with chloride or bicarbonate secretion that may lead to constipation. e.g., Cystic Fibrosis.

The compounds can also or alternatively be used alone or in combination therapy to treat calcium-induced constipation effects. Constipation is commonly found in the geriatric population, particularly patients with osteoporosis who have to take calcium supplements. Calcium supplements have shown to be beneficial in ostoporotic patients to restore bone density but compliance is poor because of constipation effects associated therewith.

The compounds of the current disclosure have can be used in combination with an opioid. Opioid use is mainly directed to pain relief, with a notable side-effect being GI disorder, e.g. constipation. These agents work by binding to opioid receptors, which are found principally in the central nervous system and the gastrointestinal tract. The receptors in these two organ systems mediate both the beneficial effects, and the undesirable side effects (e.g. decrease of gut motility and ensuing constipation). Opioids suitable for use typically belong to one of the following exemplary classes: natural opiates, alkaloids contained in the resin of the opium poppy including morphine, codeine and thebaine; semi-synthetic opiates, created from the natural opioids, such as hydromorphone, hydrocodone, oxycodone, oxymorphone, desomorphine, diacetylmorphine (Heroin), nicomorphine, dipropanoylmorphine, benzylmorphine and ethyl morphine; fully synthetic opioids, such as fentanyl, pethidine, methadone, tramadol and propoxyphene; endogenous opioid peptides, produced naturally in the body, such as endorphins, enkephalins, dynorphins, and endomorphins.

The compound of the disclosure can be used alone or in combination therapy to alleviate GI disorders encountered with patients with renal failure (stage 3-5). Constipation is the second most reported symptom in that category of patients (Murtagh et al., 2006; Murtagh et al., 2007a; Murtagh et al., 2007b). Without being held by theory, it is believed that kidney failure is accompanied by a stimulation of intestinal Na re-absorption (Hatch and Freel, 2008). A total or partial inhibition of such transport by administration of the compounds of the disclosure can have a therapeutic benefit to improve GI transit and relieve abdominal pain. In that context, the compounds of the disclosure can be used in combination with Angiotensin-modulating agents: Angiotensin Converting Enzyme (ACE) inhibitors (e.g. captopril, enalopril, lisinopril, ramipril) and Angiotensin II receptor antagonist therapy (also referred to as $AT_1$-antagonists or angiotensin receptor blockers, or ARB's); diuretics such as loop diuretics (e.g. furosemide, bumetanide), Thiazide diuretics (e.g. hydrochlorothiazide, chlorthalidone, chlorthiazide) and potassium-sparing diuretics: amiloride; beta blockers: bisoprolol, carvedilol, nebivolol and extended-release metoprolol; positive inotropes: Digoxin, dobutamine; phosphodiesterase inhibitors such as milrinone; alternative vasodilators: combination of isosorbide dinitrate/hydralazine; aldosterone receptor antagonists: spironolactone, eplerenone; natriuretic peptides: Nesiritide, a recombinant form of brain-natriuretic peptide (BNP), atrial-natriuretic peptide (ANP); vasopressin receptor antagonists: Tolvaptan and conivaptan; phosphate binder (Renagel, Renleva, Phoslo, Fosrenol); phosphate transport inhibitor such as those described in U.S. Pat. Nos. 4,806,532, 6,355,823, 6,787,528, WO 2001/005398, WO 2001/087294, WO 2001/082924, WO 2002/028353, WO 2003/048134, WO 2003/057225, U.S. Pat. No. 7,119,120, EP 1465638, US Appl. 2007/021509, WO 2003/080630, U.S. Pat. No. 7,109,184, US Appl. 2006/0280719, EP 1485391, WO 2004/085448, WO 2004/085382, US Appl. 2006/0217426, JP 2007/131532, the entire contents of which are incorporated herein by reference for all relevant and consistent purposes, or phosphate transport antagonist (Nicotinamide).

The compounds of the disclosure can be used in combination with peptides or peptide analogs that activate the Guanylate Cyclase-receptor in the intestine and results in elevation of the intracellular second messenger, or cyclic guanosine monophosphate (cGMP), with increased chloride and bicarbonate secretion into the intestinal lumen and concomitant fluid secretion. Example of such peptides are Linaclotide (MD-1100 Acetate), endogenous hormones guanylin and uroguanylin and enteric bacterial peptides of the heat stable enterotoxin family (ST peptides) and those described in U.S. Pat. Nos. 5,140,102, 5,489,670, 5,969,097, WO 2006/001931A2, WO 2008/002971A2, WO 2008/106429A2, US 2008/0227685A1 and U.S. Pat. No. 7,041,786, the entire contents of which are incorporated herein by reference for all relevant and consistent purposes.

The compounds of the disclosure can be used in combination with type-2 chloride channel agonists, such as Amitiza (Lubiprostone) and other related compounds described in U.S. Pat. No. 6,414,016, the entire contents of which are incorporated herein by reference for all relevant and consistent purposes.

The compounds of the disclosure can be used in combination with P2Y2 receptor agonists, such as those described in EP 1196396B1 and U.S. Pat. No. 6,624,150, the entire contents of which are incorporated herein by reference for all relevant and consistent purposes.

The compounds of the disclosure can be used in combination with laxative agents such as bulk-producing agents, e.g. psyllium husk (Metamucil), methylcellulose (Citrucel), polycarbophil, dietary fiber, apples, stool softeners/surfactant such as docusate (Colace, Diocto); hydrating agents (osmotics), such as dibasic sodium phosphate, magnesium citrate, magnesium hydroxide (Milk of magnesia), magnesium sulfate (which is Epsom salt), monobasic sodium phosphate, sodium biphosphate; hyperosmotic agents: glycerin suppositories, sorbitol, lactulose, and polyethylene glycol (PEG). The compounds of the disclosure can be also be used in combination with agents that stimulate gut peristalsis, such as Bisacodyl tablets (Dulcolax), Casanthranol, Senna and Aloin, from Aloe Vera.

In one embodiment, the compounds of the disclosure accelerate gastrointestinal transit, and more specifically in the colon, without substantially affecting the residence time in the stomach, i.e. with no significant effect on the gastric emptying time. Even more specifically the compounds of the invention restore colonic transit without the side-effects associated with delayed gastric emptying time, such as nausea. The GI and colonic transit are measured in patients using methods reported in, for example: Burton D D, Camilleri M, Mullan B P, et al., *J. Nucl. Med.,* 1997; 38:1807-1810; Cremonini F, Mullan B P, Camilleri M, et al., *Aliment. Pharmacol. Ther.,* 2002; 16:1781-1790; Camilleri M, Zinsmeister A R, *Gastroenterology,* 1992; 103:36-42; Bouras E P, Camilleri M, Burton D D, et al., *Gastroenterology,* 2001; 120:354-360; Coulie B, Szarka L A, Camilleri M. et al., *Gastroenterology,* 2000; 119:41-50; Prather C M, Camilleri M, Zinsmeister A R, et al., *Gastroenterology,* 2000; 118:463-468; and, Camilleri M, McKinzie S, Fox J, et al., *Clin. Gastroenterol. Hepatol.,* 2004; 2:895-904.

C. Polymer Combination Therapy

The NHE-inhibiting compounds described therein may be administered to patients in need thereof in combination with a fluid-absorbing polymer ("FAP"). The intestinal fluid-absorbing polymers useful for administration in accordance with embodiments of the present disclosure may be administered orally in combination with non-absorbable NHE-inhibiting compounds (e.g., a NHE-3 inhibitor) to absorb the intestinal fluid resulting from the action of the sodium transport inhibitors. Such polymers swell in the colon and bind fluid to impart a consistency to stools that is acceptable for patients. The fluid-absorbing polymers described herein may be selected from polymers with laxative properties, also referred to as bulking agents (i.e., polymers that retain some of the intestinal fluid in the stools and impart a higher degree of hydration in the stools and facilitate transit). The fluid-absorbing polymers may also be optionally selected from pharmaceutical polymers with anti-diarrhea function, i.e., agents that maintain some consistency to the stools to avoid watery stools and potential incontinence.

The ability of the polymer to maintain a certain consistency in stools with a high content of fluid can be characterized by its "water holding power." Wenzl et al. (in *Determinants of decreased fecal consistency in patients with diarrhea*; Gastroenterology, v. 108, no. 6, p. 1729-1738 (1995)) studied the determinants that control the consistency of stools of patients with diarrhea and found that they were narrowly correlated with the water holding power of the feces. The water holding power is determined as the water content of given stools to achieve a certain level of consistency (corresponding to "formed stool" consistency) after the reconstituted fecal matter has been centrifuged at a certain g number. Without being held to any particular theory, has been found that the water holding power of the feces is increased by ingestion of certain polymers with a given fluid absorbing profile. More specifically, it has been found that the water-holding power of said polymers is correlated with their fluid absorbancy under load (AUL); even more specifically the AUL of said polymers is greater than 15 g of isotonic fluid/g of polymer under a static pressure of 5 kPa, or under a static pressure of 10 kPa.

The FAP utilized in the treatment method of the present disclosure also has a AUL of at least about 10 g, about 15 g, about 20 g, about 25 g or more of isotonic fluid/g of polymer under a static pressure of about 5 kPa, or about 10 kPA, and may have a fluid absorbency of about 20 g, about 25 g or more, as determined using means generally known in the art. Additionally or alternatively, the FAP may impart a minimum consistency to fecal matter and, in some embodiments, a consistency graded as "soft" in the scale described in the test method below, when fecal non water-soluble solid fraction is from 10% to 20%, and the polymer concentration is from 1% to 5% of the weight of stool. The determination of the fecal non water-soluble solid fraction of stools is described in Wenz et al. The polymer may be uncharged or may have a low charge density (e.g., 1-2 meq/gr). Alternatively or in addition, the polymer may be delivered directly to the colon using known delivery methods to avoid premature swelling in the esophagus.

In one embodiment of the present disclosure, the FAP is a "superabsorbent" polymer (i.e., a lightly crosslinked, partially neutralized polyelectrolyte hydrogel similar to those used in baby diapers, feminine hygiene products, agriculture additives, etc.). Superabsorbent polymers may be made of a lightly crosslinked polyacrylate hydrogel. The swelling of the polymer is driven essentially by two effects: (i) the hydration of the polymer backbone and entropy of mixing and (ii) the osmotic pressure arising from the counter-ions (e.g., Na ions) within the gel. The gel swelling ratio at equilibrium is controlled by the elastic resistance inherent to the polymer network and by the chemical potential of the bathing fluid, i.e., the gel will de-swell at higher salt concentration because the background electrolyte will reduce the apparent charge density on the polymer and will reduce the difference of free ion concentrations inside and outside the gel that drives osmotic pressure. The swelling ratio SR (g of fluid per g of dry polymer and synonymously "fluid absorbency") may vary from 1000 in pure water down to 30 in 0.9% NaCl solution representative of physiological saline (i.e., isotonic). SR may increase with the degree of neutralization and may decrease with the crosslinking density. SR generally decreases with an applied load with the extent of reduction dependent on the strength of the gel, i.e., the crosslinking density. The salt concentration within the gel, as compared with the external solution, may be lower as a result of the Donnan effect due to the internal electrical potential.

The fluid-absorbing polymer may include crosslinked poly acrylates which are fluid absorbent such as those prepared from α,β-ethylenically unsaturated monomers, such as monocarboxylic acids, polycarboxylic acids, acrylamide and their derivatives. These polymers may have repeating units of acrylic acid, methacrylic acid, metal salts of acrylic acid, acrylamide, and acrylamide derivatives (such as 2-acrylamido-2-methylpropanesulfonic acid) along with various combinations of such repeating units as copolymers. Such derivatives include acrylic polymers which include hydrophilic grafts of polymers such as poly vinyl alcohol. Examples of suitable polymers and processes, including gel polymerization processes, for preparing such polymers are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; 4,190,562; 4,286,082; 4,857,610; 4,985,518; 5,145,906; 5,629,377 and 6,908,609 which are incorporated herein by reference for all relevant and consistent purposes (in addition, see Buchholz, F. L. and Graham, A. T., "Modern Superabsorbent Polymer Technology," John Wiley & Sons (1998), which is also incorporated herein by reference for all relevant and consistent purposes). A class of preferred polymers for treatment in combination with NHE-inhibitors is polyelectrolytes.

The degree of crosslinking can vary greatly depending upon the specific polymer material; however, in most applications the subject superabsorbent polymers are only lightly crosslinked, that is, the degree of crosslinking is such that the polymer can still absorb over 10 times its weight in physiological saline (i.e., 0.9% saline). For example, such polymers typically include less than about 0.2 mole % crosslinking agent.

In some embodiments, the FAP's utilized for treatment are Calcium Carbophil (Registry Number: 9003-97-8, also referred as Carbopol EX-83), and Carpopol 934P.

In some embodiments, the fluid-absorbing polymer is prepared by high internal phase emulsion ("HIPE") processes. The HIPE process leads to polymeric foam slabs with a very large porous fraction of interconnected large voids (about 100 microns) (i.e., open-cell structures). This technique produces flexible and collapsible foam materials with exceptional suction pressure and fluid absorbency (see U.S. Pat. Nos. 5,650,222; 5,763,499 and 6,107,356, which are incorporated herein for all relevant and consistent purposes). The polymer is hydrophobic and, therefore, the surface should be modified so as to be wetted by the aqueous fluid. This is accomplished by post-treating the foam material by a surfactant in order to reduce the interfacial tension. These materials are claimed to be less compliant to loads, i.e., less prone to de-swelling under static pressure.

In some embodiments, fluid-absorbing gels are prepared by aqueous free radical polymerization of acrylamide or a derivative thereof, a crosslinker methylene-bis-acrylamide) and a free radical initiator redox system in water. The material is obtained as a slab. Typically, the swelling radio of crosslinked polyacrylamide at low crosslinking density (e.g., 2%-4% expressed as weight % of methylene-bis-acrylamide) is between 25 and 40 (F. Horkay, *Macromolecules*, 22, pp. 2007-09 (1989)). The swelling properties of these polymers have been extensively studied and are essentially the same of those of crosslinked polyacrylic acids at high salt concentration. Under those conditions, the osmotic pressure is null due to the presence of counter-ions and the swelling is controlled by the free energy of mixing and the network elastic energy. Stated differently, a crosslinked polyacrylamide gel of same crosslink density as a neutralized polyacrylic acid will exhibit the same swelling ratio (i.e., fluid absorbing properties) and it is believed the same degree of deswelling under pressure, as the crosslinked polyelectrolyte at high salt content (e.g., 1 M). The properties (e.g., swelling) of neutral hydrogels will not be sensitive to the salt environment as long as the polymer remains in good solvent conditions. Without being held to any particular theory, it is believed that the fluid contained within the gel has the same salt composition than the surrounding fluid (i.e., there is no salt partitioning due to Donnan effect).

Another subclass of fluid-absorbing polymers that may be utilized is hydrogel materials that include N-alkyl acrylamide polymers (e.g., N-isopropylacrylamide (NIPAM). The corresponding aqueous polyNIPAM hydrogel shows a temperature transition at about 35° C. Above this temperature the hydrogel may collapse. The mechanism is generally reversible and the gel re-swells to its original swelling ratio when the temperature reverts to room temperature. This allows production of nanoparticles by emulsion polymerization (R. Pelton, *Advances in Colloid and Interface Science*, 85, pp. 1-33, (2000)). The swelling characteristics of poly-NIPAM nanoparticles below the transition temperature have been reported and are similar to those reported for bulk gel of polyNIPAM and equivalent to those found for polyacrylamide (i.e. 30-50 g/g) (W. McPhee, *Journal of Colloid and Interface Science*, 156, pp. 24-30 (1993); and, K. Oh, *Journal of Applied Polymer Science*, 69, pp. 109-114 (1997)).

In some embodiments, the FAP utilized for treatment in combination with a NHE-inhibitor is a superporous gel that may delay the emptying of the stomach for the treatment of obesity (J. Chen, *Journal of Controlled Release*, 65, pp. 73-82 (2000), or to deliver proteins. Poly acrylate-based SAP's with a macroporous structure may also be used. Macroporous SAP and superporous gels differ in that the porous structure remains almost intact in the dry state for superporous gels, but disappears upon drying for macroporous SAP's. The method of preparation is different although both methods use a foaming agent (e.g., carbonate salt that generates $CO_2$ bubbles during polymerization). Typical swelling ratios, SR, of superporous materials are around 10. Superporous gels keep a large internal pore volume in the dry state.

Macroporous hydrogels may also be formed using a method whereby polymer phase separation in induced by a non-solvent. The polymer may be poly-NIPAM and the non-solvent utilized may be glucose (see, e.g., Z. Zhang, *J. Org. Chem.*, 69, 23 (2004)) or NaCl (see, e.g., Cheng et al., *Journal of Biomedical Materials Research—Part A*, Vol. 67, Issue 1, 1 Oct. 2003, Pages 96-103). The phase separation induced by the presence of NaCl leads to an increase in swelling ratio. These materials are preferred if the swelling ratio of the material, SR, is maintained in salt isotonic solution and if the gels do not collapse under load. The temperature of "service" should be shifted beyond body temperature, e.g. by diluting NIPAM in the polymer with monomer devoid of transition temperature phenomenon.

In some embodiments, the fluid-absorbing polymer may be selected from certain naturally-occurring polymers such as those containing carbohydrate moieties. In a preferred embodiment, such carbohydrate-containing hydrogels are non-digestible, have a low fraction of soluble material and a high fraction of gel-forming materials. In some embodiments, the fluid-absorbing polymer is selected from xanthan, guar, wellan, hemicelluloses, alkyl-cellulose, hydro-alkyl-cellulose, carboxy-alkyl-cellulose, carrageenan, dextran, hyaluronic acid and agarose. In a preferred embodiment, the gel forming polymer is psyllium. Psyllium (or "ispaghula") is the common name used for several members of the plant genus *Plantago* whose seeds are used commercially for the production of mucilage. The fluid-absorbing polymer is also in the gel-forming fraction of psyllium, i.e., a neutral saccharide copolymer of arabinose (25%) and xylose (75%) as characterized in (J. Marlett, *Proceedings of the Nutrition Society*, 62, pp. 2-7-209 (2003); and, M. Fischer. *Carbohydrate Research*, 339, 2009-2012 (2004)), and further described in U.S. Pat. Nos. 6,287,609; 7,026,303; 5,126, 150; 5,445,831; 7,014,862; 4,766,004; 4,999,200, each of which is incorporated herein for all relevant and consistent purposes, and over-the-counter psillium-containing agents such as those marketed under the name Metamucil (The Procter and Gamble company). A psyllium-containing dosage form is also suitable for chewing, where the chewing action disintegrates the tablet into smaller, discrete particles prior to swallowing but which undergoes minimal gelling in the mouth, and has acceptable mouthfeel and good aesthetics as perceived by the patient.

The psyllium-containing dosage form includes physically discrete unit suitable as a unitary dosage for human subjects and other mammals, each containing a predetermined quantity of active material (e.g. the gel-forming polysaccharide) calculated to produce the desired therapeutic effect. Solid oral dosage forms that are suitable for the present compositions include tablets, pills, capsules, lozenges, chewable tablets, troches, cachets, pellets, wafer and the like.

In some embodiments, the FAP is a polysaccharide particle wherein the polysaccharide component includes xylose and arabinose. The ratio of the xylose to the arabinose may be at least about 3:1 by weight, as described in U.S. Pat. Nos. 6,287,609; 7,026,303 and 7,014,862, each of which is incorporated herein for all relevant and consistent purposes.

The fluid-absorbing polymers described herein may be used in combination with the NHE-inhibiting compound or a pharmaceutical composition containing it. The NHE-inhibiting compound and the FAP may also be administered with other agents including those described under the heading "Combination Therapies" without departing from the scope of the present disclosure. As described above, the NHE-inhibiting compound may be administered alone without use of a fluid-absorbing polymer to resolve symptoms without eliciting significant diarrhea or fecal fluid secretion that would require the co-administration of a fluid-absorbing polymer.

The fluid-absorbing polymers described herein may be selected so as to not induce any substantial interaction with the NHE-inhibiting compound or a pharmaceutical composition containing it. As used herein, "no substantial interaction" generally means that the co-administration of the FAP polymer would not substantially alter (i.e., neither substantially decrease nor substantially increase) the pharmacological property of the NHE-inhibiting compounds administered alone. For example, FAPs containing negatively charged functionality, such as carboxylates, sulfonates, and the like, may potentially interact ionically with positively charged NHE-inhibiting compounds, preventing the inhibitor from reaching its pharmacological target. In addition, it may be possible that the shape and arrangement of functionality in a FAP could act as a molecular recognition element, and sequester NHE-inhibiting compounds via "host-guest" interactions via the recognition of specific hydrogen bonds and/or hydrophobic regions of a given inhibitor. Accordingly, in various embodiments of the present disclosure, the FAP polymer may be selected, for co-administration or use with a compound of the present disclosure, to ensure that (i) it does not ionically interact with or bind with the compound of the present disclosure (by means of, for example, a moiety present therein possessing a charge opposite that of a moiety in the compound itself), and/or (ii) it does not possess a charge and/or structural conformation (or shape or arrangement) that enables it to establish a "host-guest" interaction with the compound of the present disclosure (by means of, for example, a moiety present therein that may act as a molecular recognition element and sequester the NHE inhibitor or inhibiting moiety of the compound).

D. Dosage

It is to be noted that, as used herein, an "effective amount" (or "pharmaceutically effective amount") of a compound disclosed herein, is a quantity that results in a beneficial clinical outcome of the condition being treated with the compound compared with the absence of treatment. The amount of the compound or compounds administered will depend on the degree, severity, and type of the disease or condition, the amount of therapy desired, and the release characteristics of the pharmaceutical formulation. It will also depend on the subject's health, size, weight, age, sex and tolerance to drugs. Typically, the compound is administered for a sufficient period of time to achieve the desired therapeutic effect.

In embodiments wherein both an NHE-inhibitor compound and a fluid-absorbing polymer are used in the treatment protocol, the NHE-inhibiting compound and FAP may be administered together or in a "dual-regimen" wherein the two therapeutics are dosed and administered separately. When the NHE-inhibiting compound and the fluid-absorbing polymer are dosed separately, the typical dosage administered to the subject in need of the NHE-inhibiting compound is typically from about 5 mg per day and about 5000 mg per day and, in other embodiments, from about 50 mg per day and about 1000 mg per day. Such dosages may induce fecal excretion of sodium (and its accompanying anions), from about 10 mmol up to about 250 mmol per day, from about 20 mmol to about 70 mmol per day or even from about 30 mmol to about 60 mmol per day.

The typical dose of the fluid-absorbing polymer is a function of the extent of fecal secretion induced by the non-absorbable NHE-inhibiting compound. Typically, the dose is adjusted according to the frequency of bowel movements and consistency of the stools. More specifically the dose is adjusted so as to avoid liquid stools and maintain stool consistency as "soft" or semi-formed, or formed. To achieve the desired stool consistency and provide abdominal relief to patients, typical dosage ranges of the fluid-absorbing polymer to be administered in combination with the NHE-inhibiting compound, are from about 2 g to about 50 g per day, from about 5 g to about 25 g per day or even from about 10 g to about 20 g per day. When the NHE-inhibiting compound and the FAP are administered as a single dosage regimen, the daily uptake may be from about 2 g to about 50 g per day, from about 5 g to about 25 g per day, or from about 10 g to about 20 g per day, with a weight ratio of NHE-inhibiting compound to fluid-absorbing polymer being from about 1:1000 to 1:10 or even from about 1:500 to 1:5 or about 1:100 to 1:5.

A typical dosage of the substantially impermeable or substantially systemically non-bioavailable, NHE-inhibiting compound when used alone without a FAP may be between about 0.2 mg per day and about 2 g per day, or between about 1 mg and about 1 g per day, or between about 5 mg and about 500 mg, or between about 10 mg and about 250 mg per day, which is administered to a subject in need of treatment.

The frequency of administration of therapeutics described herein may vary from once-a-day (QP) to twice-a-day (BID) or thrice-a-day (TID), etc., the precise frequency of administration varying with, for example, the patient's condition, the dosage, etc. For example, in the case of a dual-regimen, the NHE-inhibiting compound could be taken once-a-day while the fluid-absorbing polymer could be taken at each meal (TID). Furthermore, as disclosed in U.S. Application No. 61/584,753 filed Jan. 9, 2012, the NHE-inhibiting compound is administered twice-a-day (BID), or thrice-a-day (TID), and in a more specific embodiment, the NHE-inhibiting compound is administered in an amount ranging from 2-200 mg per dose BID, or 2-100 mg per dose TID. In more specific embodiments, the NHE-inhibiting compound is administered in an amount of about 15 mg per dose, about 30 mg per dose, or about 45 mg per dose, and in a more specific embodiment, in an amount of 15 mg per dose, 30 mg per dose, or 4.5 mg per dose.

E. Modes of Administration

The substantially impermeable or substantially systemically non-bioavailable NHE-inhibiting compounds of the present disclosure with or without the fluid-absorbing polymers described herein may be administered by any suitable route. The compound is administrated orally (e.g., dietary) in capsules, suspensions, tablets, pills, dragees, liquids, gels, syrups, slurries, and the like. Methods for encapsulating compositions (such as in a coating of hard gelatin or cyclodextran) are known in the art (Baker, et al., "Controlled Release of Biological Active Agents", John Wiley and Sons, 1986). The compounds can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers are biocompatible, i.e., non-toxic, non-inflammatory, non-immunogenic and devoid of other undesired reactions at the administration site. Examples of pharmaceutically acceptable carriers include, for example, saline, commercially available inert gels, or liquids supplemented with albtunin, methyl cellulose or a collagen matrix. Standard pharmaceutical formulation techniques can be employed, such as those described in Remington's Pharmaceutical Sciences, Mack Publishing Company, Easton, Pa.

In other embodiments, the NHE-3 inhibiting compounds may be systemically administered. In one embodiment, the compounds of the present invention are administered systemically to inhibit NHE-3 in the kidney. Without being held to any particular theory, the impermeable NHE-inhibiting compounds (e.g., NHE-3, -2 and/or -8 inhibitors) of the present disclosure can also be administered parenterally, by intravenous, subcutaneous or intramuscular injection or infusion to inhibit NHE3 in the kidney. NHE3 is expressed at high levels on the apical surface of the proximal tubule of the kidney and couples luminal Na reabsorption to the secretion of intracellular protons. Since NHE3 accounts for approximately 60-80% of sodium reabsorption in the kidney, it is anticipated that NHE inhibition could permit the removal of substantial quantities of systemic fluid and sodium to prevent edema and resolve congestive heart failure symptoms. This effect could be achieved by NHE inhibition in combination with other diuretics, specifically loop diuretics, like furosemide, to inhibit tubuloglomerular feedback. In addition, since sodium reabsorption via NHE3 in the proximal tubule is responsible for a large proportion of the energy requirement of the proximal tubule cell, it is anticipated that NHE inhibition in the kidney could be beneficial by reducing the energy requirement and protecting the proximal tubule cell in settings of decreased energy, availability to the proximal tubule, such as those that occur as a result of kidney hypoxia such as in kidney ischemia reperfusion injury resulting in acute kidney injury.

Pharmaceutical preparations for oral use can be obtained by combining a compound of the present disclosure with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxy propylmethycellulose, sodium carboxymethylcellulose, and/or polyvinylpyrrolidone (PVP). If desired, disintegrating agents can be added, such as crosslinked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent Mixtures. Dyestuffs or pigments can be added to the tablets or dragee coatings for identification or to characterize different combinations of active compound doses.

Pharmaceutical preparations which can be used orally include push-fit capsules made of a suitable material, such as gelatin, as well as soft, sealed capsules made of a suitable material, for example, gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

It will be understood that, certain compounds of the disclosure may be obtained as different stereoisomers (e.g., diastereomers and enantiomers) or as isotopes and that the disclosure includes all isomeric forms, racemic mixtures and isotopes of the disclosed compounds and a method of treating a subject with both pure isomers and mixtures thereof, including racemic mixtures, as well as isotopes. Stereoisomers can be separated and isolated using any suitable method, such as chromatography.

F. Delayed Release

NHE proteins show considerable diversity in their patterns of tissue expression, membrane localization and functional roles. (See, e.g., *The sodium-hydrogen exchanger—from molecule To Its Role In Disease*, Karmazyn, M., Avkiran, M., and Fliegel, L., eds., Kluwer Academics (2003).)

In mammals, nine distinct NHE genes (NHE-1 through -9) have been described. Of these nine, five (NHE-1 through -5) are principally active at the plasma membrane, whereas NHE-6, -7 and -9 reside predominantly within intracellular compartments.

NHE-1 is ubiquitously expressed and is chiefly responsible for restoration of steady state intracellular pH following cytosolic acidification and for maintenance of cell volume. Recent findings show that NHE-1 is crucial for organ function and survival (e.g., NHE-1-null mice exhibit locomotor abnormalities, epileptic-like seizures and considerable mortality before weaning).

In contrast with NHE-1 expressed at the basolateral side of the nephrons and gut epithelial cells, NHE-2 through -4 are predominantly expressed on the apical side of epithelia of the kidney and the gastrointestinal tract. Several lines of evidence show that NHE-3 is the major contributor of renal bulk Na+ and fluid re-absorption by the proximal tubule. The associated secretion of H+ by NHE-3 into the lumen of renal tubules is also essential for about ⅔ of renal $HCO3^-$ re-absorption. Complete disruption of NHE-3 function in mice causes a sharp reduction in $HCO3^-$, Na+ and fluid re-absorption in the kidney, which is consistently associated with hypovolemia and acidosis.

In one embodiment, the compounds of the disclosure are intended to target the apical NHE antiporters (e.g. NHE-3, NHE-2 and NHE-8) without substantial permeability across the layer of gut epithelial cells, and/or without substantial activity towards NHEs that do not reside predominantly in the GI tract. This invention provides a method to selectively inhibit GI apical NHE antiporters and provide the desired effect of salt and fluid absorption inhibition to correct abnormal fluid homeostasis leading to constipations states. Because of their absence of systemic exposure, said compounds do not interfere with other key physiological roles of NHEs highlighted above. For instance, the compounds of the disclosure are expected to treat constipation in patients in need thereof, without eliciting undesired systemic effects, such as for example salt wasting or bicarbonate loss leading to hyponatriemia and acidosis among other disorders.

In another embodiment, the compounds of the disclosure are delivered to the small bowel with little or no interaction with the upper GI such as the gastric compartment and the duodenum. The applicant found that an early release of the compounds in the stomach or the duodenum can have an untoward effect on gastric secretion or bicarbonate secretion (also referred to as "bicarbonate dump"). In this embodiment the compounds are designed so as to be released in an active form past the duodenum. This can be accomplished by either a prodrug approach or by specific drug delivery systems.

As used herein, "prodrug" is to be understood to refer to a modified form of the compounds detailed herein that is inactive (or significantly less active) in the upper GI, but once administered is metabolised in vivo into an active metabolite after getting past, for example, the duodenum. Thus, in a prodrug approach, the activity of the NHE-inhibiting compound can be masked with a transient protecting group that is liberated after compound passage through the desired gastric compartment. For example, acylation or alkylation of the essential guanidinyl functionality of the NHE-inhibiting compound would render it biochemically inactive; however, cleavage of these functional groups by intestinal amidases, esterases, phosphatases, and the like, as well enzymes present in the colonic flora, would liberate the active parent compound. Prodrugs can be designed to exploit the relative expression and localization of such phase I metabolic enzymes by carefully optimizing the structure of the prodrug for recognition by specific enzymes. As an example, the anti-inflammatory agent sulfasalazine is converted to 5-aminosalicylate in the colon by reduction of the diazo bond by intestinal bacteria.

In a drug delivery approach the NHE-inhibiting compounds of the disclosure are formulated in certain pharmaceutical compositions for oral administration that release the active in the targeted areas of the GI, i.e., jejunum, ileum or colon, the distal ileum and colon, or the colon.

Methods known from the skilled-in-the-art are applicable. (See, e.g., Kumar, P. and Mishra, B., Colon Targeted Drug Delivery Systems—An Overview, *Curr. Drug Deliv.*, 2008, 5 (3), 186-198; Jain, S. K. and Jain, A., Target-specific Drug Release to the Colon., *Expert Opin. Drug Deliv.*, 2008, 5 (5), 483-498; Yang, L., Biorelevant Dissolution Testing of Colon-Specific Delivery Systems Activated by Colonic Microflora, *J. Control Release,* 2008, 125 (2), 77-86; Siepmann, F.; Siepmann, J.; Walther, M.; MacRae, R. J.; and Bodmeier, R., Polymer Blends for Controlled Release Coatings, *J. Control Release* 2008, 125 (1), 1-15; Patel, M.; Shah, T.; and Amin, A., Therapeutic Opportunities in Colon-Specific Drug-Delivery Systems, *Crit. Rev. Ther. Drug Carrier Syst.,* 2007, 24 (2), 147-202; Jain, A.; Gupta, Y.; Jain, S. K., Perspectives of Biodegradable Natural Polysaccharides for Site-specific Drug Delivery to the Colon., *J. Pharm. Sci.,* 2007, 10 (1), 86-128; Van den, M. G., Colon Drug Delivery, *Expert Opin. Drug Deliv.,* 2006, 3 (1), 111-125; Basit, A. W., Advances in Colonic Drug Delivery, *Drugs* 2005, 65 (14), 1991-2007; Chourasia, M. K.; Jain, S. K., Polysaccharides for Colon-Targeted Drug Delivery, *Drug Deliv.* 2004, 11 (2), 129-148; Shareef, M. A.; Khar, R. K.; Ahuja, A.; Ahmad, F. J.; and Raghava, S., Colonic Drug Delivery: An Updated Review, *AAPS Pharm. Sci.* 2003, 5 (2), E17; Chourasia, M. K.; Jain, S. K., Pharmaceutical Approaches to Colon Targeted Drug Delivery Systems, *J. Pharm. Sci.* 2003, 6 (1), 33-66; and, Sinha, V. R.; Kumria, R., Colonic Drug Delivery: Prodrug Approach, *Pharm. Res.* 2001, 18 (5), 557-564. Typically, the active pharmaceutical ingredient (API) is contained in a tablet/capsule designed to release said API as a function of the environment (e.g., pH, enzymatic activity, temperature, etc.), or as a function of time. One example of this approach is Eudracol™ (Pharma Polymers Business Line of Degussa's Specialty Acrylics Business Unit), where the API-containing core tablet is layered with various polymeric coatings with specific dissolution profiles. The first layer ensures that the tablet passes through the stomach intact so it can continue through the small intestine. The change from an acidic environment in the stomach to an alkaline environment in the small intestine initiates the release of the protective outer layer. As it travels through the colon, the next layer is made permeable by the alkalinity and intestinal fluid. This allows fluid to penetrate to the interior layer and release the active ingredient, which diffuses from the core to the outside, where it can be absorbed by the intestinal wall. Other methods are contemplated without departing from the scope of the present disclosure.

In another example, the pharmaceutical compositions of the invention can be used with drug carriers including pectin and galactomannan, polysaccharides that are both degradable by colonic bacterial enzymes. (See, e.g., U.S. Pat. No. 6,413,494, the entire contents of which are incorporated herein by reference for all relevant and consistent purposes.) While pectin or galactomannan, if used alone as a drug carrier, are easily dissolved in simulated gastric fluid and simulated intestinal fluid, a mixture of these two polysaccharides prepared at a pH of about 7 or above produces a strong, elastic, and insoluble gel that is not dissolved or disintegrated in the simulated gastric and intestinal fluids, thus protecting drugs coated with the mixture from being released in the upper GI tract. When the mixture of pectin and galactomannan arrives in the colon, it is rapidly degraded by the synergic action of colonic bacterial enzymes. In yet another aspect, the compositions of the invention may be used with the pharmaceutical matrix of a complex of gelatin and an anionic polysaccharide (e.g., pectinate, pectate, alginate, chondroitin sulfate, polygalacturonic acid, tragacanth gum, arabic gum, and a mixture thereof), which is degradable by colonic enzymes (U.S. Pat. No. 6,319,518).

In yet other embodiments, fluid-absorbing polymers that are administered in accordance with treatment methods of the present disclosure are formulated to provide acceptable/pleasant organoleptic properties such as mouthfeel, taste, and/or to avoid premature swelling/gelation in the mouth and in the esophagus and provoke choking or obstruction. The formulation may be designed in such a way so as to ensure the full hydration and swelling of the FAP in the GI tract and avoid the formation of lumps. The oral dosages for the FAP may take various forms including, for example, powder, granulates, tablets, wafer, cookie and the like, or are delivered to the small bowel with little or no interaction with the upper GI such as the gastric compartment and the duodenum.

The above-described approaches or methods are only some of the many methods reported to selectively deliver an active in the lower part of the intestine, and therefore should not be viewed to restrain or limit the scope of the disclosure.

IV. Preparation of Compounds

The following Reaction Schemes I-IV illustrate methods for making compounds of this invention, i.e., compounds of Formula (I). It is understood that one skilled in the art may be able to make these compounds by similar methods or by combining other methods known to one skilled in the art. It is also understood that one skilled in the art would be able to make, in a similar manner as described below, other compounds of Formula (I) not specifically illustrated below by using the appropriate starting components and modifying the parameters of the synthesis as needed. The compounds described herein may be made from commercially available starting materials or synthesized using known organic, inorganic, and/or enzymatic processes. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention. The general synthetic schemes of precursors, intermediates, and final products shown below are mere illustrations of methods of preparations. The various radicals (e.g., $R^1$, $R^2$, $R^3$, $R^4$, etc. . . . ) affixed on each generic or sub-generic formula in the schemes below will be understood to represent the corresponding positional radicals in the compounds of general Formula I and I' described above. In other words, in the schemes below only the position of the radical in the structure will matter in the interpretation of the synthetic scheme rather than its labelling. For example, radicals $R^1$, $R^2$, and $R^3$ can be used interchangeably from one scheme to another without necessarily having the same meaning. Only their position in the generic structure I and I' will determine their actual substituents for the synthesis.

General Reaction Scheme I

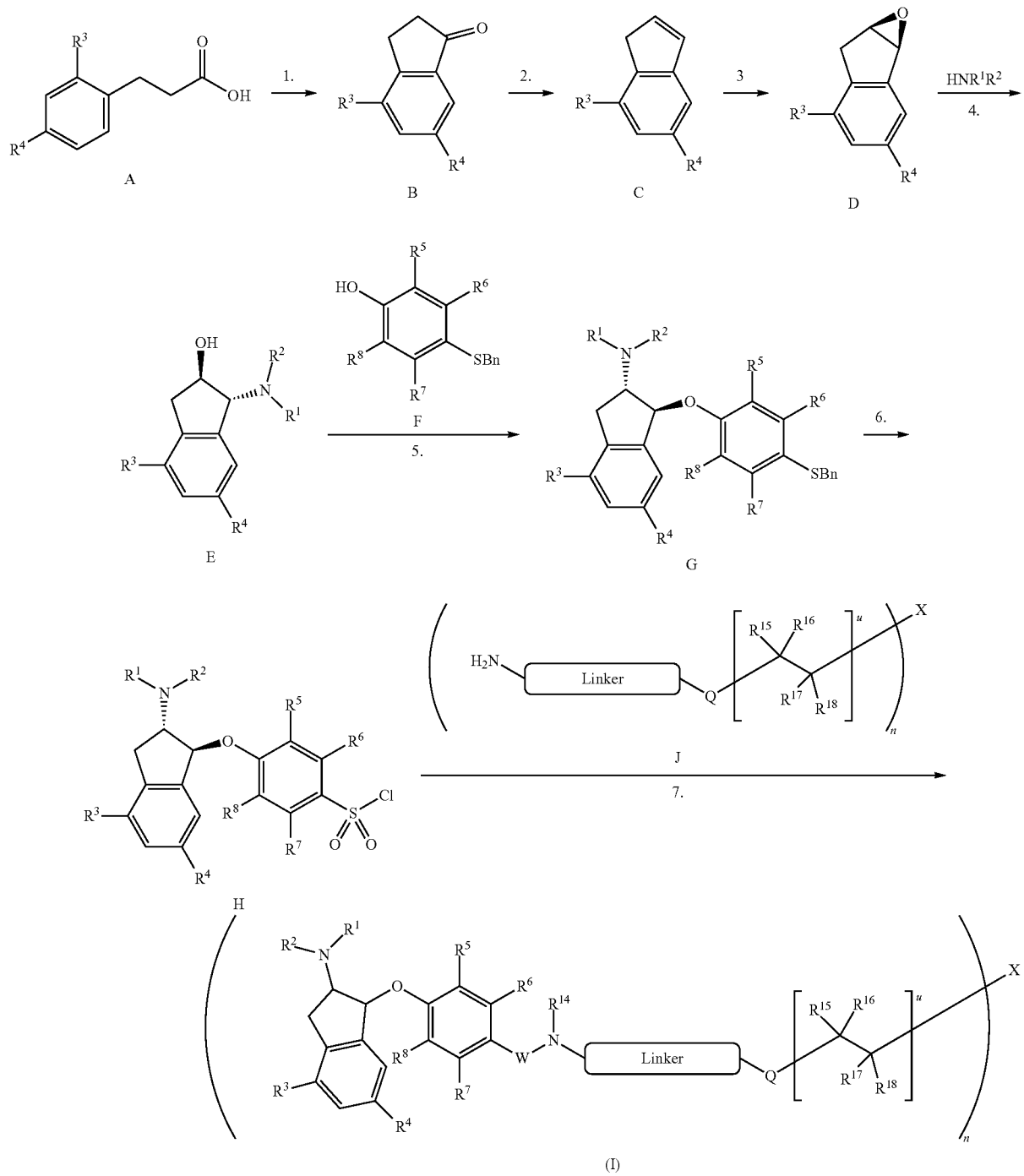

Referring to General Reaction Scheme I, an appropriate hydrocinnamic acid A, indanone B, or indene C can be obtained commercially or synthesized according to methods known in the art and converted to the enantiopure epoxide D via Jacobsen epoxidation conditions. The chiral compounds obtained (either enantiomer can be used) are then reacted with an amine HNR2R3 (where R2 and R3 are as previously defined) to provide the aminoindanol E. Further reaction with phenol F is facilitated by either formation of the mesylate or other activated intermediate of E or through activation using triphenylphosphine and an azodicarboxylate such as diisopropylazodicarboxylate, diethylazodicarboxylate, di-tert-butylazodicarboxylate, or the like, providing the rearranged aminoindanol G. Oxidation and chlorination are achieved through use of chlorinating reagents such as N-chlorosuccinimide, providing the sulfonyl chloride H. There exist multiple methods of producing the homodimers compounds (I), including reaction of H with amine dimers J.

General Reaction Scheme II

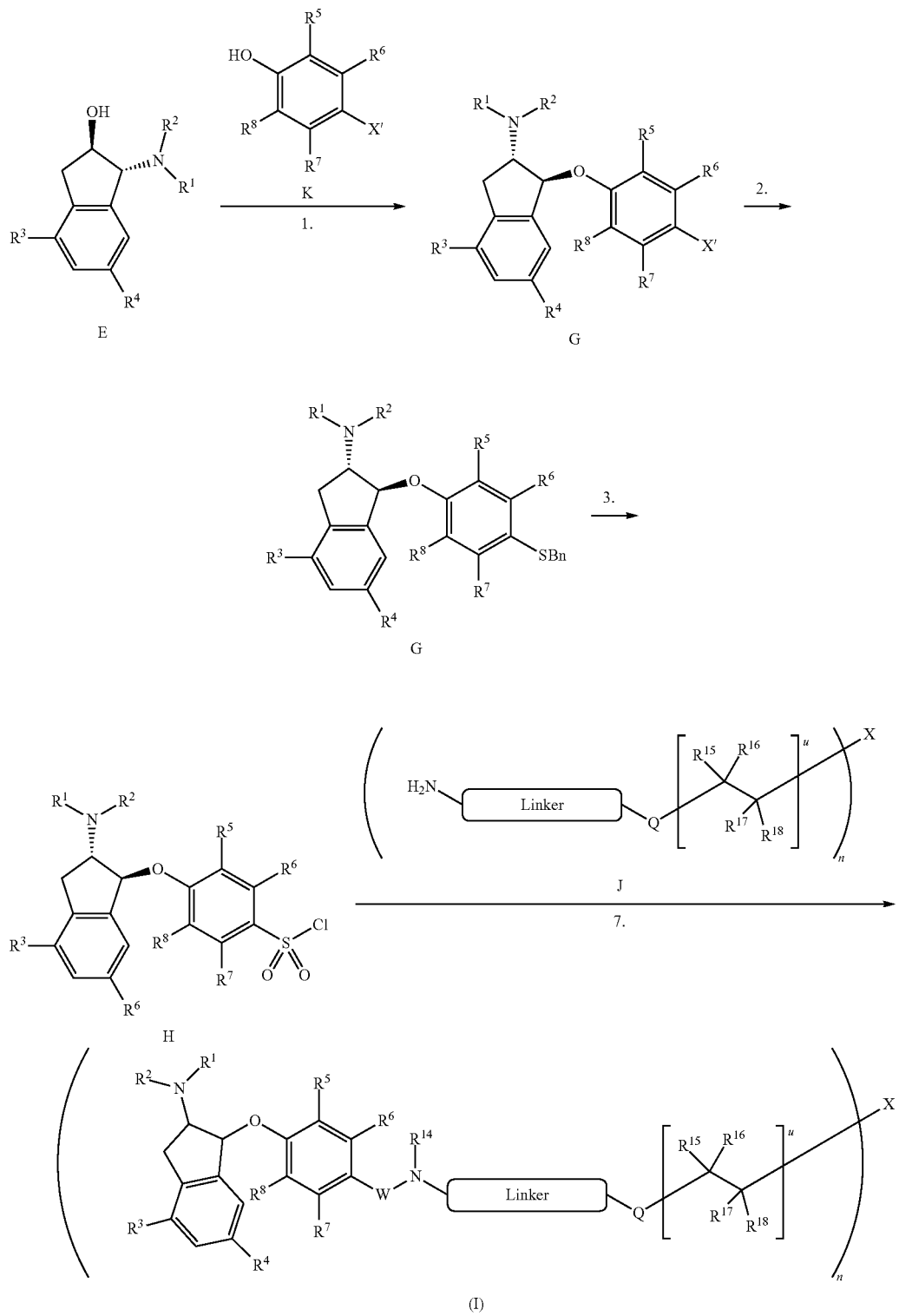

Compounds of Formula (I) may also be prepared according to General Reaction Scheme H. Aminoindanols E as obtained previously are reacted with phenols K (available commercially or synthetically via standard procedures, where X'=bromo or iodo) using conditions described in General Reaction Scheme I furnishing ether product L. Conversion of the halide to the thioether G is accomplished through palladium-mediated coupling with benzylmercaptan. Further elaboration to the compounds of structure (I) is as described in General Reaction Scheme I.

General Reaction Scheme III

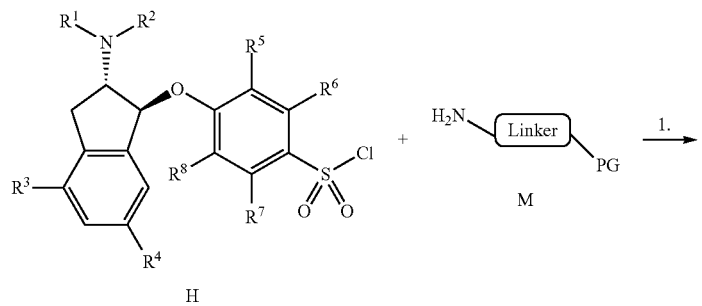

H

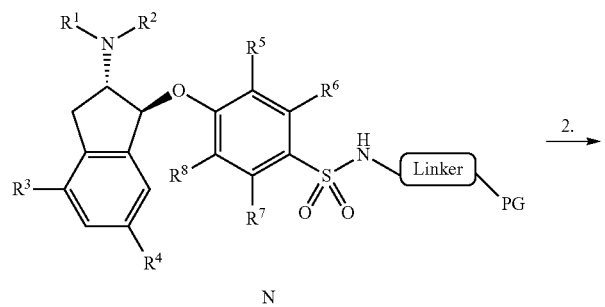

N

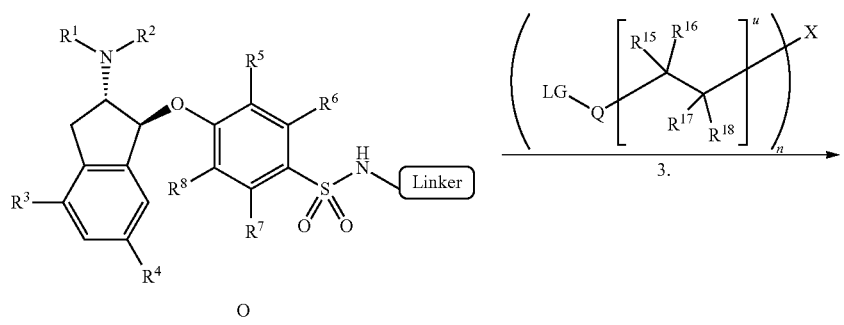

O

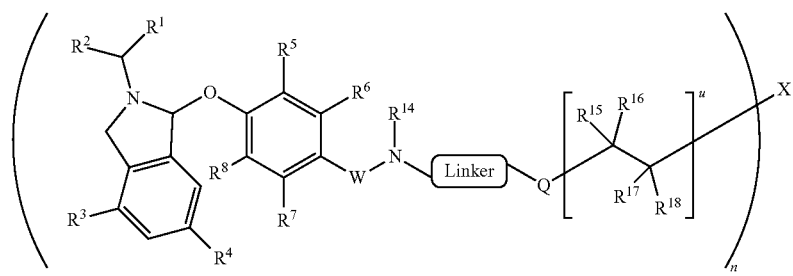

Compounds of Formula (I) are also prepared according to General Reaction Scheme III. Beginning with the sulfonyl chloride H, the product sulfonamides N are formed from reaction with an amine M where Y (with protecting group "PG", in the case where Y is a primary or secondary amine) is a protected or masked amine functionality or other functional handle. Subsequent removal of the protecting group provides the sulfonamide monomer O followed by dimerization with a bifunctional "X" moiety P generates the compounds of structure (I).

General Reaction Scheme IV
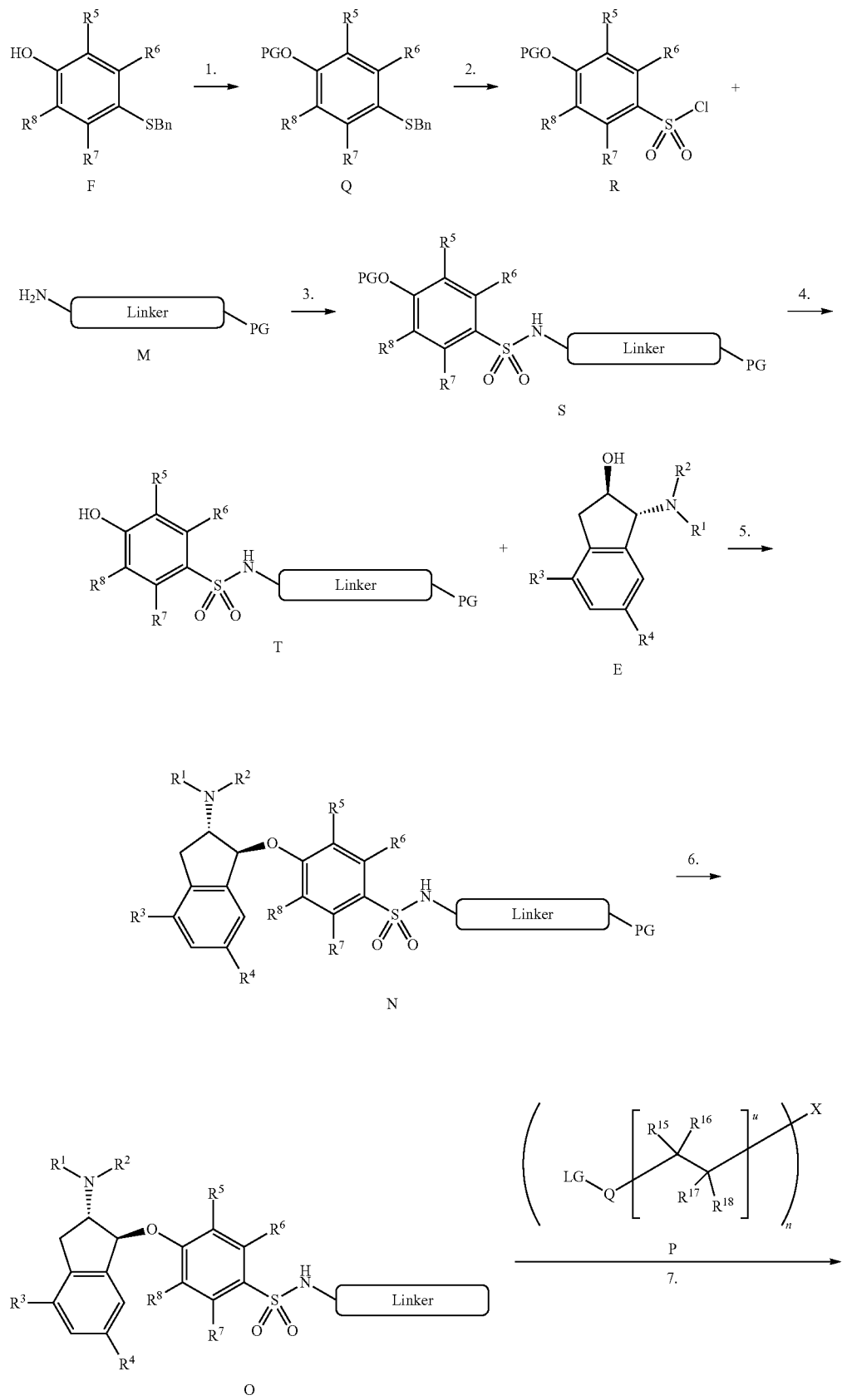

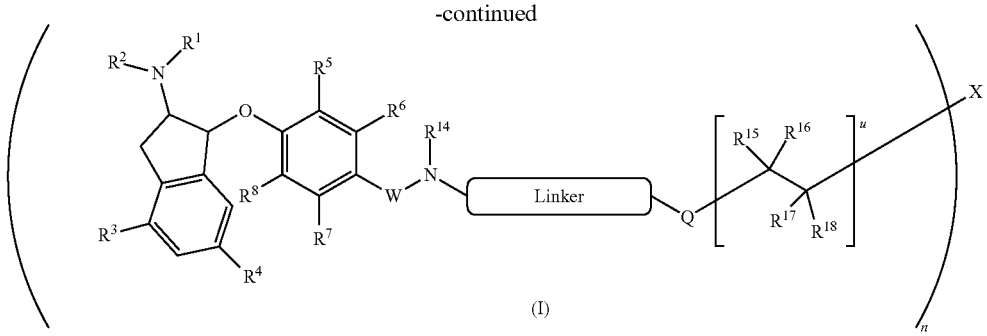

(I)

Compounds of Formula (I) can also be prepared according to the General Reaction Scheme IV, Phenols F are protected to yield thioethers Q which are then oxidized to the sulfonyl chloride R using reagents such as N-chlorosuccinimide in acetic acid. Subsequently these sulfonyl chlorides R can be coupled with amines M to yield the differentially protected derivatives S. Deprotection to yield phenol T which is then reacted with E which is activated by either formation of the mesylate or other activated intermediate of E or through using triphenylphosphine and an azodicarboxylate such as diisopropylazodicarboxylate, diethylazodicarboxylate, di-tert-butylazodicarboxylate, or the like, providing the rearranged aminoindanol N. The intermediate is deprotected to yield the monomer O followed by dimer formation with a core P with leaving groups to yield the compounds of structure (I).

General Reaction Scheme V

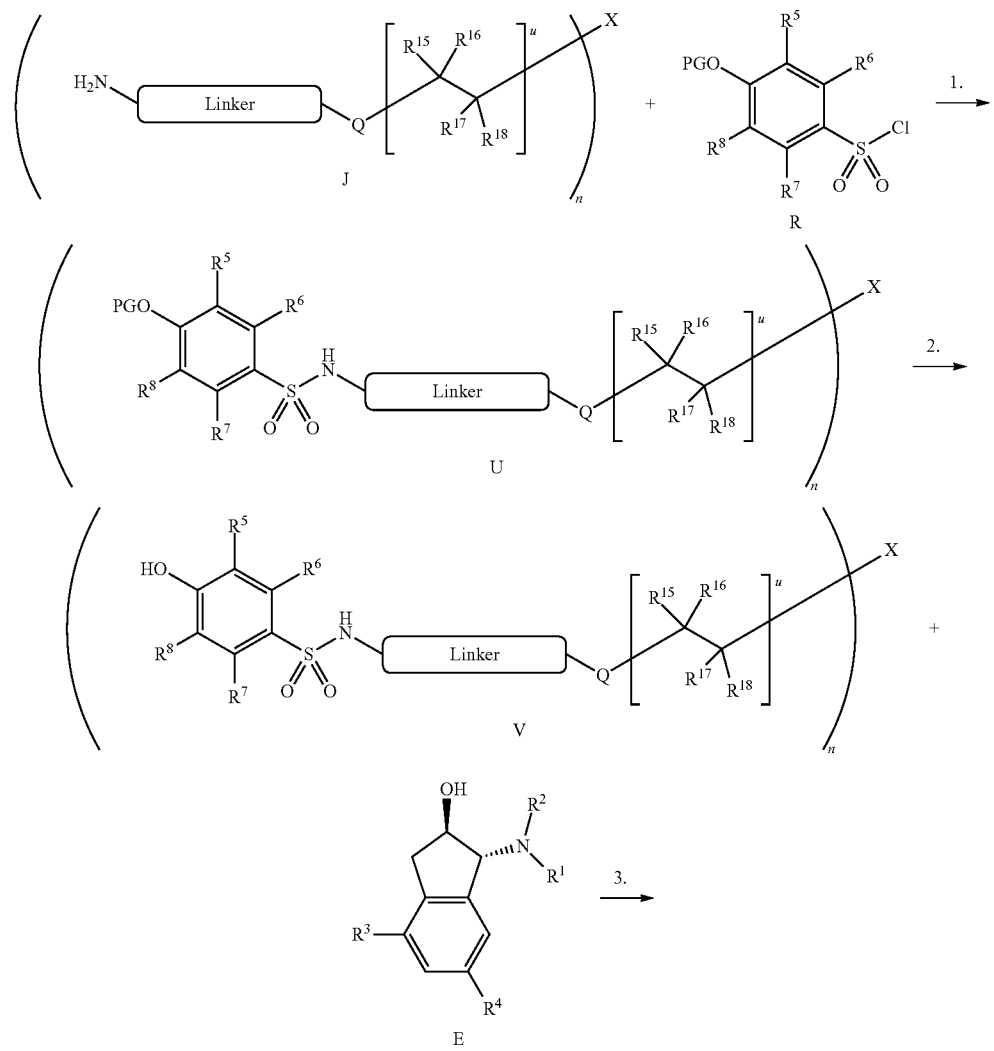

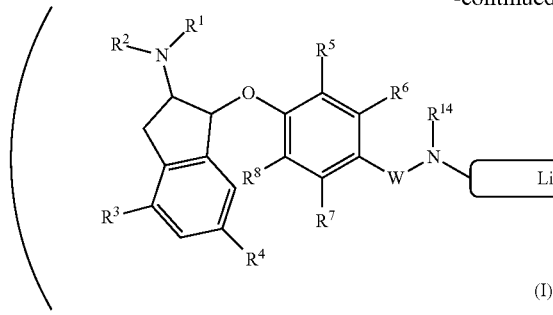
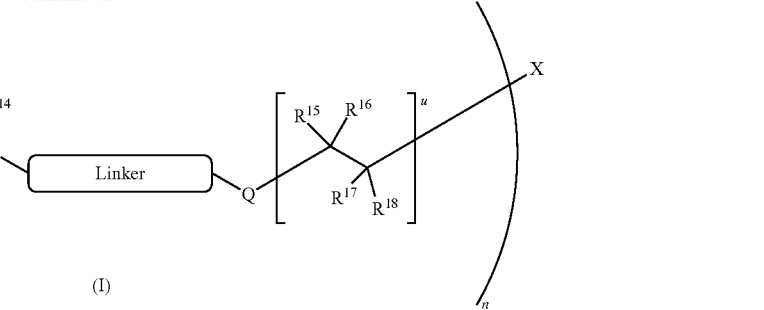

(I)

Similar to General Reaction Scheme IV, the compounds of Formula (I) can be prepared through reaction with a fully dimerized phenolic coupling partner. Reaction of the dimeric amines J with sulfonyl chlorides R can provide the dimer U under standard conditions with mild bases such as pyridine or trimethylainine. Removal of the protecting groups gives the phenol V. Intermediate of E is activated by either formation of the mesylate or using triphenylphosphine and an azodicarboxylate such as diisopropylazodicarboxylate, diethylazodicarboxylate, di-tert-butylazodicarboxylate, or the like, then reacting with phenol V providing the rearranged final compounds of structure (I).

With regard to General Reaction Schemes I-IV, typical carboxylate activation reagents include DCC, EDCI, HATU, oxalyl chloride, thionyl chloride and the like. Typical bases include TEA, DIEA, pyridine, $K_2CO_3$, NaH and the like. Typical acylation catalysts include HOBt, HOAt, 4-dimethylaminopyridine and the like. Typical catalysts for hydrogenation include palladium on carbon, rhodium on carbon, platinum on carbon, raney nickel and the like.

One skilled in the art will recognize that variations to the order of the steps and reagents discussed in reference to the Reaction Schemes are possible. Methodologies for preparation of compounds of Formula (I) are described in more detail in the following non-limiting exemplary schemes.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsityl or trimethylsilyl), tetrahydropyranyl, benzyl, and the like. Suitable protecting groups for amino, amidino and guanidino include t-butoxycarbonyl, benzyloxycarbonyl, trifluoroacetyl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following non-limiting examples are provided to further illustrate the present disclosure.

EXAMPLES

I General Scheme for Linker Synthesis

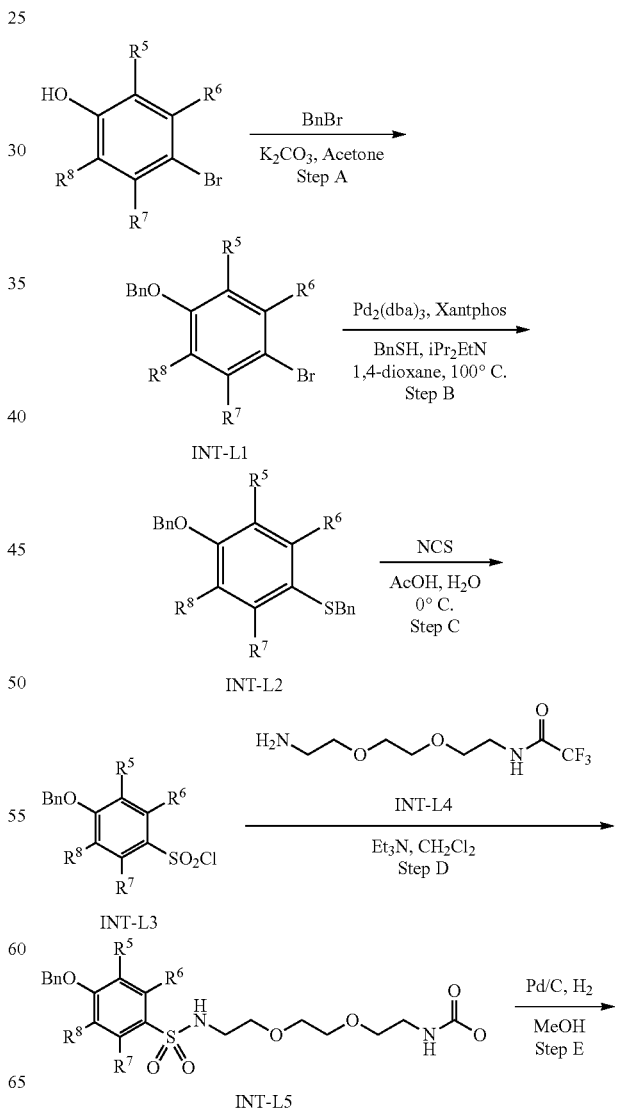

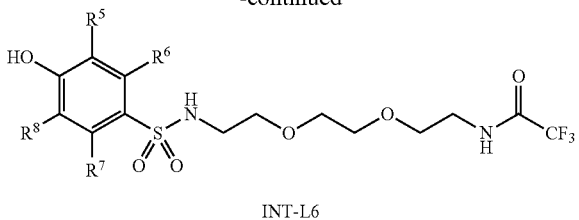

INT-L6

Step A: To a 250-mL round-bottom flask was added the desired substituted-bromophenol (1 equiv), acetone (0.45 M), potassium carbonate (5 equiv), and benzyl bromide (2.5 equiv). The resulting solution was stirred for 4 h at room temperature. The resulting solution was diluted with 30 mL of $H_2O$. The resulting mixture was concentrated under vacuum and extracted with of ethyl acetate. The organic layers were combined and washed with 3× $H_2O$ and 1× brine. The mixture was dried over anhydrous sodium sulfate, filtered, and the resulting mixture concentrated under vacuum. The residue was applied onto a silica gel column with petroleum ether providing the desired benzylethers INT-L1.

Step B: To a round-bottom flask purged and maintained with an inert atmosphere of nitrogen was added benzylether INT-L1 (1 equiv), 1,4-dioxane (0.16 M), N,N-diisopropylethylamine (2 equiv), benzylmercaptan (2 equiv), $Pd_2(dba)_3 \cdot CHCl_3$ (0.05 equiv), and Xantphos (0.10 equiv). The resulting solution was stirred overnight at 100° C. The resulting slurry was concentrated under vacuum and diluted with of $H_2O$. The resulting solution was extracted with of ethyl acetate and the organic layers combined and washed with 3× $H_2O$ and 1× brine. The mixture was dried over anhydrous sodium sulfate, filtered, and the resulting mixture was concentrated under vacuum. The residue was applied onto a silica gel column with petroleum ether providing the desired thioethers INT-L2.

Step C: To a round-bottom flask was added thioether INT-L2 (1 equiv), acetic acid (0.25 M), and water (3 equiv). This was followed by the addition of N-chlorosuccinimide (NCS, 5 equiv) in several batches at 0° C. The resulting solution was stirred for 1 h at room temperature. The resulting slurry was concentrated under vacuum and diluted with $H_2O$. The resulting solution was extracted with of ethyl acetate and the organic layers combined and washed with 3× $H_2O$ and 1× brine. The mixture was dried over anhydrous sodium sulfate, filtered, and concentrated under vacuum. The residue was applied onto a silica gel column with petroleum ether providing the sulfonyl chloride INT-L3.

Step D: To a round-bottom flask was added sulfonyl chloride INT-L3 (1 equiv), $CH_2Cl_2$ (0.2 M), triethylamine (5 equiv), and N-[2-[2-(2-aminoethoxy)ethoxy]ethyl]-2,2,2-trifluoroacetamide (INT-L4, 2 equiv). The resulting solution was stirred overnight at room temperature. The resulting mixture was concentrated under vacuum and diluted with of $H_2O$. The resulting slurry was extracted with $CH_2Cl_2$ and the organic layers combined and washed with 3× $H_2O$ and 1× brine. The mixture was dried over anhydrous sodium sulfate, filtered, and concentrated under vacuum. The residue was applied onto a silica gel column with $CH_2Cl_2$/methanol (30:1) providing the sulfonamide INT-L5.

Step E: To a round-bottom flask purged and maintained with an inert atmosphere of $H_2$, was added sulfonamide INT-L5 (1 equiv), methanol (0.1 M), and palladium on carbon (~10-20%). The resulting slurry was stirred for 1 h at room temperature. The solids were filtered out and the resulting mixture was concentrated under vacuum. The residue was applied onto a silica gel column with ethyl acetate/petroleum ether (1:1) providing the desired phenol INT-L6.

The following intermediates were made by applying the above procedures to the appropriate phenol:

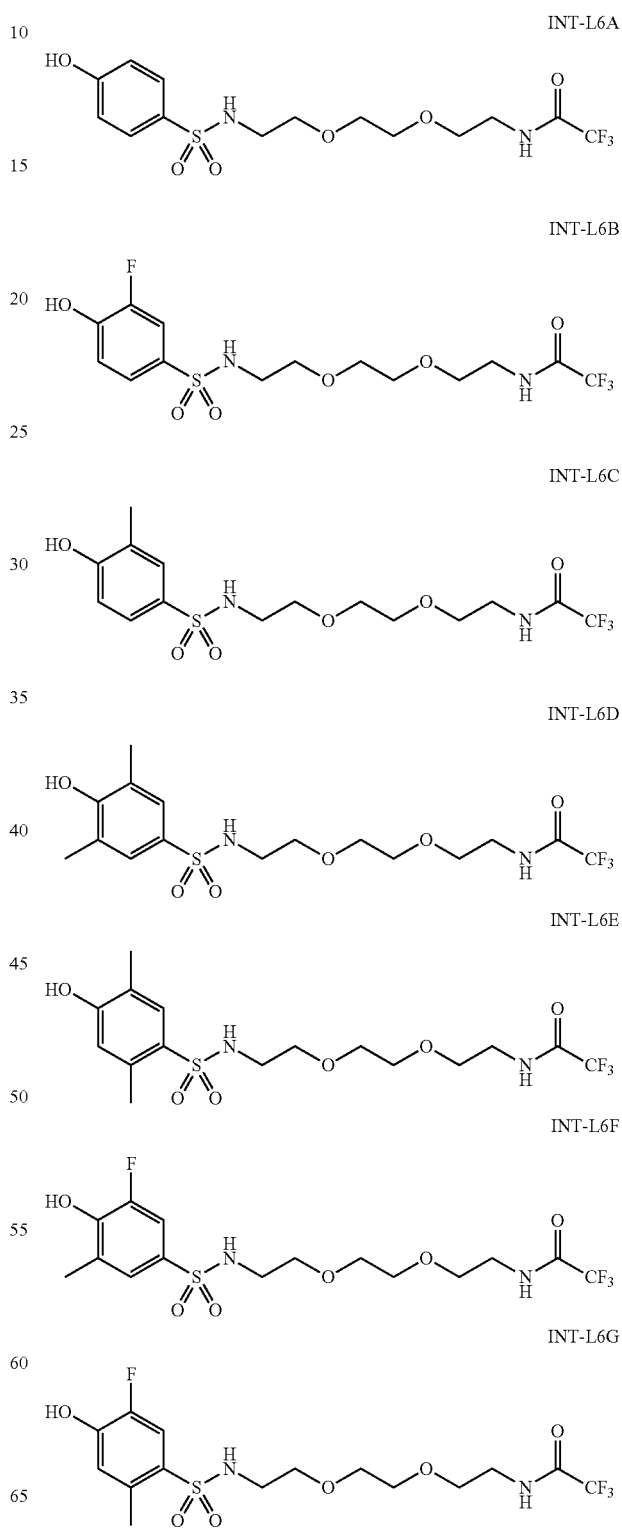

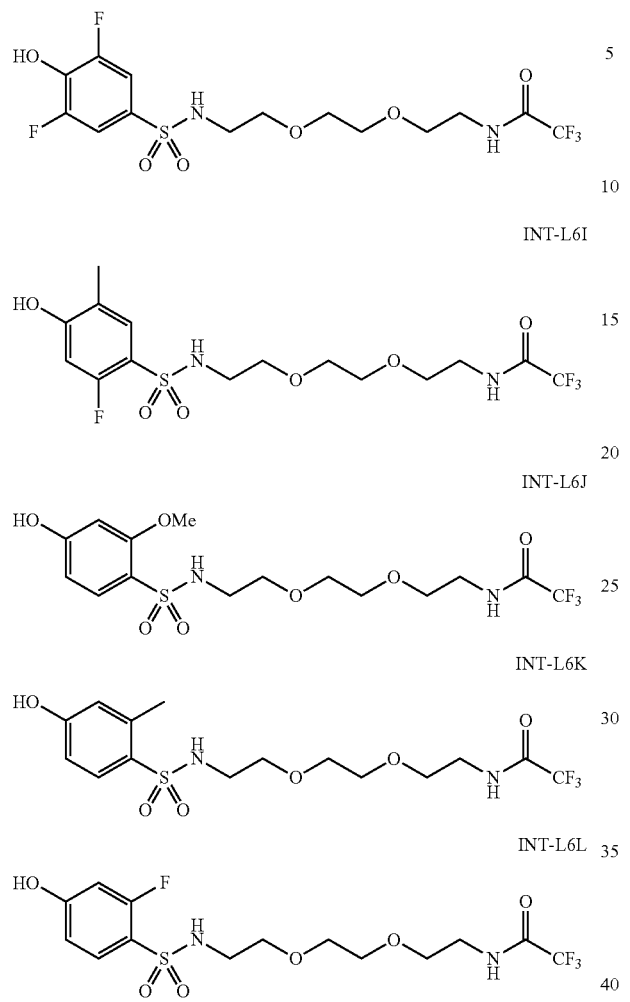

General Scheme for Indane Epoxide Synthesis

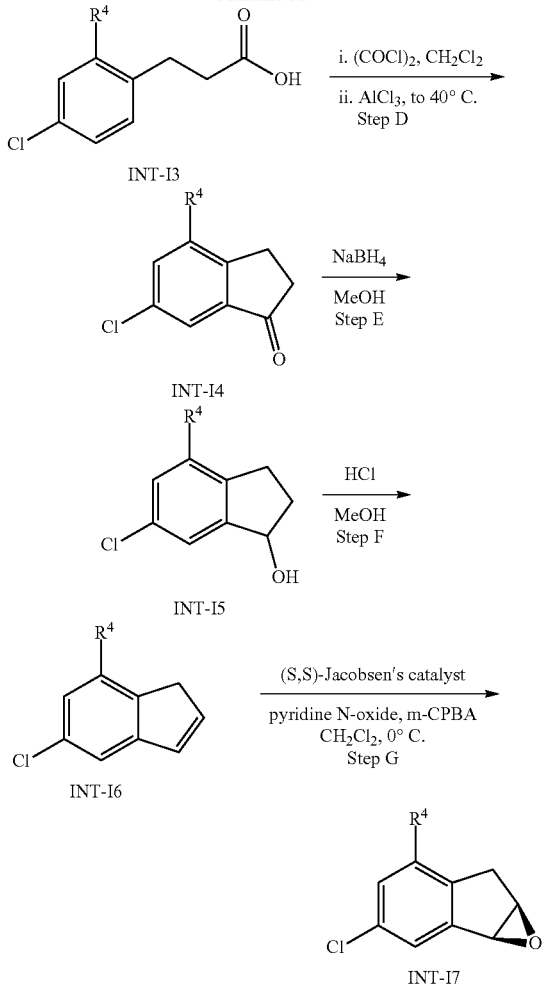

Step A: To a round-bottom flask purged and maintained with an inert atmosphere of nitrogen was added the desired Ie-substituted bromide/iodide (1 equiv), $CH_3CN$ (0.25 M), tert-butyl prop-2-enoate (equiv), diisopropylethylamine (3 equiv), $P(o\text{-tol})_3$ (0.20 equiv), and $Pd(OAc)_2$ (0.10 equiv). The resulting solution was stirred overnight at 95° C. The solids were removed by filtration and the filtrate was concentrated under vacuum. The resulting slurry was diluted with water and extracted with 3× $CH_2Cl_2$. The organic layers were combined and dried over anhydrous sodium sulfate, filtered, and concentrated. The residue was applied onto a silica gel column with ethyl acetate/petroleum ether (1:500) providing the cinnamate INT-I1.

Step B: To a round-bottom flask was cinnamate INT-I1 (1 equiv), ethyl acetate (0.1 M), and Raney Ni. The flask was purged and filled with $H_{2(g)}$, cycling three times, leaving a positive $H_2$ atmosphere. The resulting solution was stirred for 2 h at room temperature. The solids were filtered out and the resulting mixture was concentrated under vacuum providing the hydrocinnamate INT-I2.

Step C: To a round-bottom flask was added hydrocinnamate equiv) and 2:1 $CH_2Cl_2$:TFA (0.4 M). The resulting slurry was stirred for 1 h at room temperature. The resulting mixture was concentrated under vacuum and the residue was applied onto a silica gel column with ethyl acetate/petroleum ether (0-10%). The collected fractions were combined and concentrated under vacuum providing the hydrocinnamic acid INT-I3.

Step D: To a 3-necked round-bottom flask was added hydrocinnamic acid INT-I3 (1 equiv) and $CH_2Cl_2$ (0.4 M. The reaction slurry was cooled to 0° C. and treated with $(COCl)_2$ (2 equiv) dropwise. The resulting solution was stirred for 2 h at room temperature. The resulting solution was concentrated under vacuum. To a 3-necked round-bottom flask was added $AlCl_3$ (2 equiv) and $CH_2Cl_2$ (0.4 M). The product of the first step dissolved in $CH_2Cl_2$ and added dropwise to this $AlCl_3$ slurry. The resulting solution was stirred for 2 h at 40° C. in an oil bath. The reaction was then quenched by the addition of 2N $HCl_{(aq)}$. The resulting solution was extracted with 3× $CH_2Cl_2$ and the organic layers combined and concentrated under vacuum. The residue was applied onto a silica gel column with ethyl acetate/petroleum ether (0-1:10). The collected fractions were combined and concentrated under vacuum providing the indanone INT-I4.

Step E: To a round-bottom flask was indanone INT-I4 (1 equiv), methanol (0.7 M), and $NaBH_4$ (2 equiv). The resulting solution was stirred for 1 h at room temperature. The reaction was then quenched by the addition of 20 mL of water and extracted with 3× $CH_2Cl_2$. The organic layers were combined and washed with 3× brine. The organic layer was dried over anhydrous sodium sulfate, filtered, and concentrated under vacuum providing indanol INT-I5.

Step F: To a round-bottom flask was added indanol INT-I5 (1 equiv), methanol (0.5 M), and HCl (half volume of methanol). The resulting solution was stirred for 1 h at room temperature. The resulting mixture was quenched with methanol and concentrated under vacuum. The resulting slurry was extracted with 3× n-hexane and the organic layers combined. The residue was applied onto a silica gel column with n-hexane providing indene INT-I6.

Step G: To a 3-necked round-bottom flask was added indene INT-I6 (1 equiv), $CH_2Cl_2$ (0.08M, dried over magnesium sulfate), pyridine N-oxide (5 equiv in $CH_2Cl_2$ solution dried over magnesium sulfate), and (S,S)-Jacobsen's catalyst (0.05 equiv). The resulting solution was stirred for 10 min at 0° C. followed by the addition of m-CPBA (2 equiv) in portions at 0° C. The resulting slurry was stirred for an additional 1 h at 0° C. The reaction was then quenched by the addition of sodium hydroxide (3 $M_{(aq)}$), approx. 13 equiv). The resulting slurry was washed with 1× $H_2O$ and 1× brine. The mixture was dried over anhydrous sodium sulfate, filtered, and concentrated. The residue was applied onto a silica gel column with ethyl acetate/petroleum ether (1:30-1:15) providing the epoxide INT-I7.

The following intermediates were made by applying the above procedures to the appropriate starting aryl compounds (starting materials are available commercially at different stages of this sequence):

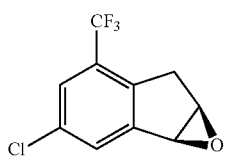
INT-I7A

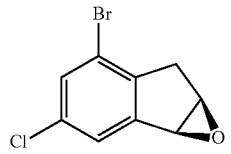
INT-I7B

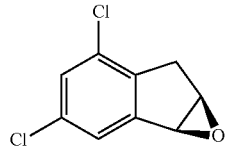
INT-I7C

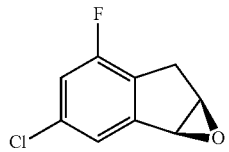
INT-I7D

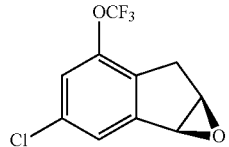
INT-I7E

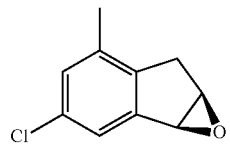
INT-I7F

General Scheme for Aminoindanol Synthesis

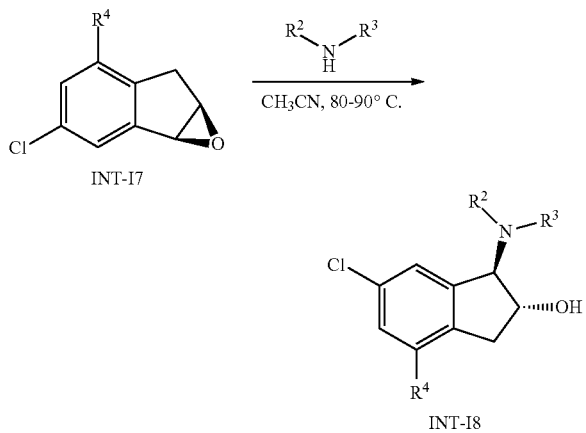

To a round-bottom flask was added epoxide INT-I7 (1 equiv), the desired amine $R^2R^3NH$ (2 equiv), and $CH_3CN$ (0.16 M). The resulting solution was heated to reflux for 16 h. The resulting mixture was concentrated under vacuum. The residue was applied onto a silica gel column with ethyl acetate/petroleum ether (1:3-1:2) providing the aminoindanol INT-I8.

The following intermediates are made by applying the above procedures to the appropriate starting epoxides and amines:

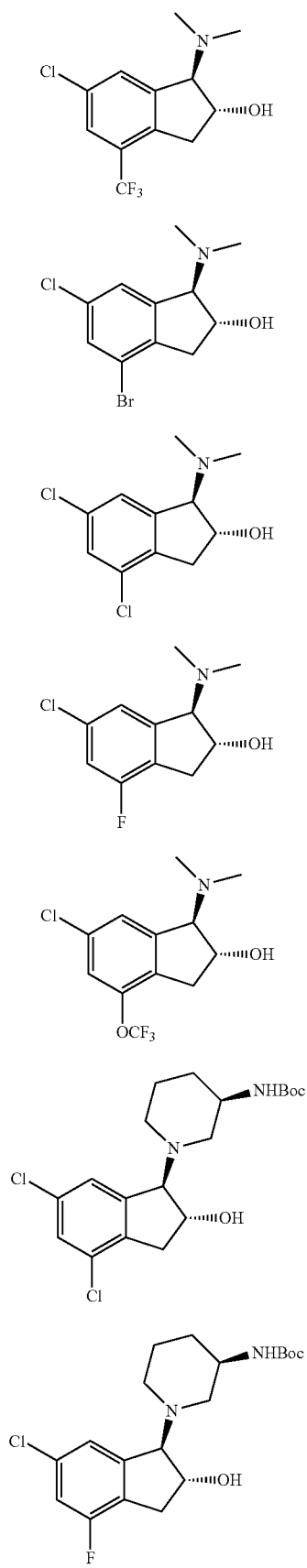
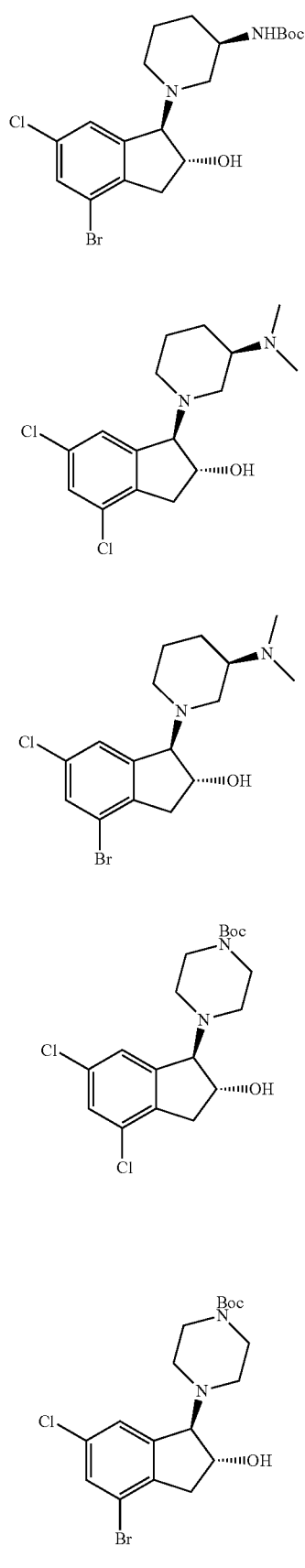

Subsequent Substitutions of Aminoindanols

Scheme 1:

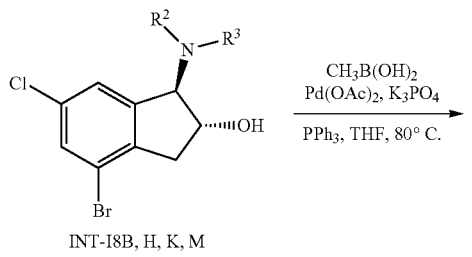

INT-I8B, H, K, M

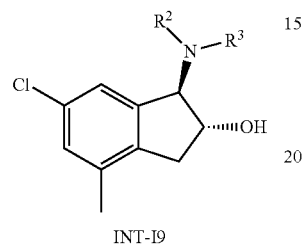

INT-I9

To a round-bottom flask purged and maintained with an inert atmosphere of nitrogen was added INT-I8 bromide (1 equiv), CH$_3$B(OH)$_2$ (1.5 equiv), PPh$_3$ (0.10 equiv), K$_3$PO$_4$ (4 equiv), tetrahydrofuran (0.3 M), and Pd(OAC)$_2$ (0.05 equiv). The resulting solution was stirred for 2 h at 80° C. The reaction was then quenched by the addition of H$_2$O and extracted with 3× ethyl acetate. The organic layers were combined, dried over anhydrous sodium sulfate, filtered, and concentrated under vacuum. The residue was applied onto a silica gel column with CH$_2$Cl$_2$/methanol (10:1). The collected fractions were combined and concentrated under vacuum providing the 4-methyl substituted aminoindanols INT-I9.

The following intermediates are made by applying the above procedures to the appropriate starting 4-bromo aminoindanols:

INT-I9A

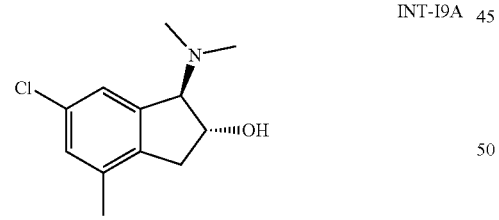

INT-I9B

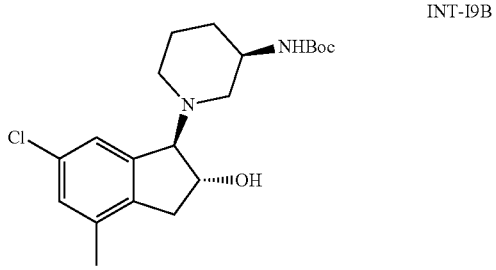

INT-I9C

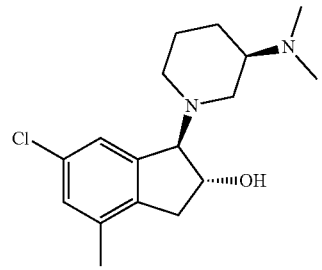

INT-I9D

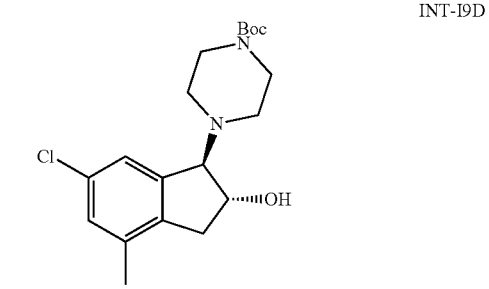

Scheme 2:

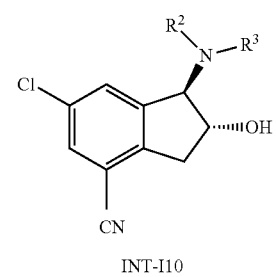

INT-I8B, H, K, M

INT-I10

To a round-bottom flask purged and maintained with an inert atmosphere of nitrogen was added 4-bromoaminoindanol INT-I8 (1 equiv), Zn(CN)$_2$ (0.60 equiv), Pd(PPh$_3$)$_4$ (0.10 equiv), and NMP (DMF on the scheme) (0.4 M). The resulting slurry was stirred overnight at 95° C. The reaction slurry was cooled and extracted with 3× ethyl acetate. The combined organic layers were washed with 3× brine, dried over anhydrous sodium sulfate, filtered, and concentrated. The residue was applied onto a silica gel column with ethyl acetate/petroleum ether (1:1) providing the 4-cyano substituted aminoindanols INT-I10.

The following intermediates are made by applying the above procedures to the appropriate starting 4-bromo aminoindanols:

INT-I10A

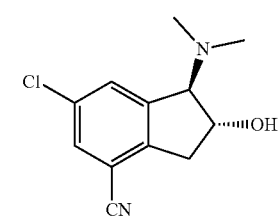

INT-I10B

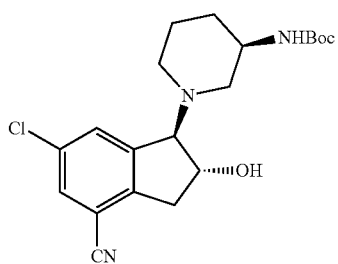

Scheme 3:

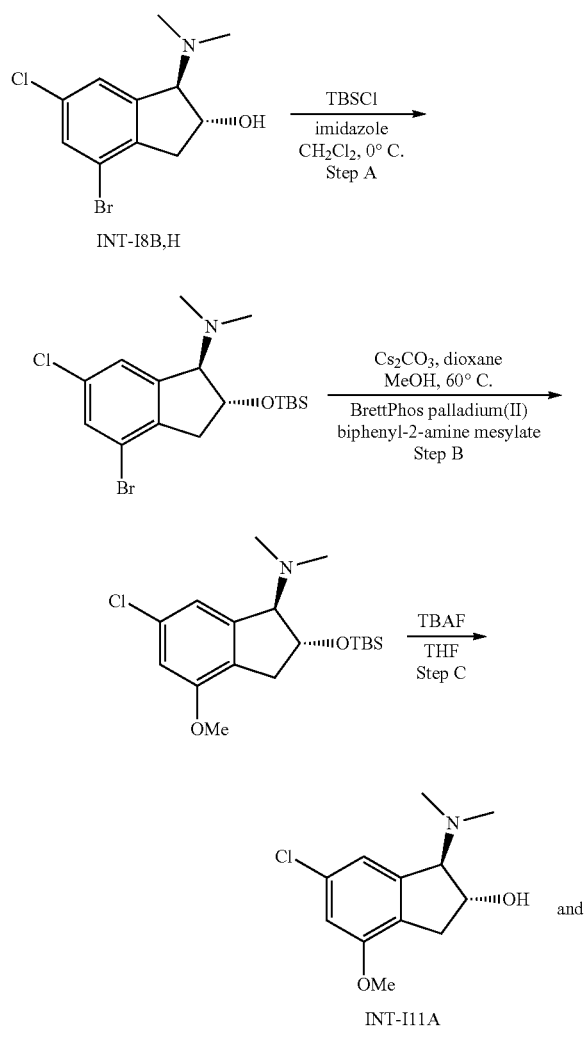

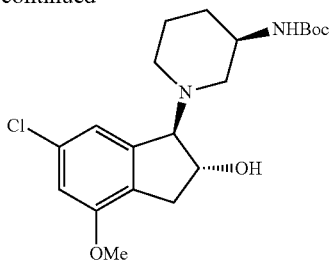

INT-I11B
from INT-I8H

Step A: To a round-bottom flask purged and maintained with an inert atmosphere of nitrogen was added 4-bromoaminoindanol INT-I8B (or INT-I8H) (1 equiv), CH$_2$Cl$_2$ (0.25 M), and imidazole (3 equiv). This was followed by the addition of TBSCl (1.5 equiv) in several batches at 0° C. The resulting slurry was stirred overnight at room temperature. The reaction was quenched by the addition of H$_2$O and extracted with 3× ethyl acetate. The organic layers were combined, washed with 1× brine, dried over anhydrous sodium sulfate, filtered, and concentrated under vacuum. The residue was applied onto a silica gel column with ethyl acetate/petroleum ether (1/10) providing the TBS-protected intermediates.

Step B: To a round-bottom flask purged and maintained with an inert atmosphere of nitrogen was added the TBS-protected aminoindanol (1 equiv), Cs$_2$CO$_3$ (3 equiv), and methanol (8 equiv). A solution of 3rd Generation BrettPhos precatalyst (0.05 equiv) in dioxane (0.5 M) was added. The resulting slurry was stirred for 2 h at 60° C. in an oil bath. The reaction was quenched by the addition of H$_2$O and extracted with 3× ethyl acetate. The organic layers were combined, washed with 1× brine, dried over anhydrous sodium sulfate, filtered, and concentrated under vacuum. The residue was applied onto a silica gel column with ethyl acetate/petroleum ether (1/5) providing the 4-methoxy substituted aminoindanol TBS-ethers.

Step C: To a round-bottom flask purged and maintained with an inert atmosphere of nitrogen was added 4-methoxy substituted aminoindanol TBS-ether (1 equiv) and tetrahydrofuran (0.5 M). TBAF (1.5 equiv, 1M THF solution) was added and the resulting solution stirred for 1 h at room temperature. The reaction slurry was diluted with 1:1 EtOAc:Et$_2$O and washed with 3× H$_2$O. The mixture was dried over anhydrous sodium sulfate, filtered, and concentrated under vacuum. The residue was applied onto a silica gel column with ethyl acetate/petroleum ether (1/1) providing 4-methoxy substituted aminoindanols INT-I11A and B.

General Scheme for Monomer Synthesis:

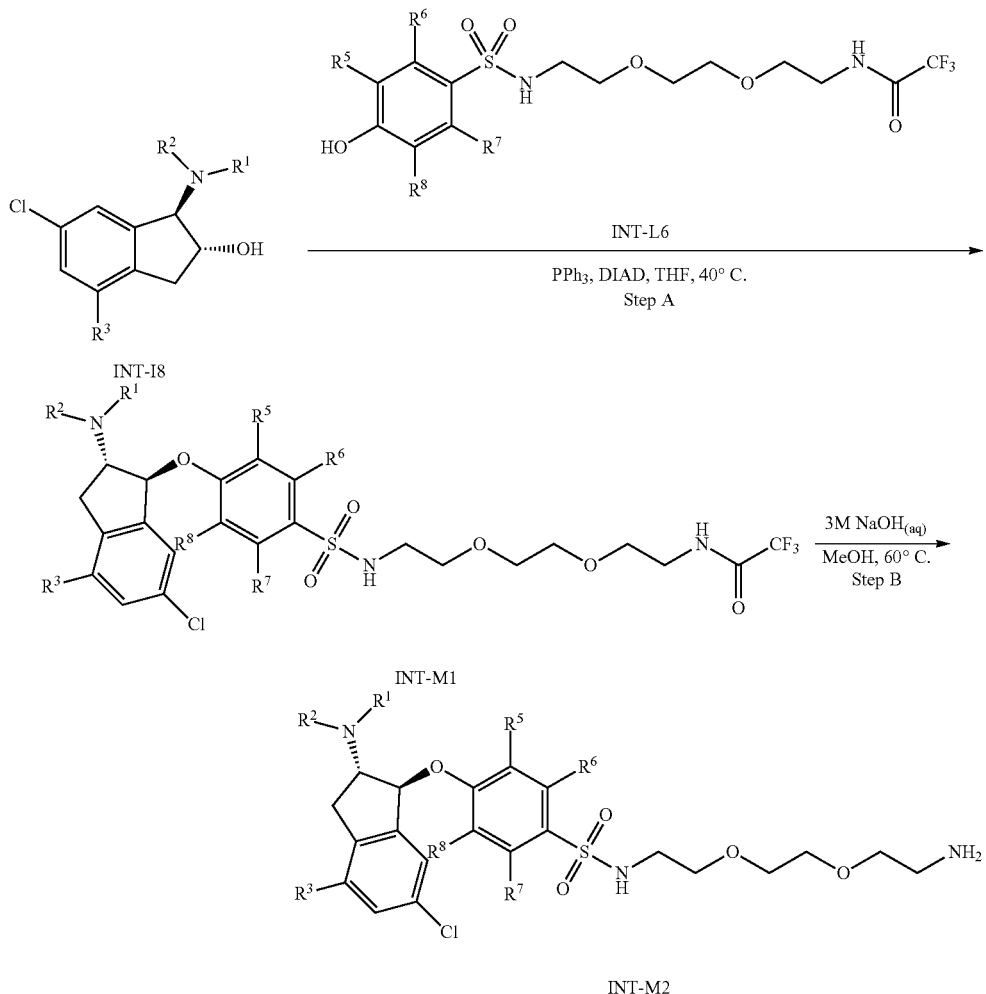

Step A: To a round-bottom flask was added aminoindanol INT-I8 (1 equiv) and tetrahydrofuran (0.2 M), followed by the addition of phenol linker INT-L6 (1.1 equiv) and heating to 40° C. To this slurry was added PPh$_3$ (2 equiv) and DIAD (1.5 equiv). The resulting solution was stirred for 1.5 h at 40° C. The resulting mixture was concentrated under vacuum and diluted with CH$_2$Cl$_2$. The residue was applied onto a silica gel column with ethyl acetate/petroleum ether (1:1) providing indane monomer INT-M1.

Step B: To a round-bottom flask was added indane monomer INT-M1 (1 equiv), methanol (0.1 M), and sodium hydroxide (3 M$_{(aq)}$, 3 equiv). The resulting solution was stirred for 1.5 h at 60° C. The resulting mixture was concentrated under vacuum and diluted with CH$_2$Cl$_2$. The residue was applied onto a silica gel column with ethyl acetate (100%) providing indane amine monomer INT-M2.

The following intermediates are made by applying the above procedures to the appropriate starting aminoindanols INT-I8 and linkers INT-L6.

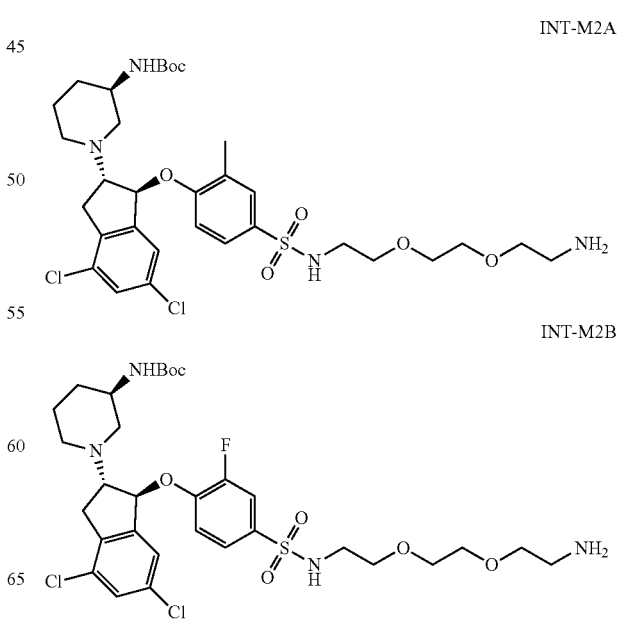

INT-M2C
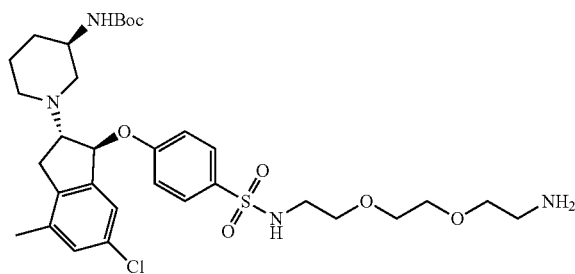
INT-M2H
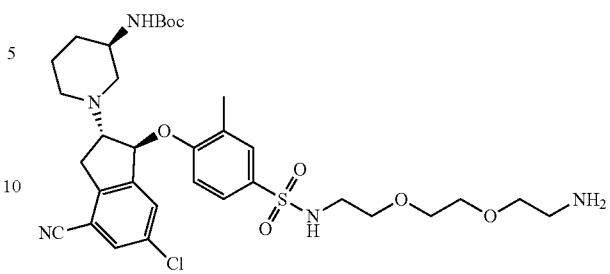
INT-M2D
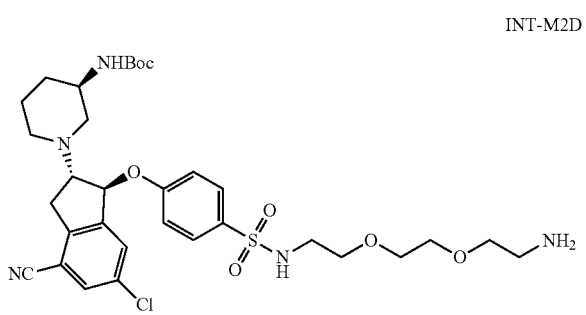
INT-M2J
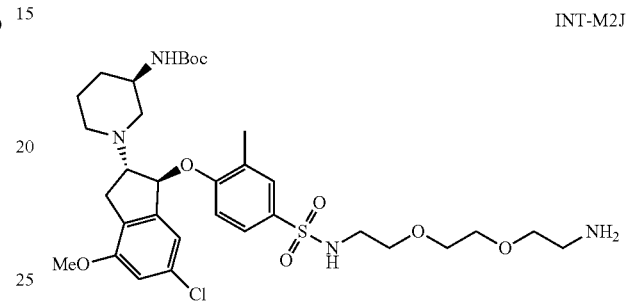
INT-M2E
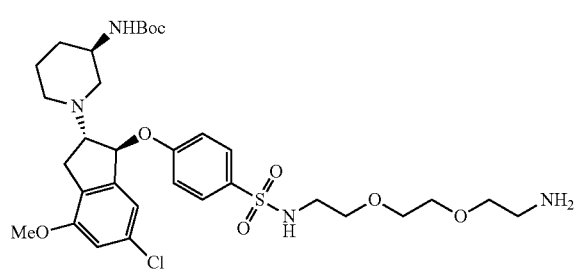
INT-M2K
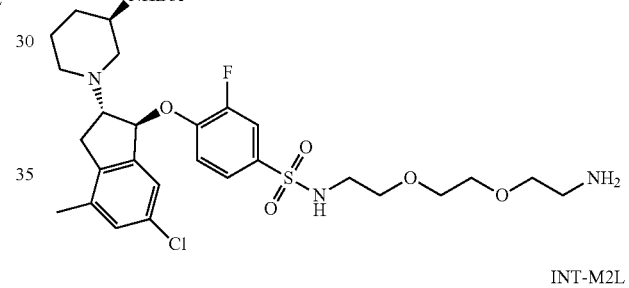
INT-M2F
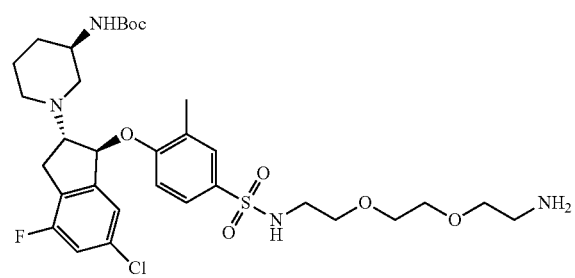
INT-M2L
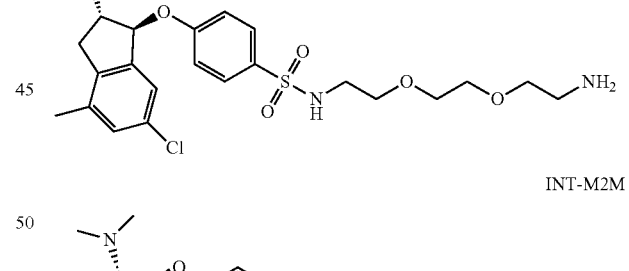
INT-M2G
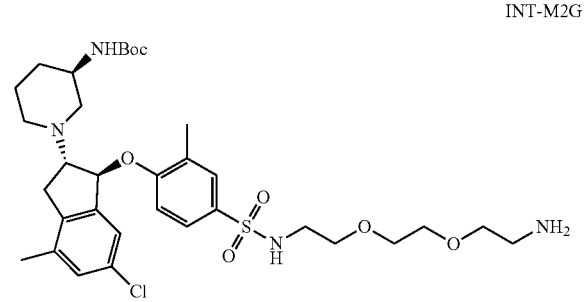
INT-M2M
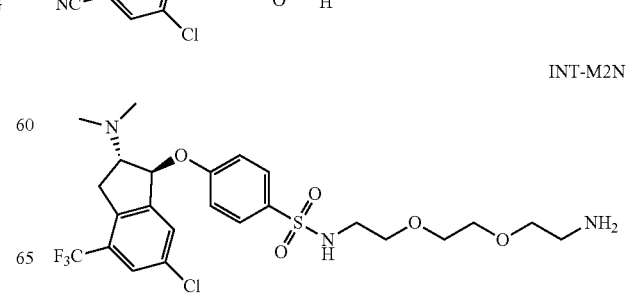
INT-M2N INT-M2O
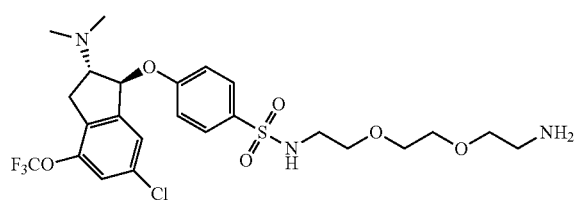
INT-M2P
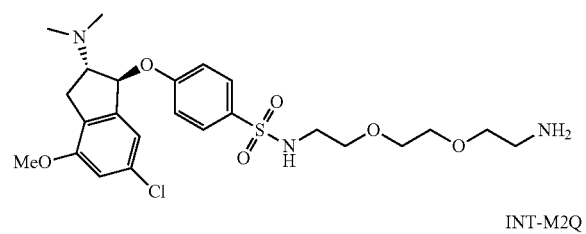
INT-M2Q
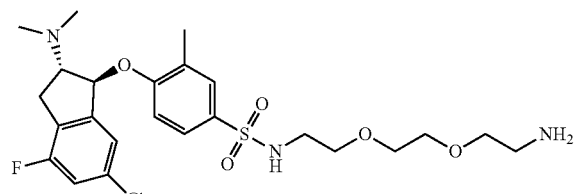
INT-M2R
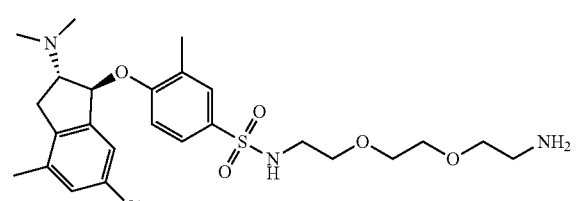
INT-M2S
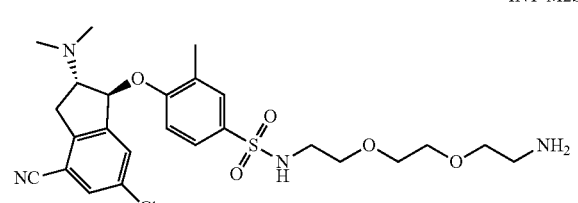
INT-M2T
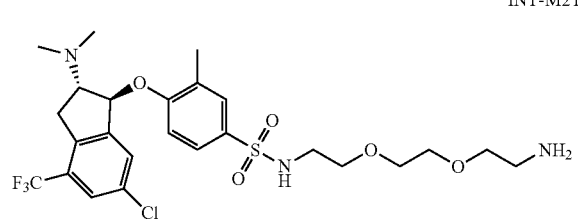
INT-M2U
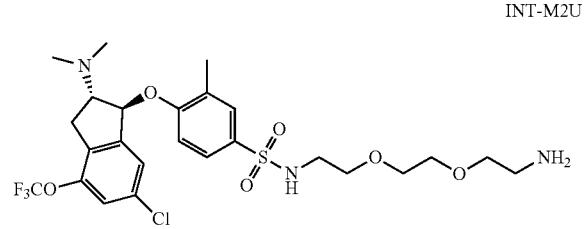
INT-M2V
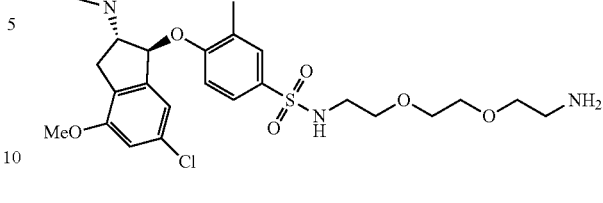
INT-M2W
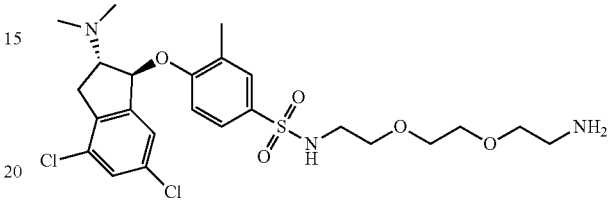
INT-M2X
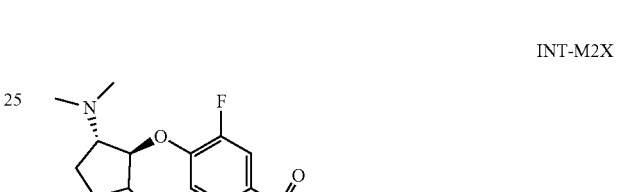
INT-M2Y
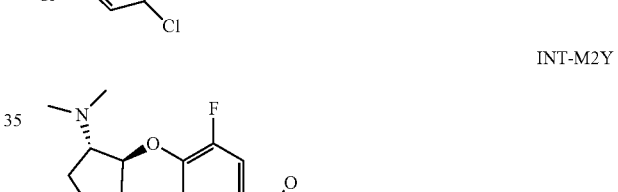
INT-M2Z
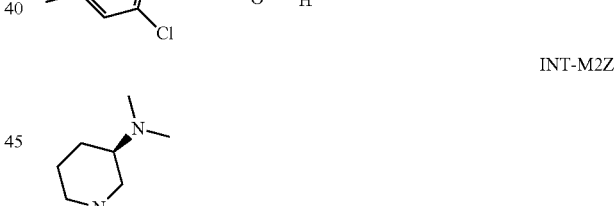
INT-M2AA
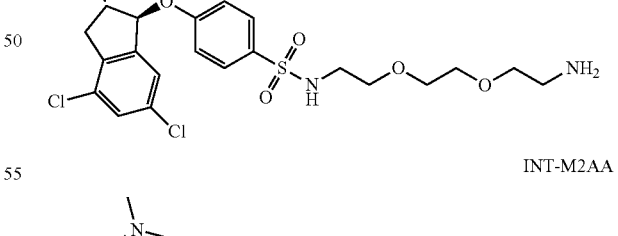
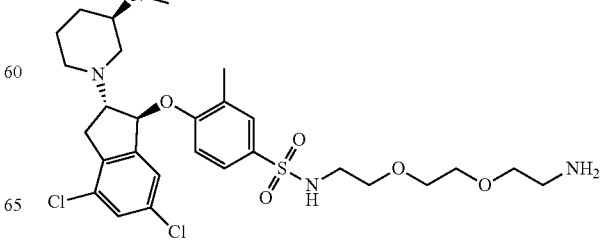

INT-M2AB
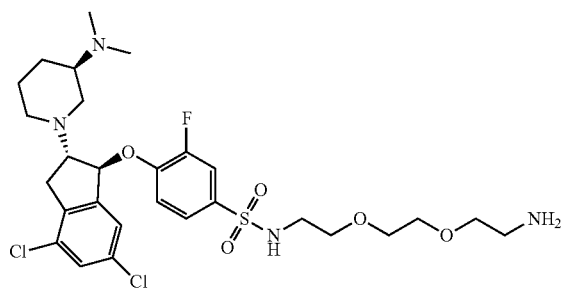
INT-M2AG
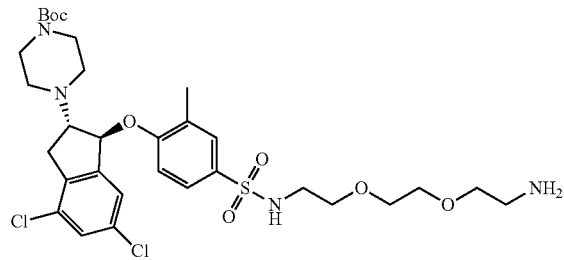
INT-M2AC
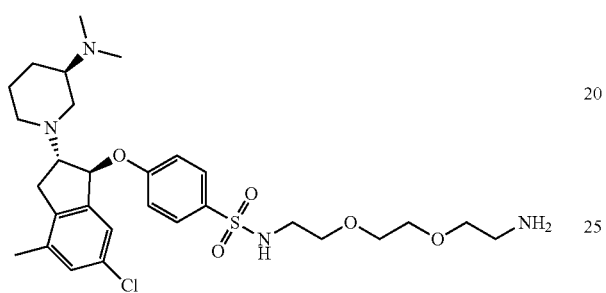
INT-M2AH
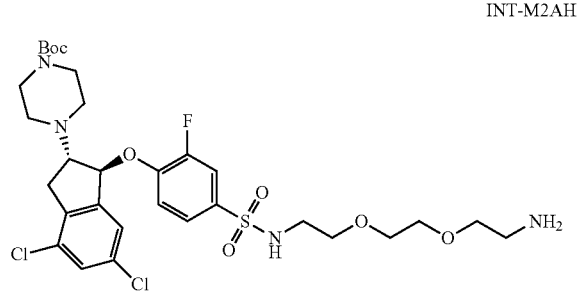
INT-M2AD
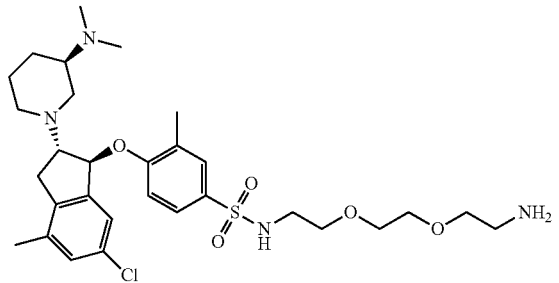
INT-M2AI
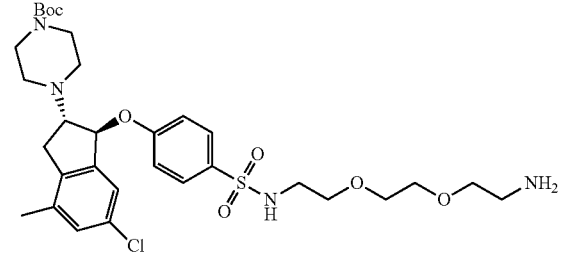
INT-M2AE
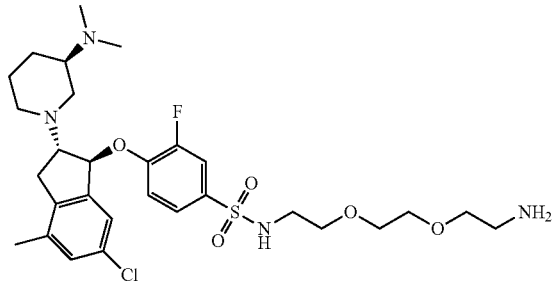
INT-M2AJ
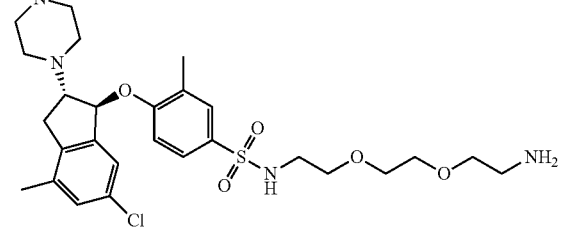
INT-M2AF
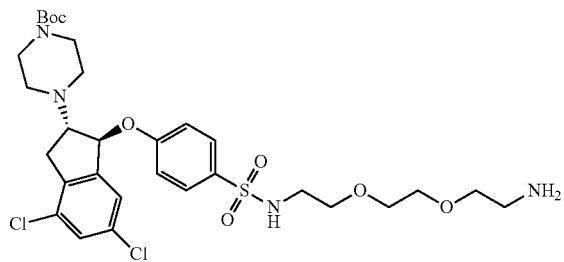
INT-M2AK
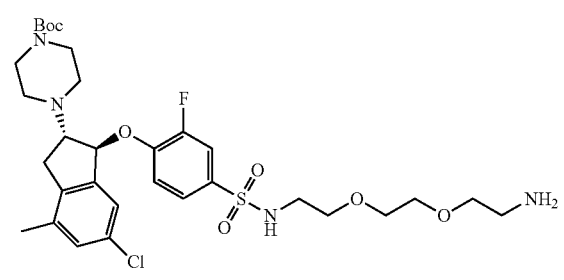

General Scheme for Dimer Formation (Non-Protected Analogs):

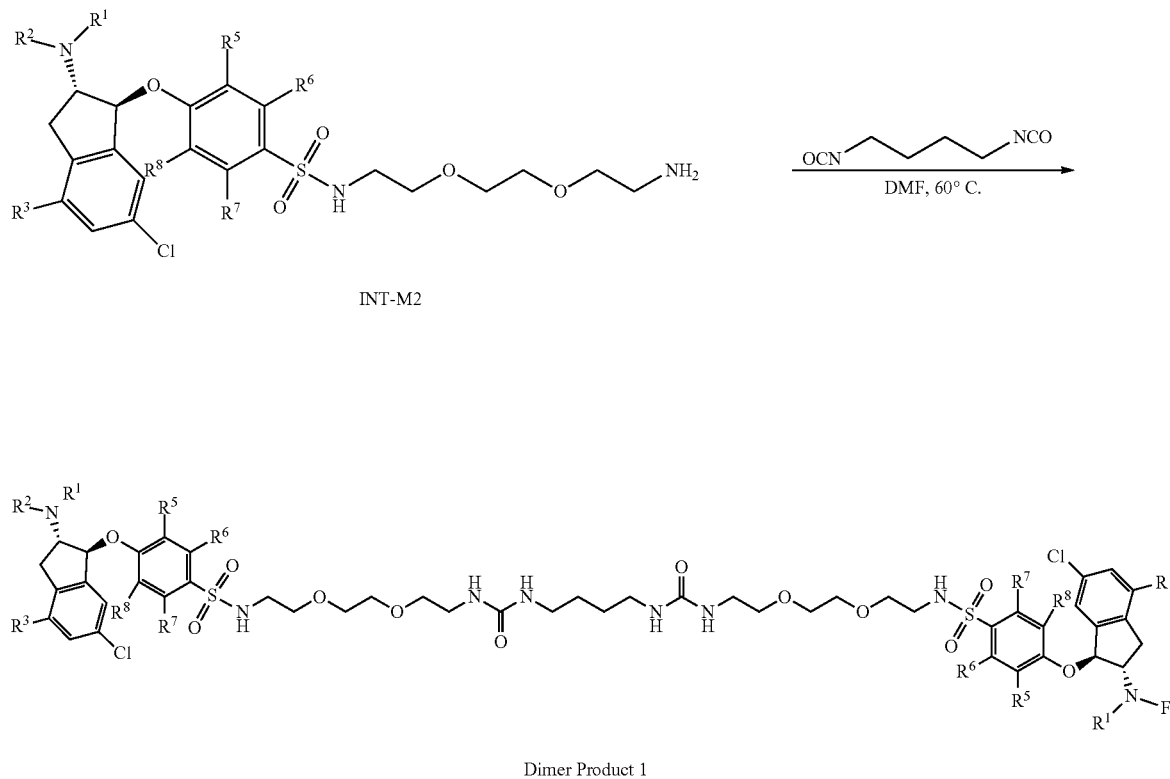

INT-M2

Dimer Product 1

To a round-bottom flask was added INT-M2 (1 equiv), N,N-dimethylformamide (DMF, 0.12 M), and 1,4-diisocyanatobutane (0.40 equiv). The resulting solution was stirred for 2 h at 60° C. The resulting mixture was concentrated under vacuum and diluted with $CH_2Cl_2$. The residue was applied onto a silica gel column with chloroform/methanol (10:1) providing the desired dimer Product 1. Final products were purified by Preparative HPLC with the following conditions: Column, XBridge C18 OBD Preparative Column, 19*250 mm, mobile phase, water (0.05% TFA) and $CH_3CN$ (10.0% $CH_3CN$ up to 70.0% in 8 min); Detector, UV 254 nm. The final products were generally isolated as the TFA salts or exchanged to the hydrochloride salts.

General Scheme for Deprotection of Dimers:

To a round-bottom flask was added Boc-protected dimers (1 equiv) and 3:1 $CH_2Cl_2$:TFA (~0.05 M). The resulting solution was stirred for 2 h at room temperature. The resulting mixture was concentrated under vacuum. The crude product was purified by Preparative HPLC with the following conditions: Column, XBridge C18 OBD Preparative Column, 19*250 mm; mobile phase, water (0.05% TFA) and $CH_3CN$ (10.0% $CH_3CN$ up to 70.0% in 8 min); Detector, UV 254 nm. The final dimer Products 1 were generally isolated as the TFA salts or exchanged to the hydrochloride salts.

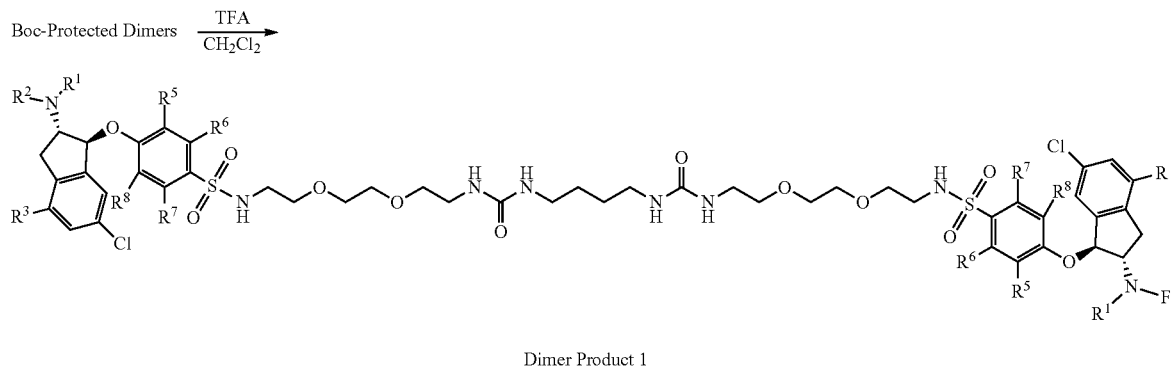

Dimer Product 1

General Scheme for Linker Synthesis

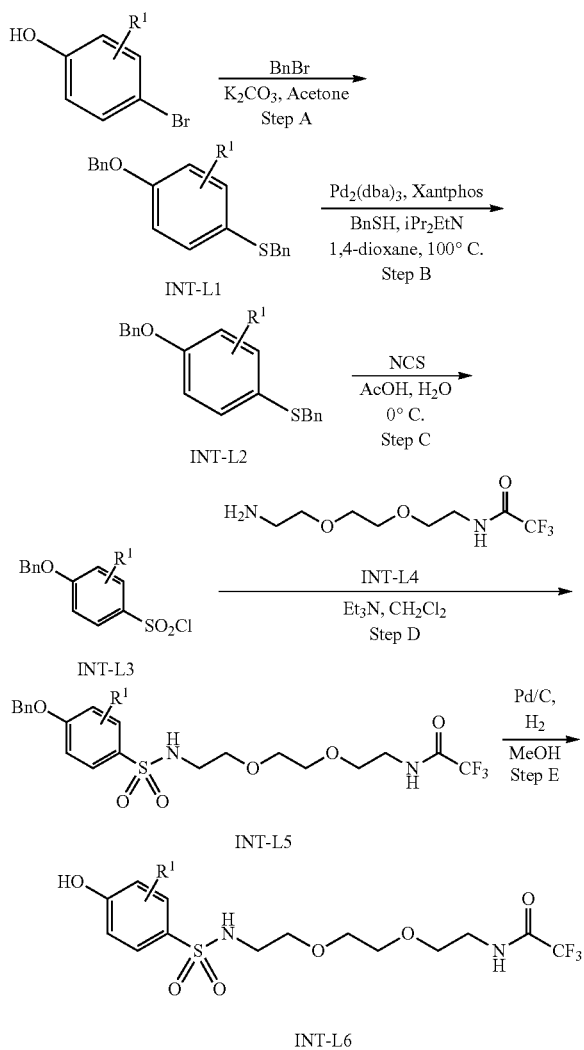

Step A: To a 250-mL round-bottom flask was added the desired substituted-bromophenol (1 equiv), acetone (0.45 M), potassium carbonate (5 equiv), and benzyl bromide (2.5 equiv). The resulting solution was stirred for 4 h at room temperature. The resulting solution was diluted with 30 mL of H$_2$O. The resulting mixture was concentrated under vacuum and extracted with of ethyl acetate. The organic layers were combined and washed with 3× H$_2$O and 1× brine. The mixture was dried over anhydrous sodium sulfate, filtered, and the resulting mixture concentrated under vacuum. The residue was applied onto a silica gel column with petroleum ether providing the desired benzylethers INT-L1.

Step B: To a round-bottom flask purged and maintained with an inert atmosphere of nitrogen was added benzylether INT-L1 (1 equiv), 1,4-dioxane (0.16 M), N,N-diisopropylethylamine (2 equiv), benzylmercaptan (2 equiv), Pd$_2$(dba)$_3$·CHCl$_3$ (0.05 equiv), and Xantphos (0.10 equiv). The resulting solution was stirred overnight at 100° C. The resulting slurry was concentrated under vacuum and diluted with of H$_2$O. The resulting solution was extracted with of ethyl acetate and the organic layers combined and washed with 3× H$_2$O and 1× brine. The mixture was dried over anhydrous sodium sulfate, filtered, and the resulting mixture was concentrated under vacuum. The residue was applied onto a silica gel column with petroleum ether providing the desired thioethers INT-L2.

Step C: To a round-bottom flask was added thioether INT-L2 (1 equiv), acetic acid (0.25 M), and water (3 equiv). This was followed by the addition of N-chlorosuccinimide (NCS, 5 equiv) in several batches at 0° C. The resulting solution was stirred for 1 h at room temperature. The resulting slurry was concentrated under vacuum and diluted with H$_2$O. The resulting solution was extracted with of ethyl acetate and the organic layers combined and washed with 3× H$_2$O and 1× brine. The mixture was dried over anhydrous sodium sulfate, filtered, and concentrated under vacuum. The residue was applied onto a silica gel column with petroleum ether providing the sulfonyl chloride INT-L3.

Step D: To a round-bottom flask was added sulfonyl chloride INT-L3 (1 equiv), CH$_2$Cl$_2$ (0.2 M), triethylamine (5 equiv), and N-[2-[2-(2-aminoethoxy)ethoxy]ethyl]-2,2,2-trifluoroacetamide (INT-L4, 2 equiv). The resulting solution was stirred overnight at room temperature. The resulting mixture was concentrated under vacuum and diluted with of H$_2$O. The resulting shiny was extracted with CH$_2$Cl$_2$ and the organic layers combined and washed with 3× H$_2$O and 1× brine. The mixture was dried over anhydrous sodium sulfate, filtered, and concentrated under vacuum. The residue was applied onto a silica gel column with CH$_2$Cl$_2$/methanol (30:1) providing the sulfonamide INT-L5.

Step E: To a round-bottom flask purged and maintained with an inert atmosphere of H$_2$, was added sulfonamide INT-L5 (1 equiv), methanol (0.1 M), and palladium on carbon (~10-20%). The resulting slurry was stirred for 1 h at room temperature. The solids were filtered out and the resulting mixture was concentrated under vacuum. The residue was applied onto a silica gel column with ethyl acetate/petroleum ether (1:1) providing the desired phenol INT-L6.

The following intermediates were made by applying the above procedures to the appropriate phenol:

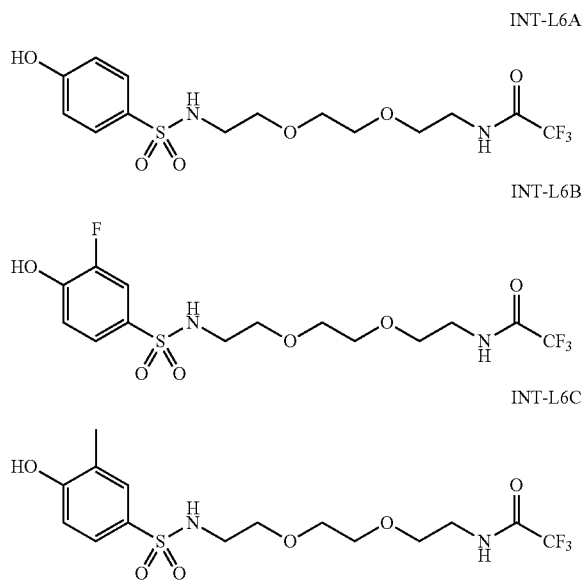

-continued
INT-L6D
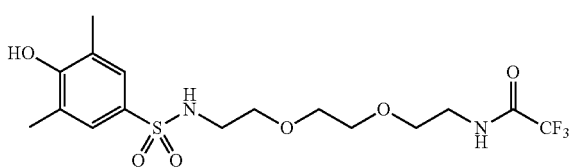
INT-L6E
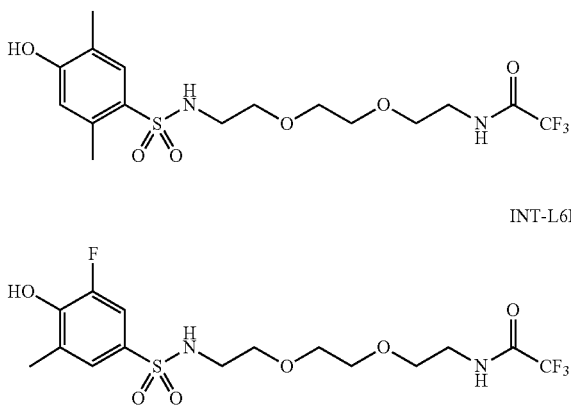
INT-L6F
INT-L6G
INT-L6H
INT-L6I
INT-L6J
INT-L6K
-continued
INT-L6L
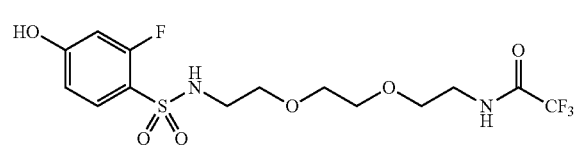
General Scheme for Indane Epoxide Synthesis
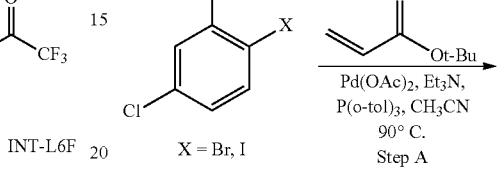
X = Br, I
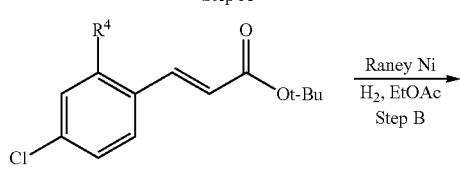
INT-I1
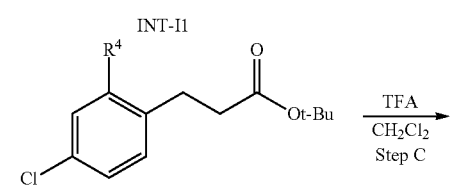
INT-I2
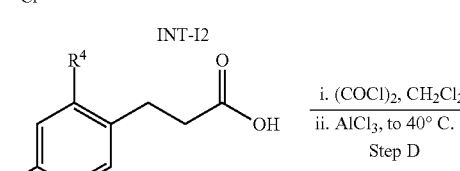
INT-I3
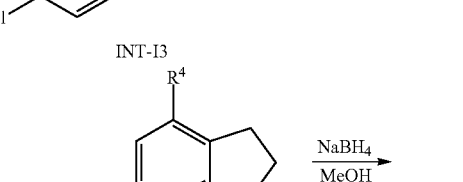
INT-I4
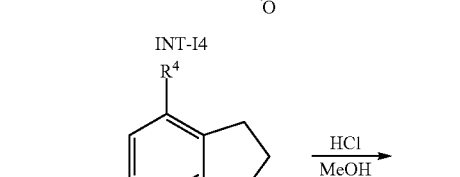
INT-I5
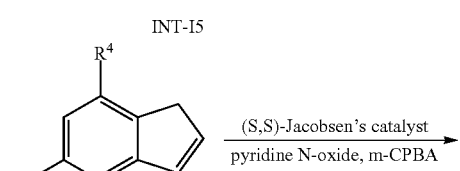
INT-I6

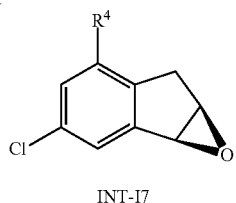

INT-I7

Step A: To a round-bottom flask purged and maintained with an inert atmosphere of nitrogen was added the desired $R^4$-substituted bromide/iodide (1 equiv), CH$_3$CN (0.25 M), tert-butyl prop-2-enoate (equiv), diisopropylethylamine (3 equiv), P(o-tol)$_3$ (0.20 equiv), and Pd(OAc)$_2$ (0.10 equiv). The resulting solution was stirred overnight at 95° C. The solids were removed by filtration and the filtrate was concentrated under vacuum. The resulting slurry was diluted with water and extracted with 3× CH$_2$Cl$_2$. The organic layers were combined and dried over anhydrous sodium sulfate, filtered, and concentrated. The residue was applied onto a silica gel column with ethyl acetate/petroleum ether (1:500) providing the cinnamate INT-I1.

Step B: To a round-bottom flask was cinnamate INT-I1 (1 equiv), ethyl acetate (0.1 M), and Raney Ni. The flask was purged and filled with H$_{2(g)}$, cycling three times, leaving a positive H$_2$ atmosphere. The resulting solution was stirred for 2 h at room temperature. The solids were filtered out and the resulting mixture was concentrated under vacuum providing the hydrocinnamate INT-I2.

Step C: To a round-bottom flask was added hydrocinnamate INT-I2 (1 equiv) and 2:1 CH$_2$Cl$_2$:TFA (0.4 M). The resulting slurry was stirred for 1 h at room temperature. The resulting mixture was concentrated under vacuum and the residue was applied onto a silica gel column with ethyl acetate/petroleum ether (0-10%). The collected fractions were combined and concentrated under vacuum providing the hydrocinnamic acid INT-I3.

Step D: To a 3-necked round-bottom flask was added hydrocinnamic acid INT-I3 (1 equiv) and CH$_2$Cl$_2$ (0.4 M). The reaction slurry was cooled to 0° C. and treated with (COCl)$_2$ (2 equiv) dropwise. The resulting solution was stirred for 2 h at room temperature. The resulting solution was concentrated under vacuum. To a 3-necked round-bottom flask was added AlCl$_3$ (2 equiv) and CH$_2$Cl$_2$ (0.4 M). The product of the first step dissolved in CH$_2$Cl$_2$ and added dropwise to this AlCl$_3$ slurry. The resulting solution was stirred for 2 h at 40° C. in an oil bath. The reaction was then quenched by the addition of 2N HCl$_{(aq)}$. The resulting solution was extracted with 3× CH$_2$Cl$_2$ and the organic layers combined and concentrated under vacuum. The residue was applied onto a silica gel column with ethyl acetate/petroleum ether (0-1:10). The collected fractions were combined and concentrated under vacuum providing the indanone INT-I4.

Step E: To a round-bottom flask was indanone INT-I4 (1 equiv), methanol (0.7 M), and NaBH$_4$ (2 equiv). The resulting solution was stirred for 1 h at room temperature. The reaction was then quenched by the addition of 20 mL of water and extracted with 3× CH$_2$Cl$_2$. The organic layers were combined and washed with 3× brine. The organic layer was dried over anhydrous sodium sulfate, filtered, and concentrated under vacuum providing indanol INT-I5.

Step F: To a round-bottom flask was added indanol INT-I5 (1 equiv), methanol (0.5 M), and HCl (half volume of methanol). The resulting solution was stirred for 1 h at room temperature. The resulting mixture was quenched with methanol and concentrated under vacuum. The resulting slurry was extracted with 3× n-hexane and the organic layers combined. The residue was applied onto a silica gel column with n-hexane providing indene INT-I6.

Step G: To a 3-necked round-bottom flask was added indene INT-I6 (1 equiv). CH$_2$Cl$_2$ (0.08M, dried over magnesium sulfate), pyridine N-oxide (5 equiv in CH$_2$Cl$_2$ solution dried over magnesium sulfate), and (S,S)-Jacobsen's catalyst (0.05 equiv). The resulting solution was stirred for 10 min at 0° C. followed by the addition of m-CPBA (2 equiv) in portions at 0° C. The resulting slurry was stirred for an additional 1 h at 0° C. The reaction was then quenched by the addition of sodium hydroxide (3 M$_{(aq)}$, approx. 13 equiv). The resulting slurry was washed with 1× H$_2$O and 1× brine. The mixture was dried over anhydrous sodium sulfate, filtered, and concentrated. The residue was applied onto a silica gel column with ethyl acetate/petroleum ether (1:30-1:15) providing the epoxide INT-I7.

The following intermediates were made by applying the above procedures to the appropriate starting aryl compounds (starting materials are available commercially at different stages of this sequence):

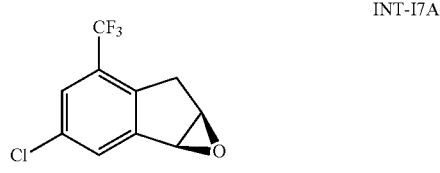

INT-I7A

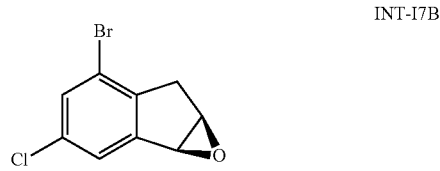

INT-I7B

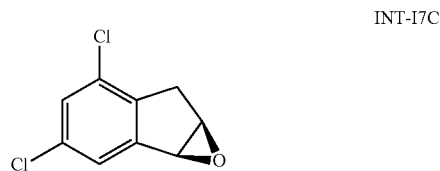

INT-I7C

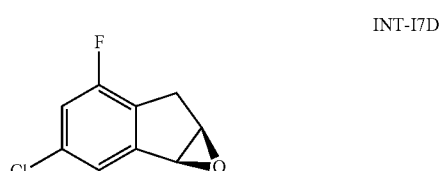

INT-I7D

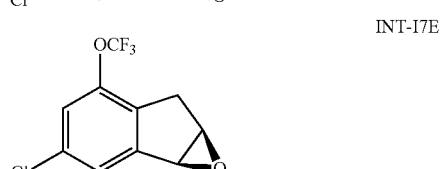

INT-I7E

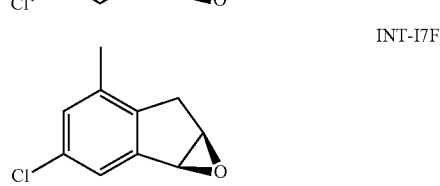

INT-I7F

General Scheme for Aminoindanol Synthesis

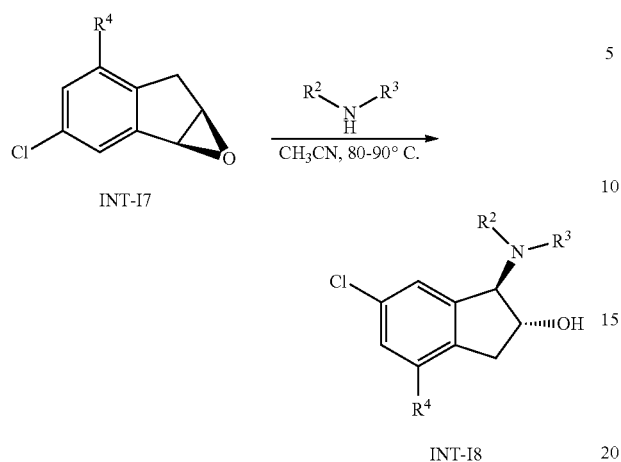

INT-I7

INT-I8

To a round-bottom flask was added epoxide INT-I7 (1 equiv), the desired amine R²R³NH (2 equiv), and CH₃CN (0.16 M). The resulting solution was heated to reflux for 16 h. The resulting mixture was concentrated under vacuum. The residue was applied onto a silica gel column with ethyl acetate/petroleum ether (1:3-1:2) providing the aminoindanol INT-I8.

The following intermediates are made by applying the above procedures to the appropriate starting epoxides and amines:

INT-I8A

INT-I8B

INT-I8C

INT-I8D

INT-I8E

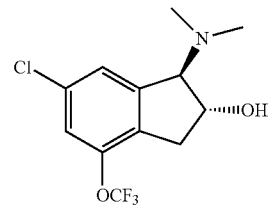

INT-I8F

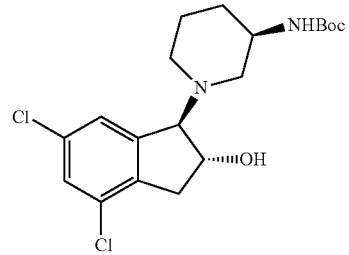

INT-I8G

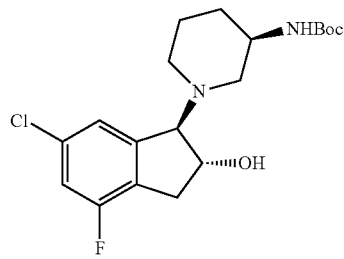

INT-I8H

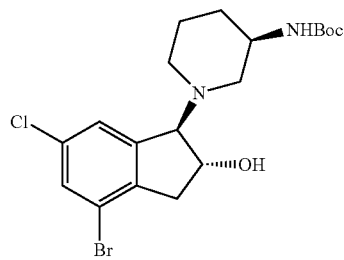

INT-I8J

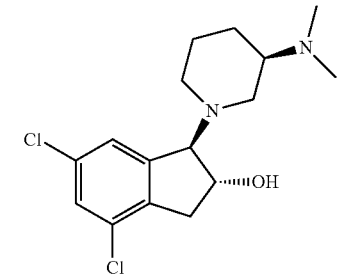

INT-I8K

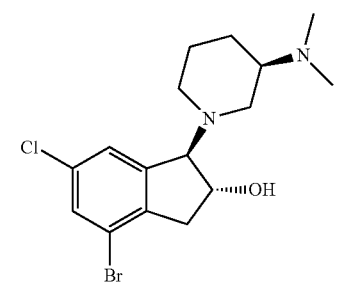

INT-I8L

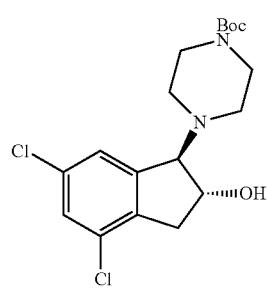

INT-I8M

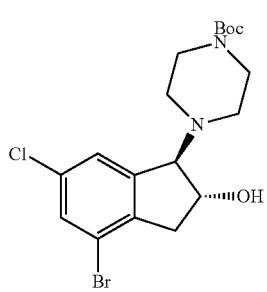

Subsequent Substitutions of Aminoindanols

Scheme 1:

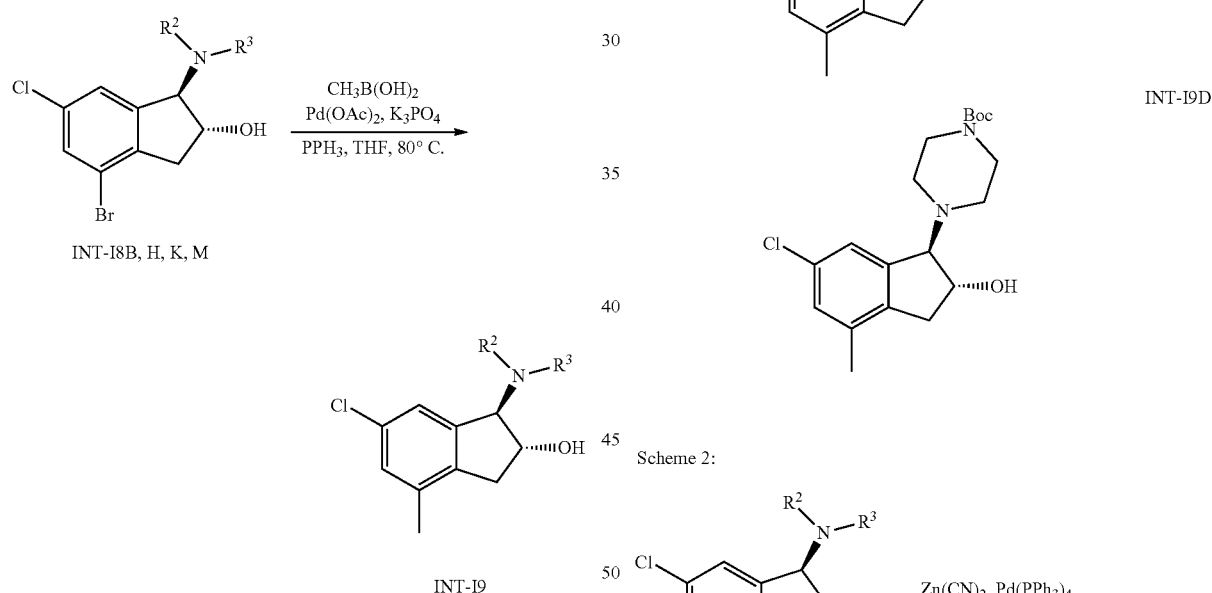

To a round-bottom flask purged and maintained with an inert atmosphere of nitrogen was added INT-I8 bromide (1 equiv), $CH_3B(OH)_2$ (1.5 equiv), $PPh_3$ (0.10 equiv), $K_3PO_4$ (4 equiv), tetrahydrofuran (0.3 M), and $Pd(OAc)_2$ (0.05 equiv). The resulting solution was stirred for 2 h at 80° C. The reaction was then quenched by the addition of $H_2O$ and extracted with 3× ethyl acetate. The organic layers were combined, dried over anhydrous sodium sulfate, filtered, and concentrated under vacuum. The residue was applied onto a silica gel column with $CH_2Cl_2$/methanol (10:1). The collected fractions were combined and concentrated under vacuum providing the 4-methyl substituted aminoindanols INT-I9.

The following intermediates are made by applying the above procedures to the appropriate starting 4-bromo aminoindanols:

Scheme 2:

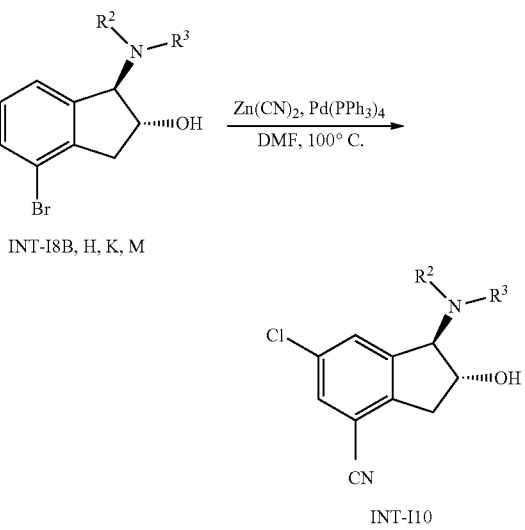

To a round-bottom flask purged and maintained with an inert atmosphere of nitrogen was added 4-bromoaminoindanol INT-I8 (1 equiv), Zn(CN)₂ (0.60 equiv), Pd(PPh₃)₄ (0.10 equiv), and NMP (DMF on the scheme) (0.4 M). The resulting slurry was stirred overnight at 95° C. The reaction slurry was cooled and extracted with 3× ethyl acetate. The combined organic layers were washed with 3× brine, dried over anhydrous sodium sulfate, filtered, and concentrated. The residue was applied onto a silica gel column with ethyl acetate/petroleum ether (1:1) providing the 4-cyano substituted aminoindanols INT-I10.

The following intermediates are made by applying the above procedures to the appropriate starting 4-bromo aminoindanols:

INT-I10A

INT-I10B

Scheme 3:

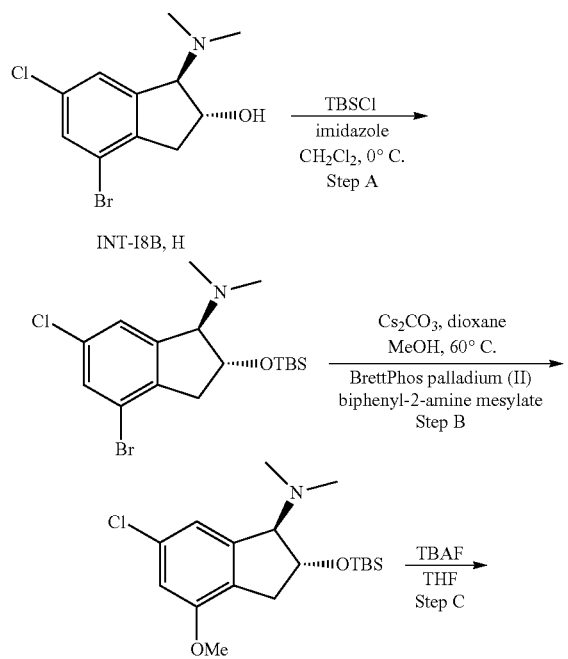

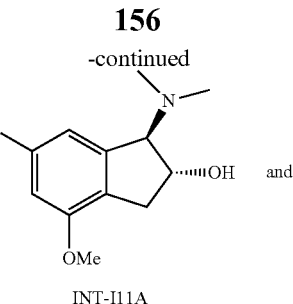

INT-I11A and

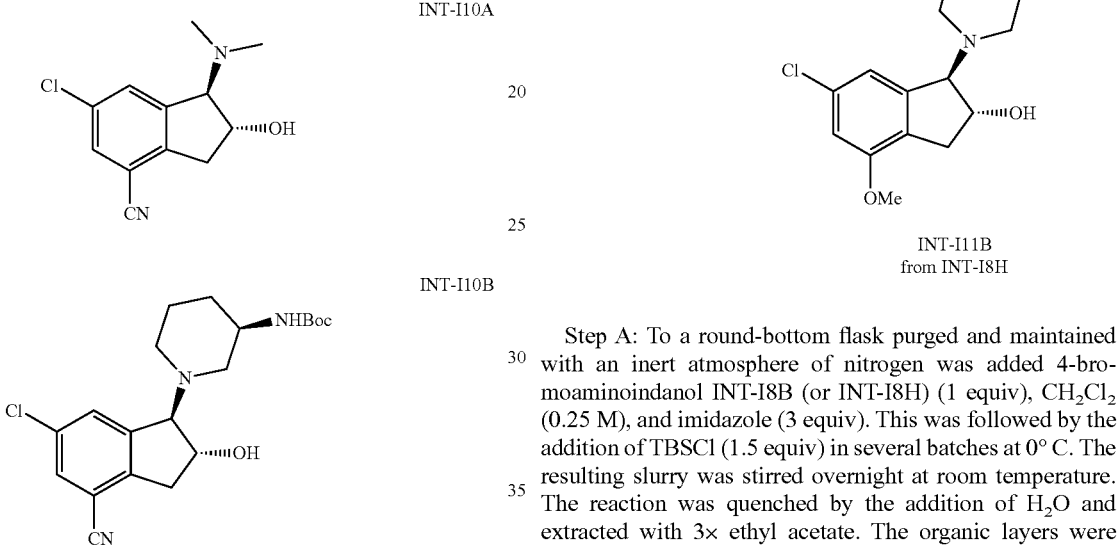

INT-I11B
from INT-I8H

Step A: To a round-bottom flask purged and maintained with an inert atmosphere of nitrogen was added 4-bromoaminoindanol INT-I8B (or INT-I8H) (1 equiv), CH₂Cl₂ (0.25 M), and imidazole (3 equiv). This was followed by the addition of TBSCl (1.5 equiv) in several batches at 0° C. The resulting slurry was stirred overnight at room temperature. The reaction was quenched by the addition of H₂O and extracted with 3× ethyl acetate. The organic layers were combined, washed with 1× brine, dried over anhydrous sodium sulfate, filtered, and concentrated under vacuum. The residue was applied onto a silica gel column with ethyl acetate/petroleum ether (1/10) providing the TBS-protected intermediates.

Step B: To a round-bottom flask purged and maintained with an inert atmosphere of nitrogen was added the TBS-protected aminoindanol (1 equiv), Cs₂CO₃ (3 equiv), and methanol (8 equiv). A solution of 3rd Generation BrettPhos precatalyst (0.05 equiv) in dioxane (0.5 M) was added. The resulting slurry was stirred for 2 h at 60° C. in an oil bath. The reaction was quenched by the addition of H₂O and extracted with 3× ethyl acetate. The organic layers were combined, washed with 1× brine, dried over anhydrous sodium sulfate, filtered, and concentrated under vacuum. The residue was applied onto a silica gel column with ethyl acetate/petroleum ether (1/5) providing the 4-methoxy substituted aminoindanol TBS-ethers.

Step C: To a round-bottom flask purged and maintained with an inert atmosphere of nitrogen was added 4-methoxy substituted aminoindanol TBS-ether (1 equiv) and tetrahydrofuran (0.5 M). TBAF (1.5 equiv. 1M THF solution) was added and the resulting solution stirred for 1 h at room temperature. The reaction slurry was diluted with 1:1 EtOAc:Et₂O and washed with 3× H₂O. The mixture was dried over anhydrous sodium sulfate, filtered, and concentrated under vacuum. The residue was applied onto a silica gel column with ethyl acetate/petroleum ether (1/1) providing 4-methoxy substituted aminoindanols INT-I11A and B.

General Scheme for Monomer Synthesis:

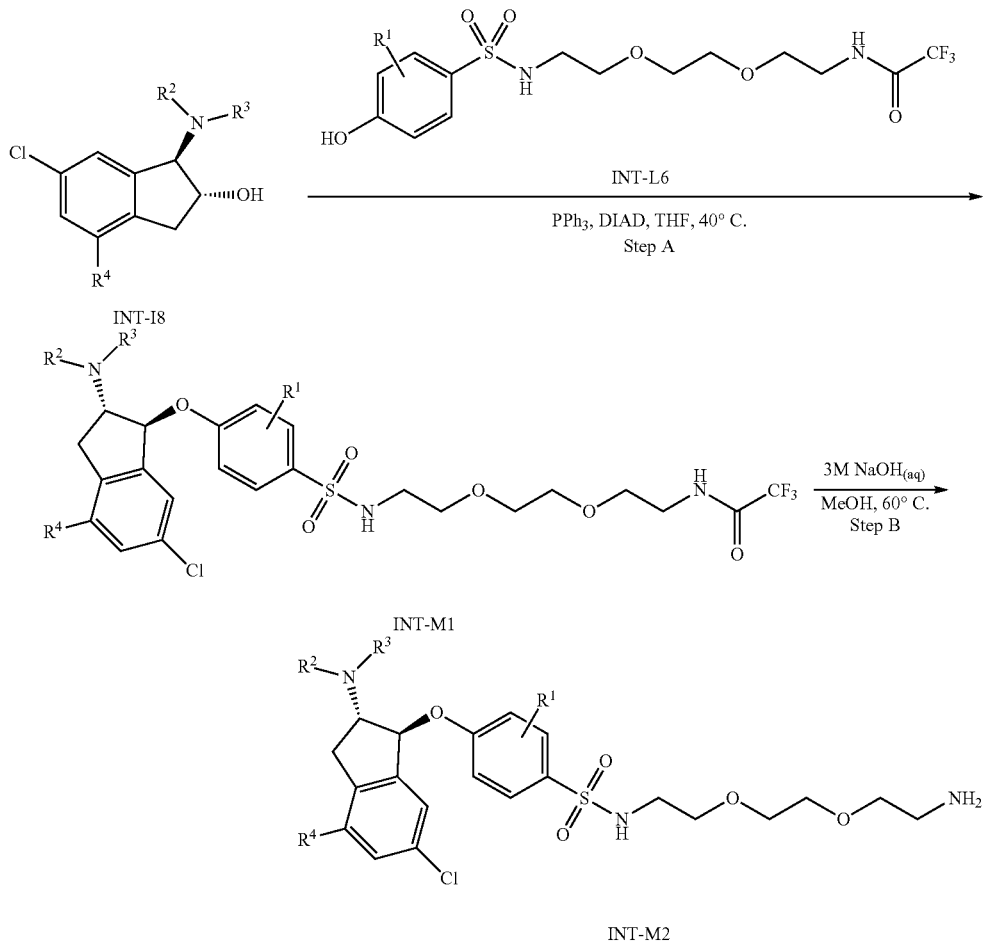

Step A: To a round-bottom flask was added aminoindanol INT-I8 (1 equiv) and tetrahydrofuran (0.2 M), followed by the addition of phenol linker INT-L6 (1.1 equiv) and heating to 40° C. To this slurry was added PPh₃ (2 equiv) and DIAD (1.5 equiv). The resulting solution was stirred for 1.5 h at 40° C. The resulting mixture was concentrated under vacuum and diluted with CH₂Cl₂. The residue was applied onto a silica gel column with ethyl acetate/petroleum ether (1:1) providing indane monomer INT-M1.

Step B: To a round-bottom flask was added indane monomer INT-M1 (1 equiv), methanol (0.1 M), and sodium hydroxide (3 M$_{(aq)}$, 3 equiv). The resulting solution was stirred for 1.5 h at 60° C. The resulting mixture was concentrated under vacuum and diluted with CH₂Cl₂. The residue was applied onto a silica gel column with ethyl acetate (100%) providing indane amine monomer INT-M2.

The following intermediates are made by applying the above procedures to the appropriate starting aminoindanols INT-I8 and linkers INT-L6:

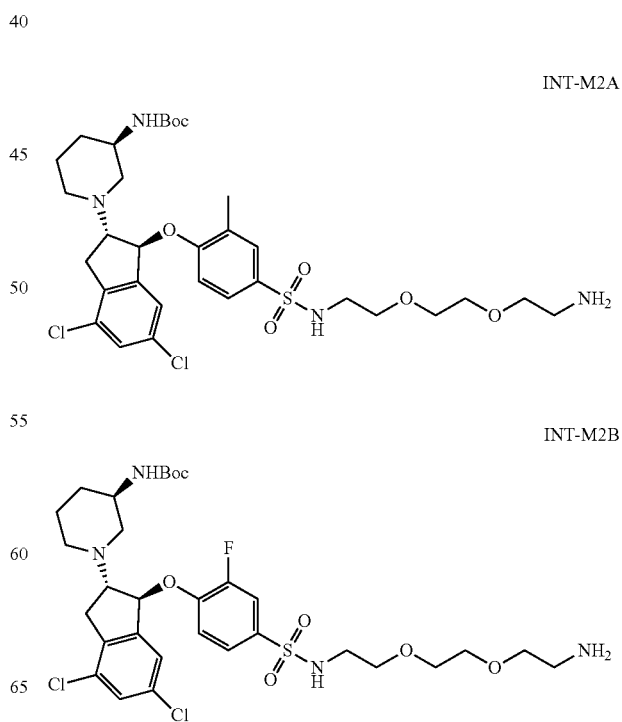

159
-continued
INT-M2C
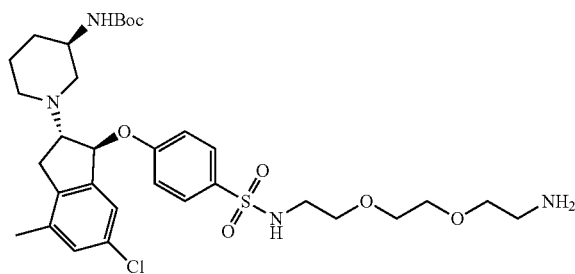
INT-M2D
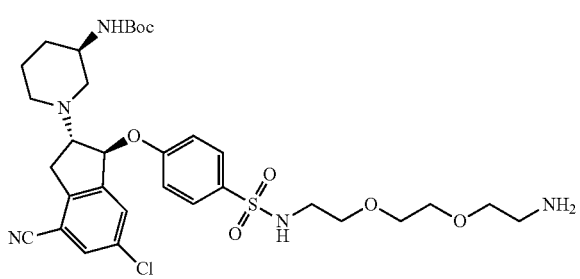
INT-M2E
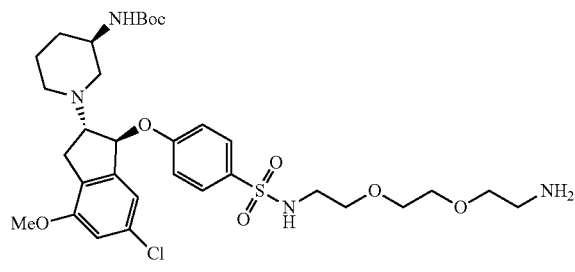
INT-M2F
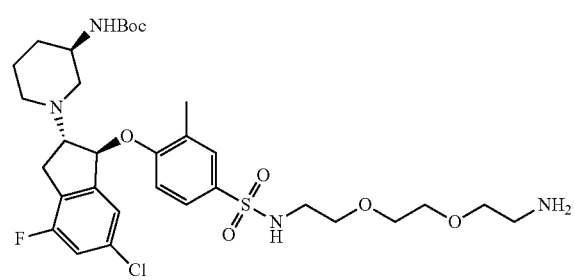
INT-M2G
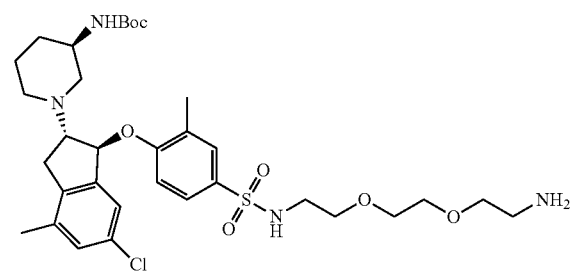
160
-continued
INT-M2H
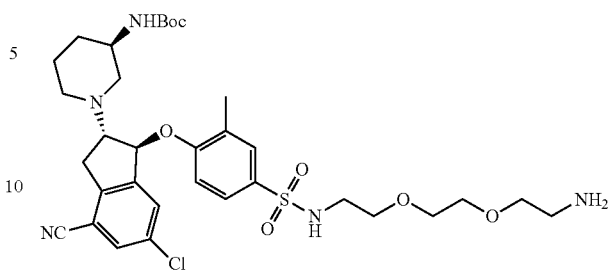
INT-M2J
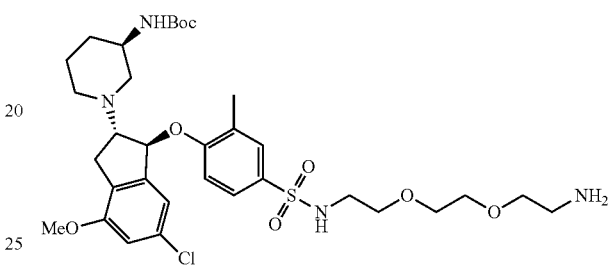
INT-M2K
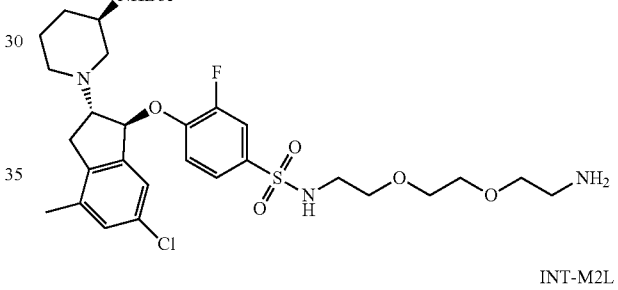
INT-M2L
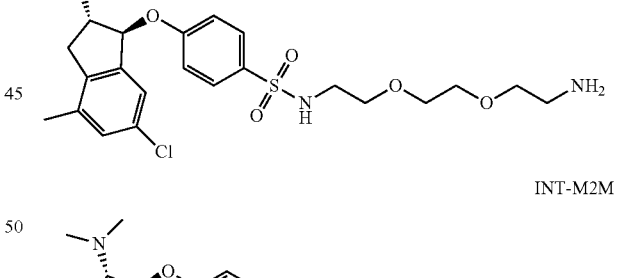
INT-M2M
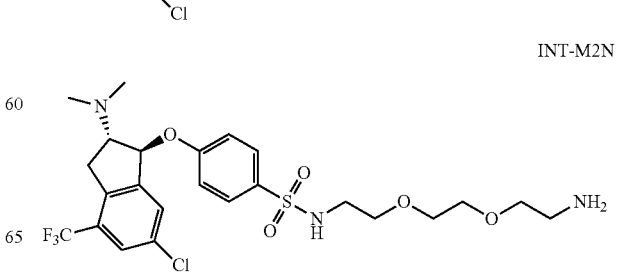
INT-M2N INT-M2O
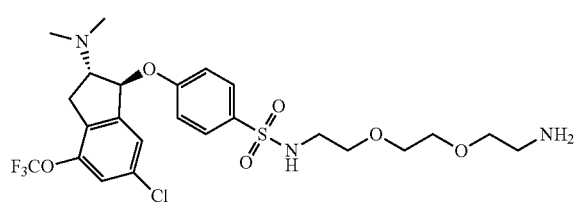
INT-M2V
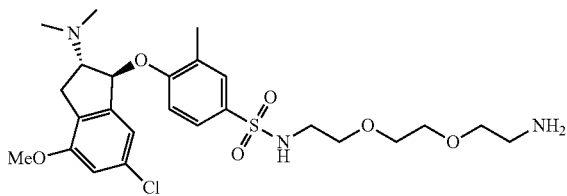
INT-M2P
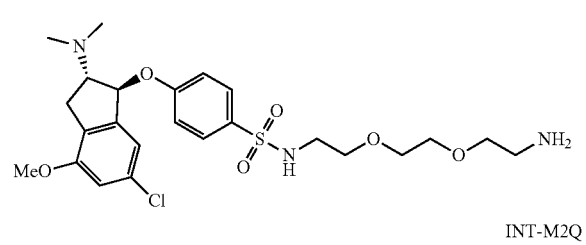
INT-M2W
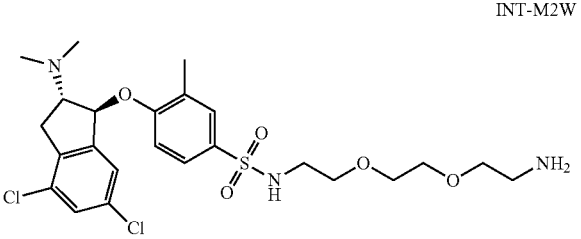
INT-M2Q
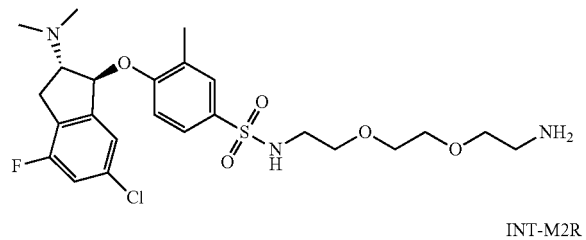
INT-M2X
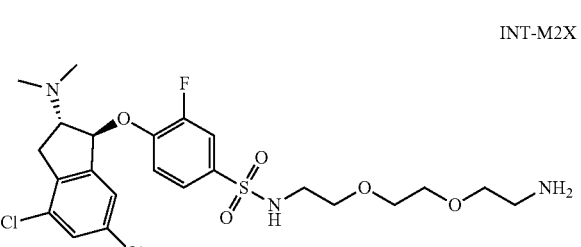
INT-M2R
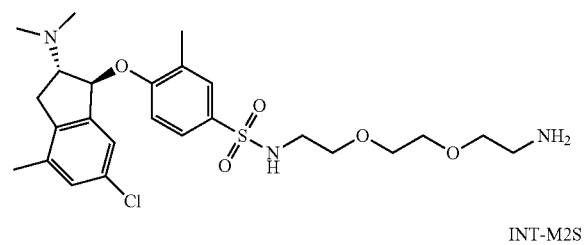
INT-M2Y
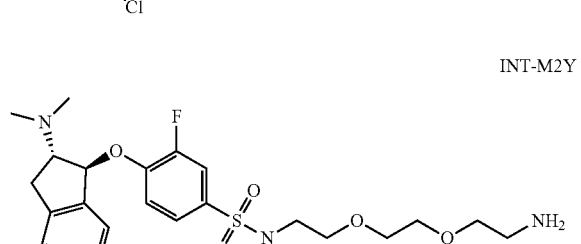
INT-M2S
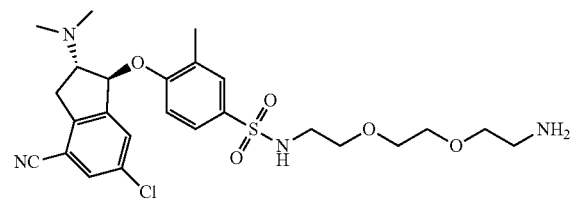
INT-M2Z
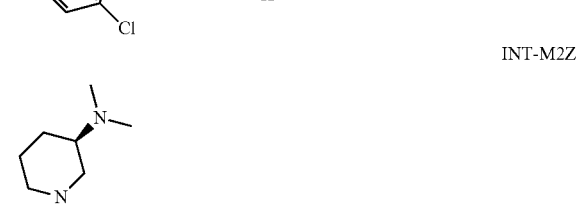
INT-M2T
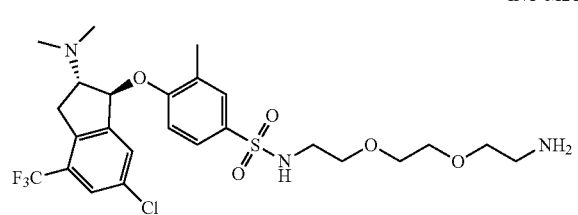
INT-M2AA
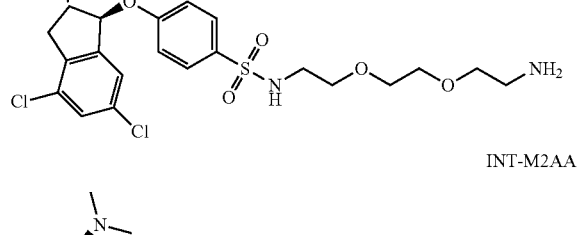
INT-M2U
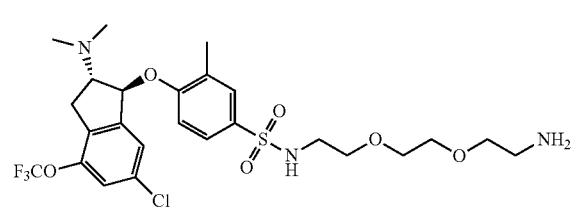
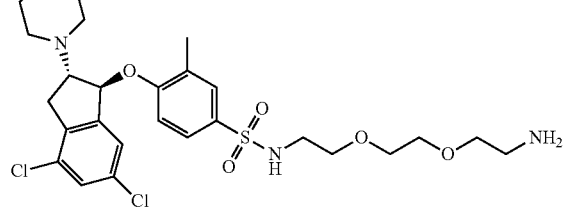

INT-M2AB
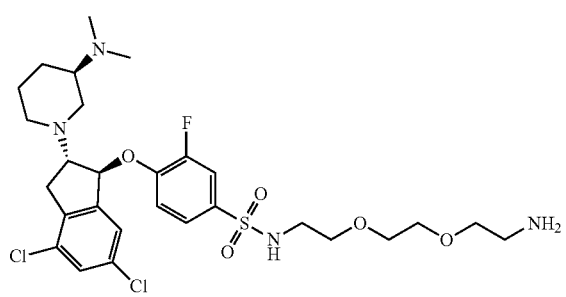
INT-M2AG
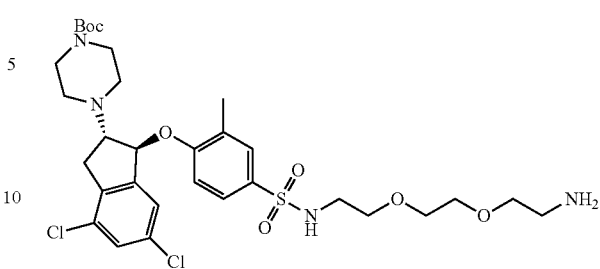
INT-M2AC
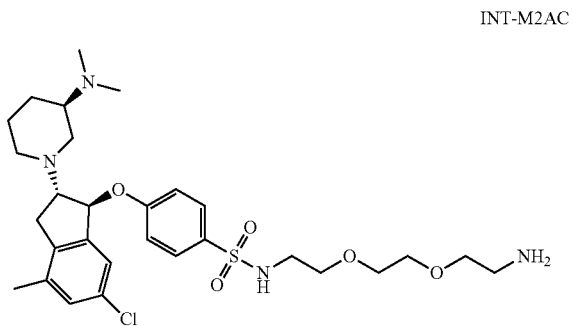
INT-M2AH
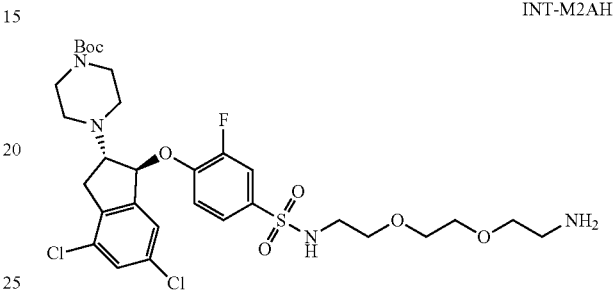
INT-M2AD
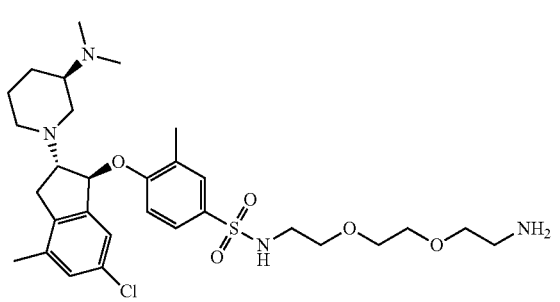
INT-M2AI
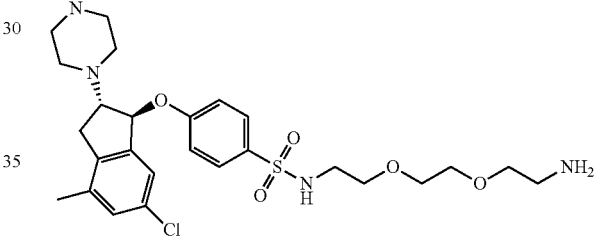
INT-M2AE
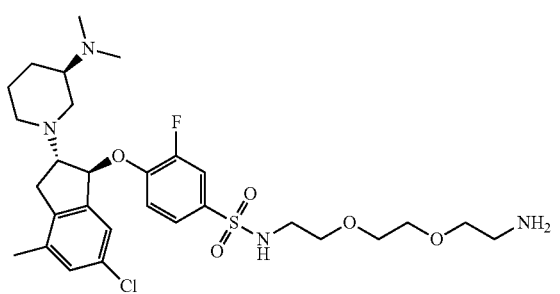
INT-M2AJ
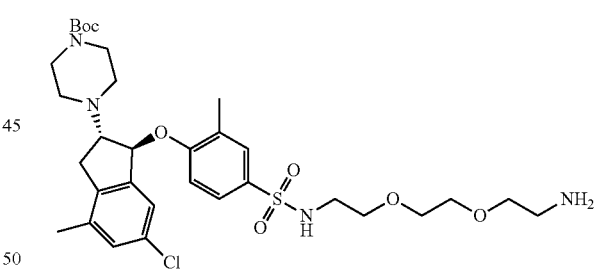
INT-M2AF
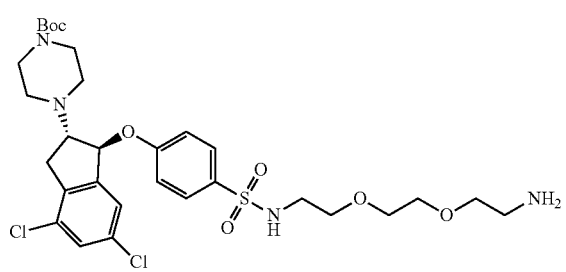
INT-M2AK
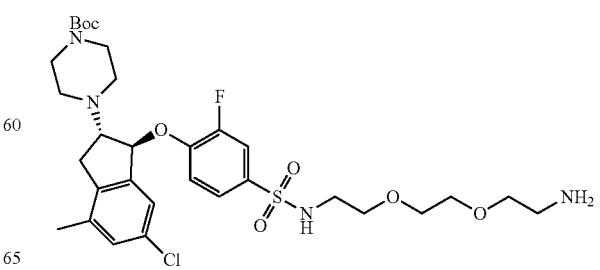

General Scheme for Dimer Formation (Non-Protected Analogs):

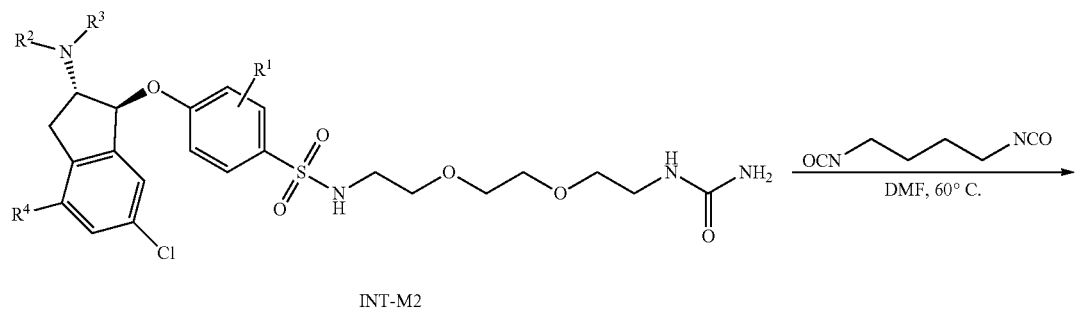

INT-M2

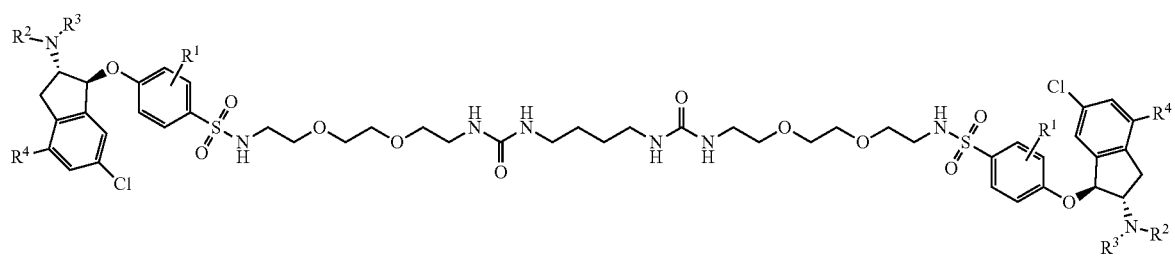

Dimer Product 1

To a round-bottom flask was added INT-M2 (1 equiv), N,N-dimethylformamide (DMF, 0.12 M), and 1,4-diisocyanatobutane (0.40 equiv). The resulting solution was stirred for 2 h at 60° C. The resulting mixture was concentrated under vacuum and diluted with $CH_2Cl_2$. The residue was applied onto a silica gel column with chloroform/methanol (10:1) providing the desired dimer Product 1. Final products were purified by Preparative HPLC with the following conditions: Column, XBridge C18 OBD Preparative Column. 19*250 mm; mobile phase, water (0.05% TFA) and $CH_3CN$ (10.0% $CH_3CN$ up to 70.0% in 8 min); Detector. UV 254 nm. The final products were generally isolated as the TFA salts or exchanged to the hydrochloride salts.

General Scheme for Deprotection of Dimers:

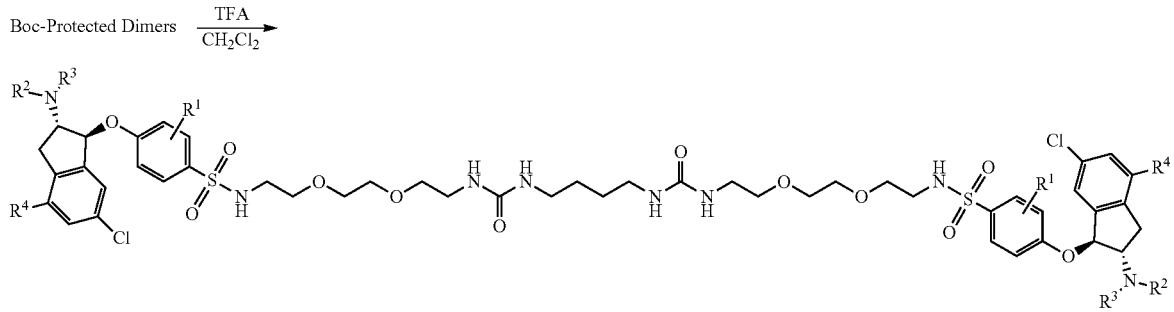

Dimer Product 1

To a round-bottom flask was added Boc-protected dimers (1 equiv) and 3:1 CH$_2$Cl$_2$:TFA (~0.05 M). The resulting solution was stirred for 2 h at room temperature. The resulting mixture was concentrated under vacuum. The crude product was purified by Preparative HPLC with the following conditions: Column, XBridge C18 OBD Preparative Column, 19*250 mm; mobile phase, water (0.05% TFA) and CH$_3$CN (10.0% CH$_3$CN up to 70.0% in 8 min); Detector, UV 254 nm. The final dimer Products 1 were generally isolated as the TFA salts or exchanged to the hydrochloride salts.

Example 1: 1-[2-(2-[2-[(4-[[(1S,2S)-2-[(3R)-3-Aminopiperidin-1-yl]-4,6-dichloro-2,3-dihydro-1H-inden-1-yl]oxy]-3-methylbenzene)sulfonamido] ethoxy]ethoxy)ethyl]-3-[4-([[2-(2-[2-([4-[[(1S,2S)-2-[(3R)-3-aminopiperidin-1-yl]-4,6-dichloro-2,3-dihydro-1H-inden-1-yl]oxy]-3-methylbenzene) sulfonamido]ethoxy]ethoxy)ethyl] carbamoyl] amino)butyl]urea Example 1

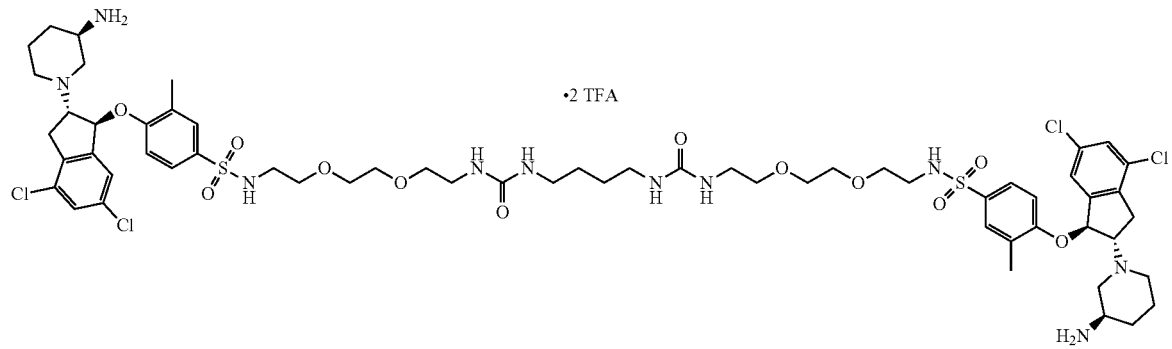

Prepared according to the General Scheme above from INT-M2A. Purification by preparative HPLC with the following conditions: Column, XBridge Shield RP18 OBD Column, 19*250 mm, 10 um; mobile phase, water (0.05% HCl) and CH$_3$CN (26.0% CH$_3$CN up to 47.0% in 8 min); Detector, UV 254 nm. This resulted in 695.3 mg (38%) of the title compound as a light yellow solid. MS (m/z): 1343.4 [M+H]$^+$. $^1$H NMR (Methanol-d4, 400 MHz) δ 7.74 (s, 2H), 7.82 (d, J=8.4 Hz, 2H), 7.49 (t, J=8.4 Hz, 4H), 7.12 (s, 2H), 6.31 (s, 2H), 4.01 (s, 2H), 3.68-3.42 (m, 20H), 3.33-3.29 (m, 6H), 3.28-3.00 (m, 12H), 2.85 (s, 4H), 2.26 (s, 6H), 2.01 (s, 4H), 1.82 (s, 2H), 1.67 (d, J=9.6 Hz, 2H), 1.50 (s, 2H).

Example 2: 3-[2-(2-[2-[(4-[[(1S,2S)-2-[(3R)-3-Aminopiperidin-1-yl]-4,6-dichloro-2,3-dihydro-1H-1-inden-1-yl]oxy]-3-fluorobenzene)sulfonamido] ethoxy]ethoxy)ethyl]-1-[4-([[2-[2-[(4-[[(1S,2S)-2-[(3R)-3-aminopiperidin-1-yl]-4,6-dichloro-2,3-dihydro-1H-inden-1-yl]oxy]-3-fluorobenzene) sulfonamido]ethoxy]ethoxy)ethyl]carbamoyl]amino) butyl]urea, bis(trifluoroacetic acid)

Example 2

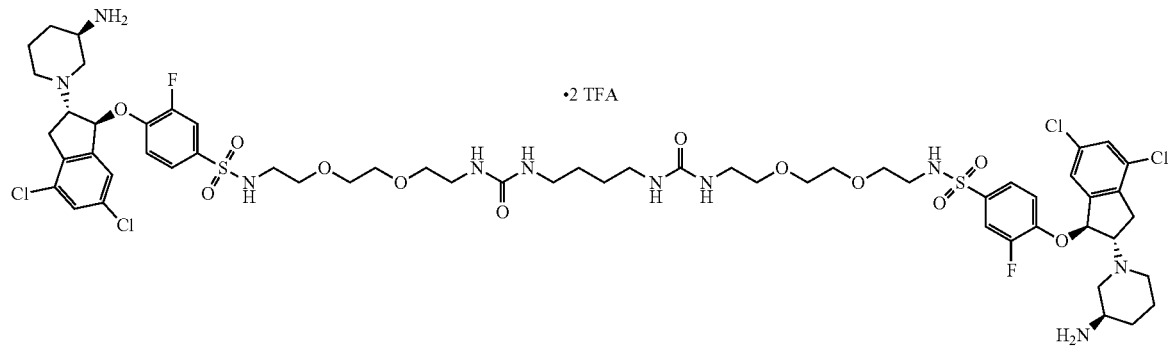

Prepared according to the General Scheme above from INT-M2B by dimer formation and Boc-deprotection. Purification by preparative HPLC with the following conditions: Column, XSelect CSH Preparative C18 OBD Column, 19*150 mm, 5 um; mobile phase, water (0.05% TFA) and CH$_3$CN (15% CH$_3$CN up to 45% in 8 min); Detector, UV 254 nm. This resulted in 192.6 mg (56%) of the title compound as a white solid. MS (m/z): 1351 [M+H]$^+$. $^1$H NMR (Methanol-d4, 400 MHz) δ 8.50 (s, 2H), 7.76-7.56 (m, 6H), 7.45 (d, J=1.7 Hz, 2H), 7.20 (d, 1.7 Hz, 2H), 6.01 (d, J=5.2 Hz, 2H), 3.71 (td, J=7.1, 5.1 Hz, 2H), 3.62-3.46 (m, 16H), 3.31-3.17 (m, 6H), 3.09 (dd, J=6.2, 4.3 Hz, 8H), 2.99 (dd, J=16.8, 6.8 Hz. 2H), 2.88 (d, J=11.4 Hz, 2H), 2.65 (s, 2H), 2.60-2.48 (m, 4H), 1.97-1.87 (m, 2H), 1.87-1.77 (m, 2H), 1.68-1.42 (m, 8H).

Example 3: 3-[2-(2-[2-[(4-[[(1S,2S)-2-[(3R)-3-Aminopiperidin-1-yl]-6-chloro-4-methyl-2,3-dihydro-1H-inden-1-yl]oxy]benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]benzene)sulfonamido]ethoxy]ethoxy)ethyl]carbamoyl]amino)butyl]urea Example 3

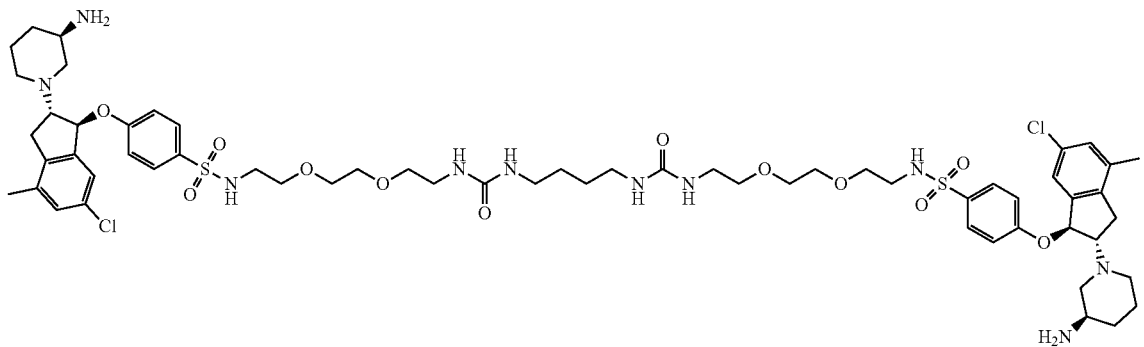

Prepared according to the General Scheme above from INT-M2C by dimer formation and Boc-deprotection. Purification by preparative HPLC with the following conditions: Column, XBridge C18 OBD Preparative Column, 19*250 mm, 5 um; mobile phase, water (0.05% TFA) and CH$_3$CN (10.0% CH$_3$CN up to 70.0% in 8 min); Detector, UV 254 nm. This resulted in 42.3 mg (26%) of the title compound as a white solid. MS (m/z): 1273 [M+H]$^+$. $^1$H NMR (Methanol-d4, 400 MHz) δ 7.91-7.83 (m, 4H), 7.32-7.25 (m, 4H), 7.18 (d, J=1.7 Hz, 2H), 7.00 (d, J=1.7 Hz, 2H), 6.00 (s, 2H), 3.68 (s, 2H), 3.61-3.46 (m, 16H), 3.38 (s, 1H), 3.27 (d, J=5.4 Hz, 3H), 3.19 (d, J=17.9 Hz, 4H), 3.09 (d, 5.2 Hz, 8H), 2.93 (s, 4H), 2.78 (s, 2H), 2.63 (s, 4H), 2.30 (s, 6H), 1.92 (s, 3H), 1.86 (s, 1H), 1.69 (s, 3H), 1.59 (d, J=10.3 Hz, 2H), 1.50-1.42 (m, 4H).

Example 4: 3-[2-(2-[2-[(4-[[(1S,2S)-2-[(3R)-3-Aminopiperidin-1-yl]-6-chloro-4-cyano-2,3-dihydro-1H-inden-1-yl]oxy]benzene)sulfonamido]ethoxy]ethoxy)ethyl]-1-[4-([[2-(2-[2-[(4-[[(1S,2)-2-[(3R)-3-aminopiperidin-1-yl]-6-chloro-4-cyano-2,3-dihydro-1H-inden-1-yl]oxy]benzene) sulfonamido]ethoxy]ethoxy)ethyl]carbamoyl]amino)butyl]urea; bis(trifluoroacetic acid)

Example 4

Prepared according to the General Scheme above from INT-M2D by dimer formation and Boc-deprotection. Purification by preparative HPLC with the following conditions: Column, XBridge C18 OBD Preparative Column, 19*250 mm, 5 um, mobile phase, water (0.05% TFA) and CH$_3$CN (25.0% CH$_3$CN up to 45.0% in 8 min); Detector, UV 254 nm. This resulted in 143.9 mg (71%) of the title compound as a white solid. MS (m/z): 1296 [M+H]$^+$. $^1$H NMR (Methanol-d4, 400 MHz) δ 7.85 (d, J=8.6 Hz, 4H), 7.75 (d, J=1.9 Hz, 2H), 7.47 (d, J=1.8 Hz, 2H), 7.29 (d, J=8.7 Hz, 4H), 6.02 (d, J=5.5 Hz, 2H), 3.72 (d, J=6.5 Hz, 2H), 3.59-3.42 (m, 16H), 3.41-3.29 (m, 1H), 3.24 (d, J=5.4 Hz, 3H), 3.20-2.99 (m, 11H), 2.89 (d, J=11.5 Hz, 2H), 2.66-2.52 (m, 7H), 1.87 (s, 4H), 1.44 (s, 4H).

Example 5: 3-[2-(2-[2-[(4-[[(1S,2S)-2-[(3R)-3-Aminopiperidin-1 yl]-6-chloro-4-methoxy-2,3-dihydro-1H-inden-1-yl]oxy]benzene)sulfonamido]ethoxy]ethoxy)ethyl]-1-[4-[[(2-(2-[2-[(4-[[(1S,2S)-2-[(3R)-3-aminopiperidin-1-yl]-6-chloro-4-methoxy-2,3-dihydro-1H-inden-1-yl]oxy]benzene)sulfonamido]ethoxy]ethoxy)ethyl]carbamoyl]amino)butyl]urea; bis(trifluoroacetic acid)

Example 5

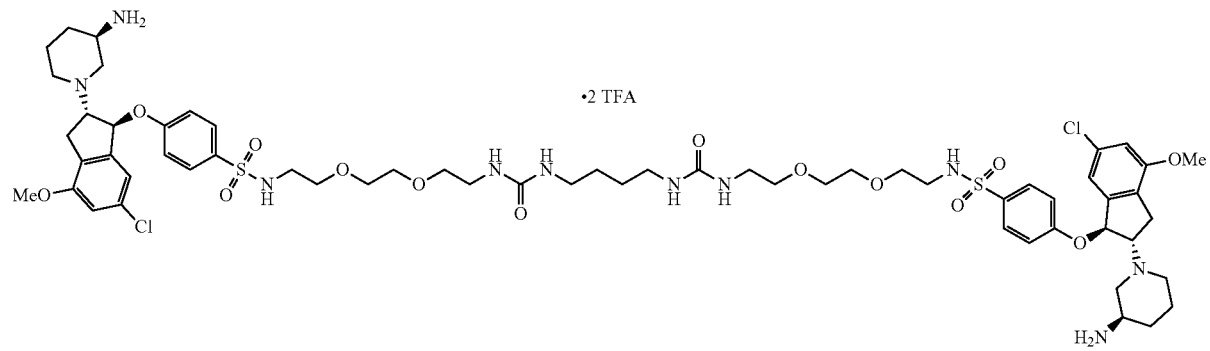

Prepared according to the General Scheme above from INT-M2E by dimer formation and Boc-deprotection. Purification by preparative HPLC with the following conditions: Column, XBridge C18 OBD Preparative Column, 19*250 mm, 5 um; mobile phase, water (0.05% TFA) and CH$_3$CN (18.0% CH$_3$CN up to 32.0% in 8 min); Detector, UV 254 nm. This resulted in 227.2 mg (74%) of the title compound as a white solid. MS (m/z): 135 [M+H]$^+$. $^1$H NMR (Methanol-d4, 400 MHz) δ 7.88 (d, J=8.3 Hz, 4H), 7.34-7.26 (m, 4H), 6.96 (s, 2H), 6.77 (s, 2H), 6.09 (d, J=19.2 Hz, 2H), 3.86 (s, 6H), 3.61-3.46 (m, 17H), 3.42 (s, 2H), 3.28 (t, J=5.4 Hz, 4H), 3.13-3.04 (m, 8H), 2.72 (s, 6H), 1.96 (s, 4H), 1.74 (s, 2H), 1.61 (s, 2H), 1.50-1.42 (m, 4H).

Example 6: 1-[2-(2-[2-[(4-[[(1S,2S)-2-[(3R)-3-Aminopiperidin-1-yl]-6-chloro-4-fluoro-2,3-dihydro-1H-inden-1-yl]oxy]-3-methylbenzene)sulfonamido]ethoxy]ethoxy)ethyl]-3-[4-[[2-(2-[2-[(4-[[(1S,2S)-2-[(3R)-3-aminopiperidin-1-yl]-6-chloro-4-fluoro-2,3-dihydro-1H-indenyl-1-yl]oxy]-3-methylbenzene)sulfonamido]ethoxy]ethoxy)ethyl]carbamoyl]amino)butyl]urea Example 6

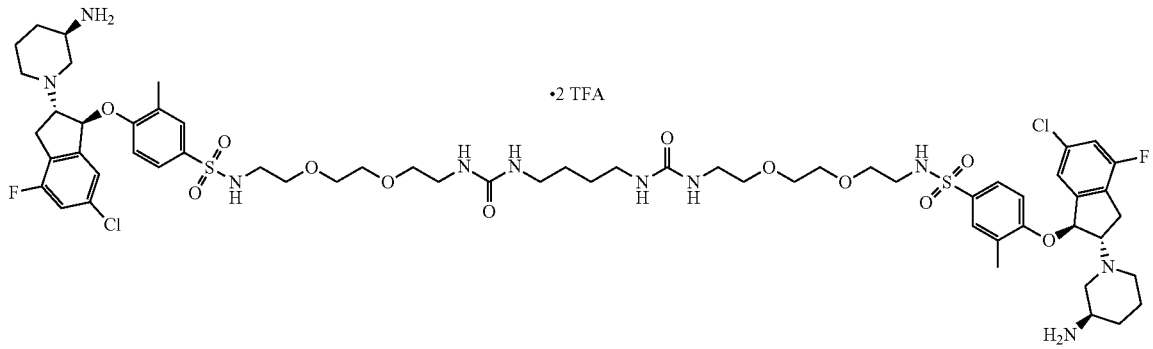

Prepared according to the General Scheme above from INT-M2F by dimer formation and Boc-deprotection. Purification by preparative HPLC with the following conditions: Column, XBridge C18 OBD Preparative Column, 19*250 mm; mobile phase, water (0.05% HCl) and CH$_3$CN (34% CH$_3$CN up to 54% in 8 min); Detector, UV 254 nm. This resulted in 168.1 mg (51%) of the titled compound as a light yellow solid. MS (m/z): 1311.45 [M+H]$^+$. $^1$H NMR (Methanol-d4, 400 MHz) δ 7.85 (d, J=2.4 Hz, 2H), 7.82 (s, 2H), 7.55 (d, J=8.8 Hz, 2H), 7.27 (d, J=8.4 Hz, 2H), 6.91 (s, 2H), 6.77 (d, J=6.4 Hz, 2H), 4.54 (d, J=6.8 Hz, 2H), 3.89-3.70 (m, 8H), 3.57-3.49 (m, 17H), 3.31-3.23 (m, 10H), 3.18-3.08 (m, 9H), 2.30 (s, 6H), 2.19-2.07 (m, 6H), 1.75 (s, 2H), 1.48 (s, 4H).

Example 7: 3-[2-(2-[2-[(4-[[(1S,2S)-2-[(3R)-3-Aminopiperidin-1-yl]-6-chloro-4-methyl-2,3-dihydro-1H-inden-1-yl]oxy]-3-methylbenzene)sulfonamido] ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-inden-1-yl]oxy]-3-methylbenzene) sulfonamido]ethoxy]ethoxy)ethyl]carbamoyl]amino) butyl]urea Example 7

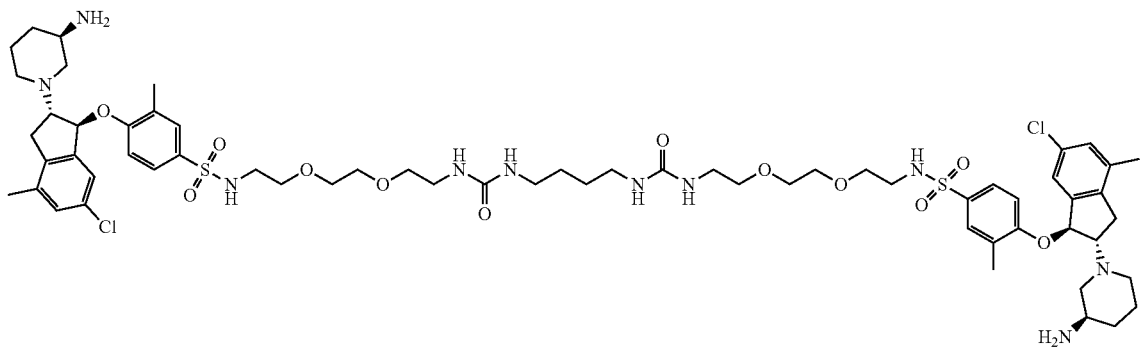

Prepared according to the General Scheme above from INT-M2G by dimer formation and Boc-deprotection. Purification by preparative HPLC with the following conditions: Column, XSelect CSH Preparative C18 OBD Column, 19*150 mm, 5 um; mobile phase, water (0.05% TFA) and CH$_3$CN (16.0% CH$_3$CN up to 40.0% in 8 min); Detector, UV 254 nm. This resulted in 157 mg (52%) of the title compound as a white solid. MS (m/z): 1301 [M+H]$^+$. $^1$H NMR (Methanol-d4, 400 MHz) δ 7.77 (d, J=9.0 Hz, 2H), 7.70 (s, 2H), 7.44 (d, J=8.5 Hz, 2H), 7.18 (s, 2H), 6.97 (d, J=6.5 Hz, 2H), 3.28 (t, J=5.4 Hz, 6H), 3.08 (dt, J=10.9, 5.5 Hz, 10H), 2.94 (s, 4H), 2.73 (s, 5H), 3.61-3.46 (m, 16H), 2.27 (d, J=22.7 Hz, 13H), 1.95 (s, 5H), 1.67 (d, J=49.5 Hz, 5H), 1.50-1.42 (m, 4H).

Example 8: 3-[2-(2-[2-[(4-[[(1S,2S)-2-[(3R)-3-Aminopiperidin-1-yl]-6-chloro-4-cyano-2,3-dihydro-1H-inden-1-yl]oxy]-3-methylbenzene)sulfonamido] ethoxy]ethoxy)ethyl]-1-[4-([[2-(2-[2-[(4-[[(1S,2S)-2-[(3R)-3-aminopiperidin-1-yl]-6-chloro-4-cyano-2,3-dihydro-1H-inden-1-yl]oxy]-3-methylbenzene) sulfonamido]ethoxy]ethoxy)ethyl]carbamoyl]amino) butyl]urea; bis(trifluoroacetic acid)

Example 8

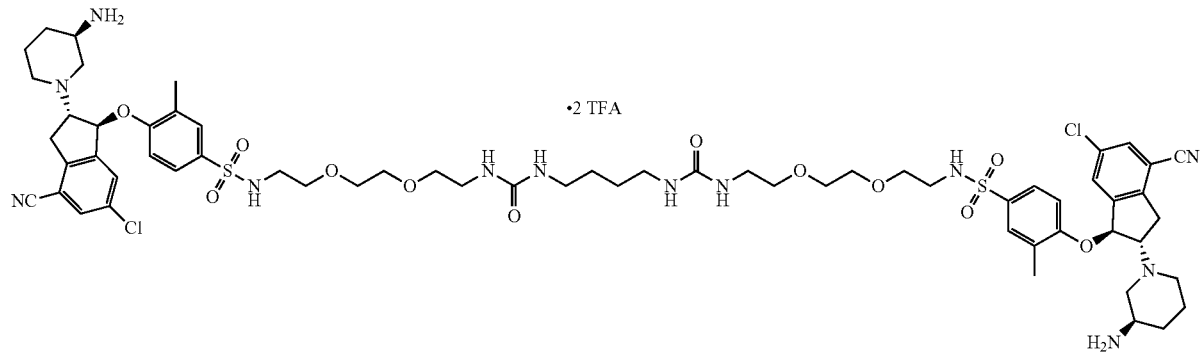

Prepared according to the General Scheme above from INT-M2H by dimer formation and Boc-deprotection. Purification by preparative HPLC with the following conditions: Column, XBridge C18 OBD Preparative Column, 19*250 mm, 5 um; mobile phase, water (0.05% TFA) and CH$_3$CN (24.0% CH$_3$CN up to 41.0% in 7 min); Detector, UV 254 nm. This resulted in 30.1 mg (25%) of the title compound as a white solid. MS (m/z): 661.7 [M/2+H]$^+$. $^1$H NMR (Methanol-d4, 400 MHz) δ 7.81-7.68 (m, 6H), 7.50-7.42 (m, 4H), 6.08 (d, J=6.6 Hz, 2H), 3.78 (d, J=8.2 Hz, 2H), 3.53 (dtd, J=22.6, 5.4, 2.5 Hz, 16H), 3.45-3.33 (m, 6H), 3.27 (d, J=5.5 Hz, 3H), 3.18 (d, J=7.6 Hz, 2H), 3.13-3.02 (m, 8H), 2.92 (s, 2H), 2.66 (d, J=27.7 Hz, 6H), 2.25 (s, 6H), 1.83 (s, 4H), 1.69-1.55 (m, 4H), 1.46 (p, J=3.2 Hz, 4H).

Example 9: 3-[2-(2-[2-[(4-[[(1S,2S)-2-[(3R)-3-Aminopiperidin-1-yl]-6-chloro-4-methoxy-2,3-dihydro-1H-inden-1-yl]oxy]-3-methylbenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methoxy-2,3-dihydro-1H-inden-1-yl]oxy]-3-methylbenzene)sulfonamido]ethoxy]ethoxy)ethyl]carbamoyl]amino)butyl]urea bis(trifluoroacetic acid)

Example 9

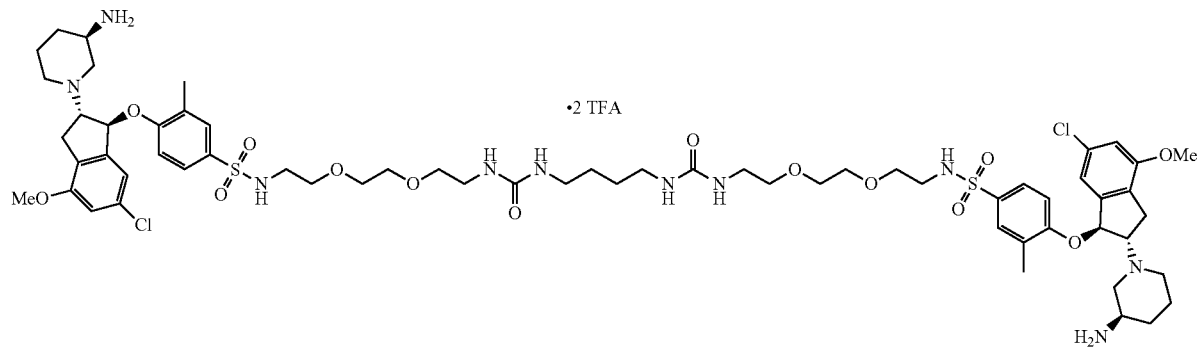

Prepared according to the General Scheme above from INT-M2J by dimer formation and Boc-deprotection. Purification by preparative HPLC with the following conditions: Column, XBridge C18 OBD Preparative Column, 19*250 mm, 5 um; mobile phase, water (0.05% TFA) and CH$_3$CN (30.0% CH$_3$CN up to 38.0% in 12 min); Detector, UV 254 nm. This resulted in 19.5 mg (13%) of the title compound as a white solid. MS (m/z): 1334 [M+H]$^+$. $^1$H NMR (Methanol-d4, 400 MHz) δ 7.81-7.73 (m, 2H), 7.70 (dd, J=2.4, 1.0 Hz, 2H), 7.43 (d, J=8.7 Hz, 2H), 6.94 (d, J=1.6 Hz, 2H), 6.75 (d, J=1.5 Hz, 2H), 6.03 (d, J=5.4 Hz, 2H), 3.86 (s, 6H), 3.75-3.67 (m, 2H), 3.61-3.46 (m, 15H), 3.38 (dd, J=7.9, 4.4 Hz, 2H), 3.32-3.16 (m, 5H), 3.08 (dt, J=11.0, 5.7 Hz, 8H), 2.98 (d, J=11.5 Hz, 2H), 2.92-2.78 (m, 4H), 2.71-2.62 (m, 4H), 2.24 (s, 6H), 1.93 (s, 4H), 1.86 (s, 2H), 1.70 (s, 2H), 1.59 (s, 2H), 1.50-1.42 (m, 4H).

Example 10: 3-[2-(2-[2-[(4-[[(1S,2S)-2-[(3R)-3-Aminopiperidin-1-yl]-6-chloro-4-methyl-2,3-dihydro-1H-inden-1-yl]oxy]-3-fluoro benzene)sulfonamido]ethoxy]ethoxy)ethyl]-1-[4-[[(2-(2-[2-[(4-[[(1S,2S)-2-[(3R)-3-aminopiperidin-1-yl]-6-chloro-4-methyl-2,3-dihydro-1H-inden-1-yl]oxy]-3-fluorobenzene)sulfonamido]ethoxy]ethoxy)ethyl]carbamoyl]amino)butyl]urea; bis(trifluoroacetic acid)

Example 10

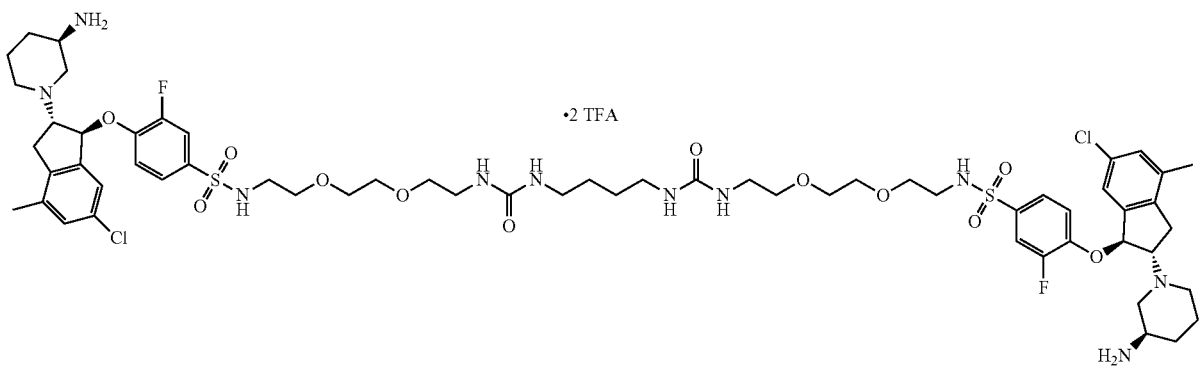

Prepared according to the General Scheme above from INT-M2K (by dimer formation and Boc-deprotection. Purification by preparative HPLC with the following conditions: Column, XBridge C18 OBD Preparative Column, 19*250 mm, 5 um; mobile phase, water (0.05% TFA) and $CH_3CN$ (29.0% $CH_3CN$ up to 33.0% in 10 min); Detector, UV 254 nm. This resulted in 302.6 mg (59%) of the title compound as a white solid. MS (m/z): 1309 [M+H]$^+$. $^1$H NMR (Methanol-d4, 400 MHz) δ 7.77-7.55 (m, 6H), 7.21 (d, J=1.8 Hz, 2H), 7.00 (d, J=1.8 Hz, 2H), 6.15 (s, 2H), 4.89 (s, 2H), 3.89 (s, 2H), 3.62-3.46 (m, 15H), 3.41 (s, 3H), 3.28 (t, J=5.4 Hz, 4H), 3.10 (q, J=5.4 Hz, 8H), 3.03-2.94 (m, 3H), 2.73 (s, 4H), 2.31 (s, 5H), 1.98 (s, 2H), 1.92 (s, 1H), 1.74 (s, 2H), 1.60 (d, J=10.8 Hz, 2H), 1.50-1.42 (m, 4H).

Example 11: 3-[2-(2-[2-[(4-[[(1S,2S)-6-Chloro-2-(dimethylamino)-4-methyl-2,3-dihydro-1H-inden-1-yl]oxy]benzene)sulfonamido]ethoxy]ethoxy)ethyl]-1-[4-([[2-(2-[2-[4-[[(1S,2S)-6-chloro-2-(dimethylamino)-4-methyl-2,3-dihydro-1H-inden-1-yl]oxy]benzene)sulfonamido]ethoxy]ethoxy)ethyl]carbamoyl]amino)butyl]urea; bis(trifluoroacetic acid)

Example 11

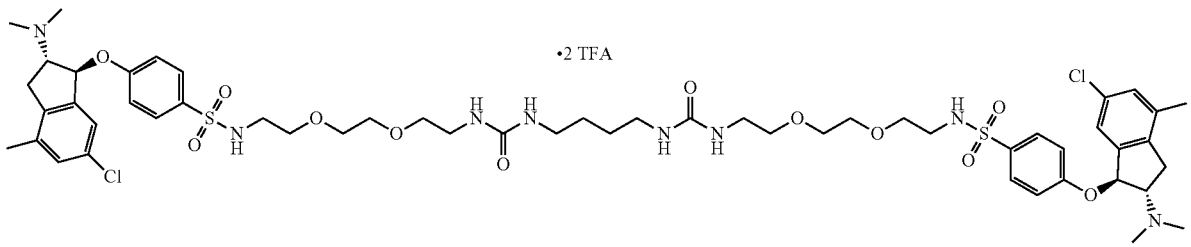

Prepared according to the General Scheme above from INT-M2L by dimer formation. Purification by preparative HPLC with the following conditions: Column, XSelect CSH Preparative C18 OBD Column, 19*150 mm, 5 um; mobile phase, water (0.05% TFA) and CH$_3$CN (25.0% CH$_3$CN up to 32.0% in 12 min); Detector, UV 254 nm. This resulted in 278.8 mg (21%) of the title compound as a white solid. MS (m/z): 1163.45) [M+H]$^+$. $^1$H NMR (Methanol-d4, 400 MHz) δ 7.96-7.88 (m, 4H), 7.39-7.30 (m, 4H), 7.26 (s, 2H), 6.98 (s, 2H), 6.39 (d, J=6.7 Hz, 2H), 4.35 (q, J=8.1 Hz, 2H), 3.62-3.45 (m, 18H), 3.27 (t, J=5.4 Hz, 4H), 3.18-3.01 (m, 22H), 2.33 (s, 6H), 1.45 (p, J=3.4 Hz, 4H).

Example 12: 3-[2-(2-[2-[(4-[[(1S,2S)-6-Chloro-4-cyano-2-(dimethylamino)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]benzene)sulfonamido]ethoxy]ethoxy)ethyl]carbamoyl]amino)butyl]urea; bis(trifluoroacetic acid)

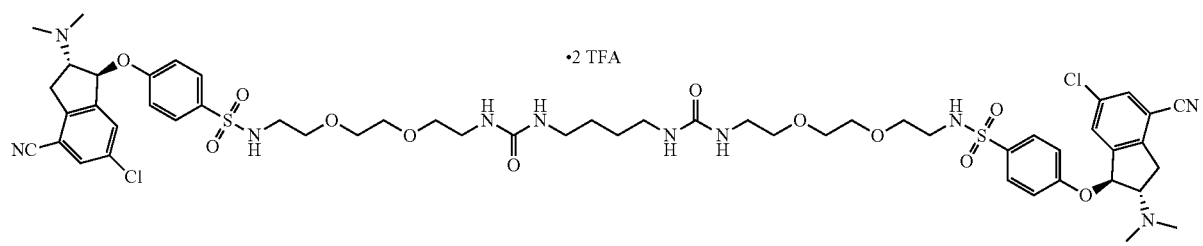

Example 12

Prepared according to the General Scheme above from INT-M2M by dimer formation. Purification by preparative HPLC with the following conditions: Column, XBridge C18 OBD Preparative Column, 19*250 mm, 5 um; mobile phase, water (0.05% TFA) and CH$_3$CN (25% CH$_3$CN up to 45% in 9 min); Detector, UV 254 nm. This resulted in 165.8 mg (41%) of the title compound as a white solid. MS (m/z): 1185 [M+H]$^+$. $^1$H NMR (Methanol-d4, 400 MHz) δ 7.98-7.86 (m, 6H), 7.45 (s, 2H), 7.43-7.34 (m, 4H), 6.48 (s, 1H), 4.50 (q, J=8.0 Hz, 2H), 3.79 (dd, J=16.6, 8.4 Hz, 2H), 3.61-3.37 (m, 18H), 3.27 (t, J=5.4 Hz, 3H), 3.07 (d, J 12.7 Hz, 20H), 1.50-1.42 (m, 4H).

Example 13: 3-[2-(2-[2-[(4-[[(1S,2S)-6-Chloro-2-(dimethylamino)-4-(trifluoromethyl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-(dimethylamino)-4-(trifluoromethyl)-2,3-dihydro-1H-inden-1-yl]oxy]benzene)sulfonamido]ethoxy]ethoxy)ethyl]carbamoyl]amino)butyl]urea

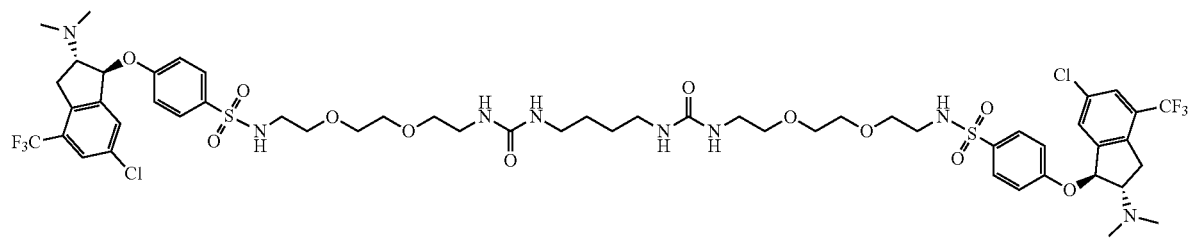

Example 13

Prepared according to the General Scheme above from INT-M2N by dimer formation. Purification by preparative HPLC with the following conditions: Column, XBridge C18 OBD Preparative Column, 19*250 mm; mobile phase, water (10 mmol/L NH$_4$HCO$_3$) and CH$_3$CN (80.0% CH$_3$CN up to 90.0% in 10 min); Detector, UV 254 nm. This resulted in 41.6 mg (7%) of the title compound as a white solid. MS (m/z): 1371.2 [M+H]$^+$. $^1$H NMR (Methanol-d4, 400 MHz) δ 8.01 (s, 2H), 7.91-7.88 (m, 4H), 7.38-7.33 (m, 6H), 5.97 (d, J=5.6 Hz, 2H), 3.71 (q, J=8.0 Hz, 2H), 3.60-3.50 (m, 19H), 3.33-3.26 (m, 5H), 3.12-3.08 (m, 8H), 2.37 (s, 12H), 1.50-1.31 (m, 5H).

Example 14: 1-[2-(2-[2-[(4-[[(1S,2S)-6-Chloro-2-(dimethylamino)-4-(trifluoromethoxy)-2,3-dihydro-1H-inden-1-yl]oxy]benzene)sulfonamido]ethoxy]ethoxy)ethyl]-3-[4-([[2-(2-[2-[(4-[[(1S,2S)-6-chloro-2-(dimethylamino)-4-(trifluoromethoxy)-2,3-dihydro-1H-inden-1-yl]oxy]benzene)sulfonamido]ethoxy]ethoxy)ethyl]carbamoyl]amino)butyl]urea

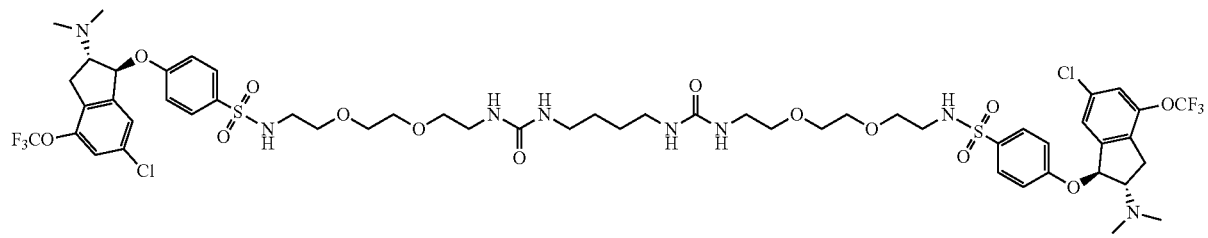

Example 14

Prepared according to the General Scheme above from INT-M2O by dimer formation. Purification by preparative HPLC with the following conditions: Column, XBridge C18 OBD Preparative Column, 19*250 mm, 5 um; mobile phase, water (10 mmol/L NH$_4$HCO$_3$) and CH$_3$CN (80.0% CH$_3$CN up to 90.0% in 10 min); Detector, UV 254 nm. This resulted in 26.5 mg (13%) of the title compound as a white solid. MS (m/z): 1403.15 [M+H]$^+$. $^1$H NMR (Methanol-d4, 400 MHz) δ 7.87 (d, J=8.8 Hz, 4H), 7.61 (s, 2H), 7.32 (d, J=8.8 Hz, 4H), 7.19 (s, 2H), 5.97 (d, J=6.0 Hz, 2H), 3.93 (q, J=8.1 Hz, 2H), 3.57-3.47 (m, 19H), 3.30 (s, 6H), 3.15-3.05 (m, 9H), 2.34 (s, 12H), 1.47 (s, 4H). $^{19}$F NMR (Methanol-d4, 376 MHz) δ: 76.92 (s, 6F).

Example 15: 3-[2-(2-[2-[(4-[[(1S,2S)-6-Chloro-2-(dimethylamino)-4-methoxy-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-(dimethylamino)-4-methoxy-2,3-dihydro-1H-inden-1-yl]oxy]benzene)sulfonamido]ethoxy]ethoxy)ethyl]carbamoyl]amino)butyl]urea; bis(trifluoroacetic acid)

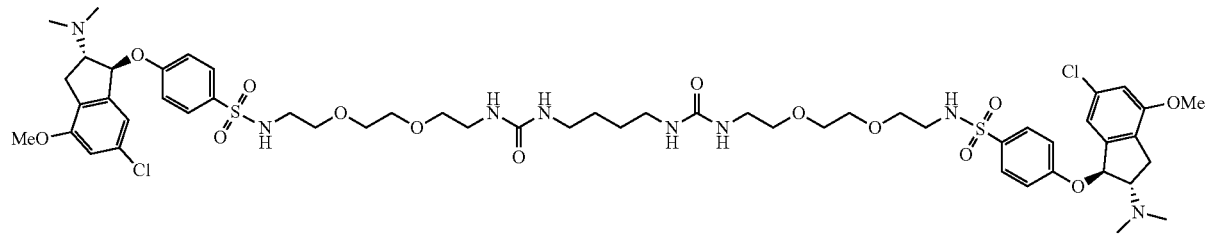

Example 15

Prepared according to the General Scheme above from INT-M2P by dimer formation. Purification by preparative HPLC with the following conditions: Column, XSelect CSH Preparative C18 OBD Column, 19*150 mm, 5 um; mobile phase, water (0.05% TFA) and CH$_3$CN (24.0% CH$_3$CN up to 33.0% in 10 min); Detector, UV 254 nm. This resulted in 159.1 mg (34%) of the title compound as a white solid. MS (m/z): 1195 [M+H]$^+$. $^1$H NMR (Methanol-d4, 400 MHz) δ 7.96-7.88 (m, 4H), 7.38-7.31 (m, 4H), 7.04 (d, J=1.5 Hz, 2H), 6.76 (s, 2H), 6.36 (d, J=6.6 Hz, 2H), 4.91 (d, J=10.0 Hz, 4H), 4.42-4.31 (m, 2H), 3.89 (s, 6H), 3.61-3.46 (m, 17H), 3.28 (t, J=5.4 Hz, 4H), 3.13-3.00 (m, 21H), 1.45 (s, 5H).

Example 16: 3-[2-(2-[2-[4-[[(1S,2S)-6-Chloro-2-(dimethylamino)-4-fluoro-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-fluoro-2,3-dihydro-1H-inden-1-yl]oxy]-3-methylbenzene)sulfonamido]ethoxy]ethoxy)ethyl]carbamoyl]amino)butyl]urea

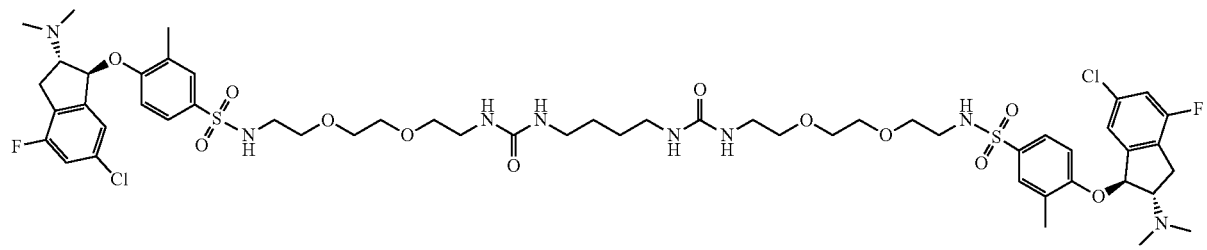

Example 16

Prepared according to the General Scheme above from INT-M2Q by dimer formation. Purification by preparative HPLC with the following conditions: Column, XBridge Preparative OBD C18 Column, 19*250 mm, 5 um; mobile phase, water (0.05% HCl) and CH$_3$CN (20.0% CH$_3$CN up to 50.0% in 8 min); Detector, UV 254 nm. This resulted in 255 mg (29%) of the title compound as a white solid. MS (m/z): 1201.35 [M+H]$^+$. $^1$H NMR (Methanol-d4, 400 MHz) δ 7.84 (q, J=3.6 Hz, 2H), 7.77 (d, J=1.6 Hz, 2H), 7.52 (d, J=8.8 Hz, 2H), 7.30 (q, J=3.2 Hz, 2H), 6.99 (s, 2H), 6.59 (d, J=6.8 Hz, 2H), 4.54-4.48 (m, 2H), 3.73 (q, J=8.4 Hz, 2H), 3.62-3.51 (m, 16H), 3.51-3.35 (m, 4H), 3.34-3.33 (m, 2H), 3.30 (s, 4H), 3.17-2.92 (m, 16H), 2.36-2.33 (m, 6H), 1.53 (s, 1H).

Example 17: 3-[2-(2-[2-[(4-[[(1S,2S)-6-Chloro-2-(dimethylamino)-4-methyl-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-methyl-2,3-dihydro-1H-inden-1-yl]oxy]-3-methylbenzene)sulfonamido]ethoxy]ethoxy)ethyl]carbamoyl]amino)butyl]urea

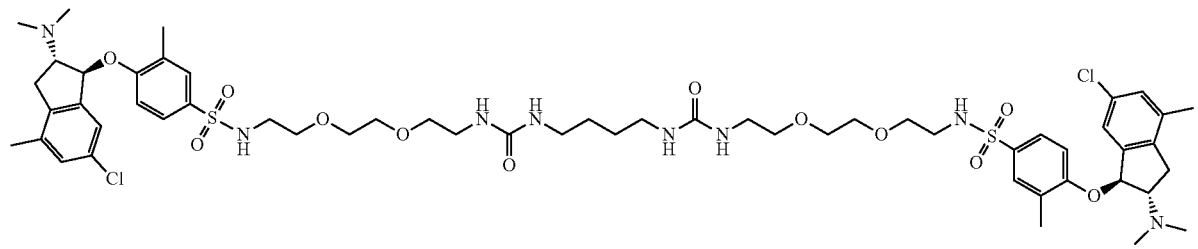

Example 17

Prepared according to the General Scheme above from INT-M2R by dimer formation. Purification by preparative HPLC with the following conditions: Column, XBridge Preparative C18 OBD Column, 19*150 mm, 5 um; mobile phase, water (0.05% NH$_4$OH) and CH$_3$CN (5.0% CH$_3$CN up to 70.0% in 1 min, up to 77.0% in 6 min); Detector, UV 254/220 nm. This resulted in 109.9 mg (12%) of the title compound as a white solid. MS (m/z): 1191 [M+H]$^+$. $^1$H NMR (Methanol-d4, 400 MHz) δ 7.80-7.67 (m, 4H), 7.40 (d, J=8.7 Hz, 2H), 7.17-7.12 (m, 2H), 6.93 (d, J=1.8 Hz, 2H), 5.91 (d, J=6.1 Hz, 2H), 3.61-3.37 (m, 19H), 3.32-3.15 (m, 6H), 3.08 (dt, J=14.5, 5.7 Hz, 8H), 2.79 (dd, J=15.9, 7.9 Hz, 2H), 2.45-2.13 (m, 25H), 1.47 (p, J=3.3 Hz, 4H).

Example 18: 3-[2-(2-[2-[(4-[[(1S,2S)-6-Chloro-4-cyano-2-(dimethylamino)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]-3-methylbenzene)sulfonamido]ethoxy]ethoxy)ethyl]carbamoyl]amino)butyl]urea; bis (trifluoroacetic acid)

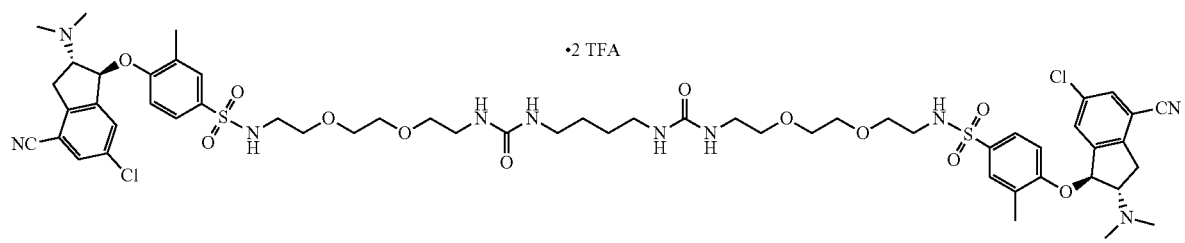

Example 18

Prepared according to the General Scheme above from INT-M2S by dimer formation. Purification by preparative HPLC with the following conditions: Column, XSelect CSH Preparative C18 OBD Column, 19*150 mm, 5 um; mobile phase, water (0.05% TFA) and CH$_3$CN (22.0% CH$_3$CN up to 38.0% in 8 min); Detector, UV 254 nm. This resulted in 75.8 mg (24%) of the title compound as a white solid. MS (m/z): 1213 [M+H]$^+$. $^1$H NMR (Methanol-d4, 300 MHz) δ 7.94-7.75 (m, 6H), 7.56-7.39 (m, 4H), 6.54 (d, J=6.7 Hz, 2H), 4.64-4.49 (m, 2H), 3.84 (dd, J=16.7, 8.5 Hz, 2H), 3.65-3.39 (m, 18H), 3.29 (d, J=5.4 Hz, 3H), 3.16-3.05 (m, 2H), 2.34 (s, 6H), 1.54-1.43 (m, 4H).

Example 19: 3-[2-[2-(2-[2-[(4-[[(1S,2S)-6-Chloro-2-(dimethylamino)-4-(trifluoromethyl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-(trifluoromethyl)-2,3-dihydro-1H-inden-1-yl]oxy]-3-methylbenzene)sulfonamido]ethoxy]ethoxy)ethyl]carbamoyl]amino)butyl]urea

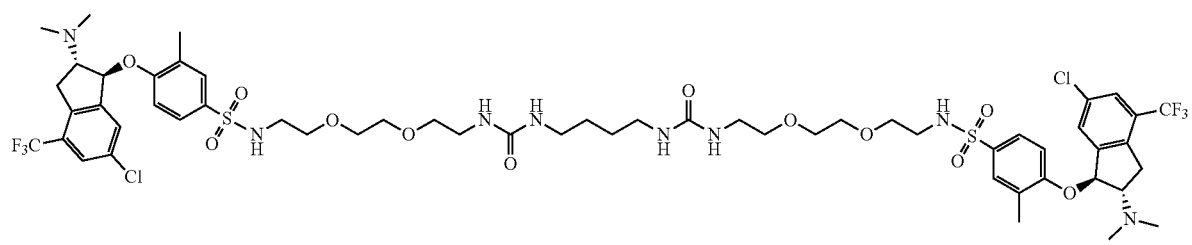

Example 19

Prepared according to the General Scheme above from INT-M2T by dimer formation. Purification by preparative HPLC with the following conditions: Column, XBridge Preparative C18 OBD Column, 19*150 min, 5 um; mobile phase, water (10 mmol/L NH₄HCO₃) and CH₃CN (75% CH₃CN up to 80% in 8 min); Detector, UV 220 nm. This resulted in 42.5 mg (16%) of the title compound as a white solid. MS (m/z): 1399.36 [M+100]⁺. ¹H NMR (Methanol-d4, 400 MHz) δ 8.00 (d, J=1.6 Hz, 2H), 7.80 (d, J=2.0 Hz, 2H), 7.78 (d, J=2.0 Hz, 2H), 7.49 (d, J=8.8 Hz, 2H), 7.34 (s, 2H), 5.98 (d, J=5.6 Hz, 2H), 3.75 (q, J=8.0 Hz, 2H), 3.59-3.50 (m, 18H), 3.33-3.26 (m, 8H), 3.12-3.07 (m, 8H), 2.38 (s, 12H), 1.49 (s, 4H), 1.31 (s, 1H), ¹⁹F NMR (Methanol-d4, 400 MHz) δ: −76.94 (s, 6F).

Example 20: 1-[2-(2-[2-[(4-[[(1S,2S)-6-Chloro-2-(dimethylamino)-4-(trifluoromethoxy)-2,3-dihydro-1H-inden-1-yl]oxy]-3-methylbenzene)sulfonamido]ethoxy]ethoxy)ethyl]-3-[4-([[2-(2-[2-[(4-[[(1S,2S)-6-chloro-2-(dimethylamino)-4-(trifluoromethoxy)-2,3-dihydro-1H-inden-1-yl]oxy]-3-methylbenzene)sulfonamido]ethoxy]ethoxy)ethyl]carbamoyl]amino)butyl]urea Example 20

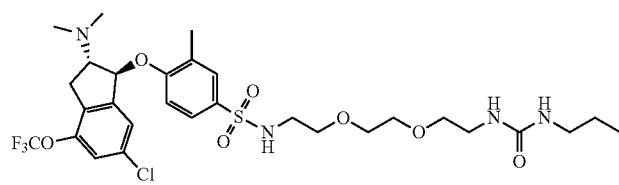
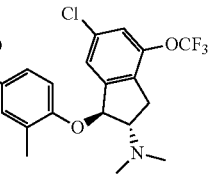

Prepared according to the General Scheme above from INT-M2U by dimer formation. Purification by preparative HPLC with the following conditions: Column, XBridge C18 OBD Preparative Column, 19*250 mm, 5 um; mobile phase, water (10 mmol/L, NH₄HCO₃) and CH₃CN (hold 90.0% CH₃CN in 10 min); Detector, UV 254 nm. This resulted in 64.5 mg (39%) of the title compound as a white solid, MS (m/z): 1431.30 [M+100]⁺. ¹H NMR (Methanol-d4, 400 MHz) δ 7.80 (d, J=2.4 Hz, 2H), 7.78 (s, 2H), 7.63 (s, 2H), 7.48 (d, J=8.8 Hz, 2H), 7.19 (s, 2H), 6.01 (d, J=6.0 Hz, 2H), 3.63-3.60 (m 4H), 3.59-3.50 (m, 14H), 3.38-3.33 (m, 4H), 3.32-3.30 (m, 4H), 3.19-3.12 (m, 4H), 3.10-3.07 (m, 4H), 2.97 (q, J=7.8 Hz, 2H), 2.37 (s, 12H), 2.28 (s, 6H), 1.49 (s, 4H). ¹⁹F NMR (Methanol-d4, 376 MHz) δ: −75.47 (s, 6F).

Example 21: 3-[2-(2-[2-[(4-[[(1S,2S)-6-Chloro-2-(dimethylamino)-4-methoxy-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-(dimethylamino)-4-methoxy-2,3-dihydro-1H-inden-1-yl]oxy]-3-methylbenzene)sulfonamido]ethoxy]ethoxy)ethyl]carbamoyl]amino)butyl]urea; bis(trifluoroacetic acid)

Example 21

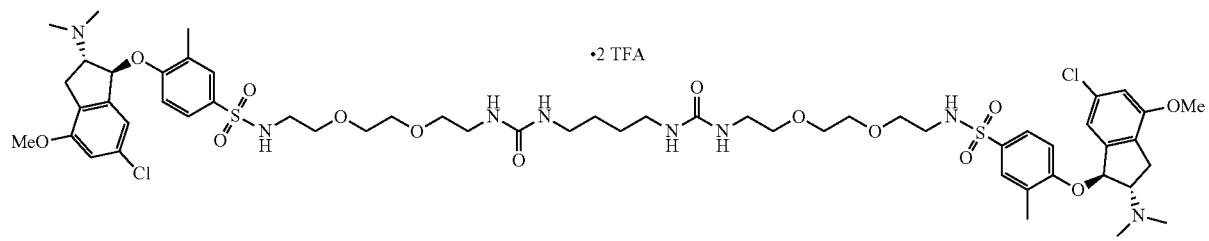

Prepared according to the General Scheme above from INT-M2V by dimer formation. Purification by preparative HPLC with the following conditions Column, XBridge C18 OBD Preparative Column, 19*250 mm, 5 um; mobile phase, water (0.05% TFA) and CH$_3$CN (15% CH$_3$CN up to 33% in 8 min); Detector, UV 254 um. This resulted in 69.6 mg (16%) of the title compound as a white solid. MS (m/z): 1225 [M+H]$^+$. $^1$H NMR (Methanol-d4, 400 MHz) δ 7.81-7.68 (m, 4H), 7.41 (d, J=8.7 Hz, 2H), 6.94 (d, J=1.6 Hz, 2H), 6.70 (d, J=1.3 Hz, 2H), 6.01 (d, J=6.2 Hz, 2H), 4.61 (s, 7H), 3.86 (s, 6H), 3.66-3.45 (m, 18H), 3.27 (d, J=5.7 Hz, 3H), 3.08 (dt, J=10.8, 5.0 Hz, 9H), 2.80 (dd, J=16.2, 8.0 Hz, 2H), 2.49 (s, 12H), 2.26 (s, 6H), 1.51-1.43 (m, 4H).

Example 22: 3-[2-(2-[2-[(4-[[(1S,2S)-4,6-Dichloro-2-(dimethylamino)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-3-methyl benzene)sulfonamido]ethoxy]ethoxy)ethyl]carbamoyl]amino)butyl]urea dihydrochloride

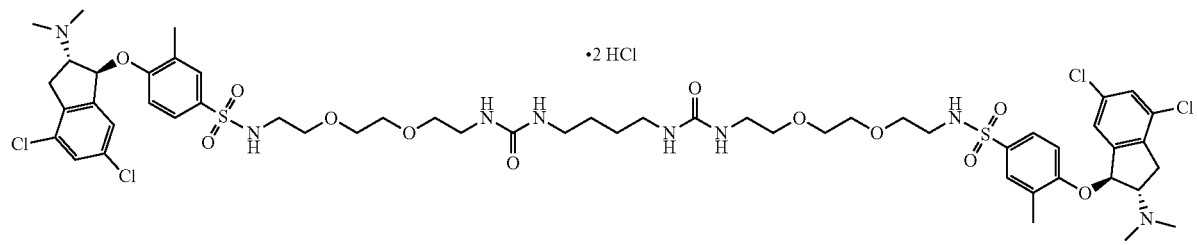

Example 21

Prepared according to the General Scheme above from INT-M2W by dimer formation. Purification by preparative HPLC with the following conditions: Column, XBridge C$_{18}$ OBD Preparative Column, 19*250 mm, 5 um; mobile phase, water (0.05% NH$_4$OH) and CH$_3$CN (80.0% CH$_3$CN up to 90.0% in 8 min); Detector, UV 220 nm. The product was treated with hydrogen chloride and lyophilized. This resulted in 566 mg (62%) of the title compound as a white solid. MS (m/z): 1233.53 [M+H]$^+$. $^1$H NMR (Methanol-d4, 400 MHz) δ 7.87-7.75 (m, 4H), 7.53 (t, J=3.6 Hz, 4H), 7.11 (s, 2H), 6.64 (d, J=6.8 Hz, 2H), 4.51 (td, J=8.4, 6.7 Hz, 2H), 3.72 (dd, J=16.4, 8.4 Hz, 2H), 3.65-3.48 (m, 16H), 3.41-3.31 (m, 6H), 3.16 (s, 4H), 3.10 (t, J=12.4 Hz, 10H), 3.01 (s, 6H), 2.33 (s, 6H), 1.53 (dt, J=6.4, 3.6 Hz, 4H).

Example 23: 3-[2-(2-[2-[(4-[[(1S,2S)-4,6-Dichloro-2-(dimethylamino)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-3-fluorobenzene)sulfonamido]ethoxy]ethoxy)ethyl]carbamoyl]amino)butyl]urea; bis(trifluoroacetic acid)

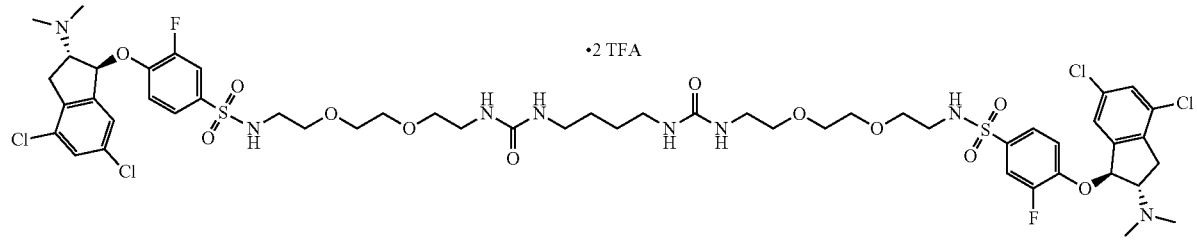

Example 22

Prepared according to the General Scheme above from INT-M2X by dimer formation. Purification by preparative HPLC with the following conditions: Column, XSelect CSH Preparative C18 OBD Column, 19*150 mm, 5 um; mobile phase, water (0.05% NH$_4$OH) and CH$_3$CN (73% CH$_3$CN up to 87% in 8 min); Detector, UV 254 nm. This resulted in 122.2 mg (23%) of the title compound as a white solid, MS (m/z): 1241.5 [M+H]$^+$. $^1$H NMR (Methanol-d4, 400 MHz) δ 7.75-7.58 (m, 6H), 7.43 (d, J=1.7 Hz, 2H), 7.18-7.12 (m, 2H), 5.97 (d, J=5.8 Hz, 2H), 3.61-3.46 (m, 17H), 3.35-3.20 (m, 7H), 3.13-3.05 (m, 7H), 2.91 (dd, J=16.7, 7.4 Hz, 2H), 2.33 (s, 12H), 1.51-1.43 (m, 4H).

Example 24: 3-[2-(2-[2-[(4-[[(1S,2S)-6-Chloro-2-(dimethylamino)-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-2-(dimethylamino)-4-methyl-2,3-dihydro-1H-inden-1-yl]oxy]-3-fluorobenzene)sulfonamido]ethoxy]ethoxy)ethyl]carbamoyl]amino)butyl]urea Example 24

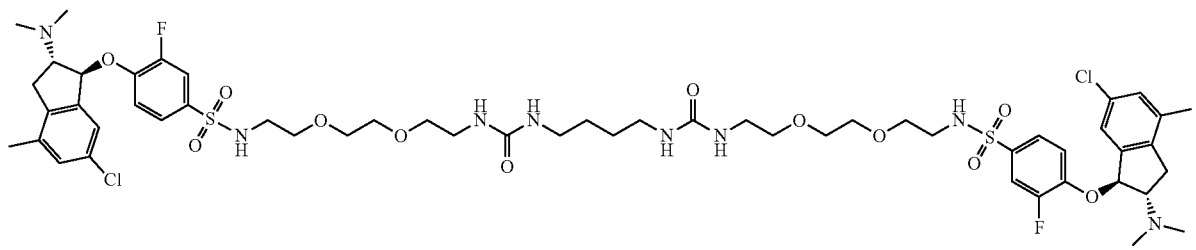

Prepared according to the General Scheme above from INT-M2Y by dimer formation. Purification by preparative HPLC with the following conditions: Column, XBridge C18 OBD Preparative Column, 19*250 mm, 5 um; mobile phase, water (0.05% NH$_4$OH) and CH$_3$CN (50.0% CH$_3$CN up to 67.0% in 8 min); Detector, UV 254 nm. This resulted in 132.5 mg (12%) of as a white solid. MS (m/z): 1200 [M+H]$^+$. $^1$H NMR (Methanol-d4, 400 MHz) δ 7.75-7.55 (m, 6H), 7.19-7.14 (m, 2H), 7.01-6.95 (m, 2H), 5.95-5.89 (d, J=5.7 Hz, 2H), 3.61-3.43 (m, 19H), 3.31-3.24 (d, J=5.4 Hz, 3H), 3.24-3.05 (m, 11H), 2.86-2.75 (dd, J=16.2, 7.4 Hz, 2H), 2.36-2.27 (d, J=18.7 Hz, 18H), 1.51-1.43 (m, 4H).

Example 25: 3-[2-(2-[2-[(4-[[(1S,2S)-1,6-Dichloro-2-[(3R)-3-(dimethylamino)piperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-1,6-dichloro-2-[(3R)-3-(dimethylamino)piperidin-1-yl]-2,3-dihydro-1H-1-inden-1-yl]oxy]benzene)sulfonamido]ethoxy]ethoxy)ethyl]carbamoyl]amino)butyl]urea; bis(trifluoroacetic acid)

Example 25

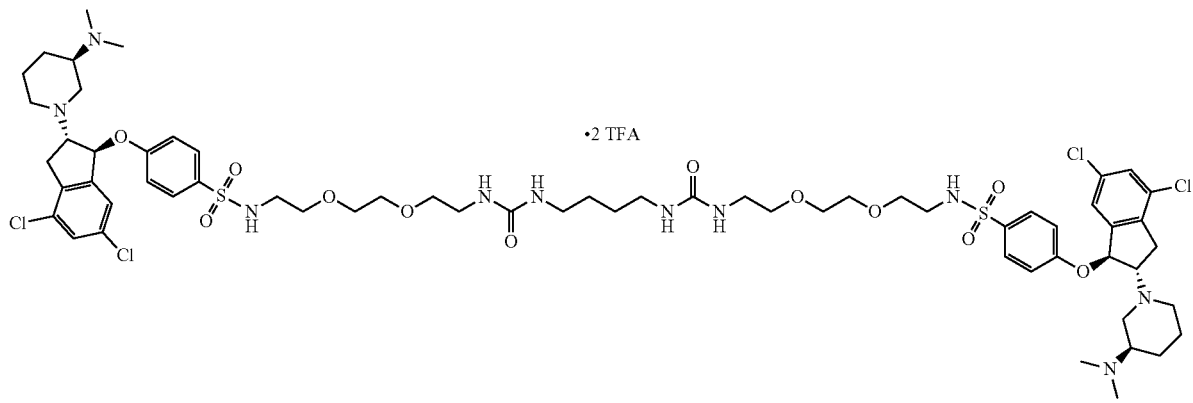

Prepared according to the General Scheme above from INT-M2Z by dimer formation. Purification by preparative HPLC with the following conditions: Column, XBridge C18 OBD Preparative Column, 19*250 mm, 5 um; mobile phase, water (0.05% TFA) and CH₃CN (30.0% CH₃CN up to 62.0% in 8 min); Detector, UV 254 nm. This resulted in 203.4 mg (58%) of the title compound as yellow oil. MS (m/z): 1371 [M+H]⁺. ¹H NMR (Methanol-d4, 400 MHz) δ 7.93-7.85 (m, 4H), 7.46 (t, J=2.1 Hz, 2H), 7.34 (d, J=8.6 Hz, 4H), 7.16-7.10 (m, 2H), 6.29 (dd, J=15.1, 6.7 Hz, 2H), 4.00 (q, J=7.6 Hz, 2H), 3.62-3.24 (m, 23H), 3.20-2.99 (m, 14), 2.92 (s, 5), 2.83 (s, 8), 2.73 (s, 1H), 2.11 (s, 2H), 1.96 (d, J=12.8 Hz, 2H), 1.79 (dd, J=10.9, 9.1 Hz, 4H), 1.41-1.51 (m, 4H).

Example 26: 3-[2-(2-[2-[(4-[[(1S,2S)-4,6-Dichloro-2-[(3R)-3-(dimethylamino)piperidin-1-yl]-2,3-dihydro-1H-inden-1-yl]oxy]-3-methylbenzene)sulfonamido]ethoxy]ethoxy)ethyl]-1-[4-([[2-(2-[2-[4-[[(1S,2S)-4,6-dichloro-2-[(3R)-3-(dimethylamino)piperidin-1-yl]-2,3-dihydro-1H-inden-1-yl]oxy]-3-methylbenzenesulfonamido]ethoxy]ethoxy)ethyl]carbamoyl]amino)butyl]urea; bis(trifluoroacetic acid)

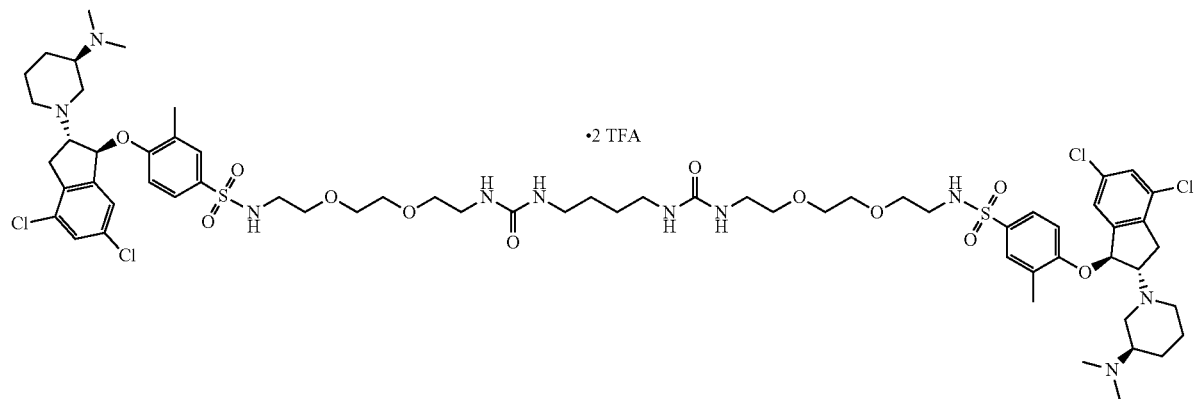

Example 26

Prepared according to the General Scheme above from INT-M2AA by dimer formation. Purification by preparative HPLC with the following conditions (Column, XBridge Shield RP18 OBD Column, 19*150 mm, 5 um; mobile phase, water (0.05% NH₄OH) and CH₃CN (isocratic 61.0% CH₃CN in 10 min); Detector, UV 254/220 nm. This resulted in 90.6 mg (13%) of the title compound as a white solid, MS (m/z): 1398.9 [M+H]⁺. ¹H NMR (Methanol-d4, 400 MHz) δ 7.80-7.67 (m, 4H), 7.50-7.38 (m, 4H), 7.16-7.10 (m, 2H), 5.99 (d, J=6.0 Hz, 2H), 3.62-3.46 (m, 18H), 3.32-3.23 (m, 6H), 3.07 (dt, J=29.7, 5.8 Hz, 10H), 2.91 (dd, J=16.4, 8.0 Hz, 4H), 2.27 (s, 8H), 2.14 (s, 16H), 1.95 (d, J=12.6 Hz, 2H), 1.84-1.75 (m, 2H), 1.64-1.52 (m, 2H), 1.52-1.44 (m, 4H) 1.28-1.15 (m, 2H).

Example 27: 3-[2-(2-[2-[(4-[[(1S,2S)-4,6-Dichloro-2-[(3R)-3-(dimethylamino)piperidin-1-yl]-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-4,6-dichloro-2-[(3R)-3-(dimethylamino)piperidin-1-yl]-2,3-dihydro-1H-inden-1-yl]oxy]-3-fluorobenzene)sulfonamido]ethoxy]ethoxy)ethyl]carbamoyl]amino)butyl]urea; bis(trifluoroacetic acid)

Example 27

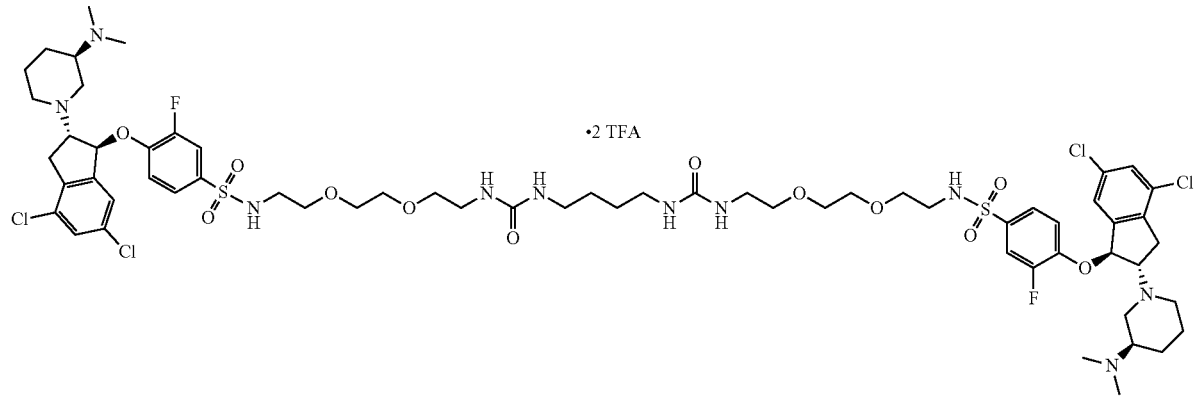

Prepared according to the General Scheme above from INT-M2AB by dimer formation. Purification by preparative HPLC with the following conditions: Column, XBridge C18 OBD Preparative Column, 19*250 min, 5 um; mobile phase, water (0.05% TFA) and $CH_3CN$ (29.0% $CH_3CN$ up to 33.0% in 10 min); Detector, UV 254 nm. This resulted in 267 mg (65%) of the title compound as colorless oil. MS (m/z): 1407 [M+H]$^+$. $^1$H NMR (Methanol-d4, 400 MHz) δ 7.76-7.57 (m, 6H), 7.45 (d, J=1.8 Hz, 2H), 7.22-7.17 (m, 2H), 6.11 (d, J=5.7 Hz, 2H), 3.86 (td, J=7.7, 5.8 Hz, 2H), 3.54 (dtd, J=21.8, 5.5, 2.6 Hz, 17H), 3.31-3.21 (m, 5H), 3.17-2.99 (m, 13H), 2.87 (s, 16H), 2.52 (t, J=9.8 Hz, 2H), 2.03 (s, 2H), 1.88 (dd, J=11.2, 6.6 Hz, 2H), 1.78-1.61 (m, 4H), 1.51-1.41 (m, 4H).

Example 28: 3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]benzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]benzene)sulfonamido]ethoxy]ethoxy)ethyl]carbamoyl]amino)butyl]urea; bis(trifluoroacetic acid)

Example 26

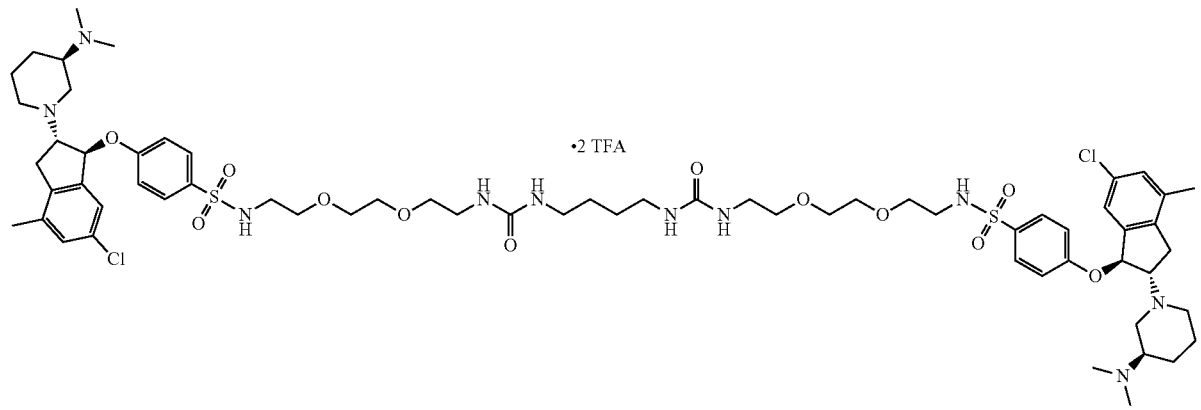

Prepared according to the General Scheme above from INT-M2AC by dimer formation. Purification by preparative HPLC with the following conditions: Column, XBridge C18 OBD Preparative Column, 19*250 mm, 5 um; mobile phase, water (0.05% TFA) and CH$_3$CN (30.0% CH$_3$CN up to 34.0% in 9 min); Detector, UV 254 nm. This resulted in 210.2 mg (18%) of the title compound as a white solid, MS (m/z): 1331.7 [M+H]$^+$. $^1$H NMR (Methanol-d4, 400 MHz) δ 7.94-7.85 (m, 4H), 7.38-7.30 (m, 4H), 7.24-7.19 (m, 2H), 6.97 (d, J=1.8 Hz, 2H), 6.36 (d, J=6.1 Hz, 2H), 4.15 (q, J=7.6 Hz, 2H), 3.66-3.33 (m, 24H), 3.32-3.20 (m, 6H), 3.16-3.04 (m, 10H), 2.82 (s, 14H), 2.31 (s, 6H), 2.18 (d, J=11.9 Hz, 2H), 2.13-2.03 (m, 2H), 1.94-1.73 (m, 4H), 1.47 (h, J=3.0 Hz, 4H).

Example 29: 3-[2-(2-[2-[4-[[(1S,2S)-6-Chloro-2-[(3R)-3-(dimethylamino)piperidin-1-yl]-4-methyl-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]-3-methylbenzene)sulfonamido]ethoxy]ethoxy)ethyl]carbamoyl]amino)butyl]urea; bis(trifluoroacetic acid)

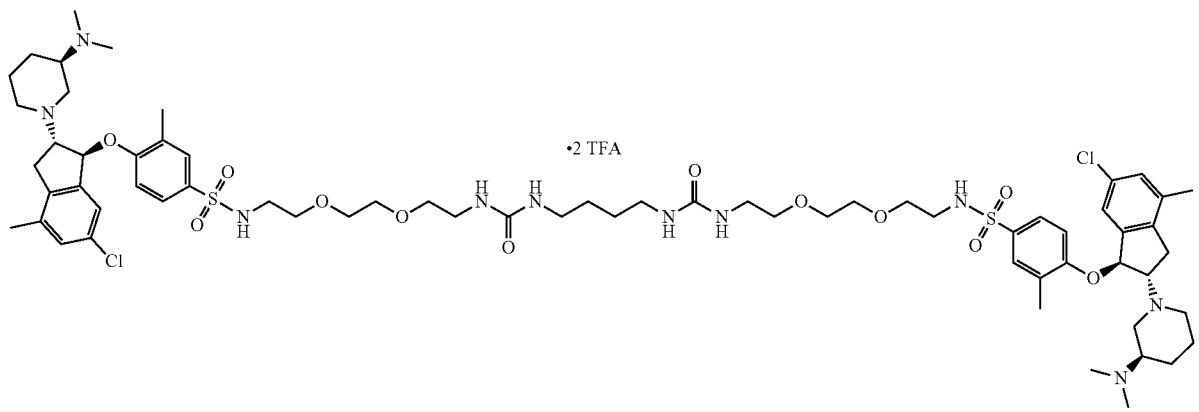

Example 29

Prepared according to the General Scheme above from INT-M2AD by dimer formation. Purification by preparative HPLC with the following conditions: Column, XBridge C18 OBD Preparative Column, 19*250 mm, 5 um; mobile phase, water (0.05% TFA) and CH$_3$CN (31.0% CH$_3$CN up to 36.0% in 10 min); Detector, UV 254 nm. This resulted in 163.7 mg (52%) of the title compound as a white solid. MS (m/z): 1359.75 [M+H]$^+$. $^1$H NMR (Methanol-d4, 300 MHz) δ 7.80-7.65 (m 4H), 7.43 (d, J=8.6 Hz, 2H), 7.21-7.14 (m, 2H), 6.92 (d, J=1.3 Hz, 2H), 6.23 (d, J=5.7 Hz, 2H), 4.00 (q, J=7.2 Hz, 2H), 3.50 (dt, J=16.7, 4.6 Hz, 19H), 3.41-3.29 (m, 4H), 3.24 (d, J=5.4 Hz, 3H), 3.16 (s, 2H), 3.03 (tt, J=12.2, 6.5 Hz, 15H), 2.80 (s, 14H), 2.26 (d, J=14.0 Hz, 12H), 2.10 (s, 2H), 1.96 (s, 2H), 1.77 (s, 4H), 1.49-1.38 (m, 4H).

Example 30: 3-[2-(2-[2-[(4-[[(1S,2S)-6-Chloro-2-[(3R)-3-(dimethylamino)piperidin-1-yl]-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-2-[(3R)-3-(dimethylamino)piperidin-1-yl]-4-methyl-2,3-dihydro-1H-inden-1-yl]oxy]-3-fluorobenzene)sulfonamido]ethoxy]ethoxy)ethyl]carbamoyl]amino)butyl]urea; bis(trifluoroacetic acid)

Example 30

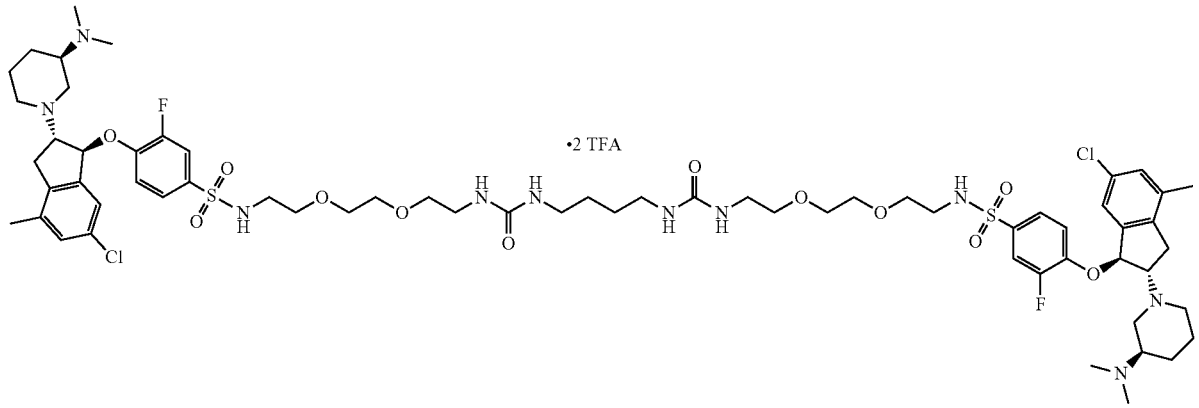

Prepared according to the General Scheme above from INT-M2AE by dimer formation. Purification by preparative HPLC with the following conditions: Column, XBridge C18 OBD Preparative Column, 19*250 mm, 5 um; mobile phase, water (0.05% TFA) and $CH_3CN$ (31.0% $CH_3CN$ up to 36.0% in 10 min); Detector, UV 254 nm. This resulted in 161.2 mg (61%) of the title compound as a white solid. MS (m/z): 1368 $[M+H]^+$. $^1H$ NMR (Methanol-d4, 300 MHz) δ 7.65 (dt, J=19.4, 8.6 Hz, 6H), 7.23-7.16 (m, 2H), 6.98 (d, J=1.9 Hz, 2H), 6.22. (s, 2H), 4.02 (s, 2H), 3.60-3.20 (m, 23H), 3.07 (t, J=5.5 Hz, 12H), 2.84 (s, 12H), 2.71 (s, 2H), 2.29 (s, 6H), 2.09 (s, 2H), 1.95 (s, 2H), 1.75 (s, 5H), 1.44 (dd, J=4.1, 2.7 Hz, 4H).

Example 31: 3-[2-(2-[2-[(4-[[(1S,2S)-4,6-Dichloro-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-(piperazin-1-yl)-2,3-dihydro-1H-inden-1-yl]oxy]benzene)sulfonamido]ethoxy]ethoxy)ethyl]carbamoyl]amino)butyl]urea; bis(trifluoroacetic acid)

Example 31

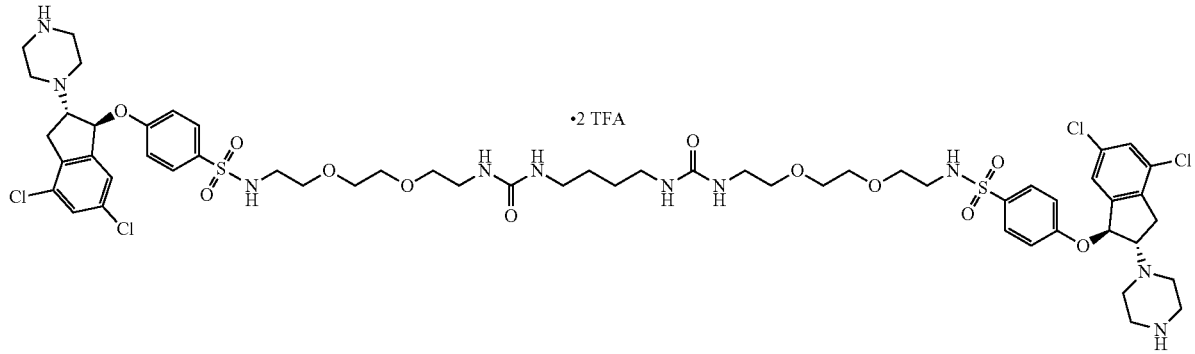

Prepared according to the General Scheme above from INT-M2AF by dimer formation and Boc-deprotection. Purification by preparative HPLC with the following conditions: Column, XBridge C18 OBD Preparative Column, 19*250 mm, 5 um; mobile phase, water (0.05% TFA) and CH$_3$CN (30.0% CH$_3$CN up to 52.0% in 8 min); Detector, UV 254 nm. This resulted in 122.7 mg (40%) of the title compound as a white solid. MS (m/z): 1287 [M+H]$^+$. $^1$H NMR (Methanol-d4, 300 MHz) δ 7.95-7.84 (m, 4H), 7.46 (d, J=1.8 Hz, 2H), 7.39-7.29 (m, 4H), 7.21-7.13 (m, 2H), 6.09 (d, J=6.0 Hz, 2H), 3.77-3.48 (m, 19H), 3.28 (dd, J=11.7, 6.7 Hz, 6H), 3.14-2.86 (m, 10H), 1.55-1.44 (m, 4H).

Example 32: 3-[2-(2-[2-[(4-[[(1S,2S)-4,6-Dichloro-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-4,6-dichloro-2-(piperazin-1-yl)-2,3-dihydro-1H-inden-1-yl]oxy]-3-methylbenzene)sulfonamido]ethoxy]ethoxy)ethyl]carbamoyl]amino)butyl]urea; bis(trifluoroacetic acid)

Example 32

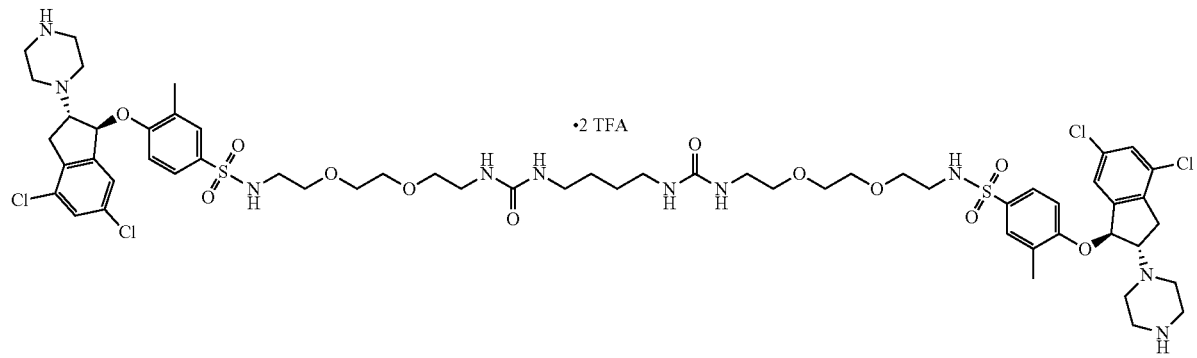

Prepared according to the General Scheme above from INT-M2AG by dimer formation and Boc-deprotection. Purification by preparative HPLC with the following conditions: Column, XBridge C18 OBD Preparative Column, 19*250 mm, 5 um; mobile phase, water (0.05% TFA) and CH$_3$CN (35.0% CH$_3$CN up to 55.0% in 8 min); Detector, UV 254 nm. This resulted in 183.2 mg (60%) of title compound as a white solid. MS (m/z): 1316.2 [M+H]$^+$. $^1$H NMR (Methanol-d4, 400 MHz) δ 7.82-7.70 (m, 4H), 7.54-7.43 (m, 5H), 7.17-7.12 (m, 2H), 6.09 (d, J=6.1 Hz, 2H), 3.72 (td, J=7.9, 6.0 Hz, 2H), 3.64-3.49 (m, 16H), 3.28 (dt, J=17.6, 5.2 Hz, 13H), 3.16-2.79 (m, 19H), 2.29 (s, 6H), 1.49 (p, J=3.4 Hz, 4H).

Example 33: 3-[2-(2-[2-[(4-[[(1S,2S)-4,6-Dichloro-2-(piperazin-1-yl)-2,3-dihydro-1H-inden-1-yl]oxy]-3-fluorobenzene)sulfonamido]ethoxy]ethoxy)ethyl]-1-[4-[[(2-(2-[2-[(4-[[(1S,2S)-4,6-dichloro-2-(piperazin-1-yl)-2,3-dihydro-1H-inden-1-y]oxy]-3-fluorobenzene)sulfonamido]ethoxy]ethoxy)ethyl]carbamoyl]amino)butyl]urea; bis(trifluoroacetic acid)

Example 33

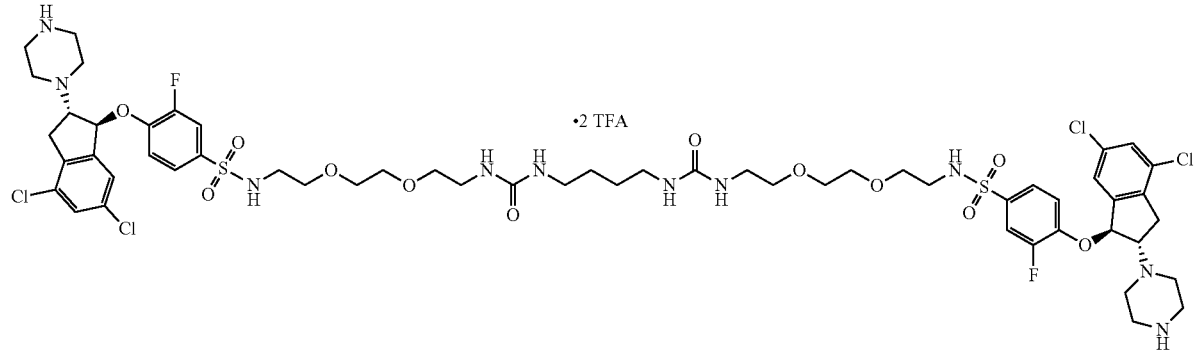

Prepared according to the General Scheme above from INT-M2AH by dimer formation and Boc-deprotection. Purification by preparative HPLC with the following conditions: Column, XBridge C18 OBD Preparative Column, 19*250 mm; mobile phase, water (0.05% TFA) and CH$_3$CN (22.0% CH$_3$CN up to 42.0% in 11 min); Detector, UV 254 nm. This resulted in 419.2 mg (69%) of the title compound as a white solid. MS (m/z): 1323 [M+H]$^+$. $^1$H NMR (Methanol-d4, 300 MHz) δ 7.75-7.52 (m, 6H), 7.42 (d, J=1.7 Hz, 2H), 7.20-7.12 (m, 2H), 6.04 (d, J=5.9 Hz, 2H), 3.72 (td, J=7.7, 5.8 Hz, 2H), 3.60-3.43 (m, 16H), 3.29-3.12 (m, 13H), 3.13-2.72 (m, 19H), 1.44 (p, J=3.3 Hz, 4H).

Example 34: 3-[2-(2-[2-[(4-[[(1S,2S)-6-Chloro-4-methyl-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]benzene)sulfonamido]ethoxy]ethyl)ethyl]carbamoyl]amino)butyl]urea; bis(trifluoroacetic acid)

Example 34

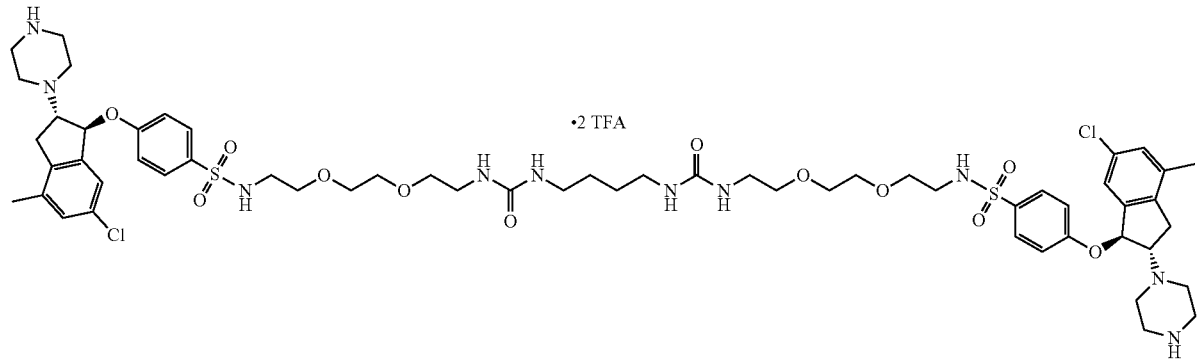

Prepared according to the General Scheme above from INT-M2AI by dimer formation and Boc-deprotection. Purification by preparative HPLC with the following conditions: Column, XBridge C18 OBD Preparative Column, 19*250 mm, 5 um, mobile phase, water (0,05% TFA) and CH$_3$CN (20% CH$_3$CN up to 38% in 8 min); Detector, UV 254 nm. This resulted in 288.6 mg (64%) of the title compound as a white solid. MS (m/z): 1245 [M+H]$^+$. $^1$H NMR (Methanol-d4, 400 MHz) δ 7.91-7.82 (m, 4H), 7.34-7.2.5 (m, 4H), 7.20-7.14 (m, 2H), 6.98 (d, J=1.9 Hz, 2H), 6.00 (d, J=5.8 Hz, 2H), 3.69-3.46 (m, 18H), 3.32-3.03 (m, 22H), 2.97-2.79 (m, 10H), 2.29 (s, 6H), 1.47 (p, J=3.3 Hz, 4H).

Example 35: 3-[2-(2-[2-[(4-[[(1S,2S)-6-Chloro-4-methyl-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]-3-methylbenzene)sulfonamido]ethoxy]ethoxy)ethyl]carbamoyl]amino)butyl]urea; bis(trifluoroacetic acid)

Example 35

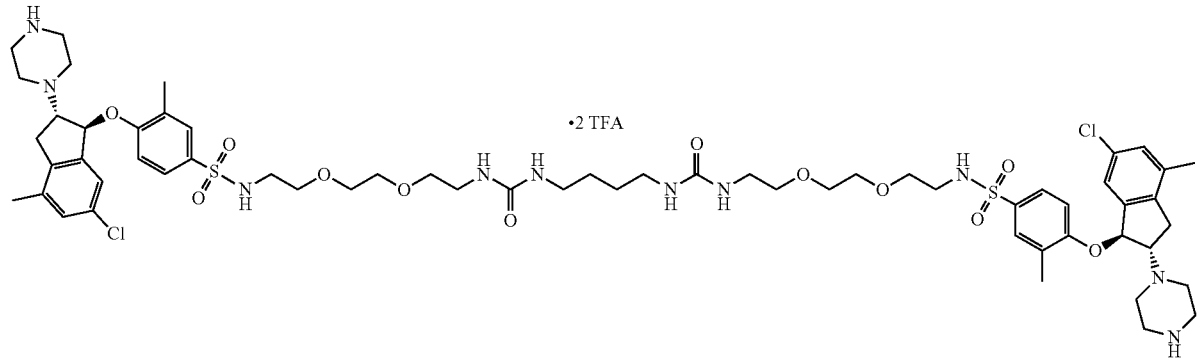

Prepared according to the General Scheme above from INT-M2AJ by dimer formation and Boc-deprotection. Purification by preparative HPLC with the following conditions: Column, XBridge C18 OBD Preparative Column, 19*250 mm, 5 um; mobile phase, water (0.05% TFA) and CH$_3$CN (22% CH$_3$CN up to 38% in 10 min); Detector, UV 254 nm. This resulted in 303.9 mg (66%) of the title compound as a white solid. MS (m/z): 638.15 [M/2+H]$^+$. $^1$H NMR (Methanol-d4, 400 MHz) δ 7.80-7.67 (m 4H), 7.43 (d, J=8.7 Hz, 2H), 7.20-7.14 (m, 2H), 6.96 (d, J=1.8 Hz, 2H), 6.02 (d, J=5.9 Hz, 2H), 3.71-3.61 (m, 2H), 3.61-3.46 (m, 16H), 3.32-3.15 (m, 14H), 3.08 (dt, J=15.4, 5.7 Hz, 8H), 2.89 (ddt, J=22.8, 13.6, 6.0 Hz, 10H), 2.28 (d, J=16.7 Hz, 12H), 1.47 (p, J=3.2 Hz, 4H).

Example 36: 3-[2-(2-[2-[(4-[[(1S,2S)-6-Chloro-4-methyl-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-methyl-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea; bis(trifluoroacetic acid)

Example 36

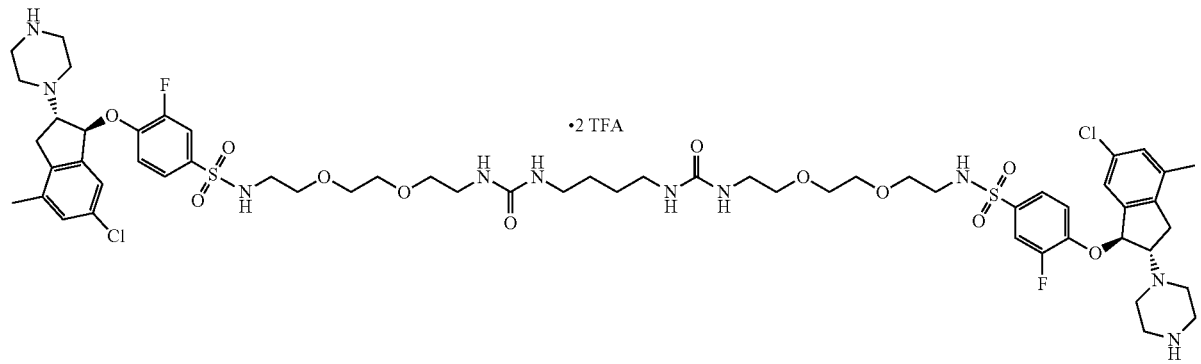

Prepared according to the General Scheme above from INT-M2AK by dimer formation and Boc-deprotection. Purification by preparative HPLC with the following condition: Column, XBridge C18 OBD Preparative Column, 19*250 mm, 5 um; mobile phase, water (0.05% TFA) and CH$_3$CN (30.0% CH$_3$CN up to 38.0% in 11 min); Detector, UV 254 nm. This resulted in 358.1 mg (59%) of the title compound as a white solid. MS (m/z): 1281 [M+H]$^+$. $^1$H NMR (Methanol-d4, 300 MHz) δ 7.74-7.51 (m, 6H), 7.20-7.13 (m, 2H), 6.99 (d, J=1.8 Hz, 2H), 6.01 (d, J=5.6 Hz, 2H), 3.69 (td, J=7.6, 5.6 Hz, 2H), 3.60-3.42 (m, 16H), 3.29-3.01 (m, 22H), 2.88 (tq, J=11.5, 6.9, 5.7 Hz, 10H), 2.27 (s, 6H), 1.50-1.39 (m, 4H).

Alternate Route to Monomer Synthesis

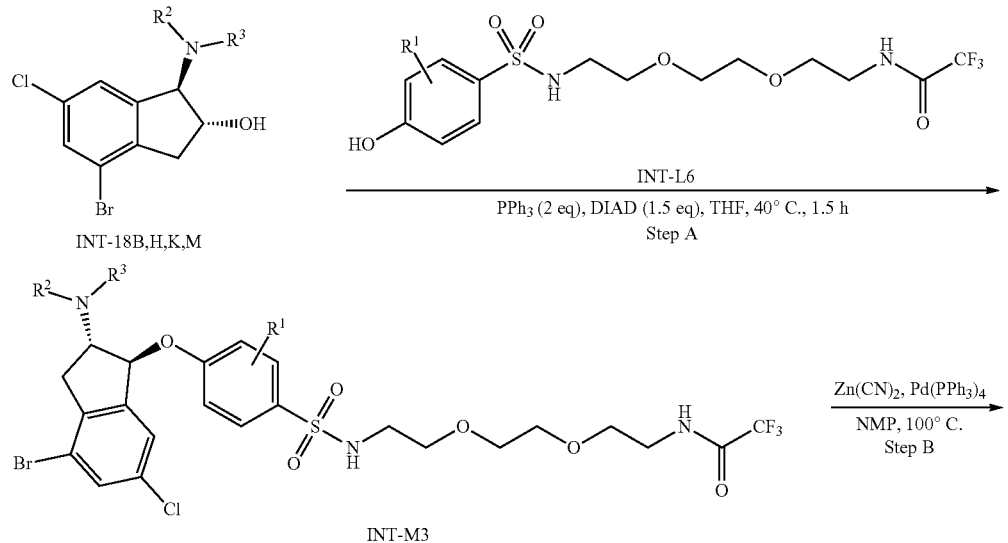

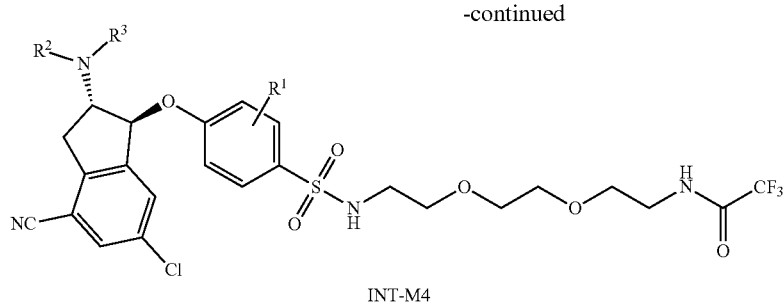

INT-M4

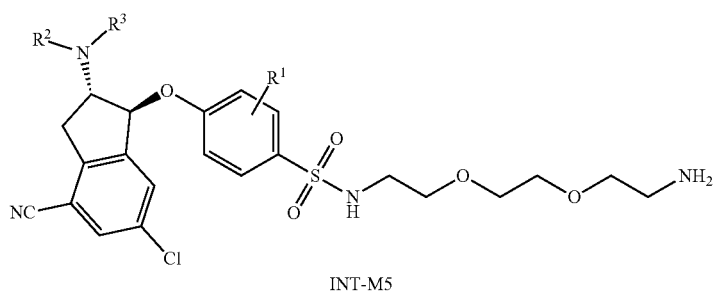

INT-M5

Step A: To a round-bottom flask was added bromoaminoindanol INT-I8 (1 equiv), phenol INT-L6 (1.2 equiv), tetrahydrofuran (0.43 M), and PPh₃ (1.5 equiv). The flask was heated to 40-45° C. followed by the addition of DIAD (1.5 equiv) dropwise over 15-20 min. The resulting slurry was stirred for 1 h at 40° C. in an oil bath. The resulting mixture was concentrated under vacuum and diluted with CH₂Cl₂. The residue was applied onto a silica gel column with ethyl acetate/petroleum ether (0-80%) providing the sulfonamide INT-M3.

Step B: To a round-bottom flask was added INT-M3 (1 equiv), NMP (0.1 M), Pd(PPh₃)₄ (0.1 equiv), and Zn(CN)₂ (0.6 equiv). The resulting solution was stirred overnight at 100° C. in an oil bath. The resulting solution was extracted with 3× ethyl acetate. The organic layers were combined, washed with 3× brine, dried over anhydrous sodium sulfate, filtered, and concentrated under vacuum. The residue was applied onto a silica gel column with ethyl acetate/petroleum ether (0-80%) providing the 4-cyano aminoindanols INT-M4.

Step C: To a round-bottom flask was added aminoindanol INT-M4 (1 equiv), tetrahydrofuran (0.066 M), and sodium hydroxide (3 M, 7.5 equiv). The resulting slurry was stirred for 1 h at room temperature. The resulting solution was extracted with 4× ethyl acetate. The organic layers were combined, dried over anhydrous sodium sulfate, filtered, and concentrated under vacuum. The residue was applied onto a silica gel column with CH₂Cl₂/methanol (5:1) providing the amine monomer INT-M5.

The following intermediates are made by applying the above procedures to the appropriate starting aminoindanols INT-I8 and linkers INT-L6:

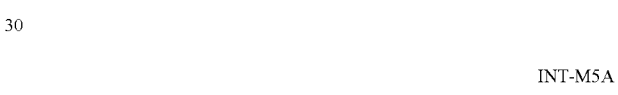

INT-M5A

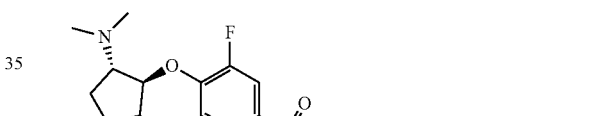

INT-M5B

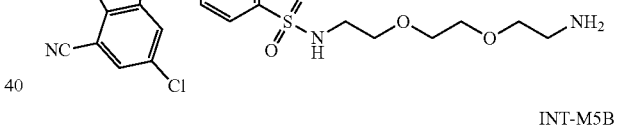

INT-M5C

INT-M5D

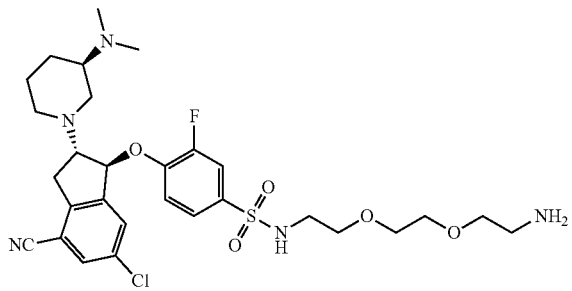

INT-M5F

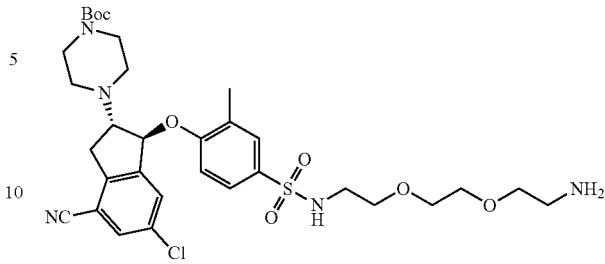

INT-M5G

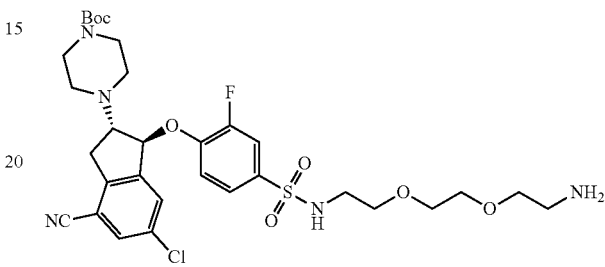

INT-M5E

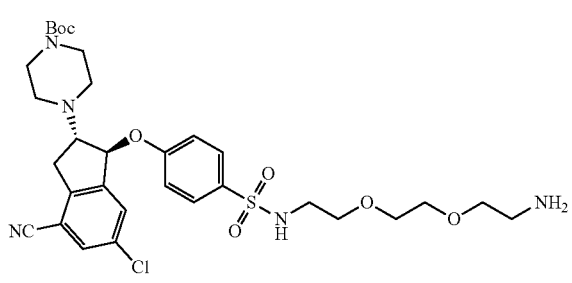

General Procedure for Dimer Product Sythesis: Conversion of monomers INT-M5 proceeded via the same sequence as the conversion of INT-M2 to the desired dimer Products 1 (with or without the follow-on Boc-deprotection as necessary).

Example 37: 3-[2-(2-[2-[(4-[[(1S,2S)-6-Chloro-4-cyano-2-(dimethylamino)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]-3-fluorobenzene)sulfonamido]ethoxy]ethoxy)ethyl]carbamoyl]amino)butyl]urea Example 37

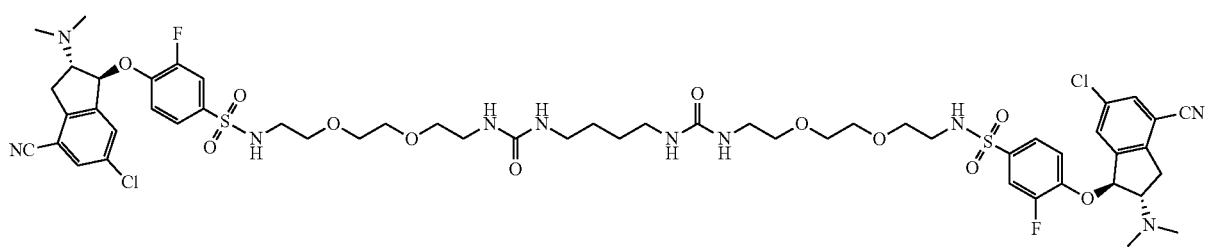

Prepared according to the General Scheme above from INT-M5A by dimer formation. Purification by preparative HPLC with the following conditions: Column, XBridge Preparative C18 OBD Column, 19*150 mm 5 um; mobile phase, water (0.05% NH$_4$OH) and CH$_3$CN (55.0% CH$_3$CN up to 59.0% in 7 min); Detector, UV 254/220 nm. This resulted in 64.8 mg (6%) of the title compound as a white solid. MS (m/z): 1223.6 [M+H]$^+$. $^1$H NMR (Methanol-d4, 400 MHz) δ 7.77 (d, J=1.8 Hz, 2H), 7.75-7.62 (m, 6H), 7.53-7.47 (m, 2H), 6.00 (d, J=5.8 Hz, 2H), 3.65 (q, J=7.3 Hz, 2H), 3.60-3.52 (m, 8H), 3.50 (td, J=5.5, 2.1 Hz, 8H), 3.31 (m, 4H), 3.28 (d, J=5.4 Hz, 3H), 3.15-3.04 (m, 10H), 2.36 (s, 12H), 1.47 (p, J=3.2 Hz, 4H).

Example 38: 3-[2-(2-[2-[(4-[[(1S,2S)-2-[(3R)-3-Aminopiperidin-1-yl]-6-chloro-4-methyl-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-methyl-2,3-dihydro-1H-1-inden-1-yl]oxy]-3-fluorobenzene)sulfonamido]ethoxy]ethoxy)ethyl]carbamoyl]amino)butyl]urea; bis(trifluoroacetic acid)

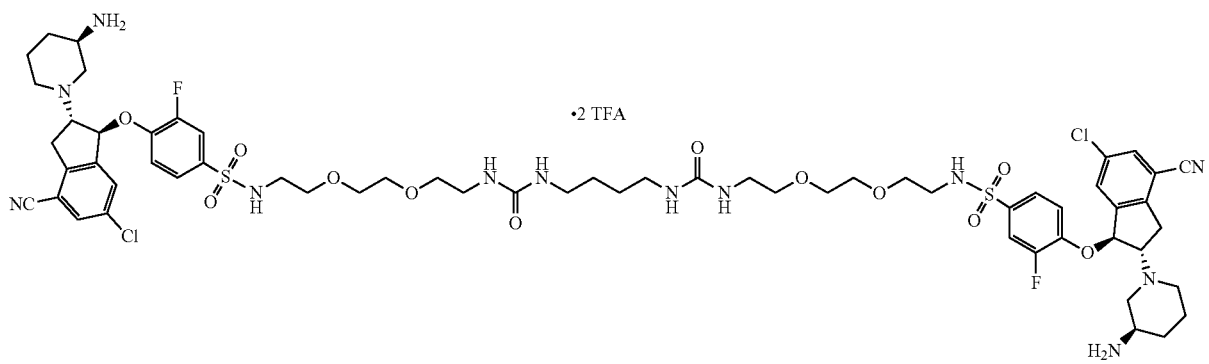

Example 38

Prepared according to the General Scheme above from INT-M5B by dimer formation and Boc-deprotection. Purification by preparative HPLC with the following conditions: Column, XBridge C18 OBD Preparative Column, 19*250 mm, 5 um; mobile phase, water (0.05% TFA) and $CH_3CN$ (29.0% $CH_3CN$ up to 33.0% in 10 min); Detector, UV 254 nm. This resulted in 302.6 mg (59%) of the title compound as a white solid. MS (m/z): 1331 [M+H]$^+$. $^1$H NMR (Methanol-d4, 400 MHz) δ 7.80 (d, J=1.9 Hz, 2H), 7.77-7.58 (m, 7H), 7.54 (d, J=2.3 Hz, 2H), 6.14-6.04 (m, 2H), 3.84 (d, J=16.5 Hz, 2H), 3.54 (dtd, J=23.1, 5.3, 3.1 Hz, 17H), 3.38 (dd, J=18.7, 7.4 Hz, 5H), 3.19 (dt, J=75.2, 5.4 Hz, 15H), 2.98 (s, 3H), 2.76 (s, 2H), 2.61 (s, 5H), 1.93 (s, 3H), 1.85 (s, 2H), 1.65 (s, 2H), 1.56 (s, 3H), 1.47 (p, J=3.3 Hz, 4H).

Example 39: 3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-methylbenzene)sulfonamido]ethoxy]ethoxy)ethyl]-1-[(4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-methylbenzene)sulfonamido]ethoxy]ethoxy)ethyl]carbamoyl]amino)butyl]urea; bis(trifluoroacetic acid)

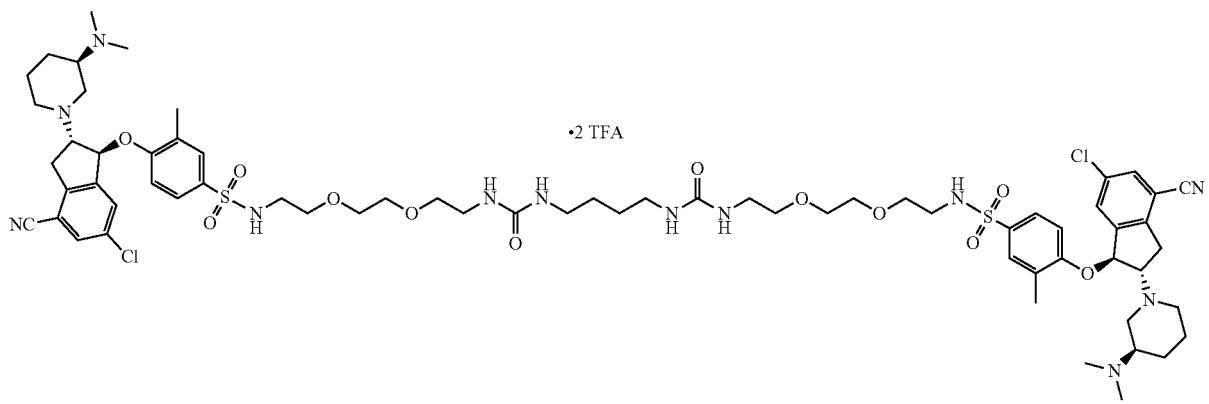

Example 39

Prepared according to the General Scheme above from INT-M5C by dimer formation. Purification by preparative HPLC with the following conditions (Column, XBridge Shield RP18 OBD Column, 19*150 mm, 5 um; mobile phase, water (0.05% NH$_4$OH) and CH$_3$CN (47.0% CH$_3$CN up to 48.0% in 15 min); Detector, UV 254/220 nm. This resulted in 52.9 mg (10%) of the title compound as a white solid. MS (m/z): 1381.85 [M+H]$^+$. $^1$H NMR (Methanol-d4, 400 MHz) δ 7.80-7.67 (m, 6H), 7.53-7.44 (m, 4H), 6.02 (d, J=6.0 Hz, 2H), 3.69-3.46 (m, 20H), 3.39 (dd, J=16.7, 8.0 Hz, 2H), 3.28 (d, J=5.4 Hz, 2H), 3.15-2.99 (m, 12H), 2.92 (d, J=11.1 Hz, 2H), 2.28 (s, 8H), 2.15 (s, 16H), 1.95 (d, J=12.9 Hz, 2H), 1.80 (dt, J=13.8, 3.4 Hz, 2H), 1.65-1.43 (m, 6H), 1.23 (ddt, J=20.4, 12,3, 6.6 Hz, 2H).

Example 40: 3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-fluorobenzene)sulfonamido]ethoxy]ethoxy)ethyl]carbamoyl]amino)butyl]urea; bis(trifluoroacetic acid)

Example 40

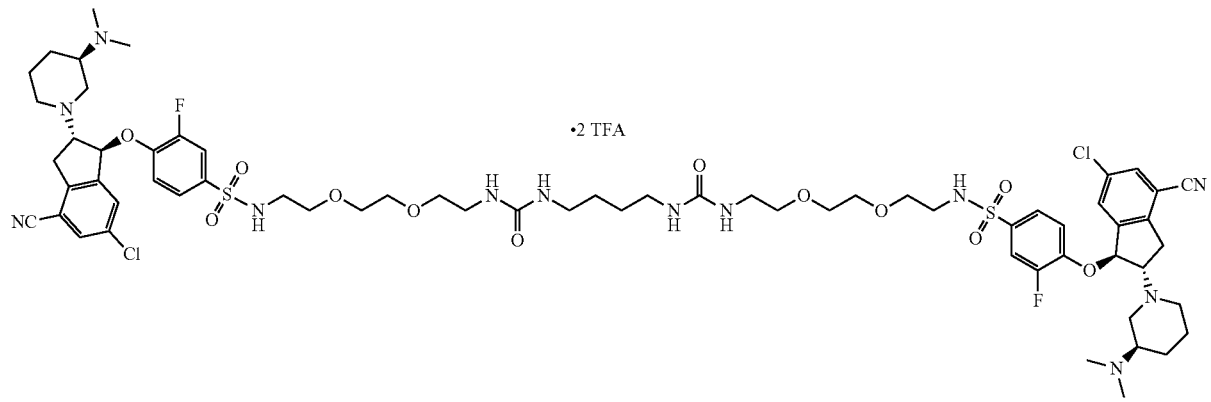

Prepared according to the General Scheme above from INT-M5D by dimer formation. Purification by preparative HPLC with the following conditions: Column, XBridge C18 OBD Preparative Column, 19*250 mm, 5 um; mobile phase, water (0.05% TFA) and CH$_3$CN (30.0% CH$_3$CN up to 40.0% in 8 min); Detector, UV 254 nm. This resulted in 334 mg (73%) of the title compound as a white solid. MS (m/z): 1387 [M+H]$^+$. $^1$H NMR (Methanol-d4, 400 MHz) δ 7.80 (d, J=1.9 Hz, 2H), 7.77-7.59 (m, 6H), 7.54 (dd, J=1.8, 0.8 Hz, 2H), 6.16 (d, J=6.0 Hz, 2H), 3.97 (q, J=7.6 Hz, 2H), 3.54 (dtd, J=22.5, 5.4, 2.9 Hz, 17H), 3.46-3.17 (m, 13H), 3.14-3.05 (m, 8H), 2.87 (s, 16H), 2.55 (t, J=9.8 Hz, 2H), 2.06 (t, J=11.1 Hz, 2H), 1.90 (dd, J=10.2, 5.1 Hz, 2H), 1.69 (q, J=10.9, 10.0 Hz, 4H), 1.53-1.41 (m, 4H).

Example 41: 3-[2-(2-[2-[(4-[[(1S,2S)-6-Chloro-4-cyano-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]benzene)sulfonamido]ethoxy]ethoxy)ethyl]carbamoyl]amino)butyl]urea; bis(trifluoroacetic acid)

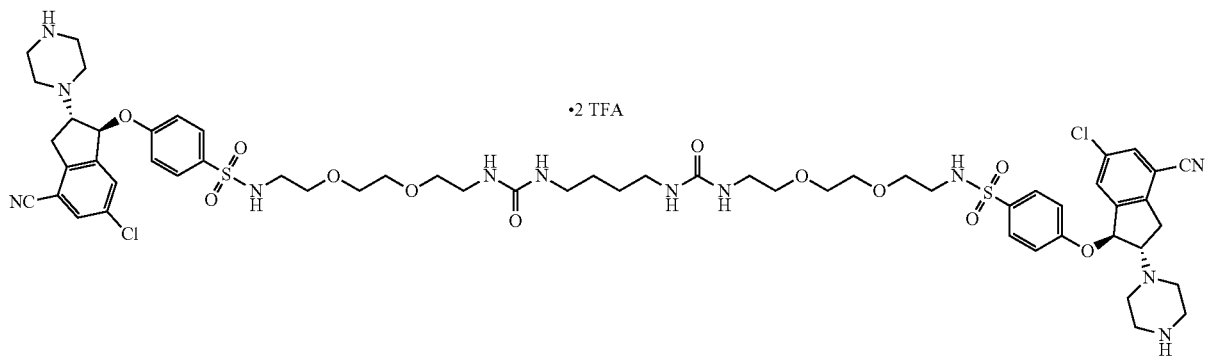

Example 41

Prepared according to the General Scheme above from INT-M5E by dimer formation and Boc-deprotection. Purification by preparative HPLC with the following conditions: Column, XBridge Preparative C18 OBD Column, 19*150 mm, 5 um; mobile phase, water (0.05% TFA) and $CH_3CN$ (28.0% $CH_3CN$ up to 29.0% in 7 min); Detector, UV 254/220 nm. This resulted in 326.1 mg (53%) of the title compound as a white solid. MS (m/z): 1267 [M+H]$^+$. $^1$H NMR (Methanol-d4, 400 MHz) δ 7.92-7.89 (m, 4H), 7.77 (d, J=1.9 Hz, 2H), 7.47 (dd, J=1.8, 0.9 Hz, 2H), 7.37-7.28 (m 4H), 6.09 (d, J=6.1 Hz, 2H), 3.76 (td, J=7.9, 6.0 Hz, 2H), 3.62-3.46 (m, 16H), 3.38 (dd, J=16.8, 8.0 Hz, 2H), 3.26 (dt, J=14.7, 5.2 Hz, 11H), 3.20-3.03 (m, 10H), 2.88 (qt, J=12.8, 4.5 Hz, 8H), 1.51-1.43 (m, 4H).

Example 42: 3-[2-(2-[2-[(4-[[(1S,2S)-6-Chloro-4-cyano-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-methylbenzene)sulfonamido]ethoxy]ethoxy)ethyl]carbamoyl]amino)butyl]urea; bis(trifluoroacetic acid)

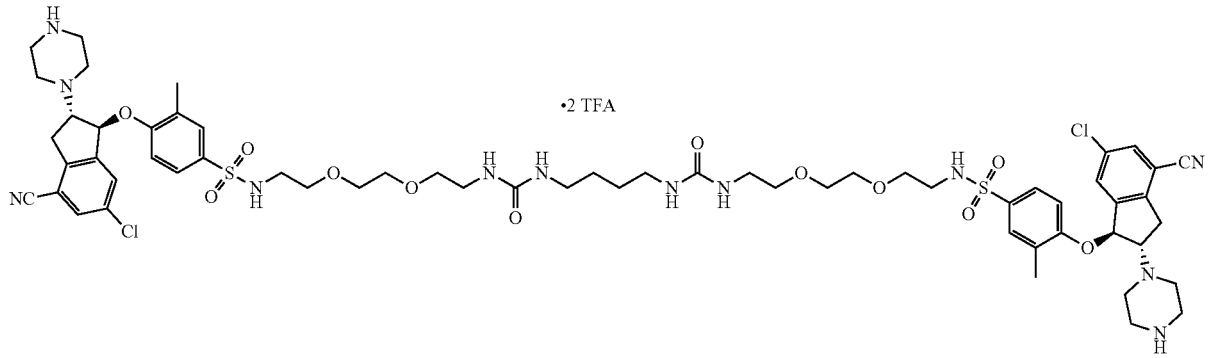

Example 42

Prepared according to the General Scheme above from INT-M5F by dimer formation and Boc-deprotection. Purification by preparative HPLC with the following conditions: Column, XSelect CSH Preparative C18 OBD Column, 19*150 mm, 5 um; mobile phase, water (0.05% TFA) and CH$_3$CN (20.0% CH$_3$CN up to 40.0% in 10 min); Detector, UV 254 nm. This resulted in 361.4 mg (59%) of the title compound as a white solid. MS (m/z): 1297.70 [M+H]$^+$. $^1$H NMR (Methanol-d4, 300 MHz) δ 7.79-7.64 (m, 6H), 7.48-7.39 (m, 4H), 6.08 (d, J=6.1 Hz, 2H), 3.76 (td, J=7.9, 6.0 Hz, 2H), 3.60-3.30 (m, 19H), 3.29-2.75 (m, 29H), 2.24 (s, 6H), 1.50-1.39 (m, 4H).

Example 43: 3-[2-(2-[2-[(4-[[(1S,2S)-6-Chloro-4-cyano-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-fluorobenzene)sulfonamido]ethoxy]ethoxy)ethyl]carbamoyl]amino)butyl]urea; bis(trifluoroacetic acid)

Example 43

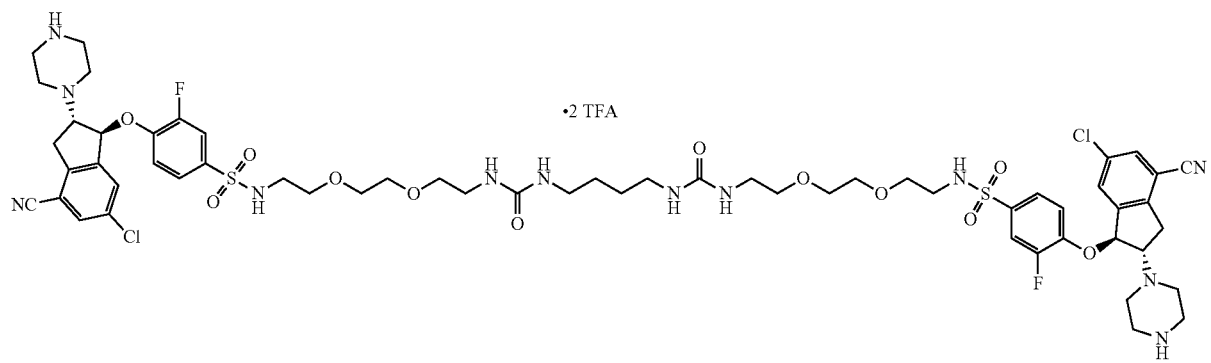

Prepared according to the General Scheme above from INT-M5G by dimer formation and Boc-deprotection. Purification by preparative HPLC with the following conditions: Column, XBridge C18 OBD Preparative Column, 19*250 mm, 5 um; mobile phase, water (0.05% TFA) and CH$_3$CN (20.0% CH$_3$CN up to 42.0% in 8 min); Detector, UV 254 nm. This resulted in 355.1 mg (81%) of the title compound as a white solid. MS (m/z): 1303 [M+H]$^+$. $^1$H NMR (Methanol-d4; 300 MHz) δ 7.80-7.47 (m, 10H), 6.06 (d, J=6.1 Hz, 2H), 3.80 (td, J=7.9, 6.0 Hz, 2H), 3.51 (dtd, J=17.3, 5.2, 2.4 Hz, 16H), 3.42-3.01 (m, 2H), 2.86 (tq, J=13.2, 7.8, 6.3 Hz, 8H), 1.50-1.39 (m, 4H).

Scheme for Hydroxymethylpyrrolidine Linker Synthesis:

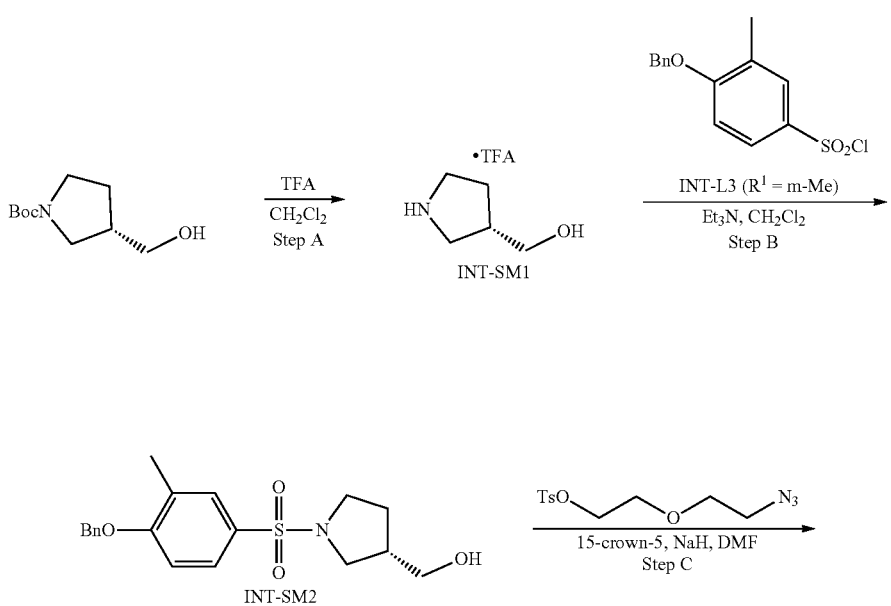

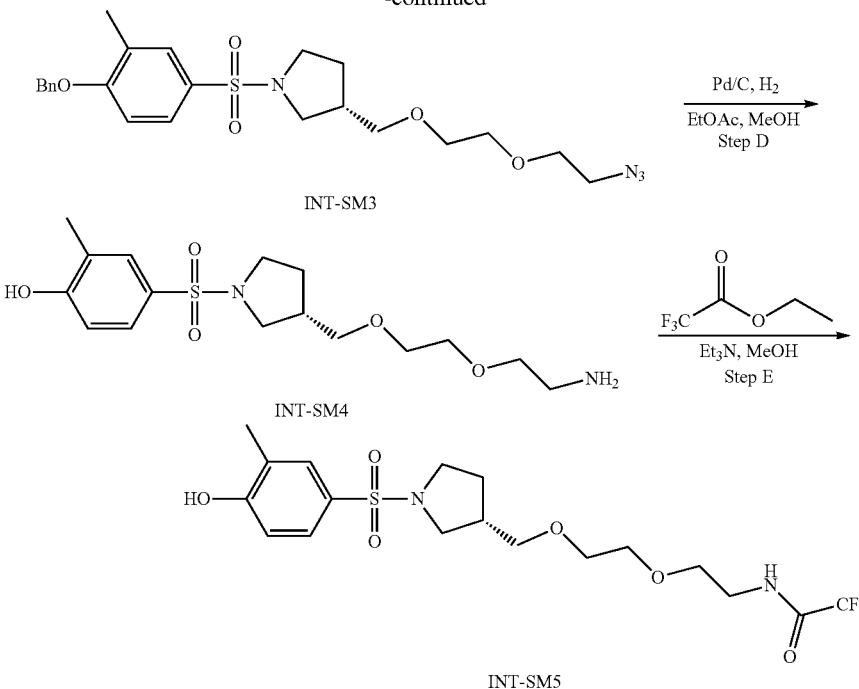

Step A: To a 250-mL round-bottom flask purged and maintained with an inert atmosphere of nitrogen was added tert-butyl (3S)-3-(hydroxymethyl)pyrrolidine-1-carboxylate (500 mg, 2.48 mmol, 1 equiv), $CH_2Cl_2$ (5 mL), and trifluoroacetic acid (1 ml). The resulting solution was stirred for 1 h at room temperature in an oil bath. The resulting mixture was concentrated under vacuum. This resulted in 250 mg (99%) of (3S)-pyrrolidin-3-ylmethanol trifluoroacetic acid salt as brown oil which was used directly in Step B.

Step B: To a 50-mL round-bottom flask purged and maintained with an inert atmosphere of nitrogen was added (3S)-pyrrolidin-3-ylmethanol (125 mg, 1.24 mmol, 1 equiv), $CH_2Cl_2$ (5 mL), and trimethylamine (0.5 mL, 3 equiv). This was followed by the dropwise addition of a solution of 4-(benzyloxy)-3-methylbenzene-1-sulfonyl chloride (INT-L3 where $R^1$=m-methyl, 360 mg, 1.21 mmol, 0.98 equiv) in $CH_2Cl_2$ (5 mL). The resulting solution was stirred for 1 h at room temperature. The resulting slurry was extracted with 3×20 mL of ethyl acetate. The organic layers were combined, washed with 1×20 mL of brine, dried over anhydrous sodium sulfate, filtered, and concentrated under vacuum. The residue was applied onto a silica gel column with ethyl acetate/petroleum ether (1/10) providing 400 mg (90%) of [(3S)-1-[[4-(benzyloxy)-3-methylbenzene]sulfonyl]pyrrolidin-3-yl]methanol as a yellow oil.

Step C: To a 250-mL round-bottom flask purged and maintained with an inert atmosphere of nitrogen was added sodium hydride (763 mg, 31.79 mmol, 3 equiv), dimethylformamide (60 mL), INT-SM2 (2.3 g, 6.36 mmol, 1 equiv), 15-crown-5 (3.8 mL, 3 equiv), and 1-[2-(2-azidoethoxy)ethoxy]sulfonyl-4-methylbenzene (2.7 g, 9.46 mmol, 1.5 equiv). The resulting solution was stirred overnight at room temperature. The reaction was then quenched by the addition of water and extracted with 3×50 mL of ethyl acetate. The organic layers combined, washed with 4×100 mL of brine, dried over anhydrous sodium sulfate, filtered, and concentrated under vacuum. The residue was applied onto a silica gel column with ethyl acetate/petroleum ether (1/3) providing 1.2 g (40%) of (3S)-3-[[2-(2-azidoethoxy)ethoxy]methyl]-1-[[4-(benzyloxy)-3-methylbenzene]sulfonyl]pyrrolidine (INT-SM3) as a yellow oil.

Step D: To a 100-mL round-bottom flask purged and maintained with an inert atmosphere of hydrogen was added azide INT-SM3 (1.2 g, 2.53 mmol, 1 equiv), ethyl acetate (6 mL), methanol (6 mL), and palladium on carbon (500 mg). The resulting slurry was stirred for 2 h at room temperature. The resulting mixture filtered to remove palladium and the filtrate concentrated under vacuum. This resulted in 740 mg (82%) of 4-[(3S)-3-[[2-(2-aminoethoxy)ethoxy] methyl]pyrrolidine-1-sulfonyl]-2-methylphenol (INT-SM4) as a yellow oil.

Step E: To a 50-mL round-bottom flask purged and maintained with an inert atmosphere of nitrogen was added amine INT-SM4 (740 mg, 2.06 mmol, 1 equiv), methanol (8 mL), triethylamine (41.7 mg, 0.41 mmol, 0.20 equiv), and ethyl 2,2,2-trifluoroacetate (0.75 mL, 3 equiv). The resulting solution was stirred for 2 h at room temperature. The resulting slurry was concentrated under vacuum. The residue was applied onto a silica gel column with ethyl acetate/petroleum ether (1/1) providing 800 mg (85%) of 2,2,2-trifluoro-N-[2-(2-[[(3S)-1-[(1-hydroxy-3-methylbenzene)sulfonyl]pyrrolidin-3-yl]methoxy]ethoxy)ethyl]acetamide (INT-SM5) as a yellow oil.

The R-enantiomer of INT-SM5 was generated from the analogous procedure beginning with tert-butyl (3R)-3-(hydroxymethyl)pyrrolidine-1-carboxylase. This provided INT-RM5:

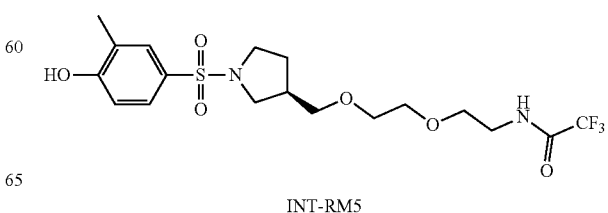

INT-RM5

Scheme for Hydroxymethylpyrrolidine Dimer Product Synthesis:

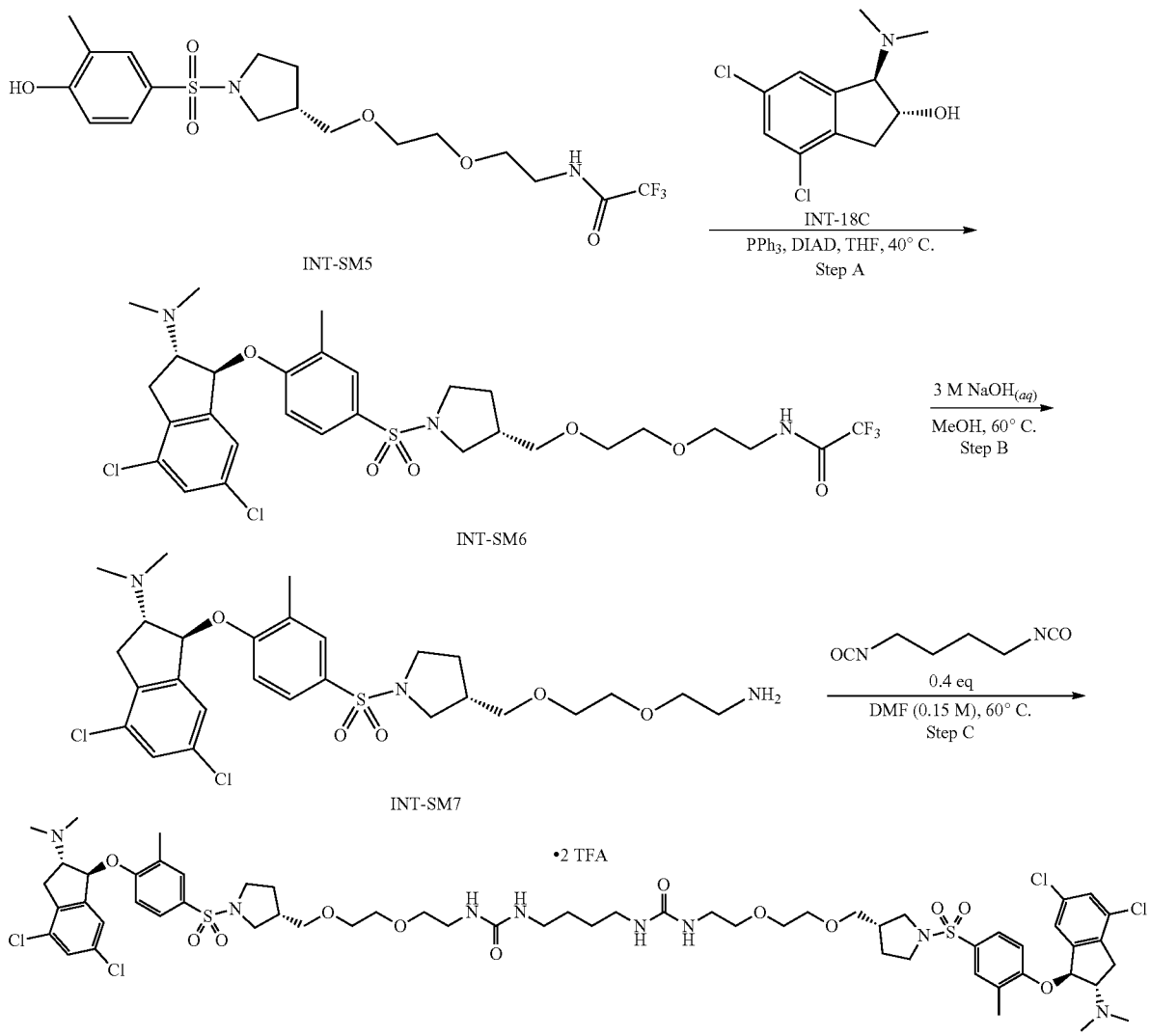

Example 44

Step A: To a 50-mL round-bottom flask purged and maintained with an inert atmosphere of nitrogen was added phenol INT-SM5 (300 mg. 0.66 mmol, 1 equiv), aminoindanol INT-I8C (162.47 mg, 0.66 mmol, 1 equiv), and tetrahydrofuran (1.5 mL). This was followed by the addition of PPh₃ (260 mg. 0.99 mmol, 1.5 equiv) at 40° C. followed by the dropwise addition of DIAD (0.195 mL, 1.5 equiv) with stirring at 40° C. The resulting solution was stirred for 1 h at 40° C. in an oil bath. The resulting slurry was concentrated tinder vacuum. The residue was applied onto a silica gel column with ethyl acetate/petroleum ether (2/1) providing 400 mg (89%) of N-[2-(2-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]-2,2,2-trifluoroacetamide (INT-SM6) as a yellow oil.

Step B: To a 250-mL round-bottom flask purged and maintained with an inert atmosphere of nitrogen, was added INT-SM6 (400 mg, 0.59 mmol, 1 equiv) and methanol (4 mL) followed by the addition of sodium hydroxide (3 M, 1 mL). The resulting slurry was stirred for 1 h at 60° C. in an oil bath. The resulting solution was extracted with 3×20 mL of ethyl acetate. The organic layers combined, washed with 1×20 mL of brine, dried over anhydrous sodium sulfate, filtered, and concentrated under vacuum. The residue was applied onto a silica gel column with CH₂Cl₂/methanol (5/1) providing 300 mg (87%) of (1S,2)-1-[4-[(3S)-3-[[2-(2-aminoethoxy)ethoxy]methyl]pyrrolidine-1-sulfonyl]-2-methylphenoxy]-4,6-dichloro-N,N-dimethyl-2,3-dihydro-1H-inden-2-amine (INT-SM7) as a yellow oil.

Step C: To a 50-mL round-bottom flask purged and maintained with an inert atmosphere of nitrogen was added amine INT-SM7 (300 mg, 0.51 mmol, 1 equiv), N,N-dimethylformamide (3.4 mL), and 1,4-diisocyanatobutane (0.029 mL, 0.45 equiv). The resulting solution was stirred for 1 h at 60° C. in an oil bath. The resulting mixture was concentrated under vacuum. The crude product was purified by preparative HPLC with the following conditions: Column, XBridge Shield RP18 OBD Column, 19*150 mm, 5 um; mobile phase, water (0.05% TFA) and CH₃CN (35.0% CH₃CN up to 48.0% in 8 min); Detector, UV 254 nm.

Example 44: 3-[2-(2-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino)butyl]urea; bis(trifluoroacetic acid)

Steps A-C provided 221.4 mg (28%) of the title compound as a white solid. MS (m/z): 1313 [M+H]+. 1H NMR (Methanol-d4, 400 MHz) δ 7.82-7.70 (m, 4H), 7.57-7.47 (m, 4H), 7.10-7.04 (m, 2H), 6.49 (d, 6.7 Hz, 2H), 4.50 (td, J=8.4, 6.6 Hz, 2H), 3.70 (dd, J=16.5, 8.6 Hz, 2H), 3.57-3.53 (m, 4H), 3.53-3.44 (m, 8H), 3.40-3.31 (m, 6H), 3.29-3.16 (m, 10H), 3.12-3.07 (m, 6H), 3.05 (s, 12H), 2.38 (p, J=6.7 Hz, 2H), 2.32 (s, 6H), 1.92 (td, J=12.8, 7.4 Hz, 2H), 1.65-1.51 (m, 2H), 1.50-1.42 (m, 4H).

Example 45: 3-[2-(2-[[(3R)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2[[(3R)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino)butyl]urea; bis(trifluoroacetic acid)

Example 45

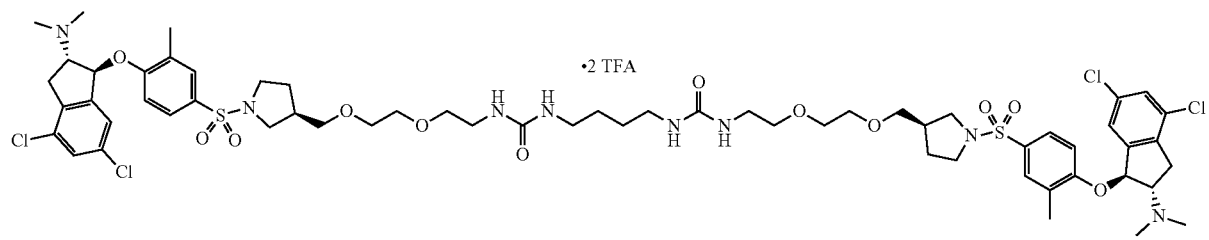

Beginning with R-enantiomer INT-RM5 and INT-I8C, Steps A-C provided 306 mg (67%) of the title compound as a white solid. MS (m/z): 1314 [M+H]+. 1H NMR (Methanol-d4, 400 MHz) δ 7.82-7.70 (m, 4H), 7.56-7.48 (m, 4H), 7.10-7.04 (m, 2H), 6.51 (d, J=6.7 Hz, 2H), 4.49 (td, J=8.5, 6.6 Hz, 2H), 3.70 (dd, J=16.5, 8.6 Hz, 2H), 3.59-3.44 (m, 12H), 3.41-3.03 (m, 33H), 2.32 (s, 8H), 1.99-1.86 (m, 2H), 1.58 (dq, J=14.5, 7.4 Hz, 2H), 1.49-1.41 (m, 4H).

Scheme for Cyano-Containing Hydroxymethylpyrrolidine Dimer Product Synthesis:

Example 46: 3-[2-(2-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino)butyl]urea; bis(trifluoroacetic acid)

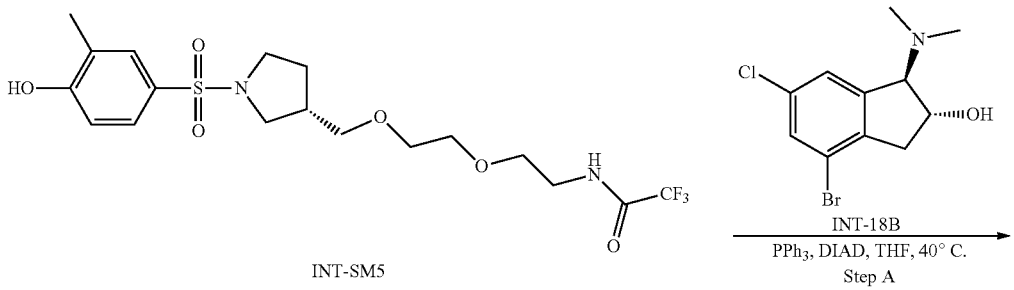

-continued
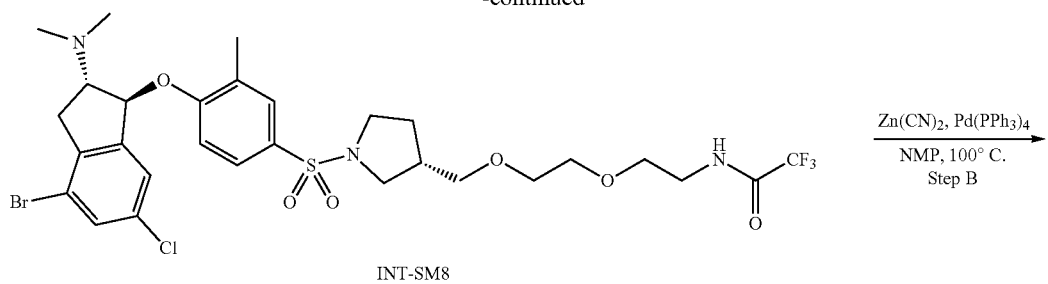
INT-SM8
Zn(CN)₂, Pd(PPh₃)₄
---
NMP, 100° C.
Step B
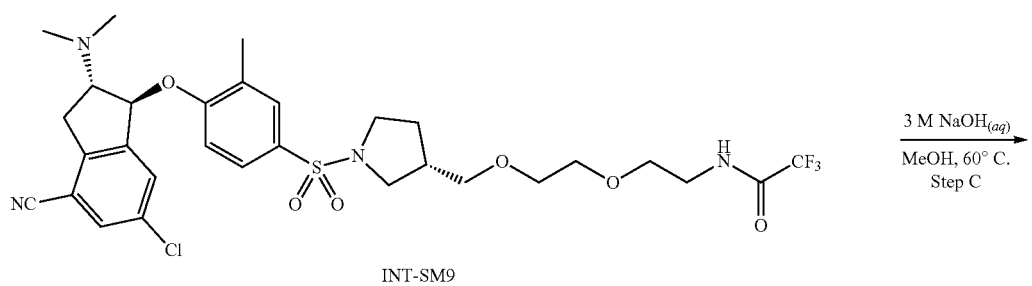
INT-SM9
3 M NaOH(aq)
---
MeOH, 60° C.
Step C
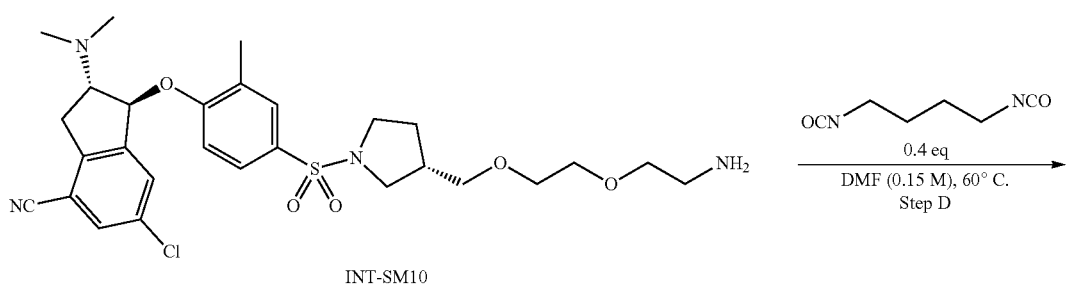
INT-SM10
OCN~~~NCO
0.4 eq
---
DMF (0.15 M), 60° C.
Step D
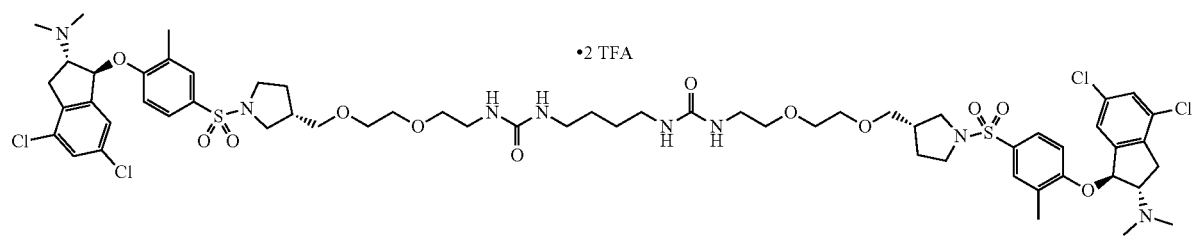
Example 46

Step A: To a 50-mL round-bottom flask purged and maintained with an inert atmosphere of nitrogen, was added phenol INT-SM5 (500 mg, 1.1 mmol, 1 equiv), aminoindanol INT-I8B (320 mg, 1.1 mmol, 1 equiv), tetrahydrofuran (2.5 mL), and PPh₃ (433 mg, 1.65 mmol, 1.5 equiv). Heating at 40° C. in an oil bath DIAD (0.33 mL, 1.5 equiv) was added dropwise with stirring. The resulting solution was stirred for 1 h. The resulting mixture was concentrated under vacuum. The residue was applied onto a silica gel column with ethyl acetate/petroleum ether (2/1) providing 700 mg (88%) of N-[2-(2-[[(3S)-1-[(4-[[(1S,2S)-4-bromo-6-chloro-2-(dimethylamino)-2,3-dihydro-1H-inden-1-yl]oxy]-3-methylbenzene)sulfonyl]pyrrolidin-3-yl]methoxy]ethoxy)ethyl]-2,2,2-trifluoroacetamide (INT-SM8) as a yellow oil.

Step B: To a 50-mL round-bottom flask purged and maintained with an inert atmosphere of nitrogen was added bromoaminoindanol INT-SM8 (640 mg, 0.88 mmol, 1.00 equiv), NMP (7 mL), Zn(CN)₂ (62 mg, 0.60 equiv), and Pd(PPh₃)₄ (102 mg, 0.09 mmol, 0.10 equiv). The resulting solution was stirred overnight at 100° C. in an oil bath. The resulting slurry was diluted with water and extracted with 3×20 mL of ethyl acetate. The organic layers were combined, washed with 3×20 mL of brine, and dried in an oven under reduced pressure. The residue was applied onto a silica gel column with ethyl acetate/petroleum ether (1/5) providing 550 mg (93%) of N-[2-(2-[[(3S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]-2,2,2-trifluoroacetamide (INT-SM9) as a yellow oil.

Step C: To a 100-mL round-bottom flask purged and maintained with an inert atmosphere of nitrogen was added INT-SM9 (550 mg, 0.82 mmol, 1 equiv) and methanol 7 mL) followed by the addition of sodium hydroxide (3 M$_{(aq)}$, 1 mL). The resulting solution was stirred for 5 h at room temperature. The reaction was then quenched by the addition of water and extracted with 3×20 mL of ethyl acetate. The organic layers were combined, washed with 1×20 ml, of brine, filtered, and concentrated to a solid under vacuum. The solid was dried in an oven under reduced pressure. The residue was applied onto a silica gel column with CH₂Cl₂/methanol (5/1) providing 460 mg (98%) of (1S,2S)-1-[4-[(3S)-3-[[2-(2-aminoethoxy)ethoxy]methyl]pyrrolidine-1-sulfonyl]-2-methylphenoxy]-6-chloro-2-(dimethylamino)-2,3-dihydro-1H-indene-4-carbonitrile (INT-SM10) as a yellow oil.

Step D: To a 50-mL round-bottom flask purged and maintained with an inert atmosphere of nitrogen was added amine INT-SM10 (460 mg, 0.80 mmol, 1 equiv), N,N-dimethylformamide (5.5 mL), and 1,4-diisocyanatobutane (52.4 mg, 0.37 mmol, 0.47 equiv). The resulting solution was stirred for 1 h at 60° C. in an oil bath. The resulting mixture was concentrated under vacuum. The crude product was purified by Preparative HPLC with the following conditions: Column, XBridge C18 OBD Preparative Column, 19*250 mm, 5 um; mobile phase, water (0.05% TFA) and CH₃CN (32.0% CH₃CN up to 54.0% in 8 min); Detector, UV 254 nm.

Example 46: 3-[2-(2-[[(3S)-1-[4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]-1-[4-([[2-(2-[[(3S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino)butyl]urea; bis (trifluoroacetic acid)

Steps A-D provided 130.6 mg (11%) of the title compound as a white solid. MS (m/z): 1295 [M+H]⁺. ¹H NMR (Methanol-d4, 400 MHz) δ 7.89 (d, J=1.9 Hz, 2H), 7.85-7.70 (m 4H), 7.54 (d, J=8.7 Hz, 2H), 7.44-7.37 (m, 2H), 6.56 (d, J=6.6 Hz, 2H), 4.63-4.49 (m, 2H), 3.83 (dd, J=16.7, 8.5 Hz, 2H), 3.61-3.04 (m, 46H), 2.33 (s, 8H), 1.94 (dt, J=13.5, 6.8 Hz, 2H), 1.59 (dd, J=13.1, 7.2 Hz, 2H), 1.47 (dd, J=3.7, 3.0 Hz, 4H).

Example 47: 3-[2-(2-[[(3R)-[4-(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl] methoxy]ethoxy)ethyl]-1-[4-([[2-(2-[[(3R)-1-[4-[[(1S,2S)-6-chloro-4-cyano-2-(dimethylamino)-2,3-dihydro-1H-inden-1-yl]oxy]-3-methylbenzene) sulfonyl]pyrrolidin-3-yl]methoxy]ethoxy)ethyl] carbamoyl]amino)butyl]urea Example 47

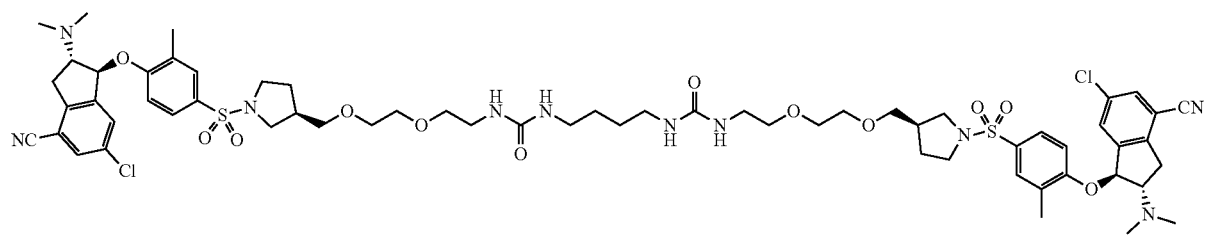

Beginning with R-enantiomer INT-RM5 and INT-I8B, Steps A-D provided 248 mg (27%) of the title compound as a white solid. MS (m/z): 1293 [M+H]⁺. ¹H NMR (Methanol-d4, 400 MHz) δ 7.78-7.65 (m, 6H), 7.51 (d, J=8.7 Hz, 2H), 7.45-7.40 (m, 2H), 6.00 (d, J=6.1 Hz, 2H), 3.64-3.45 (m, 14H), 3.44-3.14 (m, 14H), 3.14-3.02 (m, 8H), 2.35 (s, 12H), 2.27 (s, 6H), 1.91 (dtd, J=12.8, 7.5, 5.4 Hz, 2H), 1.57 (dq, J=14.3, 7.3 Hz, 2H), 1.47 (p, J=3.3 Hz, 4H).

Scheme for Pyridinyl Linker Synthesis:

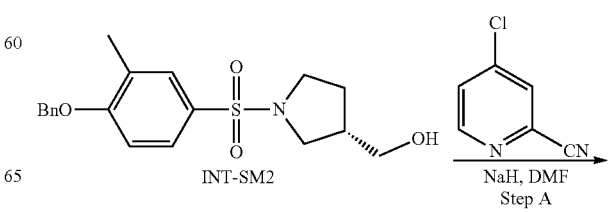

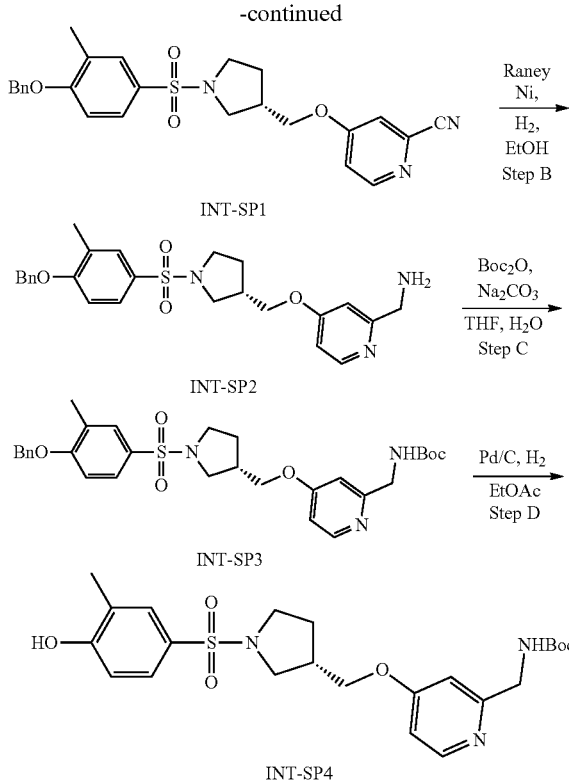

Step A: To a 50-mL round-bottom flask was added N,N-dimethylformamide (12 mL), sodium hydride (331.2 mg, 13.8 mmol, 5 equiv), 4-chloropyridine-2-carbonitrile (574.1 mg, 4.14 mmol, 1.5 equiv), sulfonamide INT-SM2 (1.0 g, 2.77 mmol 1 equiv). The resulting solution was stirred for 1.5 h at room temperature. The reaction was then quenched by the addition of 20 mL of NH$_4$Cl and extracted with 3×100 mL of ethyl acetate. The organic layers were combined, washed with 1×100 mL of brine, dried over anhydrous sodium sulfate, filtered, and concentrated under vacuum. The residue was applied onto a silica gel column with ethyl acetate/petroleum ether (1:1) providing 570 mg (44%) of 4-[[(3S)-1-[[4-(benzyloxy)-3-methylbenzene]sulfonyl]pyrrolidin-3-yl]methoxy]pyridine-2-carbonitrile (INT-SP1) as a white solid.

Step B: To a 100-mL round-bottom flask purged and maintained with an inert atmosphere of H$_2$ was added INT-SP1 (660 mg, 1.42 mmol, 1 equiv), ethanol (20 mL), and Raney Ni (660 mg). The resulting solution was stirred for overnight at room temperature. The resulting mixture was filtered and concentrated under vacuum providing 520 mg (78%) of (4-[[(3S)-1-[[4-(benzyloxy)-3-methylbenzene]sulfonyl]pyrrolidin-3-yl]methoxy]pyridin-2-yl)methanamine (INT-SP2) as a brown solid.

Step C: To a 100-mL round-bottom flask was added amine INT-SP2 (520 mg, 1.11 mmol, 1 equiv), 1:1 tetrahydrofuran: H$_2$O (20 mL), and sodium carbonate (588.3 mg, 5.55 mmol, 5 equiv). This was followed by the addition of a solution of Boc$_2$O (485 mg, 2.22 mmol, 2 equiv) in tetrahydrofuran (5 mL) dropwise with stirring at 5-10° C. in 5 min. The resulting solution was stirred for 2 h at room temperature. The resulting slurry was extracted with 3×100 mL of ethyl acetate. The organic layers were combined, washed with 1×100 mL of brine, dried over anhydrous sodium sulfate, filtered, and concentrated under vacuum. The residue was applied onto a silica gel column with CH$_2$Cl$_2$/methanol (5:1) providing 520 mg (82%) of tert-butyl N-[(4-[[(3S)-1-[[4-(benzyloxy)-3-methylbenzene]sulfonyl]pyrrolidin-3-yl]methoxy]pyridin-2-yl)methyl]carbamate (INT-SP3) as a white solid.

Step D: To a 100-mL round-bottom flask purged and maintained with an inert atmosphere of hydrogen was added a solution of INT-SP3 (520 mg, 0.92 mmol, 1 equiv), ethyl acetate (10 mL), and 10% Pd/C (520 mg). The resulting slurry was stirred for 1 h at room temperature. The solids were filtered out and the filtrate concentrated under vacuum providing 420 mg (96%) of tert-butyl N-[(4-[[(3S)-1-[(4-hydroxy-3-methylbenzene)sulfonyl]pyrrolidin-3-yl]methoxy]pyridin-2-yl)methyl]carbamate (INT-SP4) as a white solid.

The R-enantiomer of INT-SP4 was generated from the analogous procedure beginning with tert-butyl (3R)-3-(hydroxymethyl)pyrrolidine-1-carboxylate. This provided INT-RP4:

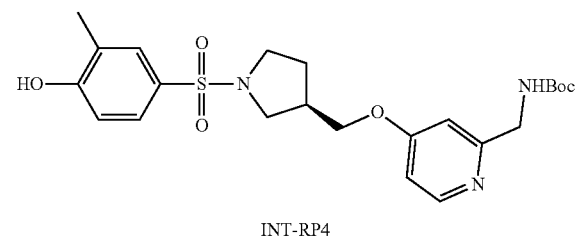 [SMILES: Cc1cc(S(=O)(=O)N2CC[C@@H](COc3ccnc(CNC(=O)OC(C)(C)C)c3)C2)ccc1O ; "INT-RP4"]

Scheme for Pyridinyl Dimer Product Synthesis:

Example 48: 3-[(4-[[(3S)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea

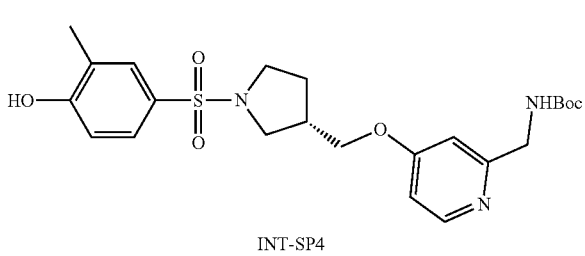

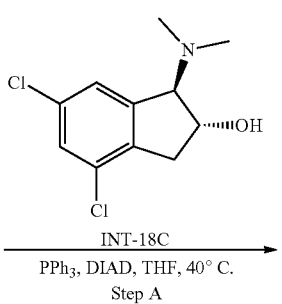

PPh$_3$, DIAD, THF, 40° C.
Step A

-continued

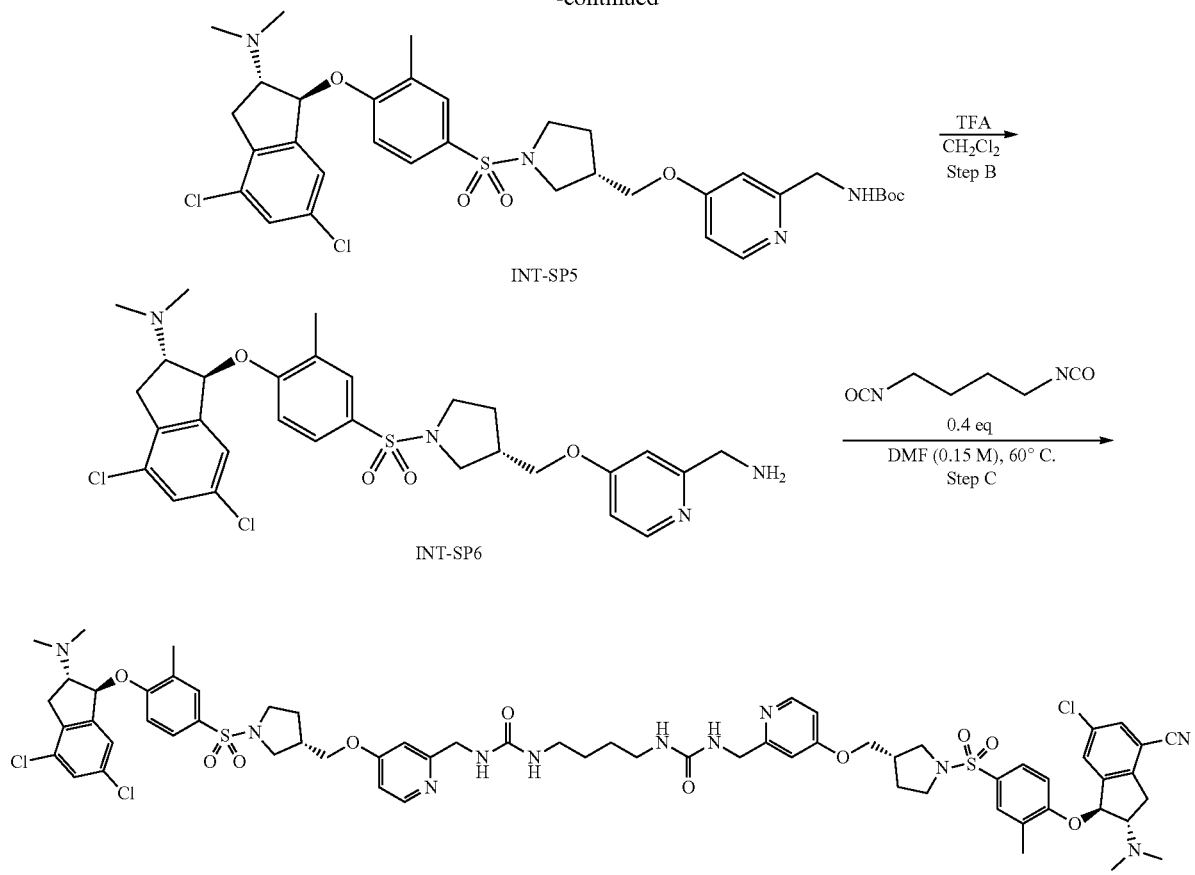

Example 48

Step A: To a 7-mL round-bottom flask was added phenol INT-SP4 (70 mg, 0.36 mmol, 1 equiv), aminoindanol INT-I8C (96.4 mg, 0.39 mmol, 1.1 equiv), tetrahydrofuran (0.83 mL and PPh$_3$ (140.1 mg, 0.53 mmol, 1.50 equiv). Heating at 40° C. in an oil bath DIAD (0.11 mL) was added dropwise with stirring over 15 min. The resulting solution was stirred for 1 h at 40-45° C. in an oil bath. The residue was applied onto a silica gel column with ethyl acetate/petroleum ether (100%) providing 200 mg (80%) of tert-butyl N-[(4-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamate (INT-SP5) as a yellow oil.

Step B: To a 100-mL round-bottom flask was added INT-SP5 (200 mg, 0.28 mmol, 1 equiv), CH$_2$Cl$_2$ (15 mL), and trifluoroacetic acid (5 mL). The resulting solution was stirred for 1 h at room temperature. The pH value of the solution was adjusted to 9.0-10.0 with sodium bicarbonate (100%) and the slurry extracted with 3×100 mL of ethyl acetate. The organic layers were combined, dried over anhydrous sodium sulfate, filtered, and concentrated under vacuum. The residue was applied onto a silica gel column with CH$_2$Cl$_2$/methanol (5:1) providing 153 mg (89%) of (1S,2S)-1-[4-[(3S)-3-([[2-(aminomethyl)pyridin-4-yl]oxy]methyl)pyrrolidine-1-sulfonyl]-2-methylphenoxy]-4,6-dichloro-N,N-dimethyl-2,3-dihydro-1H-inden-2-amine (INT-SP6) as a white solid.

Step C: To a 25-mL round-bottom flask was added amine INT-SP6 (153 mg, 0.25 mmol, 2.08 equiv), 1,4-diisocyanatobutane (17 mg, 0.12 mmol, 1 equiv), and N,N-dimethylformamide (1.7 mL). The resulting solution was stirred for 1 h at 60° C. in an oil bath. The solids were filtered out. The crude product was purified by Preparative HPLC with the following conditions: Column, XBridge C18 OBD Preparative Column, 19*250 mm, 5 um; mobile phase, water (0.05% NH$_4$OH) and CH$_3$CN (85% CH$_3$CN up to 90% in 8 min); Detector, UV 254 nm.

Example 48: 3-[(4-[[(3S)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[4-[[(3S)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea Steps A-C provided 62.3 mg (38%) of the title compound as a white solid. MS (m/z): 1351 [M+H]$^+$. $^1$H NMR (Methanol-d4, 300 MHz) δ 8.15 (d, J=5.9 Hz, 2H), 7.77-7.60 (m, 4H), 7.49-7.34 (m, 4H), 7.06 (d, J=1.1 Hz, 2H), 6.82 (d, J=2.5 Hz, 2H), 6.67 (dd, J=5.9, 2.5 Hz, 2H), 5.93 (d, J=6.2 Hz, 2H), 4.29 (s, 4H), 4.00 (s, 2H), 3.88 (dd, J=9.4, 6.0 Hz, 2H), 3.73 (t, J=8.7 Hz, 2H), 3.50-3.29 (m, 10H), 3.28-3.10 (m, 6H), 2.87 (dd, J=16.4, 7.7 Hz, 1H), 2.58 (s, 4H), 2.29 (s, 1H), 2.16 (s, 6H), 1.49 (s, 4H).

Example 49

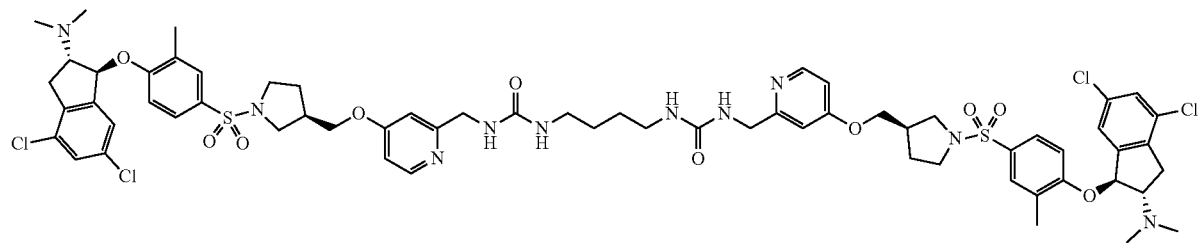

Example 49: 3-[(4-[[(3R)-1-[(4-[[(1S,2S)-4,6-Dichloro-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3R)-1-[(4-[[(1S,2S)-4,6-dichloro-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea. Beginning with R-Enantiomer INT-RP4 and INT-I8B Steps A-C provided 54.3 mg (31%) of the title compound as a white solid. MS (m/z): 1351 [M+H]$^+$. $^1$H NMR (Methanol-d4, 300 MHz) δ 8.18 (d, J=5.9 Hz, 1H), 7.77-7.61 (m, 2H), 7.49-7.33 (m, 2H), 7.04 (d, J=1.1 Hz, 1H), 6.83 (d, J=2.4 Hz, 1H), 6.71 (dd, J=5.9, 2.5 Hz, 1H), 5.92 (d, J=5.8 Hz, 1H), 4.56 (s, 5H), 4.30 (s, 2H), 3.96-3.73 (m, 2H), 3.51-3.32 (m, 3H) 3.27-3.08 (m, 5H), 2.87 (dd, J=16.6, 7.7 Hz, 1H), 2.30 (s, 7H), 2.63-2.52 (m, 1H), 2.19 (s, 4H), 2.00 (d, J=7.9 Hz, 2H), 1.67 (dd, J=13.2, 7.1 Hz, 1H), 1.50 (s, 4H), 1.30 (d, J=25.9 Hz, 6H), 0.86 (d, J=6.2 Hz, 2H).

Scheme for Cyano Containing Pyridinyl Dimer Product Synthesis:

Example 50: 3-[(4-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-[[(4-[[(3S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea

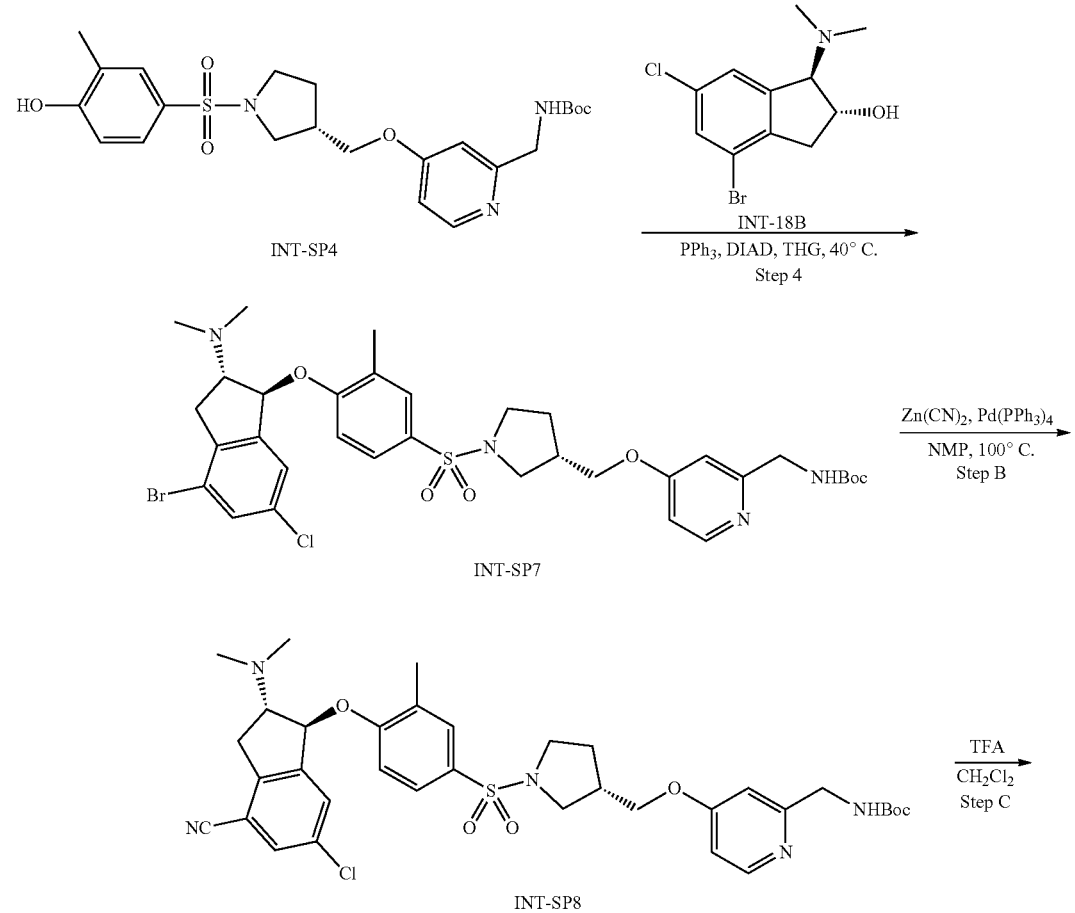

-continued

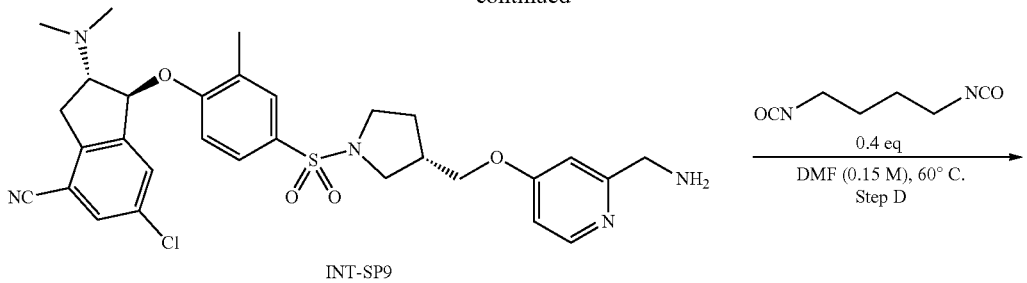

INT-SP9

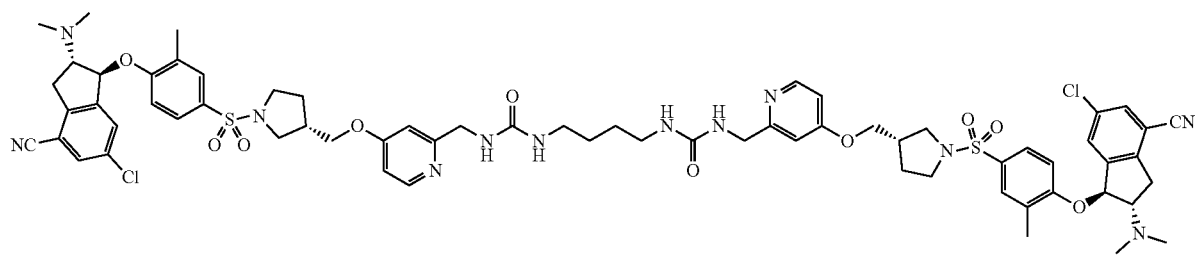

Example 50

Step A: To a 7-mL round-bottom flask was added phenol INT-SP4 (250 mg, 0.52 mmol, 1 equiv), aminoindanol INT-I8B (167.36 mg, 0.58 mmol, 1.1 equiv), tetrahydrofuran (1.22 mL), and PPh₃ (206.2 mg, 0.79 mmol, 1.50 equiv). Heating at 40° C. in an oil bath DIAD (0.16 mL) was added dropwise with stirring. The resulting solution was stirred for 1 h at 40-45° C. in an oil bath. The resulting mixture was concentrated under vacuum. The residue was applied onto a silica gel column with dichloromethane/methanol (5:1) providing 300 mg (76%) of tert-butyl N-[(4-[[(3S)-1-[(4-[[(1S,2S)-4-bromo-6-chloro-2-(dimethylamino)-2,3-dihydro-1H-inden-1-yl]oxy]-3-methylbenzene) sulfonyl]pyrrolidin-3-yl]methoxy]pyridin-2-yl)methyl]carbamate (INT-SP7) as a white solid.

Step B: To a 50-mL round-bottom flask purged and maintained with an inert atmosphere of nitrogen was added bromoaminoindanol INT-SP7 (300 mg, 0.40 mmol, 1 equiv), Zn(CN)₂ (28.16 mg, 0.24 mmol, 0.60 equiv), NMP (5 mL), and Pd(PPh₃)₄ (46.22 mg, 0.04 mmol, 0.10 equiv). The resulting solution was stirred for overnight at 100° C. in an oil bath. The resulting solution was extracted with 3×100 mL of ethyl acetate. The organic layers were combined, washed with 3×100 mL of brine, dried over anhydrous sodium sulfate, filtered, and concentrated under vacuum. The residue was applied onto a silica gel column with dichloromethane/methanol (10:1) providing 300 mg (crude) of tert-butyl N-[(4-[[(3S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamate (INT-SP8) as a white solid, used without further purification in Step C.

Step C: To a 100-mL round-bottom flask was added INT-SP8 (220 mg, 0.32 mmol, 1 equiv) and 3:1 CH₂Cl₂:TFA (20 mL). The resulting solution was stirred for 1 h at room temperature. The pH value of the solution was adjusted to 9.0-10.0 with sodium bicarbonate and extracted with 3×100 mL, of ethyl acetate. The organic layers were combined, dried over anhydrous sodium sulfate, filtered, and concentrated under vacuum. The residue was applied onto a silica gel column with CH₂Cl₂/methanol (5:1) providing 187 mg (crude) of (1S,2S)-1-[4-([3S)-3-([[2-(aminomethyl)pyridin-4-yl]oxy]methyl)pyrrolidine-1-sulfonyl]-2-methylphenoxy]-6-chloro-2-(dimethylamino)-2,3-dihydro-1H-indene-4-carbonitrile (INT-SP9) as a white solid.

Step D: To a 7-mL round-bottom flask was added amine INT-SP9 (187 mg, 0.31 mmol, 2.22 equiv), N,N-dimethylformamide (2.1 mL), and 1,4-diisocyanatobutane (19.8 mg, 0.14 mmol, 1 equiv). The resulting solution was stirred for 1 h at 60° C. in an oil bath. The solids were filtered out. The crude product was purified by preparative HPLC with the following conditions: Column, XBridge C18 OBD Preparative Column, 19*250 mm, 5 um; mobile phase, water (0.05% NH₄OH) and CH₃CN (55% CH₃CN up to 57% in 8 min); Detector, UV 254 nm.

Example 50: 3-[(4-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[4-([[(3S)-1-[(4-[[(1S,2S)-6-chloro-4-cyano-2-(dimethylamino)-2,3-dihydro-1H-inden-1-yl]oxy]-3-methylbenzene) sulfonyl]pyrrolidin-3-yl]methoxy]pyridin-2-yl) methyl]carbamoyl]amino)butyl]urea Steps A-D provided 64.5 mg (34%) of the title compound as a white solid. MS (m/z): 1333 [M+H]⁺. ¹H NMR (Methanol-d4, 300 MHz) δ 8.16 (d, J=5.7 Hz, 2H), 7.77-7.61 (m, 6H), 7.52-7.36 (m, 4H), 6.82 (d, J=2.3 Hz, 2H), 6.73-6.64 (m, 2H), 5.95 (d, J=6.0 Hz, 2H), 4.29 (s, 4H), 3.88 (dd, J=9.5, 6.0 Hz, 2H), 3.74 (dd, J=9.5, 7.7 Hz, 2H), 3.61-3.28 (m, 7H), 3.28-2.97 (m, 11H), 2.57 (dt, J=14.1, 7.0 Hz, 2H), 2.30 (s, 12H), 2.18 (s, 6H), 2.10-1.92 (m, 2H), 1.68 (dq, J=14.0, 7.2 Hz, 2H), 1.55-1.44 (m, 4H).

Example 51: 3-[(4-[[(3R)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3R)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea Example 51

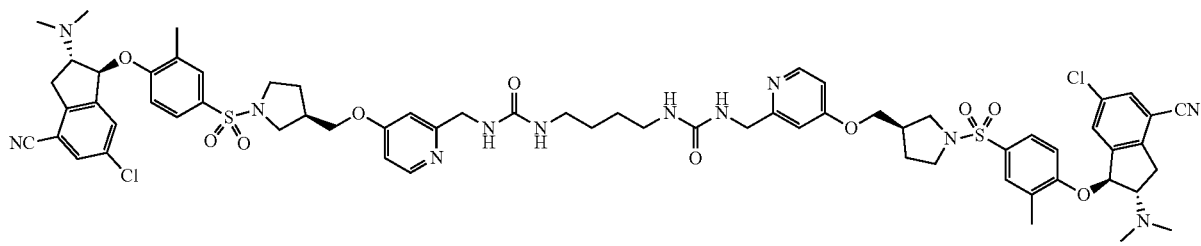

Beginning with R-enantiomer INT-RP4 and INT-I8B, Steps A-D provided 39.6 mg (37%) of the title compound as a white solid. MS (m/z): 1333 [M+H]$^+$. $^1$H NMR (DMSO-d6, 400 MHz) δ 8.23 (d, J=5.6 Hz, 2H), 7.99 (d, J=1.9 Hz, 2H), 7.70-7.60 (m, 4H), 7.58-7.49 (m, 4H), 6.76-6.66 (m, 4H), 6.32 (t, J=5.8 Hz, 2H), 6.09 (t, J=5.6 Hz, 2H), 5.93 (d, J=5.4 Hz, 2H), 4.18 (d, J=5.7 Hz, 4H), 3.80 (ddd, J=32.6, 9.6, 6.8 Hz, 4H), 3.52 (dd, J=7.7, 5.8 Hz, 2H), 3.36-2.93 (m, 16H), 2.49 (s, 2H), 2.16 (d, J=11.9 Hz, 18H), 1.91 (dt, J=13.1, 6.6 Hz, 2H), 1.58 (dq, J=14.2, 7.4 Hz, 2H), 1.38-1.29 (m, 4H).

Scheme for Hydroxyethylpyrrolidine Linker Synthesis:

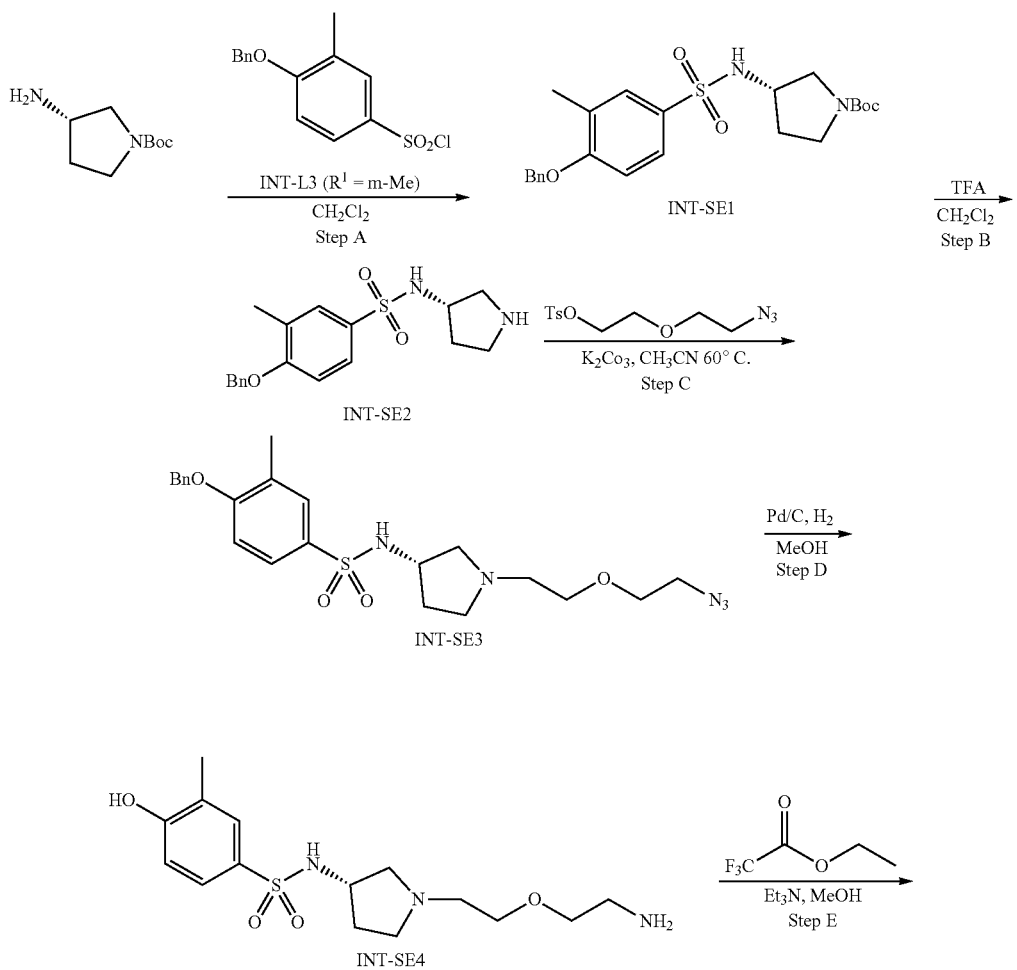

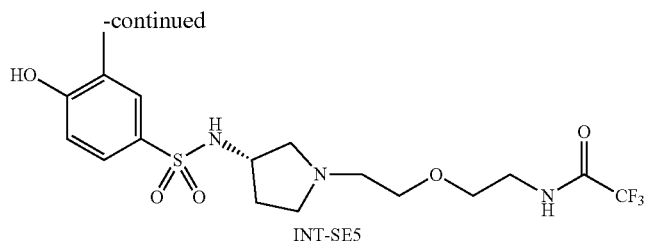

INT-SE5

Step A: To a 100-mL round-bottom flask was added text-butyl (3S)-3-aminopyrrolidine-1-carboxylate (2.5 g, 13.42 mmol, 1 equiv), CH$_2$Cl$_2$ (20 mL), and sulfonyl chloride INT-L3 (where R$^1$=m-methyl, 4.72 g, 15.90 mmol, 3 equiv). The resulting solution was stirred overnight at room temperature. The resulting mixture was concentrated under vacuum. The residue was applied onto a silica gel column with ethyl acetate/petroleum ether (1/100-100/1) providing 3.0 g (50%) of tert-butyl (3S)-3-[[4-(benzyloxy)-3-methylbenzene]sulfonamido]pyrrolidine-1-carboxylate (INT-SE1) as a yellow oil.

Step B: To a 100-mL round-bottom flask was added sulfonamide INT-SE1 (3.0 g, 6.72 mmol, 1 equiv), CH$_2$Cl$_2$ (15 mL), and trifluoroacetic acid (5 mL). The resulting solution was stirred for 1.5 h at room temperature. The pH value of the solution was adjusted to 9-10 with saturated aqueous sodium bicarbonate and extracted with 3×100 mL of ethyl acetate. The organic layers were combined and concentrated under vacuum. The residue was applied onto a silica gel column with CH$_2$Cl$_2$/methanol (10:1) providing 2.1 g (90%) of 4-(benzyloxy)-3-methyl-N-[(3S)-pyrrolidin-3-yl]benzene-1-sulfonamide (INT-SE2) as an off-white solid.

Step C: To a 100-mL round-bottom flask was added amine INT-SE2 (2.41 g, 6.96 mmol, 1 equiv), CH$_3$CN (20 mL), potassium carbonate (2.5 g, 18.09 mmol, 3 equiv), and 1-[2-(2-azidoethoxy)ethoxy]sulfonyl-4-methylbenzene (1.9 g, 6.66 mmol, 1.1 equiv). The resulting slurry was stirred overnight at 60° C. The resulting solution was diluted with water and extracted with 3×100 mL of ethyl acetate. The organic layers were combined, dried over anhydrous sodium sulfate, filtered, and concentrated under vacuum. The residue was applied onto a silica gel column with ethyl acetate/petroleum ether (1:100-100:1) providing 2.4 g (75%) of N-[(3S)-1-[2-(2-azidoethoxy)ethyl]pyrrolidin-3-yl]-4-(benzyloxy)-3-methylbenzene-1-sulfonamide (INT-SE3) as a yellow oil.

Step D: To a 100-mL round-bottom flask purged and maintained with an inert atmosphere of hydrogen was added azide INT-SE3 (1.0 g, 2.18 mmol, 1 equiv), ethyl acetate (5 mL), methanol (5 mL), and 10% palladium on carbon (500 mg). The resulting slurry was stirred for 2 h at room temperature. The solids were filtered out. The residue was applied onto a silica gel column with CH$_2$Cl$_2$/methanol (8:1) providing 420 mg (56%) of N-[(3S)-1-[2-(2-aminoethoxy)ethyl]pyrrolidin-3-yl]-4-hydroxy-3-methylbenzene-1-sulfonamide (INT-SE4) as an off-white solid.

Step E: To a 25-mL round-bottom flask was added amine INT-SE4 (400 mg, 1.16 mmol, 1 equiv), methanol (5 mL), triethylamine (24 mg, 0.24 mmol, 0.20 equiv), and ethyl 2,2,2-trifluoroacetate (653 mg, 4.60 mmol, 4 equiv). The resulting solution was stirred for 1.5 h at room temperature. The resulting slurry was diluted with water and extracted with 3×100 mL of ethyl acetate. The organic layers were combined, dried over anhydrous sodium sulfate, filtered, and concentrated under vacuum. The residue was applied onto a silica gel column with CH$_2$Cl$_2$/methanol (10:1) providing 400 mg (78%) of 2,2,2-trifluoro-N-(2-[2-[(3S)-3-[(4-hydroxy-3-methylbenzene)sulfonamido]pyrrolidin-1-yl]ethoxy]ethyl)acetamide (INT-SE5) as a yellow oil.

The R-enantiomer of INT-SE5 was generated from the analogous procedure beginning with tert-butyl (3R)-3-aminopyrrolidine-1-carboxylate. This provided INT-RE5:

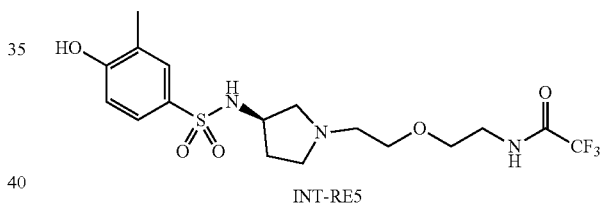

INT-RE5

Scheme for Hydroxyethylpyrrolidine Dimer Product Synthesis:

Example 52: 3-(2-[2-[(3S)-3-[(4-[[(1S,2S)-4,6-Dichloro-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3S)-3-[(4-[[(1S,2S)-4,6-dichloro-2-(dimethylamino)-2,3-dihydro-1H-inden-1-yl]oxy]-3-methylbenzene)sulfonamido]pyrrolidin-1-yl]ethoxy]ethyl) carbamoyl]amino]butyl)urea

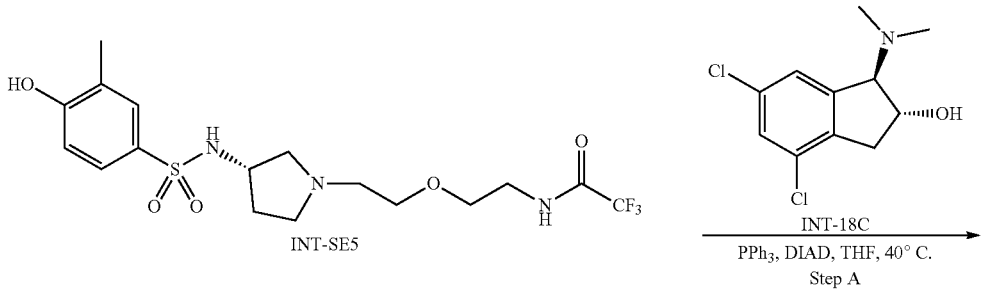

-continued

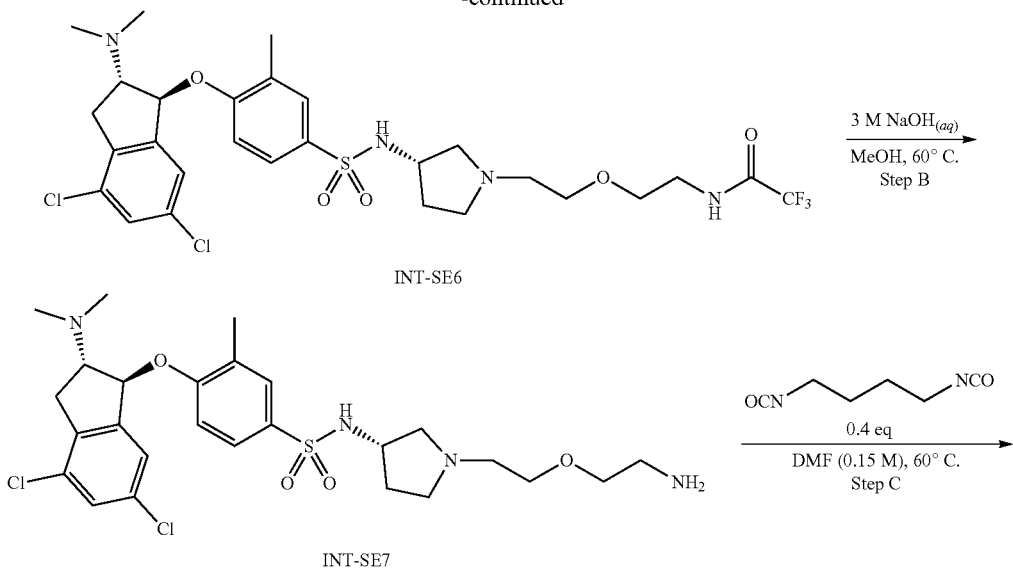

INT-SE6

INT-SE7

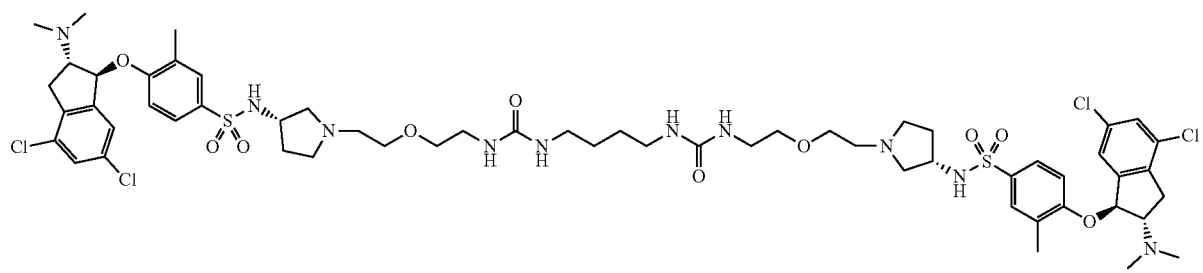

Example 52

Step A: To a 7-mL round-bottom flask was added aminoindanol INT-I8C (92.4 mg, 0.38 mmol, 1.1 equiv), tetrahydrofuran (1 mL), phenol INT-SE5 (150 mg, 0.34 mmol, 1 equiv), and PPh$_3$ (178.9 mg, 0.68 mmol, 2 equiv). Heating at 40° C. in an oil bath DIAD (103.4 mg, 0.51 mmol, 1.5 equiv) was added dropwise with stirring over 15 min. The resulting slurry was stirred for 1 h at 40-45° C. in an oil bath. The residue was applied onto a silica gel column with CH$_2$Cl$_2$/methanol (10:1) providing 200 mg (88%) of N-(2-[2-[(3S)-3-[(4-[[(1S,2S)-4,6-dichloro-2-(dimethylamino)-2,3-dihydro-1H-inden-1-yl]oxy]-3-methylbenzene)sulfonamido]pyrrolidin-1-yl]ethoxy]ethyl)-2,2,2-trifluoroacetamide (INT-SE6) as a yellow oil.

Step B: To a 25-mL round-bottom flask was added INT-SE6 (200 mg, 0.30 mmol, 1 equiv), methanol (5 mL), and sodium hydroxide (3 M$_{(aq)}$, 1 mL). The resulting solution was stirred for 1.5 h at 60° C. The resulting solution was cooled to room temperature and extracted with 3×50 mL of ethyl acetate. The organic layers were combined, dried over anhydrous sodium sulfate, filtered, and concentrated wider vacuum. The residue was applied onto a silica gel column with CH$_2$Cl$_2$/methanol (8:1) providing 100 mg (58%) of N-[(3S)-1-[(2-(2-aminoethoxy)ethyl]pyrrolidin-3-yl]-4-[[(1S,2S)-4,6-dichloro-2-(dimethylamino)-2,3-dihydro-1H-inden-1-yl]oxy]-3-methylbenzene-1-sulfonamide (INT-SE7) as a yellow oil.

Step C: To a 25-mL round-bottom flask was added amine INT-SE7 (100 mg, 0.17 mmol, 1 equiv), N,N-dimethylformamide (1 mL), and 1,4-diisocyanatobutane (0.0945 mL, 0.45 equiv). The resulting solution was stirred for 1.5 h at 60° C. The crude product was purified by preparative HPLC with the following conditions: Column, XBridge Shield RP18 OBD Column, 19*150 mm, 5 um; mobile phase, water (0.05% TFA) and CH$_3$CN (24.0% CH$_3$CN up to 40.0% in 8 min); Detector, UV 220 nm.

Example 52: 3-(2-[2-[(3S)-3-[(4-[[(1S,2S)-4,6-Dichloro-2-(dimethylamino)-2,3-dihydro-1H-inden-1-yl]oxy]-3-methylbenzene) sulfonamido]pyrrolidin-1-yl]ethoxy]ethyl)-1-(4-[[(2-[2-[(3S)-3-[(4-[[(1S,2S)-4,6-dichloro-2-(dimethylamino)-2,3-dihydro-1H-inden-1-yl]oxy]-3-methylbenzene)sulfonamido] pyrrolidin-1-yl]ethoxy]ethyl) carbamoyl]amino] butyl)urea Steps A-C provided 42.1 mg (19%) of the title compound as a colorless viscous oil. MS (m/z): 1283.7 [M+H]$^+$. $^1$H NMR (Methanol-d4, 400 MHz) δ 7.88-7.82 (m, 2H), 7.79 (s, 2H), 7.56-7.48 (m, 4H), 7.06 (d, J=1.3 Hz, 2H), 6.55 (d, J=6.7 Hz, 2H), 4.48 (q, J=8.2 Hz, 2H), 4.09-3.59 (m, 13H), 3.54 (t, J=5.3 Hz, 4H), 3.50-3.35 (m, 8H), 3.33 (s, 3H), 3.13 (m, 6H), 3.04 (s, 12H), 2.32 (m, 8H), 2.09-1.88 (m, 2H), 1.50 (s, 4H).

Example 53: 3-(2-[2-[(3R)-3-[(4-[[(1S,2S)-4,6-Dichloro-2-(dimethylamino)-2,3-dihydro-1H-inden-1-yl]oxy]-3-methylbenzene)sulfonamido]pyrrolidin-1yl]ethoxy]ethyl)-1-(4-[[(2-[2-[(3R)-3-[(4-[[(1S,2S)-4,6-dichloro-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl) urea

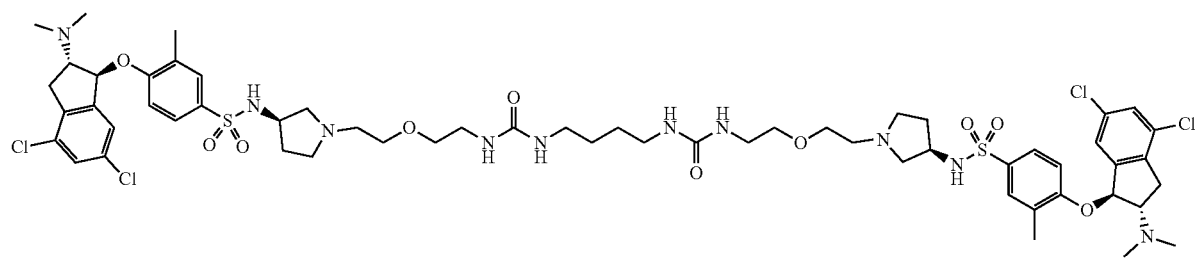

Example 53

Beginning with R-enantiomer INT-RE5 and INT-I8C, Steps A-C provided 19.4 mg (21%) of the title compound as a white solid. MS (m/z): 1283.6 [M+H]$^+$. $^1$H NMR (DMSO-d6, 300 MHz) δ 7.68-7.45 (m, 10H), 7.12 (d, J=1.8 Hz, 2H), 5.98-5.81 (m, 4H), 5.73 (t, J=5.6 Hz, 2H), 3.54 (s, 2H), 3.48-3.21 (m, 10H), 3.16-2.99 (m, 6H), 2.94-2.74 (m, 6H), 2.56 (s, 2H), 2.39 (s, 5H), 2.16 (d, J=6.0 Hz, 19H), 1.80 (s, 2H), 1.40 (d, J=7.8 Hz, 2H), 1.29-1.15 (m, 8H), Scheme for Cyano-Containing Hydroxyethylpyrrolidine Dimer Product Synthesis:

Example 54: 3-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea

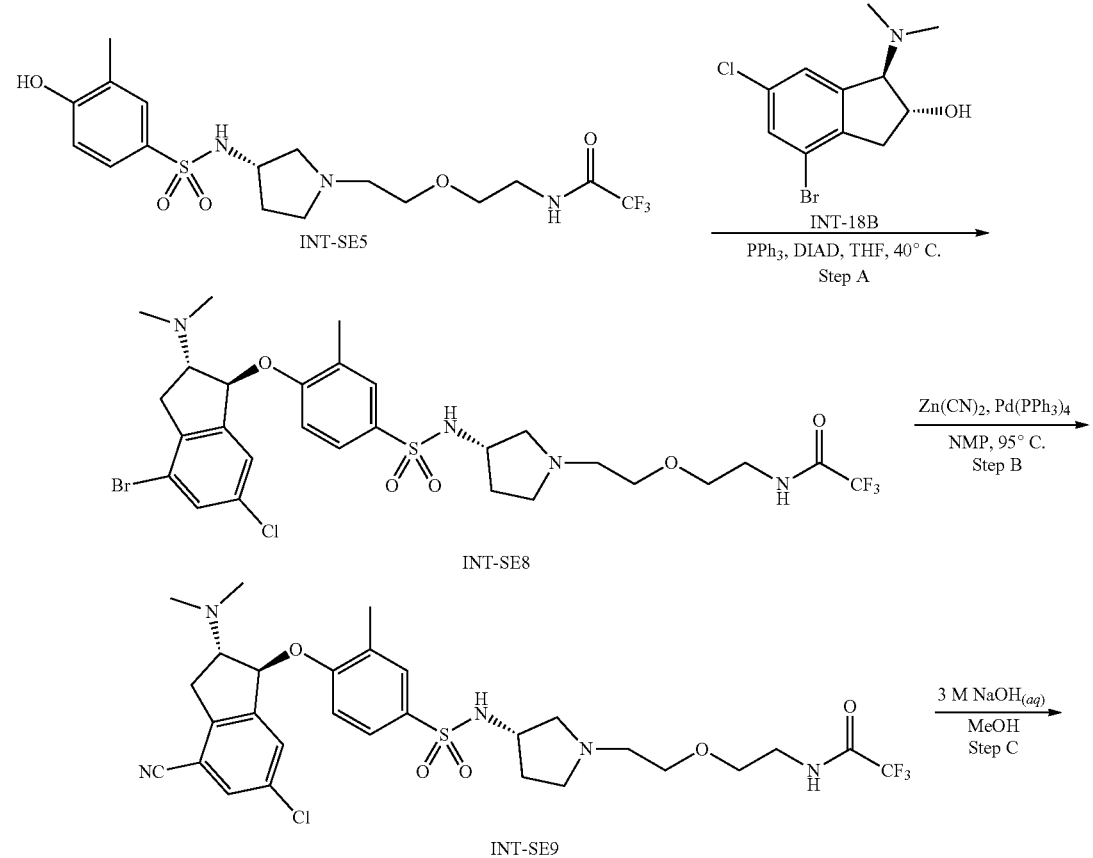

-continued

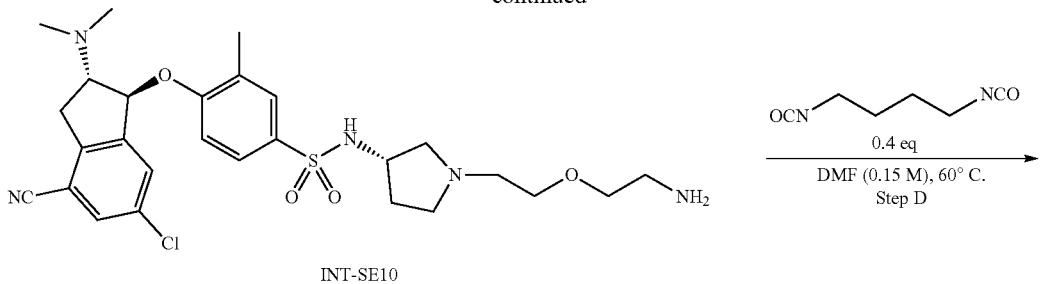

INT-SE10

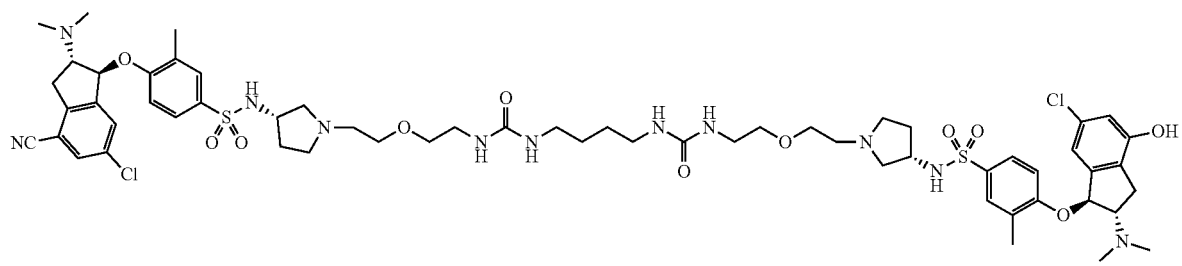

Example 54

Step A: To a 8-mL round-bottom flask was added aminoindanol INT-I8B (181.84 mg, 0.63 mmol, 1.1 equiv), tetrahydrofuran (1 mL), phenol INT-SE5 (250 mg, 0.57 mmol, 1 equiv), and PPh$_3$ (298.1 mg, 1.14 mmol, 2 equiv). Heating at 40° C. in an oil bath DIAD (172.4 mg, 0.85 mmol, 1.5 equiv) was added dropwise with stirring over 15 min. The resulting solution was stirred for 1 h at 40-45° C. in an oil bath. The residue was applied onto a silica gel column with CH$_2$Cl$_2$/methanol (10:1) providing 200 mg (49%) of N-(2-[2-[(3S)-3-[(4-[[(1S,2S)-4-bromo-6-chloro-2-(dimethylamino)-2,3-dihydro-1H-inden-1-yl]oxy]-3-methylbenzene)sulfonamido]pyrrolidin-1-yl]ethoxy]ethyl)-2,2,2-trifluoroacetamide (INT-SE8) as an off-white solid.

Step B: To a 25-mL round-bottom flask purged and maintained with an inert atmosphere of nitrogen was added bromoaminoindanol INT-SE8 (200 mg, 0.28 mmol, 1 equiv), NMP (2 mL), Zn(CN)$_2$ (19.72 mg, 0.60 equiv), and Pd(PPh$_3$)$_4$ (32.5 mg, 0.03 mmol, 0.10 equiv). The resulting solution was stirred overnight at 95° C. The resulting slurry was cooled to room temperature, diluted with water, and extracted with 3×50 mL of ethyl acetate. The organic layers were combined, dried over anhydrous sodium sulfate, filtered, and concentrated. The residue was applied onto a silica gel column with CH$_2$Cl$_2$/methanol (25:1) providing 150 mg (81%) of N-(2-[2-[(3S)-3-[(4-[[(1S,2S)-6-chloro-4-cyano-2-(dimethylamino)-2,3-dihydro-1H-inden-1-yl]oxy]-3-methylbenzene) sulfonamido]pyrrolidin-1-yl]ethoxy]ethyl)-2,2,2-trifluoroacetamide (INT-SE9) as a yellow oil.

Step C: To a 50-mL round-bottom flask was added INT-SE9 (150 mg, 0.23 mmol, 1 equiv), methanol (5 mL), and sodium hydroxide (3 M aqueous, 1 mL). The resulting solution was stirred for 1.5 h at room temperature. The resulting mixture was concentrated under vacuum. The residue was applied onto a silica gel column with ethyl acetate (100%) providing 60 mg (47%) of N-[(3S)-1-[2-(2-aminoethoxy)ethyl]pyrrolidin-3-yl]-4-[[(1S,2S)-6-chloro-4-cyano-2-(dimethylamino)-2,3-dihydro-1H-inden-1-yl]oxy]-3-methylbenzene-1-sulfonamide (INT-SE10) as a yellow oil.

Step D: To a 25-mL round-bottom flask was added amine INT-SE10 (60 mg, 0.11 mmol, 1 equiv), N,N-dimethylformamide (1 mL), and 1,4-diisocyanatobutane (0.00672 mL). The resulting solution was stirred for 1 h at 60° C. The crude product was purified by preparative HPLC with the following conditions: Column, XBridge Preparative C18 OBD Column, 19*150 mm, 5 um; mobile phase, water (0.05% NH$_4$OH) and CH$_3$CN (40.0% CH$_3$CN up to 77.0% in 7 min.) Detector, UV 254/220 nm.

Example 54: 3-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene) sulfonamido]pyrrolidin-1-yl]ethoxy]ethyl) carbamoyl]amino]butyl)urea Steps A-D provided 9.8 mg (7%) of the title compound as a white solid. MS (m/z): 1265.4 [M+H]$^+$. $^1$H NMR (Methanol-d4, 400 MHz) δ 7.79-7.74 (m, 4H), 7.72-7.68 (m, 2H), 7.48 (d, J=8.7 Hz, 2H), 7.41 (d, J=1.2 Hz, 2H), 6.00 (d, J=6.1 Hz, 2H), 4.60 (s, 5H), 3.76 (s, 2H), 3.66-3.49 (m, 6H), 3.49-3.39 (m, 5H), 3.37 (d, J=8.0 Hz, 1H), 3.32-3.21 (m, 4H), 3.15-3.03 (m, 6H), 2.83-2.74 (m, 2H), 2.63 (t, J=16.1 Hz, 8H), 2.41 (m, 2H), 2.35 (s, 12H), 2.26 (s, 6H), 2.11-1.96 (m, 2H), 1.58 (m, 2H), 1.52-1.44 (m, 4H).

Example 55: 3-(2-[2-[(3R)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3R)-3-[(4-[[(1S,2S)-6-chloro-4-cyano-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea Example 55

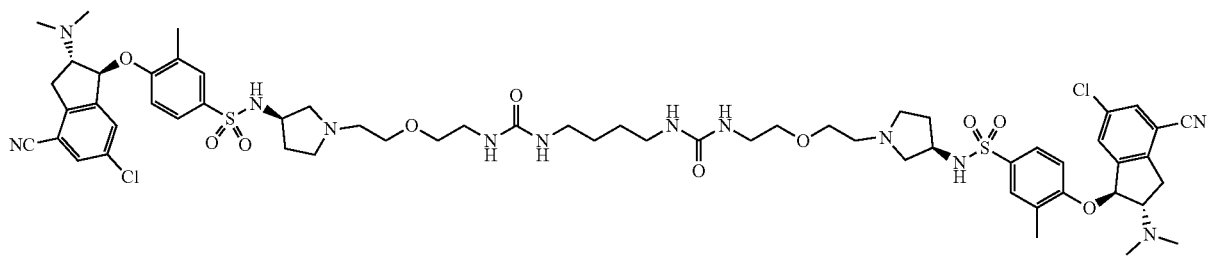

Beginning with R-enantiomer INT-RE5 and INT-I8B, Steps A-D provided 30.3 mg (27%) of the title compound as a white solid. MS (m/z): 1263 [M+H]⁺. ¹H NMR (DMSO-d6, 400 MHz) δ 8.00 (d, J=1.9 Hz, 2H), 7.69-7.58 (m, 6H), 7.57-7.47 (m, 4H), 5.92 (dd, J=29.5, 5.7 Hz, 4H), 5.76 (t, J=5.6 Hz, 2H), 3.58-3.45 (m, 5H), 3.38 (t, J=6.2 Hz, 4H), 3.31-3.18 (m, 8H), 3.12-2.87 (m, 13H), 2.59 (s, 2H), 2.42 (s, 5H), 2.18 (d, J=10.9 Hz, 18H), 1.83 (t, J=10.5 Hz, 2H), 1.43 (s, 2H), 1.32-1.19 (m, 5H).

Scheme for Synthesis of Triazole-Type Linker Compounds

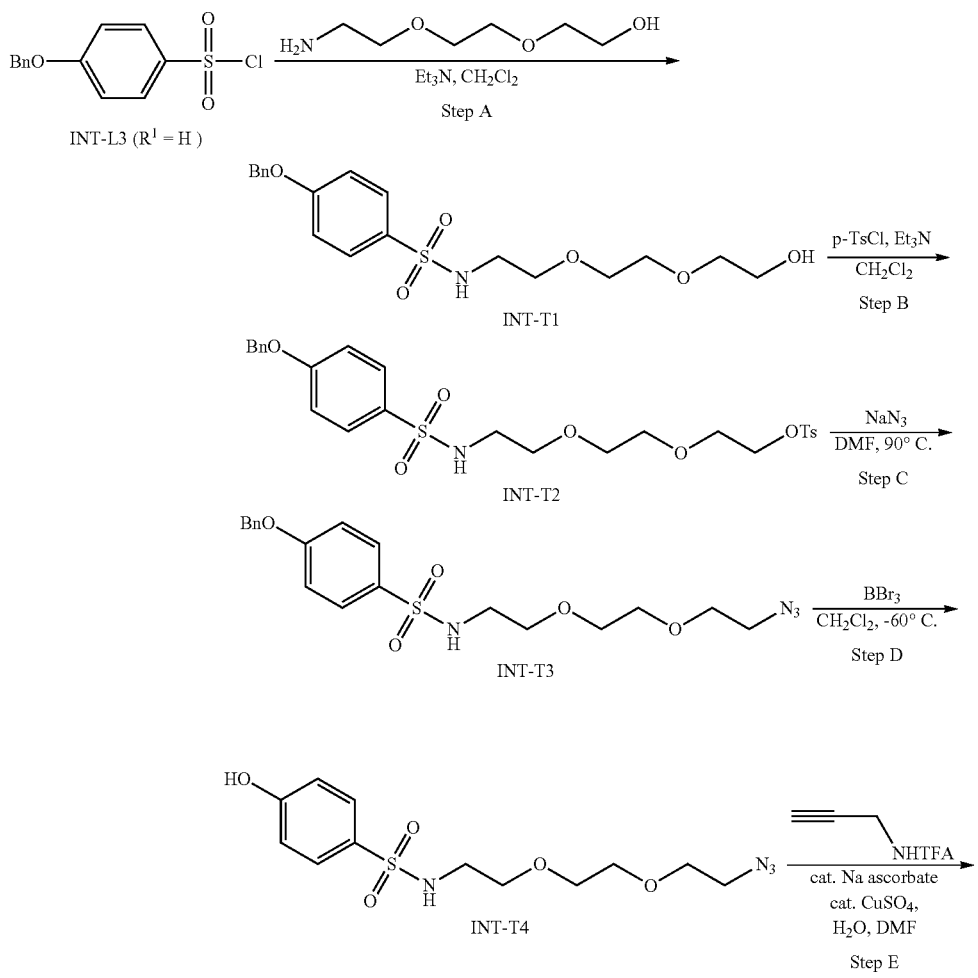

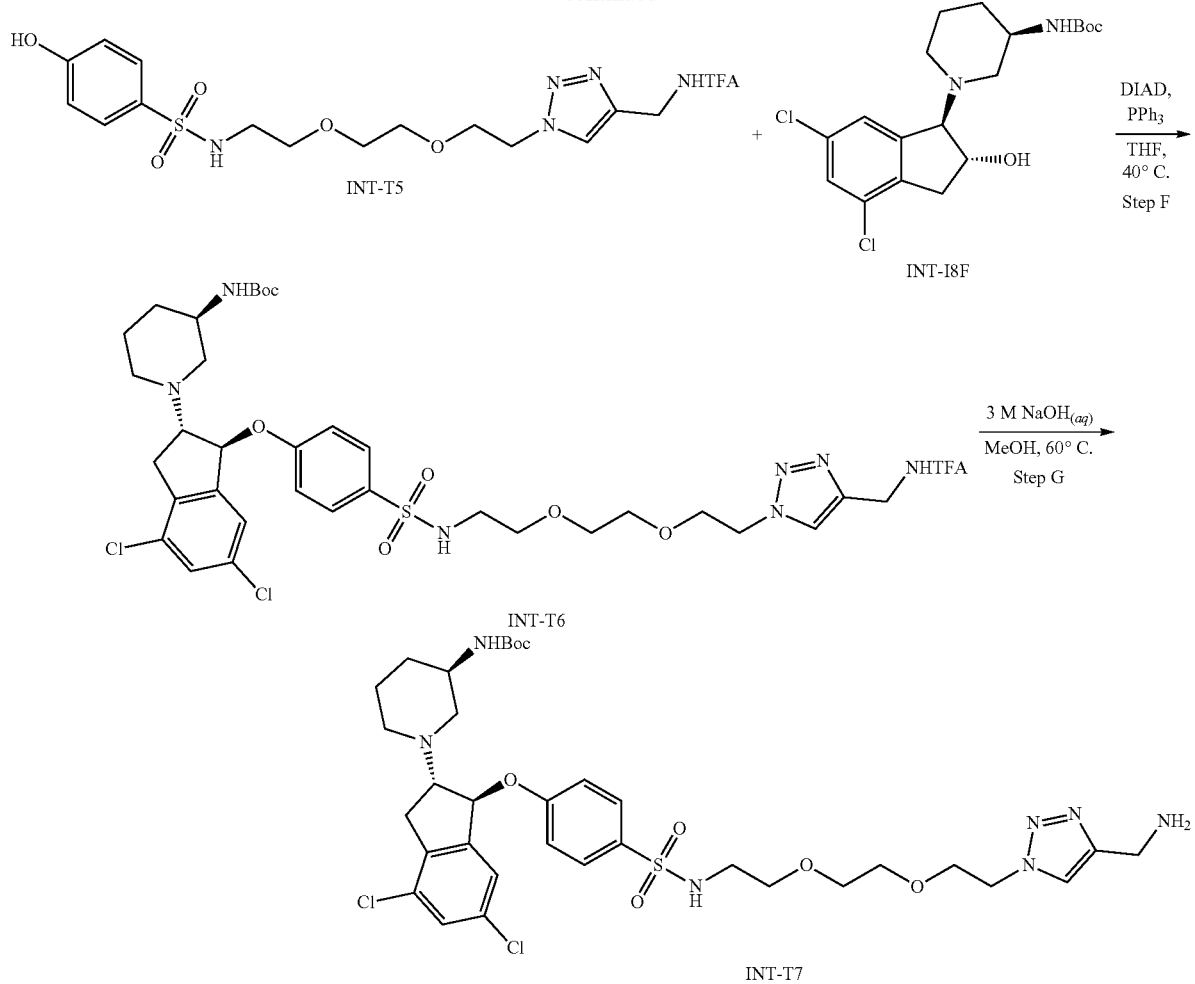

Step A: To a 250-mL round-bottom flask was added 2-[2-(2-aminoethoxy)ethoxy]ethan-1-ol (5.3 g, 35.53 mmol, 2 equiv), $CH_2Cl_2$ (50 mL), triethylamine (5.37 g, 53.07 mmol, 3 equiv), and INT-L3 ($R^1$—H, 5 g, 17.7 mmol, 1 equiv). The resulting solution was stirred overnight. The reaction was then quenched by the addition of 50 mL of water and extracted with 3×50 mL of ethyl acetate. The organic layers were combined, dried over anhydrous sodium sulfate, filtered, and concentrated under vacuum. The residue was applied onto a silica gel column with $CH_2Cl_2$/methanol (0-55%) providing 6.4 g (92%) of 2-[2-(2-[[4-(benzyloxy)benzene]sulfonamido]ethoxy)ethoxy]ethan-1-ol (INT-T1) as a white solid.

Step B: To a 250-mL round-bottom flask was added INT-T1 (6.4 g, 16.2 mmol, equiv), $CH_2Cl_2$ (50 mL), triethylamine (3.3 g, 32.6 mmol, 2 equiv), and p-TsCl (4.6 g, 24.13 mmol, 1.5 equiv). The resulting solution was stirred overnight. The reaction was quenched by the addition of 50 mL of water and extracted with 3×50 mL of $CH_2Cl_2$. The organic layers were combined, dried over anhydrous sodium sulfate, filtered, and concentrated under vacuum. The residue was applied onto a silica gel column with petroleum ether/ethyl acetate (0-50%) providing 8.3 g (93%) of 2-[2-(2-[[4-(benzyloxy)benzene]sulfonamido]ethoxy)ethoxy] ethyl 4-methylbenzene-1-sulfonate (INT-T2) as a white solid.

Step C: To a 250-mL round-bottom flask was added INT-T2 (8.3 g, 15.1 mmol, 1 equiv), N,N-dimethylformamide (20 mL), and $NaN_3$ (1.47 g, 22.6 mmol, 1.5 equiv). The resulting slurry was stirred for 5 h at 90° C. The reaction was then quenched by the addition of 50 mL of water and extracted with 3×50 mL of ethyl acetate. The organic layers were combined, dried over anhydrous sodium sulfate, filtered, and concentrated under vacuum. The residue was applied onto a silica gel column with petroleum ether/ethyl acetate (0-50%) providing 6 g (94%) of 2-[2-(2-azidoethoxy)ethoxy]-S-[4-(benzyloxy)phenyl]ethane-1-sulfonamido (INT-T3) as a white solid.

Step D: To a 100-mL round-bottom flask was added INT-T3 (6.6 g, 15.70 mmol, 1 equiv) and $CH_2Cl_2$ (2.0 mL), followed by the addition of $BBr_3$ (11.8 g, 47.1 mmol 3 equiv) dropwise with stirring at −60° C. The resulting solution was stirred for 30 min at −60° C. The reaction was then carefully quenched by the addition of 50 mL of water/ice. The resulting solution was extracted with 3×50 mL of ethyl acetate. The organic layers were combined, dried over anhydrous sodium sulfate, filtered, and concentrated under vacuum. The residue was applied onto a silica gel column with petroleum ether/ethyl acetate (0-50%) providing 5 g (crude) of 2-[2-(2-azidoethoxy)ethoxy]-S-(4-hydroxyphenyl)ethane-1-sulfonamido (INT-T4) as a yellow oil.

Step E: To a 7-mL round-bottom flask was added INT-T4 (100 mg, 0.30 mmol, 1 equiv), N,N-dimethylformamide (2 mL), 2,2,2-trifluoro-N-(prop-2-yn-1-yl)acetamide (55 mg, 0.36 mmol, 1.2 equiv), sodium ascorbate (11.97 mg), and $CuSO_4 \cdot 5H_2O$ (7.54 mg). The resulting slurry was stirred for 3 h at room temperature. The resulting solution was diluted with 20 mL of ethyl acetate and quenched by the addition of 20 mL of water. The resulting solution was extracted with 3×20 mL of ethyl acetate. The organic layers were combined, washed with 3×50 mL of brine, dried over anhydrous sodium sulfate, filtered, and concentrated under vacuum. The residue was applied onto a silica gel column with petroleum ether/ethyl acetate (100%) providing 80 mg (55%) of 2,2,2-trifluoro-N-([1-[2-(2-[2-[(4-hydroxybenzene)sulfonamido]ethoxy]ethoxy)ethyl]-1H-1,2,3-triazol-4-yl]methyl)acetamide (INT-T5) as a colorless oil.

Step F: To a 25-mL round-bottom flask was added aminoindanol INT-I8F (693 mg, 1.73 mmol, 1 equiv), phenol INT-T5 (1.0 g, 2.08 mmol, 1.2 equiv), $PPh_3$ (682 mg, 2.60 mmol, 1.51 equiv), and THF (4 mL). Heating at 40° C. in an oil bath DIAD (526 mg, 2.60 mmol, 1.51 equiv) was added in portions over 20 min. The resulting solution was stirred for 1 h at 40° C. in an oil bath. The resulting slurry was concentrated under vacuum. The residue was applied onto a silica gel column with petroleum ether/ethyl acetate (100%) providing 2.0 g (crude) of tert-butyl N-[(3R)-1-[(1S,2S)-4,6-dichloro-1-[4-([2-[2-(2-[4-[(trifluoroacetamido) methyl]-1H-1,2,3-triazol-1-yl]ethoxy)ethoxy]ethyl]sulfamoyl)phenoxy]-2,3-dihydro-1H-inden-2-yl]piperidin-3-yl]carbamate (INT-T6) as a yellow oil.

Step C: To a 100-mL round-bottom flask was added INT-T6 (2.0 g, 2.31 mmol, 1 equiv), methanol (25 mL), and sodium hydroxide (3 M (aq), 3 mL). The resulting slurry was stirred for 2 h at 60° C. in an oil bath. The resulting mixture was concentrated under vacuum. The resulting solution was extracted with 3×100 mL of ethyl acetate. The organic layers were combined, washed with 1×100 mL of brine, dried over anhydrous sodium sulfate, filtered, and concentrated under vacuum. The residue was applied onto a silica gel column with $CH_2Cl_2$/methanol (10:1) providing 1.06 g (60%) of tert-butyl N-[(3R)-1-[(1S,2S)-1-(4-[[2-(2-[2-[4-(aminomethyl)-1H-1,2,3-triazol-1-yl]ethoxy]ethoxy)ethyl]sulfamoyl]phenoxy)-4,6-dichloro-2,3-dihydro-1H-inden-2-yl]piperidin-3-yl]carbamate as an off-white solid.

Scheme for the Synthesis of Triazole-Type Dimer Products:

Example 56: 1-([1-[2-(2-[2-[(4-[[(1S,2S)-2-[(3R)-3-Aminopiperidin-1-yl]-4,6-dichloro-2,3-dihydro-1H-inden-1-yl]oxy]benzene) sulfonamido] ethoxy] ethoxy)ethyl]-1H-1,2,3-triazol-4-yl]methyl)-3-(4-[[([1-[2-(2-[2-[(4-[[(1S,2S)-2-[(3R)-3-aminopiperidin-1-yl]-4,6-dichloro-2,3-dihydro-1H-inden-1-yl]-oxy]benzene)sulfonamido]ethoxy]ethoxy)-ethyl]- 1H-1,2,3-triazol-4-yl]methyl)carbamoyl]-amino]butyl)urea

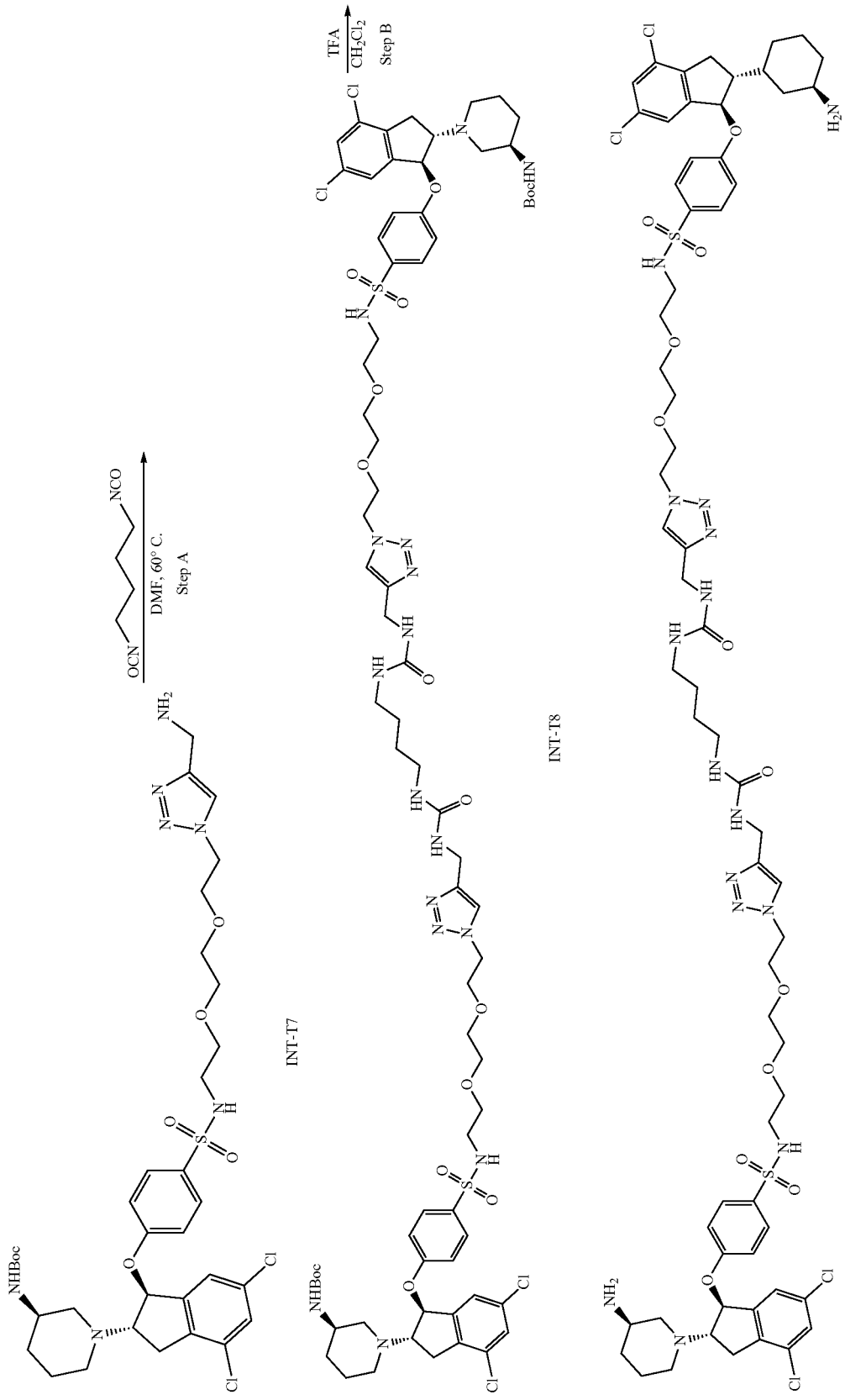
Example 56

Step A: To a 7-mL round-bottom flask was added amine INT-T7 (400 mg, 0.52 mmol, 1 equiv), DMF (3 mL), and 1,4-diisocyanatobutane (29 mg, 0.21 mmol, 0.4 equiv). The resulting solution was stirred for 2 h at 60° C. in an oil bath. The resulting solution was diluted with 50 mL of water. The resulting solution was extracted with 3×50 mL of ethyl acetate. The organic layers were combined, washed with 3×50 mL of brine, dried over anhydrous sodium sulfate, filtered, and concentrated under vacuum. The residue was applied onto a silica gel column with $CH_2Cl_2$/methanol (10:1) providing 320 mg (37%) of tert-butyl N-[(3R)-1-[(1S,2S)-1-(4-[[2-(2-[2-[4-([[(4-[[([1-[2-(2-[2-[(4-[[(1S,2S)-2-[(3R)-3-[[(tert-butoxy)carbonyl]amino]piperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)carbamoyl]amino]butyl)carbamoyl]amino]methyl)-1H-1,2,3-triazol-1-yl]ethoxy]ethoxy)ethyl]sulfamoyl]phenoxy)-4,6-dichloro-2,3-dihydro-1H-inden-2-yl]piperidin-3-yl]carbamate (INT-T8) as a brown solid.

Step B: To a 25-mL round-bottom flask was added INT-T8 (320 mg, 0.19 mmol, 1 equiv) and 20% TFA in $CH_2Cl_2$ (10 mL). The resulting solution was stirred for 1 h at room temperature. The resulting solution was diluted with 20 mL of $CH_2Cl_2$. The pH value of the solution was adjusted to 9-10 with saturated sodium bicarbonate and extracted with 3×100 mL of ethyl acetate. The organic layers were combined, washed with 1×100 mL of brine, dried over anhydrous sodium sulfate, filtered, and concentrated under vacuum. The crude product was purified by preparative HPLC with the following conditions: Column, XBridge C18 OBD Preparative Column, 19*250 mm, 5 um; mobile phase, water (0.05% TFA) and $CH_3CN$ (28.0% $CH_3CN$ up to 52.0% in 8 min); Detector, UV 254 nm.

Example 56: 1-([1-[2-(2-[2-[(4-[[(1S,2S-2-[(3R)-3-Aminopiperidin-1-yl]-4,6-dichloro-2,3-dihydro-1H-inden-1-yl]oxy]benzene) sulfonamido]ethoxy]ethoxy)ethyl]-1H-1,2,3-triazol-4-yl]methyl)-3-(4-[[([1-[2-(2-[2-[(4-[[(1S,2S)-2-[(3R)-3-aminopiperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)carbamoyl]amino]butyl)urea Steps A and B provided 137.6 mg (49%) of the title compound as an off-white solid. MS (m/z): 1477 [M+H]$^+$. $^1$H NMR (Methanol-d4, 300 MHz) δ 7.90-7.79 (m, 6H), 7.44 (d, J=1.7 Hz, 2H), 7.31-7.21 (m, 4H), 7.11-7.04 (m, 2H), 6.31 (d, J=6.0 Hz, 2H), 4.51 (t, J=4.9 Hz, 4H), 4.31 (s, 4H), 4.03 (d, J=6.8 Hz, 2H), 3.83 (t, J=5.0 Hz, 4H), 3.59-3.36 (m, 18H), 3.22-2.98 (m, 12H), 2.87 (dt, J=20.0, 10.8 Hz, 4H), 2.00 (s, 2H), 1.83 (s, 1H), 1.63 (d, J=10.2 Hz, 2H), 1.43 (s, 4H).

Scheme for Synthesis of Protected Galactaric Acid

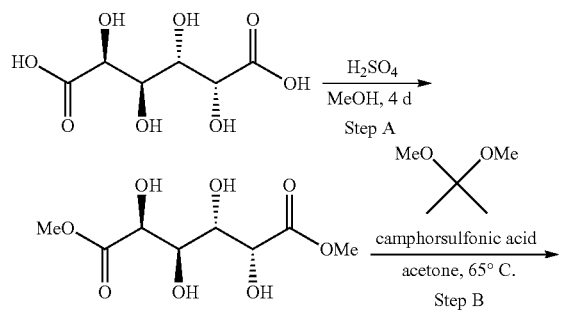

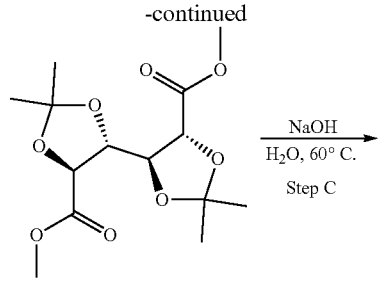

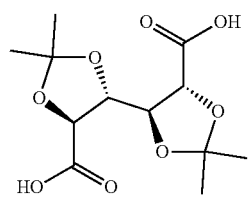

Step A: To a 1-L round-bottom flask was added (2R,3S,4R,5S)-2,3,4,5-tetrahydroxyhexanedioic acid (galactaric acid, 20 g, 95.2 mmol, 1 equiv), methanol (386 mL), and sulfuric acid (5.08 mL, 1 equiv). The resulting solution was stirred for 96 h at 70° C. The resulting solution was allowed to react, with stirring, for an additional 36 h at room temperature. The solids were collected by filtration. The resulting mixture was concentrated under vacuum. This resulted in 20.3 g (90%) of 1,6-dimethyl (2R,3S,4R,5S)-2,3,4,5-tetrahydroxyhexanedioate as a white solid.

Step B: To a 250-mL round-bottom flask was added 1,6-dimethyl (2R,3S,4R,5S)-2,3,4,5-tetrahydroxy hexanedioate (5.0 g, 21 mmol, 1 equiv), 2,2-dimethoxypropane (26 mL, 0.01 equiv), acetone (50 mL), and [(1R,4S)-7,7-dimethyl-2-oxobicyclo[2.2.1]heptan-1-yl]methanesulfonic acid (camphorsulfonic acid, 1.105 g, 4.76 mmol, 0.2 equiv). The mixture was stirred for 1 h at 65° C. The reaction was then quenched by the addition of $K_2CO_3$ (3 $M_{(aq)}$) and concentrated under vacuum. The resulting slurry was extracted with 3×100 mL of $CH_2Cl_2$. The organic layers were combined, washed with 1×100 mL of brine, dried over anhydrous sodium sulfate, filtered, and concentrated under vacuum. The crude product was purified by re-crystallization from methanol. The solids were collected by filtration providing 2.9 g (43%) of methyl (4R, 5S)-5-[(4R, 5S)-5-(methoxycarbonyl)-2,2-dimethyl-1,3-dioxolan-4-yl]-2,2-dimethyl-1,3-dioxolane-4-carboxylate as a white solid.

Step C: To a 100-mL round-bottom flask was added methyl (4R, 5S)-5-[(4R, 5S)-5-(methoxycarbonyl)-2,2-dimethyl-1,3-dioxolan-4-yl]-2,2-dimethyl-1,3-dioxolane-4-carboxylate (2.5 g, 7.85 mmol, 1 equiv), water (30 mg), and sodium hydroxide (785 mg, 19.63 mmol, 5 equiv). The resulting solution was stirred overnight at 60° C. The reaction was then quenched by the addition of 50 mL of hydrogen chloride (1 $M_{(aq)}$) in ice. The resulting solution was extracted with 3×100 mL of ethyl acetate. The organic layers were combined, dried over anhydrous sodium sulfate, filtered, and concentrated under vacuum providing 2.0 g (80%) of (4R,4'S,5S,5'R)-2,2,2',2'-tetramethyl-[4,4'-bi(1,3-dioxolane)]-5,5'-dicarboxylic acid as a white solid.

Scheme for Synthesis of Triazole-Type Dimer Products with Galactaric Acid Core:

Example 57: (2R,3S,4R,5S)—N$^1$,N$^6$-Bis([1-[2-(2-[2-[(4-[[(1S,2S)-2-[(3R)-3-aminopiperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)-2,3,4,5-tetrahydroxyhexanediamide

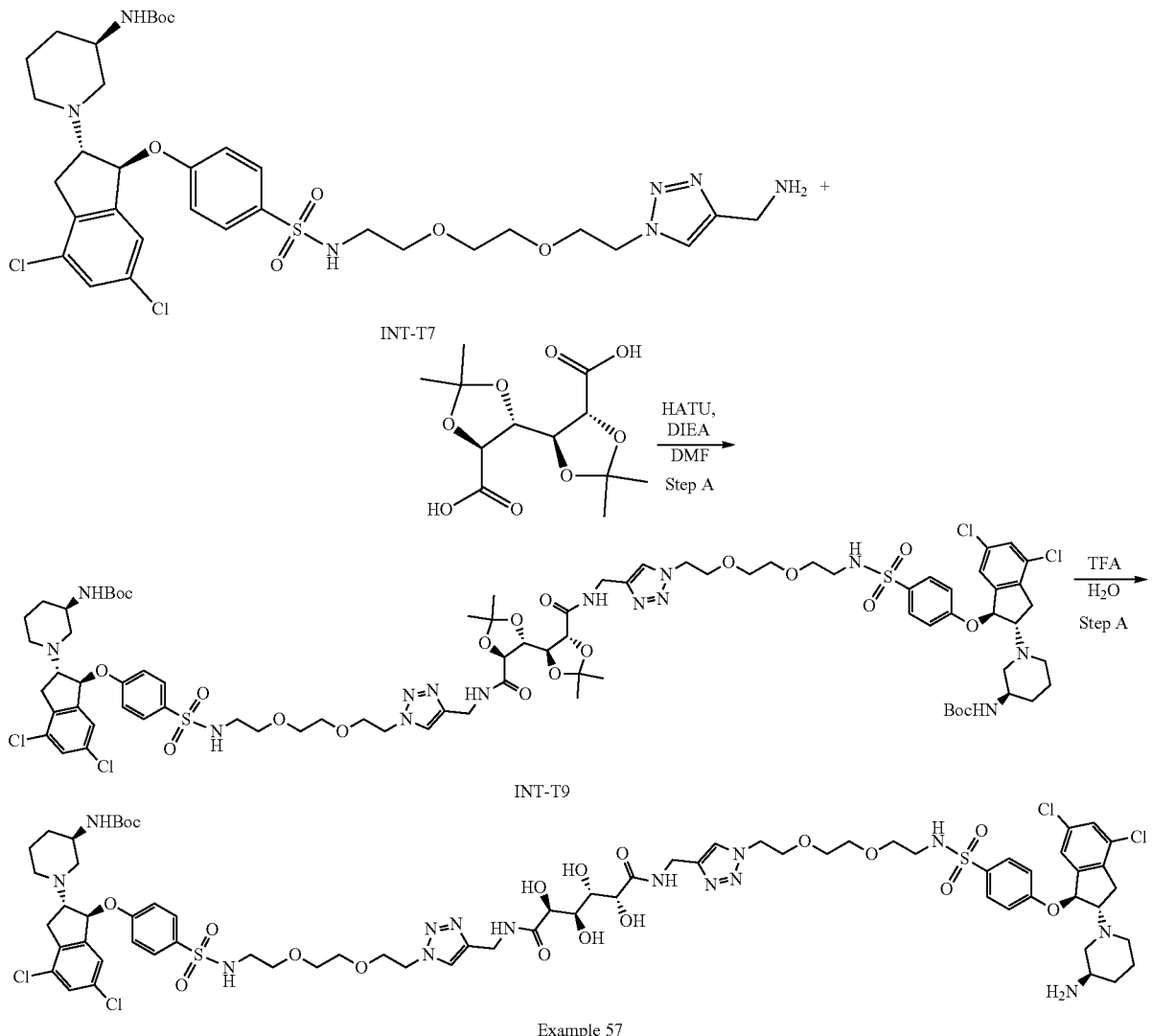

Step A: To a 25-mL round-bottom flask was added amine INT-T7 (300 mg, 0.39 mmol, 2.2 equiv), (4R,5S)-5-[(4R,5S)-5-carboxy-2,2-dimethyl-1,3-dioxolan-4-yl]-2,2-dimethyl-1,3-dioxolane-4-carboxylic acid (51.54 mg, 0.18 mmol, 1 equiv), DMF (8 mL), diisopropylethylamine (115 mg, 0.89 mmol, 5 equiv), and HATU (202.92 mg, 0.53 mmol, 3 equiv). The resulting solution was stirred for 2 h at room temperature. The reaction was quenched by the addition of 20 mL of water and the resulting solution was extracted with 3×50 mL of ethyl acetate. The organic layers were combined, washed with 3×100 mL of brine, dried over anhydrous sodium sulfate, filtered, and concentrated under vacuum. The residue was applied onto a silica gel column with CH$_2$Cl$_2$/methanol (10:1) providing 340 mg (crude) of INT-T9 as a white solid.

Step B: To a 25-mL round-bottom flask was added INT-T9 (450 mg, 0.25 mmol, 1 equiv) and TFA/H$_2$O (7/0.35 mL). The resulting solution was stirred for 3 h at room temperature. The resulting mixture was concentrated under vacuum. The crude product was purified by preparative HPLC with the following conditions: Column, XBridge C18 OBD Preparative Column, 19*250 mm, 5 um; mobile phase, water (0.05% TFA) and CH$_3$CN (28.0% CH$_3$CN up to 45.0% in 12 min); Detector, UV 254 nm.

Example 57: (2R,3S,4R,5S)—N$^1$,N$^6$-Bis([1-[2-(2-[2-[(4-[[(1S,2S)-2-[(3R)-3-aminopiperidin-1-yl]-4,6-dichloro-2,3-dihydro-1H-inden-1-yl]oxy]benzene)sulfonamido]ethoxy]ethoxy)ethyl]-1H-1,2,3-triazol-4-yl]methyl)-2,3,4,5-tetrahydroxyhexanediamide Steps A and B provided 72.3 mg (19%) of the title compound as a white solid. MS (m/z): 1511 [M+H]$^+$. $^1$H NMR (Methanol-d4, 300 MHz) δ 7.94-7.79 (m, 6H), 7.42 (s, 2H), 7.26 (d, J=8.6 Hz, 4H), 7.08 (s, 2H), 6.21 (t, J=6.3 Hz, 2H), 4.56-4.44 (m, 8H), 4.39 (d, J=1.1 Hz, 2H), 4.00 (s, 2H), 3.93-3.78 (m, 6H), 3.59-3.27 (m, 17H), 3.03 (t, J=5.4 Hz, 10H), 2.85-2.71 (m, 4H), 1.92 (d, J=18.5 Hz, 3H), 1.76 (s, 2H), 1.59 (d, J=9.8 Hz, 2H).

Scheme for Synthesis of Aliphatic Triazole-Type Intermediates:
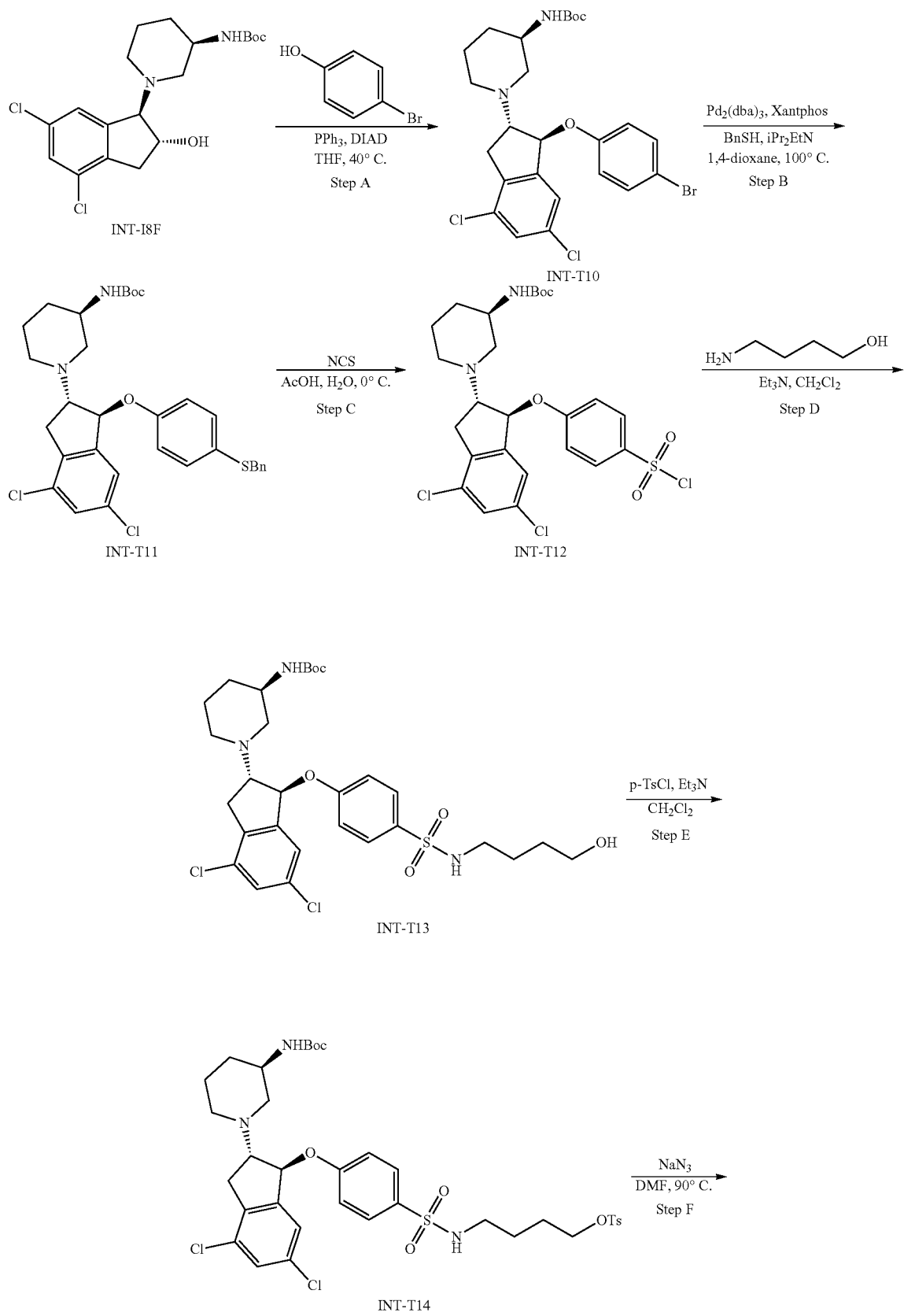

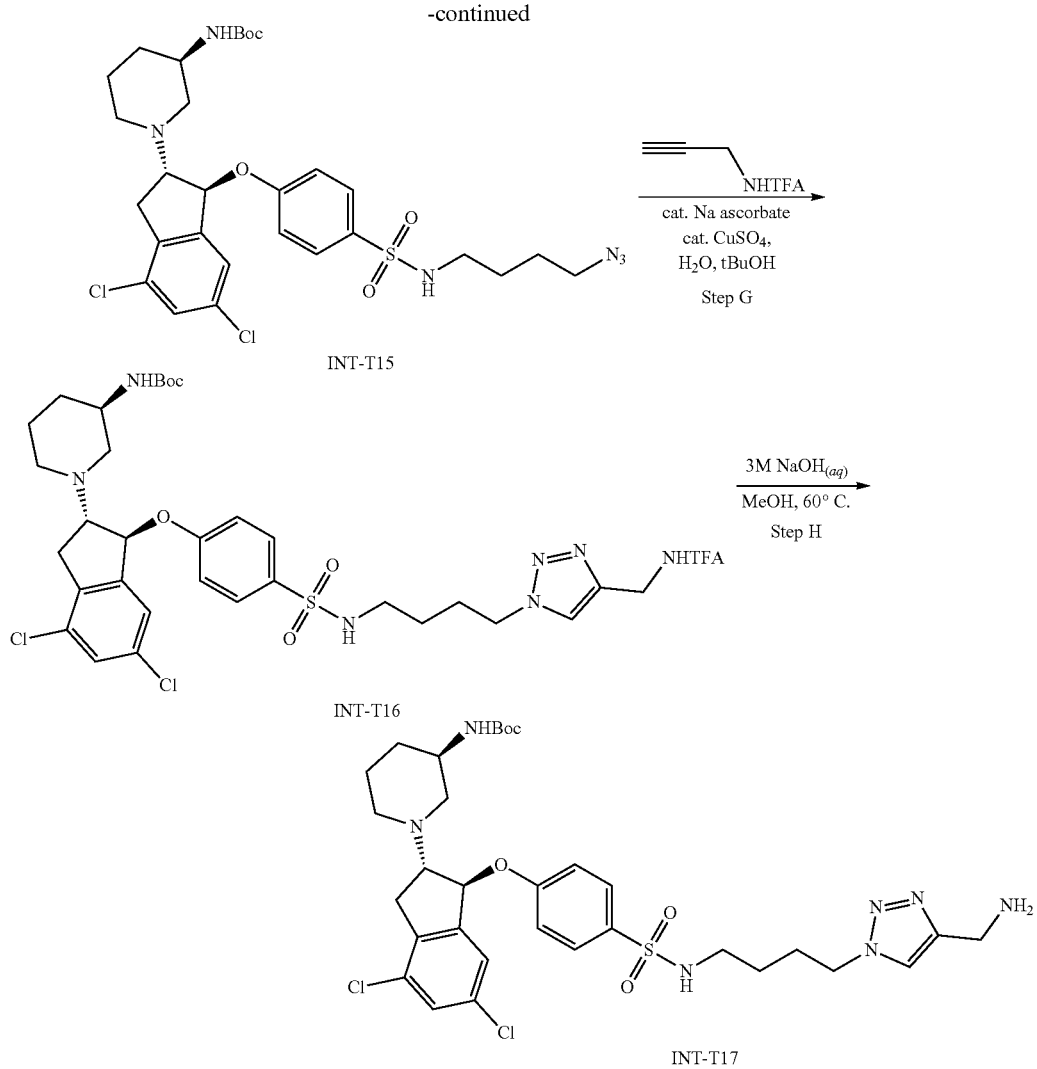

Step A: To a 250-mL round-bottom flask, was added aminoindanol INT-I8F (2.0 g, 5 mmol, 1 equiv), 4-bromophenol (1.3 g, 7.5 mmol, 1.5 equiv), PPh$_3$ (2.62 g, 10 mmol, 2 equiv), and tetrahydrofuran (100 mL). Heating at 40° C. in an oil bath DIAD (2.02 g, 10 mmol, 1.5 equiv) was added dropwise with stirring over 20 min. The resulting solution was stirred for 3 h at 40° C. The resulting mixture was concentrated under vacuum. The residue was applied onto a silica gel column with petroleum ether/ethyl acetate (10:1-8:1) providing 2.5 g (90%) of tert-butyl N-[(3R)-1-[(1S,2S)-1-(4-bromophenoxy)-4,6-dichloro-2,3-dihydro-1H-inden-2-yl]piperidin-3-yl]carbamate (INT-T10) as a light yellow solid.

Step B: To a 250-mL round-bottom flask purged and maintained with an inert atmosphere of nitrogen was added bromide INT-T10 (2.5 g, 4.14 mmol, 1 equiv), 1,4-dioxane (100 mL), benzyl mercaptan (1.12 g, 9 mmol, 2 equiv), Xantphos (260 mg, 0.45 mmol, 0.10 equiv), and diisopropylethylamine (1.46 g, 11.3 mmol, 2.73 equiv). This was followed by the addition of Pd$_2$(dba)$_3$.CHCl$_3$ (240 mg, 0.23 mmol, 0.05 equiv) in portions at room temperature. The resulting solution was stirred for 14 h at 100° C. The resulting mixture was concentrated under vacuum and the residue was dissolved in 150 mL of ethyl acetate. The resulting mixture was washed with 3×80 mL of water and 1×80 mL of saturated aqueous sodium chloride. The organic layers were combined, dried over anhydrous sodium sulfate, filtered, and concentrated under vacuum. The residue was applied onto a silica gel column with petroleum ether/ethyl acetate (10:1-3:1) providing 2.5 g (93%) of tert-butyl N-[(3R)-1-[(1S,2S)-1-[4-(benzylsulfanyl)phenoxy]-4,6-dichloro-2,3-dihydro-1H-inden-2-yl]piperidin-3-yl]carbamate (INT-T11) as a brown solid.

Step C: To a 100-mL round-bottom flask was added thioether INT-T11 (2.5 g, 4.17 mmol, 1 equiv), acetic acid (24 mL), and water (8 mL). This was followed by the addition of NCS (1.93 g, 14.45 mmol, 3.5 equiv) in portions at 0° C. The resulting solution was stirred for 4 h at room temperature. The resulting slurry was diluted with 30 mL of water. The pH value of the solution adjusted to 8 with saturated aqueous sodium bicarbonate and extracted with 3×80 mL of ethyl acetate. The organic layers were combined and washed with 1×100 mL of water and 1×100 mL of brine. The mixture was dried over anhydrous sodium sulfate, filtered, and concentrated under vacuum. This resulted in 2.0 g (83%) of crude tert-butyl N-[(3R)-1-[(1S,2S)-4,6-dichloro-1-[4-(chlorosulfonyl)phenoxy]-2,3-dihydro-1H-inden-2-yl]piperidin-3-yl]carbamate as a brown solid.

Step D: To a 250-mL round-bottom flask was added sulfonyl chloride INT-T12 (2.0 g, 3.47 mmol, 1 equiv), CH$_2$Cl$_2$ (50 mL), triethylamine (1.4 mL, 3 equiv), and 4-aminobutan-1-ol (0.64 mL, 2 equiv). The resulting solution was stirred overnight at room temperature. The resulting slurry was diluted with water and extracted with 3×150 mL of CH$_2$Cl$_2$. The organic layers were combined and washed with 1×100 mL of water and 1×100 mL of brine. The mixture was dried over anhydrous sodium sulfate, filtered, and concentrated under vacuum. The residue was applied onto a silica gel column with petroleum ether/ethyl acetate (1:2) providing 1.47 g (67%) of tert-butyl N-[(3R)-1-[(1S,2S)-4,6-dichloro-1-[4-[(4-hydroxybutyl)sulfamoyl]phenoxy]-2,3-dihydro-1H-inden-2-yl]piperidin-3-yl]carbamate (INT-T13) as a yellow oil.

Step E: To a 250-mL round-bottom flask was added alcohol INT-T13 (1.47 g, 2.34 mmol, 1 equiv). CH$_2$Cl$_2$ (30 mL), triethylamine (1.3 mL, 4 equiv), and p-toluenesulfonyl chloride (1.34 g, 7.03 mmol, 3 equiv). The resulting solution was stirred overnight at room temperature. The resulting slurry was diluted with water and extracted with 3×150 mL of CH$_2$Cl$_2$. The organic layers were combined and washed with 1×100 mL of water and 1×100 mL of brine. The mixture was dried over anhydrous sodium sulfate, filtered, and concentrated under vacuum. The residue was applied onto a silica gel column with petroleum ether/ethyl acetate (1:1) providing 1.46 g (80%) of tert-butyl N-[(3R)-1-[(1S, 2S)-4,6-dichloro-1-[4-[(4-[[(4-methylbenzene)sulfonyl] oxy]butyl)sulfamoyl]phenoxy]-2,3-dihydro-1H-inden-2-yl] piperidin-3-yl]carbamate (INT-T14) as a yellow solid.

Step F: To a 100-mL round-bottom flask was added tosylate INT-T14 (1.46 g, 1.87 mmol, 1 equiv), DMF (10 mL), and sodium azide (182 mg, 2.80 mmol, 1.5 equiv). The resulting solution was stirred overnight at 90° C. The resulting slurry was diluted with water and extracted with 3×150 mL of ethyl acetate. The organic layers were combined and washed with 1×100 mL of water and 1×100 mL of brine. The mixture was dried over anhydrous sodium sulfate, filtered, and concentrated under vacuum. The residue was applied onto a silica gel column with petroleum ether/ethyl acetate (1:1) providing 1.06 g (87%) of tert-butyl N-[(3R)-1-[(1S,2S)-1-[4-[(4-azidobutyl)sulfamoyl]phenoxy]-4,6-dichloro-2,3-dihydro-1H-inden-2-yl]piperidin-3-yl]carbamate (INT-T15) as a yellow oil.

Step G: To a 50-mL round-bottom flask was azide INT-T15 (500 mg, 0.76 mmol, 1 equiv), 2,2,2-trifluoro-N-(prop-2-yn-1-yl)acetamide (280 mg, 1.85 mmol, 2.4 equiv), 2-methylpropan-2-ol (12 mL), water (5 mL), sodium ascorbate (30 mg, 0.15 mmol, 0.2 equiv), and CuSO$_4$.5H$_2$O (20 mg, 0.08 mmol, 0.1 equiv) The resulting solution was stirred overnight at room temperature. The resulting mixture was concentrated under vacuum. The resulting solution was diluted with water and extracted with 3×100 mL of CH$_2$Cl$_2$. The organic layers were combined and washed with 1×100 mL of water and 1×100 mL of brine. The mixture was dried over anhydrous sodium sulfate, filtered, and concentrated under vacuum. The residue was applied onto a silica gel column with petroleum ether/ethyl acetate (1:1) providing 480 mg (78%) of tert-butyl N-[(3R)-1-[(1S,2S)-4,6-dichloro-1-[4-[(4-[4-[(trifluoroacetamido)methyl]-1H-1,2,3-triazol-1-yl]butyl)sulfamoyl]phenoxy]-2,3-dihydro-1H-inden-2-yl]piperidin-3-yl]carbamate (INT-T16) as a white solid.

Step H: To a 100-mL round-bottom flask was added INT-T16 (432 mg, 0.54 mmol, 1 equiv), methanol (20 mL), and sodium hydroxide (3 M$_{(aq)}$, 0.4 mL). The resulting solution was stirred for 1 h at 60° C. The resulting solution was extracted with 3×100 mL of CH$_2$Cl$_2$. The organic layers were combined and washed with 1×50 mL of water and 1×50 mL of brine. The mixture was dried over anhydrous sodium sulfate, filtered, and concentrated under vacuum. The residue was applied onto a silica gel column with CH$_2$Cl$_2$/methanol (10:1) providing 356 mg (94%) of tert-butyl N-[(3R)-1-[(1S2S)-1-[4-([4-[4-(aminomethyl)-1H-1, 2,3-triazol-1-yl]butyl]sulfamoyl)phenoxy]-4,6-dichloro-2, 3-dihydro-1H-inden-2-yl]piperidin-3-yl]carbamate (INT-T17) as a white solid.

The 6-carbon intermediate was generated from the analogous procedure beginning with 6-aminohexan-1-ol. This provided INT-T18:

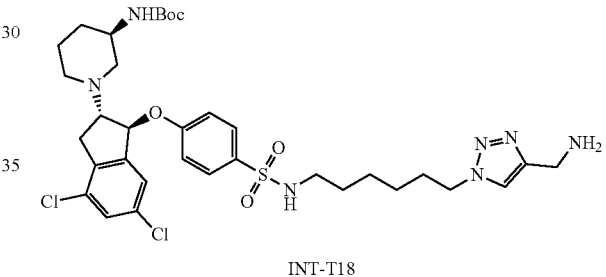

INT-T18

General Scheme for Aliphatic Triazole-Type Dimer Products:

Example 58: 3-[(1-[4-[(4-[[(1S,2S)-2-[(3R)-3-aminopiperidin-1-yl]-1,6-dichloro-2,3-dihydro-1H-1-inden-1-yl]oxy]benzene)sulfonamido]butyl]-1H-1,2, 3-triazol-4-yl)methyl]-1-[4-([[(1-[4-[(4-[[(1S,2S)-2-[(3R)-3-aminopiperidin-1-yl]-4,6-dichloro-2,3-dihydro-1H-inden-1-yl]oxy]benzene)sulfonamido] butyl]-1H-1,2,3-triazol-4-yl)methyl]carbamoyl] amino)butyl]urea

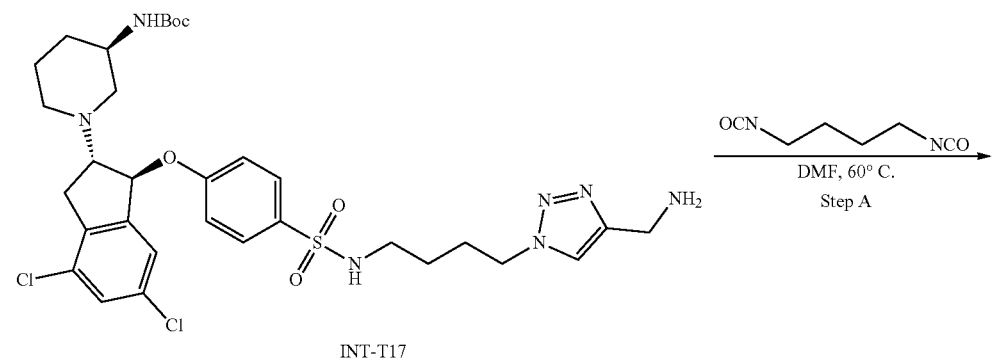

INT-T17

-continued

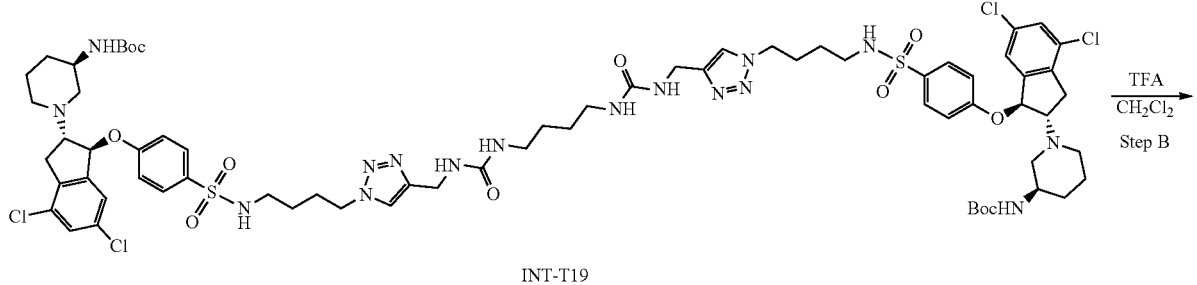

INT-T19

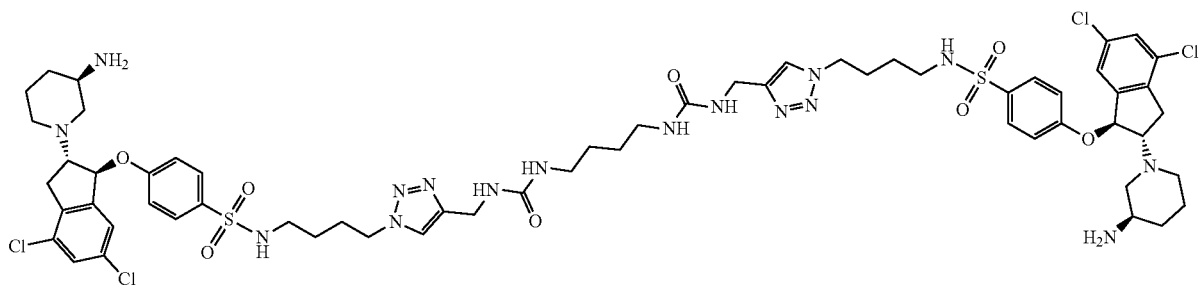

Example 58

Step A: To a 50-mL round-bottom flask was added amine INT-T17 (394 mg, 0.56 mmol, 1 equiv), DMF (4.7 mL), and 1,4-diisocyanatobutane (39 mg, 0.28 mmol, 0.5 equiv). The resulting solution was stirred for 1 h at 60° C. The resulting mixture was concentrated under vacuum. The residue was applied onto a silica gel column with $CH_2Cl_2$/methanol (10:1) providing 455 mg (crude) of tert-butyl N-[(3R)-1-[(1S,2S)-1-[4-[(4-[4-[([[4-[([[4-[([[(1-[4-[(4-[[[(1S,2S)-2-[(3R)-3-[[[(tert-butoxy)carbonyl]amino]piperidin-1-yl]-4,6-dichloro-2,3-dihydro-1H-inden-1-yl]oxy]benzene)sulfonamido]butyl]-1H-1,2,3-triazol-4-yl)methyl]carbamoyl]amino)butyl]carbamoyl]amino)methyl]-1H-1,2,3-triazol-1-yl]butyl)sulfamoyl]phenoxy]-4,6-dichloro-2,3-dihydro-1H-inden-2-yl]piperidin-3-yl]carbamate (INT-T19) as a yellow oil.

Step B: To a 50-mL round-bottom flask was added dimer INT-T19 (455 mg, 0.29 mmol 1 equiv), $CH_2Cl_2$, (10 mL), and trifluoroacetic acid (1.5 mL). The resulting solution was stirred for 1 h at room temperature. The pH value of the solution was adjusted to 8 with saturated aqueous potassium carbonate and extracted with 3×150 mL of $CH_2Cl_2$. The organic layers were combined and washed with 1×100 mL of water and 1×100 mL of brine. The mixture was dried over anhydrous sodium sulfate, filtered, and concentrated under vacuum. The crude product was purified by preparative—HPLC with the following conditions: Column, XBridge C18 OBD Preparative Column, 19*250 mm, 5 um; mobile phase, water (10 mmol/L $NH_4HCO_3$) and $CH_3CN$ (50.0% $CH_3CN$ up to 65.0% in 8 min); Detector, UV 254 nm.

Example 58: 3-[(1-[4-[(4-[[[(1S,2S)-2-[(3R)-3-Aminopiperidin-1-yl]-4,6-dichloro-2,3-dihydro-1H-inden-1-yl]oxy]benzene)sulfonamido]butyl]-1H-1,2,3-triazol-4-yl)methyl]-1-[4-([[(1-[4-[(4-[[[(1S,2S)-2-[(3R)-3-aminopiperidin-1-yl]-4,6-dichloro-2,3-dihydro-1H-inden-1-yl]oxy]benzene)sulfonamido]butyl]-1H-1,2,3-triazol-4-yl)methyl]carbamoyl]amino)butyl]urea Steps A and B provided 94 mg (24%) of the title compound as a white solid. MS (m/z): 1357.05 [M+H]$^+$. $^1$H NMR (Methanol-d4, 400 MHz) δ 7.80 (t, J=3.6 Hz, 6H), 7.40-7.15 (m, 8H), 5.95 (d, J=5.2 Hz, 2H), 4.35 (t, J=7.0 Hz, 8H), 3.59 (q, J=6.6 Hz, 2H), 3.22-3.10 (m, 6H), 3.04-2.92 (m, 2H), 2.85 (q, J=6.6 Hz, 8H), 2.72 (d, J=11.2 Hz, 2H), 2.25 (t, J=8.0 Hz, 2H), 2.15 (t, J=8.4 Hz, 2H), 1.95-1.79 (m, 6H), 1.79-1.70 (m, 2H), 1.60-1.50 (m, 2H), 1.49-1.40 (m, 8H), 1.29 (d, J=18.4 Hz, 3H), 1.18 (q, J=5.4 Hz, 2H).

Example 59

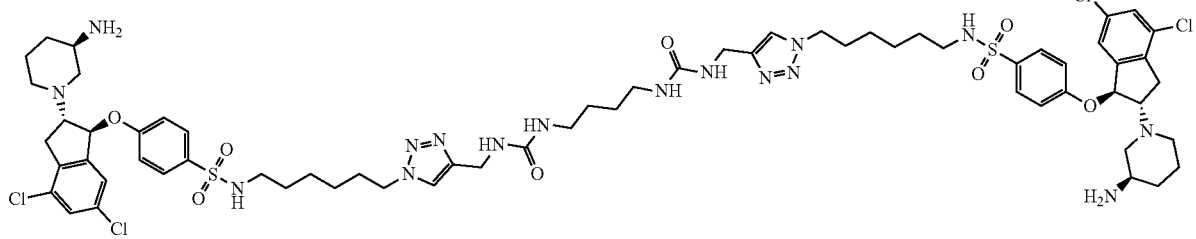

Example 59: 3-[(1-[6-[(4-[[(1S,2S)-2-[(3R)-3-Aminopiperidin-1-yl]-4,6-dichloro-2,3-dihydro-1H-inden-1-yl]oxy]benzene)sulfonamido]-hexyl]-1H-1,2,3-triazol-4-yl)methyl]-1-[4-([[(1-[6-[(4-[[(1S,2S)-2-[(3R)-3-aminopiperidin-1-yl]-4,6-dichloro-2,3-dihydro-1H-inden-1-yl]oxy]benzene)sulfonamido]hexyl]-1H-1,2,3-triazol-4-yl)methyl]carbamoyl]amino)butyl]urea. Beginning with INT-T18

Steps A and B provided 221 mg (55%) of the title compound as a white solid. MS (m/z): 1413 [M+H]+. 1H NMR (Methanol-d4, 400 MHz) δ 7.96-7.87 (m, 6H), 7.54 (d, J=1.7 Hz, 2H), 7.45-7.37 (m, 4H), 7.08-7.02 (m, 2H), 6.74 (d, J=6.5 Hz, 2H), 4.52-4.36 (m, 10H), 3.79 (s, 2H), 3.70 (q, J=7.8 Hz, 6H), 3.42 (dd, J=16.3, 8.4 Hz, 2H), 3.30-3.09 (m, 8H), 2.89 (t, J=6.8 Hz, 4H), 2.18 (d, J=15.1 Hz, 4H), 2.08 (d, J=14.3 Hz, 2H), 1.88 (p, J=7.2 Hz, 4H), 1.81-1.68 (m, 2H), 1.57-1.42 (m, 8H), 1.39-1.19 (m, 10H).

General Scheme for Synthesis of Aliphatic Triazole-Type Dimer Products with Galactaric Acid Core:

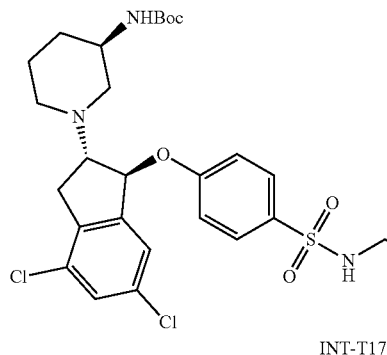

INT-T17

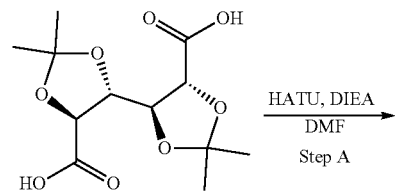

HATU, DIEA
DMF
Step A

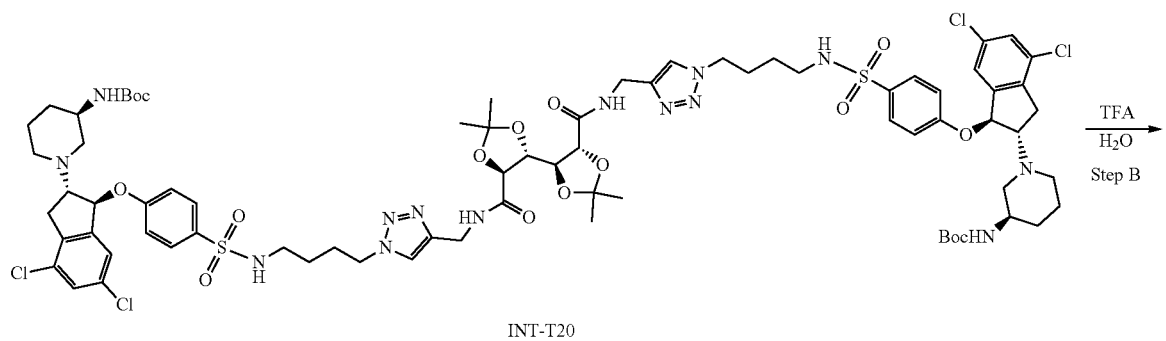

INT-T20

TFA
H2O
Step B

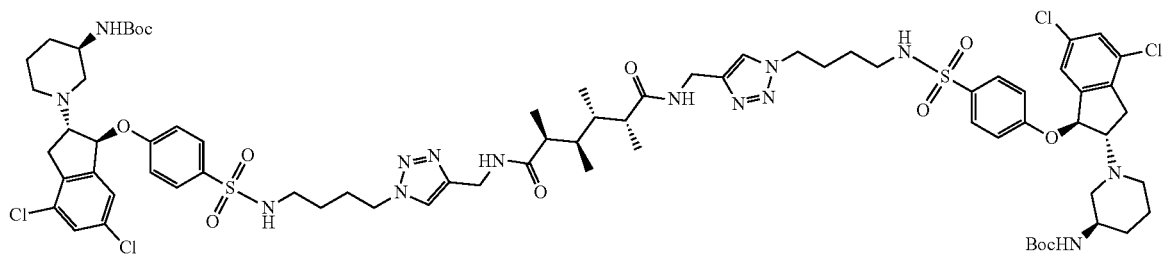

Example 60

Step A: To a 25-mL round-bottom flask was added amine INT-T17 (300 mg, 0.42 mmol, 2.2 equiv), (4R,5S)-5-[(4R,5S)-5-carboxy-2,2-dimethyl-1,3-dioxolan-4-yl]-2,2-dimethyl-1,3-dioxolane-4-carboxylic acid (55.9 mg, 0.19 mmol, 1 equiv), DMF (8 mL), diisopropylethylamine (124.5 mg, 0.96 mmol, 5 equiv), and HATU (220.02 mg, 0.58 mmol, 3 equiv). The resulting solution was stirred for 2 h at room temperature. The reaction was quenched by the addition of 20 mL of water and extracted with 3×50 mL of ethyl acetate. The organic layers were combined, washed with 3×100 mL of brine, dried over anhydrous sodium sulfate, filtered, and concentrated under vacuum. The residue was applied onto a silica gel column with $CH_2Cl_2$/methanol (10:1) providing 350 mg (crude) of tert-butyl N-[(3R)-1-[(1S,2S)-1-[4-([4-[4-([[(4S,4aR,8R,8aS)-8-[[(1-[4-[(4-[[[(1S,2S)-2-[(3R)-3-[[(tert-butoxy)carbonyl]amino]piperidin-1-yl]-(1,4,6-dichloro-2,3-dihydro-1H-inden-1-yl]oxy]benzene)sulfonamido]butyl]-1H-1,2,3-triazol-4-yl)methyl]carbamoyl]-2,2,6,6-tetramethyl-hexahydro-[1,3]dioxino[5,4-d][1,3]dioxin-4-yl]formamido]methyl)-1H-1,2,3-triazol-1-yl]butyl]sulfamoyl)phenoxy]-4,6-dichloro-2,3-dihydro-1H-inden-2-yl]piperidin-3-yl]carbamate (INT-T20) as a white solid.

Step B: To a 25-mL round-bottom flask was added dimer INT-T20 (480 mg, 0.29 mmol, 1 equiv), and TFA/$H_2O$ (7/0.35 mL). The resulting solution was stirred for 3 h at room temperature. The resulting mixture was concentrated under vacuum. The crude product was purified by preparative HPLC with the following conditions: Column, XBridge C18 OBD Preparative Column, 19*250 mm, 5 um; mobile phase, water (0.05% TFA) and $CH_3CN$ (28.0% $CH_3CN$ up to 43.0% in 8 min); Detector, UV 254 nm.

Example 60: (4R,4aS,8S,8aR)—$N^4,N^8$-Bis([1-(4-[4-((1S,2S)-2-[(3R)-3-aminopiperidin-1-yl]-4,6-dichloro-2,3-dihydro-1H-inden-1-yloxy)phenyl sulfonamide]butyl)-1H-1,2,3-traizol-4-yl]methyl)-2,2,6,6-tetramethyl-tetrahydro-[1,3]dioxino[5,4-d][1,3]dioxine-4,8-dicarboxamide Steps A and B provided 190.0 mg (48%) of the title compound as a white solid. MS (m/z): 1389 [M+H]$^+$. $^1$H NMR (Methanol-d4, 300 MHz) δ 7.85-7.76 (m, 6H), 7.45-7.38 (m, 2H), 7.27 (d, J=8.7 Hz, 4H), 7.13-7.06 (m, 2H), 6.13 (d, J=5.7 Hz, 2H), 4.61-4.26 (m, 10H), 4.00 (s, 2H), 3.82 (s, 2H), 3.37 (d, J=18.5 Hz, 4H), 3.03 (dd, J=16.6, 7.7 Hz, 4H), 2.86 (dt, J=7.2, 3.6 Hz, 6H), 2.68 (s, 4H), 1.88 (dd, J=14.5, 7.1 Hz, 8H), 1.72 (s, 2H), 1.57 (d, J=10.9 Hz, 2H), 1.40 (t, J=7.5 Hz, 4H).

Example 61: (4R,4aS,8S,8aR)—$N^4,N^8$-Bis([1-(6-[4-((1S,2S)-2-[(3R)-3-amino piperidin-1-yl]-4,6-dichloro-2,3-dihydro-1H-inden-1-yloxy)phenylsulfonamido]hexyl)-1H-1,2,3-traizol-4-yl]methyl)-2,2,6,6-tetramethyl-tetrahydro-[1,3]dioxino[5,4-d][1,3]dioxine-4,8-dicarboxamide Example 61

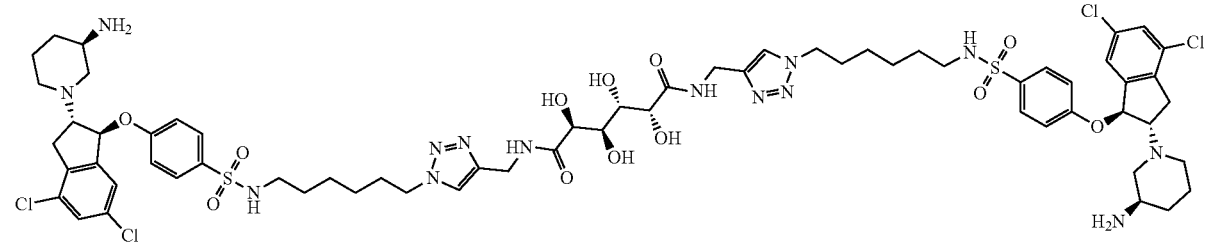

Beginning with INT-T18, Steps A and B provided 130.8 mg (52%) of the title compound as a white solid. MS (m/z): 1445 [M+H]$^+$. $^1$H NMR (Methanol-14, 400 MHz) δ 7.84 (dd, J=6.9, 1.9 Hz, 6H), 7.44 (d, J=1.8 Hz, 2H), 7.34-7.26 (m, 4H), 7.15-7.09 (m, 2H), 6.08 (d, J=5.5 Hz, 2H), 4.61-4.39 (m, 5H), 4.34 (t, J=7.0 Hz, 4H), 4.02 (s, 2H), 3.74 (q, J=7.1 Hz, 2H), 3.42-3.35 (m, 2H), 3.31-3.22 (m, 2H), 3.08-2.93 (m, 4H), 2.85 (t, J=6.8 Hz, 4H), 2.76 (s, 2H), 2.70-2.60 (m, 4H), 1.87 (tt, J=14.4, 8.2 Hz, 8H), 1.69 (s, 2H), 1.58 (s, 2H), 1.48-1.20 (m, 13H).

General Scheme for Synthesis of Alkyl Linker Monomers:

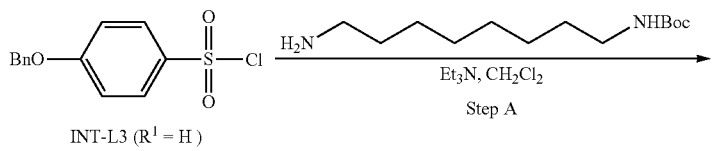

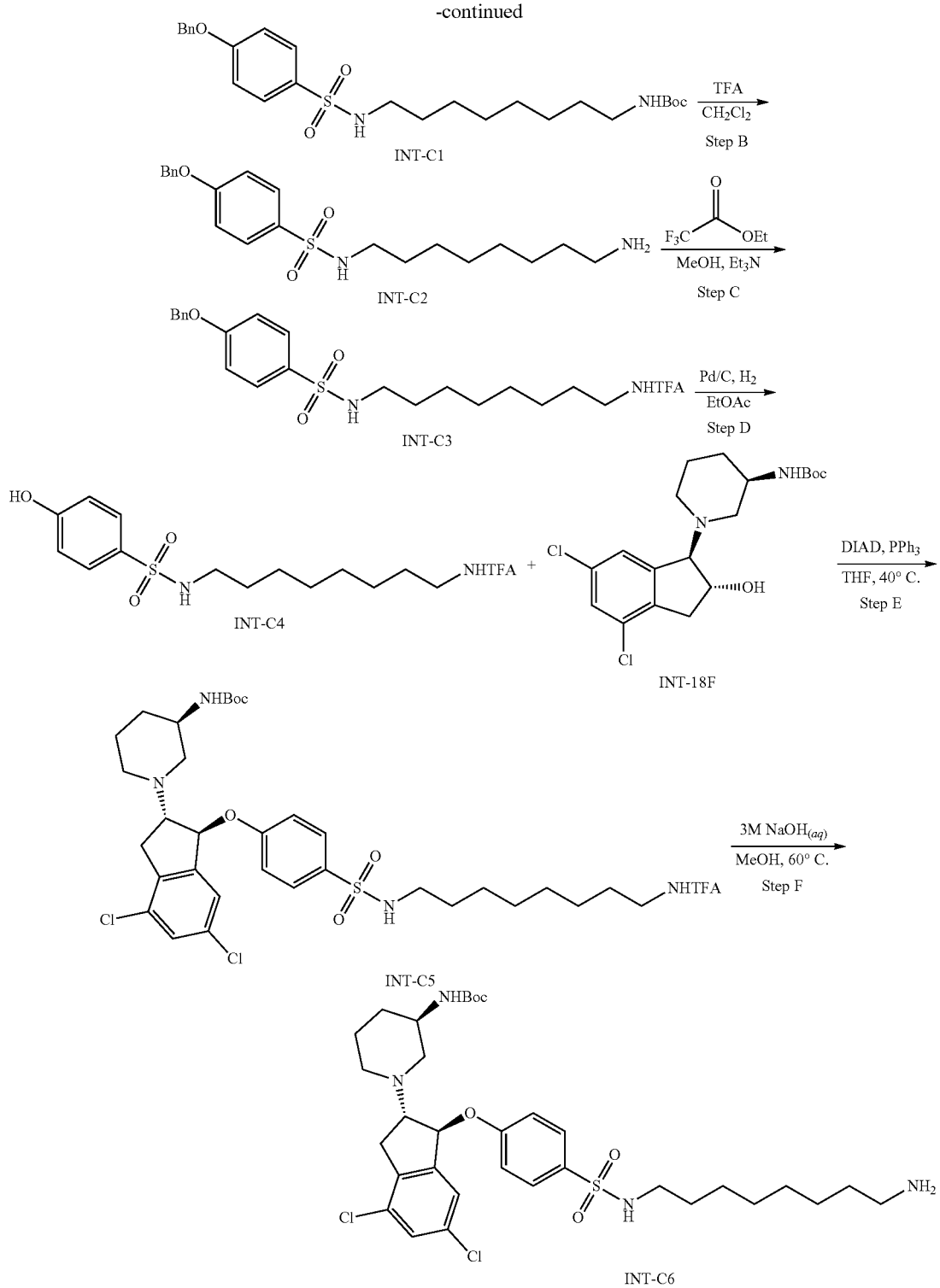

Step A: To a 250-mL round-bottom flask, was added tert-butyl N-(8-aminooctyl)carbamate (2 g, 8.18 mmol, 1.1 equiv), $CH_2Cl_2$ (30 mL), and triethylamine (3 mL, 3 equiv). This was followed by the addition of 4-(benzyloxy)benzene-1-sulfonyl chloride (INT-L3 where $R^1$=H, 2.1 g, 7.43 mmol, 1 equiv) in several portions. The resulting solution was stirred overnight at room temperature. The resulting solution was diluted with water and extracted with 3×100 mL of $CH_2Cl_2$. The organic layers were combined and washed with 2×150 mL of brine. The mixture was dried over anhydrous sodium sulfate, filtered, and concentrated under vacuum. The residue was applied onto a silica gel column with petroleum ether/ethyl acetate (2:1) providing 3.3 g (91%) of tert-butyl N-(8-[[4-(benzyloxy)benzene]sulfonamido]octyl)carbamate (INT-C1) as a white solid.

Step B: To a 250-mL round-bottom flask was added sulfonamide INT-C1 (2.7 g, 5.50 mmol, 1 equiv), CH₂Cl₂ (30 mL), and trifluoroacetic acid (4 mL). The resulting solution was stirred for 1 h at room temperature. The pH value of the solution was adjusted to 9 with saturated aqueous NaHCO₃. The solids were collected by filtration. This resulted in 1.8 g (84%) of N-(8-aminooctyl)-4-(benzyloxy)benzene-1-sulfonamide (INT-C2) as a white solid.

Step C: To a 250-mL round-bottom flask was added amine INT-C2 (1.68 g, 4.30 mmol, 1 equiv), methanol (20 mL), and triethylamine (2.3 mL, 4 equiv). This was followed by the addition of ethyl trifluoroacetate (1.2 mL, 2 equiv) dropwise with stirring at room temperature. The resulting solution was stirred for 1 h at room temperature. The resulting solution was diluted with water and extracted with 100 mL of ethyl acetate. The organic layers were combined and washed with 2×150 mL, of brine. The mixture was dried over anhydrous sodium sulfate, filtered, and concentrated under vacuum. The residue was applied onto a silica gel column with petroleum ether/ethyl acetate (2:1) providing 2 g (96%) of N-(8-[[4-(benzyloxy)benzene]sulfonamido]octyl)-2,2,2-trifluoroacetamide (INT-C3) as a white solid.

Step D: To a 250-mL round-bottom flask was added benzyl ether INT-C3 (2 g, 4.11 mmol, 1 equiv), methanol (20 mL), and 10% palladium on carbon (1 g). To the above H₂(g) was introduced in and the resulting slurry was stirred for 1 h at room temperature. The solids were filtered out and the resulting mixture concentrated under vacuum. The residue was applied onto a silica gel column with petroleum ether/ethyl acetate (1:1) providing 1.6 g (98%) of 2,2,2-trifluoro-N-[8-[(4-hydroxybenzene)sulfonamido]octyl]acetamide (INT-C4) as a white solid.

Step E: To a 50-mL round-bottom flask was added phenol INT-C4 (1.6 g, 4.04 mmol, 1 equiv), THF (18 mL), and aminoindanol INT-I8F (1.78 g, 4.44 mmol, 1.1 equiv). This was followed by the addition of PPh₃ (1.79 g, 6.82 mmol, 1.7 equiv) in several batches with heating at 40° C. To this was added DIAD (1.27 mL, 1.6 equiv) dropwise with stirring at 40° C. over 30 min. The resulting solution was stirred for 1 h at 40° C. The resulting mixture was concentrated under vacuum. The residue was applied onto a silica gel column with petroleum ether/ethyl acetate (2:1) providing 2.8 g (89%) of tert-butyl (3R)-1-((1S,2S)-4,6-dichloro-1-(4-(N-(8-(2,2,2-trifluoroacetamido)octyl)sulfamoyl)phenoxy)-2,3-dihydro-1H-inden-2-yl)piperidin-3-ylcarbamate (INT-C5) as a yellow solid.

Step F: To a 250-mL round-bottom flask was added INT-C5 (2.8 g, 3.59 mmol, 1 equiv), methanol (30 mL), and sodium hydroxide (3 M(aq), 4 mL). The resulting solution was stirred for 1 h at 60° C. The resulting solution was extracted with 3×100 mL of ethyl acetate. The organic layers combined and washed with 2×150 mL of brine. The mixture was dried over anhydrous sodium sulfate, filtered, and concentrated under vacuum. The residue was applied onto a silica gel column with CH₂Cl₂/methanol (5:1) providing 2.2 g (90%) of tert-butyl N-[(3R)-1-[(1S,2S)-1-[4-[(8-aminooctyl)sulfamoyl]phenoxy]-4,6-dichloro-2,3-dihydro-1H-inden-2-yl]piperidin-3-yl]carbamate (INT-C6) as a yellow solid.

The following intermediates are made by applying the above procedures to the appropriate starting aminoindanols INT-I8 and sulfonyl chlorides INT-L3:

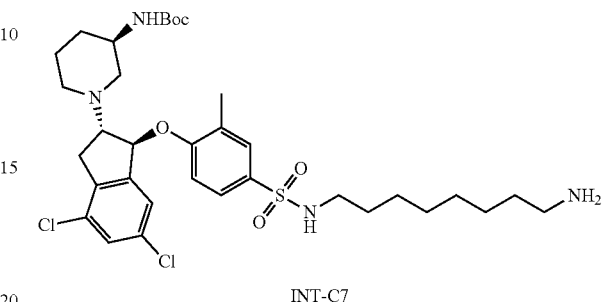

INT-C7

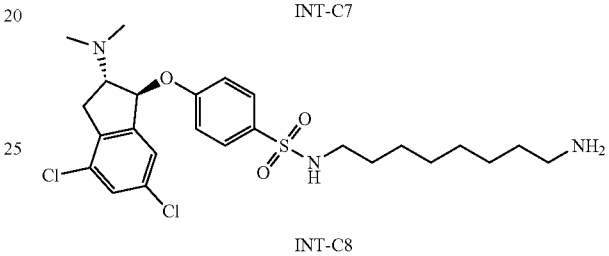

INT-C8

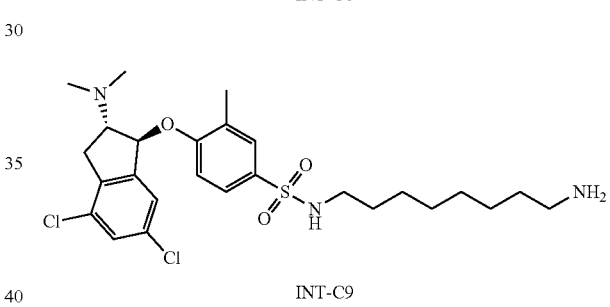

INT-C9

General Scheme for Synthesis of Alkyl Linker Dimer Products:

Example 62: 3-[8-[(4-[[(1S,2S)-2-[(3R)-3-Aminopiperidin-1-yl]-4,6-dichloro-2,3-dihydro-1H-inden-1-yl]oxy]benzene)sulfonamido]octyl]-1-[4-[([8-[(4-[[(1S,2S)-2-[(3R)-3-aminopiperidin-1-yl]-4,6-dichloro-2,3-dihydro-H-1-inden-1-yl]oxy]benzene)sulfonamido]octyl]carbamoyl)amino]butyl]urea; bis(trifluoroacetic acid)

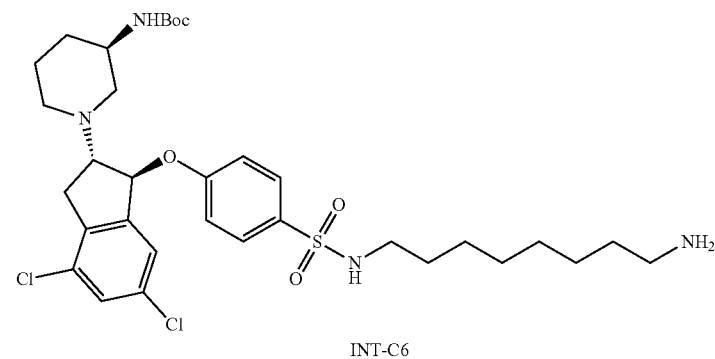

INT-C6

DMF, 60° C.

Step A

-continued

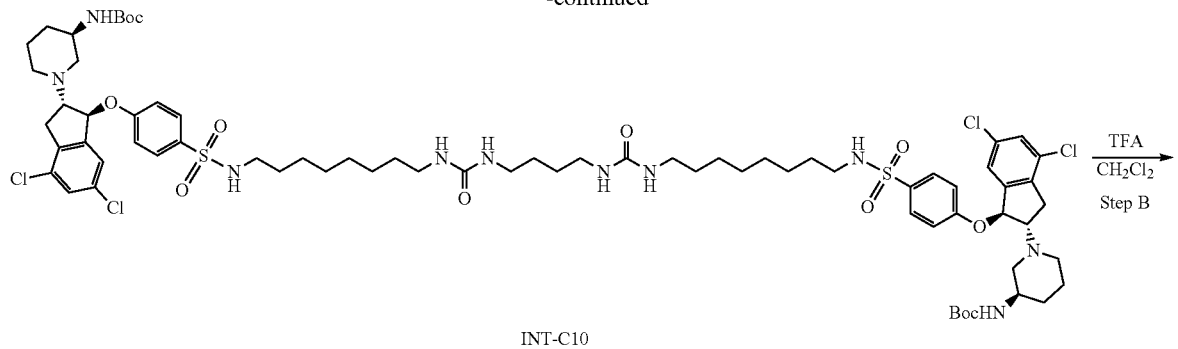

INT-C10

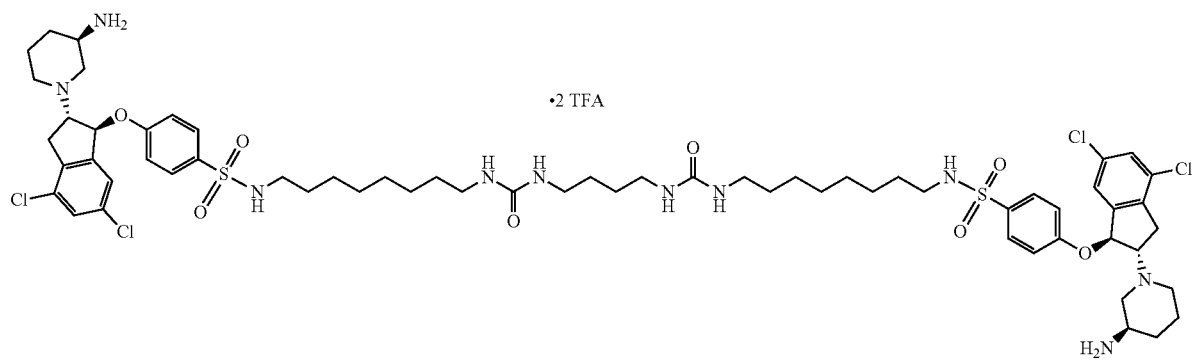

Example 62

Step A: To a 50-mL round-bottom flask, was added amine INT-C6 (300 mg, 0.44 mmol, 1 equiv), DMF (3 mL), and 1,4-diisocyanatobutane (25 mL, 0.45 equiv). The resulting solution was stirred for 1 h at 60° C. The resulting mixture was concentrated under vacuum. The resulting solution was diluted with 2 mL of $CH_2Cl_2$. The residue was applied onto a silica gel column with $CH_2Cl_2$/methanol (8:1) providing 260 mg (39%) of tert-butyl N-[(3R)-1-[(1S,2S)-1-[4-([8-[([4-[([8-[(4-[[(1S,2S)-2-[(3R)-3-[[(tert-butoxy)carbonyl]amino]piperidin-1-yl]-4,6-dichloro-2,3-dihydro-1H-inden-1-yl]oxy]benzene)sulfonamido]octyl]carbamoyl)amino]butyl]carbamoyl)amino]octyl]sulfanoyl)phenoxy]-4,6-dichloro-2,3-dihydro-1H-inden-2-yl]piperidin-3-yl]carbamate (INT-C10) as a yellow solid.

Step B: To a 25-mL round-bottom flask was added dimer INT-C10 (260 mg, 0.17 mmol, 1 equiv), $CH_2Cl_2$ (8 mL), and trifluoroacetic acid (1.5 mL). The resulting solution was stirred for 1 h at room temperature. The resulting mixture was concentrated under vacuum and diluted with 4 mL of methanol. The solids were filtered out. The crude product was purified by preparative HPLC with the following conditions: Column, XBridge C18 OBD Preparative Column, 19*250 mm, 5 um; mobile phase, water (0.05% TFA) and $CH_3CN$ (18.0% $CH_3CN$ up to 32.0% in 8 min); Detector, UV 254 nm.

Example 62: 3-[8-[(4-[[(1S,2S)-2-[(3R)-3-Aminopiperidin-1-yl]-4,6-dichloro-2,3-dihydro-1H-inden-1-yl]oxy]benzene)sulfonamido]octyl]-1-[4-[([8-[(4-[[(1S,2S)-2-[(3R)-3-aminopiperidin-1-yl]-4,6-dichloro-2,3-dihydro-1H-inden-1-yl]oxy]benzene)sulfonamido]octyl]carbamoyl)amino]butyl]urea; bis(trifluoroacetic acid)

Steps A and B provided 136.5 mg (52%) of the title compound as a white solid. MS (m/z): 1307 [M+H]$^+$. $^1$H NMR (Methanol-d4, 400 MHz) δ 7.92-7.83 (m, 4H), 7.46 (d, J=1.8 Hz, 2H), 7.37-7.28 (m, 4H), 7.17 (dd, J=1.9, 0.8 Hz, 2H), 6.08 (d, J=5.5 Hz, 2H), 3.75 (dt, J=13.6, 7.4 Hz, 2H), 3.39 (dt, J=9.8, 5.0 Hz, 4H), 3.33-3.24 (m, 2H), 3.16-2.93 (m, 13H), 2.88 (t, J=7.0 Hz, 4H), 2.77 (s, 2H), 2.71-2.61 (m, 5H), 1.92 (s, 4H), 1.71 (s, 2H), 1.61 (d, J=8.8 Hz, 3H), 1.48 (dp, J=11.6, 4.4, 3.8 Hz, 12H), 1.33-127 (m, 16H).

Example 63: 3-[8-[(4-[[(1S,2S)-2-[(3R)-3-Aminopi-peridin-1-yl]-4,6-dichloro-2,3-dihydro-1H-inden-1-yl]oxy]-3-methylbenzene) sulfonamido]octyl]-1-[4-[([8-[(4-[[(1S,2S)-2-[(3R)-3-aminopiperidin-1-yl]-4,6-dichloro-2,3-dihydro-1H-inden-1-yl]oxy]-3-methylbenzene)sulfonamide]octyl]carbamoyl)amino]butyl]urea

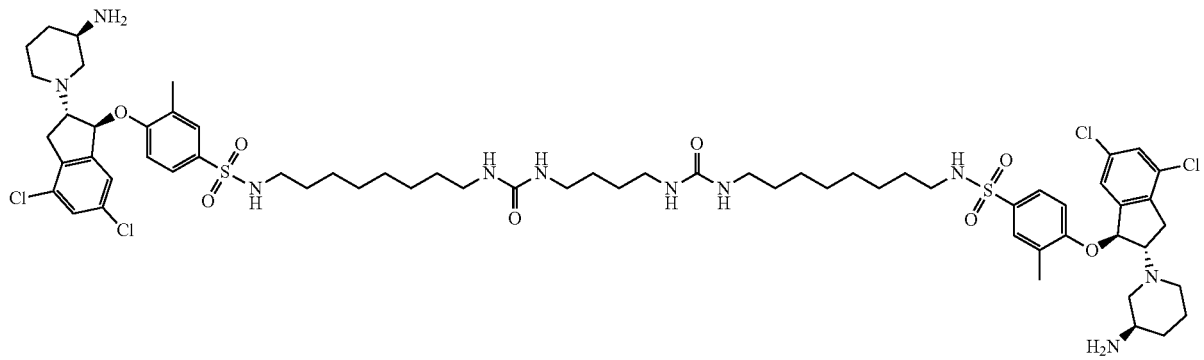

Example 63

Beginning with INT-C7 and INT-I8F, Steps A and B provided 73.6 mg (24%) of the title compound as a pink solid. MS (m/z): 1335.95 [M+H]$^+$. $^1$H NMR (Methanol-d4, 400 MHz) δ 7.87-7.74 (m, 4H), 7.63-7.52 (m, 4H), 7.02 (s, 2H), 6.87 (d, J=6.2 Hz, 2H), 4.61 (d, J=7.6 Hz, 2H), 3.92-3.70 (m, 7H), 3.49 (dd, J=24.0, 11.8 Hz, 2H), 3.35 (s, 4H), 3.19-3.06 (m, 8H), 2.90 (t, J=6.8 Hz, 4H), 2.33 (s, 6H), 2.30-2.05 (m, 6H), 1.79 (d, J=12.8 Hz, 2H), 1.55-1.44 (m, 12H), 1.30 (s, 16H).

Example 64: 3-[8-[(4-[[(1S,2S)-4,6-Dichloro-2-(di-amethylamino)-2,3-dihydro-1H-inden-1-yl]oxy]ben-zene)sulfonamido]octyl]-1-[4-[([8-[(4-[[(1S,2S)-4,6-dichloro-2-(diamethylamino)-2,3-dihydro-1H-inden-1-yl]oxy]benzene) sulfonamido]octyl]carbamoyl)amino]butyl]urea; bis(trifluoroacetic acid)

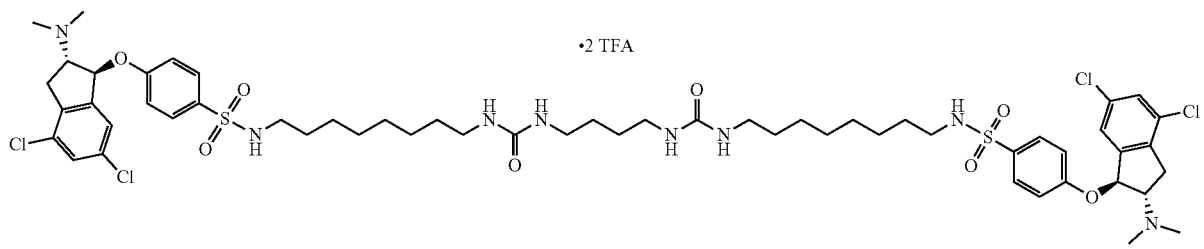

Example 64

Beginning with INT-C8 and INT-I8C, Step A provided 185 mg (48%) of the title compound as a white solid. MS (m/z): 1197 [M+H]$^+$. $^1$H NMR (Methanol-d4, 400 MHz) δ 7.95-7.87 (m, 4H), 7.57-7.51 (m, 2H), 7.41-7.32 (m, 4H), 7.11 (d, J=1.3 Hz, 2H), 6.44 (d, J=6.8 Hz, 2H), 4.44 (td, J=8.6, 6.9 Hz, 2H), 3.67 (dd, J=16.5, 8.5 Hz, 2H), 3.23 (dd, J=16.4, 8.5 Hz, 2H), 3.14-3.02 (m, 21H), 2.88 (t, J=6.9 Hz, 4H), 1.45 (dt, J=14.2, 5.0 Hz, 13H), 1.27 (s, 15H).

Example 65: 3-[8-[(4-[[(1S,2S)-4,6-Dichloro-2-(dimethylamino)-2,3-dihydro-1H-inden-1-yl]oxy]-3-methylbenzene)sulfonamido]octyl]-1-[4-[([8-[(4-[[(1S,2S)-4,6-dichloro-2-(dimethylamino)-2,3-dihydro-1H-inden-1-yl]oxy]-3-methylbenzene)sulfonamido]octyl]carbamoyl)amino]butyl]urea Example 65

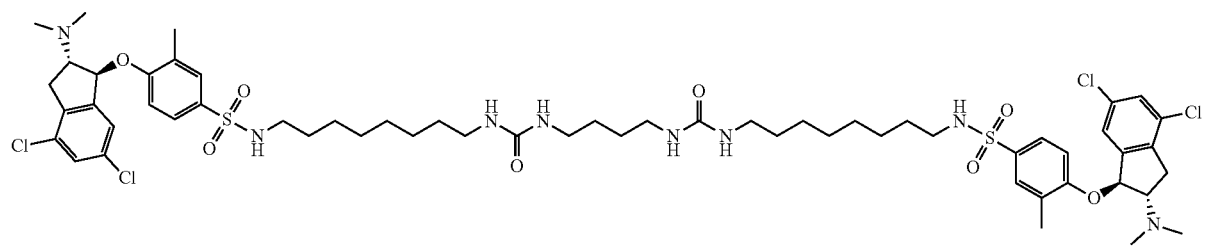

Beginning with INT-C9 and INT-I8C, Step A provided 100.3 mg (14%) of the title compound as a white solid. MS (m/z): 1227.65 [M+H]$^+$. $^1$H NMR (Methanol-d4, 400 MHz) δ 7.82 (d, J=8.8 Hz, 2H), 7.77 (s, 2H), 7.55 (s, 2H), 7.49 (d, J=8.8 Hz, 2H), 7.09 (s, 2H), 6.48 (s, 2H), 4.50-4.40 (m, 2H), 3.75-3.65 (m, 2H), 3.35-3.20 (m, 2H), 3.17-2.96 (m, 20H), 2.92-2.83 (m, 4H), 2.33 (s, 6H), 1.53-1.40 (m, 12H), 1.28 (s, 18H).

General Scheme for Synthesis of Diverse Amine Dimer Products:

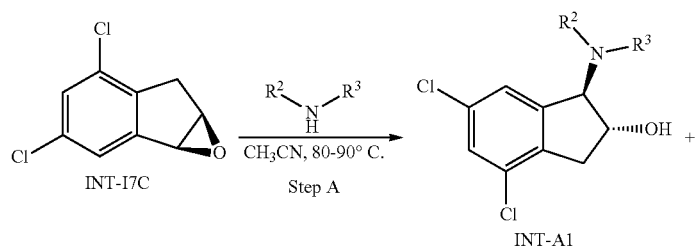

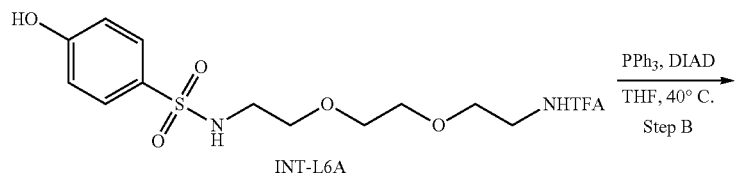

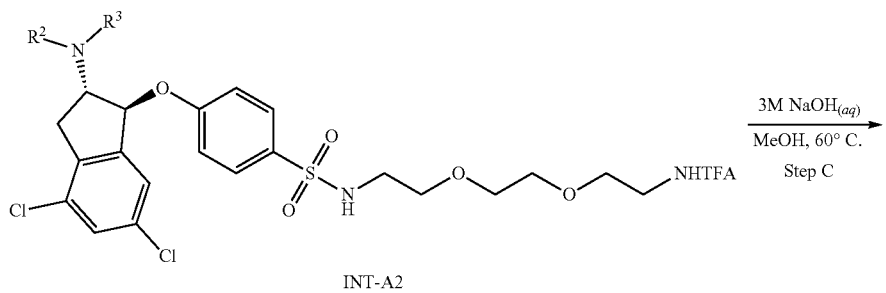

-continued

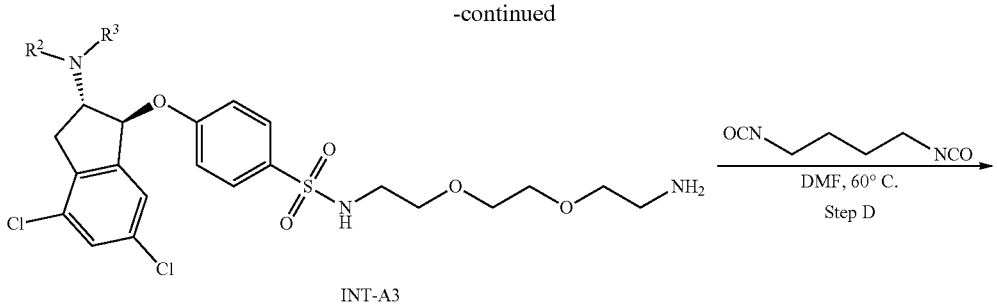

INT-A3

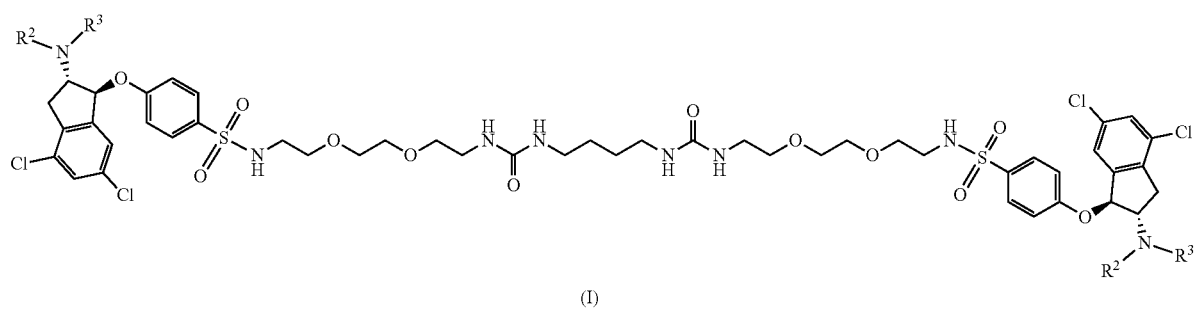

(I)

Step A: To a round-bottom flask was added epoxide INT-I7C (1 equiv), the desired amine $R^2R^3NH$ (2 equiv), and $CH_3CN$ (0.16 M). The resulting solution was heated to reflux for 16 h. The resulting mixture was concentrated wider vacuum. The residue was applied onto a silica gel column with ethyl acetate/petroleum ether (1:3-1:2) providing the aminoindanol INT-A1.

Step B: To a round-bottom flask was added aminoindanol INT-A1 (1 equiv) and tetrahydrofuran (0.2 M), followed by the addition of phenol linker INT-L6A (1.1 equiv) and heating to 40° C. To this slurry was added $PPh_3$ (2 equiv) and DIAD (1.5 equiv). The resulting solution was stirred for 1.5 h at 40° C. The resulting mixture was concentrated under vacuum and diluted with $CH_2Cl_2$. The residue was applied onto a silica gel column with ethyl acetate/petroleum ether (1:1) providing indane monomer INT-A2.

Step C: To a round-bottom flask was added indane monomer INT-A2 (1 equiv), methanol (0.1 M), and sodium hydroxide (3 $M_{(aq)}$, 3 equiv). The resulting solution was stirred for 1.5 h at 60° C. The resulting mixture was concentrated under vacuum and diluted with $CH_2Cl_2$. The residue was applied onto a silica gel column with ethyl acetate (100%) providing indane amine monomer INT-A3.

Step D: To a round-bottom flask was added INT-A3 (1 equiv), N,N-dimethylformamide (DMF, 0.12 M), and 1,4-diisocyanatobutane (0.40 equiv). The resulting solution was stirred for 2 h at 60° C. The resulting mixture was concentrated under vacuum and diluted with of $CH_2Cl_2$. The residue was applied onto a silica gel column with chloroform/methanol (10:1) providing compounds of structure (I). Final products were purified by preparative HPL with the following conditions: Column, XBridge C18 OBD Preparative Column, 19*250 mm, 5 um; mobile phase, water (0.05% TFA) and $CH_3CN$ (10.0% $CH_3CN$ up to 70.0% in 8 min); Detector, UV 254 nm. The final products were generally isolated as the free base, TFA salts, or hydrochloride salts.

Example 66: 3-[2-(2-[2-[(4-[[(1S,2S)-4,6-Dichloro-2-[(2R)-2-methylpiperidin-1-yl]-2,3-dihydro-1H-inden-1-yl]oxy]benzene)sulfonamido]ethoxy]ethyl]-1-[4-([[2-(2-[2-[(4-[[(1S,2S)-4,6-dichloro-2-[(2R)-2-methylpiperidin-1-yl]-2,3-dihydro-1H-inden-1-yl]oxy]benzene)sulfonamido]ethoxy]ethoxy)ethyl]carbamoyl]amino)butyl]urea Example 66

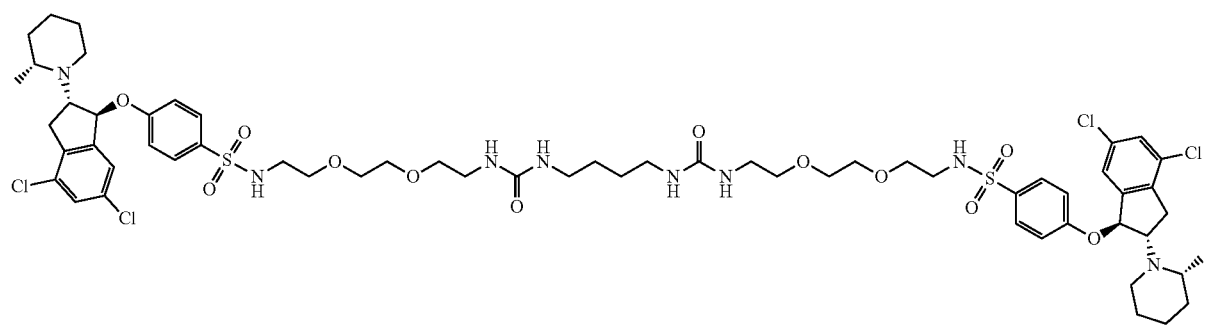

Following the General Scheme with (2R)-2-methylpiperidine, Steps A-D provided 112.8 mg (15%) of the title compound as a white solid. MS (m/z): 1313.5 [M+H]⁺. ¹H NMR (Methanol-d4, 400 MHz): δ 7.86 (d, J=8.8 Hz, 4H), 7.39 (s, 2H), 7.35 (d, J=8.8 Hz, 4H), 7.13 (s, 2H), 6.12 (d, J=5.6 Hz, 2H), 4.16-4.04 (m, 2H), 3.60-3.46 (m, 16H), 3.40-3.20 (m, 8H), 3.16-3.04 (m, 8H), 2.98-2.90 (m, 2H), 2.87-2.78 (m, 2H), 2.76-2.65 (m, 2H), 2.32 (t, J=8.8 Hz, 2H), 1.40-1.26 (m, 12H), 1.16 (d, J=6.0 Hz, 6H).

Example 67: 3-[2-(2-[2-[(4-[[(1S,2S)-4,6-Dichloro-2-[(2S)-2-methylpiperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-[(2S)-2-methylpiperidin-1-yl]-2,3-dihydro-1H-inden-1-yl]oxy]benzene)sulfonamide]ethoxy]ethoxy)ethyl]carbamoyl]amino)butyl]urea Example 67

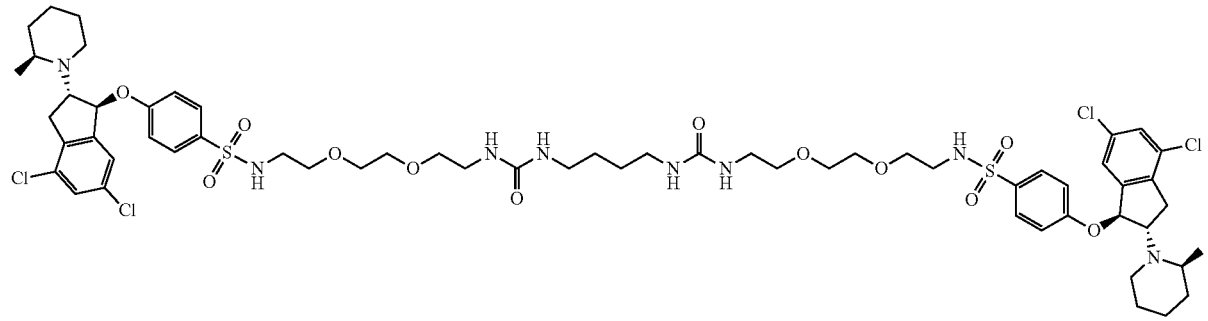

Following the General Scheme with (2S)-2-methylpiperidine, Steps A-D provided 46.8 mg (26%) of the title compound as a white solid. MS (m/z): 1313.5 [M+H]⁺. ¹H NMR (Methanol-d4, 400 MHz) δ 7.73 (d, J=6.8 Hz, 4H), 7.34 (q, J=4.8 Hz, 6H), 7.16 (d, J=1.2 Hz, 2H), 5.80 (d, J=4.0 Hz, 2H), 3.95 (q, J=4.8 Hz, 2H), 3.50-3.36 (m, 16H), 3.20-3.15 (m, 4H), 3.05-2.95 (m, 10H), 2.90-2.80 (m, 2H), 2.52 (d, 7.4 Hz, 4H), 2.10 (t, J=3.8 Hz, 2H), 1.62 (d, J=9.6 Hz, 4H), 1.54-1.43 (m, 4H), 1.39-1.32 (m, 4H), 1.31-1.20 (m, 4H), 1.18 (s, 2H), 1.00 (q, J=6.4 Hz, 6H).

Example 68: 3-[2-(2-[2-[(4-[(4-[[(1S,2S)-2-[2-Azabicyclo[2.2.1]heptan-2-yl]-4,6-dichloro-2,3-dihydro-1H-inden-1-yl]oxy]benzene)sulfonamido]ethoxy]ethoxy)ethyl]-1-[4-([[2-(2-[2-[(4-[[(1S,2S)-2-[2-azabicyclo[2.2.1]heptan-2-yl]-4,6-dichloro-2,3-dihydro-1H-inden-1-yl]oxy]benzene)sulfonamido]ethoxy]ethoxy)ethyl]carbamoyl]amino)butyl]urea Example 68

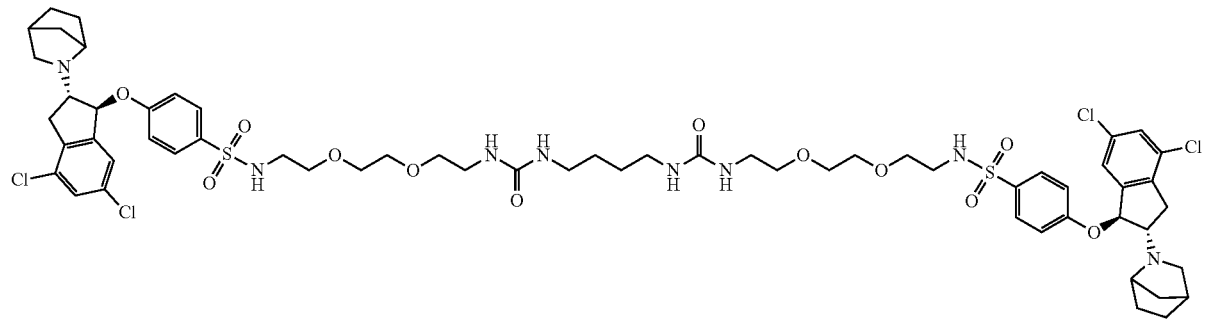

Following the General Scheme with 2-azabicyclo[2.2.1] heptane, Steps A-D provided 76.6 mg (14%) of the title compound as a white solid. MS (m/z): 1309.5 [M+H]$^+$. $^1$H NMR (Methanol-d4, 400 MHz) δ 7.90 (d, J=8.0 Hz, 2H), 7.42 (s, 2H), 7.35-7.26 (m, 4H), 7.09 (s, 2H), 6.00 (s, 2H), 3.93-3.20 (m, 28H), 3.18-3.04 (m, 8H), 3.00-2.83 (m, 3H), 2.70-2.60 (m, 1H), 2.47 (s, 3H), 2.13-1.80 (m, 2H), 1.80-1.35 (m, 15H).

Example 69: 1-[2-(2-[2-[(4-[[(1S,2S)-2-[2-Azabicyclo[2.2.2]octan-2-yl]-4,6-dichloro-2,3-dihydro-1H-inden-1-yl]oxy]benzene)sulfonamido]ethoxy]ethoxy)ethyl]-3-[4-([[2-(2-[2-[(4-[[(1S,2S)-2-[2-azabicyclo[2.2.2]octan-2-yl]-4,6-dichloro-2,3-dihydro-1H-inden-1-yl]oxy]benzene)sulfonamido]ethoxy]ethoxy)ethyl]carbamoyl]amino)butyl]urea

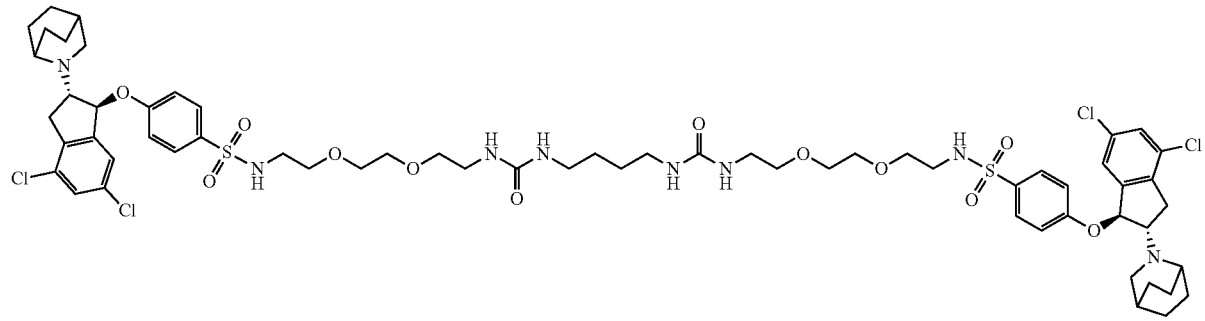

Example 69

Following the General Scheme with 2-azabicyclo[2.2.2] octane, Steps A-D provided 46.7 mg (18%) of the title compound as a white solid. MS (m/z): 1337.5 [M+H]$^+$. $^1$H NMR (Methanol-d4, 400 MHz): δ 7.86 (d, J=9.2 Hz, 4H), 7.38 (s, 2H), 7.27 (d, 8.8 Hz, 4H), 7.04 (s, 2H), 5.91 (d, J=6.8 Hz, 2H), 3.76 (q, J=7.7 Hz, 2H), 3.57-3.46 (m, 18H), 3.30-3.27 (m, 4H), 3.13-3.06 (m, 8H), 3.01 (d, J=9.6 Hz, 2H), 2.86-2.72 (m, 6H) 2.05-1.93 (m, 4H), 1.65-1.46 (m, 18H).

Example 70: 3-[2-(2-[2-[(4-[[(1S,2S)-2-[8-azabicyclo[3.2.1]octan-8-yl]-4,6-dichloro-2,3-dihydro-1H-inden-1-yl]oxy]benzene)sulfonamido]ethoxy]ethoxy)ethyl]-1-[4-([[2-(2-[2-[(4-[[(1S,2S)-2-[8-azabicyclo[3.2.1]octan-8-yl]-4,6-dichloro-2,3-dihydro-1H-inden-1-yl]oxy]benzene)sulfonamido]ethoxy]ethoxy)ethyl]carbamoyl]amino)butyl]urea

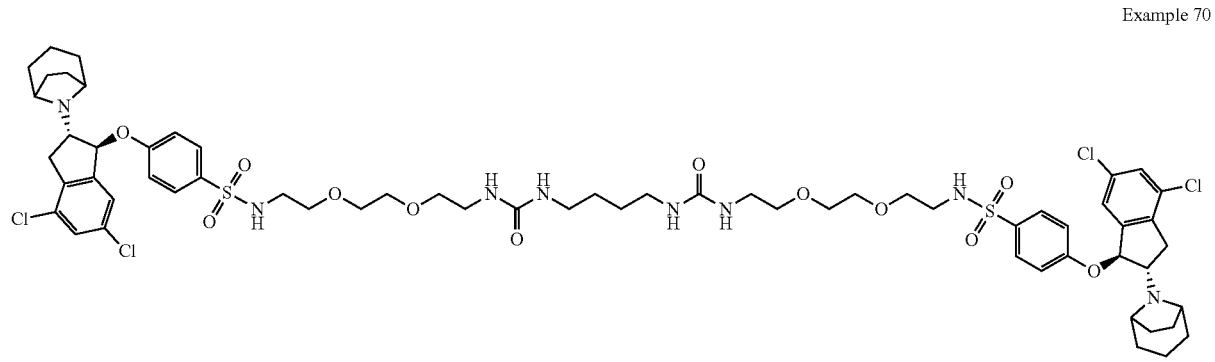 [SMILES: O=C(NCCCCNC(=O)NCCOCCOCCNS(=O)(=O)c1ccc(O[C@H]2c3cc(Cl)cc(Cl)c3C[C@@H]2N2C3CCCC2CC3)cc1)NCCOCCOCCNS(=O)(=O)c1ccc(O[C@H]2c3cc(Cl)cc(Cl)c3C[C@@H]2N2C3CCCC2CC3)cc1]

Example 70

Following the General Scheme with 8-azabicyclo[3.2.1]octane, Steps A-D provided 59.1 mg (30%) of the title compound as a white solid. MS (m/z): 1337.0 [M+H]$^+$. $^1$H NMR (Methanol-d4, 400 MHz): δ 7.78 (d, J=8.8 Hz, 4H) 7.29 (s, 2H), 7.17 (d, J=9.2 Hz, 4H), 6.93 (s, 2H), 5.85 (d, J=6.4 Hz, 2H), 3.75 (q, J=7.2 Hz, 2H), 3.50-3.47 (m, 3H), 3.47-3.35 (m, 11H), 3.29-3.22 (m, 6H), 3.21-3.18 (m, 3H), 2.98 (t, J=5.6 Hz, 7H), 2.69 (q, J=8.2 Hz, 2H), 2.00-1.83 (m, 8H), 1.72 (d, J=2.8 Hz, 2H), 1.65-1.55 (m, 6H), 1.43-1.31 (m, 6H), 1.29-1.15 (m, 6H).

Example 71: 1-[2-(2-[2-[(4-[[(1S,2S)-2-[9-Azabicyclo[3.3.1] nonan-9-yl]-4,6-dichloro-2,3-dihydro-1H-inden-1-yl]oxy]benzene)sulfonamido]ethoxy]ethoxy)ethyl]-3-[4-([[2-(2-[2-[(4-[[(1S,2S)-2-[9-azabicyclo[3.3.1]nonan-9-yl]-4,6-dichloro-2,3-dihydro-1H-inden-1-yl]oxy]benzene)sulfonamido]ethoxy]ethoxy)ethyl]carbamoyl]amino)butyl]urea Example 71

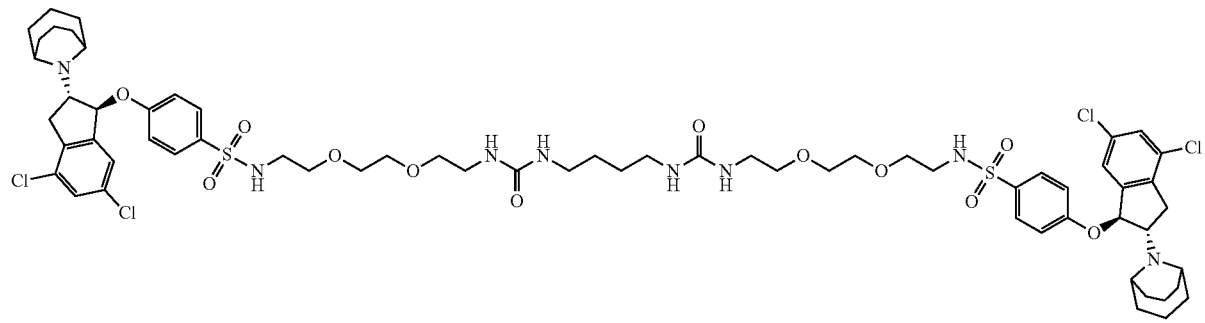

Following the General Scheme with 9-azabicyclo[3.3.1]nonane hydrochloride (and added sodium hydroxide), Steps A-D provided 59.8 mg (16%) of the title compound as a white solid. MS (m/z): 1365.5 [M+H]$^+$. $^1$H NMR (Methanol-d4, 400 MHz) δ 7.77 (d, J=8.8 Hz, 4H), 7.29 (s, 2H), 7.16 (d, J=8.8 Hz, 4H), 6.93 (s, 2H), 5.81 (d, J=6.8 Hz, 2H), 4.34 (q, J=8.0 Hz, 2H), 3.48-3.37 (m, 16H), 3.27-3.17 (m, 6H), 3.03-2.96 (m, 8H), 2.86 (s, 4H), 2.62 (q, J=8.2 Hz, 2H), 2.13-1.96 (m, 12H), 1.65-1.52 (m, 4H), 1.45-1.37 (m, 12H).

Example 72: 3-[2-(2-[2-[(4-[[(1S,2S)-4,6-Dichloro-2-(4-methylpiperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-4,6-dichloro-2-(4-methylpiperazin-1-yl)-2,3-dihydro-1H-inden-1-yl]oxy]benzene)sulfonamido]ethoxy]ethoxy)ethyl]carbamoyl]amino)butyl]urea a; bis(trifluoroacetic acid)

Example 72

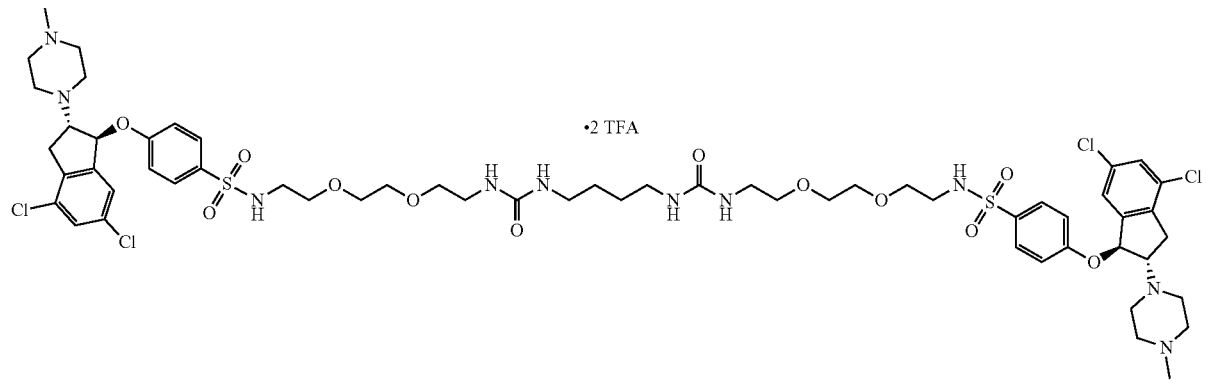

Following the General Scheme with 1-methylpiperazine, Steps A-D provided 72.8 mg (56%) of the title compound as a light yellow solid. MS (m/z): 1315 [M+H]⁺. ¹H NMR (Methanol-d4, 300 MHz) δ 7.94-7.82 (m, 4H), 7.43 (d, J=1.8 Hz, 2H), 7.37-7.25 (m, 4H), 7.18-7.10 (m, 2H), 6.06 (d, J=5.9 Hz, 2H), 3.70 (td, J=7.8, 5.9 Hz, 2H), 3.64-3.46 (m, 17H), 3.37 (s, 4H), 3.32-3.20 (m, 6H), 3.16-2.83 (m, 20H), 2.80 (s, 6H), 1.53-1.42 (m, 4H).

Example 73: 3-[2-(2-[2-[(4-[[(1S,2S)-4,6-Dichloro-2-(4-methylpiperazin-1-yl)-2,3-dihydro-1H-inden-1H-yl]oxy]-3-methylbenzene)sulfonamido]ethoxy] ethoxy)ethyl]-1-[4-([[2-(2-[2-[[(1S,2S)-4,6-dichloro-2-(4-methylpiperazin-1-yl)-2,3-dihydro-1H-inden-1-yl]oxy]-3-methylbenzene)sulfonamido]ethoxy] ethoxy)ethyl]carbamoyl]amino)butyl]urea; bis (trifluoroacetic acid)

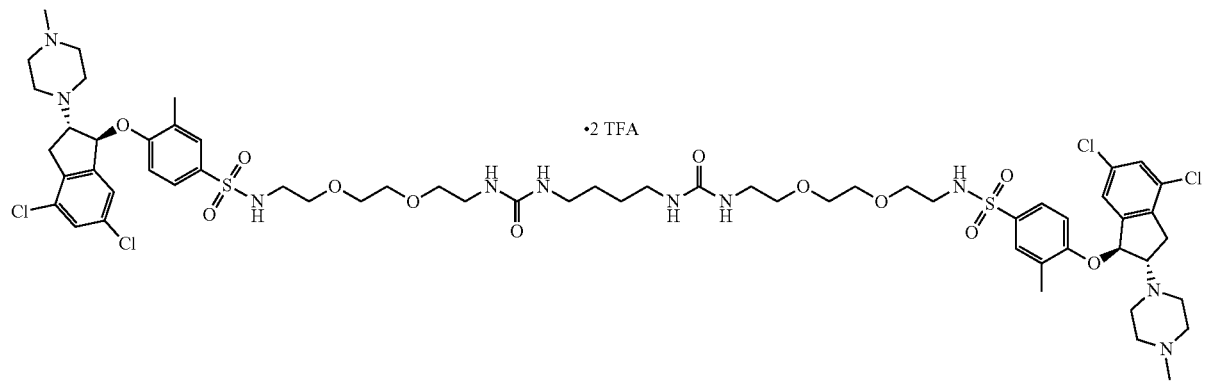

Example 73

Following the General Scheme with 1-methylpiperazine and INT-L6C, Steps A-D provided 50.4 mg (39%) of the title compound as a light yellow solid. MS (m/z): 672.5 [M/2+H]⁺. ¹H NMR (Methanol-d4, 300 MHz) δ 7.82-7.67 (m, 4H), 7.43 (dd, J=5.4, 3.5 Hz, 4H), 7.12 (s, 2H), 6.07 (d, J=6.0 Hz, 2H), 3.72 (q, J=7.3 Hz, 3H), 3.53 (dt, J=15.9, 4.7 Hz, 17H), 3.38 (s, 3H), 3.33-2.79 (m, 27H), 2.70 (s, 4H), 2.27 (s, 6H), 1.46 (d, J=5.5 Hz, 4H).

Example 74: 3-[2-(2-[2-[(4-[[(1S,2S)-2-(4-Acetylpiperazin-1-yl)-4,6-dichloro-2,3-dihydro-1H-inden-1-yl]oxy]benzene)sulfonamido]ethoxy] ethoxy)ethyl]-1-[4-([[2-(2-[2-[(4-[[(1S,2S)-2-(4-acetylpiperazin-1-yl)-4,6-dichloro-2,3-dihydro-1H-inden-1-yl]oxy]benzene)sulfonamido]ethoxy] ethoxy)ethyl]carbamoyl]amino)butyl]urea 291 292
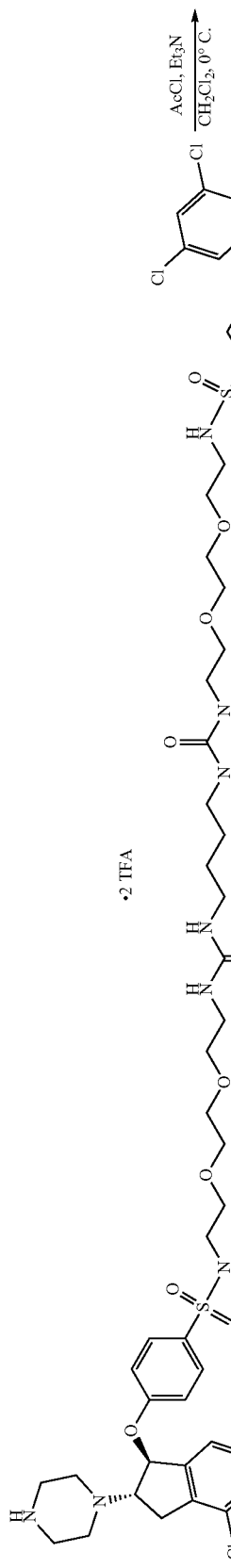
Example 31
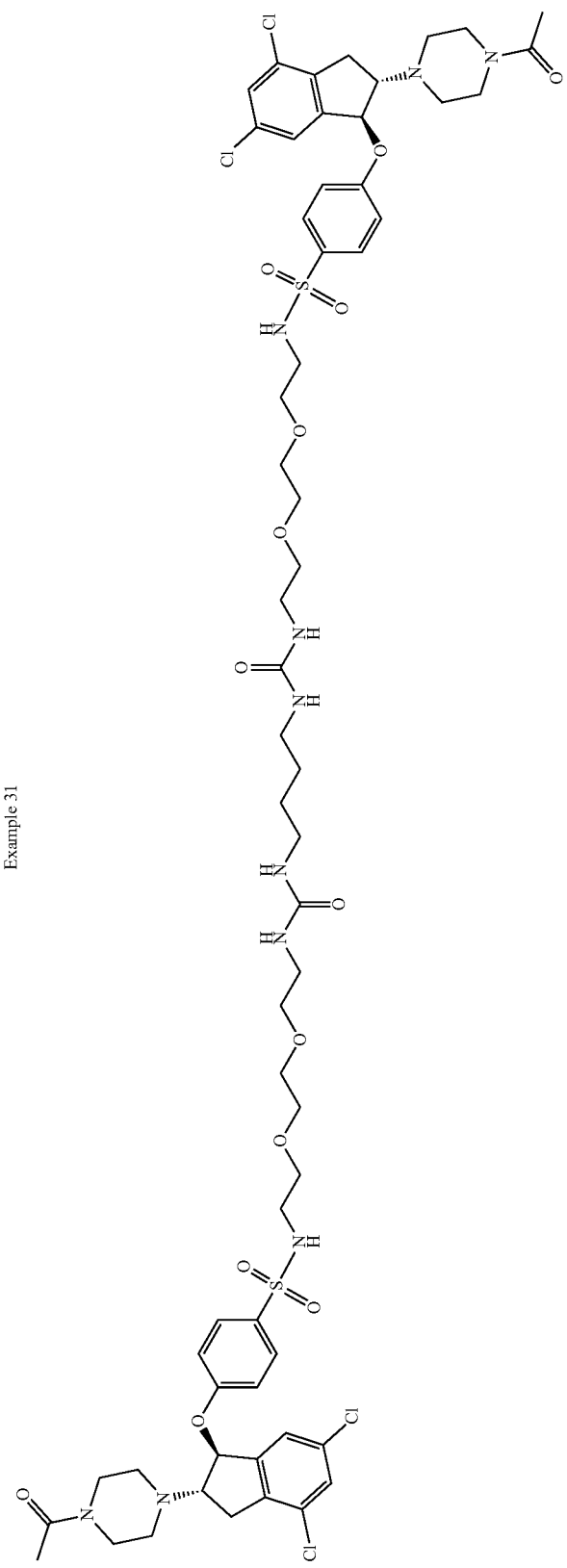
Example 74

To a 50-mL round-bottom flask was added the compound from Example 31(300 mg, 0.23 mmol, 1 equiv), $CH_2Cl_2$ (12 mL), triethylamine (0.163 mL), and acetyl chloride (0.050 mL). The resulting solution was stirred for 0.5 h at 0-5° C. in a water/ice bath. The resulting slurry was concentrated under vacuum. The crude product was purified by preparative HPLC with the following conditions: Column, XBridge C18 OBD Preparative Column, 19*250 mm, 5 um; mobile phase, water (0.05% TFA) and $CH_3CN$ (30.0% $CH_3CN$ up to 52.0% in 8 min); Detector, UV 254 nm. This resulted in 200.5 mg (63%) of the title compound as a white solid. MS (m/z): 1371 $[M+H]^+$. $^1H$ NMR (Methanol-d4, 300 MHz) δ 7.99-7.89 (m, 4H), 7.54 (d, J=1.7 Hz, 2H), 7.44-7.34 (m, 4H), 7.15 (d, J=1.0 Hz, 2H), 6.48 (d, J=6.5 Hz, 2H), 4.32 (q, J=7.9 Hz, 2H), 3.84 (s, 8H), 3.72-3.47 (m, 19H), 3.40 (s, 5H), 3.34-3.18 (m, 8H), 3.11 (t, J=5.4 Hz, 8H), 2.16 (s, 6H), 1.48 (d, J=6.2 Hz, 4H).

Example 75: 3-[2-(2-[2-[(4-[[(1S,2S)-2-(4-Acetylpiperazin-1-yl)-4,6-dichloro-2,3-dihydro-1H-inden-1-yl]oxy]-3-methylbenzene)sulfonamido] ethoxy]ethoxy)ethyl]-1-[4-([[2-(2-[2-[(4-[[(1S,2S)-2-(4-acetylpiperazin-1-yl)-4,6-dichloro-2,3-dihydro-1H-inden-1-yl]oxy]-3-methylbenzene)sulfonamido] ethoxy]ethoxy)ethyl]carbamoyl]amino)butyl]urea; bis(trifluoroacetic acid)

Example 75

Beginning with the compound in Example 32, the procedure for the synthesis of Example 74 was employed to provide 150.9 mg (41%) of the title compound as a white solid. MS (m/z): 1399 $[M+H]^+$. $^1H$ NMR (Methanol-d4, 300 MHz) δ 7.82-7.67 (m, 4H), 7.51-7.40 (m, 4H), 7.09-7.01 (m, 2H), 6.43 (d, J=6.4 Hz, 2H), 4.26 (q, J=8.0 Hz, 2H), 3.77 (s, 9H), 3.66-3.42 (m, 18H), 3.28-3.12 (m, 6H), 3.05 (q, J=5.8 Hz, 8H), 2.26 (s, 6H), 2.10 (s, 6H), 1.49-1.38 (m, 4H).

Example 76: 4-[(1S,2S)-4,6-dichloro-1-[4-[(2-[2-[2-([[4-([[2-(2-[2-[4-(4-[[(1S,2S)-4,6- dichloro-2-[4-(dimethylcarbamoyl)piperazin-1-yl]-2,3-dihydro-1H-inden-1-yl]oxy]benzene) sulfonamido]ethoxy] ethoxy)ethyl]carbamoyl]amino)butyl]carbamoyl] amino)ethoxy]ethoxy]ethyl)sulfamoyl]phenoxy]-2,3-dihydro-1H-inden-2-yl]-N,N-dimethylpiperazine-1-carboxamide

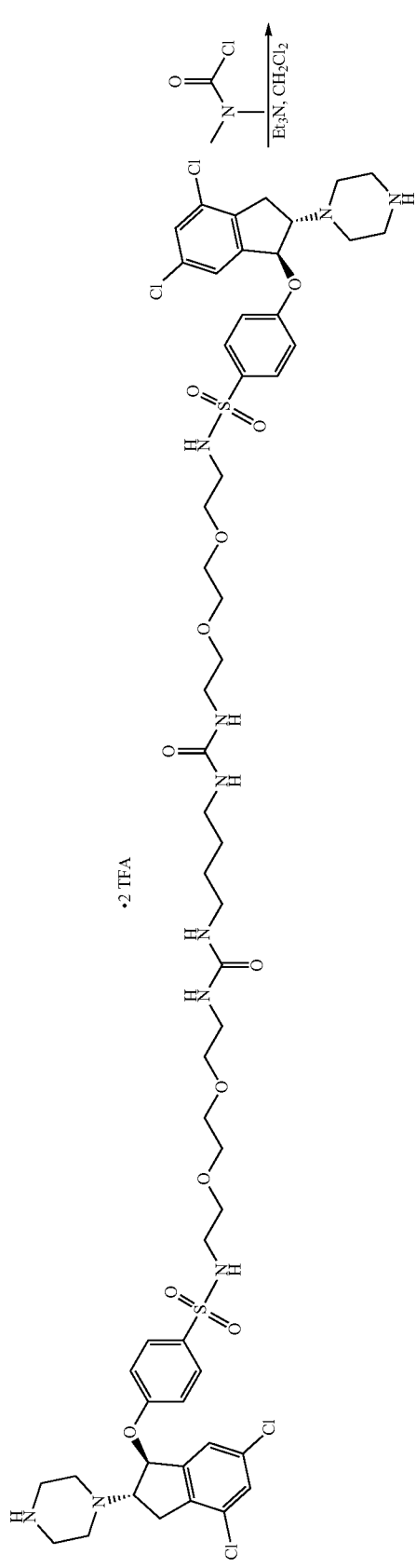
Example 31
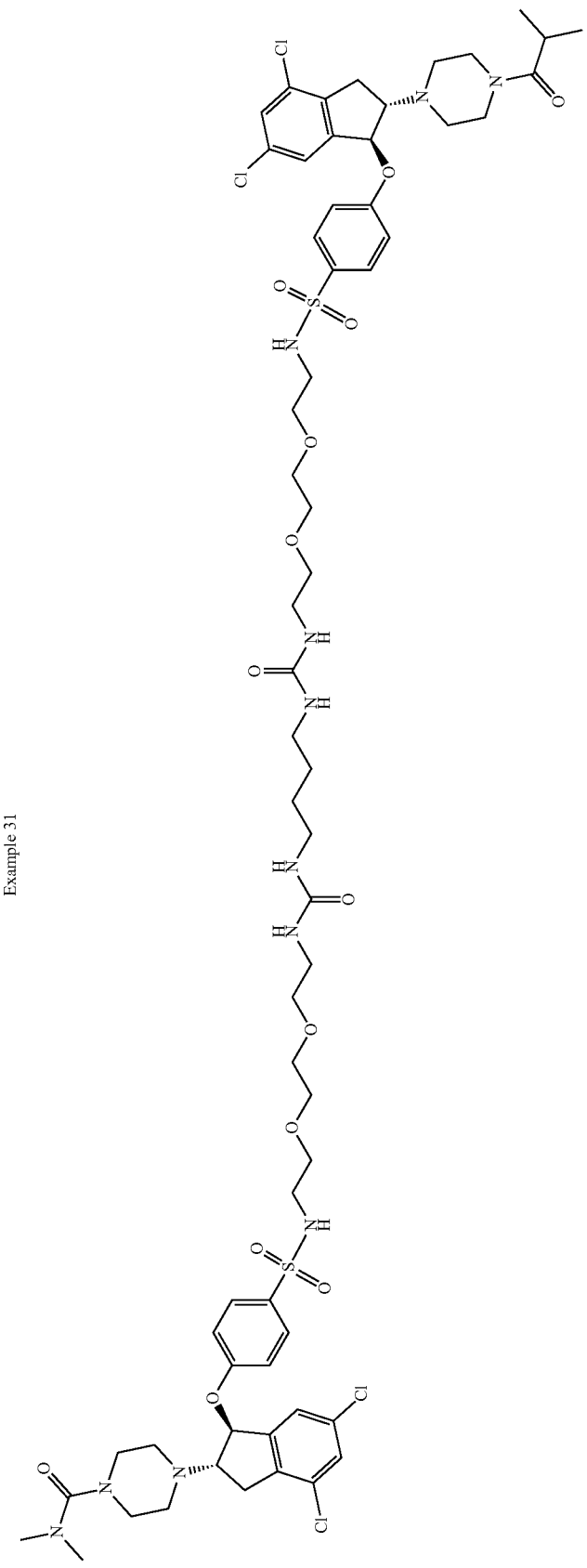
Example 76

To a 50-mL round-bottom flask was added the compound from Example 31 (300 mg, 0.23 mmol 1 equiv), CH$_2$Cl$_2$ (8 mL), N,N-dimethylcarbamoyl chloride (75.2 mg, 0.70 mmol, 3 equiv), and triethylamine (0.162 mL). The resulting solution was stirred for 1 h at room temperature. The resulting mixture was concentrated under vacuum. The crude product was purified by preparative HPLC with the following conditions: Column, XBridge C18 OBD Preparative Column, 19*250 mm, 5 um; mobile phase, water (0.05% TFA) and CH$_3$CN (30% CH$_3$CN up to 52% in 8 min); Detector, UV 254 nm. This resulted in 236.9 mg (71%) of the title compound as a white solid. MS (m/z): 1429 [M+H]$^+$. $^1$H NMR (Methanol-d4, 300 MHz) δ 8.01-7.89 (m, 4H), 7.56 (d, J=1.7 Hz, 2H), 7.45-7.34 (m, 4H), 7.17-7.10 (m, 2H), 6.58 (d, J=6.9 Hz, 2H), 4.48 (q, J=8.2 Hz, 2H), 3.80-3.23 (m, 39H), 3.12 (t, J=5.5 Hz, 9H), 2.91 (s, 12H), 1.54-1.43 (m, 4H).

Example 77: 4-[(1S,2S)-4,6-dichloro-1-[4-[(2-[2-[2-([[4-([[2-(2-[2-[(4-[[(1S,2S)-4,6-dichloro-2-[4-(dimethylcarbamoyl)piperazin-1-yl]-2,3-dihydro-1H-inden-1-yl]oxy]-3-methylbenzene)sulfonamido]ethoxy]ethoxy)ethyl]carbamoyl]amino)butyl]carbamoyl]amino)ethoxy]ethoxy]ethyl)sulfamoyl]-2-methylphenoxy]-2,3-dihydro-1H-inden-2-yl]-N,N-dimethylpiperazine-1-carboxamide; bis(trifluoroacetic acid)

Example 77

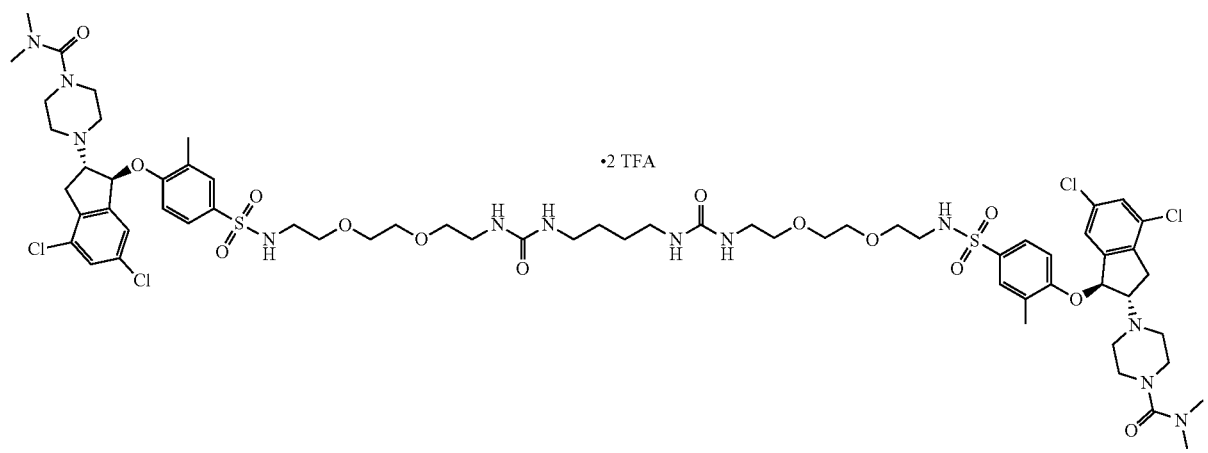

Beginning with the compound in Example 32, the procedure for the synthesis of Example 76 was employed to provide 198 mg (52%) of the title compound as a white solid. MS (m/z): 1455 [M+H]$^+$. $^1$H NMR (Methanol-d4, 300 MHz) δ 7.83-7.68 (m, 4H), 7.53-7.40 (m, 4H), 7.03 (d, J=1.7 Hz, 2H), 6.54 (d, J=6.6 Hz, 2H), 4.45 (q, J=8.1 Hz, 2H), 3.68 (dd, J=16.4, 8.6 Hz, 3H), 3.60-3.42 (m, 28H), 3.36 (d, J=9.1 Hz, 5H), 3.24 (d, J=5.4 Hz, 4H), 3.05 (q, J=5.6 Hz, 8H), 2.86 (s, 12H), 2.27 (s, 6H), 1.48-1.38 (m, 4H).

Scheme for the Synthesis of Example 78

Example 78: 3-[2-(2-[2-[(4-[[(1S,2S)-4,6-Dichloro-2-[(3R)-3-[methyl(propan-2-yl)amino]piperidin-1-yl]-2,3-dihydro-1H-inden-1-yl]oxy]benzene) sulfonamido]ethoxy]ethoxy)ethyl]-1-[4-([[2-(2-[2-[(4-[[(1S,2S)-4,6-dichloro-2-[(3R)-3-[methyl(propan-2-yl)amino]piperidin-1-yl]-2,3-dihydro-1H-inden-1-yl]oxy]benzene)sulfonamido]ethoxy]ethoxy)ethyl]carbamoyl]amino)butyl]urea; bis(trifluoroacetic acid)

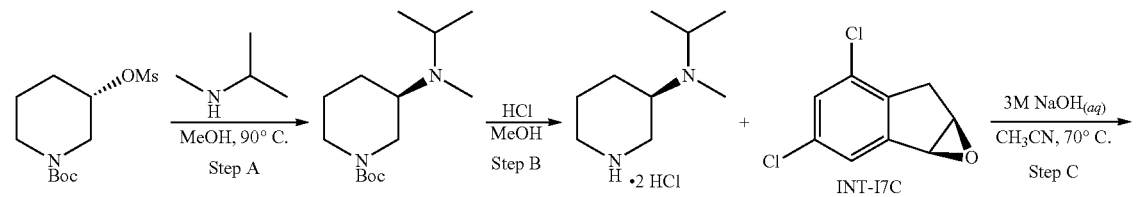

-continued
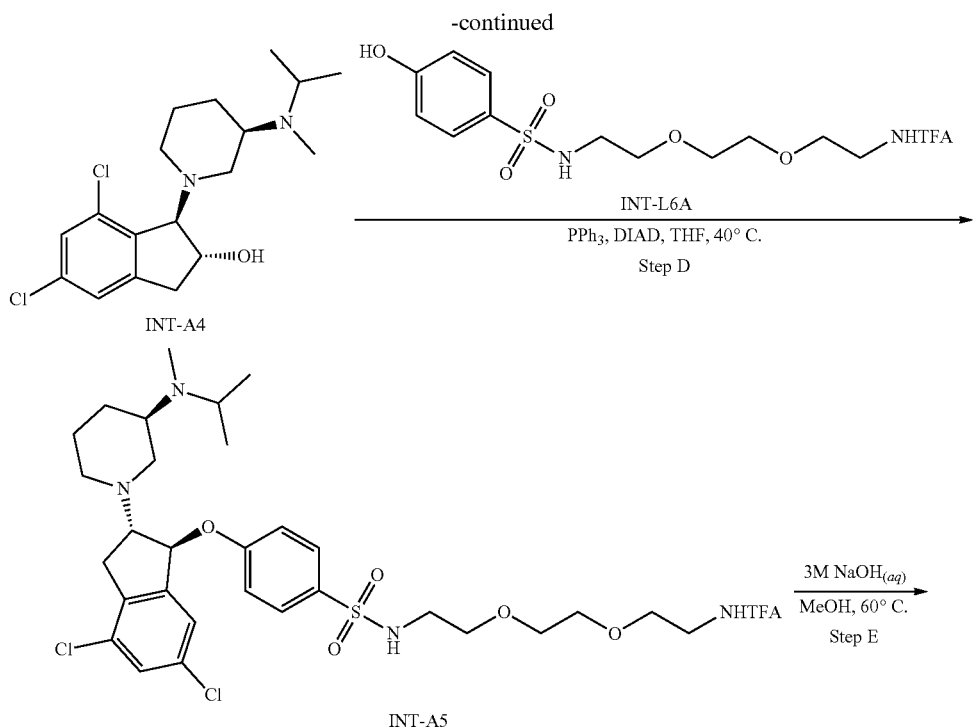
INT-A4
INT-A5
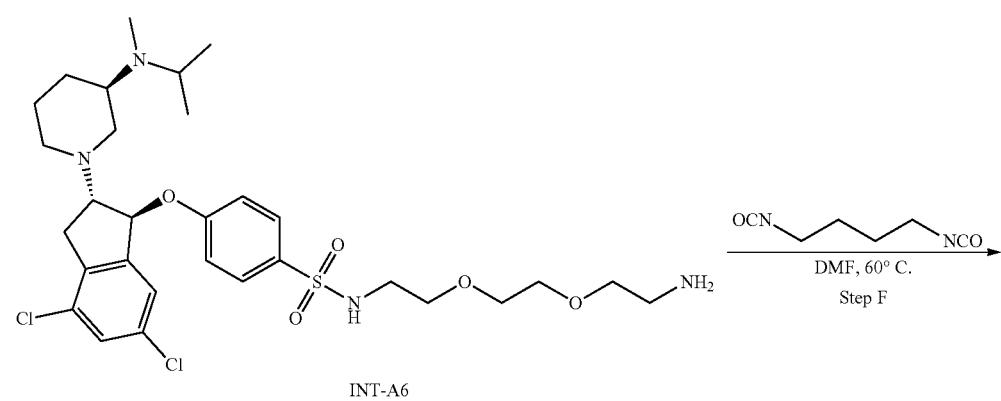
INT-A6
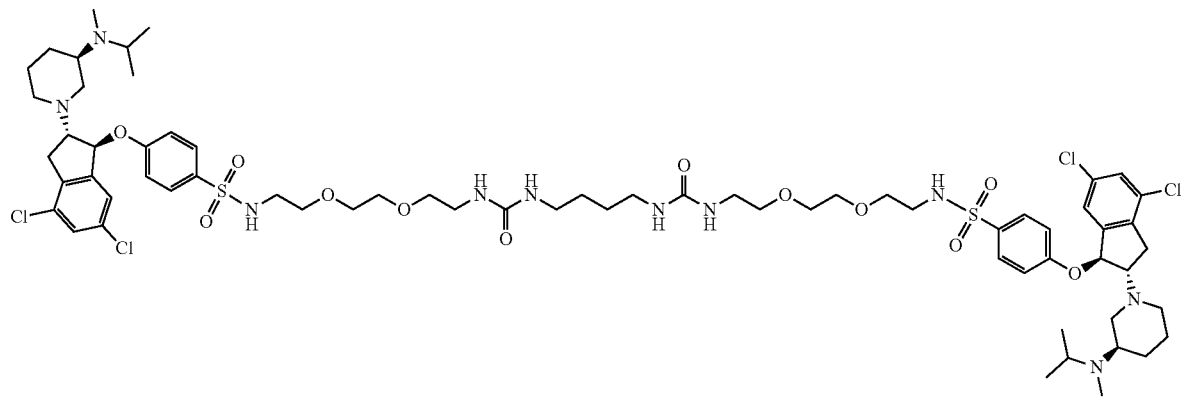
Example 78

Step A: To a 50-mL sealed tube was added tert-butyl (3S)-3-(methanesulfonyloxy)piperidine-1-carboxylate (5 g, 17.9 mmol, 1 equiv), methanol (15 mL), and methyl(propan-2-yl)amine (3.9 g, 53.3 mmol, 3 equiv). The resulting solution was stirred for 72 hrs at 90° C. The resulting mixture was concentrated under vacuum. The residue was applied onto a silica gel column with CH$_2$Cl$_2$/methanol (0-5%) providing 2 g (44%) of tert-butyl(3R)-3-[methyl (propan-2-yl)amino]piperidine-1-carboxylate as a yellow oil.

Step B: To a 100-mL round-bottom flask was added tert-butyl (3R)-3-[methyl(propan-2-yl)amino]piperidine-1-carboxylate (1.7 g, 6.63 mmol, 1 equiv) and hydrogen chloride in methanol (40 mL). The final reaction mixture was stirred overnight at room temperature. The resulting mixture was concentrated under vacuum to provide 1.52 g (100%) of (3R)—N-isopropyl-N-methylpiperidin-3-amine dihydrochloride as a white solid.

Step C: To a 50-mL round-bottom flask was added epoxide INT-I7C (300 mg, 1.49 mmol, 1 equiv), (3R)—N-isopropyl-N-methylpiperidin-3-amine dihydrochloride (684 mg, 2.98 mmol, 2 equiv), MeCN (10 mL), and sodium hydroxide(3 M$_{(aq)}$, 3 mL). The resulting solution was stirred for 1 h at 70° C. in an oil bath. The resulting solution was extracted with 3×50 mL of ethyl acetate and the organic layers combined and concentrated under vacuum. The residue was applied onto a silica gel column with CH$_2$Cl$_2$/methanol (8:1) providing 530 mg (99%) of (1R,2R)-4,6-dichloro-1-[(3R)-3-[methyl(propan-2-yl)amino]piperidin-1-yl]-2,3-dihydro-1H-inden-2-ol (INT-A4) as a red oil.

Step D: To a 50-mL round-bottom flask was added aminoindanol INT-A4 (570 mg, 1.60 mmol, 1 equiv), phenol INT-L6A (716 mg, 1.77 mmol, 1.1 equiv), THF (3.7 mL), and PPh$_3$ (627 mg, 2.39 mmol, 1.5 equiv). Heating at 40° C. in an oil bath DIAD (0.47 mL, 1.5 equiv) was added dropwise with stirring over 30 min. The resulting solution was stirred for 1 h at 40° C. in an oil bath. The residue was applied onto a silica gel column with CH$_2$Cl$_2$/methanol (10:1) providing 600 mg (51%) of tert-butyl N-[2-(2-[2-[(4-[[(1S,2S)-4,6-dichloro-2-[(3R)-3-[methyl(propan-2-yl) amino]piperidin-1-yl]-2,3-dihydro-1H-inden-1-yl]oxy]benzene)sulfonamido]ethoxy]ethoxy)ethyl]carbamate (INT-A5) as a yellow oil.

Step E: To a 100-mL round-bottom flask was added INT-A5 (600 mg, 0.81 mmol, 1 equiv), CH$_2$Cl$_2$ (10 mL), and TFA (2 mL). The resulting solution was stirred for 1 h at room temperature. The pH value of the solution was adjusted to 8 with saturated aqueous sodium bicarbonate and extracted with 3×50 mL of CH$_2$Cl$_2$. The organic layers were combined and concentrated under vacuum. The residue was applied onto a silica gel column with CH$_2$Cl$_2$/methanol (8:1) providing 420 mg (81%) of N-[2-[2-(2-aminoethoxy) ethoxy]ethyl]-4-[[(1S,2S)-4,6-dichloro-2-[(3R)-3-[methyl (propan-2-yl)amino]piperidin-1-yl]-2,3-dihydro-1H-inden-1-yl]oxy]benzene-1-sulfonamide (INT-A6) as a yellow oil.

Step F: To a 50-mL round-bottom flask was added amine INT-A6 (400 mg, 0.62 mmol, 1 equiv), DMF (5 mL), and 1,4-diisocyanatobutane (68 mg, 0.25 mmol, 0.40 equiv). The resulting solution was stirred for 1 h at 60° C. in an oil bath. The resulting mixture was concentrated under vacuum. The crude product was purified by preparative HPLC with the following conditions: Column, Bridge C18 OBD Preparative Column, 19*250 mm, 5 um; mobile phase, water (0.05% TFA) and CH$_3$CN (25.0% CH$_3$CN up to 45.0% in 8 min); Detector, UV 254 nm.

Example 78: 3-[2-(2-[2-[(4-[[(1S,2S)-4,6-Dichloro-2-[(3R)-3-[methyl(propan-2-yl)amino]piperidin-1-yl]-2,3-dihydro-1H-inden-1-yl]oxy]benzene) sulfonamido]ethoxy]ethoxy)ethyl]-[4-([[2-(2-[2-[(4-[[(1S,2S)-4,6-dichloro-2-[(3R)-3-[methyl(propan-2-yl) amino]piperidin-1-yl]-2,3-dihydro-1H-inden-1-yl] oxy]benzene)sulfonamido]ethoxy]ethoxy)ethyl] carbamoyl]amino)butyl]urea; bis(trifluoroacetic acid)

Steps A-F provided 203.1 mg (20%) of the title compound as a white solid. MS (m/z): 714.5 [M/2+H]$^+$. $^1$H NMR (Methanol-d4, 300 MHz) δ 7.91-7.81 (m, 4H), 7.42 (d, J=1.7 Hz, 2H), 7.30 (d, J=8.5 Hz, 4H), 7.11 (d, J=2.4 Hz, 2H), 6.18 (m, 2H), 3.98-3.66 (m, 4H), 3.54 (dq, J=5.6, 2.0 Hz, 8H), 3.47 (t, J=5.5 Hz, 10H), 3.29 (m, 3H), 3.27-3.23 (m, 4H), 3.12-2.99 (m, 10H), 2.94 (m, 4H), 2.77-2.62 (m, 6H), 2.58 (m, 3H), 2.08 (m, 2H), 1.89 (m, 2H), 1.70 (m, 4H), 1.49-1.38 (m, 4H), 1.31 (m, 10H), 1.20 (d, J=6.5 Hz, 2H).

General Scheme for Synthesis of Disubstituted Sulfonamide Dimer Products:

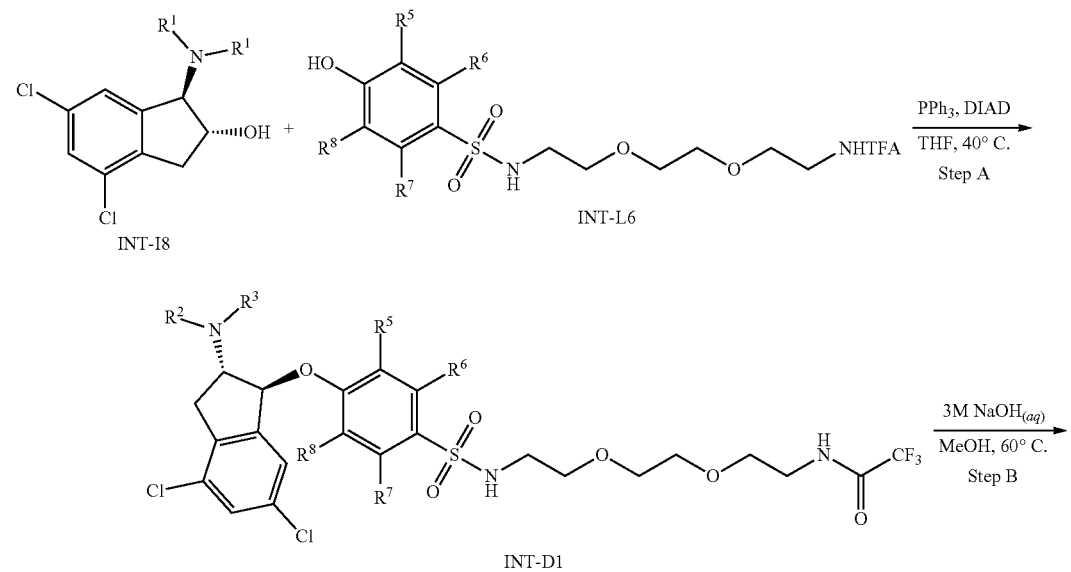

-continued

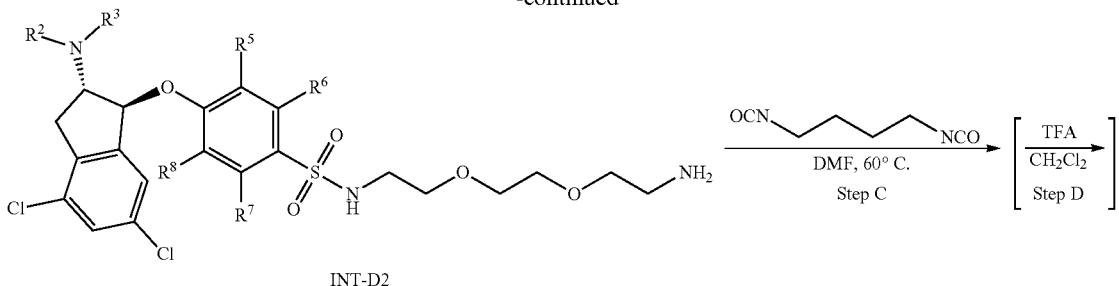

INT-D2

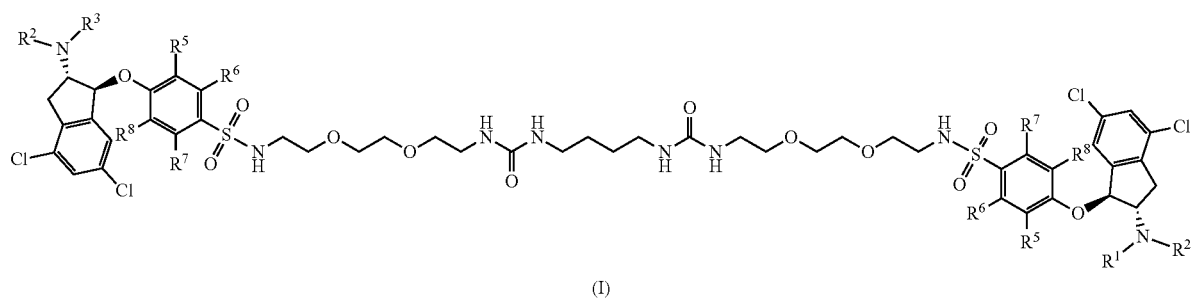

(I)

Step A: To a round-bottom flask was added aminoindanol INT-I8 (1 equiv) and tetrahydrofuran (0.2 M), followed by the addition of phenol linker INT-L6 (1.1 equiv) and heating to 40° C. To this slurry was added PPh$_3$ (2 equiv) and DIAD (1.5 equiv). The resulting solution was stirred for 1-3 h at 40° C. The resulting mixture was concentrated under vacuum and diluted with CH$_2$Cl$_2$. The residue was applied onto a silica gel column with petroleum ether/ethyl acetate (1:1) providing indane monomer INT-D1.

Step B: To a round-bottom flask was added indane monomer INT-D1 (1 equiv), methanol (0.1 M), and sodium hydroxide (3 M$_{(aq)}$, 3-5 equiv). The resulting solution was stirred for 1-2 h at 60° C. The resulting mixture was concentrated under vacuum and diluted with CH$_2$Cl$_2$. The residue was applied onto a silica gel column with CH$_2$Cl$_2$/methanol (10:1) providing indane amine monomer INT-D2.

Step C: To a round-bottom flask was added INT-D2 (1 equiv), N,N-dimethylformamide (DMF, 0.1 M), and 1,4-diisocyanatobutane (0.4-0.5 equiv). The resulting solution was stirred for 2 h at 60° C. The resulting mixture was concentrated under vacuum and diluted with of CH$_2$Cl$_2$. The residue was applied onto a silica gel column with chloroform/methanol (10:1) providing the desired dialer of structure (I). Final products were purified by preparative HPLC. The final products were generally isolated as the free based amines, TFA salts, or hydrochloride salts.

Step D (for Boc-protected intermediates): To a round-bottom flask was added Boc-protected dimer (I) (1 equiv) and 5:1 CH$_2$Cl$_2$:TFA (~0.05 M). The resulting solution was stirred for 2 h at room temperature. The resulting mixture was concentrated under vacuum. The crude product was purified by preparative HPLC. The final products were generally isolated as the free based amines, TFA salts, or hydrochloride salts.

Example 79: 3-[2-(2-[2-[(4-[[(1S,2S)-2-[(3R)-3-Aminopiperidin-1-yl]-4,6-dichloro-2,3-dihydro-1H-inden-1-yl]oxy]-3,5-dimethylbenzene)sulfonamido] ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]3,5-dimethylbenzene) sulfonamido]ethoxy]ethoxy)ethyl]carbamoyl]amino) butyl]urea; hydrochloride Example 79

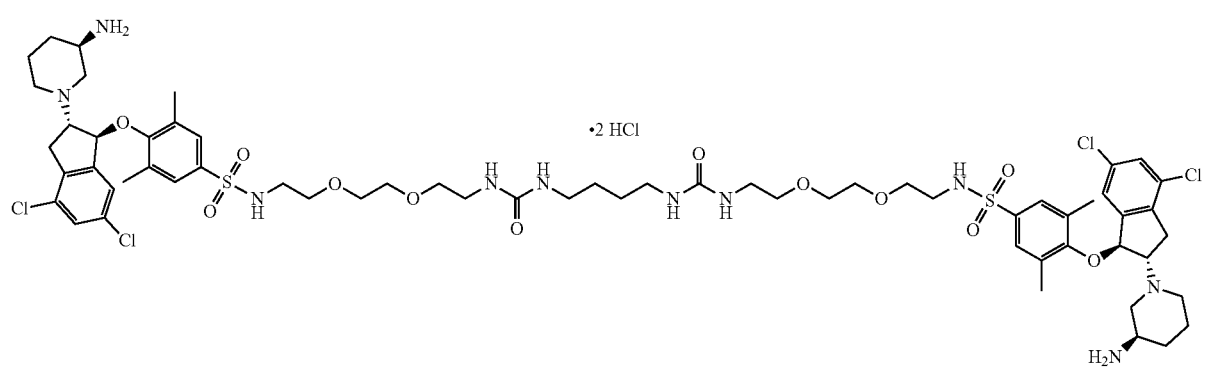

Beginning with INT-L6D and INT-I8F, Steps A-D provided Example 79 which was purified by preparative HPLC with the following conditions: Column, XBridge Preparative OBD C18 Column, 19*250 mm, 5 um; mobile phase, water (0.05% HCl) and CH$_3$CN (40.0% CH$_3$CN up to 70.0% in 8 min); Detector, UV 254 nm. This resulted in 129.2 mg (48%) of the title compound as a yellow solid. MS (m/z): 1370.85 [M+H]$^+$. $^1$H NMR (Methanol-d4, 400 MHz) δ 7.60 (d, J=15.2 Hz, 6H), 6.45 (s, 2H), 6.30 (s, 2H), 4.70 (d, J=3.2 Hz, 2H), 3.95-3.80 (m, 6H), 3.70-3.50 (m, 20H), 3.40-3.35 (m, 8H), 3.17 (s, 4H), 3.05 (t, J=5.4 Hz, 4H), 2.30-2.10 (m, 18H), 1.88 (s, 2H), 1.54 (s, 4H).

Example 80: 1-[2-(2-[2-[(3-[[(1S,2S)-4,6-dichloro-2-(dimethylamino)-2,3-dihydro-1H-inden-1-yl]oxy]-2,4-dimethylbenzene)sulfonamide]ethoxy]ethoxy) ethyl]-3-[4-([[2-(2-[2-[4-[[(1S,2S)-4,6-dichloro-2-(dimethylamino)-2,3-dihydro-1H-inden-1-yl]oxy]-3,5-dimethylbenzene)sulfonamido]ethoxy]ethoxy) ethyl]carbamoyl]amino)butyl]urea Example 80

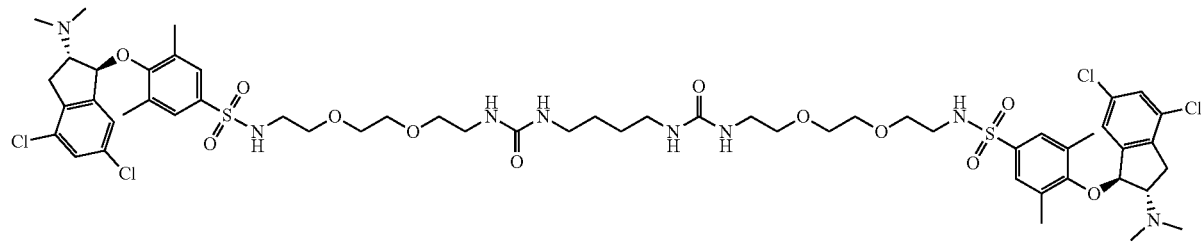

Beginning with INT-L6D and INT-I8C, Steps A-C provided Example 80 which was purified by preparative HPLC with the following conditions: Column, XBridge BEH130 Preparative C18 OBD Column, 19*150 mm, 5 um; mobile phase, water (0.05% NH$_4$OH) and CH$_3$CN (75.0% CH$_3$CN up to 84.0% in 9 min), Detector, UV 254 nm. This resulted in 91.5 mg (28%) of the title compound as a white solid. MS (m/z): 1261.20 [M+H]$^+$. $^1$H NMR (Methanol-d4, 400 MHz) δ 7.56 (s, 4H), 7.43 (d, J=1.6 Hz, 2H), 6.50 (d, J=1.2 Hz, 2H), 5.68 (d, J=2.4 Hz, 2H), 4.82-4.78 (m, 2H), 3.58 (q, J=5.0 Hz, 8H), 3.55-3.50 (m, 8H), 3.42-3.37 (m, 2H), 3.35-3.30 (m, 4H), 3.13 (s, 4H), 3.08-2.96 (m, 6H), 2.30 (s, 12H), 2.15 (d, J=9.6 Hz, 12H), 1.50 (s, 4H).

Example 81: 3-[2-(2-[2-[(4-[[(1S,2S)-2-[(3R)-3-Aminopiperidin-1-yl]-4,6-dichloro-2,3-dihydro-1H-inden-1-yl]oxy]-2,5-dimethylbenzene) sulfonamido] ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-2,5-dimethylbenzene) sulfonamido]ethoxy]ethoxy)ethyl] carbamoyl] amino)butyl]urea Example 81

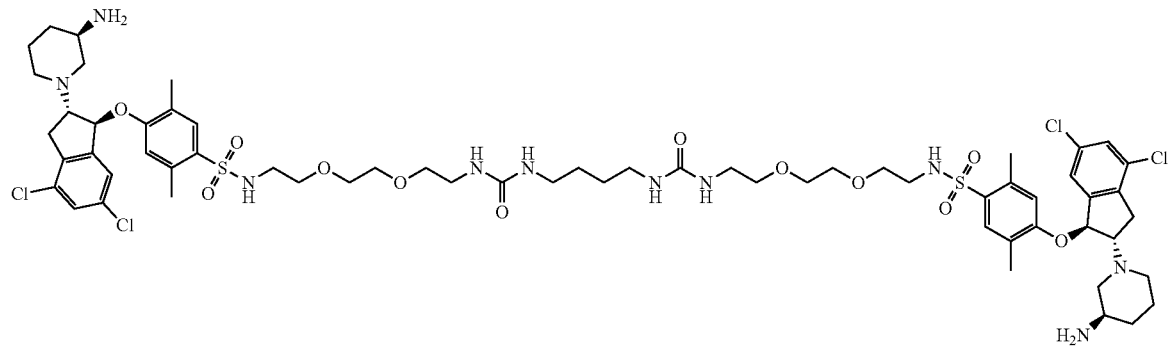

Beginning with INT-L6E and INT-I8F, Steps A-D provided Example 81 which was purified by preparative HPLC with the following conditions: Column, XBridge Preparative OBD $C_{18}$ Column, 19*250 mm, 5 um; mobile phase, water (10 mmol/L $NH_4HCO_3$+0.1% $NH_4OH$) and $CH_3CN$ (50.0% $CH_3CN$ up to 60.0% in 13 min); Detector, UV 254 nm. This resulted in 113.6 mg (30%) of the title compound as a light yellow solid. MS (m/z): 1371.75 [M+H]+. 1H NMR (Methanol-d4, 400 MHz) δ 7.83 (s, 2H), 7.54 (s, 2H), 7.48 (s, 2H), 7.01 (d, J=1.8 Hz, 2H), 6.88 (d, J=6.0 Hz, 2H), 4.61 (d, J=8.0 Hz, 2H), 3.87-3.71 (m, 8H), 3.70-3.51 (m, 20H), 3.50-3.33 (m, 8H), 3.21 (d, J=6.0 Hz, 4H), 3.11 (t, J=5.6 Hz, 4H), 2.71 (s, 6H), 2.30-2.11 (m, 10H), 1.83 (s, 2H), 1.56 (s, 5H).

Example 82: 3-[2-(2-[2-[(4-[[(1S,2S)-4,6-Dichloro-2-(dimethylamino)-2,3-dihydro-1H-inden-1-yl]oxy]-2,5-dimethylbenzene)sulfonamido]ethoxy]ethoxy)ethyl]-[4-([[2-(2-[2-[(4-[[(1S,2S)-4,6-dichloro-2-(dimethylamino)-2,3-dihydro-1H-inden-1-yl]oxy]-2,5-dimethylbenzene)sulfonamido]ethoxy]ethoxy)ethyl]carbamoyl]amino)butyl]urea Example 82

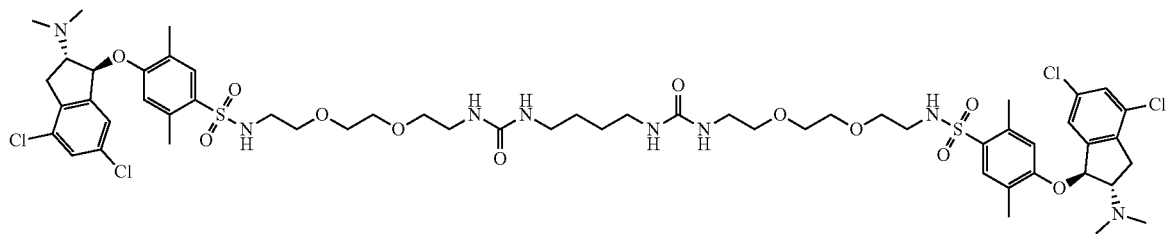

Beginning with INT-L6E and INT-I8C, Steps A-C provided Example 82 which was purified by preparative HPLC with the following conditions (2#-AnalyseHPLC-SHIMADZU(HPLC-10)): Column, XBridge C18 OBD Preparative Column, 19*250 mm, 5 um; mobile phase, water (0.05% $NH_4OH$) and $CH_3CN$ (85.0% $CH_3CN$ up to 89.0% in 11 min); Detector, UV 254 nm. This resulted in 74.8 mg (14%) of the title compound as a white solid, MS (m/z): 1261.55 [M+H]+. 1H NMR (Methanol-d4, 400 MHz) δ 7.77 (s, 2H), 7.42 (s, 2H) 7.30 (s, 2H), 7.09 (s, 2H), 5.99 (d, J=6.2 Hz, 2H), 3.63-3.42 (m, 18H), 3.30 (q, J=5.6 Hz, 6H), 3.20-3.04 (m, 8H), 2.91 (dd, J=16.4, 8.0 Hz, 2H), 2.66 (s, 6H), 2.37 (s, 12H), 2.22 (s, 6H), 1.53 (s, 4H).

Example 83: 1-[2-(2-[2-[(4-[[(1S,2S)-2-[(3R)-3-Aminopiperidin-1-yl]-4,6-dichloro-2,3-dihydro-1H-inden-1-yl]oxy]-3-fluoro-5-methylbenzene)sulfonamido]ethoxy]ethoxy)ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]-3-fluoro-5-methylbenzene)sulfonamido]ethoxy]ethoxy)ethyl]carbamoyl]amino)butyl]urea; hydrochloride Example 83

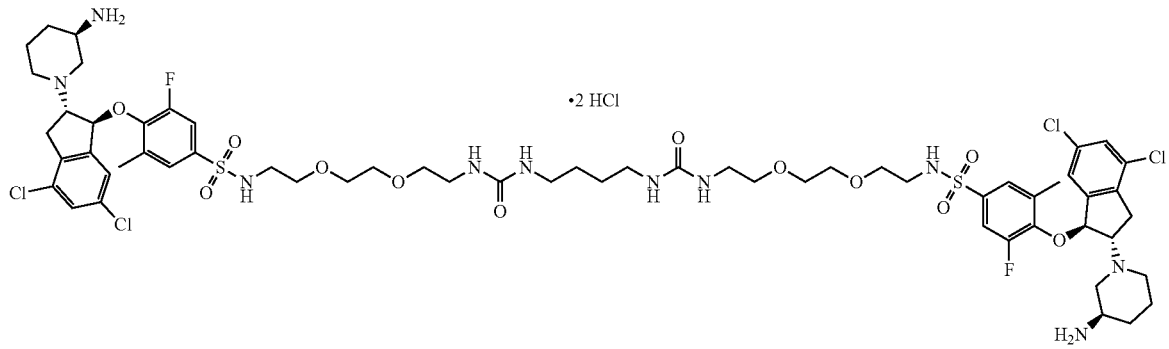

Beginning with INT-L6F and INT-I8F, Steps A-D provided Example 83 which was purified by preparative HPLC with the following conditions: Column, XBridge Preparative OBD C18 Column, 19*250 mm, 5 um; mobile phase, water (0.05% HCl) and CH$_3$CN (20.0% CH$_3$CN up to 70.0% in 8 min); Detector, UV 254 nm. This resulted in 317.6 mg (64%) of the title compound as a light yellow solid. MS (m/z): 1380.80 [M+H]$^+$. $^1$H NMR (Methanol-d4, 400 MHz) δ 7.66 (d, J=11.2 Hz, 2H), 7.65 (s, 2H), 7.62 (s, 2H), 6.70 (s, 4H), 4.67 (s, 2H), 3.99-3.80 (m, 8H), 3.68-3.48 (m, 19H), 3.46-3.28 (m, 7H), 3.21 (s, 4H), 3.11 (t, J=5.2 Hz, 4H), 2.14 (s, 6H), 2.30-2.10 (m, 6H), 1.93-1.78 (m, 2H), 1.57 (s, 4H).

Example 84: 1-[2-(2-[2-[(4-[[(1S,2S)-4,6-Dichloro-2-(dimethylamino)-2,3-dihydro-1H-inden-1-yl]oxy]-3-fluoro-5-methylbenzene)sulfonamido]ethoxy]ethoxy)ethyl]-3-[4-([[2-(2-[2-[(4-[[(1S,2S)-4,6-dichloro-2-(dimethylamino)-2,3-dihydro-1H-inden-1-yl]oxy]-3-fluoro-5-methylbenzene)sulfonamido]ethoxy]ethoxy)ethyl]carbamoyl]amino)butyl]urea

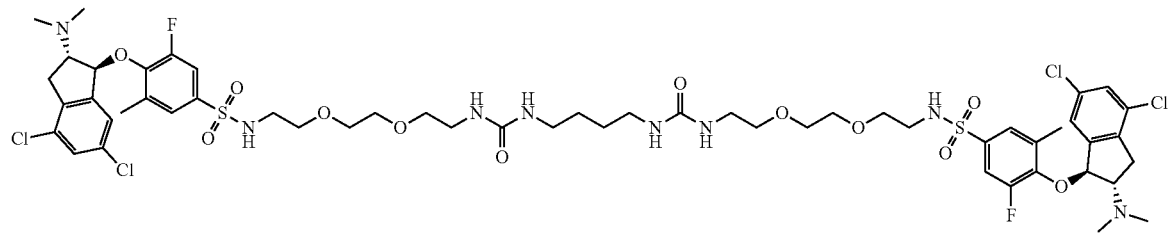

Example 84

Beginning with INT-L6F and INT-I8C, Steps A-C provided Example 84 which was purified by preparative HPLC with the following conditions: Column, XBridge C18 OBD Preparative Column, 19*250 mm, 5 um; mobile phase, water (0.05% TFA) and CH$_3$CN (45.0% CH$_3$CN up to 65.0% in 8 min); Detector, UV 254 nm. This resulted in 109.6 mg (30%) of the title compound as a white solid. MS (m/z): 1269.45 [M+H]$^+$. $^1$H NMR (Methanol-d4, 400 MHz) δ 7.59 (t, J=13.4 Hz, 4H), 7.44 (s, 2H), 6.93 (s, 2H), 5.92 (d, J=4.0 Hz, 2H), 3.72-3.65 (m, 3H), 3.60-3.50 (m, 16H), 3.38-3.29 (m, 5H), 3.13-3.08 (m, 8H), 2.93 (dd, J=16.8, 5.6 Hz, 2H), 2.32 (s, 12H), 2.15 (s, 6H), 1.49 (s, 4H).

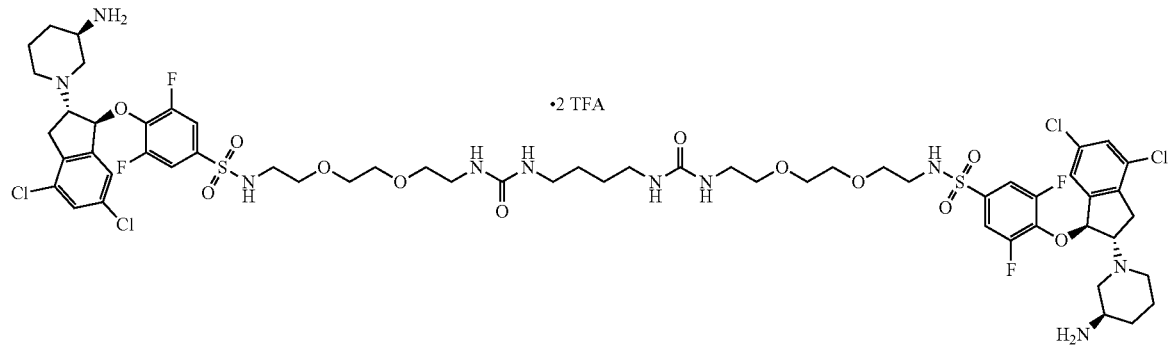

Example 85

Example 85: 3-[2-(2-[2-[(4-[[(1S,2S)-2-[(3R)-3-Aminopiperidin-1-yl]-4,6-dichloro-2,3-dihydro-1H-1-inden-1-yl]oxy]-3,5-difluorobenzene) sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-3,5-difluorobenzene)sulfonamido]ethoxy]ethoxy)ethyl]carbamoyl]amino)butyl]urea; bis(trifluoroacetic acid)

Beginning with INT-L6H and INT-I8F, Steps A-D provided Example 85 which was purified by preparative HPLC with the following conditions: Column, XBridge C18 OBD Preparative Column, 19 mm*250 mm, 5 um; mobile phase, water (0.05% TFA) and $CH_3CN$ (25% $CH_3CN$ up to 65% in 8 min); Detector, UV 254 nm. This resulted in 192.3 mg (57%) of the title compound as a white solid. MS (m/z): 1387 [M+H]$^+$. $^1$H NMR (Methanol-d4, 400 MHz) δ 7.59 (d, J=7.2 Hz, 4H), 7.46 (d, J=1.8 Hz, 2H), 7.22-7.16 (m, 2H), 5.89 (d, J=4.9 Hz, 2H), 3.89 (q, J=6.4 Hz, 2H), 3.62-3.47 (m, 17H), 3.31-3.22 (m, 5H), 3.20-3.06 (m, 10H), 3.04-2.93 (m, 4H), 2.69 (s, 2H), 2.56-2.40 (m, 4H), 1.97-1.88 (m, 2H), 1.78 (d, J=12.4 Hz, 2H), 1.54-1.36 (m, 8H).

Example 86: 4-([1S,2S)-4,6-dichloro-2-(dimethylamino)-2,3-dihydro-1H-inden-1-yl]oxy)-N-[26-([4-([(1S,2S)-4,6-dichloro-2-(dimethylamino)-2,3-dihydro-1H-inden-1-yl]oxy)-3,5-difluorophenyl]sulfonamido)-10,17-dioxo-3,6,21,24-tetraoxa-9,11,16,18-tetraazahexacosyl]-3,5-difluorobenzenesulfonamide; bis(trifluoroacetic acid)

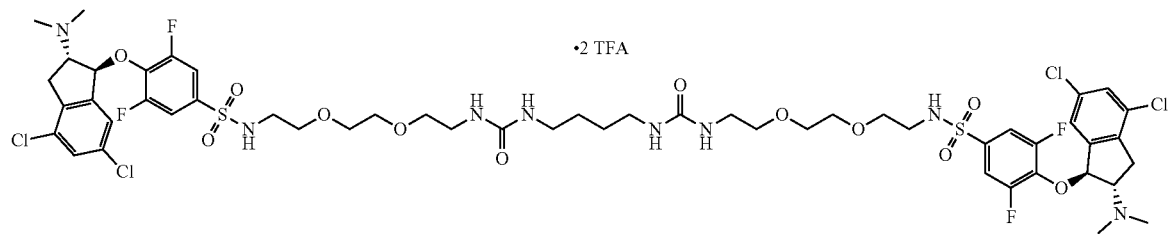

Example 86

Beginning with INT-L6H and INT-I8C, Steps A-C provided Example 86 which was purified by preparative HPLC with the following conditions: Column, XBridge C18 OBD Preparative Column, 19*250 mm, 5 um; mobile phase, water (0.05% TFA) and $CH_3CN$ (25.0% $CH_3CN$ up to 38.0% in 9 min); Detector, UV 254 nm. This resulted in 225.1 mg (52%) of the title compound as a white solid. MS (m/z): 1277 [M+H]$^+$. $^1$H NMR (Methanol-d4, 400 MHz) δ 7.70-7.59 (m, 4H), 7.57 (d, J=1.8 Hz, 2H), 7.07-7.01 (m, 2H), 6.31 (d, J=4.1 Hz, 2H), 4.54 (ddd, J=8.4, 5.7, 4.1 Hz, 2H), 3.72 (dd, J=17.5, 8.5 Hz, 2H), 3.61-3.46 (m, 17H), 3.27 (t, J=5.4 Hz, 5H), 3.16-3.05 (m, 8H), 3.02 (s, 12H), 1.47 (p, J=3.3 Hz, 4H).

Example 87: 3-[2-(2-[2-[(4-[[(1S,2S)-2-[(3R)-3-Aminopiperidin-1-yl]-4,6-dichloro-2,3-dihydro-1H-inden-1-yl]oxy]-5-fluoro-2-methylbenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-5-fluoro-2-methylbenzene)sulfonamido]ethoxy]ethoxy)ethyl]carbamoyl]amino)butyl]urea; bis(trifluoroacetic acid)

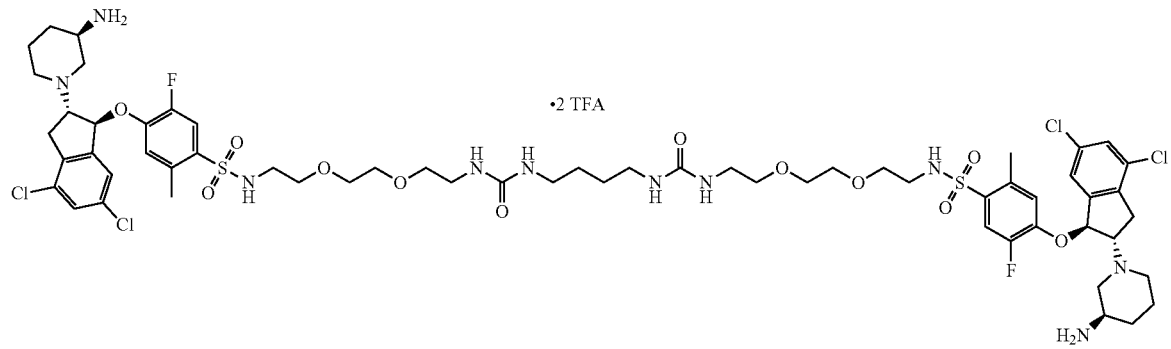

Example 87

Beginning with INT-L6G and INT-I8F, Steps A-D provided Example 87 which was purified by preparative HPLC with the following conditions: Column, XBridge C18 OBD Preparative Column, 19 mm*250 mm, 5 um; mobile phase, water (0.05% TFA) and CH$_3$CN (15.0% CH$_3$CN up to 65.0% in 8 min); Detector, UV 254 nm. This resulted in 254 mg (50%) of the title compound as a white solid. MS (m/z): 1379 [M+H]$^+$. $^1$H NMR (Methanol-d4, 400 MHz) δ 7.74 (d, J=11.1 Hz, 2H), 7.49-7.42 (m, 4H), 7.17-7.12 (m, 2H), 6.17 (d, J=5.8 Hz, 2H), 3.86 (q, J=7.4 Hz, 2H), 3.62-3.42 (m, 16H), 3.41-3.24 (m, 8H), 3.15-2.98 (m, 13H), 2.88 (s, 2H), 2.64 (s, 8H), 1.97 (s, 3H), 1.88 (s, 1H), 1.58 (dd, J=12.8, 8.9 Hz, 2H), 1.51-1.42 (m, 4H).

Example 88: 3-[2-(2-[2-[(4-[[(1S,2S)-4,6-Dichloro-2-(dimethylamino)-2,3-dihydro-1H-inden-1-yl]oxy]-5-fluoro-2-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-5-fluoro-2-methylbenzene)sulfonamido]ethoxy]ethoxy)ethyl]carbamoyl]amino)butyl]urea Example 88

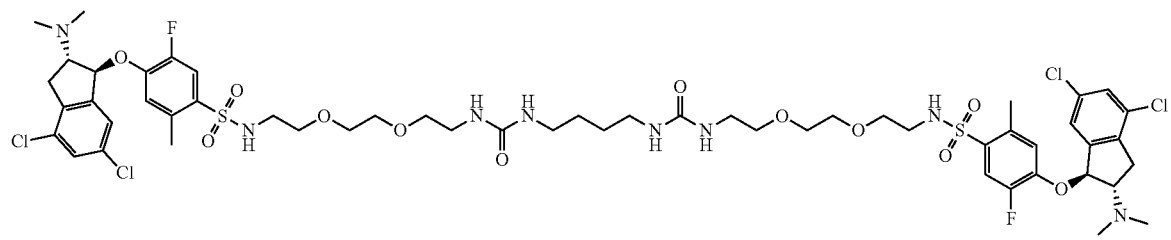

Beginning with INT-L6G and INT-I18C, Steps A-C provided Example 88 which was purified by preparative HPLC with the following conditions: Column, XBridge Preparative C18 OBD Column, 19*150 mm, 5 um; mobile phase, water (0.05% NH$_4$OH) and CH$_3$CN (5.0% CH$_3$CN up to 75.0% in 1 min, up to 86.0% in 6 min); Detector, UV 254/220 nm. This resulted in 80.2 mg (18%) of the title compound as a white solid. MS (m/z): 1269 [M+H]$^+$. $^1$H NMR (Methanol-d4, 400 MHz) δ 7.72 (d, J=11.2 Hz, 2H), 7.50-7.39 (m, 4H), 7.16-7.10 (m, 2H), 5.97 (d, J=5.8 Hz, 2H), 3.61-3.41 (m, 19H), 3.37-3.20 (m, 6H), 3.10 (t, J=5.4 Hz, 9H), 2.90 (dd, J=16.6, 7.4 Hz, 2H), 2.63 (s, 6H), 2.34 (s, 12H), 1.51-1.43 (m, 4H).

Example 89: 3-[2-(2-[2-[(4-[[(1S,2S)-2-[(3R)-3-Aminopiperidin-1-yl]-4,6-dichloro-2,3-dihydro-1H-inden-1-yl]oxy]-2-fluoro-5-methylbenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-2-fluoro-5-methylbenzene)sulfonamido]ethoxy]ethoxy)ethyl]carbamoyl]amino)butyl]urea; bis(trifluoroacetic acid)

Example 89

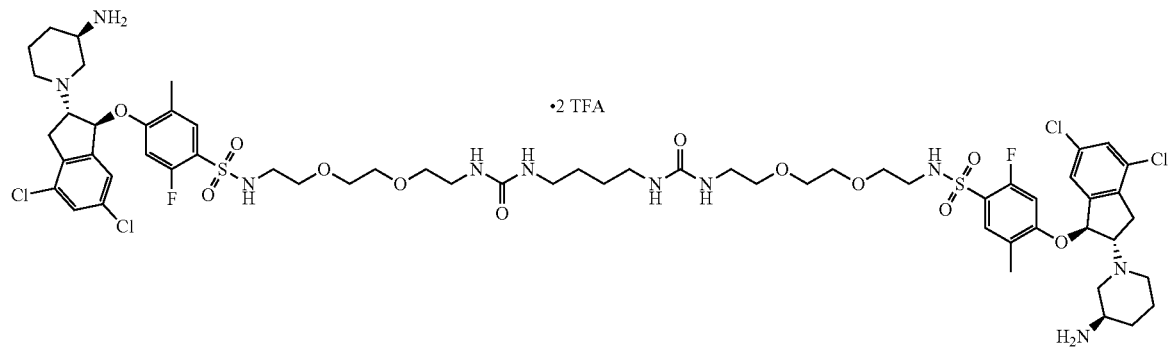

Beginning with INT-L6I and INT-I8F, Steps A-D provided Example 89 which was purified by preparative HPLC with the following conditions: Column, XBridge Preparative OBD C18 Column, 19*250 mm, 5 um; mobile phase, water (0.05% TFA) and CH₃CN (55.0% CH₃CN up to 80.0% in 8 min); Detector, UV 254 nm. This resulted in 234.1 mg (74%) of the title compound as a white solid. MS (m/z): 690.5 [M+H]⁺. ¹H NMR (Methanol-d4, 400 MHz) δ 7.66 (d, J=8.1 Hz, 2H), 7.45 (d, J=1.7 Hz, 2H), 7.38 (d, J=12.2 Hz, 2H), 7.19-7.14 (m, 2H), 6.04 (d, J=5.5 Hz, 2H), 3.74 (s, 2H), 3.63-3.46 (m, 15H), 3.31-3.22 (m, 4H), 3.19-2.92 (m, 13H), 2.75 (s, 2H), 2.63 (d, J=9.6 Hz, 2H), 2.54 (s, 3H), 2.19 (s, 5H), 1.95 (s, 3H), 1.85 (s, 2H), 1.68 (s, 2H), 1.55 (d, J=10.6 Hz, 2H), 1.47 (d, J=3.7 Hz, 3H).

Example 90: 3-[2-(2-[2-[(4-[[(1S,2S)-4,6-Dichloro-2-(dimethylamino)-2,3-dihydro-1H-inden-1-yl]oxy]-2-fluoro-5-methylbenzene)sulfonamido]ethoxy]ethoxy)ethyl]-1-[4-([[2-(2-[2-[(4-[[(1S,2S)-4,6-dichloro-2-(dimethylamino)-2,3-dihydro-1H-inden-1-yl]oxy]-2-fluoro-5-methylbenzene)sulfonamido]ethoxy]ethoxy)ethyl]carbamoyl]amino)butyl]urea; bis(trifluoroacetic acid)

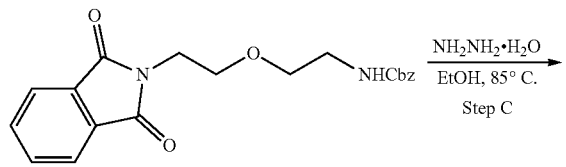

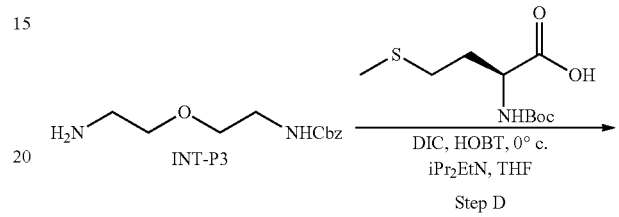

Example 89

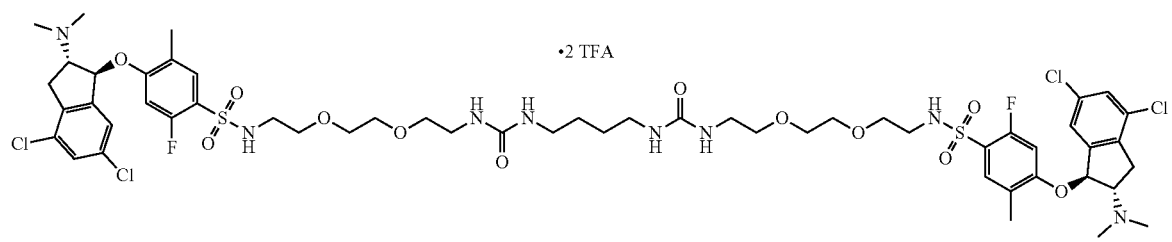

Beginning with INT-L6I and INT-I8C, Steps A-C provided Example 90 which was purified by preparative HPLC with the following conditions: Column, XSelect CSH Preparative C18 OBD Column, 19*250 mm, 5 um; mobile phase, water (0.05% TFA) and CH₃CN (25.0% CH₃CN up to 40.0% in 10 min); Detector, UV 254 nm. This resulted in 216.8 mg (58%) of the title compound as a white solid. MS (m/z): 1291 [M+Na]⁺. ¹H NMR (Methanol-d4, 400 MHz) δ 7.75-7.67 (m, 2H), 7.55 (d, J=1.7 Hz, 2H), 7.41 (d, J=11.6 Hz, 2H), 7.17-7.07 (m, 2H), 6.46 (d, J=6.7 Hz, 2H), 4.50 (td, J=8.5, 6.6 Hz, 2H), 3.74-3.63 (m, 3H), 3.61-3.46 (m, 18H), 3.31-3.20 (m, 6H), 3.20-3.01 (m, 25H), 2.26 (d, J=7.6 Hz, 7H), 1.46 (td, J=6.4, 3.2 Hz, 4H).

Scheme for the Synthesis of Pyrrolidinone Linkers:

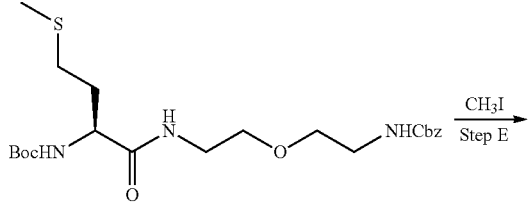

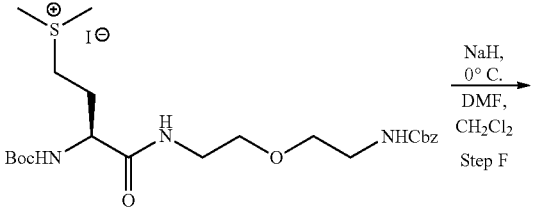

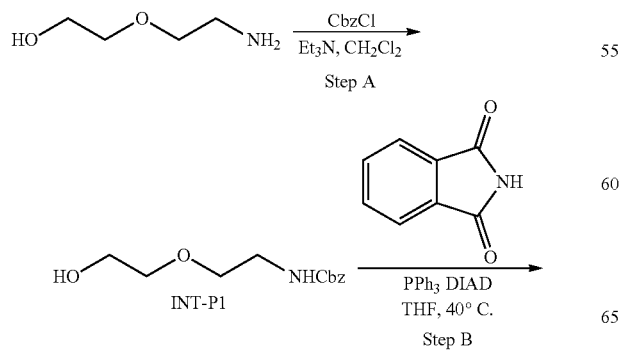

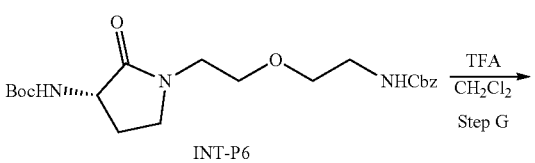

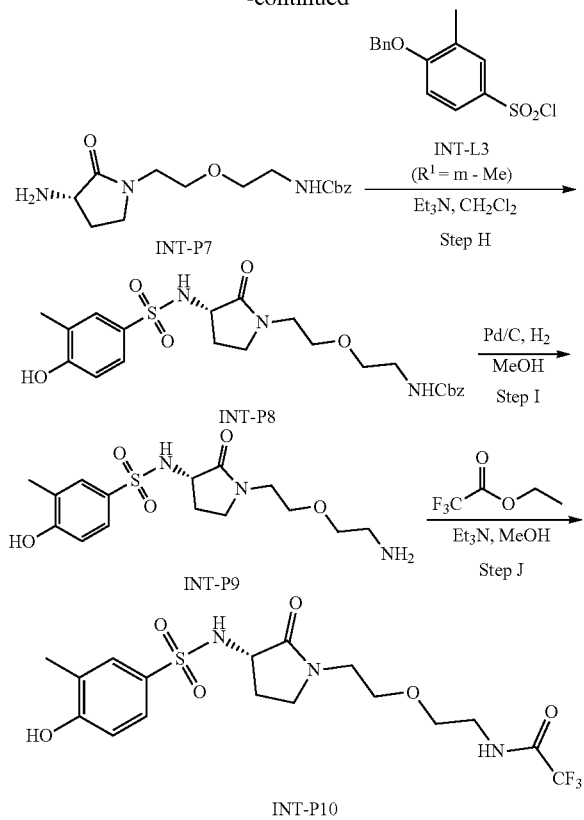

Step A: To a 500-mL round-bottom flask purged and maintained with an inert atmosphere of nitrogen was added 2-(2-aminoethoxy)ethan-1-ol (16.1 g, 153 mmol, 1 equiv), CH₂Cl₂ (160 mL), and triethylamine (22.4 mL, 1.05 equiv). This was followed by the addition of CbzCl (28.7 g, 168.24 mmol, 1.1 equiv) dropwise with stirring at 5-10° C. The resulting solution was stirred overnight at room temperature. The reaction was then quenched by the addition of 100 mL of water and extracted with 3×100 mL of CH₂Cl₂. The organic layers were combined and washed with 1×100 mL of brine, dried over anhydrous sodium sulfate, filtered, and concentrated under vacuum. The solid was dried in an oven under reduced pressure. The residue was applied onto a silica gel column with petroleum ether/ethyl acetate (1:1) providing 32 g (87%) of benzyl N-[2-(2-hydroxyethoxy) ethyl]carbamate (INT-P1) as a yellow oil.

Step B: To a 250-mL round-bottom flask purged and maintained with an inert atmosphere of nitrogen was added alcohol INT-P1 (5 g, 20.90 mmol, 1 equiv), phthalimide (3.07 g, 20.9 mmol, 1 equiv), and tetrahydrofuran (49 mL). This was followed by the addition of PPh₃ (8.22 g, 31.34 mmol, 1.5 equiv) in several portions at 40° C. To this was added DIAD (6.17 mL, 1.5 equiv) dropwise with stirring at 40° C. over 30 min. The resulting solution was stirred for 1 h at 40° C. in an oil bath. The resulting slurry was diluted with water and extracted with 3×100 mL of ethyl acetate. The organic layers combined and concentrated under vacuum. The residue was applied onto a silica gel column with petroleum ether/ethyl acetate (1:1) providing 6.5 g (84%) of benzyl N-[2-[2-(1,3-dioxo-2,3-dihydro-1H-isoindol-2-yl)ethoxy]ethyl]carbamate (INT-P2) as a yellow oil.

Step C: To a 1-L round-bottom flask purged and maintained with an inert atmosphere of nitrogen was added phthalimide INT-P2 (6.5 g, 17.6 mmol, 1 equiv), ethanol (500 mL), and NH₂NH₂·H₂O (8.8 g, 10 equiv). The resulting solution was stirred for 3 h at 85° C. in an oil bath. The resulting mixture was concentrated under vacuum. The residue was applied onto a silica gel column with CH₂Cl₂/methanol (5:1) providing 4 g (95%) of benzyl N-[2-(2-aminoethoxy)ethyl]carbamate (INT-P3) as a yellow oil.

Step D: To a 250-mL round-bottom flask purged and maintained with an inert atmosphere of nitrogen was added Boc-Met-OH (3.77 g, 15.1 mmol, 1 equiv), amine INT-P3 (3.6 g, 15.1 mmol, 1 equiv), THF (54 mL), HOBT (2.04 g, 15.1 mmol, 1 equiv), and diisopropylethylamine (5 mL, 2 equiv). This was followed by the addition of DIC (2.5 mL, 1.05 equiv) dropwise with stirring at 0° C. The resulting solution was stirred for 1 h at room temperature. The resulting mixture was concentrated under vacuum. The residue was applied onto a silica gel column with H₂O/CH₃CN (3:2) providing 5.2 g (73%) of tert-butyl N-[(1S)-1-[[2-(2-[[(benzyloxy)carbonyl]amino]ethoxy)ethyl]carbamoyl]-3-(methylsulfanyl)propyl]carbamate (INT-P4) as a yellow oil.

Step E: To a 250-mL round-bottom flask purged and maintained with an inert atmosphere of nitrogen was added INT-P4 (5.2 g, 11.07 mmol, 1 equiv) and iodomethane (50 mL). The resulting solution was stirred for 3 days at room temperature. The resulting mixture was concentrated under vacuum. This resulted in 5.3 g (99%) of tert-butyl N-[(1S)-1-[[2-(2-[[(benzyloxy)carbonyl]amino]ethoxy)ethyl]carbamoyl]-3-(dimethylsulfaniumyl)propyl]carbamate (INT-P5) as a light yellow oil.

Step F: To a 250-mL round-bottom flask purged and maintained with an inert atmosphere of nitrogen was added INT-P5 (5.3 g, 11.8 mmol, 1 equiv), DMF (60 mL), CH₂Cl₂ (60 mL), and lastly sodium hydride (900 mg, 37.5 mmol, 3.2 equiv) in portions. The resulting slurry was stirred for 2.5 h at 0° C. in an ice/salt bath. The resulting mixture was concentrated under vacuum. The residue was diluted with CH₂Cl₂ and washed with 3×100 mL of brine. The organic layer was dried over anhydrous sodium sulfate, filtered, and concentrated under vacuum providing 4.6 g (93%) of benzyl N-(2-[2-[(3S)-3-[[(tert-butoxy)carbonyl]amino]-2-oxopyrrolidin-1-yl]ethoxy]ethyl)carbamate (INT-P6) as a yellow oil.

Step G: To a 250-mL round-bottom flask purged and maintained with an inert atmosphere of nitrogen was added pyrrolidinone INT-P6 (4.5 g, 10.68 mmol, 1 equiv), CH₂Cl₂ (50 mL), and trifluoroacetic acid (8 mL). The resulting solution was stirred for 3 h at room temperature. The resulting mixture was concentrated under vacuum. The reaction was quenched by the addition of 100 mL of water. The pH of the solution was adjusted to 8 with saturated aqueous sodium bicarbonate and extracted with 5×100 mL of ethyl acetate. The organic layers were combined, dried over anhydrous sodium sulfate, filtered, and concentrated under vacuum. This resulted in 3.4 g (100%) of benzyl N-(2-[2-[(3S)-3-amino-2-oxopyrrolidin-1-yl]ethoxy]ethyl) carbamate (INT-P7) as a yellow oil.

Step H: To a 250-mL round-bottom flask purged and maintained with an inert atmosphere of nitrogen was added CH₂Cl₂ (20 mL), triethylamine (4.6 mL, 2.9 equiv), and amine INT-P7 (3.3 g, 10.3 mmol, 0.9 equiv). To this mixture was added a solution of 4-(benzyloxy)-3-methylbenzene-1-sulfonyl chloride (INT-L3 with R¹=m-Me, 3.4 g, 11.5 mmol, 1 equiv) in CH₂Cl₂ (30 mL) dropwise with stirring over 20 min. The resulting solution was stirred for 2 h at room temperature. The reaction was quenched by the addition of 100 mL of water and extracted with 3×200 mL of ethyl acetate. The organic layers were combined and washed with 1×100 mL of brine. The organic layer was dried over anhydrous sodium sulfate, filtered, and concentrated under vacuum. The residue was applied onto a silica gel column with petroleum ether/ethyl acetate (3:7) providing 4.2 g (63%) of benzyl N-(2-[2-[(3S)-3-[[4-(benzyloxy)-3-methylbenzene]sulfonamido]-2-oxopyrrolidin-1-yl]ethoxy]ethyl) carbamate (INT-P8) as a yellow oil.

Step I: To a 500-mL round-bottom flask purged and maintained with an inert atmosphere of hydrogen was added benzyl ether INT-P8 (4.2 g, 7.22 mmol, 1 equiv) and methanol (50 mL). This was followed by the addition of palladium on carbon (2.1 g, 60% of water). The resulting slurry was stirred for 2 days at room temperature. The solids were filtered out. The mixture was dried over anhydrous sodium sulfate, filtered, and concentrated under vacuum. This resulted in 2.3 g (88%) of N-[(3S)-1-[2-(2-aminoethoxy)ethyl]-2-oxopyrrolidin-3-yl]-4-hydroxy-3-methylbenzene-1-sulfonamide (INT-P9) as a white solid.

Step J: To a 500-mL round-bottom flask purged and maintained with an inert atmosphere of nitrogen was added amine INT-P9 (2.3 g, 6.43 mmol, 1 equiv), methanol (30 mL), triethylamine (0.2 mL, 0.20 equiv), and ethyl 2,2,2-trifluoroacetate (2.35 mL, 3 equiv). The resulting solution was stirred for 3 h at room temperature. The resulting mixture was concentrated under vacuum. The residue was applied onto a silica gel column with hexane/ethyl acetate (3:7) providing 2 g (69%) of 2,2,2-trifluoro-N-(2-[2-[(3S)-3-[(4-hydroxy-3-methylbenzene)sulfonamido]-2-oxopyrrolidin-1-yl]ethoxy]ethyl)acetamide (INT-P10) as a white solid.

Scheme for the Synthesis of Pyrrolidinone Dimer Products:

Example 91: 1-(2-[2-[(3S)-3-[(4-[[(1S,2S)-4,6-Dichloro-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3S)-3-[(4-[[(1S,2S)-4,6-dichloro-2-(dimethylamino)-2,3-dihydro-1H-inden-1-yl]oxy]-3-methylbenzene)sulfonamido]-oxopyrrolidin-1-yl]ethoxy]ethyl)carbamoyl]amino)butyl]urea

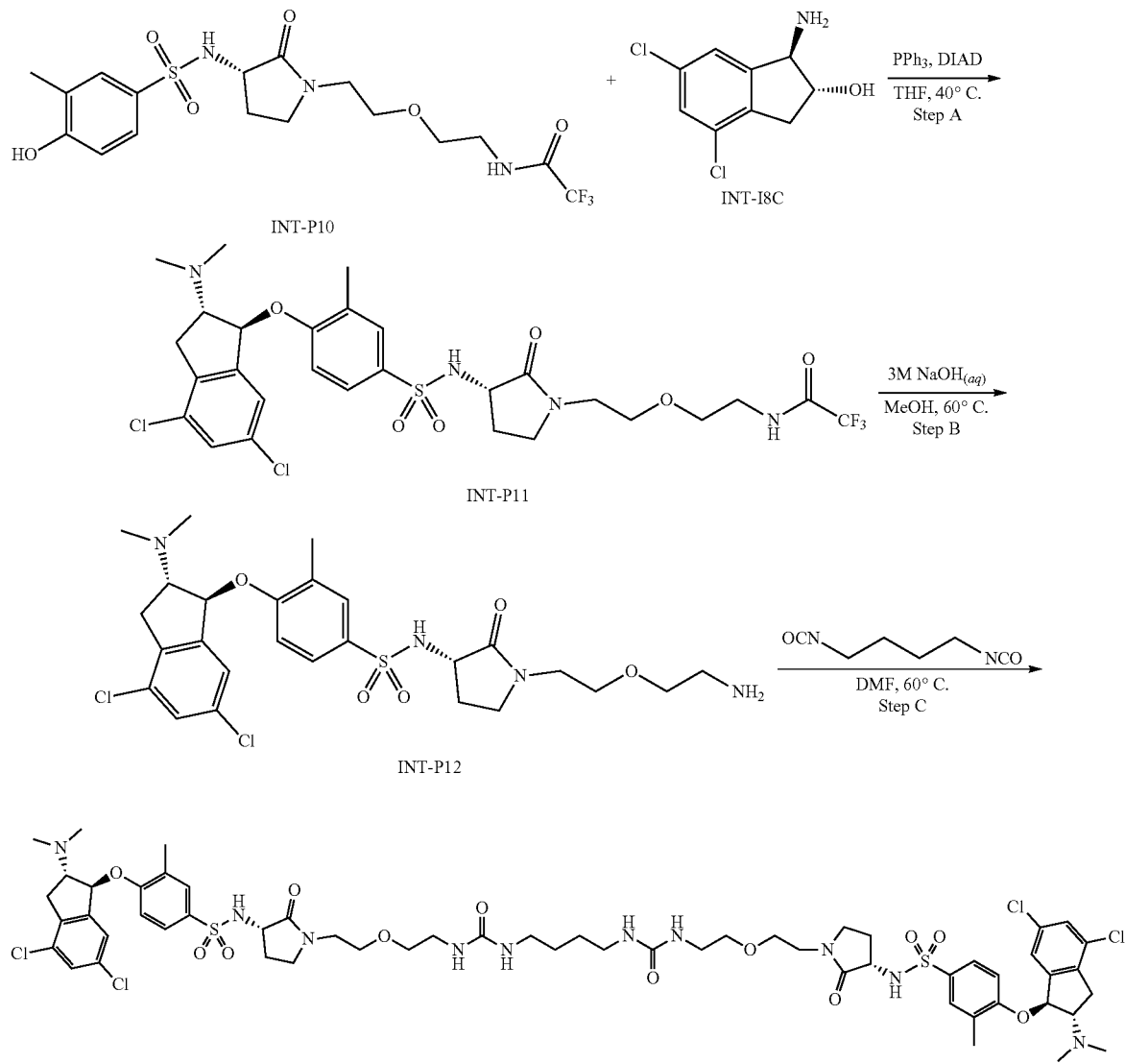

Example 91

Step A: To a 50-mL round-bottom flask purged and maintained with an inert atmosphere of nitrogen was added phenol INT-P10 (300 mg, 0.66 mmol, 1 equiv), aminoindanol INT-18C (163 mg, 0.66 mmol, 1 equiv), and THF (1.5 mL). This was followed by the addition of PPh$_3$ (260 mg, 0.99 mmol, 1.5 equiv) at 40° C. To this was added DIAD (0.2 mL, 1.5 equiv) dropwise with stirring at 40° C. over 30 min. The resulting solution was stirred for 1 h at 40° C. in an oil bath. The resulting mixture was concentrated tinder vacuum. The residue was applied onto a silica gel column with hexane/ethyl acetate (1:2) providing 400 mg (89%) of N-(2-[2-[(3S)-3-[(4-[[(1S,2S)-4,6-dichloro-2-(dimethylamino)-2,3-dihydro-1H-inden-1-yl]oxy]-3-methylbenzene)sulfonamido]-2-oxopyrrolidin-1-yl]ethoxy]ethyl)-2,2,2-trifluoroacetamide (INT-P11) as a yellow oil.

Step B: To a 250-mL round-bottom flask purged and maintained with an inert atmosphere of nitrogen was added monomer intermediate INT-P11 (400 mg, 0.59 mmol, 1 equiv) and methanol (10 mL). This was followed by the addition of sodium hydroxide (3 M$_{(aq)}$, 1.5 mL). The resulting solution was stirred for 1 h at 60° C. in an oil bath. The resulting solution was diluted with water and extracted with 3×100 mL of ethyl acetate. The organic layers were combined and washed with 1×100 mL of brine. The organic layer was dried over anhydrous sodium sulfate, filtered, and concentrated under vacuum. The residue was applied onto a silica gel column with CH$_2$Cl$_2$/methanol (5:1) providing 320 mg (93%) of N-[(3S)-1-[2-(2-aminoethoxy)ethyl]-2-oxopyrrolidin-3-yl]-4-[[(1S,2S)-4,6-dichloro-2-(dimethylamino)-2,3-dihydro-1H-inden-1-yl]oxy]-3-methylbenzene-1-sulfonamide (INT-P12) as a yellow oil.

Step C: To a 100-mL round-bottom flask purged and maintained with an inert atmosphere of nitrogen was added amine INT-P12 (320 mg, 0.55 mmol, 1 equiv), DMF (3.6 mL), and 1,4-diisocyanatobutane (34.5 mg, 0.25 mmol, 0.45 equiv). The resulting solution was stirred for 2 h at 60° C. in an oil bath. The resulting mixture was concentrated under vacuum and purified by preparative HPLC as below.

Example 91: 1-(2-[2-[(3S)-3-[(4-[[(1S,2S)-4,6-Dichloro-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3S)-3-[(4-[[(1S,2S)-4,6-dichloro-2-(dimethylamino)-2,3-dihydro-1H-inden-1-yl]oxy]-3-methylbenzene)sulfonamido]-2-oxopyrrolidin-1-yl]ethoxy]ethyl)carbamoyl]amino]butyl)urea Crude compound of Steps A-C was purified by preparative HPLC with the following conditions: Column, XBridge Preparative OBD C18 Column, 19*250 mm, 5 um; mobile phase, water (0.05% NH$_4$OH) and CH$_3$CN (73.0% CH$_3$CN to 86.0% in 8 min); Detector, UV 220 nm. This resulted in 139 mg (19%) of the title compound as a white solid. MS (m/z): 1311 [M+H]$^+$. $^1$H NMR (Methanol-d4, 400 MHz) δ 7.85-7.74 (m, 4H), 7.46-7.37 (m, 4H), 7.11-7.06 (m, 2H), 5.96 (d, J=6.1 Hz, 2H), 4.05 (dd, J=9.8, 8.5 Hz, 2H), 3.60-3.31 (m, 18H), 3.31-3.20 (m, 6H), 3.12. (t, J=5.3 Hz, 4H), 2.89 (dd, J=16.5, 7.8 Hz, 2H), 2.34 (s, 12H), 2.25 (s, 8H), 1.78 (dq, J=12.4, 9.3 Hz, 2H), 1.49 (p, J=3.2 Hz, 4H).

Scheme for Synthesis of Cyano-Containing Pyrrolidinone Dimer Product:

Example 92: 1-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)carbamoyl]amino]butyl)urea; bis(trifluoroacetic acid)

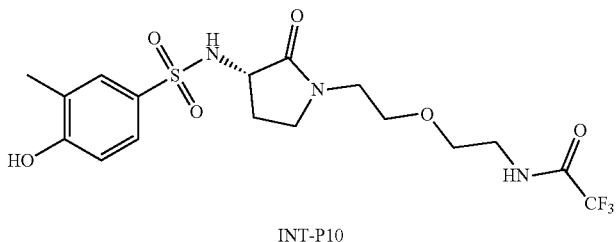

INT-P10

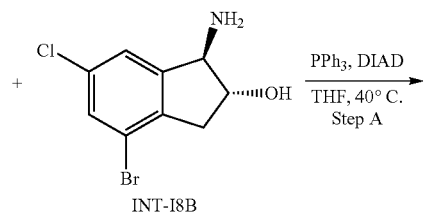

INT-I8B

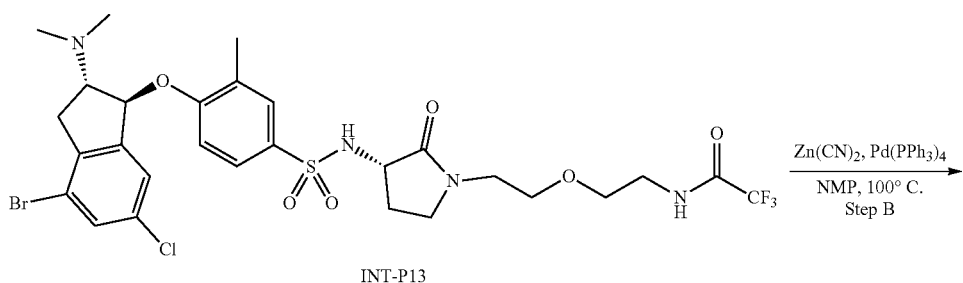

INT-P13

-continued

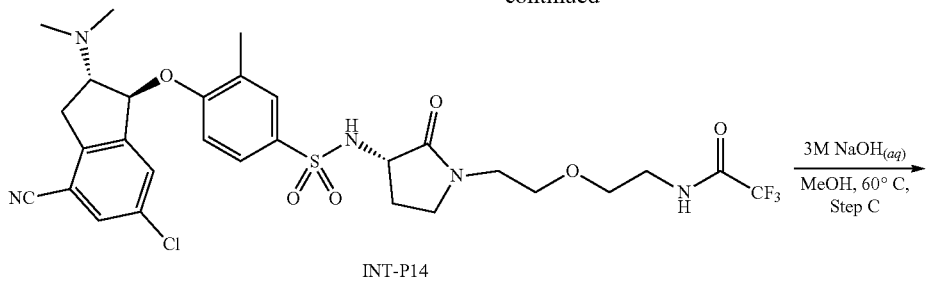

INT-P14

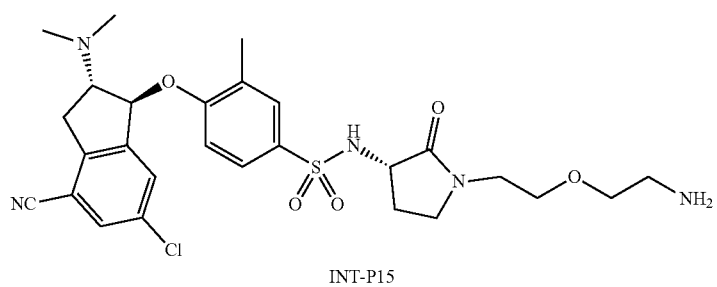

INT-P15

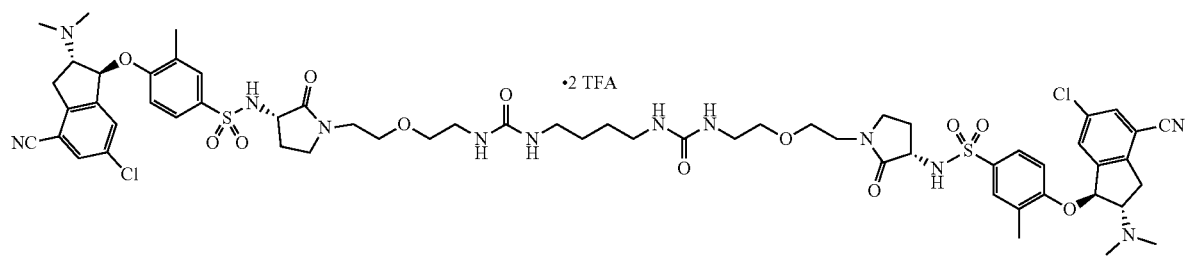

Example 92

Step A: To a 50-mL, round-bottom flask purged and maintained with an inert atmosphere of nitrogen was added phenol INT-P10 (500 mg, 1.1 mmol, 1 equiv), aminoindanol INT-I8B (320 mg, 1.1 mmol, 1 equiv), and THF (2.6 mL). This was followed by the addition of PPh$_3$ (434 mg, 1.65 mmol, 1.5 equiv) at 40° C. To this slurry was added DIAD (0.33 mL) dropwise with stirring at 40° C. over 30 min. The resulting solution was stirred for 1 h at 40° C. in an oil bath. The resulting mixture was concentrated under vacuum. The residue was applied onto a silica gel column with petroleum ether/ethyl acetate (2/1) providing 570 mg (71%) of N-2-[2-[(3S)-3-[(4-[[(1S,2S)-4-bromo-6-chloro-2-(dimethylamino)-2,3-dihydro-1H-inden-1-yl]oxy]-3-methylbenzene)sulfonamido]-2-oxopyrrolidin-1-yl]ethoxy]ethyl)-2,2,2-trifluoroacetamide (INT-P13) as a yellow oil.

Step B: To a 50-mL round-bottom flask purged and maintained with an inert atmosphere of nitrogen was added INT-P13 (570 mg, 0.79 mmol, 1.00 equiv), NMP (6 mL), Zn(CN)$_2$ (55.4 mg, 0.6 equiv), and Pd(PPh$_3$)$_4$ (91 mg, 0.08 mmol, 0.1 equiv). The resulting solution was stirred for overnight at 100° C. in an oil bath. The reaction was then quenched by the addition of 10 mL of water and extracted with 3×20 mL of ethyl acetate. The organic layers were combined and washed with 3×50 mL of brine. The organic layer was dried over anhydrous sodium sulfate, filtered, and concentrated under vacuum. The residue was applied onto a silica gel column with ethyl acetate/petroleum ether (1/1) providing 400 mg (76%) of N-(2-[2-[(3S)-3-[(4-[[(1S,2S)-6-chloro-4-cyano-2-(dimethylamino-2,3-dihydro-1H-inden-1-yl]oxy]-3-methylbenzene)sulfonamido]-2-oxopyrrolidin-1-yl]ethoxy]ethyl)-2,2,2-trifluoroacetamide (INT-P14) as a yellow oil.

Step C: To a 100-mL round-bottom flask purged and maintained with an inert atmosphere of nitrogen was added INT-P14 (400 mg, 0.60 mmol, 1 equiv), methanol (7 mL), and sodium hydroxide (3 M$_{(aq)}$, 1 mL). The resulting solution was stirred for 2 h at room temperature. The resulting solution was extracted with 3×50 mL of ethyl acetate and the organic layers combined. The resulting mixture was washed with 1×50 mL of brine, dried over anhydrous sodium sulfate, filtered, and concentrated under vacuum. The residue was applied onto a silica gel column with CH$_2$Cl$_2$/methanol (5/1) providing 300 mg (87%) of N-[(3S)-1-[2-(2-aminoethoxy)ethyl]-2-oxopyrrolidin-3-yl]-4-[[(1S,2S)-6-chloro-4-cyano-2-(dimethylamino)-2,3-dihydro-1H-inden-1-yl]oxy]-3-methylbenzene-1-sulfonamide (INT-P15) as a yellow oil.

Step D: To a 50-mL round-bottom flask purged and maintained with an inert atmosphere of nitrogen, was added amine INT-P15 (144 mg, 0.25 mmol, 1 equiv), DMF (2 mL), and 1,4-diisocyanatobutane (0.012 mL, 0.4 equiv). The resulting solution was stirred for 2 h at 60° C. in an oil bath. The resulting mixture was concentrated under vacuum and purified by preparative HPLC as below.

Example 92: 1-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)carbamoyl]amino]butyl)urea; bis (trifluoroacetic acid)

Crude compound of Steps A-D was purified by preparative HPLC with the following conditions: Column, XBridge Shield RP18 OBD Column, 19*150 mm, 5 um; mobile phase, water (0.05% TFA) and $CH_3CN$ (15.0% $CH_3CN$ up to 40.0% in 10 min); Detector, UV 254 nm. This resulted in 51.5 mg (14%) of the title compound as a white solid. MS (m/z): 1293 [M+H]$^+$. $^1$H NMR (Methanol-d4, 400 MHz) δ 7.91-7.79 (m, 6H), 7.49 (d, J=8.8 Hz, 2H), 7.45-7.39 (m, 2H), 6.52 (d, J=6.7 Hz, 2H), 4.54 (td, J=8.5, 6.6 Hz, 2H), 4.07 (dd, J=9.9, 8.5 Hz, 2H), 3.81 (dd, J=16.7, 8.5 Hz, 2H), 3.59-3.32 (m, 19H), 3.22 (t, J=5.4 Hz, 4H), 3.07 (s, 17H), 2.31 (s, 8H), 1.80 (dq, J=12.6, 9.3 Hz, 2H), 1.52-1.44 (m, 4H).

Representative Scheme for Synthesis of Cyclic-Substituted Sulfonamide Linkers:

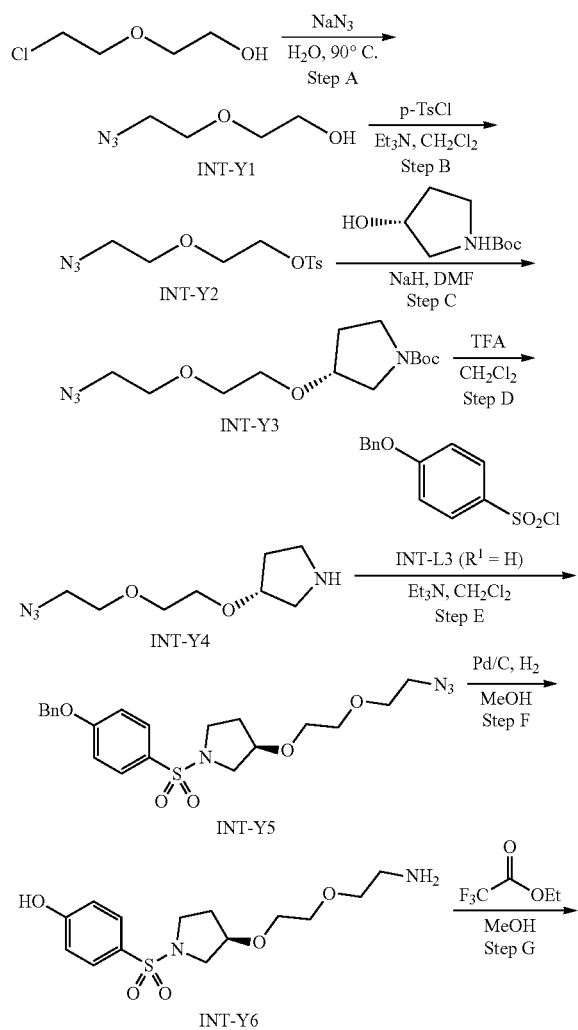

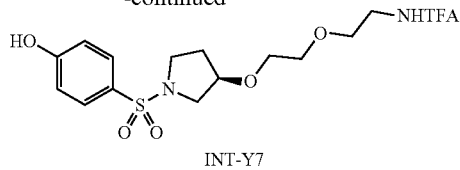

INT-Y7

Step A: To a 250-mL round-bottom flask was added 2-(2-chloroethoxy)ethan-1-ol (7.8 g, 62.62 mmol, 1 equiv) and water (300 mL). This was followed by the addition of a solution of sodium azide (7.7 g, 118.4 mmol, 2 equiv) in water (40 mL) dropwise with stirring. The resulting solution was stirred overnight at 80° C. The reaction mixture was cooled to 0° C. with a water/ice bath and extracted with 3×500 mL, of $CH_2Cl_2$. The organic layers were combined, dried over anhydrous sodium sulfate, filtered, and concentrated under vacuum providing 10 g (crude) of 2-(2-azidoethoxy)ethan-1-ol (INT-Y1) as a colorless oil.

Step B: To a 500-mL round-bottom flask was added azidoalcohol INT-Y1 (10 g crude from Step A, theoretical 62.6 mmol, 1 equiv), dichloromethane (300 mL), 4-methylbenzene-1-sulfonyl chloride (18 g, 94.42 mmol, 1.3 equiv), and triethylamine (10 mL, 1.15 equiv). The resulting solution was stirred for 2 h at room temperature. The reaction was then quenched by the addition of 50 mL of water and extracted with 3×300 mL of dichloromethane. The organic layers were combined, dried over anhydrous sodium sulfate, filtered, and concentrated under vacuum. The residue was applied onto a silica gel column with petroleum ether/ethyl acetate (1:3) providing 15 g (69%) of 1-[[2-(2-azidoethoxy)ethoxy]sulfonyl]-4-methylbenzene (INT-Y2) as a colorless oil.

Step C: To a 100-mL round-bottom flask was added tert-butyl (3R)-3-hydroxypyrrolidine-1-carboxylate (700 mg, 3.74 mmol, 1 equiv), DMF (30 mL), and tosylate INT-Y2 (900 mg, 3.15 mmol, 0.84 equiv). This was followed by the addition of sodium hydride (300 mg. 12.50 mmol, 3.34 equiv) in several portions at 0° C. The resulting slurry was stirred overnight at 40° C. The resulting mixture was diluted with 50 mL of ethyl acetate and quenched by the addition of 50 mL of water. The resulting solution was extracted with 2×150 mL, of ethyl acetate and the organic layers combined. The resulting mixture was washed with 2×150 mL of brine, dried over anhydrous sodiumسulfate, filtered, and concentrated under vacuum. This resulted in 940 mg (84%) of tert-butyl (3R)-3-[2-(2-azidoethoxy)ethoxy]pyrrolidine-1-carboxylate (INT-Y3) as a light brown solid.

Step D: To a 100-mL round-bottom flask was added azide INT-Y3 (940 mg, 3.13 mmol, 1 equiv), $CH_2Cl_2$ (50 mL), and trifluoroacetic acid (12 mL). The resulting solution was stirred for 30 min at room temperature. The pH value of the solution was adjusted to 12 with saturated aqueous potassium carbonate and extracted with 2×150 mL of $CH_2Cl_2$. The combined organic layers were washed with 2×150 mL of brine, dried over anhydrous sodium sulfate, filtered, and concentrated under vacuum. This resulted in 630 mg (crude) of (3R)-3-[2-(2-azidoethoxy)ethoxy]pyrrolidine (INT-Y4) as a light brown oil.

Step E: To a 250-mL round-bottom flask was added amine INT-Y4 (702 mg, 3.5 mmol, 1 equiv), $CH_2Cl_2$ (50 mL), 4-(benzyloxy)benzene-1-sulfonyl chloride (INT-L3 with $R^1$=H, 1 g, 3.5 mmol, 1 equiv), and triethylamine (2.8 mL). The resulting solution was stirred for 30 min at room temperature. The resulting solution was diluted with water and extracted with 3×200 mL of CH$_2$Cl$_2$. The combined organic layers were washed with 2×200 mL of brine, dried over anhydrous sodium sulfate, filtered, and concentrated under vacuum. The residue was applied onto a silica gel column with petroleum ether/ethyl acetate (3:1) providing 380 mg (24%) of (3R)-3-[2-(2-azidoethoxy)ethoxy]-1-[[4-(benloxy)benzene]sulfonyl]pyrrolidine (INT-Y5) as a light yellow oil.

Step F: To a 250-mL round-bottom flask purged and maintained with an inert atmosphere of H$_2$ was added azide INT-Y5 (700 mg, 1.57 mmol, 1 equiv), methanol (40 mL), and palladium on carbon (200 mg). The resulting slurry was stirred overnight at room temperature. The resulting solution was diluted with 200 mL of methanol, filtered, and concentrated under vacuum. The residue was applied onto a silica gel column with CH$_2$Cl$_2$:methanol:triethylamine (100:10:1) providing 380 mg (73%) of 4-[(3R)-3-[2-(2-aminoethoxy)ethoxy]pyrrolidine-1-sulfonyl]phenol (INT-Y6) as a light brown oil.

Step G: To a 250-mL round-bottom flask was added amine INT-Y6 (380 mg, 1.15 mmol, 1 equiv), methanol (30 mL), and ethyl 2,2,2-trifluoroacetate (817.6 mg, 6.48 mmol, 5.6 equiv). The resulting solution was stirred overnight at room temperature. The resulting mixture was concentrated under vacuum. The residue was applied onto a silica gel column with petroleum ether/ethyl acetate (1:2). This resulted in 390 mg (80%) of 2,2,2-trifluoro-N-[2-(2-[[(3R)-1-[(4-hydroxybenzene)sulfonyl]pyrrolidin-3-yl]oxy]ethoxy)ethyl]acetamide (INT-Y7) as a light brown oil.

Other cyclic amine intermediates were generated from the analogous procedure beginning with the appropriate Boc-aminoalcohol starting materials.

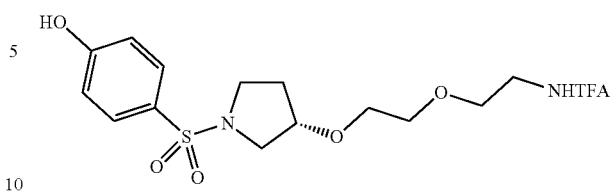

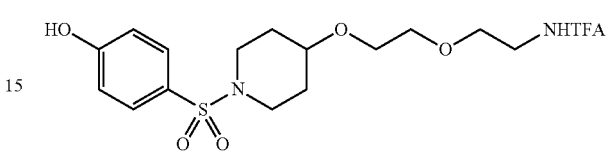

Representative Scheme for Synthesis of Cyclic-Substituted Dimer Products:

Example 93: 3-[2-(2-[[(3R)-1-[(4-[[(1S,2S)-2-[(3R)-3-Aminopiperidin-1-yl]-4,6-dichloro-2,3-dihydro-1H-inden-1-yl]oxy]benzene)sulfonyl]pyrrolidin-3-yl]oxy]ethoxy)ethyl]-1-[4-([[2-(2-[[(3R)-1-[(4-[[(1S,2S)-2-[(3R)-3-aminopiperidin-1-yl]-4,6-dichloro-2,3-dihydro-1H-inden-1-yl]oxy]benzene)sulfonyl]pyrrolidin-3-yl]oxy]ethoxy)ethyl]carbamoyl]amino)butyl]urea

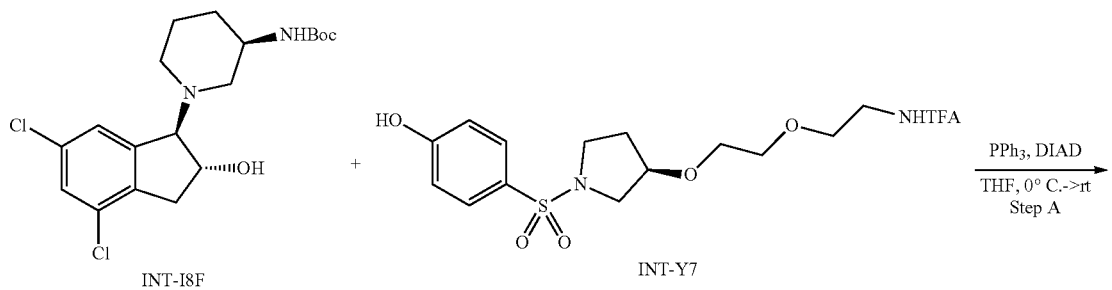

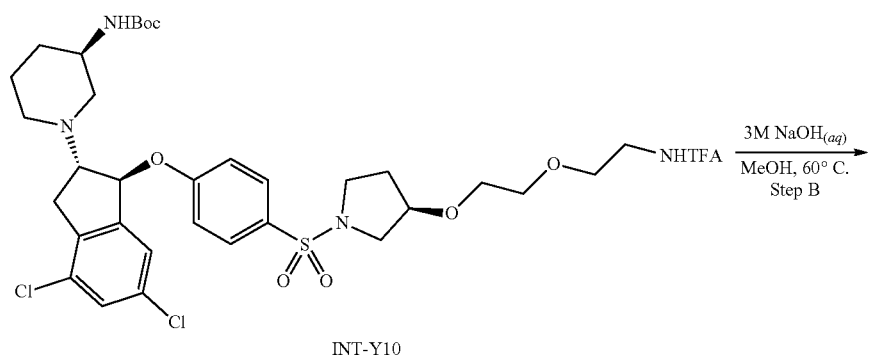

-continued

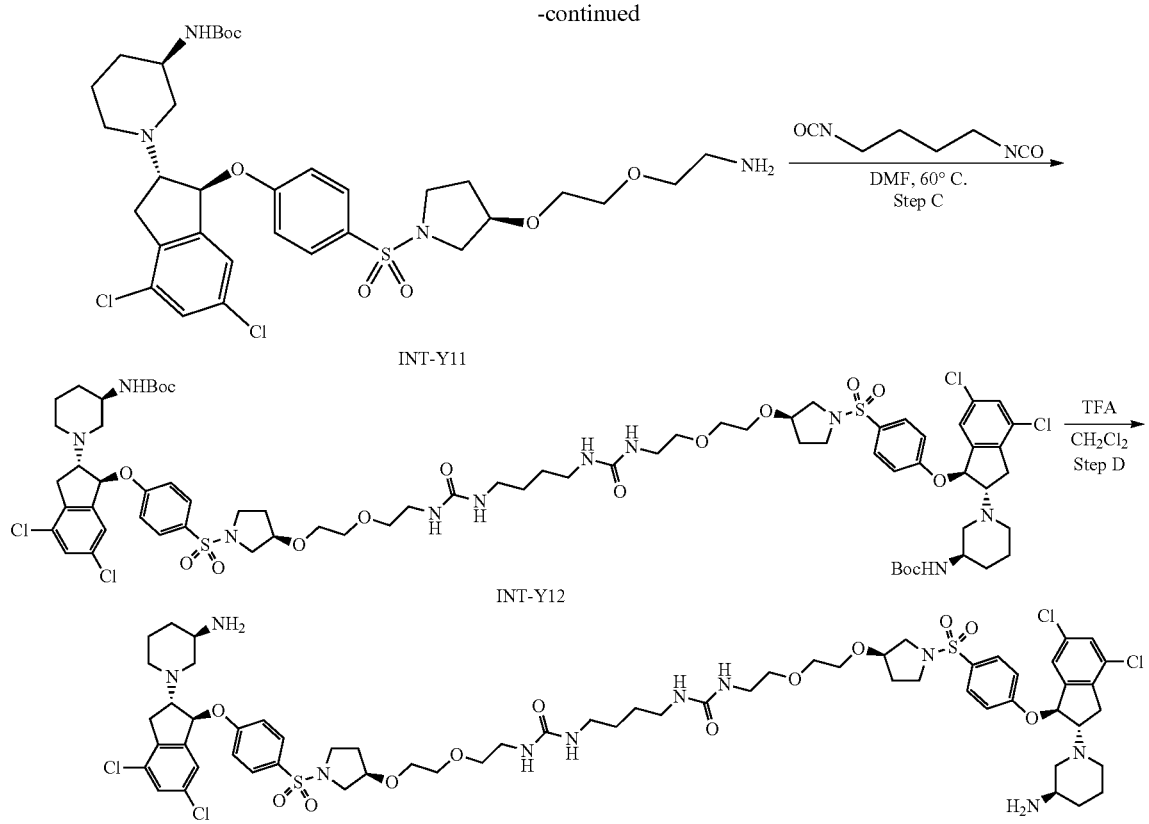

Example 93

Step A: To a 50-mL round-bottom flask was added phenol INT-Y7 (390 mg, 0.91 mmol, 1 equiv), tetrahydrofuran (20 mL), and aminoindanol INT-I8F (369 mg, 0.92 mmol, 1 equiv). This was followed by the addition of PPh$_3$ (480 mg, 1.83 mmol, 2 equiv) in several portions at 0° C. and subsequently DIAD (370 mg, 1.83 mmol, 2 equiv) dropwise at 0° C. The resulting solution was stirred for 40 min at room temperature. The resulting mixture was concentrated under vacuum. The residue was applied onto a silica gel column with CH$_2$Cl$_2$:methanol:triethylamine (100:10:1) providing 2 g of tert-butyl N-[(3R)-1-[(1S,2S)-4,6-dichloro-1-[4-[(3R)-3-[2-[2-(trifluoroacetamido)ethoxy]ethoxy]pyrrolidine-1-sulfonyl] phenoxy]-2,3-dihydro-1H-inden-2-yl]piperidin-3-yl]carbamate (INT-Y10) as a dark oil.

Step B: To a 250-mL round-bottom flask was added INT-Y10 (2 g, 2.47 mmol, equiv) and methanol (60 mL). This was followed by the addition of sodium hydroxide (3 M$_{(aq)}$, 10 mL). The resulting solution was stirred for 1 h at 60° C. The resulting solution was extracted with 2×200 mL of CH$_2$Cl$_2$. The combined organic layers were washed with 1×150 mL of brine, dried over anhydrous sodium sulfate, filtered, and concentrated under vacuum. The residue was applied onto a silica gel column with ethyl acetate/petroleum ether (150:120) providing 370 mg (21%) of tert-butyl N-[(3R)-1-[(1S,2S)-1-[4-[(3R)-3-[2-(2-aminoethoxy) ethoxy]pyrrolidine-1-sulfonyl]phenoxy]-4,6-dichloro-2,3-dihydro-1H-inden-2-yl]piperidin-3-yl]carbamate (INT-Y11) as a light brown oil.

Step C: To a 100-mL round-bottom flask was added amine INT-Y11 (370 mg, 0.52 mmol, 1 equiv), DMF (15 mL), and 1,4-diisocyanatobutane (36.3 mg. 0.26 mmol, 0.5 equiv). The resulting solution was stirred for 1 h at 60° C. The resulting mixture was concentrated under vacuum. The residue was applied onto a silica gel column with CH$_2$Cl$_2$:methanol:triethylamine (100:10:1). This resulted in 210 mg (26%) of tert-butyl N-[(3R)-1-[(1S,2S)-1-[4-[(3R)-3-[2-[2-([[4-([[2-(2-[[(3R)-1-[(4-[[(1S,2S)-2-[(3R)- 3-[[(tert-butoxy)carbonyl]amino]piperidin-1-yl]-4,6-dichloro-2,3-dihydro-1H-inden-1-yl]oxy]benzene)sulfonyl]pyrrolidin-3-yl]oxy]ethoxy)ethyl]carbamoyl]amino)butyl]carbamoyl] amino)ethoxy]ethoxy]pyrrolidine-1-sulfonyl]phenoxy]-4,6-dichloro-2,3-dihydro-1H-inden-2-yl]piperidin-3-yl] carbamate (INT-Y12) as an off-white solid.

Step D: To a 100-mL round-bottom flask was added dimer INT-Y12 (210 mg, 0.13 mmol, 1 equiv), CH$_2$Cl$_2$ (10 mL), and trifluoroacetic acid (1.5 mL). The resulting solution was stirred for 1 h at room temperature. The pH value of the solution was adjusted to 12 with saturated aqueous potassium carbonate and extracted with 2×200 mL of CH$_2$Cl$_2$. The combined organic layers were washed with 1×200 mL of brine and concentrated under vacuum to provide crude compound Example 93.

Example 93: 3-[2-(2-[[(3R)-1-[(4-[[(1S,2S)-2-[(3R)-3-Aminopiperidin-1-yl]-4,6-dichloro-2,3-dihydro-1H-inden-1-yl]oxy]benzene)sulfonyl]pyrrolidin-3-yl]oxy]ethoxy)ethyl]-1-[4-([[2-(2-[[(3R)-1-[(4-[[(1S,2S)-2-[(3R)-3-aminopiperidin-1-yl]-4,6-dichloro-2,3-dihydro-1H-inden-1-yl]oxy]benzene)sulfonyl] pyrrolidin-3-yl]oxy]ethoxy)ethyl]carbamoyl]amino) butyl]urea Crude product of Steps A-D was purified by preparative HPLC with the following conditions: Column, XBridge Shield RP18 OBD Column, 19*150 mm, 5 um; mobile phase, water (0.05% TFA) and CH₃CN (28.0% CH₃CN up to 39.0% in 10 min); Detector, UV 254 nm. This resulted in 81.4 g (38%) of the title compound as an off-white solid. MS (m/z): 1367.33 [M+H]⁺. ¹H NMR (Methanol-d4, 400 MHz) δ 7.86 (d, J=8.8 Hz, 4H), 7.45 (s, 2H), 7.34 (d, 8.8 Hz, 4H), 7.15 (s, 2H), 6.14 (d, 5.6 Hz, 2H), 4.06 (s, 2H), 3.88-3.84 (m, 2H), 3.50-3.40 (m, 16H), 3.40-3.37 (m, 6H), 3.29-3.22 (m, 7H), 3.09-3.03 (m, 8H), 2.86 (s, 2H), 2.75-2.67 (m, 4H), 1.99-1.87 (m, 8H), 1.79-1.68 (m, 2H), 1.64-1.62 (m, 2H), 1.60 (s, 4H), 1.29 (s, 1H).

Example 94: 3-[2-(2-[[(3S)-1-[(4-[[(1S,2S)-2-[(3R)-3-Aminopiperidin-1-yl]-4,6-dichloro-2,3-dihydro-1H-inden-1-yl]oxy] benzene)sulfonyl]pyrrolidin-3-yl]oxy]ethoxy)ethyl]-1-[4-([[2-(2-[[(3S)-1-[(4-[[(1S,2S)-2-[(3R)-3-aminopiperidin-1-yl]-4,6-dichloro-2,3-dihydro-1H-inden-1-yl]oxy]benzene)sulfonyl]pyrrolidin-3-yl]oxy]ethoxy)ethyl]carbamoyl]amino)butyl]urea Example 94

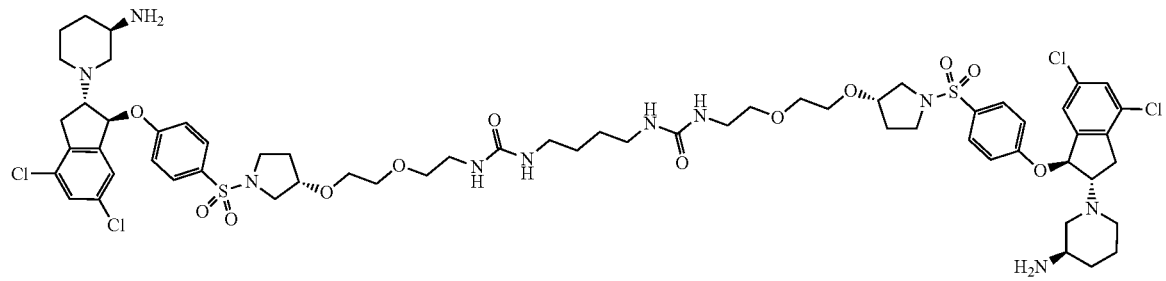

Beginning with INT-I8F and INT-Y8, the crude product of Steps A-D was purified by preparative HPLC with the following conditions: Column, XBridge C18 OBD Preparative Column, 19*250 mm, 5 um; mobile phase, water (0.05% TFA) and CH₃CN (30.0% CH₃CN up to 36.0% in 9 min); Detector, UV 220 nm. This resulted in 22 mg (13%) of the title compound as a brown solid. MS (m/z): 1368 [M+H]⁺. ¹H NMR (Methanol-d4, 400 MHz): δ 7.87 (d, J=8.8 Hz, 5H), 7.46 (s, 2H), 7.35 (d, J=8.8 Hz, 5H), 7.20 (s, 2H), 6.03 (d, J=7.8 Hz, 2H), 4.08 (s, 2H), 3.70 (s, 2H), 3.55 (s, 3H), 3.51-3.49 (m, 11H), 3.49-3.35 (m, 8H), 3.19-2.91 (m, 10H), 2.90-2.80 (m, 2H), 2.70-2.61 (m, 7H), 1.95-1.80 (m, 8H), 1.70-1.48 (m, 5H) 1.40 (s, 4H), 1.32 (s, 2H).

Example 95: 3-[2-[2-([1-[(4-[[(1S,2S)-2-[(3R)-3-Aminopiperidin-1-yl]-4,6-dichloro-2,3-dihydro-1H-inden-1-yl]oxy]benzene)sulfonyl]piperidin-4-yl]oxy)ethoxy]ethyl]-1-[4-[([2-[2-([1-[(4-[[(1S,2S)-2-[(3R)-3-aminopiperidin-1-yl]-4,6-dichloro-2,3-dihydro-1H-inden-1-yl]oxy]benzene)sulfonyl]piperidin-4-yl]oxy)ethoxy]ethyl]carbamoyl)amino]butyl]urea Example 95

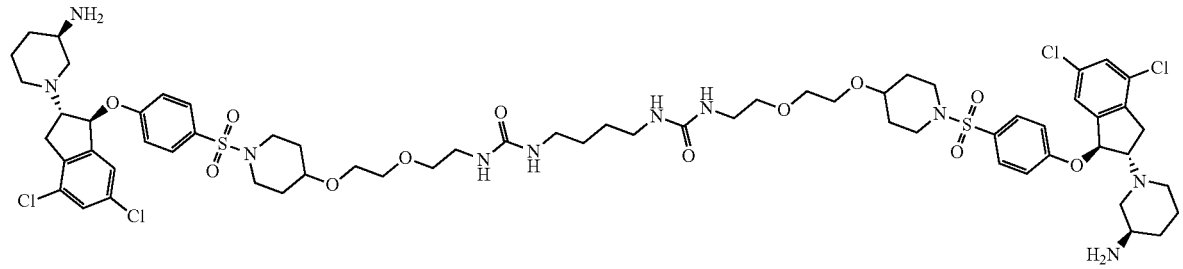

Beginning with INT-I8F and INT-Y9, the crude product of Steps A-D was purified by preparative HPLC with the following conditions: Column, XBridge Shield RP18 OBD Column, 5 um, 19*150 mm, 5 um; mobile phase, water (0.05% TFA) and CH₃CN (29.0% CH₃CN up to 36.0% in 13 min); Detector, UV 254 nm. This resulted in 112.8 mg (28%) of the title compound as an off-white solid. MS (m/z): 1395.4 [M+H]⁺. ¹H NMR (Methanol-d4, 400 MHz): δ 7.80 (d, J=6.8 Hz, 4H), 7.44 (s, 2H), 7.34 (d, J=8.8 Hz, 4H), 7.17 (s, 2H), 6.04 (d, J=5.2 Hz, 2H), 3.75-3.72 (m, 2H), 3.69 (s, 8H), 3.55-3.35 (m, 6H), 3.31-3.21 (m, 11H), 3.13-3.01 (m, 6H), 2.99-2.72 (m, 7H), 2.71 (s, 2H), 2.65-2.60 (m, 6H), 1.93-1.84 (m, 8H), 1.70-1.46 (m, 8H), 1.29 (s, 4H).

Representative Scheme for Synthesis of α-Alkyl-Substituted Sulfonamide Linkers:

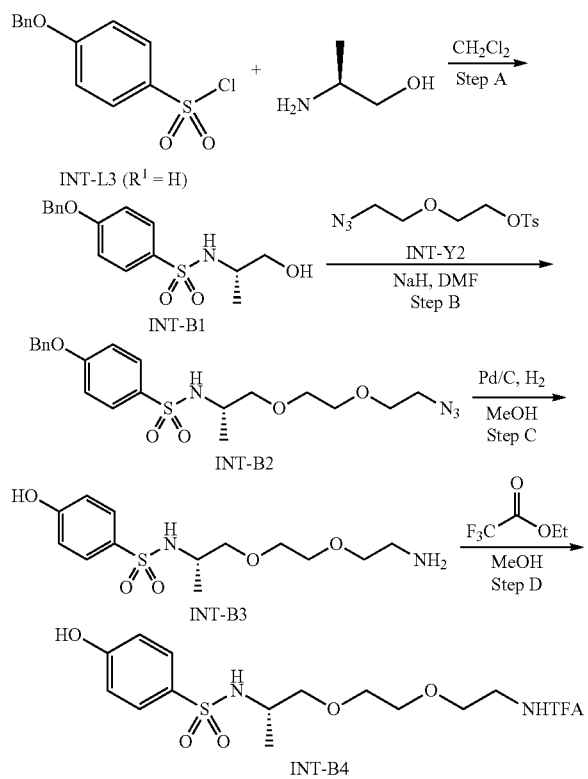

Step A: To a 250-mL round-bottom flask, was added (2S)-2-aminopropan-1-ol (2.1 g, 28 mmol, 4 equiv) and CH₂Cl₂ (50 mL). This was followed by the dropwise addition of a solution of 4-(benzyloxy)benzene-1-sulfonyl chloride (INT-L3 with R¹=H, 2 g, 7.07 mmol, 1 equiv) in CH₂Cl₂ (50 mL). The resulting solution was stirred for 40 min at room temperature. The resulting mixture was concentrated under vacuum. The residue was applied onto a silica gel column with ethyl acetate (100%) providing 2.33 g of (S)-4-(benzyloxy)-N-(1-hydroxypropan-2-yl)benzenesulfonamide (INT-B1) as a white solid.

Step B: To a 250-mL round-bottom flask, was added alcohol INT-B1 (960 mg, 3 mmol, 1 equiv azidotosylate INT-Y2 (870 mg, 3 mmol, 1 equiv), DMF (40 mL), and lastly sodium hydride (360 mg, 15.00 mmol, 5 equiv) in portions. The resulting slurry was stirred overnight at room temperature. The reaction was quenched by the addition of 100 mL of water and extracted with 3×150 mL of ethyl acetate. The combined organic layers were dried over anhydrous sodium sulfate, filtered, and concentrated under vacuum. The residue was applied onto a silica gel column with ethyl acetate/petroleum ether (1:1) providing 300 mg (23%) of N-[(2S)-1-[2-(2-azidoethoxy)ethoxy]propan-2-yl]-4-(benzyloxy)benzene-1-sulfonamide (INT-B2) as a yellow oil.

Step C: To a 250-mL round-bottom flask was added azide INT-B2 (200 mg, 0.46 mmol, 1 equiv), methanol (20 mL), and palladium on carbon (100 mg). Hydrogen gas was introduced into the flask. The resulting slurry was stirred for 3 h at room temperature. The solids were removed by filtration and the filtrate concentrated under vacuum. The residue was applied onto a silica gel column with ethyl acetate (100%) providing 100 mg (68%) of [(2S)-1-[2-(2-aminoethoxy)ethoxy]propan-2-yl]-4-hydroxybenzene-1-sulfonamide (INT-B3) as a colorless oil.

Step D: To a 250-mL round-bottom flask, was added amine INT-B3 (400 mg, 1.26 mmol, 1 equiv), methanol (35 mL), and ethyl 2,2,2-trifluoroacetate (892 mg). The resulting solution was stirred for 30 min at room temperature. The resulting mixture was concentrated under vacuum. The residue was applied onto a silica gel column with ethyl acetate/petroleum ether (1:2) providing 430 mg (83%) of (S)-2,2,2-trifluoro-N-(2-[2-(2-[(4-hydroxyphenyl)sulfonamide]propoxy)ethoxy]ethyl)acetamide (INT-B4) as a light yellow oil.

Other α-alkyl-substituted sulfonamide intermediates were generated from the analogous procedure beginning with the appropriate aminoalcohol starting materials.

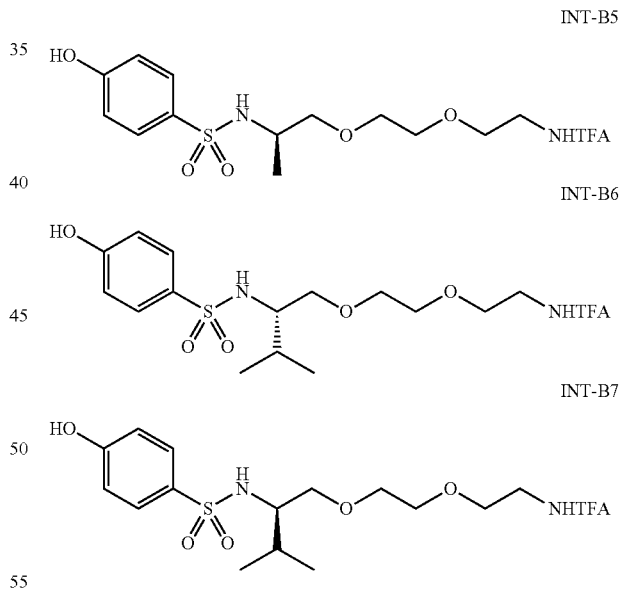

The germinal dimethyl version of these α-alkyl-substituted sulfonamide linkers was made through the following procedure.

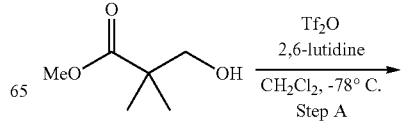

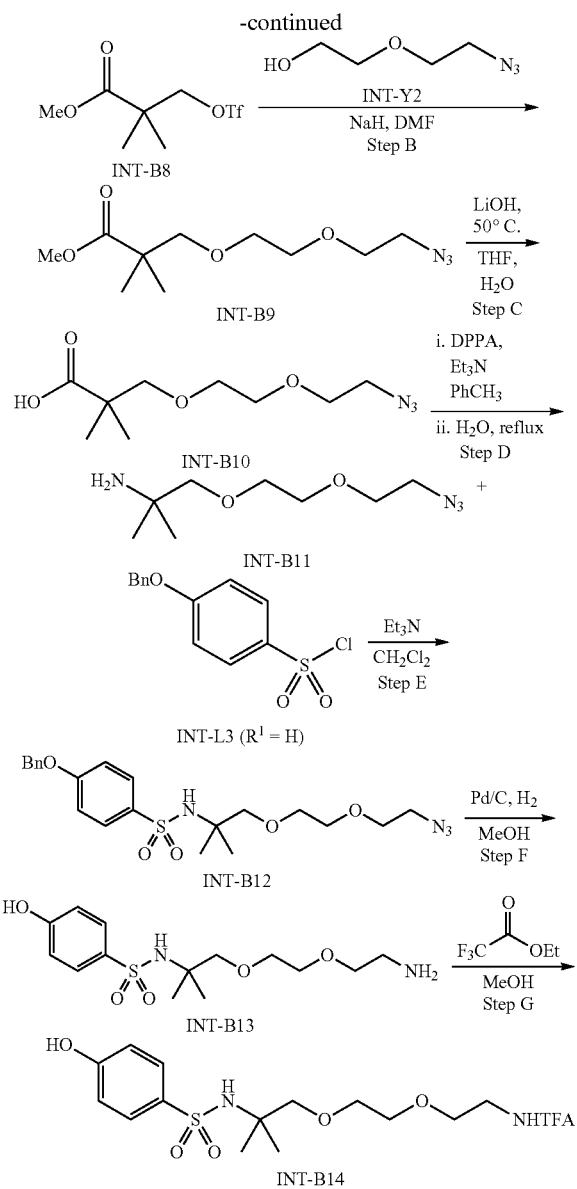

Step A: To a 100-mL 3-necked round-bottom flask purged and maintained with an inert atmosphere of nitrogen was added methyl 3-hydroxy-2,2-dimethylpropanoate (1.32 g, 10 mmol, 1 equiv), CH$_2$Cl$_2$ (40 mL), and 2,6-lutidine (1.6 g, 15 mmol, 1.5 equiv). This was followed by the dropwise addition of triflic anhydride (Tf$_2$O, 3.39 g, 12 mmol, 1.2 equiv) −78° C. The resulting solution was stirred for 15 min at −78° C. and then gradually warmed to room temperature over 3 h. The resulting solution was diluted with 100 mL of ethyl acetate and sequentially washed with 1×50 mL of water, 2×40 mL of 2 M hydrogen chloride, and 2×40 mL of brine. The mixture was dried over anhydrous sodium sulfate, filtered, and concentrated under vacuum. This resulted in 2.64 g (100% crude) of methyl 2,2-dimethyl-3-[(trifluoromethane)sulfonyloxy]propanoate INT-98 as a brown oil.

Step B: To a 100-mL round-bottom flask was added triflate INT-B8 (2.64 g, 10 mmol, 2 equiv), 2-(2-azidoethoxy)ethan-1-ol (INT-Y2, 650 mg, 5 mmol, 1 equiv), and DMF (40 mL). This was followed by the addition of sodium hydride (60% in oil, 400 mg, 10 mmol, 2 equiv) in portions at 0° C. The resulting slurry was stirred for 14 h at room temperature. The reaction was quenched by the slow addition of 100 mL of water and extracted with 3×50 mL of ethyl acetate. The combined organic layers were washed with 1×100 mL of water and 1×100 mL of brine, dried over anhydrous sodium sulfate, filtered, and concentrated under vacuum. This resulted in 1.23 g (100% crude) of methyl 3-[2-(2-azidoethoxy)ethoxy]-2,2-dimethylpropanoate (INT-B9) as a brown oil.

Step C: To a 100-mL round-bottom flask was added ester INT-B9 (3.68 g, 15 mmol, 1 equiv), tetrahydrofuran (30 mL), and water (20 mL). This was followed by the addition of LiOH—H$_2$O (1.26 g, 30 mmol, 2 equiv) in portions at room temperature. The resulting solution was stirred for 4 h at 50° C. The reaction mixture was cooled to room temperature and diluted with of water. The volatiles were removed under vacuum and the resulting mixture washed with 2×30 mL of petroleum ether. The pH of the aqueous layer was adjusted to 1-2 with 3 M aqueous hydrogen chloride and extracted with 3×40 mL of CH$_2$Cl$_2$. The combined organic layers were washed with 1×50 mL of water and 1×50 mL of brine, dried over anhydrous sodium sulfate, filtered, and concentrated under vacuum. This resulted in 2.4 g (69% crude) of 3-[2-(2-azidoethoxy)ethoxy]-2,2-dimethylpropanoic acid (INT-B10) as a light yellow oil.

Step D: To a 100-mL round-bottom flask was added carboxylic acid INT-B10 (2.4 g, 10.4 mmol, 1 equiv), toluene (30 mL), and triethylamine (2.1 g, 20.8 mmol, 2 equiv). This was followed by the dropwise addition of DPPA (4.1 g, 14.9 mmol, 1.5 equiv) with stirring at room temperature. The resulting solution was stirred for 1 h at room temperature. Water (10 mL) was added and the resulting slurry allowed to react with stirring for an additional 14 h at reflux. The resulting solution was diluted with 40 mL of water and hydrogen chloride (3 M$_{(aq)}$, 20 mL). The resulting mixture was washed with 1×50 mL of petroleum ether. The pH value of the aqueous layer was adjusted to 13-14 with sodium hydroxide and extracted with 3×50 mL of CH$_2$Cl$_2$. The combined organic layers were washed with 1×50 mL of water and 1×50 mL of brine, dried over anhydrous sodium sulfate, filtered, and concentrated under vacuum. This resulted in 1.5 g (71% crude) of 1-(2-amino-2-methylpropoxy)-2-(2-azidoethoxy)ethane (INT-B11) as a light yellow oil.

Step E: To a 100-mL round-bottom flask was amine INT-B11 (1.5 g, 7.42 mmol, 1.5 equiv), CH$_2$Cl$_2$ (40 mL), and triethylamine (1.5 g, 14.8 mmol, 2 equiv). This was followed by the addition of 4-(benzyloxy)benzene-1-sulfonyl chloride (INT-L3 with 1.41 g, 5 mmol, 1 equiv) in portions at room temperature. The resulting solution was stirred overnight at room temperature. The resulting solution was diluted with 200 mL of ethyl acetate and washed with 2×100 mL of water and 1×100 mL of brine. The mixture was dried over anhydrous sodium sulfate, filtered, and concentrated under vacuum. The residue was applied onto a silica gel column with petroleum ether/ethyl acetate (8:1-2:1) providing 1.8 g (80%) of N-[1-[2-(2-azidoethoxy)ethoxy]-2-methylpropan-2-yl]-4-(benzyloxy)benzene-1-sulfonamide (INT-B12) as a light yellow oil.

Step F: To a 100-mL round-bottom flask was added azide INT-B12 (1.8 g, 4.0 mmol, 1 equiv), methanol (40 mL), and palladium on carbon (180 mg, 0.10 equiv). To the above, hydrogen (1 atm) was introduced in and the resulting slurry stirred overnight at room temperature. The solids were filtered out. The resulting mixture was concentrated under vacuum providing 1.33 g (100%) of N-[1-[2-(2-aminoethoxy)ethoxy]-2-methylpropan-2-yl]-4-hydroxybenzene-1-sulfonamide (INT-B13) as a colorless oil.

Step G: To a 100-mL round-bottom flask was added amine INT-B13 (1.33 g, 4.0 mmol, 1 equiv) and CH$_2$Cl$_2$ (40 Ml) followed by the dropwise addition of ethyl 2,2,2-trifluoroacetate (2.84 g, 20 mmol, 5 equiv) at room temperature. To this was added triethylamine (40 mg, 0.40 mmol, 0.1 equiv). The resulting solution was stirred for 1 h at room temperature. The resulting mixture was concentrated under vacuum. The residue was applied onto a silica gel column with petroleum ether/ethyl acetate (4:1-2:1) providing 1.57 g, (92%) of 2,2,2-trifluoro-N-[2-(2-[2-[(4-hydroxybenzene) sulfonamido]-2-methylpropoxy]ethoxy)ethyl]acetamide (INT-B14) as a light yellow oil.

Representative Scheme for Synthesis of α-Alkyl-Substituted Dimer Products:

Example 96: 1-(2-[2-[(2S)-2-[(4-[[(1S,2S)-2-[(3R)-3-Aminopiperidin-1-yl]-4,6-dichloro-2,3-dihydro-1H-inden-1-yl]oxy]benzene)sulfonamido]propoxy] ethoxy]ethyl)-3-(4-[[(2-[2-[(2S)-2-[(4-[[(1S,2S)-2-[(3R)-3-aminopiperidin-1-yl]-4,6-dichloro-2,3-dihydro-1H-inden-1-yl]oxy]benzene)sulfonamido] propoxy]ethoxy]ethyl)carbamoyl]amino]butyl)urea; hydrochloride

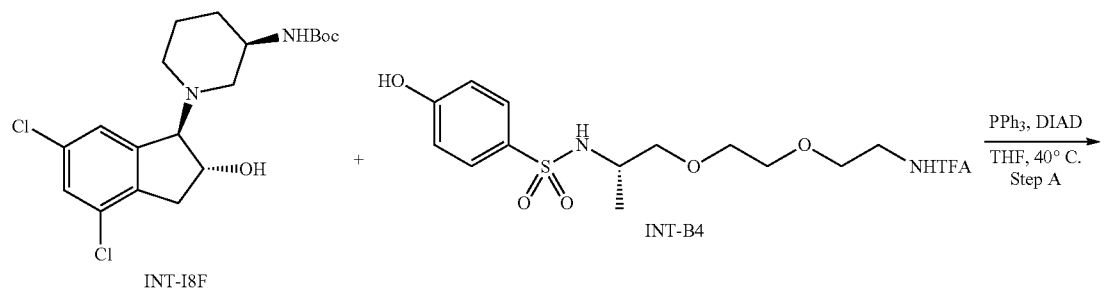

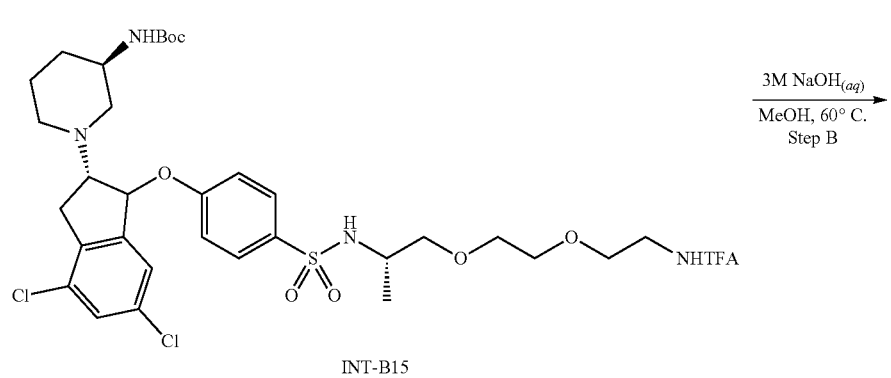

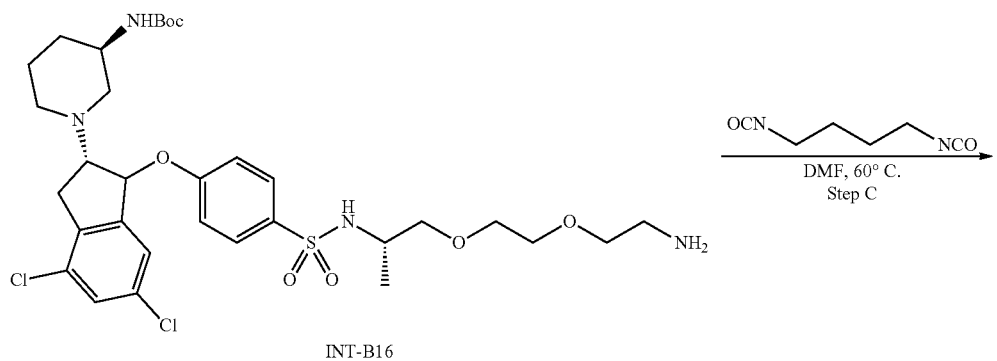

-continued

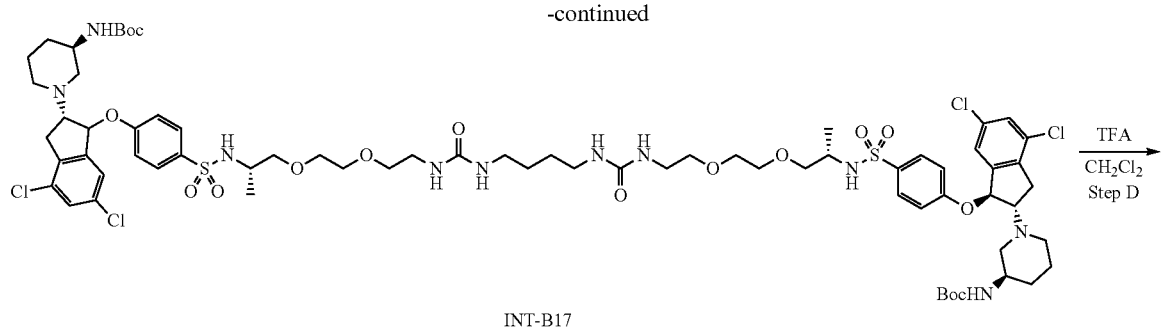

INT-B17

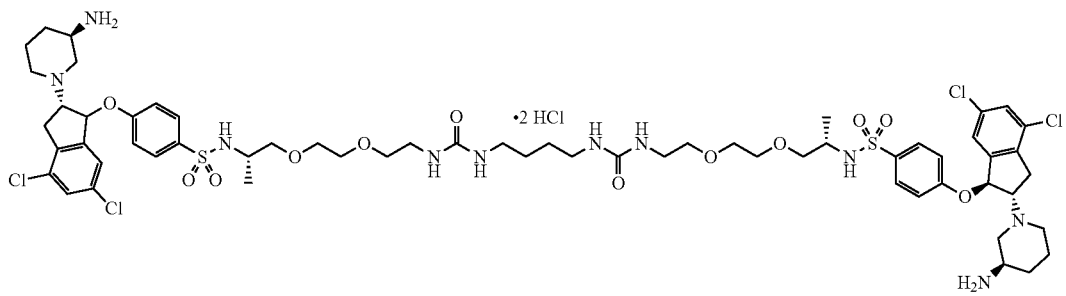

Example 96

Step A: To a 100-mL round-bottom flask was added phenol INT-B4 (430 mg, 1.04 mmol, 1 equiv), tetrahydrofuran (25 mL), aminoindanol INT-I8F (416 mg, 1.04 mmol, 1 equiv), and PPh$_3$ (408 mg, 1.56 mmol, 1.5 equiv). This was followed by the dropwise addition of a solution of DIAD (314 mg, 1.55 mmol, 1.5 equiv) in tetrahydrofuran (2 mL) over 20 min. The resulting solution was stirred for 40 min at 40° C. The resulting mixture was concentrated under vacuum. The residue was applied onto a silica gel column with ethyl acetate (100%) providing 1 g of tert-butyl N-[(3R)-1-[(1S,2S)-4,6-dichloro-1-(4-[[(2S)-1-[2-[2-(trifluoroacetamido)ethoxy]ethoxy]propan-2-yl]sulfamoyl]phenoxy)-2,3-dihydro-1H-inden-2-yl]piperidin-3-yl]carbamate (INT-B15) as a brown oil.

Step B: To a 250-mL round-bottom flask was added INT-B15 (1 g, 1.25 mmol, 1 equiv) and methanol (50 mL) followed by the addition of sodium hydroxide (3 M$_{(aq)}$, 8 mL). The resulting solution was stirred for 45 min at 60° C. The resulting slurry was extracted with 3×150 mL of CH$_2$Cl$_2$. The combined organic layers were dried over anhydrous sodium sulfate, filtered, and concentrated under vacuum. This resulted in 230 mg (26%) of tert-butyl N-[(3R)-1-[(1S,2S)-1-(4-[[(2S)-1-[2-(2-aminoethoxy)ethoxy]propan-2-yl]sulfamoyl]phenoxy)-4,6-dichloro-2,3-dihydro-1H-inden-2-yl]piperidin-3-yl]carbamate (INT-B16) as a light yellow solid.

Step C: To a 100-mL round-bottom flask was added amine monomer INT-B16 (230 mg, 0.33 mmol, 1 equiv), DMF (20 mL), and 1,4-diisocyanatobutane (23 mg, 0.16 mmol, 0.5 equiv). The resulting solution was stirred for 1 h at 60° C. The resulting mixture was concentrated under vacuum. The residue was applied onto a silica gel column with CH$_2$Cl$_2$/methanol (10:1) providing 150 mg (30%) of tert-butyl N-[(3R)-1-[(1S,2S)-1-(4-[[(2S)-1-[2-(2-[[(4-[[(2-[2-[(2S)-2-[(4-[[(1S,2S)-2-[(3R)-3-[[(tert-butoxy)carbonyl]amino]piperidin-1-yl]-4,6-dichloro-2,3-dihydro-1H-inden-1-yl]oxy]benzene)sulfonamido]propoxy]ethoxy]ethyl)carbamoyl]amino]butyl)carbamoyl]amino]ethoxy)ethoxy]propan-2-yl]sulfamoyl]phenoxy)-4,6-dichloro-2,3-dihydro-1H-inden-2-yl]piperidin-3-yl]carbamate (INT-B17) as a light brown solid.

Step D: To a 100-mL round-bottom flask was added Boc-dimer B17 (150 mg, 0.10 mmol, 1 equiv), CH$_2$Cl$_2$ (10 mL), and trifluoroacetic acid (1.5 mL). The resulting solution was stirred for 1 h at room temperature. The pH value of the solution was adjusted to 12 with saturated aqueous potassium carbonate and extracted with 100 mL of CH$_2$Cl$_2$. The organic layer was washed with 2×100 mL of brine, dried over anhydrous sodium sulfate, filtered, and concentrated under vacuum to provide crude compound Example 96.

Example 96: 1-(2-[2-[(2S)-2-[(4-[[(1S,2S)-2-[(3R)-3-Aminopiperidin-1-yl]-4,6-dichloro-2,3-dihydro-1H-inden-1-yl]oxy]benzene)sulfonamido]propoxy]ethoxy]ethyl)-3-(4-[[(2-[2-[(2S)-2-[(4-[[(1S,2S)-2-[(3R)-3-aminopiperidin-1-yl]-4,6-dichloro-2,3-dihydro-1H-inden-1-yl]oxy]benzene)sulfonamido]propoxy]ethoxy]ethyl)carbamoyl]amino]butyl)urea; hydrochloride Crude product of Steps A-D was purified by preparative HPLC with the following conditions: Column, XBridge Preparative C18 OBD Column, 19*150 mm, 5 um; mobile phase, water (0.05% HCl) and CH$_3$CN (25.0% CH$_3$CN up to 55.0% in 10 min); Detector, UV 254 nm. This resulted in 20.8 mg (16%) of the title compound as a light yellow solid. MS (m/z): 1343.7 [M+H]$^+$. $^1$H NMR (Methanol-d4, 400 MHz) δ 7.96 (d, J=8.8 Hz, 4H), 7.52 (s, 2H), 7.40 (d, J=8.8 Hz, 4H), 7.04 (s, 2H), 6.78 (d, J=4.0 Hz, 2H), 4.60-4.42 (m, 2H), 3.90-3.66 (m, 8H), 3.55-3.49 (m, 18H), 3.32-3.10 (m, 10H), 3.09 (s, 4H), 2.28-2.00 (m, 6H), 1.78-1.66 (m, 2H), 1.46 (s, 4H), 1.30-1.28 (m, 1H), 1.07 (d, J=6.4 Hz, 6H).

Example 97: 3-(2-[2-[(2R)-2-[(4-[[(1S,2S)-2-[(3R)-3-Aminopiperidin-1-yl]-4,6-dichloro-2,3-dihydro-1H-inden-1-yl]oxy]benzene)sulfonamido]propoxy]ethoxy]ethyl)-1-(4-[[(2-[2-[(2R)-2-[(4-[[(1S,2S)-2-[(3R)-3-aminopiperidin-1-yl]-4,6-dichloro-2,3-dihydro-1H-inden-1-yl]oxy]benzene)sulfonamido]propoxy]ethoxy]ethyl)carbamoyl]amino]butyl)urea Example 97

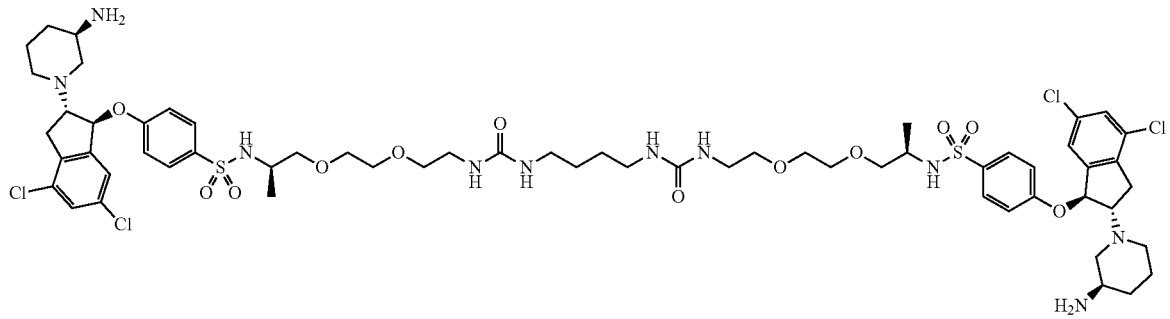

Beginning with INT-I8F and INT-B5, the crude product of Steps A-D was purified by preparative HPLC with the following conditions: Column, XBridge C18 OBD Preparative Column, 19*250 mm, 5 um; mobile phase, waters (0.05% TFA) and CH$_3$CN (17.0% CH$_3$CN up to 60.0% in 8 min); Detector, UV 254 nm. This resulted in 150.7 mg (43%) of the title compound as a white solid. MS (m/z): 1343.25 [M+H]$^+$. $^1$H NMR (Methanol-d4, 400 MHz) δ 7.96-7.86 (m, 4H), 7.45 (d, J=1.6 Hz, 2H), 7.30 (d, J=8.8 Hz, 4H), 7.12 (s, 2H), 6.20 (d, J=5.6 Hz, 2H), 3.92-3.78 (m, 2H), 3.56-3.50 (m, 12H), 3.50-3.30 (m, 8H), 3.29-3.26 (m, 6H), 3.13-3.04 (m, 8H), 3.04-2.82 (m, 2H), 2.78-2.73 (m, 4H), 1.96-1.88 (m, 4H), 1.63-1.61 (m, 2H), 1.61-1.55 (m, 2H), 1.44 (s, 4H), 1.06 (d, J=6.4 Hz, 6H).

Example 98: 3-(2-[2-[(2S)-2-[(4-[[(1S,2S)-2-[(3R)-3-Aminopiperidin-1-yl]-4,6-dichloro-2,3-dihydro-1H-inden-1-yl]oxy]benzene)sulfonamido]-3-methylbutoxy]ethoxy]ethyl)-1-(4-[[(2-[2-[(2S)-2-[(4-[[(1S,2S)-2-[(3R)-3-aminopiperidin-1-yl]-4,6-dichloro-2,3-dihydro-1H-inden-1-yl]oxy]benzene)sulfonamido]-3-methylbutoxy]ethoxy]ethyl)carbamoyl]amino]butyl)urea dihydrochloride Example 98

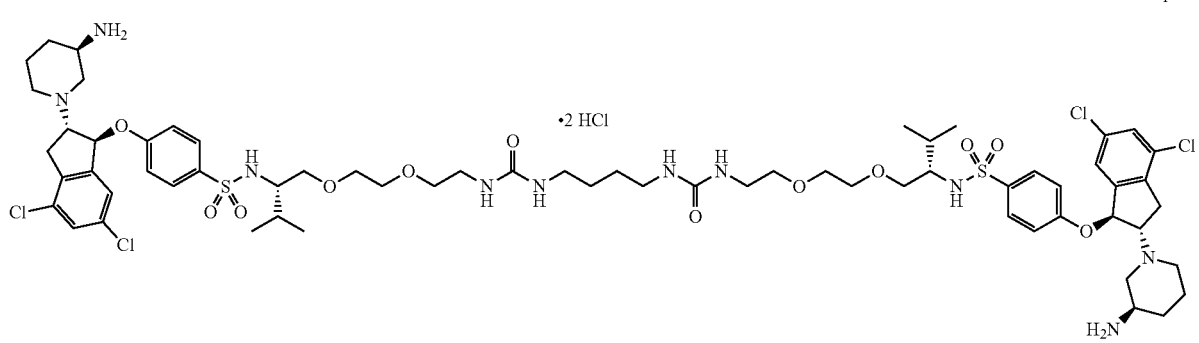

Beginning with INT-I8F and INT-B6, the crude product of Steps A-D was purified by preparative HPLC with the following conditions: Column, XBridge Preparative C18 OBD Column, 19*150 mm, 5 um; mobile phase, water (0.05% HCl) and CH₃CN (40.0% CH₃CN up to 60.0% in 10 min); Detector, UV 254 nm. This resulted in 82.8 mg (18%) of the title compound as a white solid. MS (m/z): 1400 [M+H]⁺. ¹H NMR (Methanol-d4, 400 MHz) δ 7.98 (d, J=8.4 Hz, 4H), 7.55 (s, 2H), 7.42 (d, J=8.4 Hz, 4H), 7.05 (s, 2H), 6.86 (d, J=6.4 Hz, 2H), 4.57 (q, J=8.0 Hz, 2H), 3.84-3.71 (m, 8H), 3.59-3.27 (m, 24H), 3.22 (q, J=5.4 Hz, 2H), 3.12 (s, 4H), 2.33-2.19 (m, 6H), 1.97-1.69 (m, 4H), 1.50 (s, 4H), 0.90 (t, J=6.4 Hz, 12H).

Example 99: 3-(2-[2-[(2R)-2-[(4-[[(1S,2S)-2-[(3R)-3-Aminopiperidin-1-yl]-4,6-dichloro-2,3-dihydro-1H-inden-1-yl]oxy]benzene)sulfonamido]-3-methylbutoxy]ethoxy]ethyl)-1-(4-[[(2-[2-[(2R)-2-[(4-[[(1S,2S)-2-[(3R)-3-aminopiperidin-1-yl]-4,6-dichloro-2,3-dihydro-1H-inden-1-yl]oxy]benzene)sulfonamido]-3-methylbutoxy]ethoxy]ethyl)carbamoyl]amino]butyl)urea Example 99

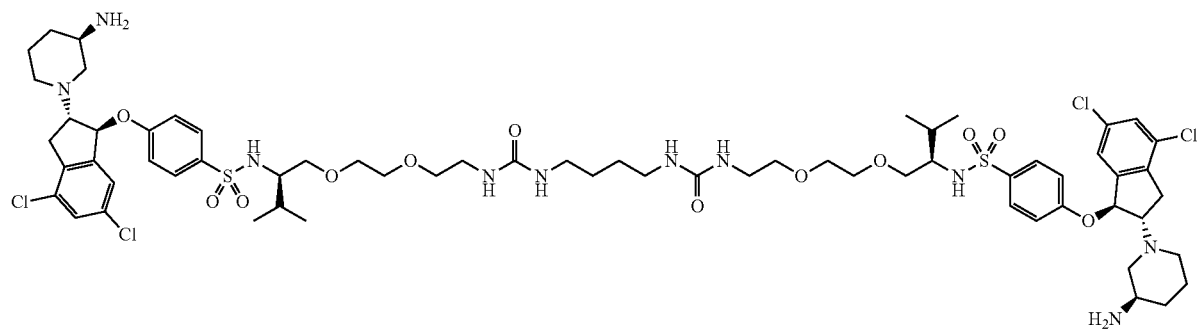

Beginning with INT-I8F and INT-B7, the crude product of Steps A-D was purified by preparative HPLC with the following conditions: Column, XBridge Shield RP18 OBD Column, 19*150 mm, 5 um; mobile phase, water (0.05% TFA) and CH₃CN (30.0% CH₃CN up to 47.0% in 8 min); Detector, UV 254 nm. This resulted in 48.6 mg (56%) of the title compound as a white solid. MS (m/z): 1400 [M+H]⁺. ¹H NMR (Methanol-d4, 400 MHz): δ 7.95-7.87 (d, J=9.2 Hz, 4H), 7.46 (d, J=1.6 Hz, 2H), 7.30 (d, J=6.4 Hz, 4H), 7.14 (s, 2H), 6.15 (d, J=8.8 Hz, 2H), 3.80 (q, J=5.6 Hz, 2H), 3.56-3.34 (m, 18H), 3.34-3.26 (m, 4H), 3.22-3.18 (m, 2H), 3.13-2.99 (m, 8H), 2.83 (s, 2H), 2.78-2.66 (m 4H), 2.03-1.82 (m, 6H), 1.79-1.57 (m, 4H), 1.46 (s, 4H), 0.89 (t, J=6.4 Hz, 12H).

Example 100: 1-[2-(2-[2-[(4-[[(1S,2S)-2-[(3R)-3-Aminopiperidin-1-yl]-4,6-dichloro-2,3-dihydro-1H-inden-1 yl]oxy]benzene)sulfonamido]-2-methylpropoxy]ethoxy)ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]benzene)sulfonamido]-2-methylpropoxy]ethoxy)ethyl]carbamoyl]amino)butyl]urea; hydrochloride Example 100

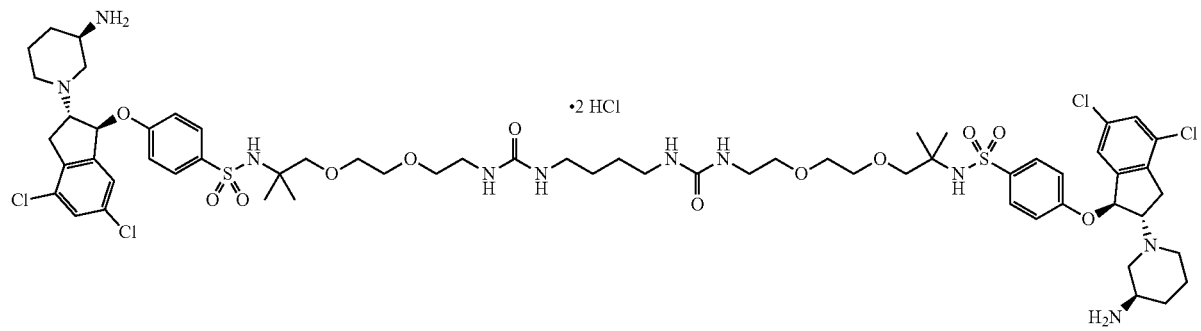

Beginning with INT-I8F and INT-B14 the crude product of Steps A-D was purified by preparative HPLC with the following conditions: Column, XBridge Preparative C18 OBD Column, 19*150 mm, 5 um; mobile phase, water (0.05% HCl) and CH$_3$CN (30% CH$_3$CN up to 60% in 10 min); Detector, UV 254 nm. This resulted in 217.6 mg (45%) of the title compound as a light yellow solid. MS (m/z): 1371.25 [M+H]$^+$. $^1$H NMR (Methanol-d$_4$, 400 MHz) δ 7.99 (d, J=8.8 Hz, 4H), 7.54 (s, 2H), 7.42 (d, J=8.8 Hz, 4H), 7.05 (s, 2H), 6.85 (d, J=6.0 Hz, 2H), 4.55 (q, J=7.8 Hz, 2H), 3.92-3.73 (m, 8H), 3.64-3.56 (m, 12H), 3.47 (q, J=8.2 Hz, 2H), 3.42-3.29 (m, 14H), 3.10 (s, 4H), 2.26-2.12 (m, 6H), 1.85-1.70 (m, 2H), 1.48 (s, 4H), 1.23 (s, 12H).

General Scheme for Synthesis of Ortho-Substituted Sulfonamide Dimer Products:

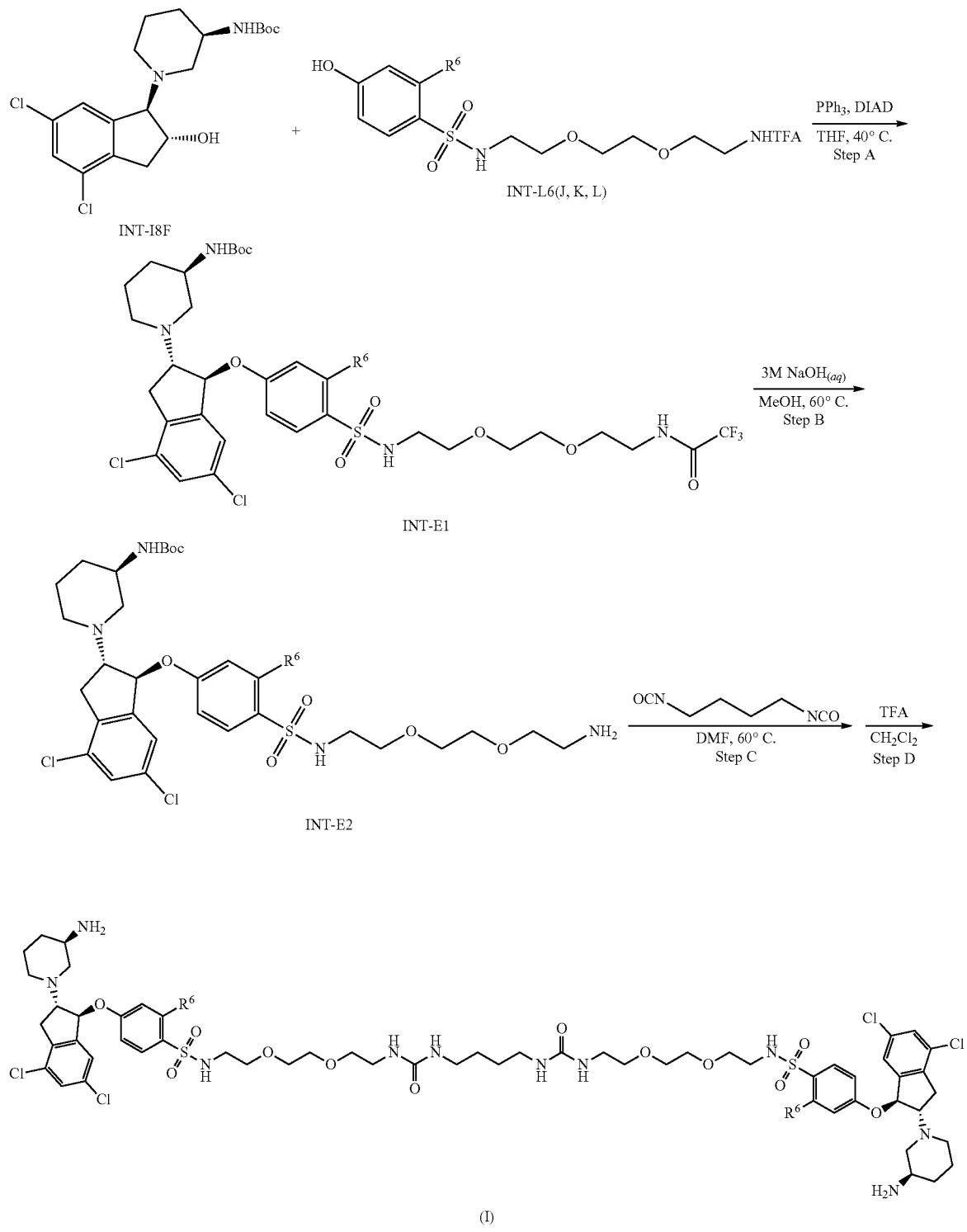

Step A: To a round-bottom flask was added aminoindanol INT-I8F (1 equiv) and tetrahydrofuran (0.2 M), followed by the addition of phenol linker INT-L6 (1.1 equiv) and heating to 40° C. To this slurry was added PPh₃ (2 equiv) and DIAD (1.5 equiv). The resulting solution was stirred for 1-3 h at 40° C. The resulting mixture was concentrated under vacuum and diluted with CH₂Cl₂. The residue was applied onto a silica gel column with petroleum ether/ethyl acetate (1:1) providing indane monomer INT-E1.

Step B: To a round-bottom flask was added indane monomer INT-E1 (1 equiv), methanol (0.1 M), and sodium hydroxide (3 M$_{(aq)}$, 3-5 equiv). The resulting solution was stirred for 1-2 h at 60° C. The resulting mixture was concentrated under vacuum and diluted with CH₂Cl₂. The residue was applied onto a silica gel column with CH₂Cl₂/methanol (10:1) providing indane amine monomer INT-D2.

Step C: To a round-bottom flask was added INT-E2 (1 equiv), N,N-dimethylformamide (DMF, 0.1 M), and 1,4-diisocyanatobutane (0.4-0.5 equiv). The resulting solution was stirred for 2 h at 60° C. The resulting mixture was concentrated under vacuum and diluted with of CH₂Cl₂. The residue was applied onto a silica gel column with chloroform methanol (10:1) providing the desired dimer of structure (I). Final products were purified by preparative HPLC. The final products were generally isolated as the free based amines, TFA salts, or hydrochloride salts.

Step D: To a round-bottom flask was added Boc-protected dimer (I) (1 equiv) and 5:1 CH₂Cl₂:TFA (~0.05 M). The resulting solution was stirred for 2 h at room temperature. The resulting mixture was concentrated under vacuum. The crude product was purified by preparative HPLC. The final products were generally isolated as the free based amines, TFA salts, or hydrochloride salts.

Example 101: 1-[2-(2-[2-[(4-[[(1S,2S)-2-[(3R)-3-Aminopiperidin-1-yl]-4,6-dichloro-2,3-dihydro-1H-inden-1-yl]oxy]-2-methoxybenzene)sulfonamido]ethoxy]ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]-2-methoxybenzene)sulfonamido]ethoxy]ethoxy)ethyl]carbamoyl]amino)butyl]urea Example 101

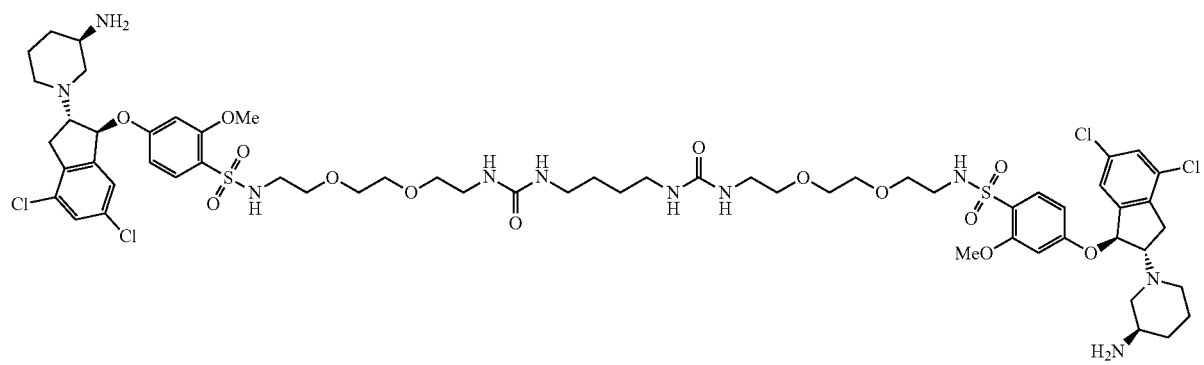

Beginning with INT-L6J and INT-I8F, Steps A-D provided Example 101 which was purified by preparative HPLC with the following conditions: Column, XBridge Shield RP18 OBD Column, 19*150 mm, 5 um, mobile phase, water (0.05% TFA) and CH₃CN (15.0% CH₃CN up to 50.0% in 8 min); Detector, UV 254 nm. This resulted in 0.146 g (100%) of the title compound as a white solid. MS (m/z): 1375.80 [M+H]⁺. ¹H NMR (Methanol-d₄, 400 MHz): δ 7.83 (d, J=8.8 Hz, 2H), 7.44 (s, 2H), 7.18 (s, 2H), 6.93-6.86 (m, 4H), 6.05 (s, 2H), 3.96 (s, 6H), 3.70 (s, 2H), 3.60-3.53 (m, 9H), 3.51-3.48 (m, 9H), 3.40-3.31 (m, 8H), 3.12-3.09 (m, 6H), 3.03 (t, J=5.4 Hz, 6H), 2.71 (d, J=8.0 Hz, 2H), 2.62-2.58 (m, 4H), 1.96-1.91 (m, 2H), 1.84 (s, 2H), 1.80-1.68 (m, 2H), 1.65-1.50 (m, 2H), 1.46 (s, 4H).

Example 102: 3-[2-(2-[2-[(4-[[(1S,2S)-2-[(3R)-3-Aminopiperidin-1-yl]-4,6-dichloro-2,3-dihydro-1H-inden-1-yl]oxy]-2-methylbenzene)sulfonamido]ethoxy]ethoxy)ethyl]-1-[4-([[2-(2-[2-[(4-[[(1S,2S)-2-[(3R)-3-aminopiperidin-1-yl]-4,6-dichloro-2,3-dihydro-1H-inden-1-yl]oxy]-2-methylbenzene)sulfonamido]ethoxy]ethoxy)ethyl]carbamoyl]amino)butyl]urea Example 102

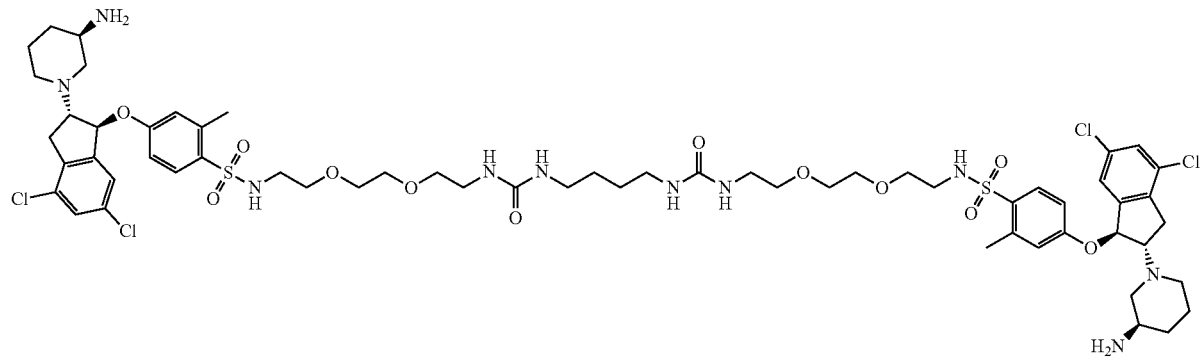

Beginning with INT-L6K and INT-I8F, Steps A-D provided Example 102 which was purified by preparative HPLC with the following conditions: Column, XSelect CSH Preparative C18 OBD Column, 19*150 mm, 5 um; mobile phase, water (0.05% TFA) and $CH_3CN$ (25.0% $CH_3CN$ up to 37.0% in 10 min); Detector, UV 254 nm. This resulted in 30.4 mg (20%) of the title compound as a solid. MS (m/z): 1343.4 [M+H]$^+$. $^1$H NMR (Methanol-d4, 400 MHz) δ 7.95 (d, J=8.8 Hz, 2H), 7.46 (s, 2H), 7.19-7.11 (m, 6H), 6.12 (d, J=5.8 Hz, 2H), 3.78 (q, J=7.4 Hz, 2H), 3.63-3.45 (m, 17H), 3.41-3.35 (m, 2H), 3.35-3.25 (m, 8H), 3.13-3.05 (m, 8H), 3.05-2.98 (m, 4H), 2.85 (s, 2H), 2.70-2.60 (m, 9H), 2.00-1.85 (m, 4H), 1.73 (d, J=9.0 Hz, 2H), 1.59 (d, J=8.8 Hz, 2H), 1.46 (s, 4H), 1.33 (t, J=8.8 Hz, 2H).

Example 103: 1-[2-(2-[2-[(4-[[(1S,2S)-2-[(3R)-3-Aminopiperidin-1-yl]-4,6-dichloro-2,3-dihydro-1H-inden-1-yl]oxy]-2-fluorobenzene)sulfonamido]ethoxy]ethoxy)ethyl]-3-[4-([[2-(2-[2-[(4-[[(1S,2S)-2-[(3R)-3-aminopiperidin-1-yl]-4,6-dichloro-2,3-dihydro-1H-inden-1-yl]oxy]-2-fluorobenzene)sulfonamido]ethoxy]ethoxy)ethyl]carbamoyl]amino)butyl]urea Example 103

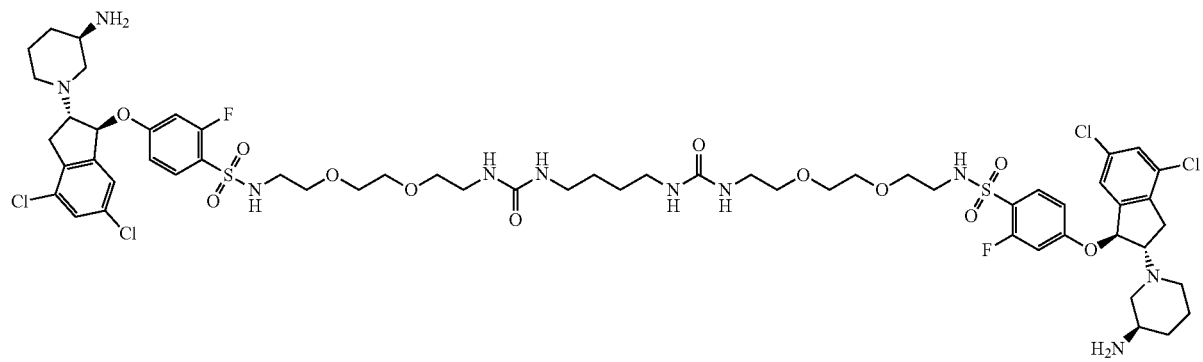

Beginning with INT-L6L and INT-I8F, Steps A-D provided Example 103 which was purified by preparative HPLC with the following conditions: Column, XSelect CSH Preparative C18 OBD Column, 19*150 mm, 5 um; mobile phase, water (0.05% TFA) and $CH_3CN$ (23.0% $CH_3CN$ up to 41.0% in 8 min); Detector, UV 254 nm. This resulted in 53.2 mg (69%) of the title compound as a white solid. MS (m/z): 1351.75 [M+H]$^+$. $^1$H NMR (Methanol-d4, 400 MHz) δ 7.88 (t, J=8.6 Hz, 2H), 7.47 (d, J=1.8 Hz, 2H), 7.23-7.10 (m, 6H), 6.11 (d, J=16.4 Hz, 2H), 3.76 (s, 2H), 3.63-3.49 (m, 16H), 3.42-3.36 (m, 4H), 3.36-3.29 (m, 6H), 3.29-3.20 (m, 4H), 3.20-3.10 (m, 4H), 3.10-2.96 (m, 4H), 2.96-2.56 (m, 6H), 1.94 (d, J=32.2 Hz, 4H), 1.66 (d, J=46.6 Hz, 4H), 1.49 (s, 4H).

Scheme for Synthesis of Example 104
Example 104: 4-([(1S,2S)-2-[(R)-3-Aminopiperidin-1-yl]-1,6-dichloro-2,3-dihydro-1H-inden-1-yl]oxy)-N-[26-([(4-([(1S,2S)-2-[(R)-3-aminopiperidin-1-yl]-4,6-dichloro-2,3-dihydro-1H-inden-1-yl]oxy)-2-chlorophenyl]sulfonamido)-10,17-dioxo-3,6,21,24-tetraoxa-9,11,16,18-tetraazahexacosyl]-2-chlorobenzenesulfonamide; bis(trifluroacetic acid)
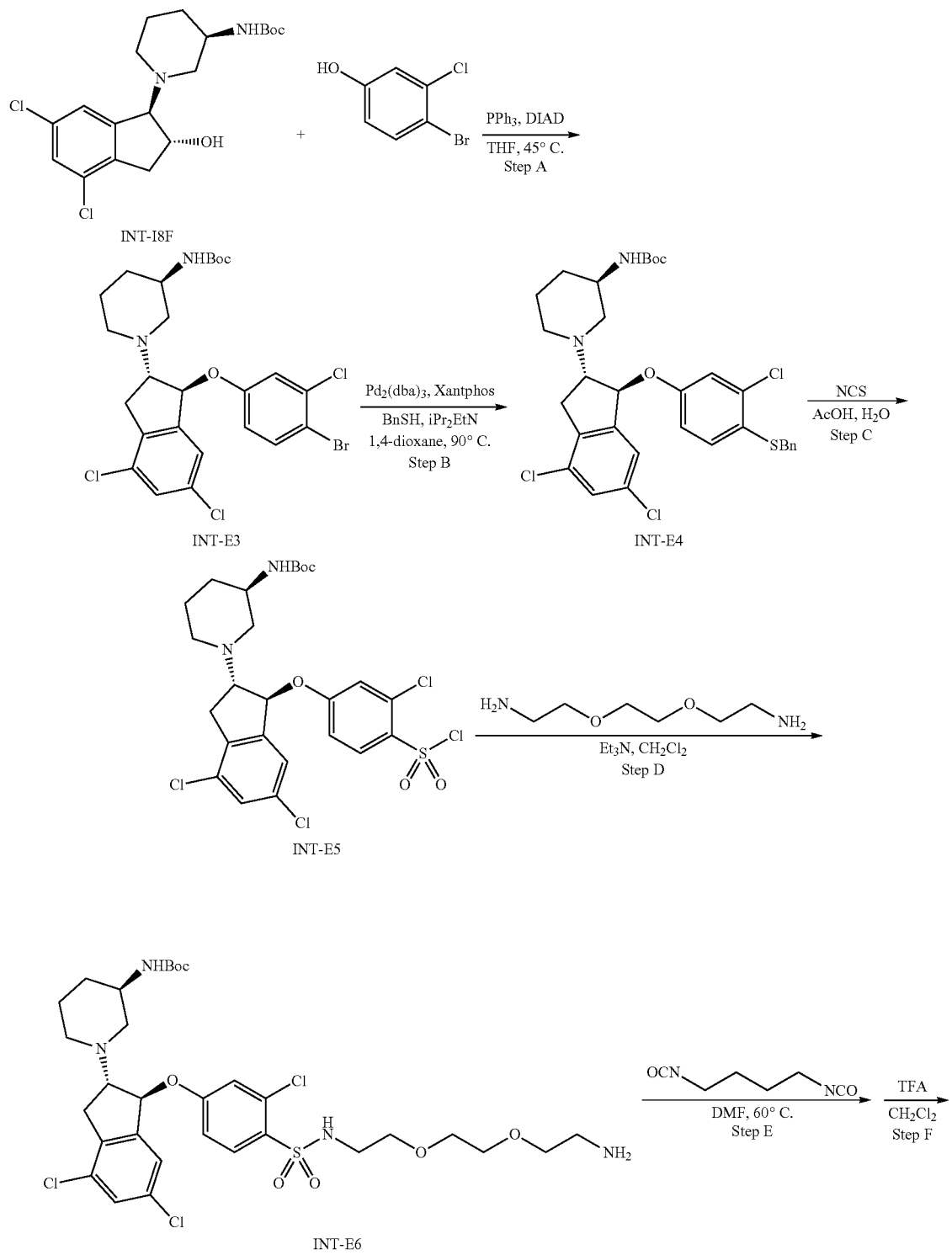

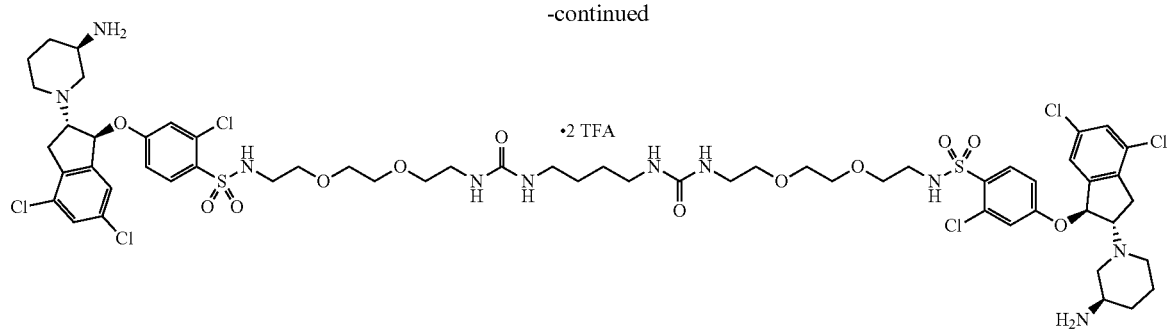

Example 104

Step A: To a round-bottom flask was added aminoindanol INT-I8F (0.602 g, 1.5 mmol, 1 equiv) and tetrahydrofuran (3.5 mL), followed by the addition of 4-bromo-3-chlorophenol (0.374 g, 1.8 mmol, 1.2 equiv) and heating to 45° C. To this slurry was added PPh$_3$ (0.590 g, 2.25 mmol, 1.5 equiv) followed DIAD (0.443 mL, 2.25 mmol, 1.5 equiv) dropwise. The resulting solution was stirred for 3 h at 40° C. The resulting mixture was concentrated under vacuum and diluted with CH$_2$Cl$_2$. The residue was applied onto a silica gel column with hexanes/ethyl acetate (0-50%) providing 0.886 g (99%) of tert-butyl [(R)-1-[(1S,2S)-1-(4-bromo-3-chlorophenoxy)-4,6-dichloro-2,3-dihydro-1H-inden-2-yl]piperidin-3-yl]carbamate (INT-E3) as a pale pink foam.

Step B: To a round-bottom flask purged and maintained with an inert atmosphere of nitrogen was added arylbromide INT-E3 (0.870 g, 1.47 mmol, 1 equiv), 1,4-dioxane (7.4 mL), N,N-diisopropylethylamine (0.381 g, 2.95 mmol, 2 equiv), Pd$_2$(dba)$_3$.CHCl$_3$ (33.7 mg, 0.037 mmol, 0.025 equiv), and Xantphos (38.9 mg, 0.067 mmol 0.05 equiv). The solution was degassed with nitrogen bubbling for 5 min before the addition of benzylmercaptan (0.219 g, 1.76 mmol, 1.2 equiv) in one portion. The resulting solution was stirred overnight at 90° C. The resulting slurry was concentrated under vacuum. The residue was applied onto a silica gel column with hexanes/acetone (0-20%) providing 0.607 g (65%) of tert-butyl [(R)-1-[(1S,2S)-1-(4-(benzylthio)-3-chlorophenoxy)-4,6-dichloro-2,3-dihydro-1H-inden-2-yl]piperidin-3-yl]carbamate (INT-E4) as a light orange solid.

Step C: To a round-bottom flask was added thioether INT-E4 (0.607 g, 0.95 mmol, 1 equiv), acetic acid (3 mL), and water (1 mL). This was followed by the addition of N-chlorosuccinimide (0.384, 2.87 mmol, 3 equiv) in several batches at room temperature. The resulting solution was stirred for 2 h at room temperature. The resulting slurry was diluted with 50 mL of ethyl acetate and treated with 4.6 g of sodium bicarbonate. Water (50 mL) was added and the layers separated. The organic layer was washed with 1×50 mL saturated aqueous sodium bicarbonate and 1×50 mL brine. The organic layer was dried over anhydrous sodium sulfate, filtered, and concentrated under vacuum. This provided 740 mg of crude tert-butyl [(R)-1-[(1S,2S)-4,6-dichloro-1-[3-chloro-4-(chlorosulfonyl)phenoxy]-2,3-dihydro-1H-inden-2-yl]piperidin-3-yl]carbamate (INT-E5) as a pasty solid that was used without further purification.

Step D: To a round-bottom flask was added crude sulfonyl chloride INT-E5 (theoretical 0.95 mmol) from Step C and CH$_2$Cl$_2$ (1 mL). To this mixture was added 2,2'-(ethane-1,2-diylbis(oxy))bis(ethan-1-amine) (1.04 g, 7 mmol, 7 equiv) dropwise over 2 min. The reaction solution was stirred overnight at room temperature. The reaction slurry was diluted with 15 mL of CH$_2$Cl$_2$ and 10 mL of ethyl acetate. The organic layer was washed with 3×30 mL of water and 2×30 mL of brine. The resulting mixture was concentrated under vacuum and diluted with of CH$_2$Cl$_2$. The residue was applied onto a silica gel column with CH$_2$Cl$_2$/methanol (0-15%) providing 0.335 g (49% over 2 steps) of tert-butyl [(R)-1-[(1S,2S)-1-(4-[N-(2-[2-(2-aminoethoxy)ethoxy]ethyl)sulfamoyl]-3-chlorophenoxy)-4,6-dichloro-2,3-dihydro-1H-inden-2-yl]piperidin-3-yl]carbamate (INT-E6) as a white foam.

Step E: To a round-bottom flask was added INT-E6 (0.181 g, 0.25 mmol, 1 equiv), DMF (5 mL), and 1,4-diisocyanatobutane (15.8 mg, 0.113 mmol, 0.45 equiv). The resulting solution was stirred for 4 h at room temperature. The resulting mixture was concentrated under vacuum and used directly in Step F.

Step F: The crude material from Step E (theoretical 0.113 mmol) was diluted in 3:1 CH$_2$Cl$_2$:TFA (4 mL). The resulting solution was stirred for 1 h at room temperature. The resulting mixture was concentrated under vacuum. The crude product was purified by preparative HPLC.

Steps A-F provided Example 104 which was purified by Preparative HPLC with the following conditions: Column, Atlantis T3 OBD Column, 19*150 mm, 10 um; mobile phase, water (0.1% TFA) and CH$_3$CN (0.1% TFA, 20% CH$_3$CN up to 70.0% in 40 min); Detector, UV 254 nm. This resulted in 0.174 g (100%) of the title compound as a white solid. MS (m/z): 1383 [M+H]$^+$. $^1$H NMR (Methanol-d4, 400 MHz): δ 8.06 (d, J=8.9 Hz, 2H), 7.48-7.40 (m, 4H), 7.27 (dd, J=8.9, 1.8 Hz, 2H), 7.16 (s, 2H), 6.20 (d, J=5.4 Hz, 2H), 3.89 (dd, J=13.4, 7.3 Hz, 2H), 3.74-3.43 (m, 19H), 3.43-3.28 (m, 15H), 3.20-3.10 (m, 16H), 2.95 (s, 2H), 2.84-2.58 (m, 4H), 2.00 (s, 2H), 1.92 (s, 2H), 1.77 (d, J=9.6 Hz, 1H), 1.74-1.30 (m, 7H).

Representative Scheme for the Synthesis of Linker Amine Dimers:

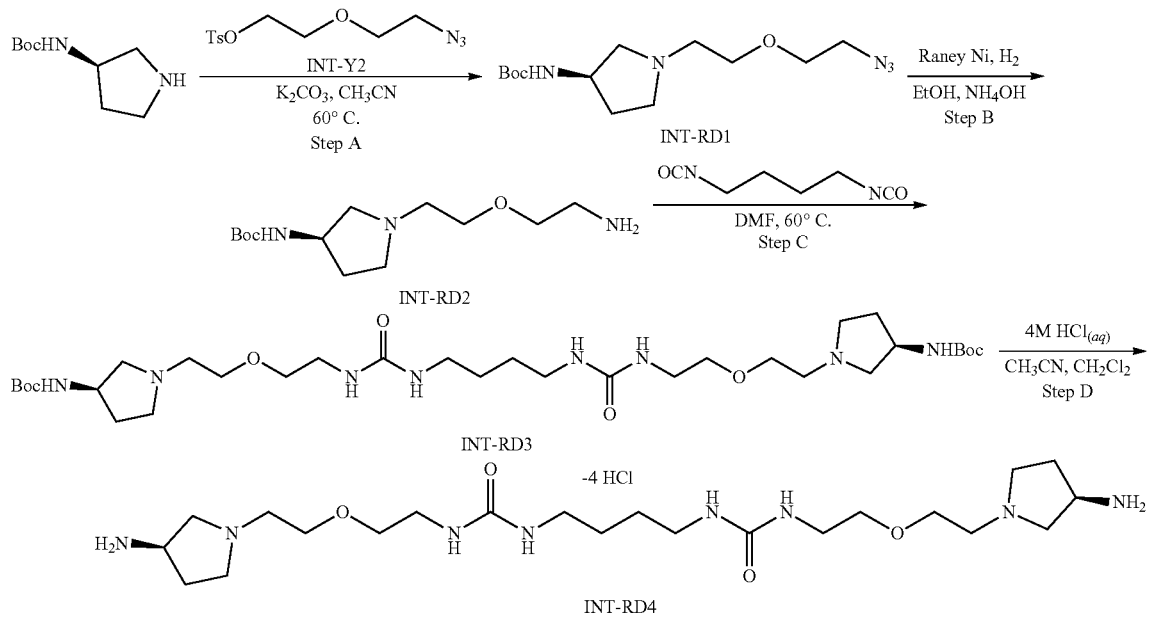

Step A: To a 500-mL round-bottom flask was added tert-butyl N-[(3R)-pyrrolidin-3-yl]carbamate (10 g, 53.7 mmol, 1 equiv), 1-[[2-(2-azidoethoxy)ethoxy]sulfonyl]-4-methylbenzene (INT-Y2, 16.85 g, 59.1 mmol, 1.1 equiv), $CH_3CN$ (100 mL), and potassium carbonate (22.26 g, 161 mmol, 3 equiv). The resulting solution was stirred overnight at 60° C. The solids were filtered out and the resulting mixture was concentrated under vacuum providing 13 g (81%) of tert-butyl N-[(3R)-1-[2-(2-azidoethoxy)ethyl]pyrrolidin-3-yl]carbamate (INT-RD1) as a yellow oil.

Step B: To a 250-mL round-bottom flask flushed with $N_2$ was added ethanol (100 mL), Raney Ni (10 g), azide INT-RD1 (6 g, 20 mmol, 1 equiv), and $NH_4OH$ (28%, 10 mL). To the above $H_{2(g)}$ was introduced in followed by a purging/filling cycle, leaving the slurry under an atmosphere of $H_{2(g)}$. The resulting slurry was stirred for 2 h at room temperature. The solids were filtered out and the resulting mixture concentrated under vacuum providing 4.8 g (88%) of tert-butyl N-[(3R)-1-[2-(2-aminoethoxy)ethyl]pyrrolidin-3-yl]carbamate (INT-RD2) as a yellow oil.

Step C: To a 500-mL round-bottom flask purged and maintained with an inert atmosphere of nitrogen was added amine INT-RD2 (10 g, 36.6 mmol, 1 equiv), DMF (250 mL), and 1,4-diisocyanatobutane (2.6 mL, 0.45 equiv). The resulting solution was stirred for 2 h at 60° C. The resulting slurry was concentrated under vacuum. The residue was applied onto a silica gel column with $CH_3CN:H_2O$ (35:65) providing 9.0 g of tert-butyl N-[(3R)-1-[2-(2-[[(4-[[(2-[2-[(3R)-3-[[(tert-butoxy)carbonyl]amino]pyrrolidin-1-yl]ethoxy]ethyl)carbamoyl]amino]butyl)carbamoyl]amino]ethoxy)ethyl]pyrrolidin-3-yl]carbamate (INT-RD3) as a white solid.

Step D: 3-(2-[2-[(3R)-3-Aminopyrrolidin-1-yl]ethoxy]ethyl)-1-(4-[[(2-[2-[(3R)-3-aminopyrrolidin-1-yl]ethoxy]ethyl)carbamoyl]amino]butyl)urea hydrochloride. To a 250-mL round-bottom flask was added Boc-diamine INT-RD3 (3.0 g, 4.37 mmol, 1 equiv), $CH_2Cl_2$ (15 mL), $CH_3CN$ (15 mL), and hydrogen chloride (4 $M_{(aq)}$, 15 mL). The resulting solution was stirred for 2 h at room temperature. The resulting mixture was concentrated under vacuum. This resulted in 2.2099 g (91%) of the title compound as a brown oil. MS (m/z): 487 [M+H]$^+$. $^1$H NMR (Methanol-d4, 300 MHz) δ 4.29-4.12 (m, 3H), 4.01-3.73 (m, 7H), 3.75-3.48 (m, 10H), 3.40 (t, J=4.9 Hz, 6H), 3.19 (d, J=5.8 Hz, 4H), 2.70 (tt, J=24.7, 11.1 Hz, 2H), 2.30 (qd, J=8.0, 3.7 Hz, 2H), 1.60-1.49 (m, 4H).

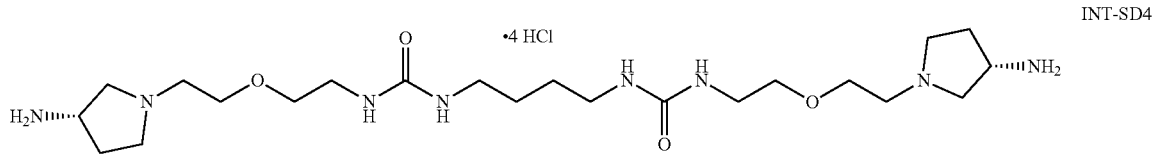 [SMILES: N[C@H]1CCN(CCOCCNC(=O)NCCCCNC(=O)NCCOCCN2CC[C@H](N)C2)C1]

INT-SD4

Through Steps A-D, 2.2449 g (92%) of 3-(2-[2-[(3S)-3-aminopyrrolidin-1-yl]ethoxy]ethyl)-1-(4-[[(2-[2-[(3S)-3-aminopyrrolidin-1-yl]ethoxy]ethyl)carbamoyl]amino]butyl)urea hydrochloride (INT-SD4) was prepared as a brown solid. MS (m/z): 487 [M+H]$^+$. $^1$H NMR (Methanol-d4, 300 MHz) δ 4.26 (s, 2H), 4.18 (s, 1H), 3.98 (d, J=12.5 Hz, 2H), 3.83 (t, J=4.5 Hz, 5H), 3.77-3.50 (m, 10H), 3.41 (t, J=5.2 Hz, 5H), 3.26-3.16 (m, 4H), 2.74 (s, 2H), 2.31 (ddd, J=13.8, 8.4, 5.0 Hz, 2H), 1.62-1.51 (m, 4H).

Representative Scheme for the Synthesis of Thioether Indane Scaffolds:

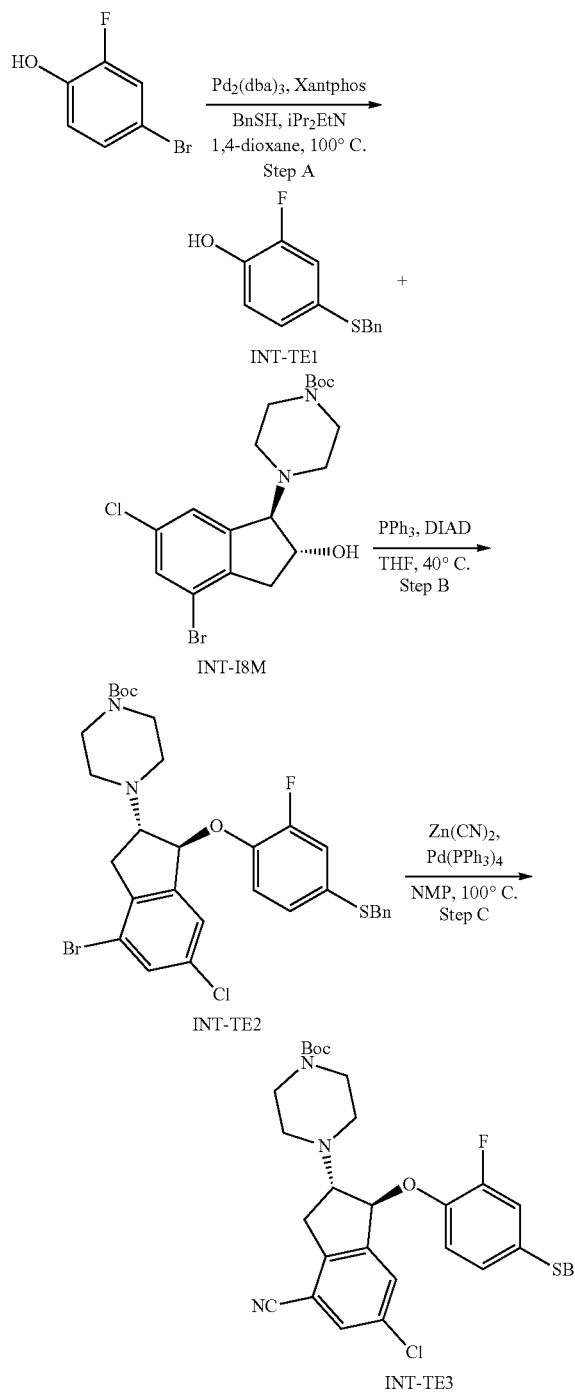

Step A: To a 1000-mL round-bottom flask purged and maintained with an inert atmosphere of nitrogen was added 4-bromo-2-fluorophenol (20 g, 104.7 mmol, 1 equiv), dioxane (240 mL), Xantphos (7.28 g, 12.6 mmol, 0.12 equiv), diisopropylethylamine (34.6 mL), Pd$_2$(dba)$_3$.CHCl$_3$ (6.52 g), and benzylmercaptan (24.6 mL). The resulting solution was stirred overnight at 100° C. in an oil bath. The resulting mixture was concentrated under vacuum. The resulting residue was slurried in water and extracted with 3×500 mL of ethyl acetate. The combined organic layers were washed with 3×500 mL of brine, dried over anhydrous sodium sulfate, filtered, and concentrated under vacuum. The residue was applied onto a silica gel column with hexane/ethyl acetate (0-10%) providing 14 g (57%) of 4-(benzylsulfanyl)-2-fluorophenol (INT-TE1) as a yellow solid.

Step B: To a 100-mL round-bottom flask purged and maintained with an inert atmosphere of nitrogen was added aminoindanol INT-I8M (3 g, 6.95 mmol, 1 equiv), tetrahydrofuran (16.2 mL), phenol INT-TE1 (1.71 g, 7.30 mmol, 1.05 equiv), and PPh$_3$ (2.92 g, 11.1 mmol, 1.6 equiv). This was followed by the dropwise addition of DIAD (2.12 g, 10.5 mmol, 1.55 equiv) at 40° C. over 45 min. The resulting solution was stirred for 1 h at 40° C. in an oil bath. The resulting mixture was concentrated under vacuum. The residue was applied onto a silica gel column with ethyl acetate/petroleum ether (1:40) providing 3.3 g (73%) of tert-butyl 4-[(1S,2S)-1-[4-(benzylsulfanyl)-2-fluorophenoxy]-4-bromo-6-chloro-2,3-dihydro-1H-inden-2-yl]piperazine-1-carboxylate (INT-TE2) as a purple solid.

Step C: To a 100-mL round-bottom flask purged and maintained with an inert atmosphere of nitrogen was added arylbromide INT-TE2 (3.3 g, 5.09 mmol 1 equiv), NMP (33 mL), Zn(CN)$_2$ (312 mg, 0.52 equiv), and Pd(PPh$_3$)$_4$ (589 mg, 0.10 equiv). The resulting solution was stirred overnight at 100° C. in an oil bath. The resulting solution was diluted with water and extracted with 3×30 mL of ethyl acetate. The combined organic layers were washed with 3×30 mL of brine and concentrated under vacuum. The residue was applied onto a silica gel column with petroleum ether/ethyl acetate (7:1) providing 2.05 g (68%) of tert-butyl 4-[(1S,2S)-1-[4-(benzylsulfanyl)-2-fluorophenoxy]-6-chloro-4-cyano-2,3-dihydro-1H-inden-2-yl]piperazine-1-carboxylate (INT-TE3) as a gray solid. MS (m/z): 594 [M+H]$^+$. $^1$H NMR (Methanol-d4, 300 MHz) δ 7.71 (d, J=2.0 Hz, 1H), 7.49-7.41 (m, 1H), 7.33-7.02 (m, 8H), 5.80 (d, J=6.1 Hz, 1H), 4.07 (s, 2H), 3.70-3.56 (m, 1H), 3.34 (t, J=4.8 Hz, 4H), 3.02 (dd, J=16.7, 7.8 Hz, 1H), 2.51 (qd, J=11.6, 5.3 Hz, 4H), 1.42 (s, 9H).

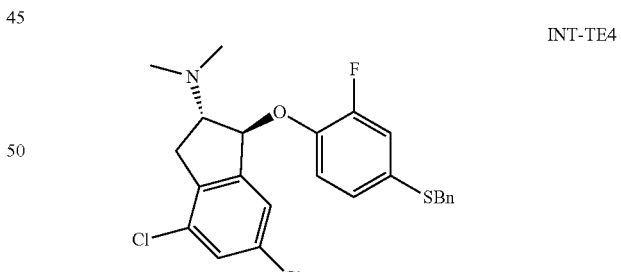

INT-TE4

Using INT-I8C, Steps A and B provided crude INT-TE4. The residue was applied onto a silica gel column with ethyl acetate/petroleum ether (1:10) providing 3.2 g (62%) of (1S,2S)-1-[4-(benzyl sulfanyl)-2-fluorophenoxy]-4,6-dichloro-N,N-dimethyl-2,3-dihydro-1H-inden-2-amine (INT-TE4) as a white solid. MS (m/z): 462 [M+H]$^+$. $^1$H NMR (Methanol-d4, 400 MHz) δ 7.40 (d, J=1.7 Hz, 1H), 7.30-7.15 (m, 6H), 7.17-7.04 (m, 3H), 5.78 (d, J=5.7 Hz, 1H), 4.09 (s, 2H), 3.46 (td, J=7.7, 5.8 Hz, 1H), 3.26 (dd, J=16.6, 8.1 Hz, 1H), 2.85 (dd, J=16.6, 7.4 Hz, 1H), 2.31 (s, 6H).

INT-TE5

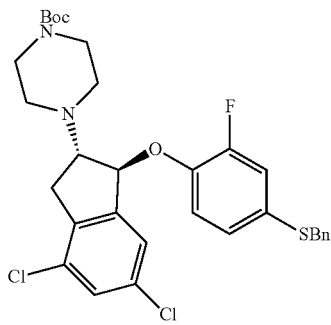

Using INT-I8L, Steps A-C provided crude INT-TE5. The residue was applied onto a silica gel column with ethyl acetate/petroleum ether (1:10) providing 231 g (59%) of tert-butyl 4-[(1S,2S)-1-[4-(benzylsulfanyl)-2-fluorophenoxy]-4,6-dichloro-2,3-dihydro-1H-inden-2-yl]piperazine-1-carboxylate (INT-TE5) as a light purple solid. MS (m/z): 603 [M+H]⁺. ¹H NMR (DMSO-d6, 400 MHz) δ 7.57 (d, J=1.8 Hz, 1H), 7.45 (t, J=8.8 Hz, 1H), 7.33-7.09 (m, 8H), 5.89 (d, J=5.6 Hz, 1H), 4.19 (s, 2H), 3.61-3.51 (m, 1H), 3.30 (s, 4H), 3.08 (dd, J=16.7, 8.0 Hz, 1H), 2.83 (dd, J=16.7, 7.1 Hz, 1H), 2.40 (dp, J=21.7, 5.6, 4.9 Hz, 4H), 1.36 (s, 9H).

INT-TE6

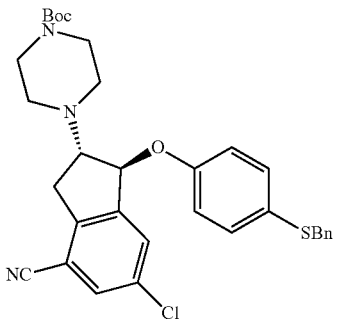

Using INT-I8M, and 4-bromophenol, Steps A-C provided crude INT-TE6. The residue was applied onto a silica gel column with petroleum ether/ethyl acetate (10%) providing 2.05 g (79%) of tert-butyl 4-[(1S,2S)-1-[4-(benzylsulfanyl)phenoxy]-6-chloro-4-cyano-2,3-dihydro-1H-inden-2-yl]piperazine-1-carboxylate (INT-TE6) as a gray solid. MS (m/z): 576 [M+H]⁺. ¹H NMR (Methanol-d4, 300 MHz) δ 8.10-8.01 (m, 1H), 7.46 (d, J=8.5 Hz, 1H), 3.94 (t, J=6.2 Hz, 1H), 3.05 (t, J=6.9 Hz, 1H), 2.64 (d, J=13.8 Hz, 1H), 2.22 (d, J=11.8 Hz, 1H), 2.02 (s, 1H), 1.73 (q, J=13.3, 9.8 Hz, 3H), 1.43 (d, J=13.6 Hz, 3H), 1.33-1.11 (m, 2H), 086 (s, 1H).

Scheme for the Synthesis of Thioether INT-TE8

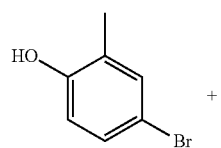

+

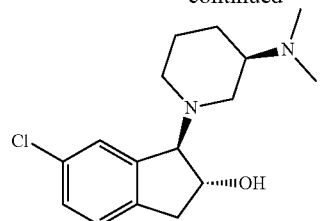

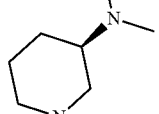

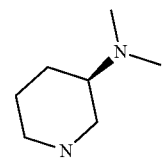

The thioether INT-TE8 was synthesized by reversing the steps from the previous method as shown in the scheme above.

Step A: To a 100-mL 3-necked round-bottom flask purged and maintained with an inert atmosphere of nitrogen was added aminoindanol INT-I9C (2.5 g, 8 mmol, 1 equiv), 4-bromo-2-methylphenol (1.82 g, 9.73 mmol, 1.2 equiv), tetrahydrofuran (19 mL), and PPh₃ (3.2 g, 12.2 mmol, 1.5 equiv). This was followed by the dropwise addition of DIAD (2.4 mL) at 40-45° C. over 15 min. The resulting solution was stirred for 2 h at 40-45° C. in an oil bath. The resulting mixture was concentrated under vacuum. The residue was applied onto a silica gel column with CH₂Cl₂/methanol (5:1) providing 3.25 g (84%) of (3R)-1-[(1S,2S)-1-(4-bromo-2-methylphenoxy)-6-chloro-4-methyl-2,3-dihydro-1H-inden-2-yl]-N,N-dimethylpiperidin-3-amine (INT-TE7) as a red oil.

Step B: To a 250-mL round-bottom flask purged and maintained with an inert atmosphere of nitrogen was added arylbromide INT-TE7 (4.58 g, 9.58 mmol, 1 equiv), dioxane (66 mL), benzylmercaptan (2.38 g, 192 mmol, 2 equiv), Xantphos (665 mg, 1.15 mmol, 0.12 equiv), and diisopropylethylamine (2.48 g, 19.2 mmol, 2 equiv), and Pd₂

(dba)₃·CHCl₃ (595 mg). The resulting solution was stirred overnight at 100° C. in an oil bath. The resulting mixture was concentrated under vacuum. The resulting solution was diluted with water and extracted with 3×100 mL of ethyl acetate. The combined organic layers were washed with 2×200 mL of brine, dried over anhydrous sodium sulfate, filtered, and concentrated under vacuum. The residue was applied onto a silica gel column with hexane/ethyl acetate (10%) providing 2.07 g (42%) of (3R)-1-[(1S,2S)-1-[4-(benzylsulfanyl)-2-methylphenoxy]-6-chloro-4-methyl-2,3-dihydro-1H-inden-2-yl]-N,N-dimethylpiperidin-3-amine (INT-TE8) as a light red oil. MS (m/z): 521 [M+H]⁺. ¹H NMR (Methanol-d4, 300 MHz) δ 7.33-7.08 (m, 9H), 6.95 (d, J=1.1 Hz, 1H), 5.79 (d, J=6.3 Hz, 1H), 4.04 (s, 2H), 3.43 (td, J=8.1, 6.2 Hz, 1H), 3.24 (dd, J=15.8, 8.1 Hz, 1H), 3.06 (dd, J=30.1, 11.1 Hz, 2H), 2.77 (dd, J=15.9, 8.1 Hz, 1H), 2.30 (s, 5H), 2.20-1.88 (m, 12H), 1.88-1.77 (m, 1H), 1.62 (t, J=12.8 Hz, 1H), 1.28 (ddd, J=14.5, 6.8, 4.2 Hz, 2H).

Representative Scheme for the Synthesis of Dimer Products from Diamine Linkers:

Example 105: 4-([(1S,2S)-4,6-Dichloro-2-(piperazin-1-yl)-2,3-dihydro-1H-inden-1-yl]oxy)-N—[(R)-1-(20-[(R)-3-([4-([(1S2S)-4,6-dichloro-2-(piperazin-1-yl)-2,3-dihydro-1H-inden-1-yl]oxy)-3-fluorophenyl]sulfonamido)pyrrolidin-1-yl]-7,14-dioxo-3,18-dioxa-6,8,13,15-tetraazaicosyl) pyrrolidin-3-yl]-3-fluorobenzenesulfonamide; tetra (trifluoroacetate)

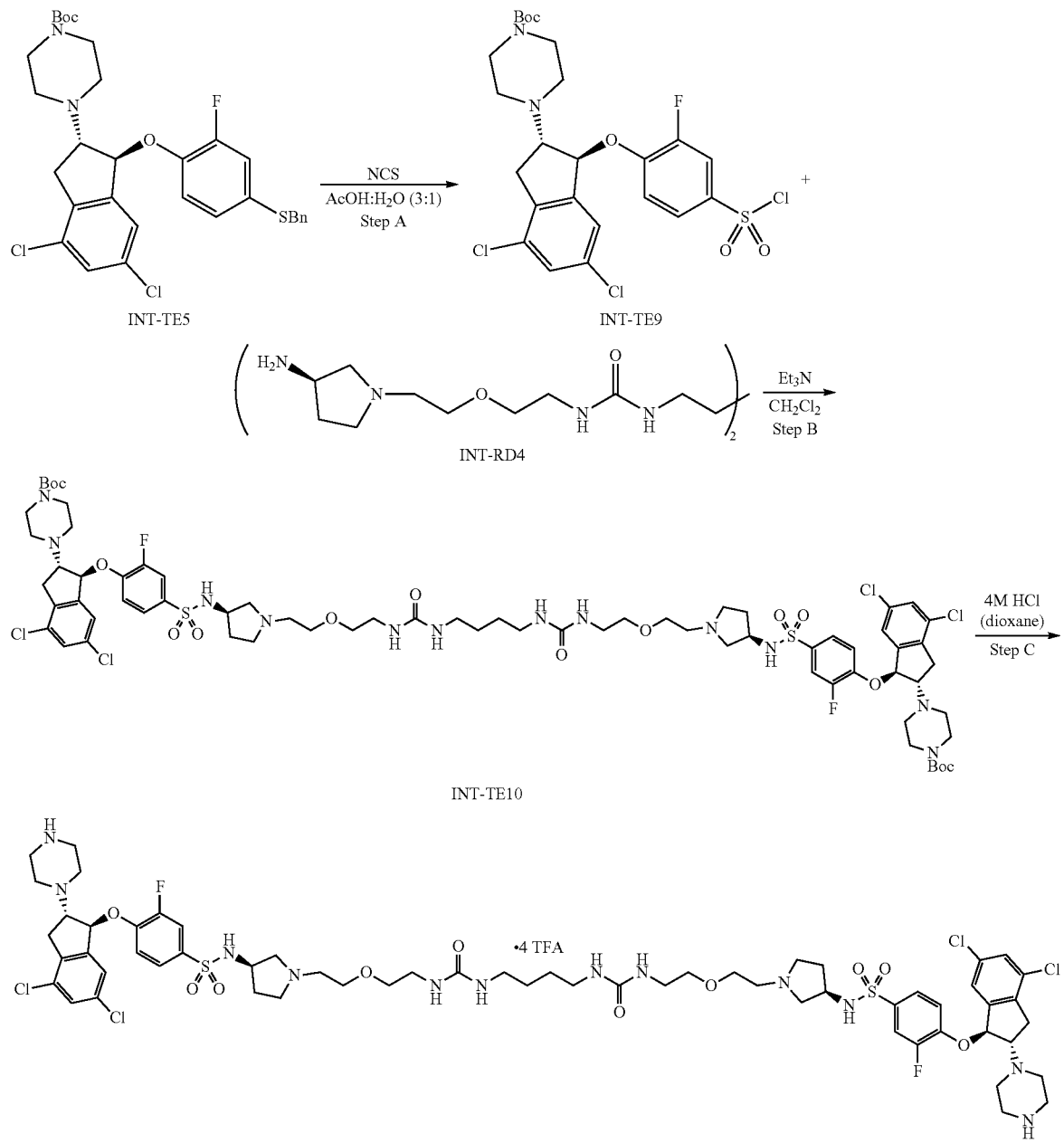

Example 105

Step A: To a 20 mL glass vial was added thioether INT-TE5 (0.530 g, 0.88 mmol, 1 equiv), acetic acid (6.75 mL), and water (2.25 mL). Then N-chlorosuccinimide (0.350, 2.62 mmol, 3 equiv) was added at room temperature. The resulting solution was stirred for 2 h at room temperature. The slimy was diluted with 50 mL of ethyl acetate and organic solution was washed with 2×15 mL saturated aqueous sodium bicarbonate and 1×15 mL brine. The organic layer was dried over anhydrous sodium sulfate, filtered, and concentrated under vacuum. The residue was applied onto a silica gel column with hexanes/ethyl acetate (0-30%) providing 0.429 g (84%) of tert-butyl 4-((1S,2S)-1-(4-(benzylthio)-2-fluorophenoxy)-4,6-dichloro-2,3-dihydro-1H-inden-2-yl)piperazine-1-carboxylate (INT-TE9) as a white solid.

Step B: To a 5 mL glass vial was added of 3-(2-[2-[(3R)-3-aminopyrrolidin-1-yl]ethoxy]ethyl)-1-(4-[[(2-[2-[(3R)-3-aminopyrrolidin-1-yl]ethoxy]ethyl)carbamoyl]amino]butyl) urea hydrochloride (INT-RD4, 96 mg, 0.15 mmol, 1 equiv), CH$_2$Cl$_2$ (0.5 mL), and triethylamine (0.15 mL, 1.10 mmol, 8 equiv). The mixture stirred for 15 minutes at room temperature, then solution of sulfonyl chloride INT-TE9 (0.198 g, 0.34 mmol, 2.3 equiv) in CH$_2$Cl$_2$ (1.0 mL) was added dropwise. The reaction mixture stirred for 3 h at room temperature. The resulting mixture was concentrated under vacuum providing 0.270 g of crude tert-butyl 4-((1S,2S)-1-(4-(N—((R)-1-(20-((R)-3-((4-(((1S,2S)-2-(4-(tert-butoxycarbonyl)piperazin-1-yl)-4,6-dichloro-2,3-dihydro-1H-inden-1-yl)oxy)-3-fluorophenyl)sulfonamido)pyrrolidin-1-yl)-7,14-dioxo-3,18-dioxa-6,8,13,15-tetraazaicosyl) pyrrolidin-3-yl)sulfamoyl)-2-fluorophenoxy)-4,6-dichloro-2,3-dihydro-1H-inden-2-yl)piperazine-1-carboxylate (INT-TE10) as a tan foam which was used for the next step without purification.

Step C: To the crude material from Step B (theoretical 0.15 mmol) was added 4 M hydrochloric acid in dioxane (1 mL) and the mixture was stirred for 2 h at room temperature. The resulting slurry was concentrated under vacuum. The crude product was purified by preparative HPLC to provide the desired product.

Steps A-C provided the crude product which was purified by preparative HPLC with the following conditions: Column, Atlantis Preparative T3 OBD Column, 19*150 mm, 10 um; mobile phase, water (0.1% TFA) and CH$_3$CN (10.0% CH$_3$CN up to 70.0% in 40 min); Detector, UV 214 nm. This resulted in 0.061 g (22%) of the title compound as a white solid, MS (m/z): 686.2 [M/2+H]$^+$. $^1$H NMR (Methanol-d4, 400 MHz) δ 7.81-7.61 (m, 6H), 7.46 (d, J=1.7 Hz, 2H), 7.17 (s, 2H), 6.08 (d, J=5.7 Hz, 2H), 3.79-3.68 (m, 10H), 3.54 (t, J=5.4 Hz, 5H), 3.40 (m, 6H), 3.28-3.18 (m, 16H), 3.13 (s, 6H), 2.99 (dd, J=16.6, 7.5 Hz, 2H), 2.90-2.75 (m, 10H), 1.50 (s, 4H).

Example 106: 4-([(1S,2S)-4,6-Dichloro-2-(piperazin-1-yl)-2,3-dihydro-1H-inden-1-yl]oxy)-N—[(S)-1-(20-[(S)-3-([4-([(1S,2S)-4,6-dichloro-2-(piperazin-1-yl)-2,3-dihydro-1H-inden-1-yl]oxy)-3-fluorophenyl]sulfonamido)pyrrolidin-1-yl]-7,14-dioxo-3,18-dioxa-6,8,13,15-tetraazaicosyl) pyrrolidin-3-yl]-3-fluorobenzenesulfonamide; tetra (trifluoroacetate)

Example 106

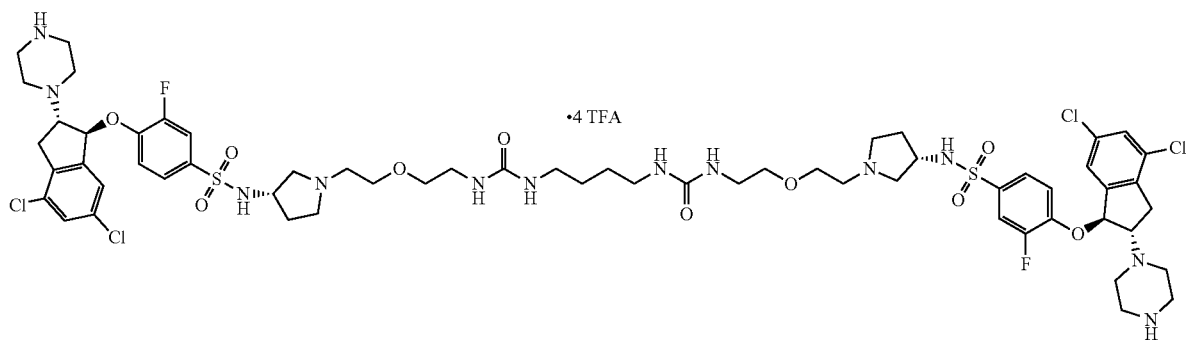

Beginning with INT-TE5 and INT-SD4, Steps A-C provided 121.8 mg (48%) of the title compound as a white solid. MS (m/z): 686.2 [M+H]$^+$. $^1$H NMR (Methanol-d4, 400 MHz) δ 7.77-7.65 (m, 6H), 7.44 (d, J=1.7 Hz, 2H), 7.16 (d, J=1.2 Hz, 2H), 6.06 (d, J=5.7 Hz, 2H), 3.81-3.61 (m, 10H), 3.52 (t, J=5.3 Hz, 5H), 3.43 (m, 6H), 3.25-3.18 (m, 16H), 3.11 (s, 6H), 2.98 (dd, J=16.6, 7.2 Hz, 2H), 2.91-2.76 (m, 10H), 1.48 (s, 4H).

Example 107: 4-([(1S,2S)-6-Chloro-4-cyano-2-(piperazin-1-yl)-2,3-dihydro-1H-inden-1-yl]oxy)-N—[(S)-1-(20-[(S)-3-([4-([[(1S,2S)-6-chloro-4-cyano-2-(piperazin-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; tetra(trifluoroacetate)

Example 107

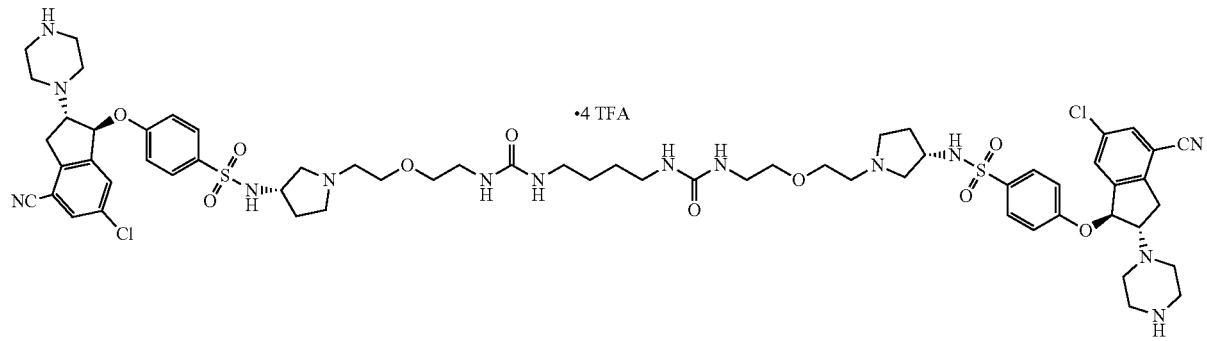

Beginning with INT-TE6 and INT-SD4, Steps A-C provided 84.9 mg (34%) of the title compound as a white solid. MS (m/z): 659.4 [M/2+H]$^+$. $^1$H NMR (Methanol-d4, 400 MHz) δ 7.91 (d, J=8.9 Hz, 4H), 7.79 (d, J=1.7 Hz, 2H), 7.46 (d, J=1.3 Hz, 2H), 7.36 (d, J=8.9 Hz, 4H), 6.09 (d, J=6.0 Hz, 2H), 3.80-3.70 (m, 10H), 3.54 (t, J=5.4 Hz, 5H), 3.48-3.33 (m, 11H), 3.24 (t, J=5.1 Hz, 10H), 3.19-3.08 (m, 8H), 2.94-2.79 (m, 10H), 1.50 (s, 4H).

Example 108: 4-([[(1S,2S)-6-Chloro-4-cyano-2-(piperazin-1-yl)-2,3-dihydro-1H-inden-1-yl]oxy)-N—[(R)-1-(20-[(R)-3-([4-([[(1S2S)-6-chloro-4-cyano-2-(piperazin-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; tetra(trifluoroacetate)

Example 108

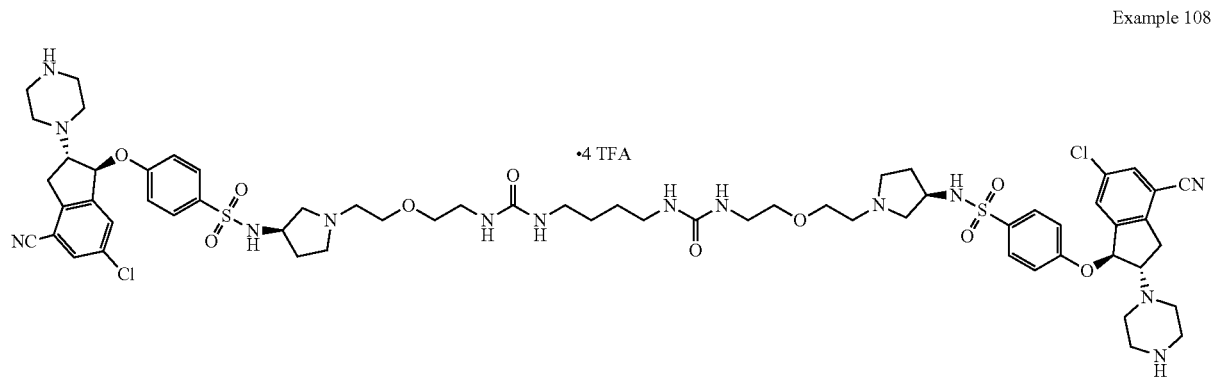 [SMILES: N#Cc1cc(Cl)cc2c1C[C@H](N1CCNCC1)[C@H]2Oc1ccc(S(=O)(=O)N[C@@H]2CCN(CCOCCNC(=O)NCCCCNC(=O)NCCOCCN3CC[C@@H](NS(=O)(=O)c4ccc(O[C@H]5c6cc(Cl)cc(C#N)c6C[C@@H]5N5CCNCC5)cc4)C3)C2)cc1]

Beginning with INT-TE6 and INT-RD4, Steps A-C provided 71.0 mg (26%) of the title compound as a white solid. MS (m/z): 659.3 [M/2+H]$^+$. $^1$H NMR (Methanol-d4, 400 MHz) δ 7.91 (d, J=8.9 Hz, 4H), 7.79 (d, J=1.9 Hz, 2H), 7.46 (s, 2H), 7.36 (d, J=8.9 Hz, 4H), 6.09 (d, J=6.0 Hz, 2H), 3.78-3.71 (m, 10H), 3.54 (t, J=5.3 Hz, 5H), 3.49-3.34 (m, 11H), 3.24 (t, J=5.2 Hz, 10H), 3.19-3.08 (m, 8H), 2.94-2.78 (m, 10H), 1.50 (s, 4H).

Example 109: 4-([(1S,2S)-6-Chloro-4-cyano-2-(piperazin-1-yl)-2,3-dihydro-1H-inden-1-yl]oxy)-N—[(R)-1-(20-[(R)-3-[(4-([(1S,2S)-6-chloro-4-cyano-2-(piperazin-1-yl)-2,3-dihydro-1H-inden-1-yl]oxy)-3-fluorophenyl)sulfonamide)pyrrolidin-1-yl]-7,14-dioxo-3,18-dioxa-6,8,13,15-tetraazaicosyl)pyrrolidin-3-yl]-3-fluorobenzenesulfonamide; tetra (trifluoroacetate)

Example 109

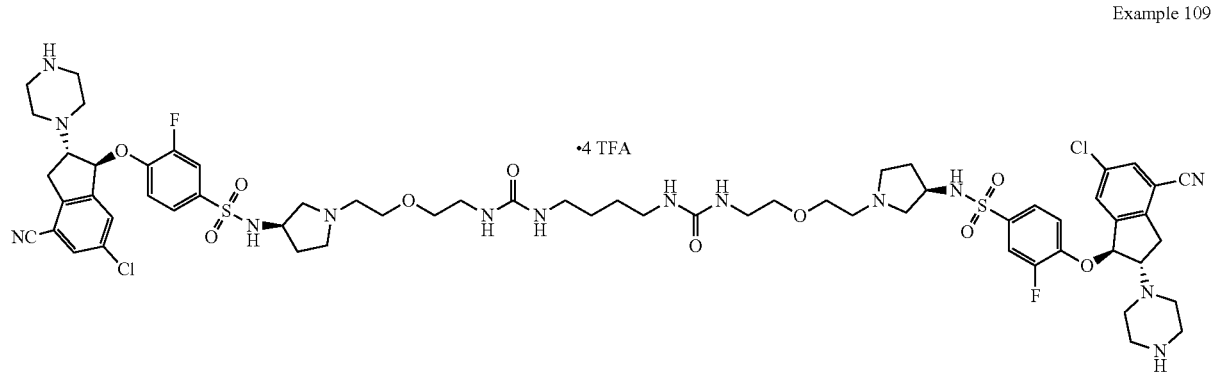 [SMILES: N#Cc1cc(Cl)cc2c1C[C@H](N1CCNCC1)[C@H]2Oc1ccc(S(=O)(=O)N[C@@H]2CCN(CCOCCNC(=O)NCCCCNC(=O)NCCOCCN3CC[C@@H](NS(=O)(=O)c4ccc(O[C@H]5c6cc(Cl)cc(C#N)c6C[C@@H]5N5CCNCC5)c(F)c4)C3)C2)cc1F]

Beginning with INT-TE3 and INT-RD4, Steps A-C provided 74.0 mg (36%) of the title compound as a white solid. MS (m/z): 677.3 [M/2+H]$^+$. $^1$H NMR (Methanol-d4, 400 MHz) δ 7.78 (d, J=1.8 Hz, 2H), 7.77-7.62 (m, 6H), 7.50 (d, J=1.7 Hz, 2H), 6.08 (d, J=5.8 Hz, 2H), 3.81 (dd, J=13.8, 7.8 Hz, 2H), 3.74 (t, J=5.0 Hz, 6H), 3.53 (t, J=5.3 Hz, 5H), 3.46-3.31 (m, 11H), 3.21 (m, 13H), 3.14 (dd, J=16.6, 7.4 Hz, 9H), 2.93-2.77 (m, 10H), 1.46 (s, 4H).

Example 110: 4-([(1S,2S)-6-Chloro-4-cyano-2-(piperazin-1-yl)-2,3-dihydro-1H-inden-1-yl]oxy)-N—[(S)-1-(20-[(S)-3-[(4-([(1S,2S)-6-chloro-4-cyano-2-(piperazin-1-yl)-2,3-dihydro-1H-inden-1-yl]oxy)-3-fluorophenyl)sulfonamide)pyrrolidin-1-yl]-7,14-dioxo-3,18-dioxa-6,8,13,15-tetraazaicosyl)pyrrolidin-3-yl]-3-fluorobenzenesulfonamide; tetra (trifluoroacetate)

Example 110

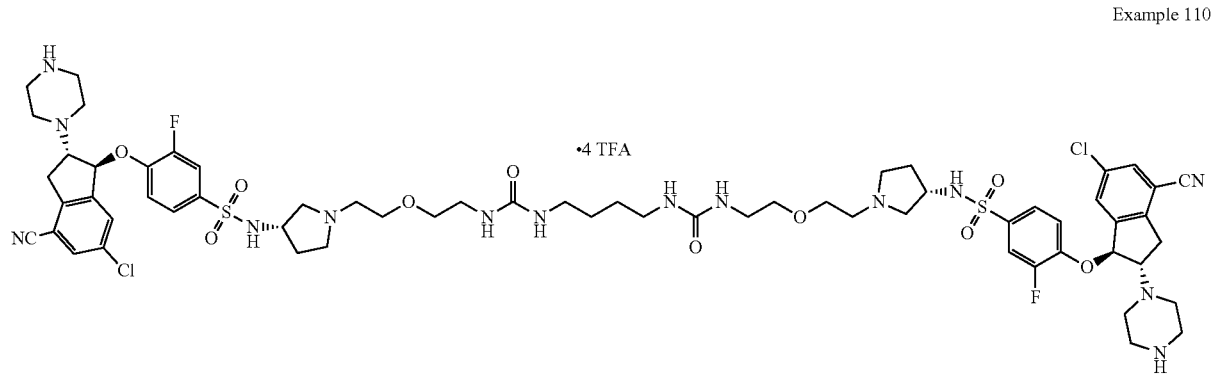 [SMILES: N#Cc1cc(Cl)cc2c1C[C@H](N1CCNCC1)[C@H]2Oc1ccc(S(=O)(=O)N[C@H]2CCN(CCOCCNC(=O)NCCCCNC(=O)NCCOCCN3CC[C@H](NS(=O)(=O)c4ccc(O[C@H]5c6cc(Cl)cc(C#N)c6C[C@@H]5N5CCNCC5)c(F)c4)C3)C2)cc1F]

Beginning with INT-TE3 and INT-SD4, Steps A-C provided 44.9 mg (17%) of the title compound as a white solid, MS (m/z): 677.3 [M/2+H]$^+$. $^1$H NMR (Methanol-d4, 400 MHz) δ 7.78 (d, J=1.8 Hz, 2H), 7.77-7.62 (m, 6H), 7.49 (d, J=1.7 Hz, 2H), 6.07 (d, J=5.8 Hz, 2H), 3.81 (dd, J=13.8, 7.8 Hz, 2H), 3.74 (t, J=5.0 Hz, 6H), 3.53 (t, J=5.4 Hz, 5H), 3.47-3.31 (m, 11H), 3.22 (dd, J=11.9, 7.3 Hz, 13H), 3.14 (dd, J=16.6, 7.4 Hz, 9H), 2.94-2.77 (m, 10H), 1.45 (s, 4H).

Example 111: 4-([(1S,2S)-4,6-Dichloro-2-(dimethylamino)-2,3-dihydro-1H-inden-1-yl]oxy)-N—[(S)-1-(20-[(S)-3-([4-([(1S,2S)-4,6-dichloro-2-(dimethylamino)-2,3-dihydro-1H-inden-1-yl]oxy)-3-fluorophenyl]sulfonamido)pyrrolidin-1-yl]-7,14-dioxo-3,18-dioxa-6,8,13,15-tetraazaicosyl)pyrrolidin-3-yl)-3-fluorobenzenesulfonamide; tetra (trifluoroacetate)

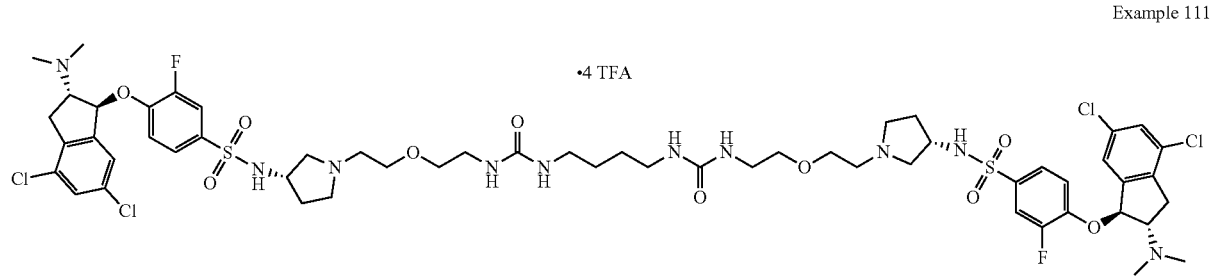 [SMILES: CN(C)[C@H]1Cc2c(Cl)cc(Cl)cc2[C@@H]1Oc1ccc(S(=O)(=O)N[C@H]2CCN(CCOCCNC(=O)NCCCCNC(=O)NCCOCCN3CC[C@H](NS(=O)(=O)c4ccc(O[C@H]5c6cc(Cl)cc(Cl)c6C[C@@H]5N(C)C)c(F)c4)C3)C2)cc1F]

Example 111

Beginning with INT-TE4 and INT-SD4, Steps A-B provided Example 111 which was purified by preparative HPLC with the following conditions: Column, Atlantis Preparative T3 OBD Column, 19*150 mm, 10 um; mobile phase, water (0.1% TFA) and CH$_3$CN (10.0% CH$_3$CN up to 60.0% in 40 min); Detector, UV 214 nm. This resulted in 15.9 mg (5.4%) of the title compound as a white solid. MS (m/z): 645.3 [M/2+H]$^+$. $^1$H NMR (Methanol-d4, 400 MHz): δ 7.83-7.74 (m, 4H), 7.67 (t, J=8.5 Hz, 2H), 7.56 (d, J=1.7 Hz, 2H), 7.13 (s, 2H), 6.53 (d, J=6.3 Hz, 2H), 3.76 (t, J=5.0 Hz, 7H), 3.68 (dd, J=16.8, 8.6 Hz, 2H), 3.55 (t, J=5.3 Hz, 7H), 3.45 (m, 6H), 3.29-3.22 (m, 2H), 3.13 (s, 4H), 3.03 (s, 23H), 1.50 (s, 4H).

Example 112: 4-([(1S,2S)-4,6-Dichloro-2-(dimethylamino)-2,3-dihydro-1H-inden-1-yl]oxy)-N—[(R)-1-(20-[(R)-3-([4-([(1S,2S)-4,6-dichloro-2-(dimethylamino)-2,3-dihydro-1H-inden-1-yl]oxy)-3-fluorophenyl]sulfonamido)pyrrolidin-1 yl]-7,14-dioxo-3,18-dioxa-6,8,13,15-tetraazaicosyl)pyrrolidin-3-yl)-3-fluorobenzenesulfonamide; tetra (trifluoroacetate)

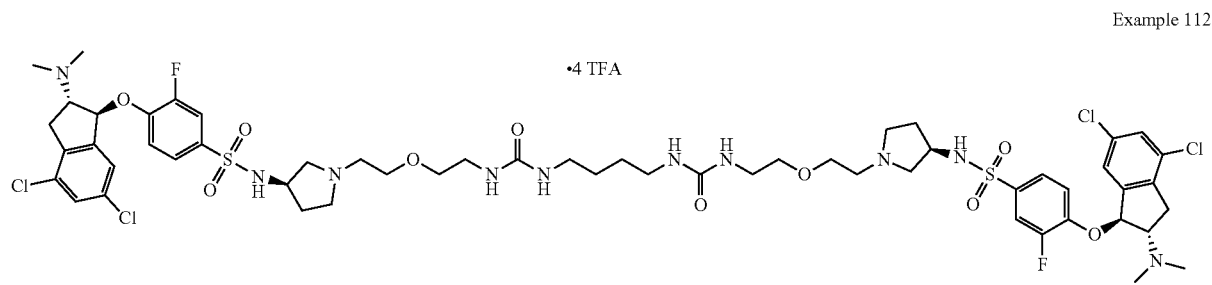 [SMILES: CN(C)[C@H]1Cc2c(Cl)cc(Cl)cc2[C@@H]1Oc1ccc(S(=O)(=O)N[C@@H]2CCN(CCOCCNC(=O)NCCCCNC(=O)NCCOCCN3CC[C@@H](NS(=O)(=O)c4ccc(O[C@H]5c6cc(Cl)cc(Cl)c6C[C@@H]5N(C)C)c(F)c4)C3)C2)cc1F]

Example 112

Beginning with INT-TE4 and INT-RD4, Steps A-B provided Example 112 which was purified by preparative HPLC with the following conditions: Column, Atlantis Preparative T3 OBD Column, 19*150 mm, 10 um; mobile phase, water (0.1% TFA) and CH$_3$CN (10.0% CH$_3$CN up to 60.0% in 40 min); Detector, UV 214 nm. This resulted in 10.9 mg (3.1%) of the title compound as a white solid. MS (m/z): 645.3 [M/2+H]$^+$. $^1$H NMR (Methanol-d4, 400 MHz): δ 7.83-7.75 (m, 4H), 7.67 (t, J=8.2 Hz, 2H), 7.56 (d, J=1.6 Hz, 2H), 7.13 (s, 2H), 6.52 (d, J=6.1 Hz, 2H), 3.76 (t, J=5.0 Hz, 7H), 3.68 (dd, J=16.8, 8.7 Hz, 2H), 3.55 (t, J=5.4 Hz, 7H), 3.46 (m, 6H), 3.30-3.20 (m, 2H), 3.14 (s, 4H), 3.03 (s, 23H), 1.48 (s, 4H).

Example 113: 4-([(1S,2S)-6-Chloro-2-[(R)-3-(dimethylamino)piperidin-1-yl]-4-methyl-2,3-dihydro-1H-inden-1-yl]oxy)-N—[(R)-1-(20-[(R)-3-([4-([(1S,2S)-6-chloro-2-[(R)-3-(dimethylamino)piperidin-1-yl]-4-methyl-2,3-dihydro-1H-inden-1-yl]oxy)-3-methylphenyl]sulfonamido)pyrrolidin-1-yl]-7,14-dioxo-3,18-dioxa-6,8,13,15-tetraazaicosyl)pyrrolidin-3-yl]-3-methylbenzenesulfonamide; tetra(trifluoroacetate)

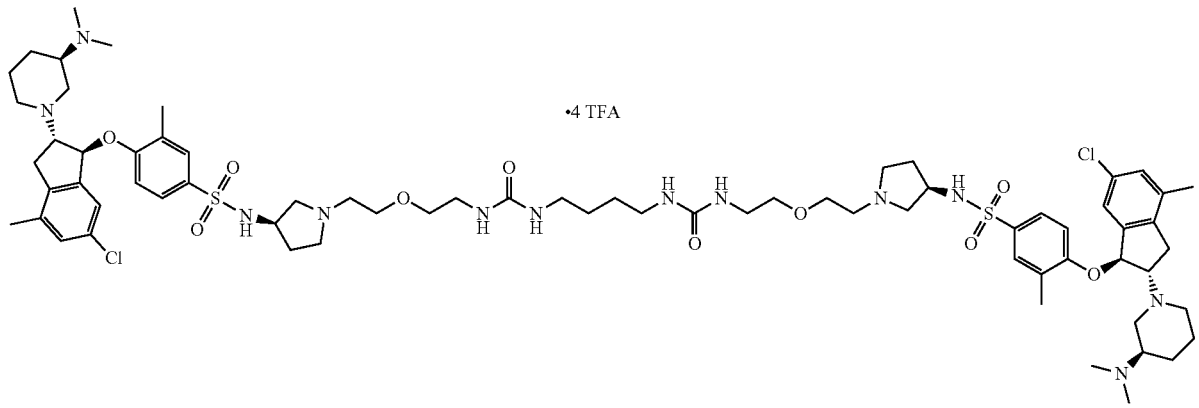

Example 113

Beginning with INT-TE8 and INT-RD4 Steps A-B provided Example 113 which was purified by preparative HPLC with the following conditions: Column, Atlantis Preparative T3 OBD Column, 19*150 mm, 10 um; mobile phase, water (0.1% TFA) and CH$_3$CN (10.0% CH$_3$CN up to 60.0% in 40 min); Detector, UV 214 nm. This resulted in 16.9 mg (4.8%) of the title compound as a white solid. MS (m/z): 704.4 [M/2+H]$^+$. $^1$H NMR (Methanol-d4, 400 MHz): δ 7.80 (d, J=8.8 Hz, 2H), 7.73 (s, 2H), 7.47 (t, J=8.8 Hz, 2H), 7.18 (s, 2H), 6.96 (s, 2H), 6.05 (s, 2H), 3.82-3.69 (m, 13H), 3.54 (m, 6H), 3.48-3.34 (m, 6H), 3.21 (dd, J=16.2, 8.0 Hz, 2H), 3.13 (s, 4H), 2.92 (m, 2H), 2.87 (m, 23H), 2.28 (m, 25H), 1.50 (s, 4H).

Example 114: 4-([(1S,2S)-6-Chloro-2-[(R)-3-(dimethylamino)piperidin-1-yl]-4-methyl-2,3-dihydro-1H-inden-1-yl]oxy)-N—[(S)-1-(20-[(S)-3-([4-([(1S,2S)-6-chloro-2-[(R)-3-(dimethylamino)piperidin-1-yl]-4-methyl-2,3-dihydro-1H-inden-1-yl]oxy)-3-methylphenyl]sulfonamido)pyrrolidin-1-yl]-7,14-dioxo-3,18-dioxa-6,8,13,15-tetraazaicosyl)pyrrolidin-3-yl]-3-methylbenzenesulfonamide; tetra(trifluoroacetate)

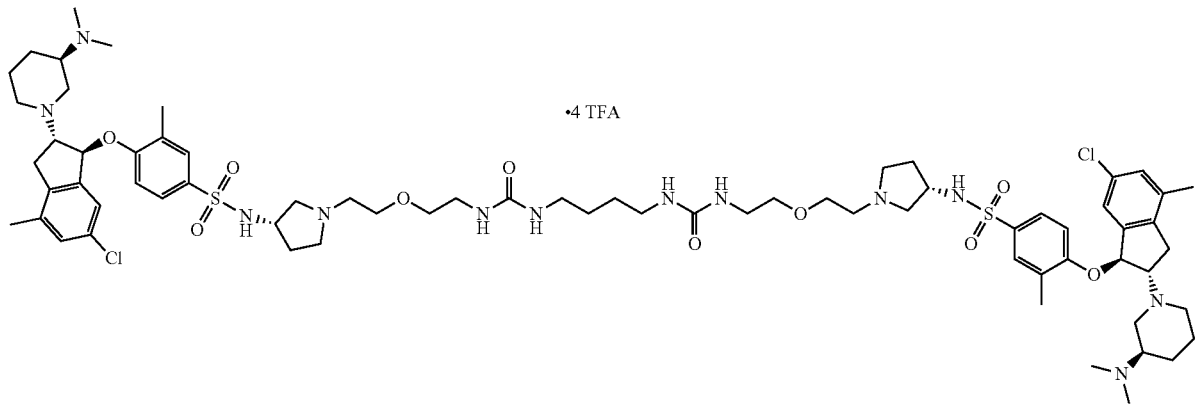

Example 114

Steps A-C were followed to prepare Example 114 with the addition of a free-basing of the initial amine INT-SD4 with basic resin (Dowex Monosphere 550A hydroxide form) prior to addition of the sulfonyl chloride in Step B. The crude product obtained was purified by preparative HPLC with the following conditions: Column, Atlantis Preparative T3 OBD Column, 19*150 mm, 10 um; mobile phase, water (0.1% TFA) and CH$_3$CN (10% CH$_3$CN up to 60.0% in 40 min); Detector, UV 214 nm. This resulted in 68.0 mg (16%) of the title compound as a white solid, MS (m/z): 704.4 [M/2+H]$^+$. $^1$H NMR (Methanol-d4, 400 MHz): δ 7.84-7.67 (m, 4H), 7.48 (t, J=8.8 Hz, 2H), 7.18 (s, 2H), 6.95 (s, 2H), 6.07 (d, J=5.8 Hz, 2H), 3.82-3.69 (m, 13H), 3.54 (t, J=5.3 Hz, 6H), 3.48-3.34 (m, 6H), 3.22 (dd, J=16.2, 8.0 Hz, 2H), 3.19 (s, 4H), 2.90 (m, 2H), 2.83 (m, 23H), 2.29 (m, 25H), 1.47 (s, 4H).

Scheme for Dimer Product Synthesis via Stepwise Linker Construction:

Example 115: 4-([(1S,2S)-6-Chloro-4-cyano-2-(piperazin-1-yl)-2,3-dihydro-1H-inden-1-yl]oxy)-N-[1-(18-[4-([4-[(1S,2S)-6-chloro-4-cyano-2-(piperazin-1-yl)-2,3-dihydro-1H-inden-1-yl]oxy)phenyl]sulfonamido)piperidin-1-yl]-6,13,18-trioxo-5,7,12,14-tetraazaoctadecanoyl)piperidin-4-yl]benzenesulfonamide; bis(trifluoroacetate)

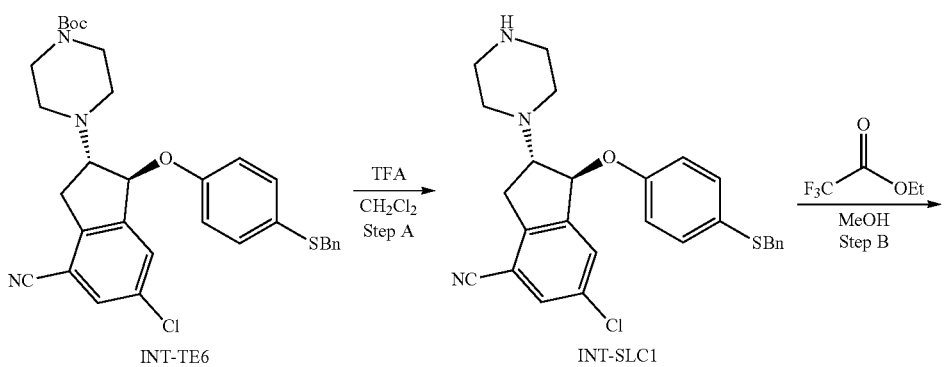

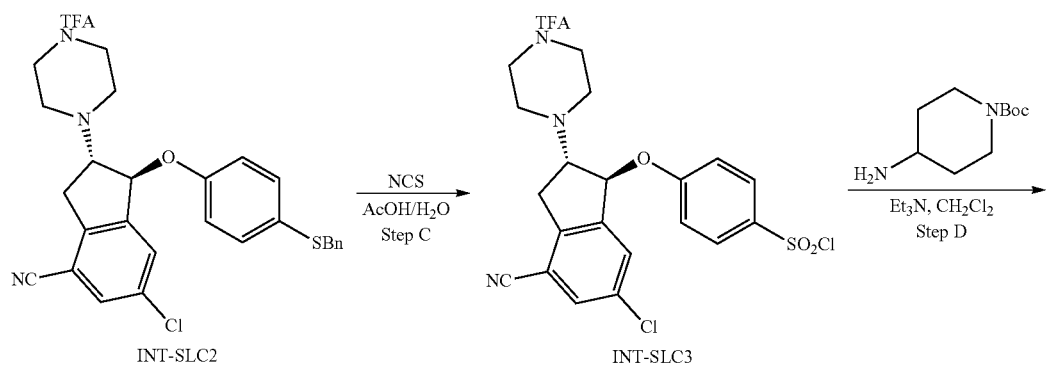

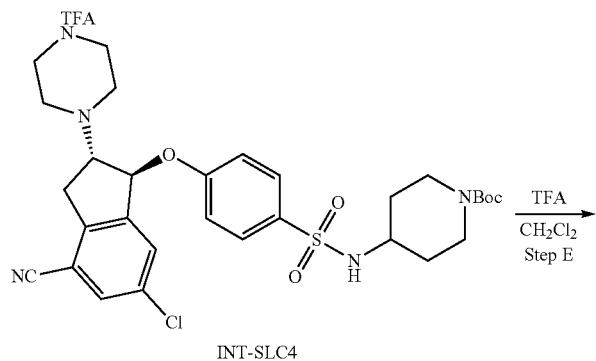

-continued
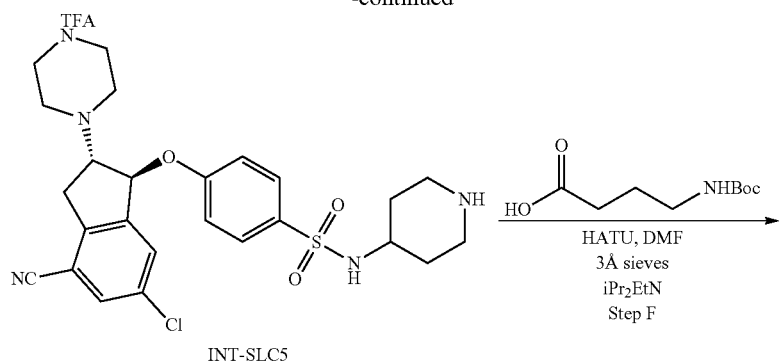
INT-SLC5
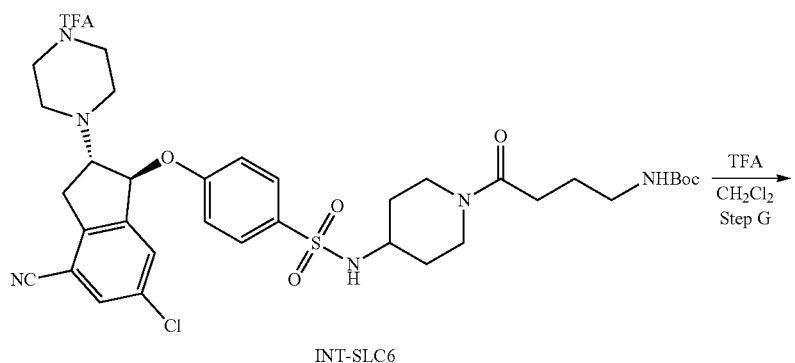
INT-SLC6
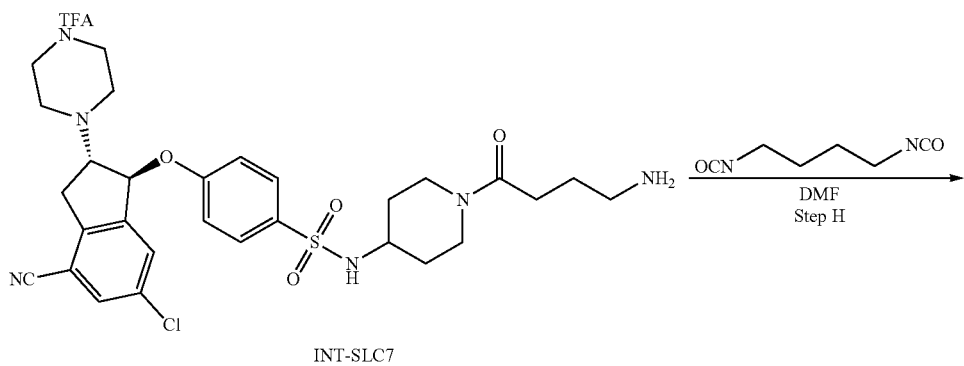
INT-SLC7
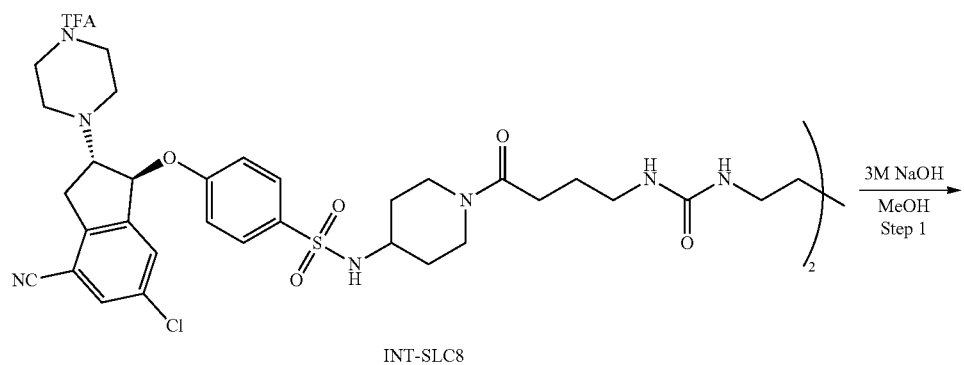
INT-SLC8

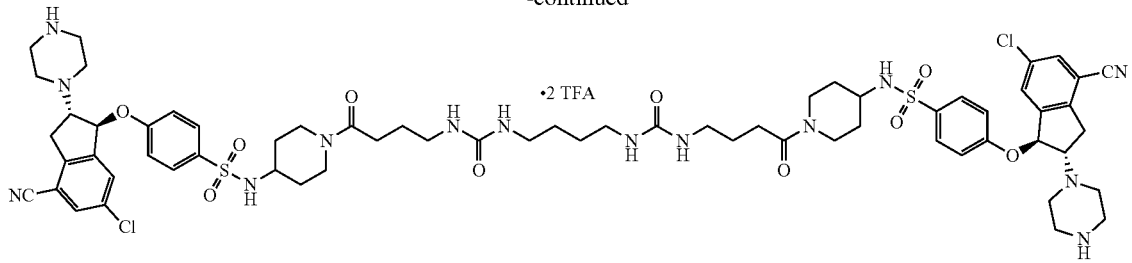

Example 115

Step A: tert-Butyl 4-((1S,2S)-1-(4-(benzylthio)phenoxy)-6-chloro-4-cyano-2,3-dihydro-1H-inden-2-yl)piperazine-1-carboxylate (580 mg, 1.00 mmol) was dissolved in $CH_2Cl_2$ (3 mL) and trifluoroacetic acid (0.5 mL, 6.52 mmol, 6.5 equiv) was added at 0° C. The reaction mixture was allowed to warm to room temperature and stirred for 18 h. The reaction mixture was diluted with ethyl acetate (50 mL) and washed with 1 M aqueous sodium hydroxide (2×10 mL), water (10 mL), and brine (10 mL). The aqueous layers were back-extracted with ethyl acetate (20 mL). The combined organic layers were dried over sodium sulfate, filtered, and concentrated providing 500 mg of crude (1S,2S)-1-(4-(benzylthio)phenoxy)-6-chloro-2-(piperazin-1-yl)-2,3-dihydro-1H-indene-4-carbonitrile (INT-SLC1) as a brownish resin. MS (m/z): 476.2 $[M+H]^+$.

Step B: To a solution of crude material INT-SLC1 from Step A (theoretical 1 mmol) in methanol (3 mL) was added ethyl trifluoroacetate (0.5 mL, 4.2 mmol) at room temperature. After stirring at room temperature for 1.5 h another portion of ethyl trifluoroacetate (0.3 mL, 2.5 mmol) was added, followed by triethylamine (50 µL, 0.36 mmol). The reaction mixture stirred for 1 h and then concentrated under vacuum. The residue was applied onto a silica gel column with hexanes/ethyl acetate (0-35%) providing 556 mg (97%) of (1S,2S)-1-[4-(benzylthio)phenoxy]-6-chloro-2-[4-(2,2,2-trifluoroacetyl)piperazin-1-yl]-2,3-dihydro-1H-indene-4-carbonitrile (INT-SLC2) as a clear brownish oil. MS (m/z): 572.1 $[M+H]^+$.

Step C: To a solution of thioether INT-SLC2 (556 mg, 0.97 mmol) in a mixture of acetic acid (6.75 mL) and water (2.25 mL), N-chlorosuccinimide (388 mg, 2.91 mmol, 3 equiv) was added at room temperature. The reaction mixture stirred for 2 h at room temperature and diluted with ethyl acetate (50 mL). The resulting solution was washed with saturated aqueous sodium bicarbonate (2×15 mL) and brine (15 mL). The organic layer was dried over anhydrous sodium sulfate, filtered, and concentrated under vacuum providing 760 mg of crude 4-([(1S,2S)-6-chloro-4-cyano-2-[4-(2,2,2-trifluoroacetyl)piperazin-1-yl]-2,3-dihydro-1H-inden-1-yl]oxy)benzene-1-sulfonyl chloride (INT-SLC3) as a yellowish oil. MS (m/z): 548.0 $[M+H]^+$.

Step D: To a solution of crude material INT-SLC3 from Step C (theoretical 0.48 mmol) in $CH_2Cl_2$ (2 mL) was added tert-butyl 4-aminopiperidine-1-carboxylate (147 mg, 0.74 mmol), followed by triethylamine (95 µL, 0.67 mmol). The reaction mixture stirred for 20 h at room temperature and concentrated under vacuum. The residue was applied onto a silica gel column with hexanes/ethyl acetate (0-50%) providing 221 mg (65%) of tert-butyl 4-([4-([(1S,2S)-6-chloro-4-cyano-2-[4-(2,2,2-trifluoroacetyl)piperazin-1-yl]-2,3-dihydro-1H-inden-1-yl]oxy)phenyl]sulfonamido)piperidine-1-carboxylate (INT-SLC4) as a white solid. MS (m/z): 734.2 $[M+Na]^+$.

Step E: To a solution of sulfonamide INT-SLC4 (50 mg, 0.07 mmol) in $CH_2Cl_2$ (0.7 mL) was added trifluoroacetic acid (0.05 mL, 0.87 mmol, 12.3 equiv) and the mixture stirred for 20 h at room temperature. The reaction mixture was diluted with $CH_2Cl_2$ (5 mL) and washed with 1 M aqueous sodium hydroxide (2×2 mL) and brine (3 mL). The organic layer was dried over anhydrous sodium sulfate, filtered, and concentrated providing 50 mg of crude 4-([(1S,2S)-6-chloro-4-cyano-2-[4-(2,2,2-trifluoroacetyl)piperazin-1-yl]-2,3-dihydro-1H-inden-1-yl]oxy)-N-(piperidin-4-yl)benzenesulfonamide (INT-SLC5) as a white solid. MS (m/z): 612.2 $[M+H]^+$.

Step F: The crude material INT-SLC5 from Step E (theoretical 0.07 mmol), 4-[(tert-butoxycarbonyl)amino]butanoic acid (24.7 mg, 0.122 mmol, 1.7 equiv), HATU (61.9 mg, 0.163 mmol, 2.3 equiv), and crushed 3 Å molecular sieves were suspended in DMF (0.8 mL). To this slurry was added diisopropylethylamine (56.7 µL, 0.326 mmol, 4.6 equiv) and the reaction mixture stirred for 2 h. The volatiles were removed under vacuum and the residue was applied onto a silica gel column with $CH_2Cl_2$/methanol (0-10%) providing 50 mg (77%) of tert-butyl [4-(4-[4-([(1S,2S)-6-chloro-4-cyano-2-[4-(2,2,2-trifluoroacetyl)piperazin-1-yl]-2,3-dihydro-1H-inden-1-yl]oxy)phenylsulfonamido]piperidin-1-yl)-4-oxobutyl]carbamate (INT-SLC6) as a brownish solid. MS (m/z): 797.3 $[M+H]^+$.

Step G: Trifluoroacetic acid (50 µL, 0.65 mmol, 10 equiv) was added to a solution of Boc-amine INT-SLC6 (50 mg, 0.063 mmol) in $CH_2Cl_2$ (0.7 mL). The reaction mixture stirred for 5 h at room temperature. After completion (TLC and LCMS), the reaction mixture was diluted in $CH_2Cl_2$ (4 mL) and washed with 1 M aqueous sodium hydroxide (2×1.5 mL) and brine (1.5 mL). The organic layer was dried over anhydrous sodium sulfate, filtered, and concentrated under vacuum providing 45 mg of crude N-[1-(4-aminobutanoyl)piperidin-4-yl]-4-([(1S,2S)-6-chloro-4-cyano-2-[4-(2,2,2-trifluoroacetyl)piperazin-1-yl]-2,3-dihydro-1H-inden-1-yl]oxy)benzenesulfonamide (INT-SLC7) as a tan solid. MS (m/z): 697.2 $[M+H]^+$.

Step H: To the solution of crude material INT-SLC7 from Step G (theoretical 0.063 mmol) in DMF (0.6 mL) was added 1,4-diisocyanatobutane (3.5 mg, 0.025 mmol, 0.4 equiv). The reaction mixture was stirred for 15 h at room temperature. The reaction mixture was concentrated under vacuum and the residue was applied onto a silica gel column with $CH_2Cl_2$/methanol (0-12%) providing 7 mg (18%) of 4-([(1S,2S)-6-chloro-4-cyano-2-[4-(2,2,2-trifluoroacetyl)piperazin-1-yl]-2,3-dihydro-1H-inden-1-yl]oxy)-N-[1-(18-[4-([4-([(1S,2S)-6-chloro-4-cyano-2-[4-(2,2,2-trifluoroacetyl)piperazin-1-yl]-2,3-dihydro-1H-inden-1-yl]oxy)phenyl]sulfonamido)piperidin-1-yl]-6,13,18-trioxo-5,7,12, 14-tetraazaoctadecanoyl)piperidin-4-yl]benzenesulfonamide (INT-SLC8) as a white solid. MS (m/z): 767.3 [M/2+H]$^+$.

Step I: To a solution of dimer INT-SLC8 from Step H (7 mg, 0.0046 mmol) in methanol (0.3 mL) was added aqueous sodium hydroxide (3 M, 10 μL, 0.03 mmol, 6.5 equiv) at room temperature. The reaction mixture stirred for 16 h at room temperature, concentrated under vacuum, and the residue purified by reverse phase chromatography.

Compound 115

4-([(1S,2S)-6-Chloro-4-cyano-2-(piperazin-1-yl)-2,3-dihydro-1H-inden-1-yl]oxy)-N-[1-(18-[4-([4-([(1S,2S)-6chloro-4-cyano-2-(piperazin-1-yl)-2,3-dihydro-1H-inden-1-yl]oxy)phenyl]sulfonamido)piperidin-1-yl]-6,13,18-trioxo-5,7,12,14-tetraazaoctadecanoyl)piperidin-4-yl]benzenesulfonamide, bis(trifluoroacetate)

The crude product obtained through Steps A-I was purified by preparative HPLC with the following conditions: Column, Atlantis Preparative T3 OBD, 19*150 mm, 10 um; mobile phase, water (0.1% TFA) and CH$_3$CN (10.0% CH$_3$CN up to 70.0% in 40 min); Detector, UV 214 nm. This procedure provided 2.9 mg (40%) of the title compound as a white solid. MS (m/z): 671.3 [M/2+H]$^+$. $^1$H NMR (Methanol-d4, 400 MHz) δ 7.88 (d, J=8.8 Hz, 4H), 7.76 (m, 2H), 7.45 (m, 2H), 7.31 (d, J=8.9 Hz, 4H), 6.05 (d, J=5.8 Hz, 2H), 3.48-3.44 (m, 2H), 3.40-3.33 (m, 8H), 3.25-3.20 (m, 8H), 3.15-3.08 (m, 14H), 2.92-2.76 (m, 16H), 2.39-2.32 (m, 4H), 1.74-1.66 (m, 4H), 1.47 (s, 4H).

General Scheme for the Synthesis of Dimers with Peptidic Linkers:

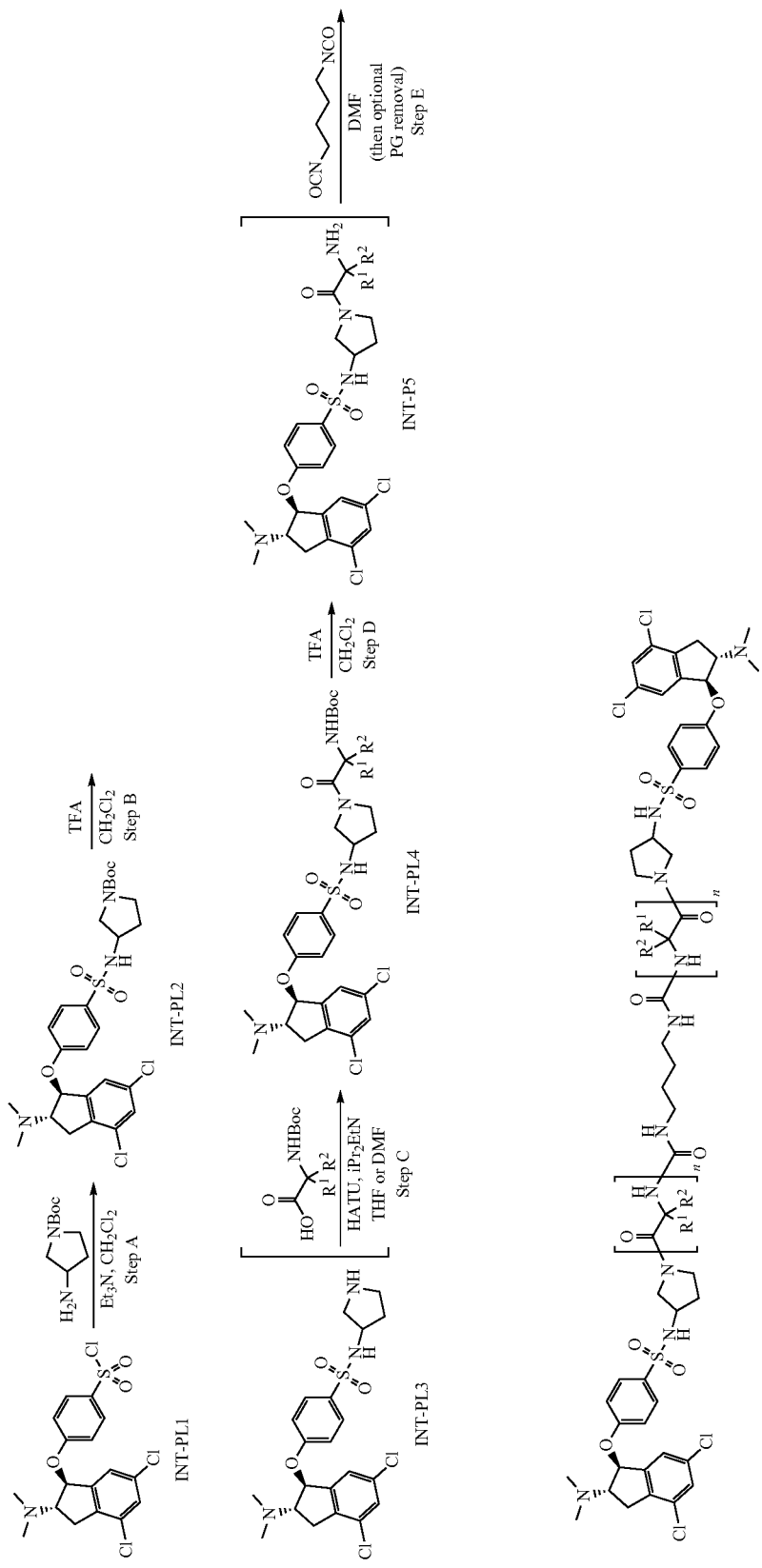

Indane dimer products such are synthesized with amino acid/peptidic linkers using the following methods.

Step A: The sulfonyl chloride INT-PL1, synthesized as outlined in this work, is combined with tert-butyl 3-amino-pyrrolidine-1-carboxylate in CH$_2$Cl$_2$ with trimethylamine to provide the desired sulfonamide adduct INT-PR2. The crude material is washed with water and brine, dried over anhydrous sodium sulfate, filtered, and concentrated under vacuum. The product is purified by normal phase chromatography to provide clean INT-PL2.

Step B: The Boc-protected amine INT-PL2 is slurried in CH$_2$Cl$_2$ and treated with trifluoroacetic acid. Once removal of the protecting group is complete based on TLC and/or LCMS, the volatiles are removed under vacuum and the residue dissolved in ethyl acetate. The organic layer is washed with saturated sodium bicarbonate and brine, dried over dried over anhydrous sodium sulfate, filtered, and concentrated under vacuum. The product is purified by normal phase chromatography to provide clean INT-PL3.

Step C: The amine product INT-PL3 is diluted in a suitable solvent such as tetrahydrofuran or DMF and treated with a Boc-protected amino acid, diisopropylethylamine, and a coupling reagent such as HATU. Once reaction is complete based on TLC and/or LCMS, the volatiles are removed under vacuum and the residue dissolved in CH$_2$Cl$_2$ or other suitable solvent. The organic layer is washed with saturated sodium bicarbonate and brine, dried over dried over anhydrous sodium sulfate, filtered, and concentrated under vacuum. The product is purified by normal phase chromatography to provide clean INT-PL4.

Step D: The Boc-protected amine INT-PL4 is slurried in CH$_2$Cl$_2$ and treated with trifluoroacetic acid. Once removal of the protecting group is complete based on TLC and/or LCMS, the volatiles are removed under vacuum and the residue dissolved in ethyl acetate. The organic layer is washed with saturated sodium bicarbonate and brine, dried over dried over anhydrous sodium sulfate, filtered, and concentrated under vacuum. The product is purified by normal phase chromatography to provide clean INT-PL5.

Steps C and D can be repeated to extend the linker peptide with more amino acids as desired.

Step E: The amine INT-PL5 is diluted in DMF and treated with a limiting amount of 1,4-diisocyanatobutane. The resulting solution was stirred at room temperature (or heated as required to drive completion). The resulting mixture was concentrated under vacuum to provide crude INT-PR6. If the product contains protecting groups such as tert-butyl carbamates or trifluoroacetamides, they are deprotected with the appropriate conditions at this stage. The final product of structure (II) is purified by preparative HPLC in water/CH$_3$CN and lyophilized to provide the pure products as salts.

Through Steps A-E for the synthesis of compound of structure (II), the following Examples are prepared.

Example 116: 4-([(1S,2S)-6-Chloro-4-cyano-2-(piperazin-1-yl)-2,3-dihydro-1H-inden-1-yl]oxy)-N—[(S)-1-(14-[(S)-3-([4-([(1S,2S)-6-chloro-4-cyano-2-(piperazin-1-yl)-2,3-dihydro-1H-inden-1-yl]oxy)phenyl]sulfonamido)pyrrolidin-1-yl]-4,11,14-trioxo-3,5,10,12-tetraazatetradecanoyl)pyrrolidin-3-yl]benzenesulfonamide Example 116

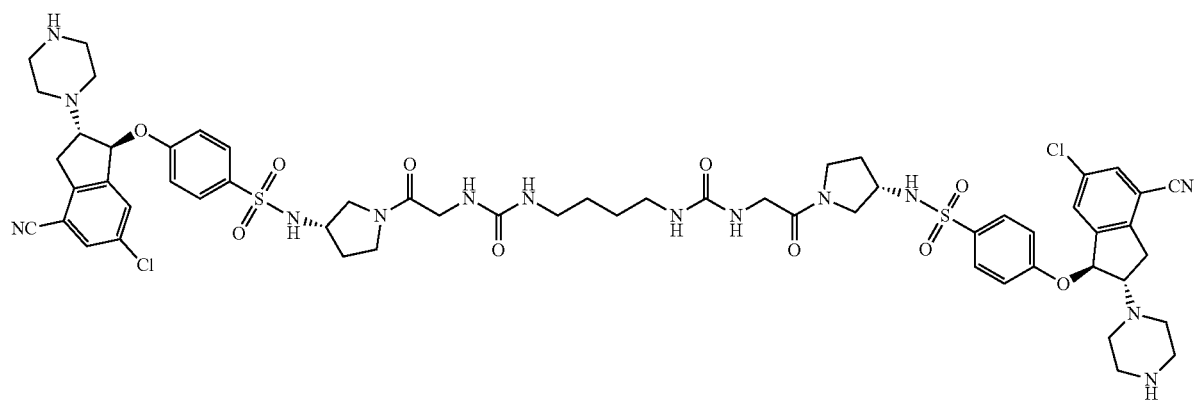

The title compound was prepared from INT-TE6 and Boc-Gly-OH. MS (m/z): 629.3 [M/2+H]+. $^1$H NMR (Methanol-d4, 400 MHz) δ 7.80 (dd, J=13.3, 5.1 Hz, 4H), 7.68 (t, J=2.0 Hz, 2H), 7.40 (d, J=6.4 Hz, 2H), 7.25 (dd, J=9.0, 7.0 Hz, 5H), 5.99 (d, J=6.7 Hz, 2H), 3.85-3.60 (m, 9H), 3.27 (d, J=16.6 Hz, 8H), 3.18-2.94 (m, 21H), 2.86-2.68 (m, 10H), 1.96-1.81 (m, 1H), 1.40 (s, 4H).

Example 117: 4-([(1S,2S)-6-Chloro-4-cyano-2-(piperazin-1-yl)-2,3-dihydro-1H-inden-1-yl]oxy)-N—[(S)-1-[(2S,13S)-14-[(S)-3-([4-([(1S,2S)-6-chloro-4-cyano-2-(piperazin-1-yl)-2,3-dihydro-1H-inden-1-yl]oxy)phenyl]sulfonamido)pyrrolidin-1-yl]-2,13-dimethyl-4,11,14-trioxo-3,5,10,12-tetraazatetradecanoyl]pyrrolidin-3-yl]benzenesulfonamide

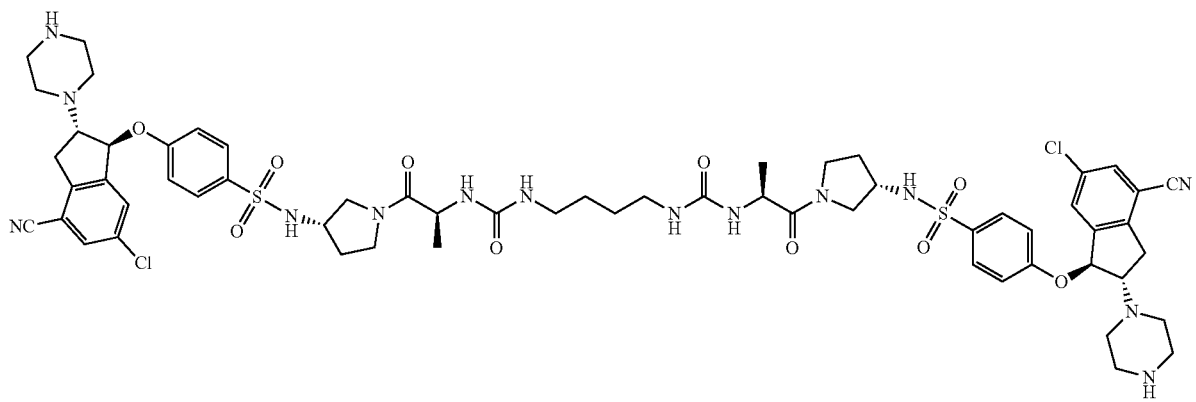

Example 117

The title compound is prepared from INT-TE6 and Boc-Ala-OH.

Example 118: $N^1,N^{14}$-bis(2-[(S)-3-([4-([(1S,2S)-6-chloro-4-cyano-2-(piperazin-1-yl)-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide

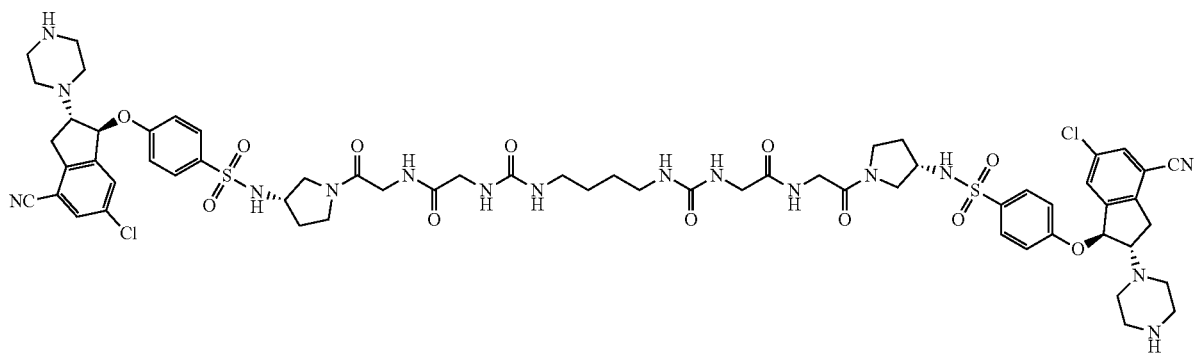

Example 118

The title compound was prepared from INT-TE6 and Boc-Gly-Gly-OH. MS (m/z): 686.3 [M/2+H]$^+$. $^1$H NMR (Methanol-d4, 400 MHz) δ 7.88 (t, J 8.5 Hz, 4H), 7.75 (s, 2H), 7.50-7.45 (m, 2H), 7.32 (t, J=8.4 Hz, 4H), 6.07 (s, 2H), 3.96-3.81 (m, 5H), 3.78 (d, J=4.1 Hz, 7H), 3.59-3.41 (m, 3H), 3.18 (dt, J=32.4, 6.6 Hz, 20H), 2.87 (s, 9H), 1.50 (s, 4H).

Example 119: N$^1$,N$^{14}$-bis(2-[(R)-3-([4-([(1S,2S)-6-chloro-4-cyano-2-(piperazin-1-yl)-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide Example 119

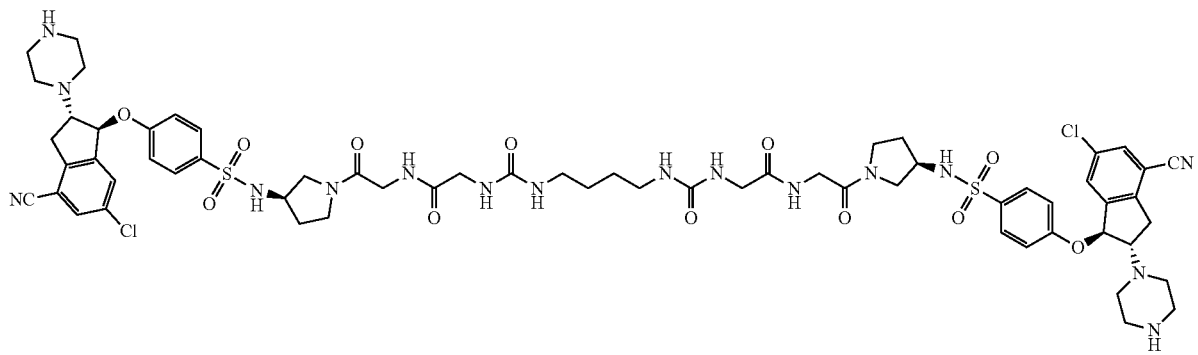

The title compound was prepared from INT-TE6 and Boc-Gly-Gly-OH. MS (m/z): 686.3 [M/2+H]+. 1H NMR (Methanol-d4, 400 MHz) δ 7.87 (d, J=8.9 Hz, 4H), 7.77-7.73 (m, 2H), 7.49-7.45 (m, 2H), 7.31 (d, J=8.9 Hz, 4H), 6.09-6.03 (m, 2H), 3.78 (d, J=4.3 Hz, 11H), 3.58-3.32 (m, 2H), 3.26-3.04 (m, 21H), 2.87 (s, 10H), 1.51 (s, 4H).

Example 120: N$^1$,N$^{18}$-Bis(1-([4-([(1S,2S)-6-chloro-4-cyano-2-(piperazin-1-yl)-2,3-dihydro-1H-inden-1-yl]oxy)phenyl]sulfonyl)piperidin-4-yl)-6,13-dioxo-5,7,12,14-tetraazaoctadecanediamide Example 120

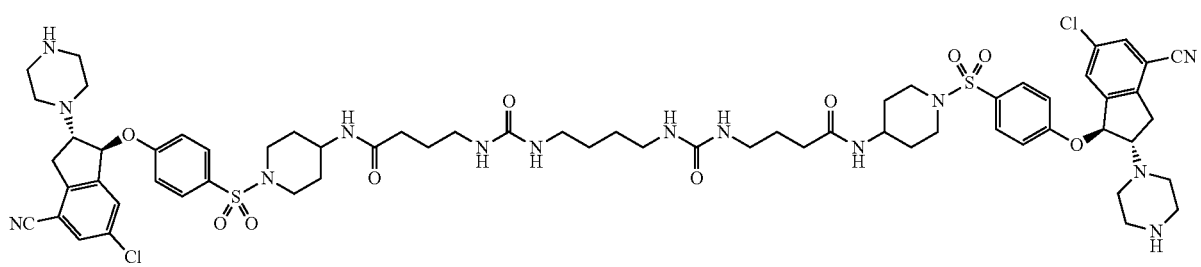

The title compound is prepared from 4-[(tert-butoxycarbonyl)amino]butanoic acid, tert-butyl piperidin-4-ylcarbamate, and INT-TE6.

Scheme for the Synthesis of Diastereomeric Dimethylaminopiperidine Analogs:
Example 121: 4-([(1S,2S)-6-Chloro-4-cyano-2-[(R)-3-(dimethylamino)piperidin-1-yl]-2,3-dihydro-1H-inden-1-yl]oxy)-N-[26-([4-([(1S,2S)-6-chloro-4-cyano-2-[(1)-3-(dimethylamino)piperidin-1-yl]-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide
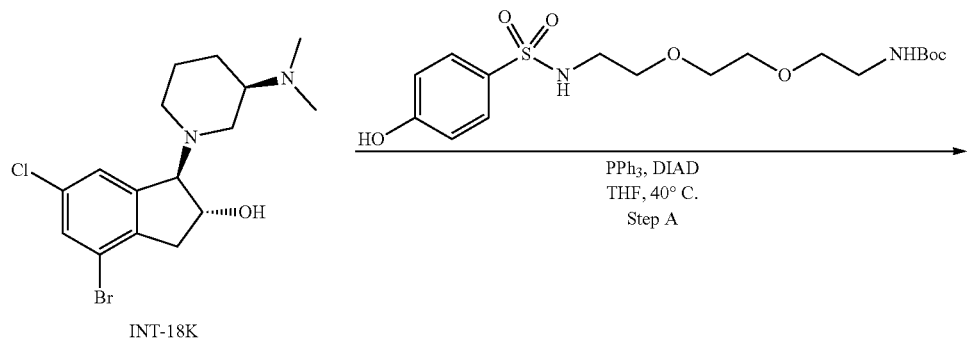
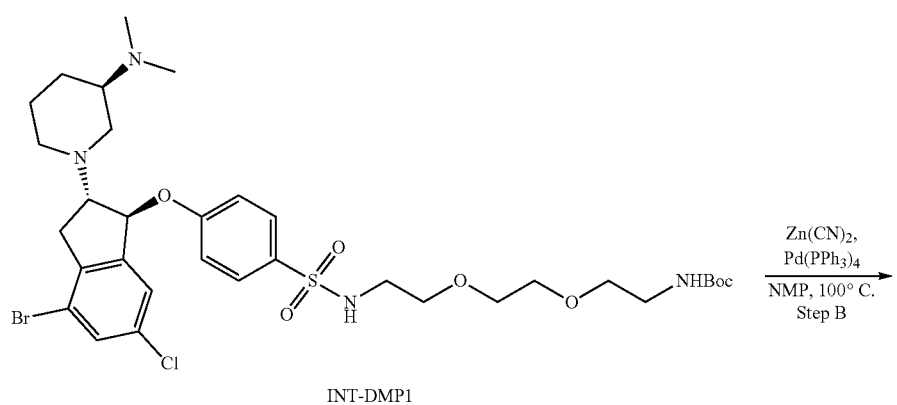
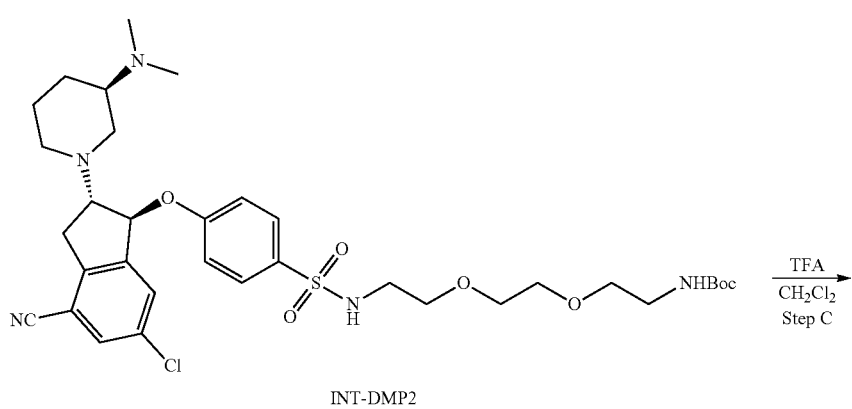

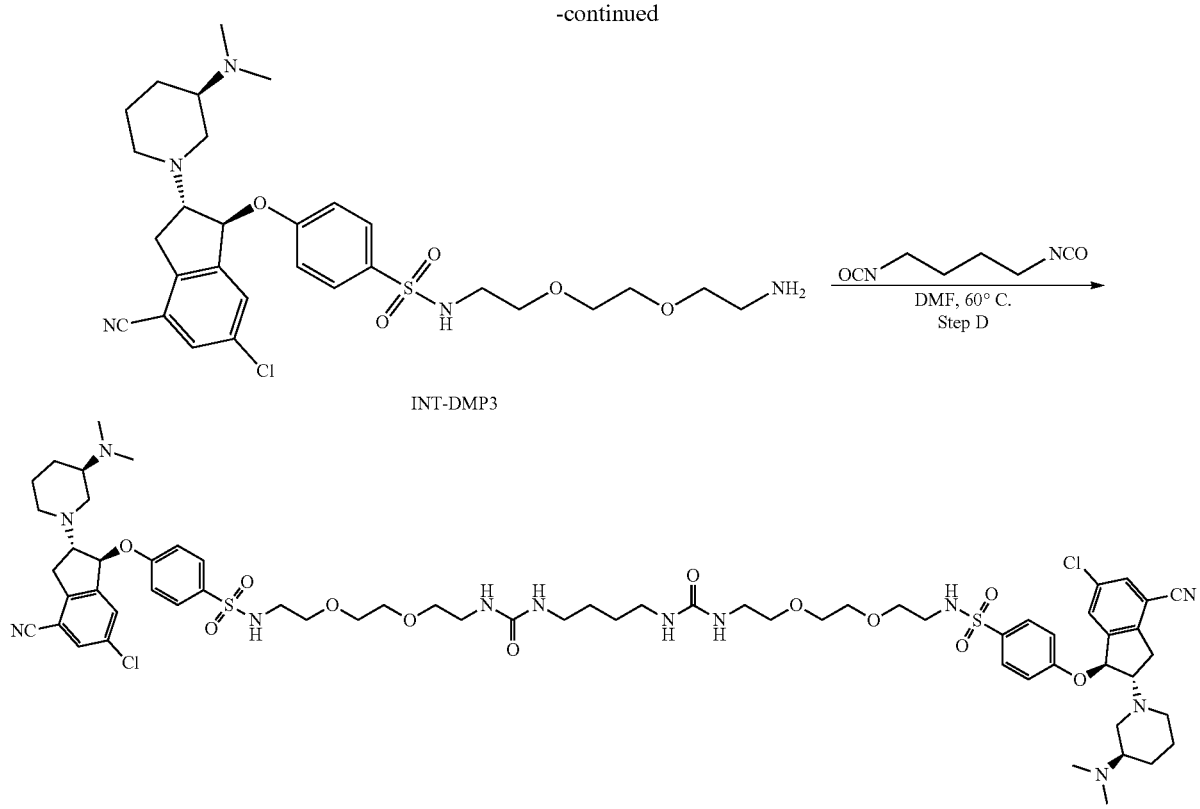

Example 121

Step A: To a 25-mL round-bottom flask was added aminoindanol INT-I8K (600 mg, 1.61 mmol 1 equiv), tert-butyl N-[2-(2-[2-[(4-hydroxybenzene)sulfonamido]ethoxy]ethoxy)ethyl]carbamate (736 mg, 1.82 mmol, 1.1 equiv), PPh₃ (629 mg, 2.40 mmol, 1.5 equiv), and THF (3.7 mL). To the above was added DIAD (485 mg, 2.40 mmol, 1.50 equiv) slowly at 45° C. over 25 min. The resulting solution was stirred for 3 h at 45° C. and then concentrated under vacuum after diluting with CH₂Cl₂. The residue was applied onto a silica gel column with CH₂Cl₂/methanol (10:1) providing 920 mg (75%) of tert-butyl N-[2-(2-[2-[(4-[[(1S,2S)-4-bromo-6-chloro-2-[(3R)-3-(dimethylamino)piperidin-1-yl]-2,3-dihydro-1H-inden-1-yl]oxy]benzene)sulfonamido]ethoxy]ethoxy)ethyl]carbamate (INT-DMP1) as a yellow oil.

Step B: To a To a 50-mL round-bottom flask purged and maintained with an inert atmosphere of nitrogen was added arylbromide INT-DMP1 (960 mg, 1.26 mmol, 1 equiv), Zn(CN)₂ (82 mg, 0.55 equiv), NMP (10 mL), and Pd(PPh₃)₄ (147 mg, 0.13 mmol, 0.1 equiv). The resulting solution was stirred overnight at 100° C. The resulting solution was diluted with water and extracted with 3×50 mL of ethyl acetate. The combined organic layers were dried over anhydrous sodium sulfate, filtered, and concentrated under vacuum. The residue was applied onto a silica gel column with CH₂Cl₂/methanol (10:1) providing 600 mg (67%) of tert-butyl N-[2-(2-[2-[(4-[[(1S,2S)-6-chloro-4-cyano-2-[(3R)-3-(dimethylamino)piperidin-1-yl]-2,3-dihydro-1H-inden-1-yl]oxy]benzene)sulfonamido]ethoxy]ethoxy)ethyl]carbamate (INT-DMP2) as a yellow oil.

Step C: To a To a 100-mL round-bottom flask was added Boc-amine INT-DMP2 (600 mg, 0.85 mmol, 1 equiv), CH₂Cl₂ (5 mL), and trifluoroacetic acid (1 mL). The resulting slurry was stirred for 30 min at room temperature. The pH value of the solution was adjusted to 9 with saturated aqueous sodium bicarbonate and extracted with 5×20 mL of CH₂Cl₂. The combined organic layers were dried over anhydrous sodium sulfate, filtered, and concentrated under vacuum. The residue was applied onto a silica gel column with CH₂Cl₂/methanol (10:1) providing 470 mg (91% of N-[2-[2-(2-aminoethoxy)ethoxy]ethyl]-4-[[(1S,2S)-6-chloro-4-cyano-2-[(3R)-3-(dimethylamino)piperidin-1-yl]-2,3-dihydro-1H-inden-1-yl]oxy]benzene-1-sulfonamide (INT-DMP3) as a yellow oil.

Step D: To a To a 25-mL round-bottom flask was added amine INT-DMP3 (470 mg, 0.78 mmol, 1 equiv), DMF (2 mL), and 1,4-diisocyanatobutane (48 mg, 0.34 mmol, 0.45 equiv). The resulting solution was stirred for 1 h at 60° C. The crude product was purified by preparative HPLC.

Example 121: 4-([[(1S,2S)-6-Chloro-4-cyano-2-[(R)-3-(dimethylamino)piperidin-1-yl]-2,3-dihydro-1H-inden-1-yl]oxy)-N-[26-([4-([[(1S,2S)-6-chloro-4-cyano-2-[(R)-3-(dimethylamino)piperidin-1-yl]-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide The crude product was purified by Preparative HPLC with the following conditions: Column, XBridge Preparative C18 OBD Column, 19*150 mm 5 um; mobile phase, Water (0.05% NH₄OH) and ACN (hold 47.0% ACN in 10 min); Detector, UV 254/220 nm. This resulted in 275.9 mg (26%) of 3-[2-(2-[2-[(4-[[(1S,2S)-6-chloro-4-cyano-2-[(3R)-3-(dimethylamino) piperidin-1-yl]-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]benzene)sulfonamido]ethoxy]ethoxy)ethyl]carbamoyl]amino) butyl]urea as a white solid. MS (m/z): 1353.7 [M+H]⁺. ¹H NMR (Methanol-d4, 300 MHz) δ 7.89-7.78 (m, 4H), 7.72

(d, J=2.0 Hz, 2H), 7.50-7.42 (m, 2H), 7.37-7.26 (m, 4H), 5.99 (d, J=5.9 Hz, 2H), 3.67-3.42 (m, 18H), 3.40-3.21 (m, 5H), 3.14-2.97 (m, 12H), 2.86 (d, J=11.1 Hz, 2H), 2.35-2.22 (m, 2H), 2.15 (s, 16H), 1.93 (d, J=11.8 Hz, 2H), 1.77 (d, J=13.4 Hz, 2H), 1.60-1.39 (m, 6H), 1.29-1.13 (m, 3H).

Example 122: 4-([(1S,2S)-6-Chloro-4-cyano-2-[(S)-3-(dimethylamino)piperidin-1-yl]-2,3-dihydro-1H-inden-1-yl]oxy)-N-[26-([4-([(1S,2S)-6-chloro-4-cyano-2-[(S)-3-(dimethylamino)piperidin-1-yl]-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide

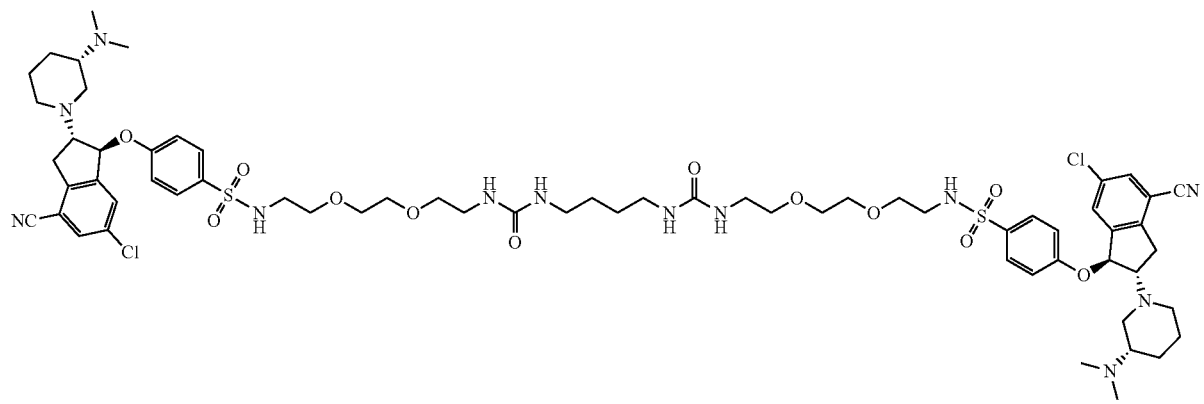

Example 122

The title compound was prepared in the same manner as Example 121, beginning with the enantiomer (S)—N,N-dimethylpiperidin-3-amine. The crude product was purified by preparative HPLC with the following conditions: Column, XBridge Shield RP18 OBD Column, 5 um, 19*150 mm; mobile phase, water (0.05% NH₄OH) and ACN (42.0% ACN up to 56.0% in 10 min); Detector, UV 254 nm. This resulted in 93.7 mg (56%) of the title compound as a white solid. MS (m/z): 1353 [M+H]⁺. ¹H NMR (Methanol-d4, 400 MHz) δ 7.91-7.83 (m, 4H), 7.76 (d, J=1.9 Hz, 2H), 7.52-7.47 (m, 2H), 7.38-7.29 (m, 4H), 6.05 (d, J=5.9 Hz, 2H), 3.75 (td, J=7.9, 5.9 Hz, 2H), 3.61-3.46 (m, 18H), 3.28 (d, J=5.4 Hz, 3H), 3.20-3.01 (m, 13H), 2.91 (s, 2H), 2.76 (d, J=11.3 Hz, 2H), 2.62 (s, 12H), 2.50 (d, J=11.0 Hz, 2H), 2.42 (d, J=10.8 Hz, 2H), 1.94 (s, 2H), 1.79 (d, J=12.8 Hz, 2H), 1.56 (s, 4H), 1.51-1.43 (m, 4H).

Scheme for the Synthesis of Example 123

Example 123: 4-([(1S,2S)-6-Chloro-4-cyano-2-(piperazin-1-yl)-2,3-dihydro-1H-inden-1-yl]oxy)-N-[1-(20-[4-([(1S,2S)-6-chloro-4-cyano-2-(piperazin-1-yl)-2,3-dihydro-1H-inden-1-yl]oxy)phenyl]sulfonamide]piperidin-1-yl)-7,14-dioxo-3,18-dioxa-6,8,13,15-tetraazaicosyl]piperidin-4-yl)benzenesulfonamide

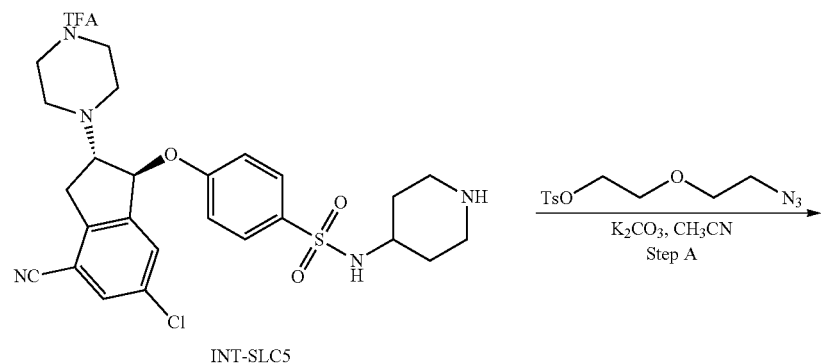

-continued

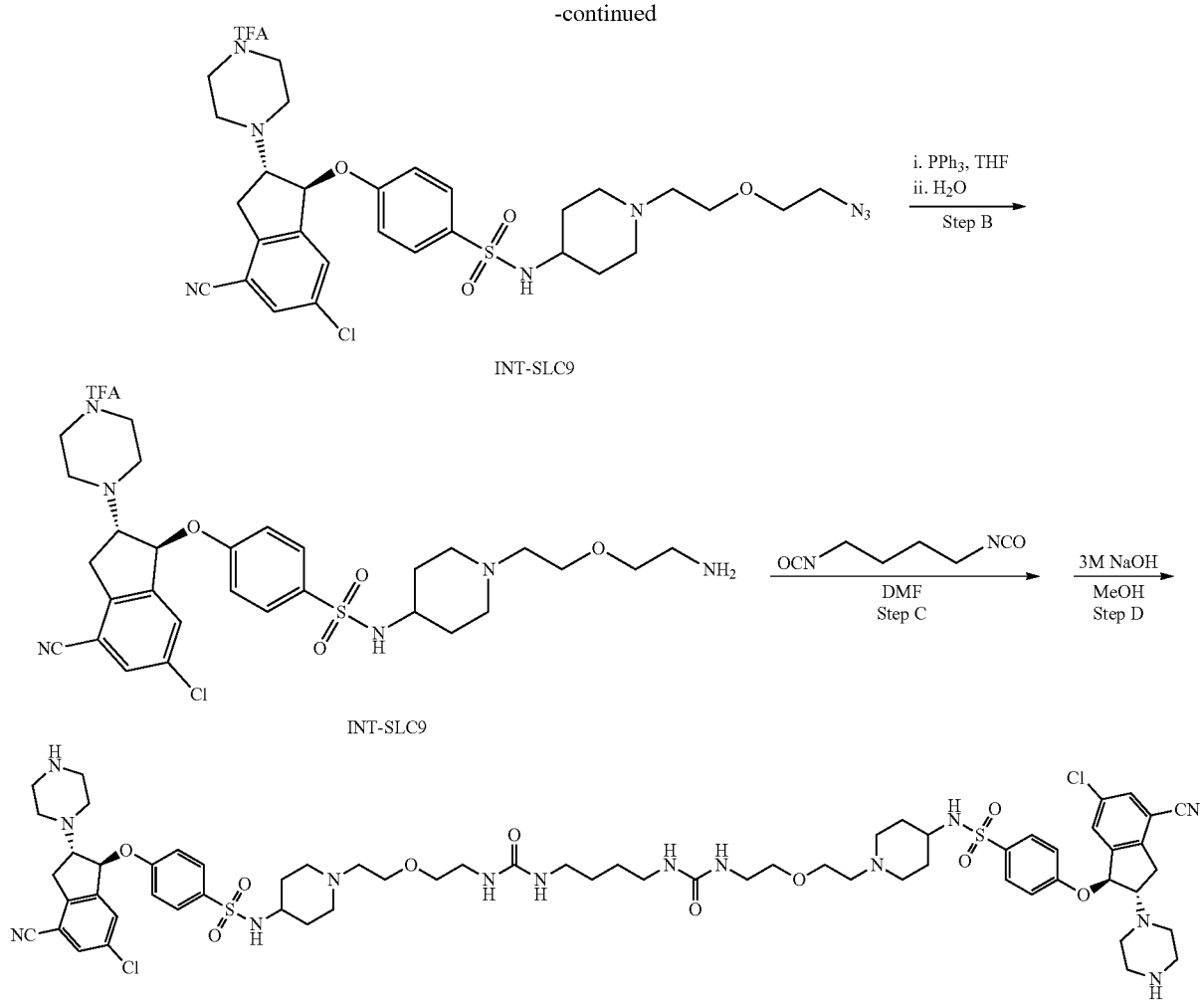

Example 123

Step A: 4-([(1S,2S)-6-Chloro-4-cyano-2-[4-(2,2,2-trifluoroacetyl)piperazin-1-yl]-2,3-dihydro-1H-inden-1-yl]oxy)-N-(piperidin-4-yl)benzenesulfonamide (INT-SLC5, 164 mg, 0.27 mmol), 2-(2-azidoethoxy)ethyl 4-methylbenzenesulfonate (91.3 mg, 0.32 mmol, 1.2 equiv), and potassium carbonate (110 mg, 0.80 mmol, 3 equiv) were suspended in acetonitrile (2.5 mL) and the mixture stirred for 46 h at 50° C. The reaction mixture was concentrated under vacuum and the residue was applied on silica gel column dichloromethane/methanol (0-10%) providing 112 mg (58%) of N-(1-[2-(2-azidoethoxy)ethyl]piperidin-4-yl)-4-([(1S,2S)-6-chloro-4-cyano-2-[4-(2,2,2-trifluoroacetyl)piperazin-1-yl]-2,3-dihydro-1H-inden-1-yl]oxy)benzenesulfonamide was collected as a white solid. MS (m/z): 725.2 [M+H]⁺.

Step B: Platinum on carbon 5 wt. % (25 mg) was added to a solution of INT-SLC9 (63 mg, 0.087 mmol) in ethyl acetate (2 mL). Three vacuum/hydrogen cycles were performed and the reaction mixture stirred under hydrogen (1 atm) for 2 h at room temperature. The reaction mixture was diluted with ethyl acetate and filtered through 0.2 μm Acrodisc® filter. The filtrates were concentrated under vacuum providing 55 mg of crude N-(1-[2-(2-aminoethoxy)ethyl]piperidin-4-yl)-4-([(1S,2S)-6-chloro-4-cyano-2-[4-(2,2,2-trifluoroacetyl)piperazin-1-yl]-2,3-dihydro-1H-inden-1-yl]oxy)benzenesulfonamide product (INT-SLC10) as a white solid. MS (m/z): 699.3 [M+H]⁺.

Step C: Solution of 1,4-diisocyanatobutane (4.3 mg, 0.031 mmol, 0.39 equiv) in dichloromethane (0.1 mL) was added to a solution of amine INT-SLC10 (55 mg, 0.079 mmol) in dichloromethane (1.2 mL) followed by triethylamine (10 μL, 0.078 mmol). The reaction mixture stirred for 3 h at room temperature and concentrated under vacuum. The residue was applied onto a silica gel column gradient wash with dichloromethane/methanol (0-20%) followed by dichloromethane/methanol/triethylamine (80:20:2.5) providing 38 mg (80%) of 4-([(1S,2S)-6-chloro-4-cyano-2-[4-(2,2,2-trifluoroacetyl)piperazin-1-yl]-2,3-dihydro-1H-inden-1-yl]oxy)-N-[1-(20-[4-([4-([(1S,2S)-6-chloro-4-cyano-2-[4-(2,2,2-trifluoroacetyl)piperazin-1-yl]-2,3-dihydro-1H-inden-1-yl]oxy)phenyl]sulfonamido)piperidin-1-yl]-7,14-dioxo-3,18-dioxa-6,8,13,15-tetraazaicosyl)piperidin-4-yl]benzenesulfonamide as a white solid. MS (m/z): 770.0 [M/2+H]⁺.

Step D: Aqueous sodium hydroxide (3 M, 24 μL, 0.07 mmol, 3 equiv) was added to a solution of dimer from Step C (37 mg, 0.024 mmol) in tetrahydrofuran/methanol (0.5: 0.05 mL). The reaction mixture stirred for 1.5 h at room temperature and then quenched with trifluoroacetic acid (50 μL) at 0° C. The mixture was concentrated under vacuum and the residue purified by reverse phase chromatography to yield 4-([(1S,2S)-6-Chloro-4-cyano-2-(piperazin-1-yl)-2,3-dihydro-1H-inden-1-yl]oxy)-N-[1-(20-[4-([4-([(1S,2S)-6-chloro-4-cyano-2-(piperazin-1-yl)-2,3-dihydro-1H-inden-1-yl]oxy)phenyl]sulfonamide]piperidin-1-yl)-7,14-dioxo-3,18-dioxa-6,8,13,15-tetraazaicosyl]piperidin-4-yl)benzenesulfonamide (Example 123).

Representative Scheme for the Synthesis of N-Acylsulfonamide Dimer Products:

Example 124: N$^1$,N$^{18}$-Bis([4-([(1S,2S)-6-chloro-4-cyano-2-(piperazin-1-yl)-2,3-dihydro-1H-inden-1-yl]oxy)phenyl]sulfonyl)-6,13-dioxo-5,7,12,14-tetraazaoctadecanediamide

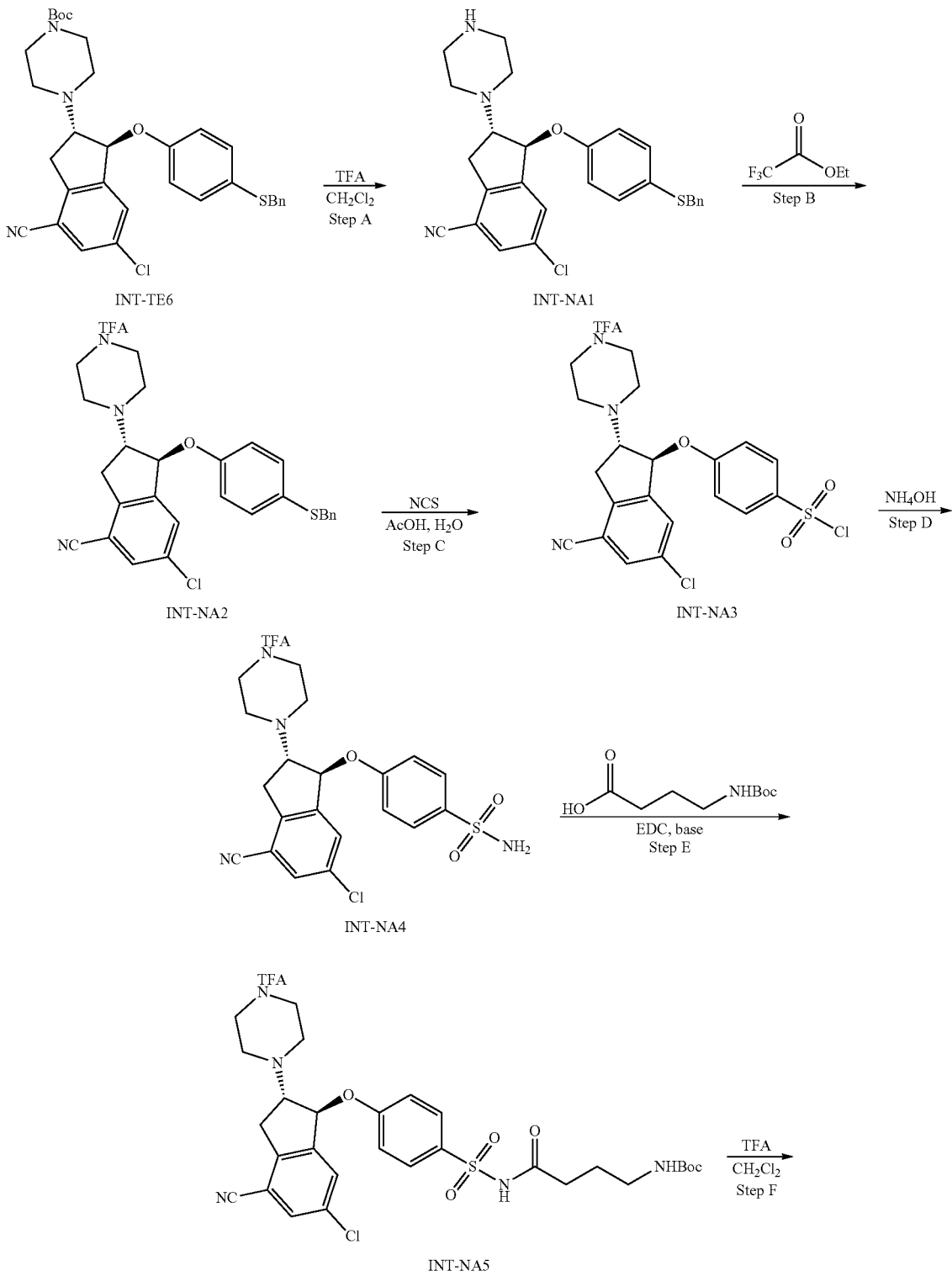

399 400
-continued
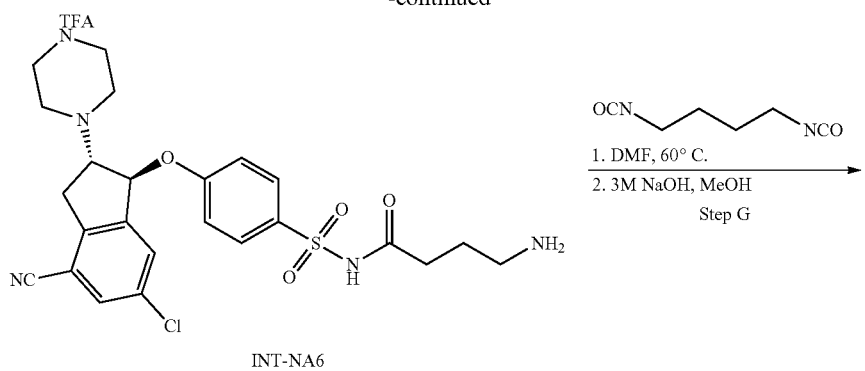
INT-NA6
1. DMF, 60° C.
2. 3M NaOH, MeOH
Step G
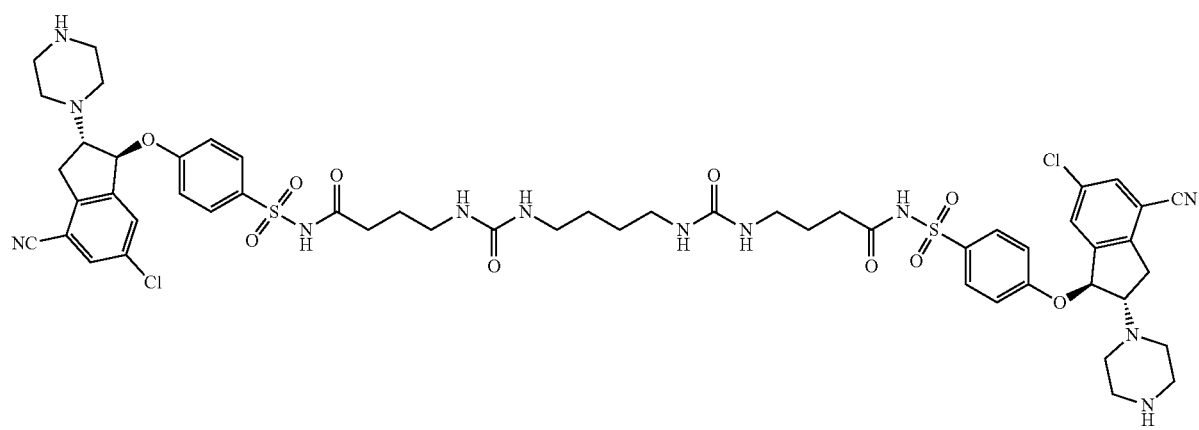
Example 124

Step A: The thioether intermediate INT-TE6 is deprotected by treatment with a protic acid such as trifluoroacetic acid or HCl.

Step B: The secondary amine of INT-NA1 is protected as a trifluroacetamide by treatment with ethyl trifluoroacetate in the presence of a base such as triethylamine or pyridine.

Step C: The sulfonyl chloride INT-NA3 is obtained by oxidative chlorination with NCS or chlorine gas.

Step D: Treatment of the sulfonyl chloride with an ammonia equivalent through addition of ammonia in methanol or ammonium hydroxide yields sulfonamide INT-NA4.

Step E: The N-acylsulfonamide is obtained through standard coupling conditions with the carboxylic acid using reagents including EDC, DCC, CDI, HATU, and the like, or alternatively, through reactions with acid chlorides, all in the presence of a suitable base such as triethylamine or pyridine.

Step F: The Boc-intermediate INT-NA5 is deprotected by treatment with a protic acid such as trifluoroacetic acid or HCl.

Step G: Reaction of the amine INT-NA5 with a dual functional reagent such as 1,4-diisocyanatobutane yields the dimer product from which protecting groups are removed through treatment with appropriate reagents (such as 3 M sodium hydroxide in methanol) to provide the final dimer product.

Example 125: N-([4-([(1S,2S)-6-chloro-4-cyano-2-(piperazin-1-yl)-2,3-dihydro-1H-inden-1-yl]oxy)phenyl]sulfonyl)-1-[16-(4-[([4-([(1S,2S)-6-chloro-4-cyano-2-(piperazin-1-yl)-2,3-dihydro-1H-inden-1-yl]oxy)phenyl]sulfonyl)carbamoyl]piperidin-1-yl)-5,12-dioxo-4,6,11,13-tetraazahexadecyl]piperidin-4-carboxamide Example 125

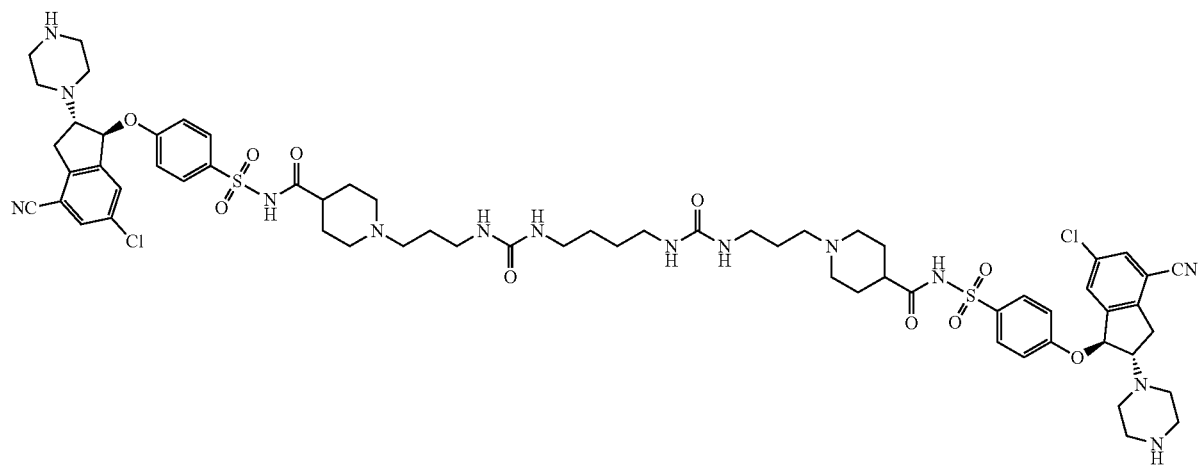

Representative Scheme for Synthesis of Piperazine Dimer Products:

Example 126: 4-([[(1S,2S)-6-Chloro-4-cyano-2-(1,4-diazepan-1-yl)-2,3-dihydro-1H-inden-1-yl]oxy)-N—[(S)-1-(20-[(S)-3-([4-([(1S,2S)-6-chloro-4-cyano-2-(1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide

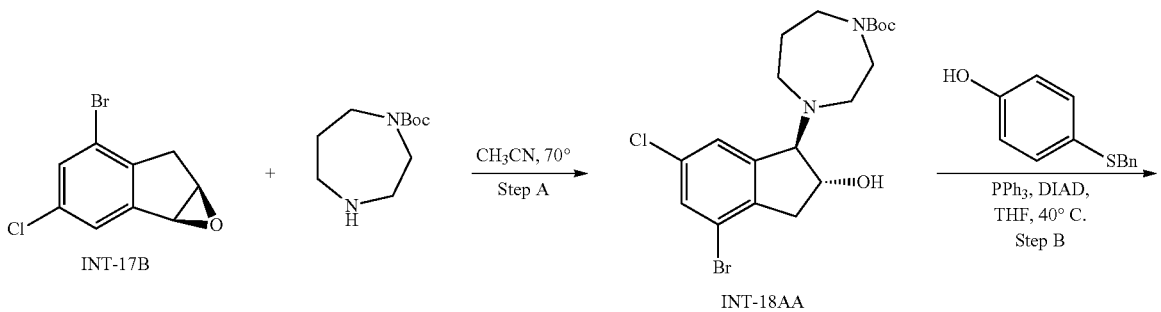

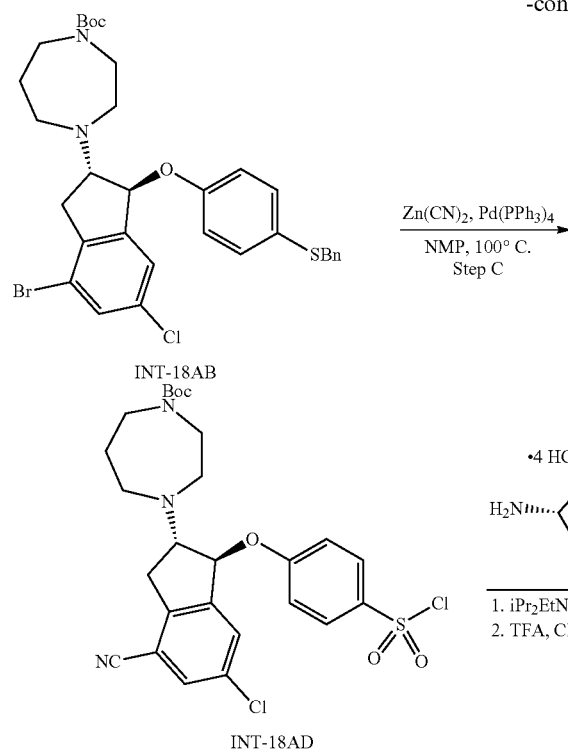
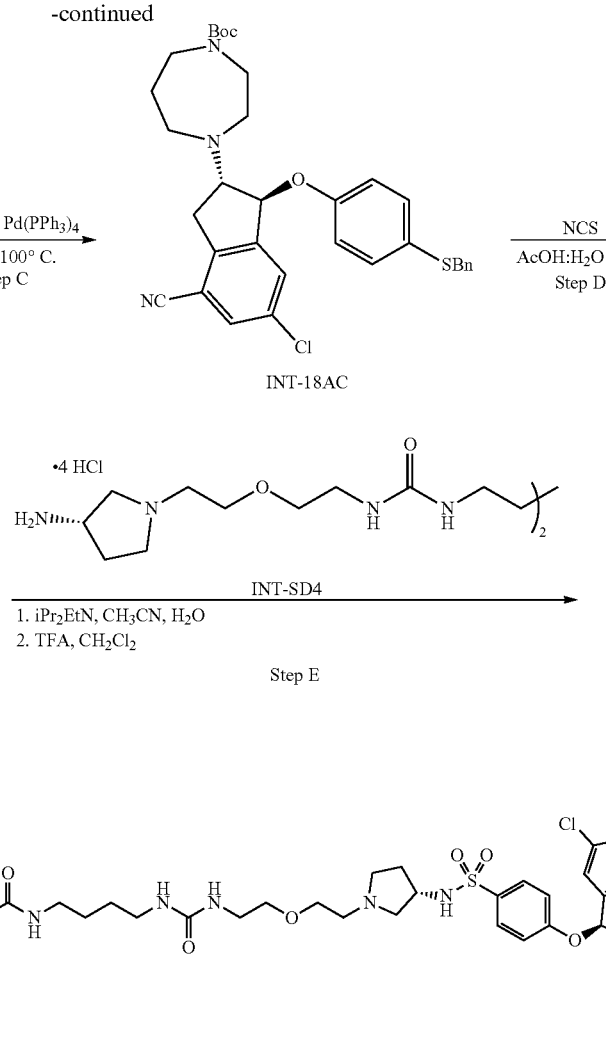

Example 126

Step A: As described previously in this work, epoxide INT-I7B is reacted with Boc-homopiperazine in CH₃CN at elevated temperature. The resulting mixture is concentrated under vacuum and purified on a silica gel column to provide the aminoindanol INT-I8AA.

Step B: Aminoindanol INT-I8AA (1 equiv) and the thiophenol are mixed in tetrahydrofuran (0.2 M), heating to 40° C. To this slurry is added PPh₃ (2 equiv) and DIAD (1.5 equiv). Upon completion of the reaction (LCMS or TLC), the resulting mixture is concentrated under vacuum and purified on a silica gel column to provide ether INT-I8AB.

Step C: Aminoindanol INT-I8AB (1 equiv), Zn(CN)₂ (0.60 equiv), Pd(PPh₃)₄ (0.10 equiv), and NMP (0.4 M) are combined at 95° C. Upon completion, the reaction slurry is cooled and extracted with 3× ethyl acetate. The combined organic layers are washed with 3× brine, dried over anhydrous sodium sulfate, filtered, and concentrated. The residue is purified on a silica gel column providing the 4-cyano substituted aminoindanol INT-I8AC.

Step D: Thioether INT-I8AC (1 equiv) and acetic acid and water (9:1) are combined in a flask followed by the addition of N-chlorosuccinimide (NCS, 5 equiv) in several batches. Upon completion, the resulting slurry is concentrated under vacuum and diluted with H₂O. The resulting solution is extracted with of ethyl acetate and the organic layers combined and washed with 3× H₂O and 1× brine. The mixture is dried over anhydrous sodium sulfate, filtered, and concentrated under vacuum. The residue is purified on a silica gel column to provide the sulfonyl chloride INT-I8AD.

Step E: Amine dimer INT-SD4 is slurried in CH₃CN and water (added as necessary for solubility) followed by the addition of sulfonyl chloride INT-I8AD and diisopropylethylamine. The reaction mixture is agitated until completion (as determined by TLC or LCMS) and concentrated under vacuum. The residue is diluted in CH₂Cl₂ and washed with 2×1 M NaHSO₄ and brine, dried over anhydrous sodium sulfate, filtered, and concentrated under vacuum. The residue is purified on a silica gel column providing the Boc-protected dimer product. Subsequently, the material is treated with trifluoracetic acid in CH₂Cl₂ to remove the protecting groups and the resulting mixture purified by reverse phase preparative HPLC.

The crude product was purified by preparative HPLC with the following conditions: Column, XBridge Shield RP18 OBD Column, 5 um, 19*150 mm; mobile phase, water (0.05% TFA) and ACN (13.0% ACN up to 36.0% in 8 min);

Detector, UV 254 nm. This resulted in 188 mg (69%) of the title compound as a white solid. MS (m/z): 1345.65 [M+H]+. 1H NMR (Methanol-d4, 400 MHz) δ 7.94 (d, J=8.6 Hz, 2H), 7.80 (d, J=1.9 Hz, 1H), 7.51 (d, J=1.7 Hz, 1H), 7.39 (d, J=8.8 Hz, 2H), 6.09 (d, J=5.9 Hz, 1H), 4.00 (q, J=7.4 Hz, 2H), 3.78 (t, J=4.9 Hz, 2H), 3.56 (t, J=5.3 Hz, 2H), 3.50-3.36 (m, 2H), 3.33-3.23 (m, 2H), 3.20-3.05 (m, 5H), 2.95 (t, J=6.0 Hz, 2H), 2.37 (s, 1H), 2.04 (dd, J=10.1, 4.0 Hz, 3H), 1.52 (s, 2H).

Example 127: 4-([(1S,2S)-6-Chloro-4-cyano-2-(1,4-diazepan-1-yl)-2,3-dihydro-1H-inden-1-yl]oxy)-N—[(R)-1-(20-[(R)-3-([4-([(1S,2S)-6-chloro-4-cyano-2-(1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; bis(trifluoroacetic acid)

Example 127

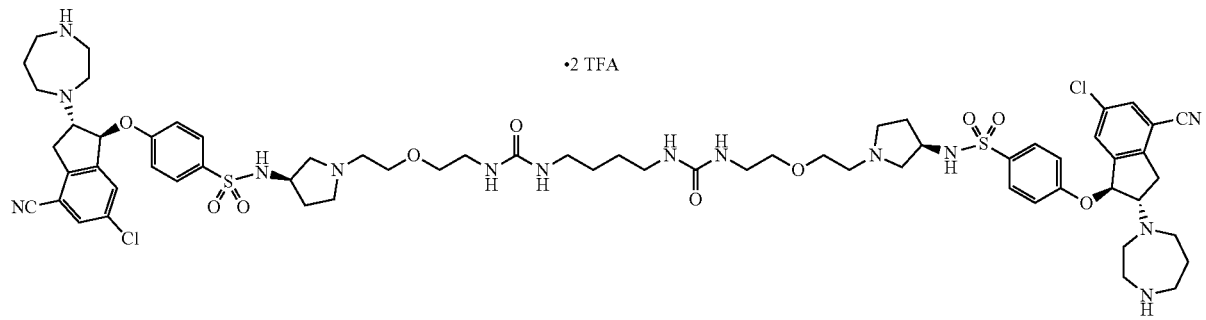

The crude product was purified by preparative HPLC with the following conditions: Column, XBridge C18 OBD Preparative Column, 19 mm*250 mm, 5 μm; mobile phase, water (0.05% TFA) and ACN (24.0% ACN up to 42.0% in 9 min); Detector, UV 254 nm. This resulted in 128.3 mg (70%) of the title compound as a white solid. MS (m/z): 1348 [M+H]+. 1H NMR (Methanol-d4, 300 MHz) δ 7.89 (d, J=8.8 Hz, 2H), 7.75 (d, J=1.9 Hz, 1H), 7.46 (s, 1H), 7.34 (d, J=8.8 Hz, 2H), 6.03 (d, J=5.8 Hz, 1H), 4.87-4.77 (m, 1H), 4.00-3.89 (m, 2H), 3.73 (t, J=4.9 Hz, 2H), 3.52 (t, J=5.2 Hz, 2H), 3.43-3.31 (m, 3H), 3.28-3.01 (m, 6H), 2.89 (t, J=6.0 Hz, 2H), 2.04-1.94 (m, 3H), 1.47 (s, 2H).

Example 128: 4-([(1S,2S)-6-Chloro-4-cyano-2-(4-methyl-1,4-diazepan-1-yl)-2,3-dihydro-1H-inden-1-yl]oxy)-N—[(S)-1-(20-[(S)-3-([4-([(1S,2S)-6-chloro-4-cyano-2-(4-methyl-1,4-diazepan-1-yl)-2,3-dihydro-1H-inden-1-yl]oxy)phenyl]sulfonamido)pyrrolidin-1-yl]-7,14-diaxo-3,18-dioxa-6,8,13,15-tetraazaicosyl)pyrrolidin-3-yl]benzenesulfonamide Example 128

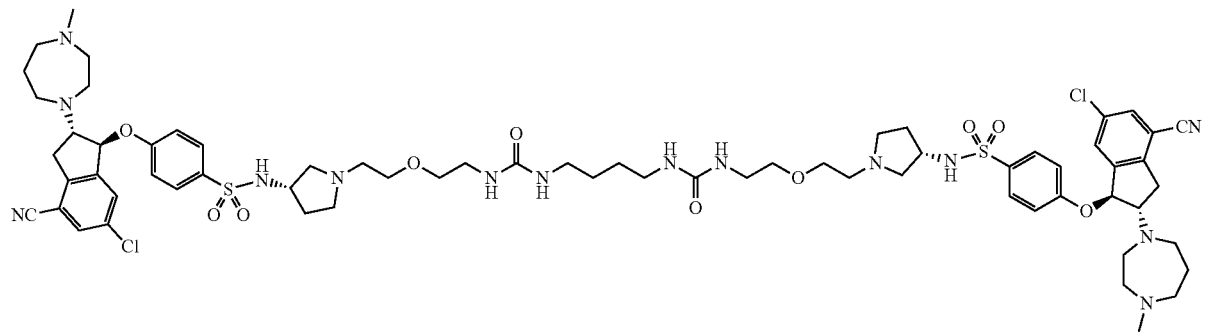

Example 129: 4-([(1S,2S)-6-Chloro-4-cyano-2-(4-methyl-1,4-diazepan-1-yl)-2,3-dihydro-1H-inden-1-yl]oxy)-N—[(R)-1-(20-[(R)-3-([4-([1S,2S)-6-chloro-4-cyano-2-(4-methyl-1,4-diazepan-1-yl)-2,3-dihydro-1H-inden-1-yl]oxy)phenyl]sulfonamido)pyrrolidin-1-yl]-7,14-diaxo-3,18-dioxa-6,8,13,15-tetraazaicosyl)pyrrolidin-3-yl]benzenesulfonamide Example 129

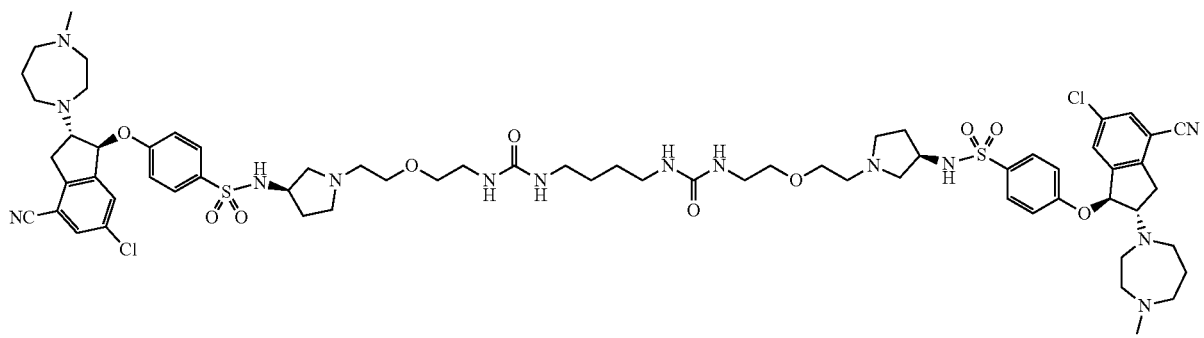

Example 130: 4-([(1S,2S)-2-[(1S,4S)-2,5-Diazabicyclo[2.2.1]heptan-2-yl]-6-chloro-4-cyano-2,3-dihydro-1H-inden-1-yl]oxy)-N—[(S)-1-(20-[(S)-3-[(4-([(1S,2S)-2-[(1S,4S)-2,5-diazabicyclo[2.2.1]heptan-2-yl]-6-chloro-4-cyano-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; bis (trifluoroacetic acid)

Example 130

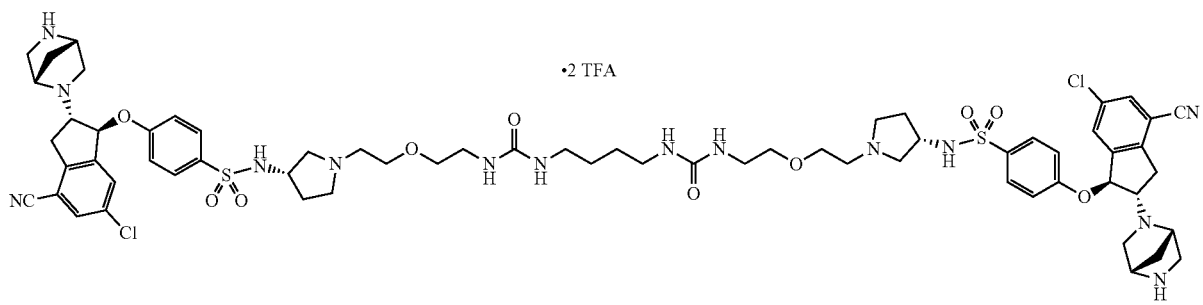

The crude product was purified by Preparative HPLC with the following conditions: Column, XBridge C18 OBD Preparative Column, 10 μm, 19*250 mm; mobile phase, water (0.05% TFA) and ACN (23.0% ACN up to 41.0% in 8 min); Detector, UV 254 nm. This resulted in 209 mg (51%) of the title compound as a white solid. MS (m/z): 1343 [M+H]$^+$. $^1$H NMR (Methanol-d$^4$, 400 MHz) δ 7.96-7.88 (m, 4H), 7.76 (d, J=1.9 Hz, 2H), 7.40-7.32 (m, 6H), 6.05 (d, J=6.9 Hz, 2H), 4.27 (s, 2H), 3.99 (s, 4H), 3.91-3.80 (m, 4H), 3.75 (t, J=5.0 Hz, 6H), 3.64-3.40 (m, 14H), 3.21 (dd, J=11.5, 2.4 Hz, 6H), 3.15-3.01 (m, 10H), 2.95-2.87 (m, 2H), 2.47-2.07 (m, 4H), 2.01 (s, 2H), 1.85 (d, J=11.6 Hz, 2H), 1.49 (s, 4H).

Example 131: 4-([(1S,2S)-2-[(1S,4S)-2,5-Diazabi-
cyclo[2.2.1]heptan-2-yl]-6-chloro-4-cyano-2,3-di-
hydro-1H-inden-1-yl]oxy)-N—[(R)-1-(20-[(R)-3-
([4-([(1S,2S)-2-[(1S,4S)-2,5-diazabicyclo[2.2.1]
heptan-2-yl]-6-chloro-4-cyano-2,3-dihydro-1H-
inden-1-yl]oxy)phenyl]sulfonamido)pyrrolidin-1-yl]-
7,14-dioxo-3,18-dioxa-6,8,13,15-tetraazaicosyl)
pyrrolidin-3-yl]benzenesulfonamide; bis
(trifluoroacetic acid)

Example 131

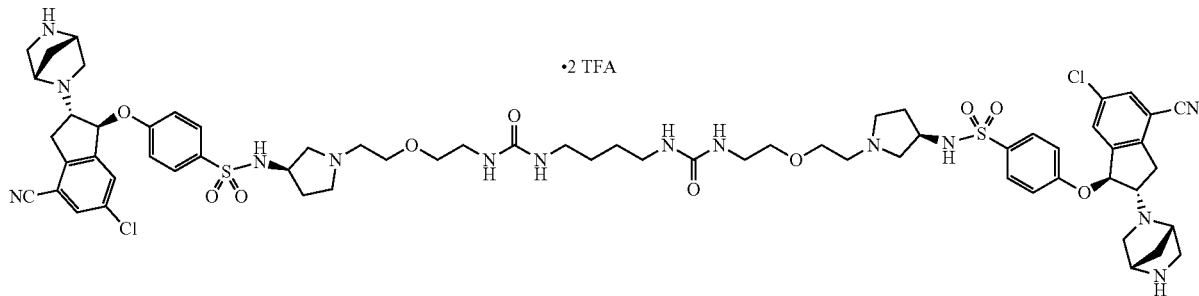

The crude product was purified by preparative HPLC with the following conditions: Column, XBridge C18 OBD Preparative Column, 10 μm, 19 mm×250 mm; mobile phase, water (0.05% TFA) and ACN (23.0% ACN up to 41.0% in 8 min); Detector, UV 254 nm. This resulted in 288.8 mg (63%) of the title compound as a white solid. MS (m/z): 1343 [M+H]$^+$. $^1$H NMR (Methanol-d4, 400 MHz) δ 7.96-7.88 (m, 4H), 7.77 (d, J=1.8 Hz, 2H), 7.40-7.32 (m, 6H), 6.06 (d, J=6.9 Hz, 2H), 4.30-4.25 (m, 2H), 3.99 (s, 2H), 3.93-3.81 (m, 5H), 3.75 (t, J=5.0 Hz, 7H), 3.65-3.36 (m, 16H), 3.21 (dd, J=11.6, 2.4 Hz, 4H), 3.15-3.01 (m, 10H), 2.97-2.89 (m, 2H), 2.49-2.06 (m, 4H), 2.00 (s, 2H), 1.86 (d, J=11.3 Hz, 2H), 1.49 (s, 4H).

Example 132: 4-([(1S,2S)-6-Chloro-4-cyano-2-[(R)-
3-methylpiperazin-1-yl]-2,3-dihydro-1H-inden-1-yl]
oxy)-N—[(S)-1-(20-[(S)-3-([4-([(1S,2S)-6-chloro-4-
cyano-2-[(R)-3-methylpiperazin-1-yl]-2,3-dihydro-
1H-inden-1-yl]oxy)phenyl]sulfonamido)pyrrolidin-
1-yl]-7,14-diaxo-3,18-dioxa-5,8,13,15-
tetraazaicosyl)pyrrolidin-3-yl]benzenesulfonamide;
bis(trifluoroacetic acid)

Example 132

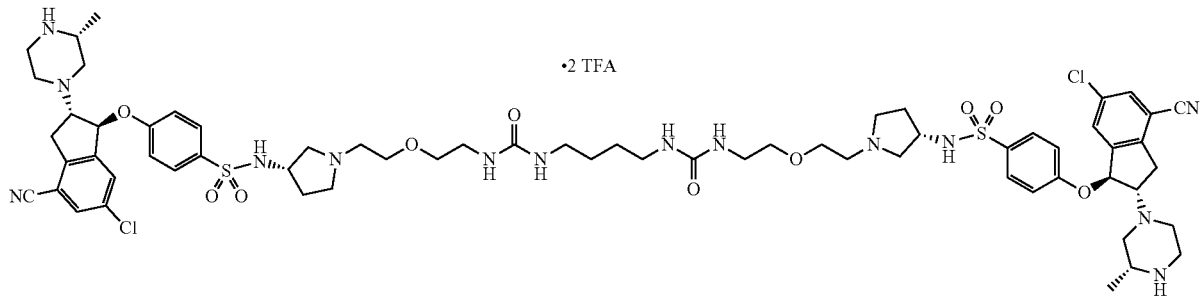

The crude product was purified by Preparative HPLC with the following conditions: Column, XBridge Shield RP18 OBD Column, 5 um, 19*150 mm; mobile phase, water (0.05% TFA) and ACN (12% ACN up to 38% in 8 min); Detector, UV 220 nm. This resulted in 180.1 mg (59%) of the title compound as a white solid. MS (m/z): 1347.7 [M+H]$^+$. $^1$H NMR (Methanol-d4, 300 MHz) δ 7.93-7.83 (m, 4H), 7.75 (d, J=1.9 Hz, 2H), 7.43 (d, J=1.8 Hz, 2H), 7.38-7.29 (m, 4H), 6.12-6.03 (m, 2H), 3.96 (s, 2H), 3.74 (q, J=6.6, 5.1 Hz, 10H), 3.51 (t, J=5.2 Hz, 4H), 3.43-3.27 (m, 16H), 3.19-2.97 (m, 15H), 2.63 (t, J=10.8 Hz, 2H), 2.41-2.27 (m, 3H), 2.00 (s, 1H), 1.47 (s, 4H), 1.27 (d, J=6.6 Hz, 6H).

Example 133: 4-([(1S,2S)-6-Chloro-4-cyano-2-[(R)-3-methylpiperazin-1-yl]-2,3-dihydro-1H-inden-1-yl]oxy)-N—[(R)-1-(20-[(R)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; bis(trifluoroacetic acid)

Example 133

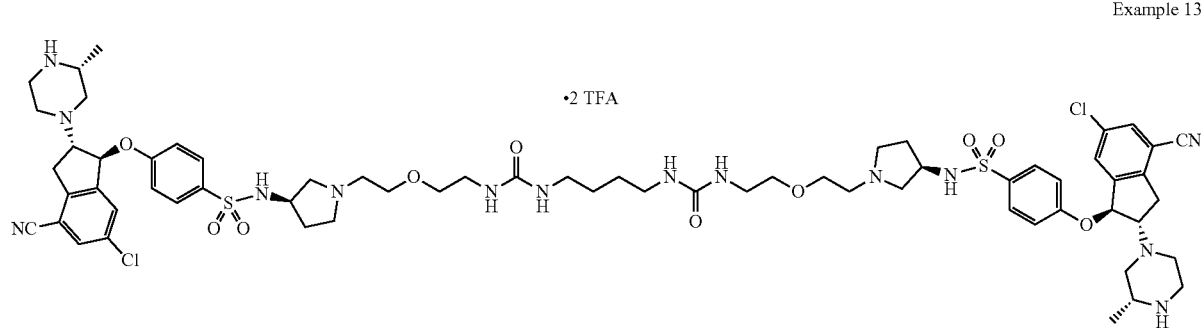 [SMILES: C[C@@H]1CN([C@H]2Cc3c(C#N)cc(Cl)cc3[C@@H]2Oc2ccc(S(=O)(=O)N[C@@H]3CCN(CCOCCNC(=O)NCCCCNC(=O)NCCOCCN4CC[C@@H](NS(=O)(=O)c5ccc(O[C@H]6c7cc(Cl)cc(C#N)c7C[C@@H]6N6CCN[C@H](C)C6)cc5)C4)C3)cc2)CCN1]

The crude product was purified by preparative HPLC with the following conditions: Column, XBridge Preparative OBD C18 Column, 19*250 mm, 5 μm; mobile phase, water (0.05% TFA) and ACN (25% ACN up to 40% in 9 min); Detector, UV 220 nm. This resulted in 218.9 mg (54%) of the title compound as a white solid. MS (m/z): 1348 [M+H]$^+$. $^1$H NMR (Methanol-d4, 300 MHz) δ 7.88 (d, J=8.8 Hz, 4H), 7.75 (d, J=1.9 Hz, 2H), 7.47-7.40 (m, 2H), 7.38-7.29 (m, 4H), 6.08 (d, J=6.0 Hz, 2H), 3.74 (q, J=6.8, 5.2 Hz, 8H), 3.51 (t, J=5.2 Hz, 7H), 3.43-3.27 (m, 10H), 3.19-2.97 (m, 21H), 2.63 (t, J=11.2 Hz, 2H), 2.34 (dd, J=12.6, 10.2 Hz, 2H), 2.00 (s, 0H), 1.47 (s, 4H), 1.27 (d, J=6.6 Hz, 6H).

Example 134: 4-([(1S,2S)-6-Chloro-4-cyano-2-[(S)-3-methylpiperazin-1-yl]-2,3-dihydro-1H-inden-1-yl]oxy)-N—[(S)-1-(20-[(S)-3-([4-([(1S,2S)-6-chloro-4-cyano-2-[(S)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; bis(trifluoroacetic acid)

Example 134

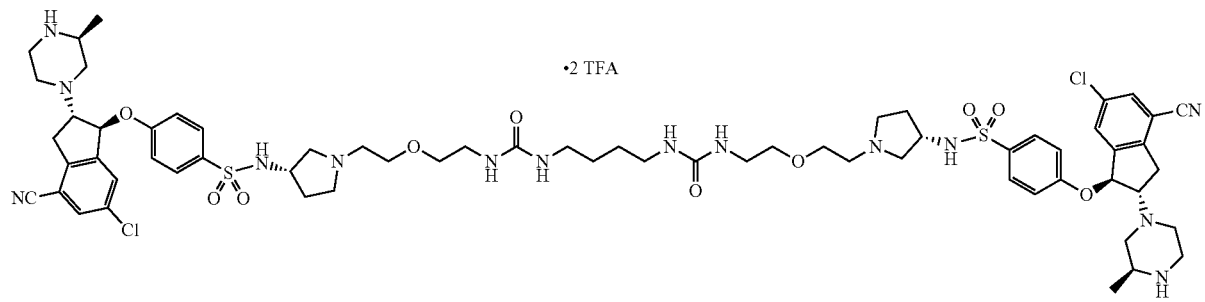

The crude product was purified by preparative HPLC with the following conditions: Column, XBridge Shield RP18 OBD Column, 5 μm, 19*150 mm; mobile phase, water (0.05% TFA) and ACN (12.0% ACN up to 38.0% in 8 min); Detector, UV 220 nm. This resulted in 257.5 mg (51%) of the title compound as a white solid. MS (m/z): 1346 [M+H]$^+$. $^1$H NMR (Methanol-d4, 400 MHz) δ 7.97-7.89 (m, 4H), 7.80 (d, J=1.8 Hz, 2H), 7.53-7.48 (m, 2H), 7.42-7.34 (m, 4H), 6.10 (d, J=5.9 Hz, 2H), 4.01 (s, 2H), 3.86-3.71 (m, 10H), 3.56 (t, J=5.3 Hz, 5H), 3.50-3.40 (m, 15H), 3.24-3.05 (m, 14H), 2.67-2.56 (m, 2H), 2.49 (dd, J=12.8, 10.2 Hz, 2H), 2.36 (s, 2H), 2.02 (s, 2H), 1.52 (s, 4H), 1.29 (d, J=6.6 Hz, 6H).

Example 135: 4-([(1S,2S)-6-Chloro-4-cyano-2-[(S)-3-methylpiperazin-1-yl]-2,3-dihydro-1H-inden-1-yl]oxy)-N—[(R)-1-(20-[(R)-3-([4-([(1S,2S)-6-chloro-4-cyano-2-[(S)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; bis(trifluoroacetic acid

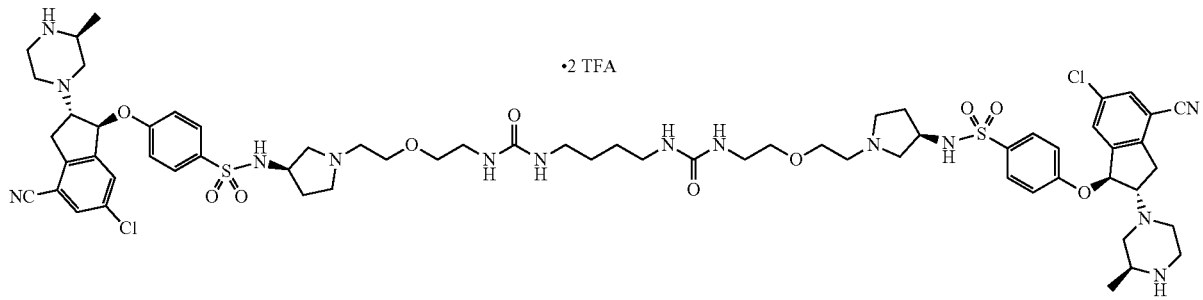

Example 135

The crude product was purified by preparative HPLC with the following conditions: Column, XBridge C18 OBD Preparative Column, 19*250 mm, 5 μm; mobile phase, water (0.05% TFA) and ACN (25.0% ACN up to 43.0% in 9 min); Detector, UV 254 nm. This resulted in 226.5 mg (44%) of the title compound as a white solid. MS (m/z): 1346 [M+H]$^+$. $^1$H NMR (Methanol-d4, 400 MHz) δ 7.97-7.89 (m, 4H), 7.80 (d, J=1.9 Hz, 2H), 7.53-7.48 (m, 2H), 7.42-7.34 (m, 4H), 6.10 (d, J=5.9 Hz, 2H), 4.01 (s, 2H), 3.86-3.74 (m, 10H), 3.56 (t, J=5.3 Hz, 4H), 3.44-3.34 (m, 16H), 3.24-3.06 (m, 14H), 2.68-2.56 (m, 2H), 2.54-2.43 (m, 2H), 2.36 (s, 2H), 2.01 (s, 2H), 1.51 (d, J=5.9 Hz, 4H), 1.29 (d, J=6.6 Hz, 6H).

Example 136: 4-([(1S,2S)-6-Chloro-4-cyano-2-[(3S,5R)-3,5-dimethylpiperazin-1-yl]-2,3-dihydro-1H-inden-1-yl]oxy)-N—[(S)-1-(20-[(S)-3-[(4-([(1S,2S)-6-chloro-4-cyano-2-[(3S,5R)-3,5-dimethylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; bis(trifluoroacetic acid

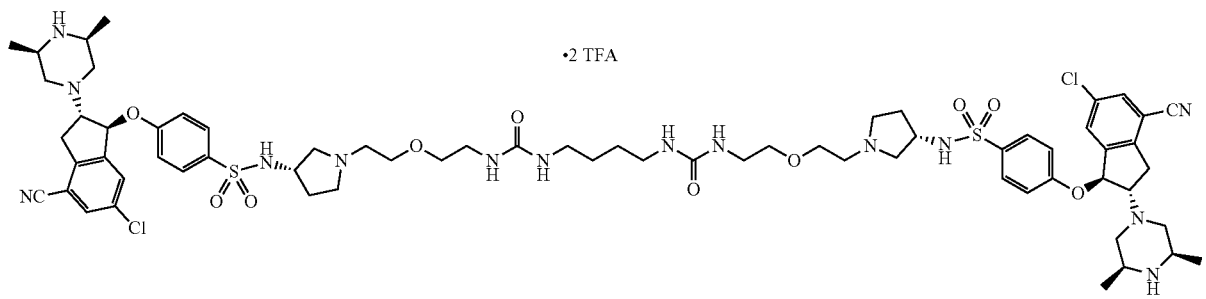

Example 136

The crude product was purified by preparative HPLC with the following conditions: Column, XBridge C18 OBD Preparative Column, 10 μm, 19*250 mm; mobile phase, water (0.05% TFA) and ACN (25% ACN up to 43% in 8 min); Detector, UV 254 nm. This resulted in 254 mg (84%) of the title compound as a white solid, MS (m/z): 1376 [M+H]$^+$. $^1$H NMR (Methanol-d4, 300 MHz) δ 7.88 (d, J=8.7 Hz, 4H), 7.76 (d, J=1.9 Hz, 2H), 7.45 (s, 2H), 7.33 (d, J=8.9 Hz, 4H), 6.07 (d, J=6.0 Hz, 2H), 3.96 (s, 3H), 3.74 (dt, J=9.6, 5.6 Hz, 10H), 3.51 (t, J=5.2 Hz, 4H), 3.41-3.28 (m, 14H), 3.20-3.07 (m, 12H), 2.30 (dt, J=28.3, 11.9 Hz, 5H), 1.99 (s, 3H), 1.47 (s, 4H), 1.25 (dd, J=9.3, 6.6 Hz, 13H).

Example 137: 4-([(1S,2S)-6-Chloro-4-cyano-2-[(3S,5R)-3,5-dimethylpiperazin-7-yl]-2,3-dihydro-1H-inden-1-yl]oxy)-N—[(R)-1-(20-[(R)-3-([4-([(1S,2S)-6-chloro-4-cyano-2-[(3S,5R)-3,5-dimethylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; bis(trifluoroacetic acid)

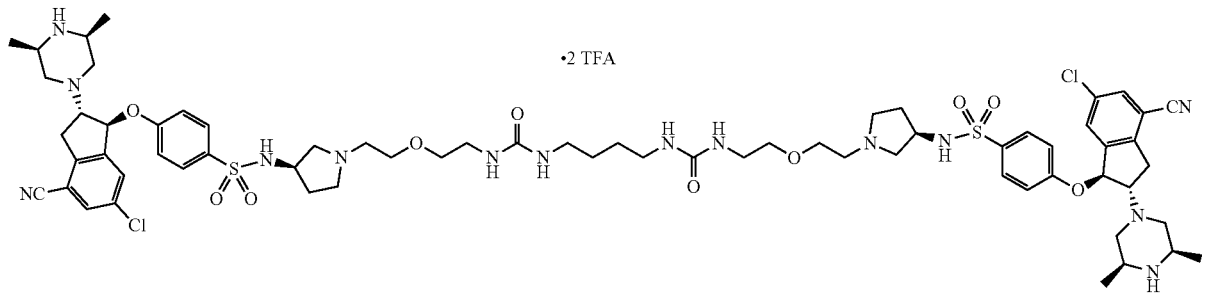

Example 137

The crude product was purified by preparative HPLC with the following conditions: Column, XBridge Shield RP18 OBD Column, 5 um, 19*150 mm; mobile phase, water (0.05% TFA) and ACN (13% ACN up to 40% in 8 min); Detector, UV 220 nm. This resulted in 171 mg (42%) of the title compound as a white solid. MS (m/z): 1375.6 [M+H]$^+$. $^1$H NMR (Methanol-d4, 300 MHz) δ 7.88 (d, J=8.7 Hz, 4H), 7.76 (d, J=1.8 Hz, 2H), 7.46 (d, J=1.8 Hz, 2H), 7.38-7.29 (m, 4H), 6.07 (d, J=5.9 Hz, 2H), 3.96 (s, 2H), 3.74 (dt, J=9.9, 5.6 Hz, 10H), 3.51 (t, J=5.2 Hz, 5H), 3.41-3.28 (m, 13H), 3.20-3.06 (m, 13H), 2.30 (dt, J=27.3, 11.9 Hz, 6H), 1.97 (s, 2H), 1.48 (d, J=5.3 Hz, 4H), 1.25 (dd, J=9.7, 6.6 Hz, 13H).

Example 138: 4-([(1S,2S)-6-Chloro-4-cyano-2-(piperazin-1-yl)-2,3-dihydro-1H-inden-1-yl]oxy)-N—[(S)-1-(20-[(S)-([4-([(1S,2S)-6-chloro-4-cyano-2-(piperazin-1-yl)-2,3-dihydro-1H-inden-1-yl]oxy)phenyl]sulfonamido)-2-oxopiperidin-1-yl]-7,14-dioxo-3,18-dioxa-6,8,13,15-tetraazaicosyl)-2-oxopiperidin-3-yl]benzenesulfonamide

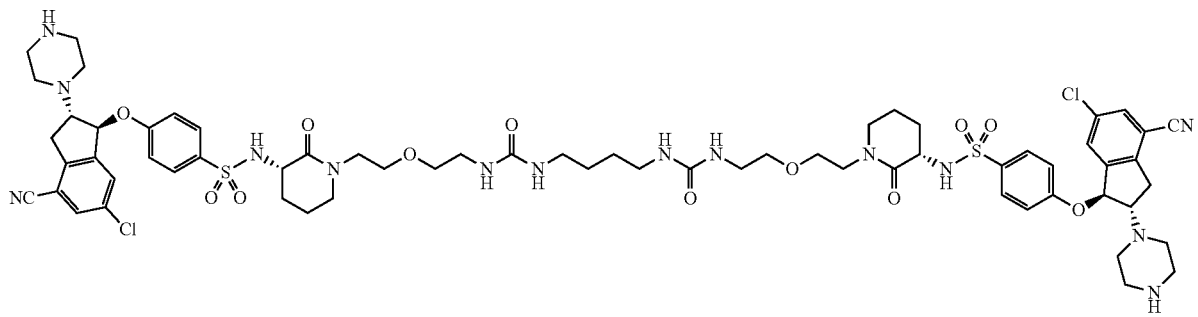

Example 138

Example 139: 4-([(1S,2S)-6-Chloro-4-cyano-2-(piperazin-1-yl)-2,3-dihydro-1H-inden-1-yl]oxy)-N-[1-(20-[3-([4-([[(1S,2S)-6-chloro-4-cyano-2-(piperazin-1-yl)-2,3-dihydro-1H-inden-1-yl]oxy)phenyl]sulfonamido)-2-oxoazepan-1-yl]-7,14-dioxo-3,18-dioxa-6,8,13,15-tetraazaicosyl)-2-oxoazepan-3-yl]benzenesulfonamide Example 139

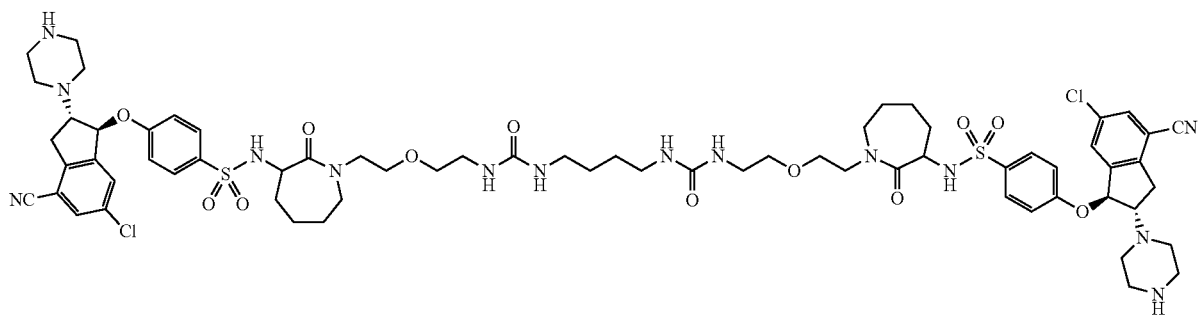

Scheme for the Synthesis of Cyclohexyl Core Dimer Products:

Example 140: 4-([(1S,2S)-6-Chloro-4-cyano-2-(piperazin-1-yl)-2,3-dihydro-H-1-inden-1-yl]oxy)-N-[2-(2-[2-(3-[(1s,4s)-4-(3-[2-(2-[2-([4-([[(1S,2S)-6-chloro-4-cyano-2-(piperazin-1-yl)-2,3-dihydro-1H-inden-1-yl]oxy)phenyl]sulfonamido)ethoxy]ethoxy)ethyl]ureido)cyclohexyl]ureido)ethoxy]ethoxy)ethyl]benzenesulfonamide

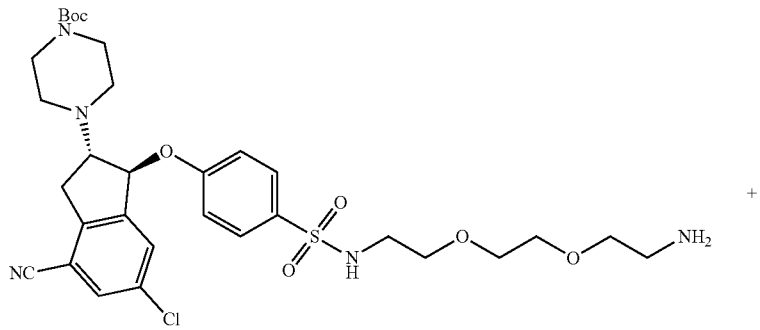

INT-M5E

+

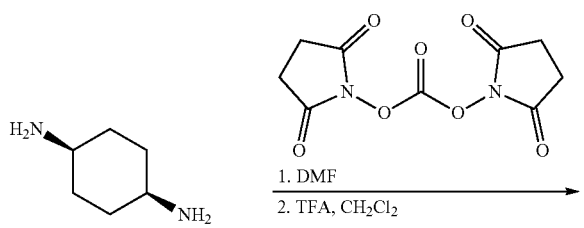

1. DMF
2. TFA, CH₂Cl₂

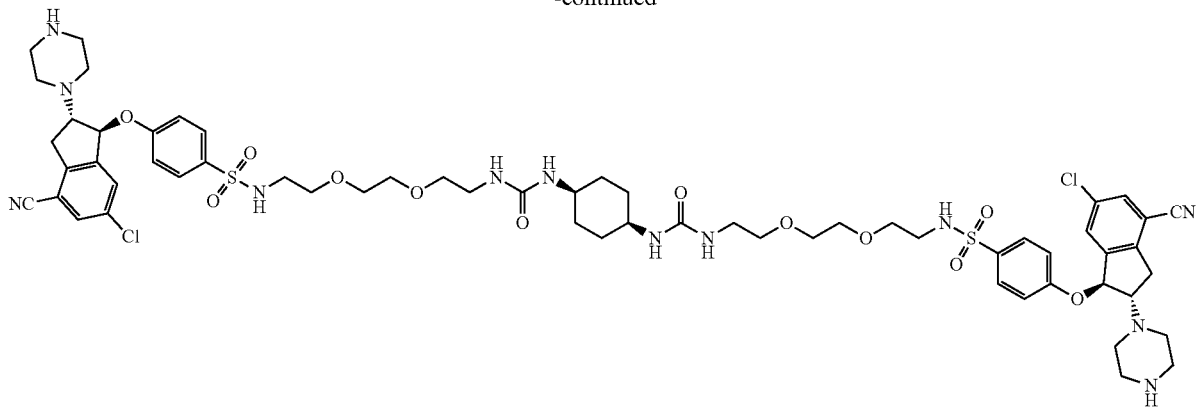

Example 140

Step 1: The amine INT-M5E is treated with disuccinimidyl carbonate (DSC) or similar activating agent (others including 1,1'-carbonyldiimidazole p-nitrophenylchloroformate, etc) in DMF, followed by addition of the desired diamine, with (1s,4s)-cyclohexane-1,4-diamine shown. Bis (2,5-dioxopyrrolidin-1-yl)carbonate (85 mg, 0.33 mmol, 1.1 eq) and tert-butyl 4-((1S,2S)-2-(4-(N-(2-(2-(2-aminoethoxy)ethoxy)ethyl)sulfamoyl)phenoxy)-4-chloro-6-cyano-2,3-dihydro-1H-inden-1-yl)piperazine-1-carboxylate (200 mg, 0.3 mmol) were stirred in DMF (1 mL) for 1.5 hours before a solution of (1s,4s)-cyclohexane-1,4-diamine (15.5 mg, 0.135 mmol, 0.45 eq) in DMF (0.2 mL) was added. The mixture was stirred for 2 h at 60° C. LCMS showed significant amount of monourea side-product, example 155. The DMF was removed under vacuum, residue dissolved in 4:1 MeCN:H2O, filtered, and purified by prep-HPLC with the following conditions: Column, Atlantis Prep T3 OBD, 50*250 mm, 10 um; mobile phase, water (0.1% TFA) and CH$_3$CN (25.0% CH$_3$CN up to 80.0% in 60 min); Detector, UV 214 nm. Product eluted ~62% MeCN. Boc-protected cyclohexyl diamine product: 143 mg (61%); LCMS: ret time 3.3 min. MS (m/z): [M/2+H]+ 747.4. The product was deprotected in the following step.

Step 2: The product was deprotected under acidic conditions yielding Example 140. LCMS: ret time 2.40 min, [M/2+H]+ 647.3. $^1$H NMR (Methanol-d4, 400 MHz) δ 7.86 (d, J=9.0 Hz, 4H), 7.76 (d, J=1.9 Hz, 2H), 7.45 (d, J=1.2 Hz, 2H), 7.31 (d, J=9.0 Hz, 4H), 6.06 (d, J=6.2 Hz, 2H), 3.79-3.67 (m, 1H), 3.62-3.44 (m, 22H), 3.33 (s, 3H), 3.22 (t, J=5.1 Hz, 8H), 3.05 (t, J=5.5 Hz, 4H), 2.85 (d. J=14.3 Hz, 5H), 1.70-1.46 (m, 4H)

Example 141: 4-([(1S,2S)-6-Chloro-4-cyano-2-(piperazin-1-yl)-2,3-dihydro-1H-inden-1-yl]oxy)-N-[2-(2-[2-(3-[(1r,4r)-4-(3-[2-(2-[2-([4-([(1S,2S)-6-chloro-4-cyano-2-(piperazin-1-yl)-2,3-dihydro-1H-inden-1-yl]oxy)phenyl]sulfonamido)ethoxy]ethoxy)ethyl]ureido)cyclohexyl]ureido)ethoxy]ethoxy)ethyl]benzenesulfonamide

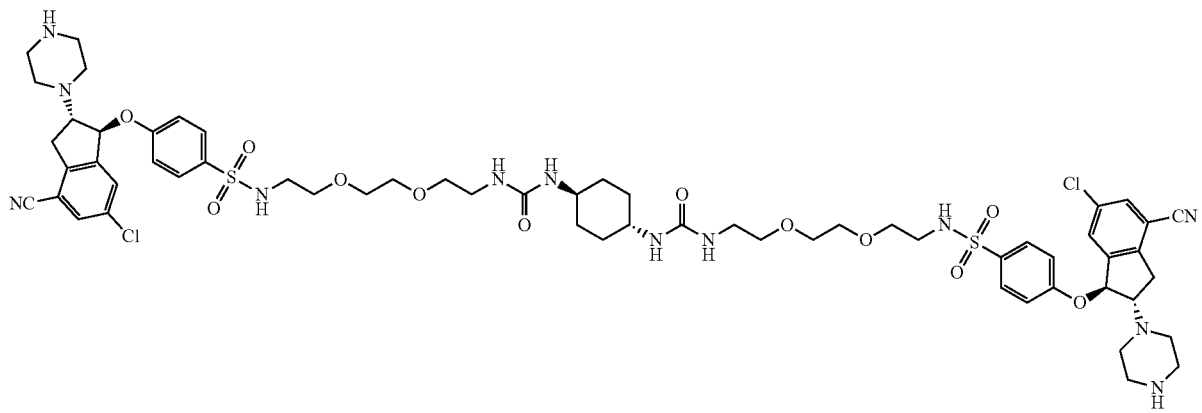

Example 141

The title compound was prepared from (1r,4r)-cyclohexane-1,4-diamine and INT-M5E through the route to prepare Example 140. LCMS: ret time 2.37 min. MS (m/z): [M/2+H]+ 647.3. ¹H NMR (Methanol-d4, 400 MHz) δ 7.91-7.82 (m, 4H), 7.76 (d, J=1.9 Hz, 2H), 7.46 (d, J=1.2 Hz, 2H), 7.38-7.23 (m, 4H), 6.07 (d, J=6.1 Hz, 2H), 3.80-3.66 (m, 2H), 3.61-3.44 (m, 18H), 3.36 (dd, J=16.7, 8.0 Hz, 4H), 3.24 (dt, J=15.3, 5.4 Hz, 13H), 3.12 (dd, J=16.6, 8.1 Hz, 2H), 3.05 (t, J=5.5 Hz, 4H), 2.86 (qd, J=13.0, 7.9 Hz, 8H), 1.88 (d, J=6.3 Hz, 4H), 1.21 (dd, J=10.9, 9.2 Hz, 4H).

Example 142: 4-([(1S,2S)-6-Chloro-4-cyano-2-(piperazin-1-yl)-2,3-dihydro-1H-inden-1-yl]oxy)-N—[(R)-1-(18-[(R)-3-([4-([(1S,2S)-6-chloro-4-cyano-2-(piperazin-1-yl)-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide Example 142

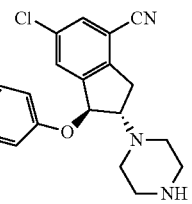
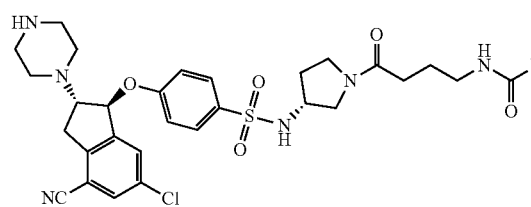

The title compound is prepared through the sequence employed in preparation of Example 116, but beginning with Boc-4-aminobutyric acid and 1-Boc-(R)-3-aminopyrrolidine.

Example 143: 4-([(1S,2S)-6-Chloro-4-cyano-2-(piperazin-1-yl)-2,3-dihydro-1H-inden-1-yl]oxy)-N—[(S)-1-(18-[(S)-3-([4-([(1S,2S)-6-chloro-4-cyano-2-(piperazin-1-yl)-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide Example 143

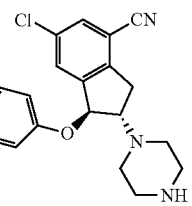
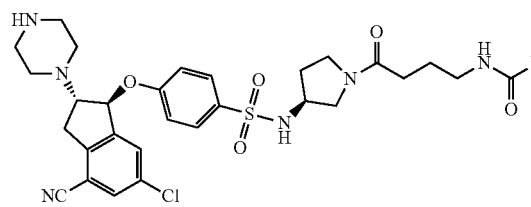

The title compound is prepared through the sequence employed in preparation of Example 116, but beginning with Boc-4-aminobutyric acid and 1-Boc-(S)-3-aminopyrrolidine.

Example 144: (S)—N-([4-([(1S,2S)-6-Chloro-4-cyano-2-(piperazin-1-yl)-2,3-dihydro-1H-inden-1-yl]oxy)phenyl]sulfonyl)-1-(20-[(S)-3-[([4-([(1S,2S)-6-chloro-4-cyano-2-piperazin-1-yl)-2,3-dihydro-1H-inden-1-yl]oxy)phenyl]sulfonyl)carbamoyl]pyrrolidin-1-yl]-7,14-dioxo-3,18-dioxa-6,8,13,15-tetraazaicosyl)pyrrolidine-3-carboxamide Example 144

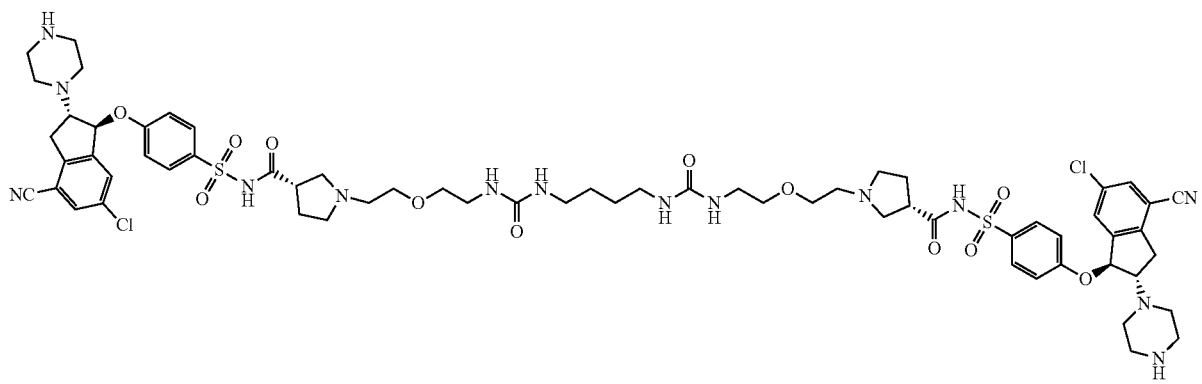

The title compound was prepared through the procedure provided for Example 124 beginning with N-Boc-L-beta-proline. MS (m/z): 687.3 [M/2+H]$^+$. $^1$H NMR (Methanol-d4, 400 MHz) δ 8.12-7.98 (m, 4H), 7.81-7.77 (m, 2H), 7.48-7.44 (m, 2H), 7.41-7.28 (m, 4H), 6.12-6.06 (m, 2H), 3.76 (s, 9H), 3.59-3.50 (m, 6H), 3.25 (s, 14H), 3.19-3.07 (m, 9H), 2.96-2.74 (m, 9H), 1.57-1.43 (m, 4H).

Example 145: (R)—N-([4-([4-([(1S,2S)-6-Chloro-4-cyano-2-(piperazin-1-yl)-2,3-dihydro-1H-inden-1-yl]oxy)phenyl]sulfonyl)-1-(20-[(R)-3-[([4-([(1S,2S)-6-chloro-4-cyano-2-(piperazin-1-yl)-2,3-dihydro-1H-inden-1-yl]oxy)phenyl]sulfonyl)carbamoyl]pyrrolidin-1-yl]-7,14-dioxo-3,18-dioxa-6,8,13,15-tetraazaicosyl)pyrrolidine-3-carboxamide Example 145

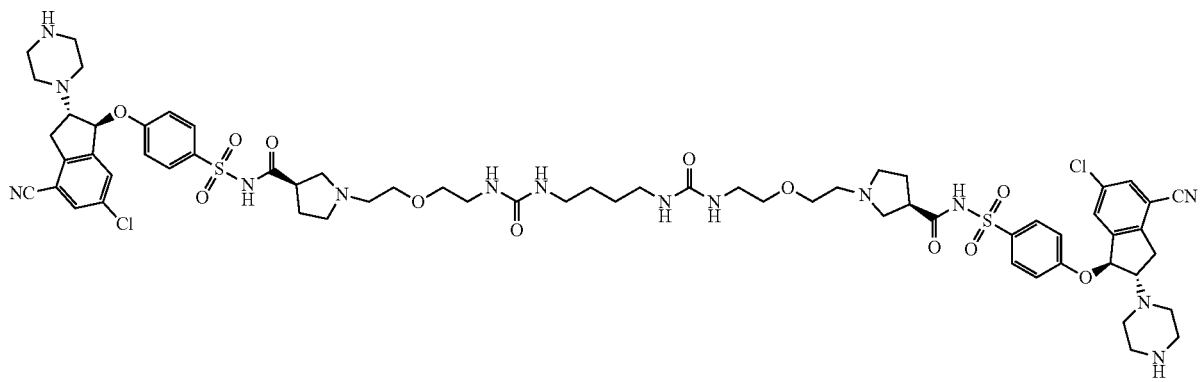

The title compound is prepared through the procedure provided for Example 124 beginning with N-Boc-D-beta-proline.

425

Scheme for the Synthesis of Monomer Products:

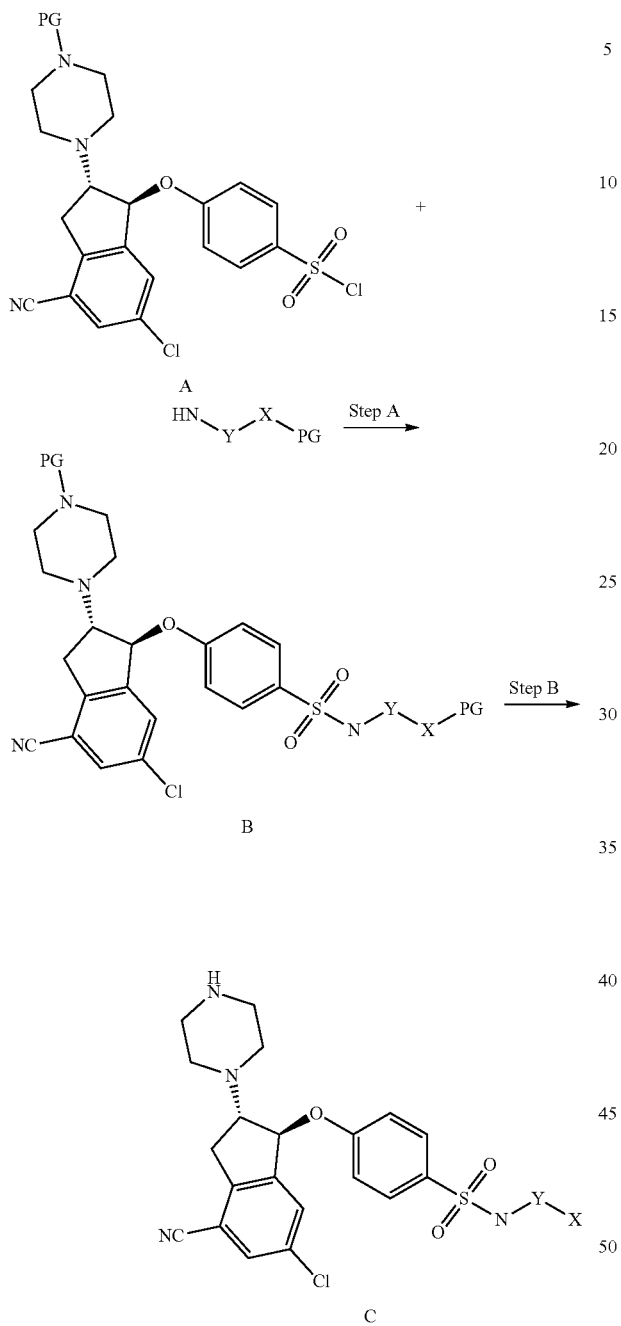

"Monomer" final products are described previously in this work or obtained through deprotection (as necessary) of analogs such as the INT-M2 series of compounds. Additionally, "monomers" are obtained through the steps listed in the above scheme, beginning with sulfonyl chloride A, prepared through oxidative chlorination as previously described in this work. These materials A are reacted with any commercial or synthetic amine (primary or secondary) compounds, including those with protecting groups PG, in the presence of bases like triethylamine, pyridine, or metal carbonates. The product sulfonamides B are deprotected as necessary to produce "monomer" products of structure C.

426

The following Example of products can also be prepared using the synthetic routes described herein:

Example 146: 4-([(1S,2S)-6-Chloro-4-cyano-2-(piperazin-1-yl)-2,3-dihydro-1H-inden-1-yl]oxy)benzenesulfonamide

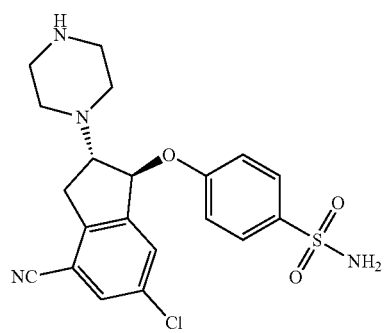

Example 146

Example 147: N-(2-[2-(2-Aminoethoxy)ethoxy]ethyl)-4-([(1S,2S)-6-chloro-4-cyano-2-(piperazin-1-yl)-2,3-dihydro-1H-inden-1-yl]oxy)benzenesulfonamide

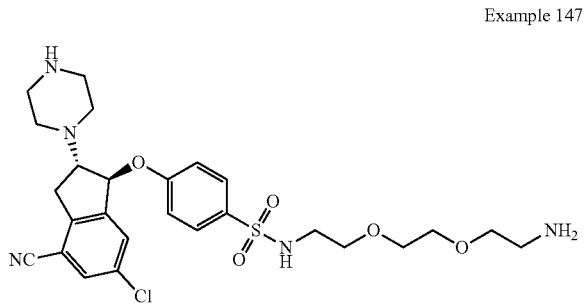 [SMILES: N#Cc1cc(Cl)cc2c1C[C@H](N1CCNCC1)[C@H]2Oc1ccc(S(=O)(=O)NCCOCCOCCN)cc1]

Example 147

Example 148: N-[1-(4-Aminobutanoyl)piperidin-4-yl]-4-([(1S,2S)-6-chloro-4-cyano-2-(piperazin-1-yl)-2,3-dihydro-1H-inden-1-yl]oxy)benzenesulfonamide

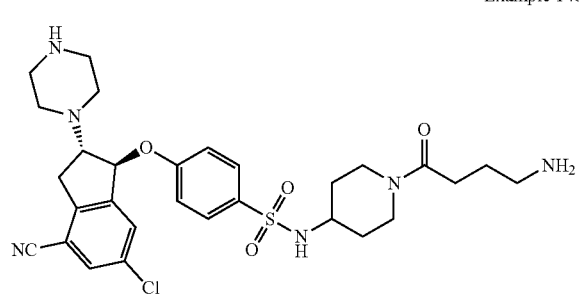

Example 148

Example 149: 4-([(1S,2S)-6-Chloro-4-cyano-2-(piperazin-1-yl)-2,3-dihydro-1H-inden-1-yl]oxy)-N-(3-oxo-7,10-dioxa-2,4-diazadodecan-12-yl)benzenesulfonamide Example 149

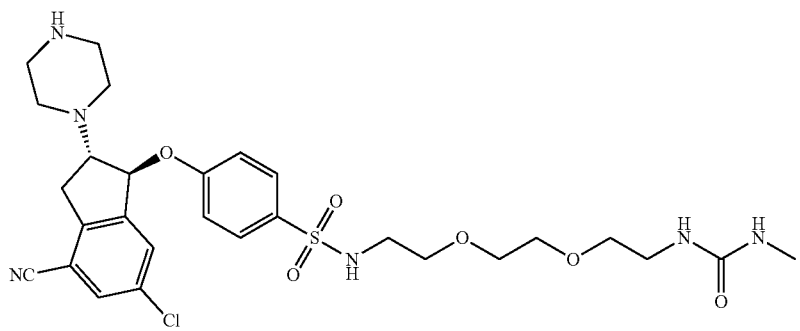

Example 150: 4-([(1S,2S)-6-Chloro-4-cyano-2-(piperazin-1-yl)-2,3-dihydro-1H-inden-1-yl]oxy)-N-(1-[4-(3-methylureido)butanoyl]piperidin-4-yl)benzenesulfonamide Example 151: 4-([(1S,2S)-6-Chloro-4-cyano-2-(piperazin-1-yl)-2,3-dihydro-1H-inden-1-yl]oxy)-N-[(2S,3R,4S,5R)-1,3,4,5,6-pentahydroxyhexan-2-yl]benzenesulfonamide Example 150

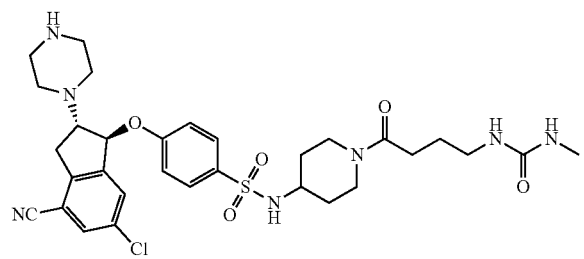

Example 151

Example 152: 4-([4-([(1S,2S)-6-Chloro-4-cyano-2-(piperazin-1-yl)-2,3-dihydro-1H-inden-1-yl]oxy)phenyl]sulfonamido)-N-[(2S,3R,4S,5R)-1,3,4,5,6-pentahydroxyhexan-2-yl]piperidine-1-carboxamide Example 152

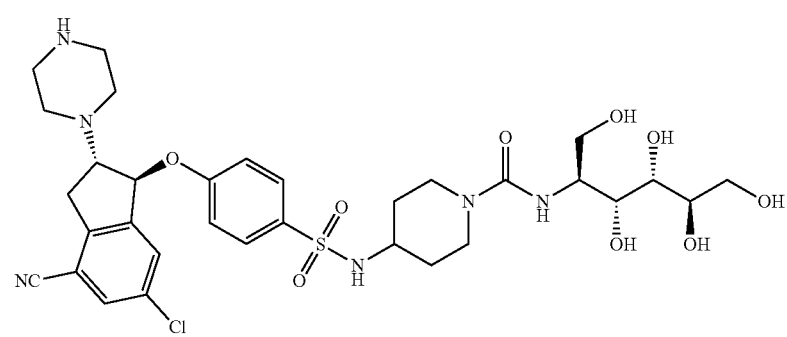

Other Synthetic Schemes

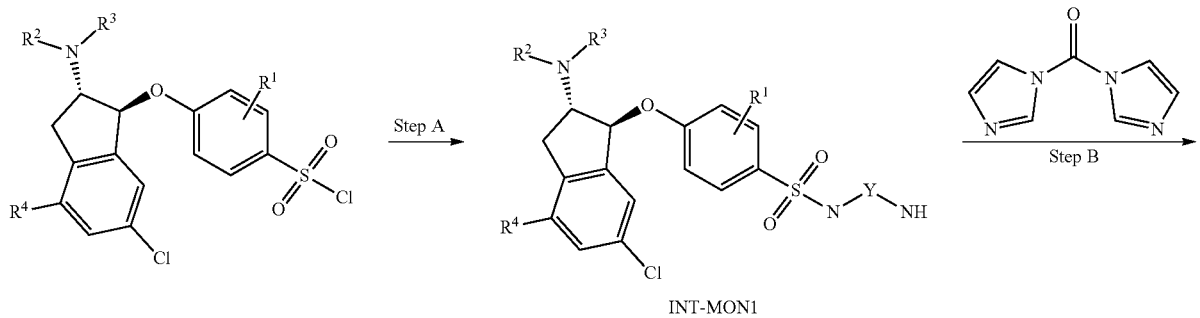

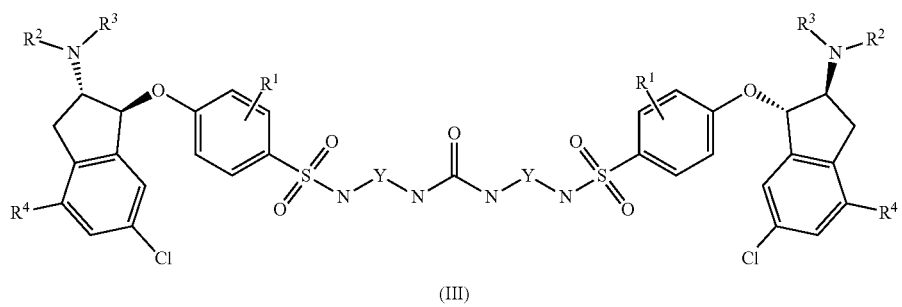

According to the General Scheme for the synthesis of compounds of structure the elaborated structures such as INT-MON1, "monomers", are dimerized to the symmetric urea (III) through reaction with 1,1'-carbonyldiimidazole or p-nitrophenylchloroformate or the like. Through this step, compounds such as Example 153-155 are prepared.

Example 153: 4-(3-[4-([4-([(1S,2S)-6-Chloro-4-cyano-2-(piperazin-1-yl)-2,3-dihydro-1H-inden-1-yl]oxy)phenyl]sulfonamido)-4-oxobutyl]ureido)-N-([4-([(1S,2S)-6-chloro-4-cyano-2-(piperazin-1-yl)-2,3-dihydro-1H-inden-1-yl]oxy)phenyl]sulfonyl)butanamide Example 153

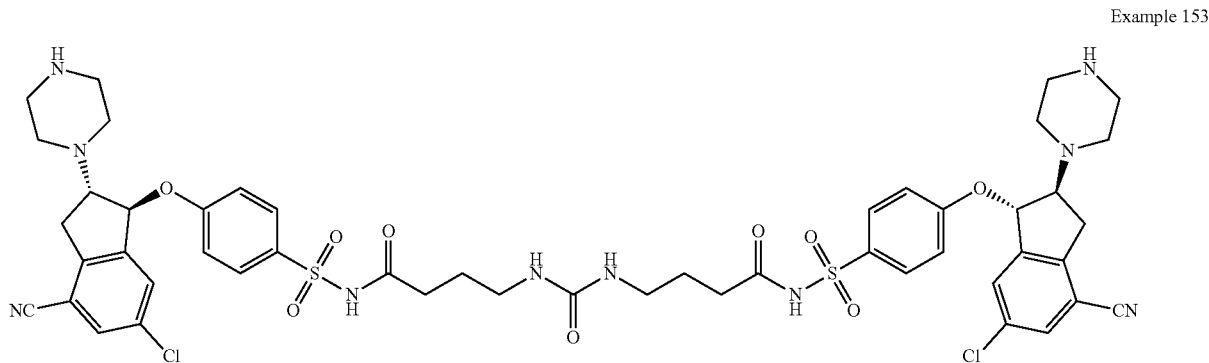 [SMILES: N#Cc1cc(Cl)cc2c1C[C@H](N1CCNCC1)[C@H]2Oc1ccc(S(=O)(=O)NC(=O)CCCNC(=O)NCCCC(=O)NS(=O)(=O)c2ccc(O[C@H]3c4cc(Cl)cc(C#N)c4C[C@@H]3N3CCNCC3)cc2)cc1]

Example 154: 4-([[(1S,2S)-6-Chloro-4-cyano-2-(piperazin-1-yl)-2,3-dihydro-1H-inden-1-yl]oxy)-N-[1-(4-[3-(4-[4-([4-([[(1S,2S)-6-chloro-4-cyano-2-(piperazin-1-yl)-2,3-dihydro-1H-inden-1-yl]oxy)phenyl]sulfonamido)piperidin-1-yl]-4-oxobutyl)ureido]butanoyl)piperidin-4-yl]benzenesulfonamide

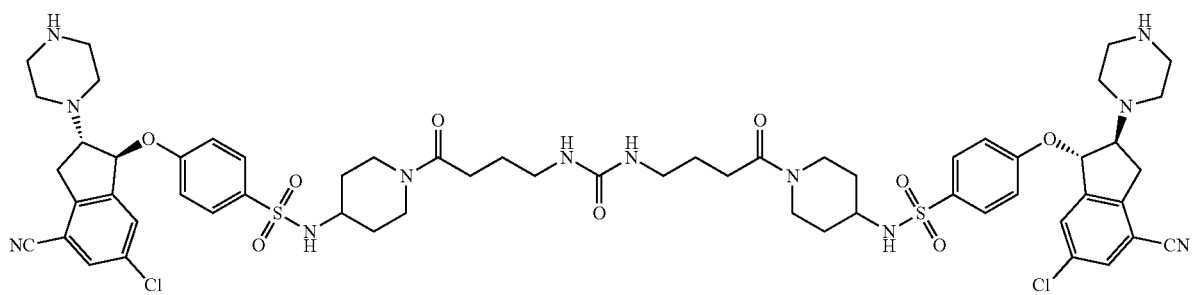

Example 154

Example 155: 4-([[(1S,2S)-6-Chloro-4-cyano-2-(piperazin-1-yl)-2,3-dihydro-1H-inden-1-yl]oxy)-N-[19-([4-([[(1S,2S)-6-chloro-4-cyano-2-(piperazin-1-yl)-2,3-dihydro-1H-inden-1-yl]oxy)phenyl]sulfonamido)-10-oxo-3,6,14,17-tetraoxa-9,11-diazanonadecyl]benzenesulfonamide

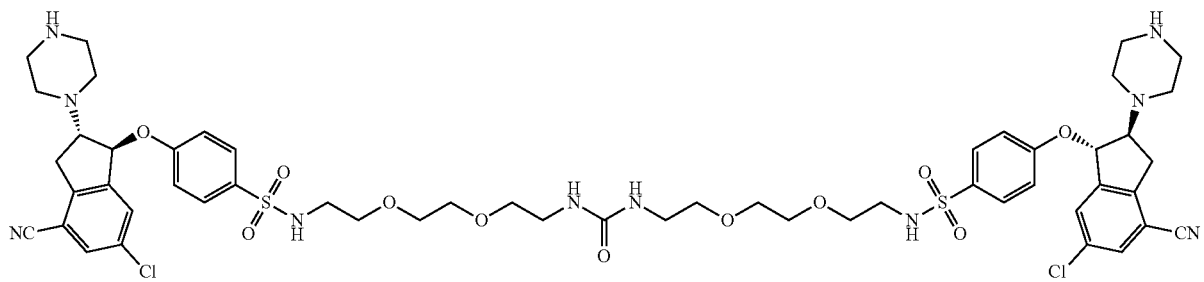

Example 155

Step A: Bis(2,5-dioxopyrrolidin-1-yl)carbonate (85 mg, 0.33 mmol, 1.1 eq) and tert-butyl 4-((1S,2S)-2-(4-(N-(2-(2-(2-aminoethoxy)ethoxy)ethyl)sulfamoyl)phenoxy)-4-chloro-6-cyano-2,3-dihydro-1H-inden-1-yl)piperazine-1-carboxylate (200 mg, 0.3 mmol) were stirred in DMF (1 mL) for 1.5 hours before a solution of (1s,4s)-cyclohexane-1,4-diamine (15.5 mg. 0.135 mmol, 0.45 eq) in DMF (0.2 mL) was added. The mixture was stirred for 2 h at 60° C. LCMS showed significant amount of monourea side-product, example 155. The DMF was removed under vacuum, residue dissolved in 4:1 MeCN:H2O, filtered, and purified by prep-HPLC with the following conditions: Column, Atlantis Prep T3 OBD, 50*250 mm, 10 um; mobile phase, water (0.1% TFA) and CH$_3$CN (25.0% CH$_3$CN up to 80.0% in 60 min); Detector, UV 214 nm. Product eluted ~62% MeCN. Cyclohexyl diamine product: 143 mg (61%); LCMS: ret time 3.3 min. MS (m/z): [M/2+H]+ 747.4. Symmetric urea product: 47 mg (22%); LCMS: ret time 3.4 min MS (m/z): [M/2+H]+ 677.3. The products were each deprotected in the following step.

Step B: Representative procedure (Example 155): TFA (150 μL, 1.95 mmol, 69 eq) was added to a solution of tert-butyl 4-((1S,2S)-1-(4-(N-(19-((4-(((1S,2S)-2-(4-(tert-butoxycarbonyl)piperazin-1-yl)-6-chloro-4-cyano-2,3-dihydro-1H-inden-1-yl)oxy)phenyl)sulfonamido)-10-oxo-3,6,14,17-tetraoxa-9,11-diazanonadecyl)sulfamoyl) phenoxy)-6-chloro-4-cyano-2,3-dihydro-1H-inden-2-yl)piperazine-1-carboxylate (45 mg, 0.028 mmol) in DCM (1.0 mL). The mixture was stirred for 4 hours (complete by LCMS). The volatiles were removed under vacuum and the residue dissolved in 4:1 MeCN:H2O and purified by prep-HPLC with the following conditions: Column, Atlantis Prep T3 OBD, 50*250 mm, 10 um; mobile phase, water (0.1% TFA) and CH$_3$CN (25.0% CH$_3$CN up to 60.0% in 50 min); Detector, UV 214 nm. Product eluted at 50% MeCN, 25 mg (55%) was collected Example 155 as a white solid. LCMS: ret time 2.40 min. MS: [M/2+H]+ 577.3. $^1$H NMR (Methanol-d4, 400 MHz) δ 7.86 (d, J=9.0 Hz, 4H), 7.76 (d, J=1.9 Hz, 2H), 7.47-7.44 (m, 2H), 7.31 (d, J=9.0 Hz, 4H), 6.08-6.04 (m, 2H), 3.78-3.67 (m, 1H), 3.61-3.43 (m, 2H), 3.40-3.32 (m, 2H), 3.27 (s, 4H), 3.22 (t, J=5.2 Hz, 10H), 3.16-3.08 (m, 1H), 3.05 (s, 5H), 2.93-2.77 (m, 8H).

Example 156: 4-([(1S,2S)-6-Chloro-4-amido-2-(piperazin-1-yl)-2,3-dihydro-1H-inden-1-yl]oxy)-N-[26-([4-([(1S,2S)-6-chloro-4-amido-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide Example 156

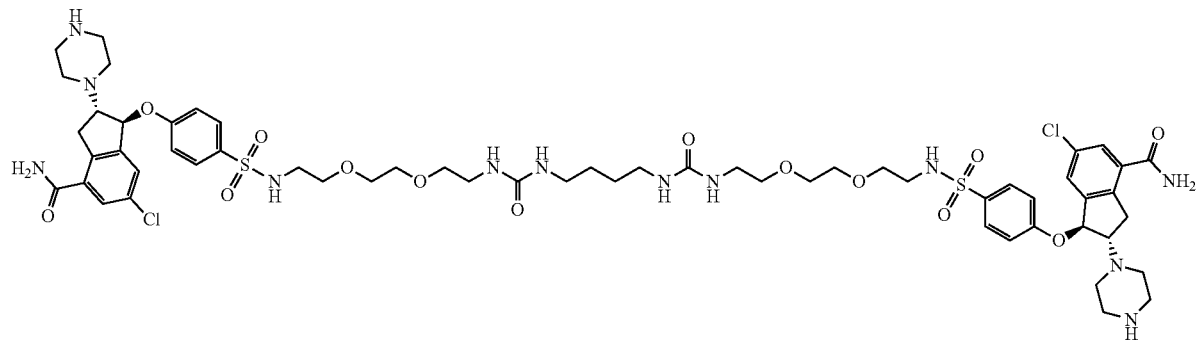

The title compound is prepared through controlled hydrolysis of Example 41, via the use of either protic acids including sulfuric acid or hydrogen chloride or aqueous bases such as sodium hydroxide.

Example 157: 4-([(1S,2S)-4-Cyano-6-methyl-2-(piperazin-1-yl)-2,3-dihydro-1H-inden-1-yl]oxy)-N-[26-([4-([(1S,2S)-4-cyano-6-methyl-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide Example 157

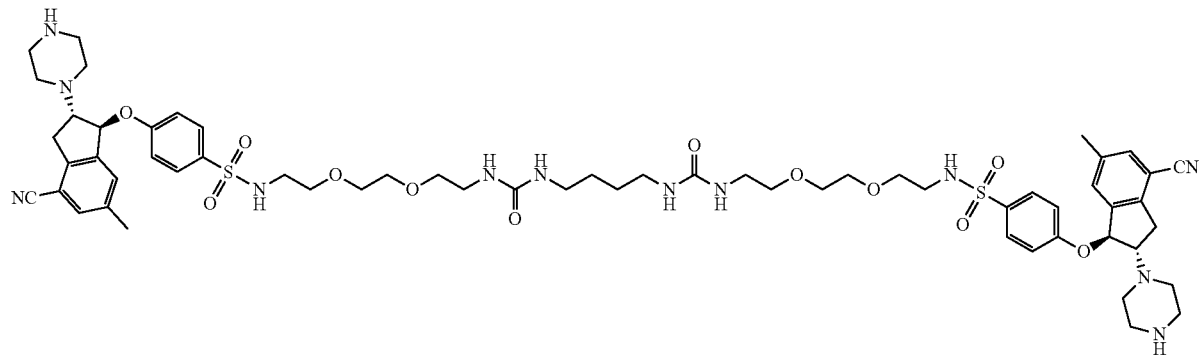

The title compound is prepared through the same procedures as yield Example 41, beginning with the 4-methyl-2-bromobenzaldehyde or similar appropriate starting material.

Scheme for the Synthesis of Bicyclic Analogs:

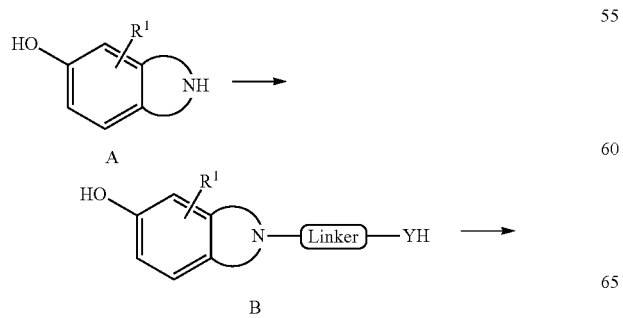

-continued

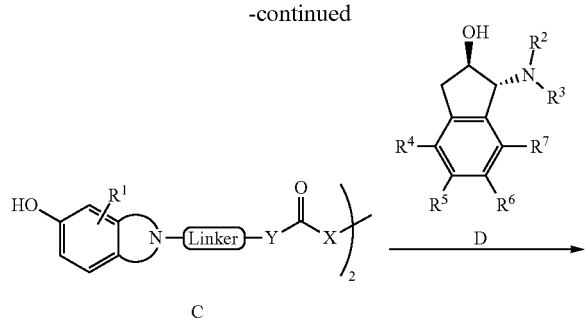

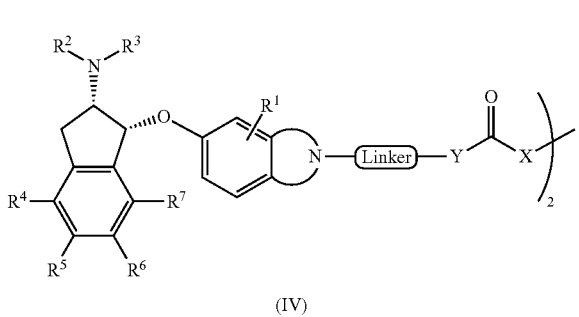

(IV)

According to the General Scheme for the Synthesis of Bicyclic Analogs, compounds of structure (IV) are prepared from starting materials such as phenol A. With or without protection of the phenolic oxygen, compounds B are prepared via alkylation or acylation with a suitable reagent such as alkyl halides, carboxylic acids, isocyanates, etc using bases or coupling agents known to those in the art. Subsequently the linker of compound B, containing a reactive or masked substituent Y, is reacted with a bifunctional reagent such as 1,4-diisocyanatobutane or the like to generate a dimer C. Compounds of structure (IV) are generated by coupling of C with D under Mitsunobu conditions with diazocarboxylate reagents (DEAD, DIAD, etc) and triphenylphosphine or through mesylation/displacement in the presence of base.

Example 158: 1,1'-(Butane-1,4-diyl)bis[3-(4-[6-([(1S,2S)-6-chloro-4-cyano-2-(piperazin-1-yl)-2,3-dihydro-1H-inden-1-yl]oxy)-3,4-dihydroisoquinolin-2(1H)-yl]-4-oxobutyl)urea]

Example 158

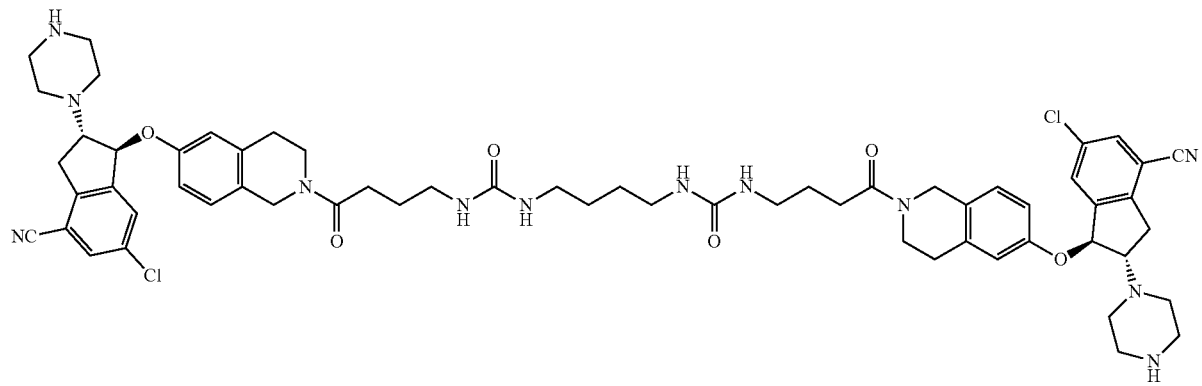

Example 159: 1,1'-(Butane-1,4-diyl)bis[3-(4-[7-([(1S,2S)-6-cyano-2-(piperazin-1-yl)-2,3-dihydro-1H-inden-1-yl]oxy)-3,4-dihydroisoquinolin-2(1H)-yl]-4-oxobutyl)urea]

Example 159

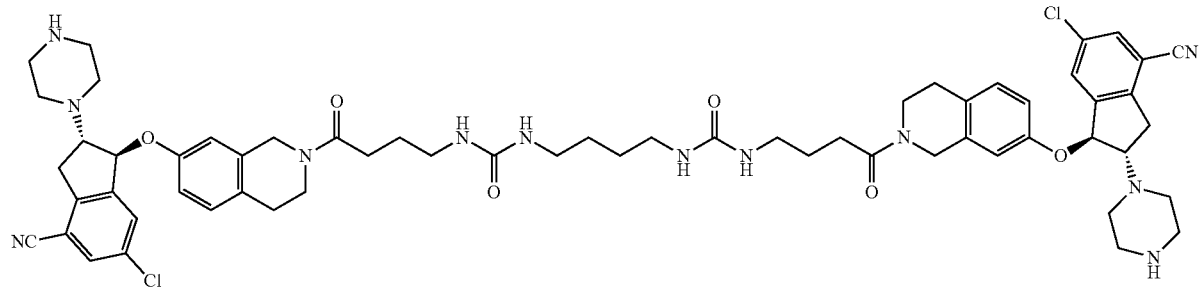

Example 160: N,N'-(6,14-Dioxo-10-oxa-5,7,13,15-tetraazanonadecane-1,19-diyl)bis[6-([(1S,2S)-6-chloro-4-cyano-2-(piperazin-1-yl)-2,3-dihydro-1H-inden-1-yl]oxy)-3,4-dihydroisoquinoline-2(1H)-carboxamide]

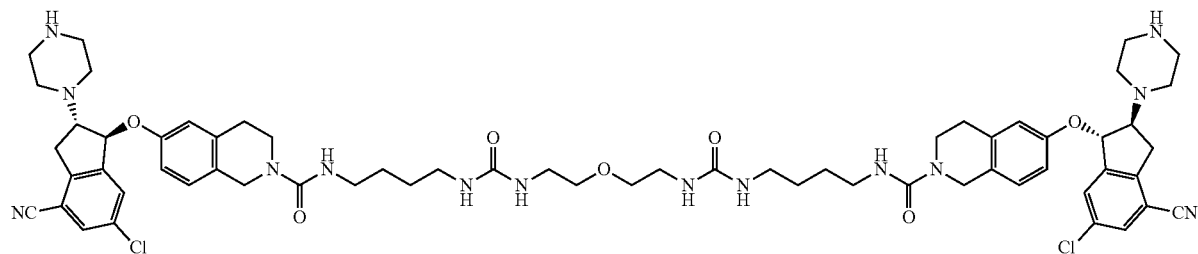

Example 160

Example 161: N,N'-(6,14-Dioxo-10-oxa-5,7,13,15-tetraazanonadecane-1,19-diyl)bis[7-([(1S,2S)-6-chloro-4-cyano-2-(piperazin-1-yl)-2,3-dihydro-1H-inden-1-yl]oxy)-3,4-dihydroisoquinoline-2(1H)-carboxamide]

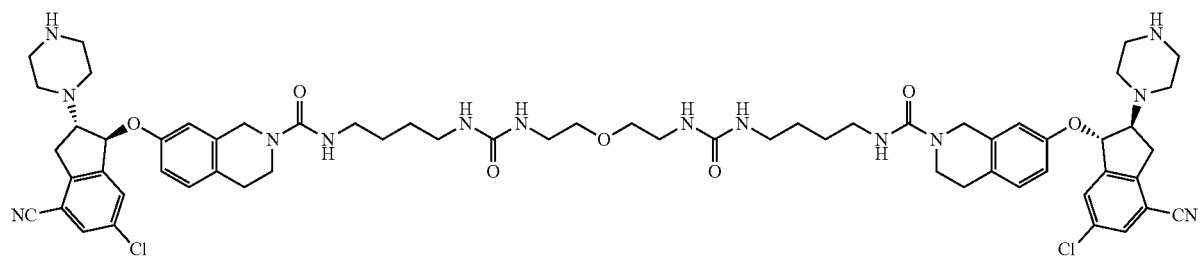

Example 161

Example 162: 1,1'-(Butane-1,4-diyl)bis(3-[2-(2-[6-([(1S,2S)-6-chloro-4-cyano-2-(piperazin-1-yl)-2,3-dihydro-1H-inden-1-yl]oxy)-1-oxoisoindolin-2-yl]ethoxy)ethyl]urea)

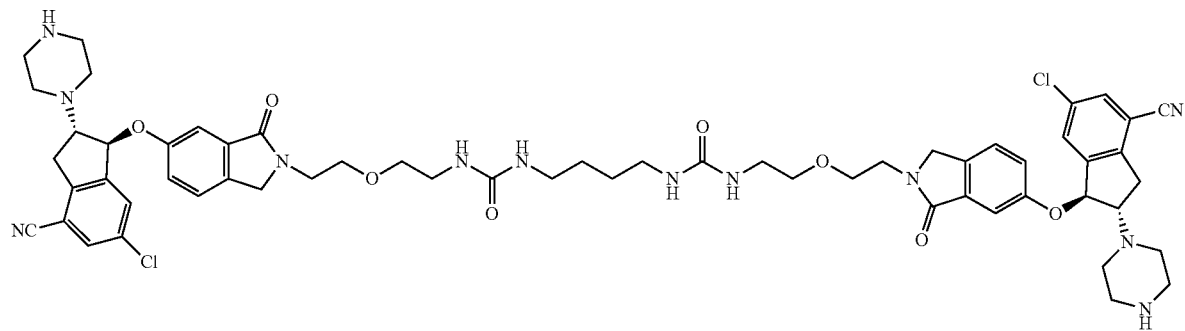

Example 162

Example 163: 1,1'-(Butane-1,4-diyl)bis(3-[2-(2-[5-([(1S,2S)-6-chloro-4-cyano-2-(piperazin-1-yl)-2,3-dihydro-1H-inden-1-yl]oxy)-1-oxoisoindolin-2-yl]ethoxy)ethyl]urea)

Example 163

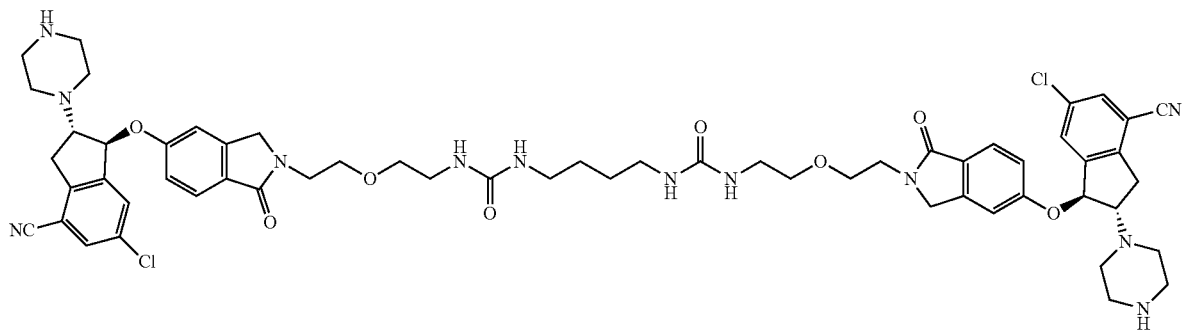

Example 164: 4-([(1S,2S)-6-Chloro-4-cyano-2-[(R)-3-methylpiperazin-1-yl]-2,3-dihydro-1H-inden-1-yl]oxy)-N—[(S)-1-(18-[(S)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide Example 164

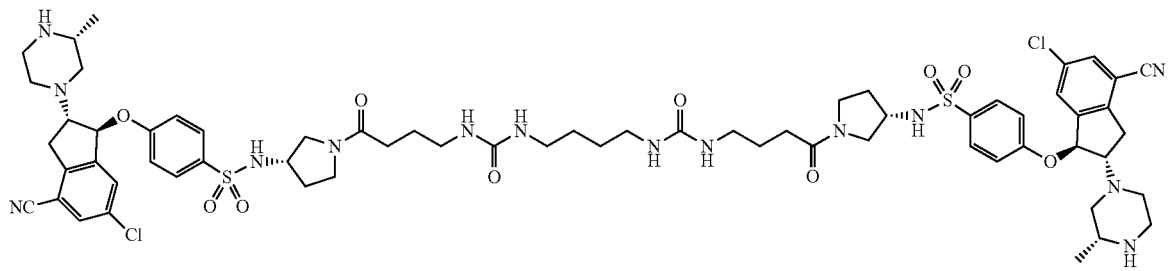

Example 165: 4-([(1S,2S)-6-Chloro-4-cyano-2-[(R)-3-methylpiperazin-1-yl]-2,3-dihydro-1H-inden-1-yl]oxy)-N—[(R)-1-(18-[(R)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide Example 165

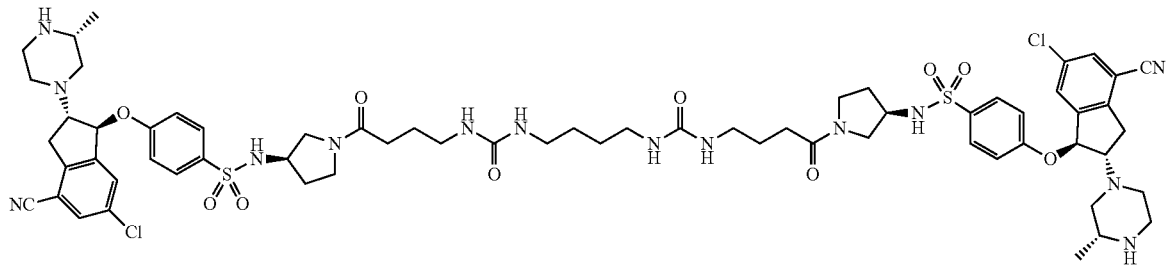

Example 166: 4-([(1S,2S)-6-Chloro-4-cyano-2-[(R)-3-methylpiperazin-1-yl]-2,3-dihydro-1H-inden-1-yl]oxy)-N-[1-(18-[4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-4-yl]benzenesulfonamide Example 166

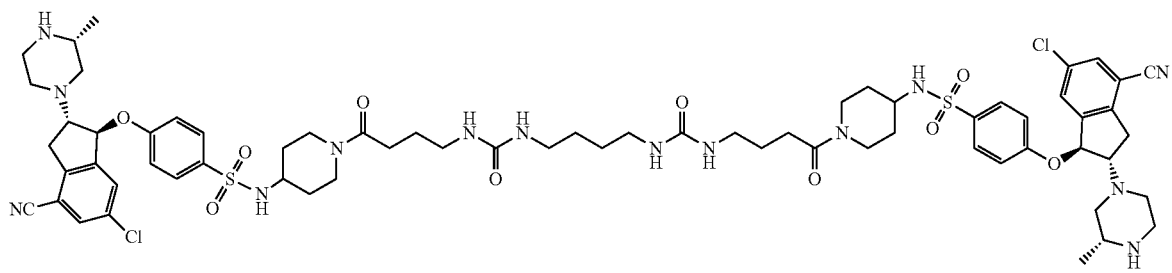

Example 167: $N^1,N^{14}$-Bis(2-[(S)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide Example 167

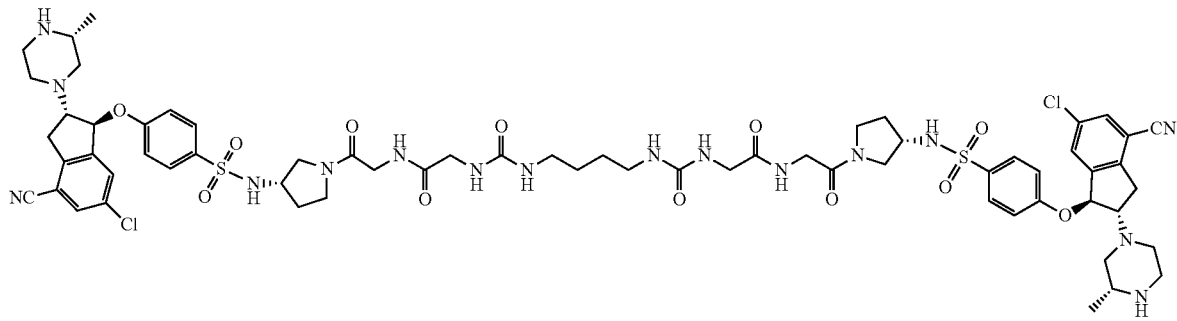

Example 168: 4-([(1S,2S)-6-Chloro-4-cyano-2-[(R)-3-methylpiperazin-1-yl]-2,3-dihydro-1H-inden-1-yl]oxy)-N-[1-(20-[4-([(1S,2S)-6-chloro-4-cyano-2-[(R)-3-methylpiperazin-1-yl]-2,3-dihydro-1H-inden-1-yl]oxy)phenyl]sulfonamido)piperidin-1-yl]-7,14-dioxo-3,18-dioxa-6,8,13,15-tetraazaicosyl)piperidin-4-yl]benzenesulfonamide Exanoke 168

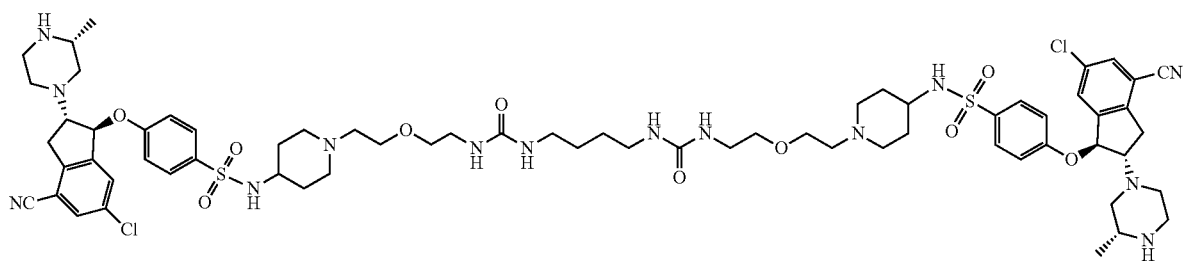

Example 169: 4-([(1S,2S)-4,6-Dichloro-2-[(R)-3-methylpiperazin-1-yl]-2,3-dihydro-1H-inden-1-yl]oxy)-N—[(S)-1-(20-[(S)-3-([4-([(1S,2S)-4,6-dichloro-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide

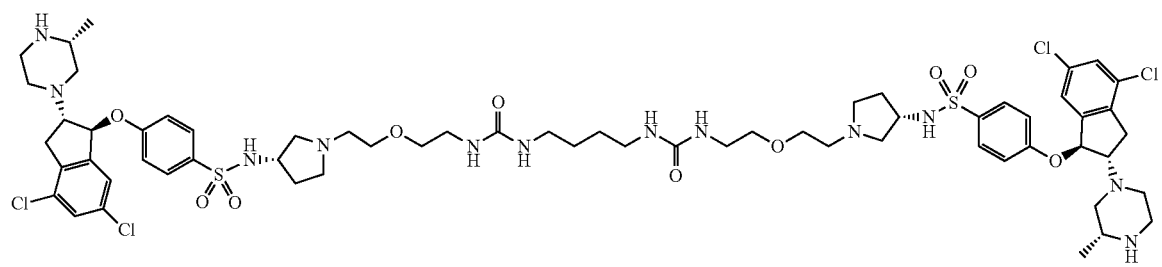

Example 169

Example 170: $N^1,N^{14}$-Bis(2-[(S)-3-([4-([(1S,2S)-4,6-dichloro-2-[(R)-3-methylpiperazin-1-yl]-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide

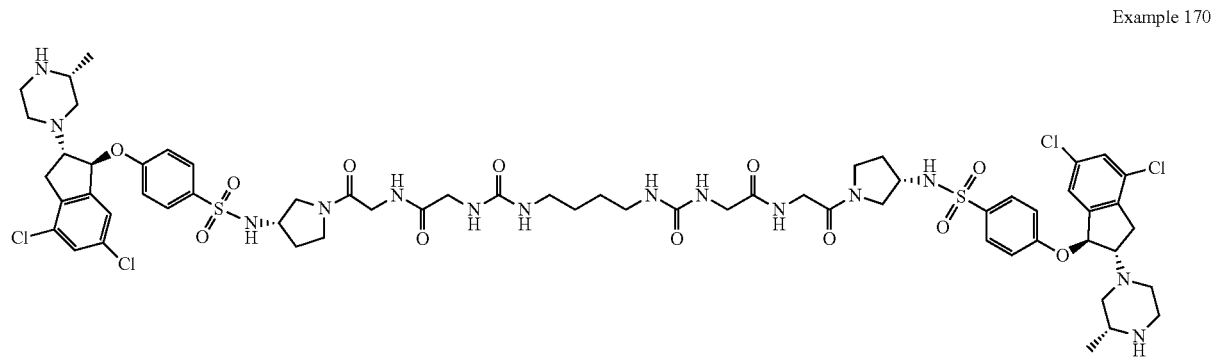 [SMILES: C[C@@H]1CN([C@H]2Cc3c(Cl)cc(Cl)cc3[C@@H]2Oc2ccc(S(=O)(=O)N[C@H]3CCN(C(=O)CNC(=O)CNC(=O)NCCCCNC(=O)NCC(=O)NCC(=O)N4CC[C@H](NS(=O)(=O)c5ccc(O[C@H]6c7cc(Cl)cc(Cl)c7C[C@@H]6N6CCN[C@H](C)C6)cc5)C4)C3)cc2)CCN1]

Example 170

Example 171: 4-([(1S,2S)-6-Chloro-4-cyano-2-[(R)-3-methylpiperazin-1-yl]-2,3-dihydro-1H-inden-1-yl]oxy)-N—[(S)-1-(18-[(S)-3-([4-([(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]-benzenesulfonamide

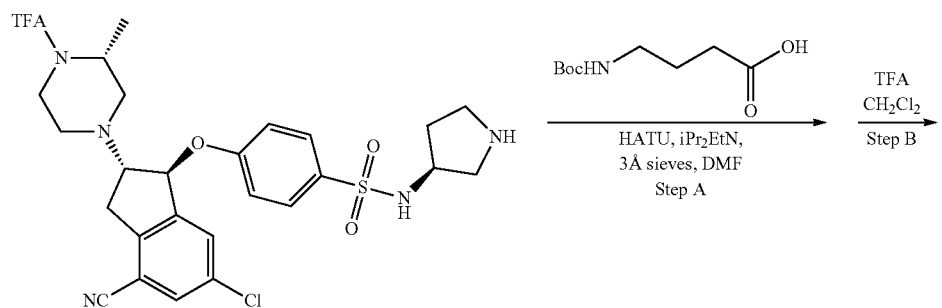

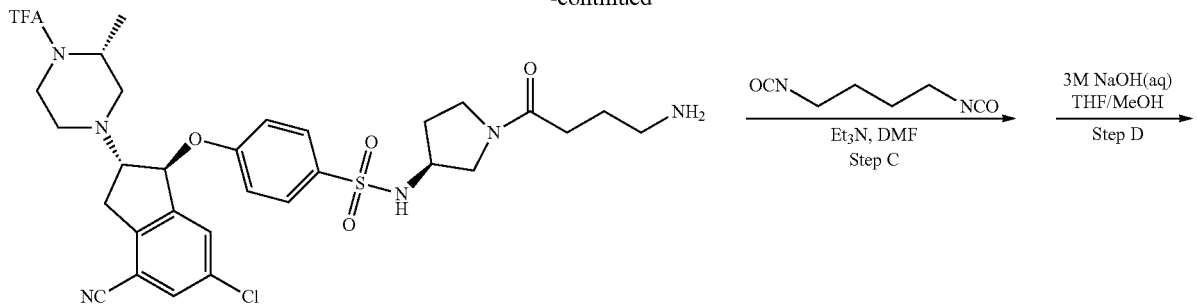

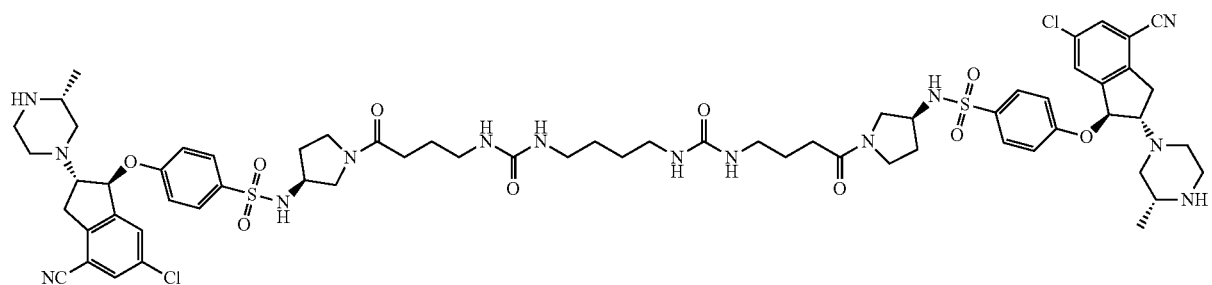

Example 169

Step A: 4-(((1S,2S)-6-Chloro-4-cyano-2-((R)-3-methyl-4-(2,2,2-trifluoroacetyl)piperazin-1-yl)-2,3-dihydro-1H-inden-1-yl)oxy)-N—((S)-pyrrolidin-3-yl)benzenesulfonamide (prepared by procedures analogous to the INT-SLC5, 200 mg, 0.33 mmol), 4-((tert-butoxycarbonyl)amino)butanoic acid (100 mg, 0.49 mmol, 1.5 equiv), HATU (247 mg, 0.65 mmol, 2 equiv), and crushed molecular sieves (3 Å) were suspended in dimethylformamide (1.0 mL), then diisopropylethylamine (226 µL, 1.3 mmol, 4 equiv) was added at room temperature. The mixture was stirred for 30 min at room temperature at which point the reaction was complete by LC/MS. The reaction mixture was concentrated under vacuum and the residue was purified by silica gel chromatography with DCM:MeOH 0 to 8%. Product eluted ~6% MeOH; 250 mg (97%) was collected as tan solid. LC/MS: retention time 4.06 minutes. MS (m/z): [M+H]+ 797.2.

Step B: TFA (190 µL, 2.5 mmol, 8.0 equiv) was added to a solution of tert-butyl (4-((S)-3-(4-(((1S,2S)-6-chloro-4-cyano-2-((R)-3-methyl-4-(2,2,2-trifluoroacetyl)piperazin-1-yl)-2,3-dihydro-1H-inden-1-yl)oxy)phenylsulfonamido)pyrrolidin-1-yl)-4-oxobutyl)carbamate (250 mg, 0.31 mmol) in DCM (1.0 mL). The reaction mixture was stirred for 16 h at rt, then concentrated under vacuum (azeotroping TFA with DCE) providing crude product (theoretical 0.31 mmol) as a white foam, which was used for the next step without purification. LCMS: retention time 3.22 minutes. MS (m/z): [M+H]+ 697.2.

Step C: 1,4-Diisocyanatobutane (18.6 mg, 0.13 mmol, 0.43 equiv) was added to a solution of 2N—((S)-1-(4-aminobutanoyl)pyrrolidin-3-yl)-4-(((1S,2S)-6-chloro-4-cyano-2-((R)-3-methyl-4-(2,2,2-trifluoroacetyl)piperazin-1-yl)-2,3-dihydro-1H-inden-1-yl)oxy)benzenesulfonamide (216 mg, 0.31 mmol) in DMF (1.0 mL) and Et$_3$N (213 µL, 1.54 mmol, 5 equiv). The reaction mixture was stirred for 4 h at room temperature, diluted with H$_2$O/MeCN, and purified by prep-HPLC with the following conditions: Column, Atlantis Prep T3 OBD, 19*150 mm, 10 um; mobile phase, water (0.1% TFA) and CH$_3$CN (20.0% CH$_3$CN up to 80.0% in 40 min); Detector, UV 214 nm. Product eluted ~77% MeCN. This procedure provided 170.1 mg (83%) of the title compound as a white solid. LC/MS: retention time 4.31 minutes. MS (m/z): [M/2+H]+ 767.3.

Step D: 3M aq NaOH (185 µL, 0.55 mmol, 5.0 eq) was added to a solution of (S,S,R)—N,N'-((3S,3'S)-1,1'-(6,13-dioxo-5,7,12,14-tetraazaoctadecane-1,18-dioyl)bis(pyrrolidine-3,1-diyl))bis(4-(((1S,2S)-6-chloro-4-cyano-2-((R)-3-methyl-4-(2,2,2-trifluoroacetyl)piperazin-1-yl)-2,3-dihydro-1H-inden-1-yl)oxy)benzenesulfonamide) (170 mg, 0.11 mmol) in THF/methanol (0.9:0.1 mL). The reaction mixture was stirred for 4 h at rt—complete by LC/MS. The reaction mixture was diluted in H$_2$O/MeCN and purified by prep-HPLC with the following conditions: Column, Atlantis Prep T3 OBD, 19*150 mm, 10 µm; mobile phase, water (0.1% TFA) and CH$_3$CN (10.0% CH$_3$CN up to 60.0% in 40 min); Detector, UV 214 nm. Product eluted ~48% MeCN. This procedure provided 124 mg (72%) of the title compound as a white solid. LC/MS: retention time 2.9 minutes. MS (m/z): [M/2+H]+ 671.3. $^1$H NMR (Methanol-d4, 400 MHz) δ 7.92-7.83 (m, 4H), 7.76 (s, 2H), 7.49-7.45 (m, 2H), 7.37-7.25 (m, 4H), 6.09-6.05 (m, 2H), 3.86-3.69 (m, 2H), 3.34 (dd, J=14.5, 6.4 Hz, 19H), 3.11 (t, J=8.6 Hz, 22H), 2.69-2.55 (m, 1H), 2.41-2.04 (m, 1H), 1.98-1.62 (m, 1H), 1.47 (s, 4H), 1.28 (dd, J=6.5, 3.7 Hz, 7H).

Example 172: 4-([(1S,2S)-6-Chloro-4-cyano-2-[(R)-3-methylpiperazin-1-yl]-2,3-dihydro-1H-inden-1-yl]oxy)-N-[1-(18-[4-([4-([[(1S,2S)-6-chloro-4-cyano-2-[(R)-3-methylpiperazin-1-yl]-2,3-dihydro-1H-inden-1-yl]oxy)phenyl]sulfonamido)piperidin-1-yl]-6,13,18-trioxo-5,7,12,14-tetraazaoctadecanoyl)piperidin-4-yl]benzenesulfonamide Step B: TFA (160 μL, 2.06 mmol, 8.0 equiv) was added to a solution of tert-butyl (4-(4-(4-(((1S,2S)-6-chloro-4-cyano-2-((R)-3-methyl-4-(2,2,2-trifluoroacetyl)piperazin-1-yl)-2,3-dihydro-1H-inden-1-yl)oxy)phenylsulfonamido)piperidin-1-yl)-4-oxobutyl)carbamate (210 mg, 0.26 mmol) in DCM (1.0 mL). The reaction mixture was stirred for 18 h at rt, then concentrated under vacuum (azeotroping TFA with

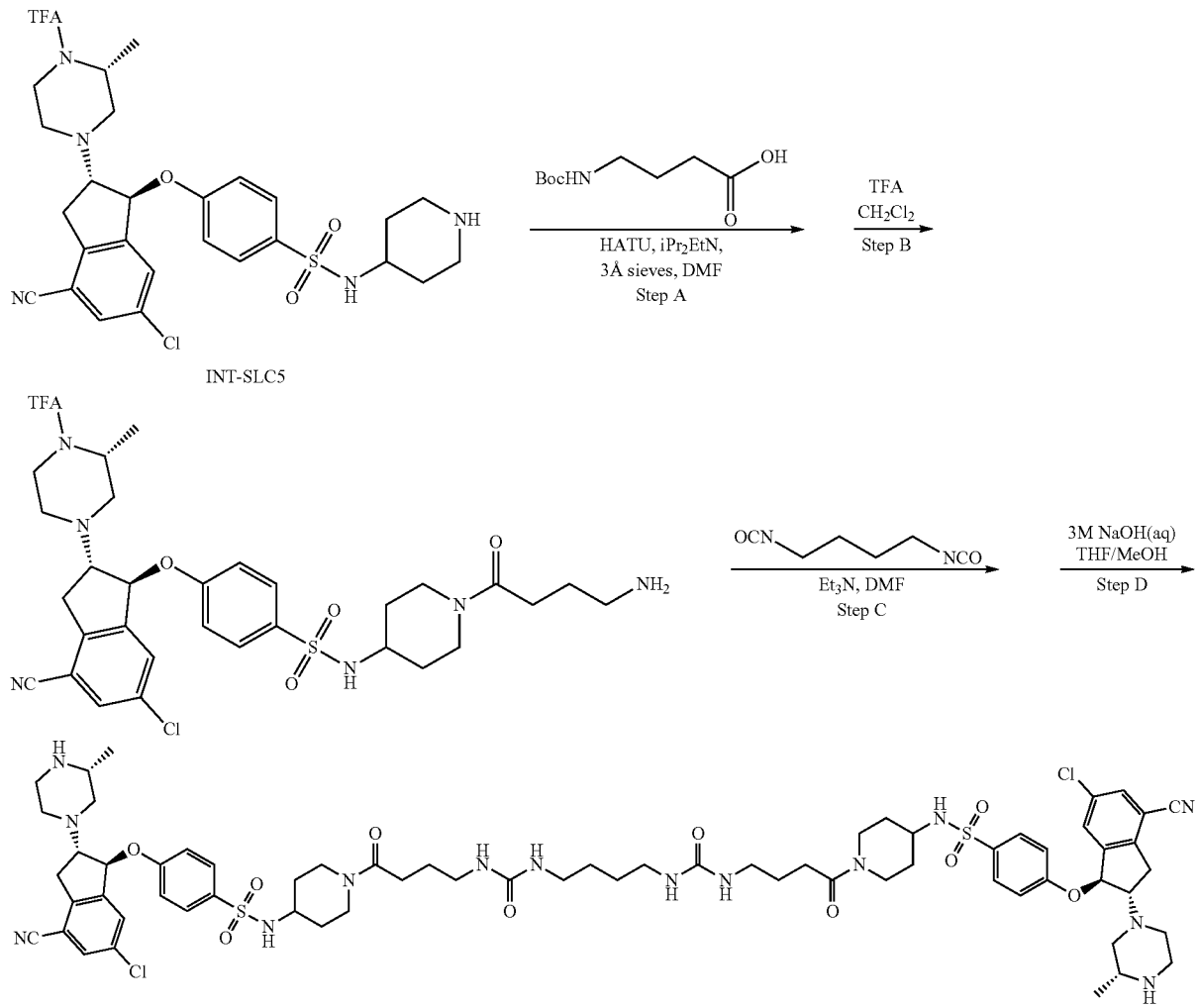

Example 170

Step A: 4-(((1S,2S)-6-Chloro-4-cyano-2-((R)-3-methyl-4-(2,2,2-trifluoroacetyl)piperazin-1-yl)-2,3-dihydro-1H-inden-1-yl)oxy)-N-(piperidin-4-yl)benzenesulfonamide (prepared by procedures analogous to INT-SLC5, 170 mg, 0.27 mmol), 4-((tert-butoxycarbonyl)amino)butanoic acid (83 mg, 0.40 mmol, 1.5 equiv). HATU (206 mg, 0.54 mmol, 2 equiv) and crushed molecular sieves (3 Å) were suspended in dimethylformamide (1.0 mL), then diisopropylethylamine (190 μL, 1.1 mmol, 4 equiv) was added at room temperature. The reaction mixture was stirred for 1 h at room temperature—complete by LC/MS. The reaction mixture was concentrated under vacuum and the residue was purified by silica gel chromatography with DCM:MeOH 0 to 8%. Product eluted ~6% MeOH; 210 mg (96%) was collected as a tan solid. LC/MS: retention time 4.11 minutes. MS (m/z): [M+H]+ 811.2.

DCE) providing crude product (theoretical 0.26 mmol) as a white foam, which was used for the next step without purification. LCMS: retention time 3.24 minutes. MS (m/z): [M+H]+ 711.2.

Step C: 1,4-Diisocyanatobutane (15.1 mg, 0.11 mmol, 0.43 equiv) was added to a solution of N-(1-(4-aminobutanoyl)piperidin-4-yl)-4-(((1S,2S)-6-chloro-4-cyano-2-((R)-3-methyl-4-(2,2,2-trifluoroacetyl)piperazin-1-yl)-2,3-dihydro-1H-inden-1-yl)oxy)benzenesulfonamide (180 mg, 0.25 mmol) in DMF (0.8 mL) and Et₃N (175 μL, 1.26 mmol, 5 equiv). The reaction mixture was stirred for 4 h at room temperature diluted with H₂O/MeCN and purified by prep-HPLC with the following conditions: Column, Atlantis Prep T3 OBD, 19*150 mm, 10 um; mobile phase, water (0.1% TFA) and CH₃CN (20.0% CH₃CN up to 80.0% in 40 min); Detector, UV 214 nm. Product eluted ~77% MeCN. This procedure provided 145 mg (86%) of the title compound as a white solid. LC/MS: retention time 4.37 minutes. MS (m/z): [M/2+H]+ 781.3.

Step D: 3M aq NaOH (185 μL, 0.55 mmol, 6.0 eq) was added to a solution of (S,S,R)—N,N'-(1,1'-(6,13-dioxo-5,7,12,14-tetraazaoctadecane-1,18-dioyl)bis(piperidine-4,1-diyl)bis(4-(((1S,2S)-6-chloro-4-cyano-2-((R)-3-methyl-4-(2,2,2-trifluoroacetyl)piperazin-1-yl)-2,3-dihydro-1H-inden-1-yl)oxy)benzenesulfonamide) (145 mg, 0.9 mmol) in THF/methanol (0.9:0.1 mL). The reaction mixture was stirred for 1 h at rt—complete by LC/MS. The reaction mixture was diluted in H2O/MeCN and purified by prep-HPLC with the following conditions: Column, Atlantis Prep T3 OBD, 19*150 mm, 10 um; mobile phase, water (0.1% TFA) and CH3CN (10.0% CH3CN up to 60.0% in 40 min); Detector, UV 214 nm. Product eluted ~48% MeCN. This procedure provided 108.8 mg (73%) of the title compound as a white solid. LC/MS: retention time 2.93 minutes. MS (m/z): [M/2+H]+ 685.3. $^1$H NMR (Methanol-d4, 400 MHz) δ 7.88 (d, J=8.9 Hz, 4H), 7.76 (d, J=1.9 Hz, 2H), 7.44 (s, 2H), 7.31 (d, J=8.9 Hz, 4H), 6.06 (s, 2H), 4.24-4.16 (m, 1H), 3.84-3.70 (m, 3H), 3.41-3.30 (m, 17H), 3.24-3.01 (m, 15H), 2.40-2.30 (m, 5H), 1.85-1.76 (m, 1H), 1.71 (d, J=7.2 Hz, 4H), 1.46 (s, 5H), 1.28 (d, J=6.6 Hz, 7H).

Example 173: 4-([(1S,2S)-6-Chloro-4-cyano-2-[(R)-3-methylpiperazin-1-yl]-2,3-dihydro-1H-inden-1-yl]oxy)-N-[1-(20-[4-([4-([(1S,2S)-6-chloro-4-cyano-2-[(R)-3-methylpiperazin-1-yl]-2,3-dihydro-1H-inden-1-yl]oxy)phenyl]sulfonamido)piperidin-1-yl]-7,14-dioxo-3,18-dioxa-6,8,13,15-tetraazaicosyl)piperidin-4-yl]benzenesulfonamide Exanoke 171

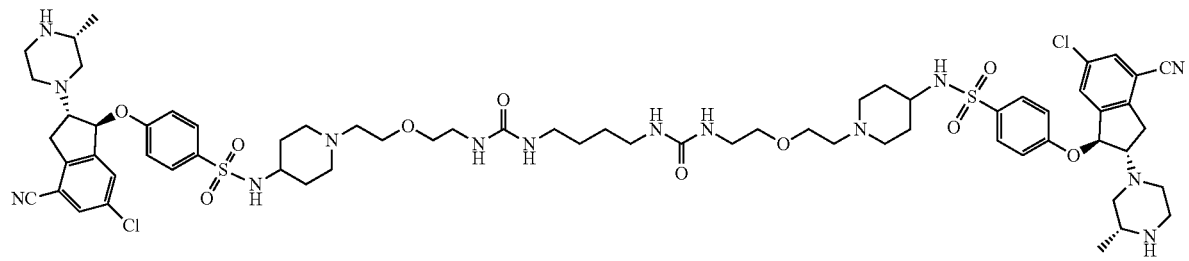

The title compound was prepared following the procedure from Example 123. The residue purified by Column, Atlantis Prep T3 OBD, 19*150 mm, 10 um; mobile phase, water (0.1% TFA) and CH3CN (10.0% CH3CN up to 60.0% in 40 min); Detector, UV 214 nm. Product eluted ~43% MeCN. This procedure provided 28 mg (41%) of the title compound as a white solid. LCMS: ret. time 1.89 min. MS (m/z): [M/2+H]+ 687.3. $^1$H NMR (Methanol-d4, 400 MHz) δ 7.89 (d, J=9.0 Hz, 4H), 7.78-7.75 (m, 2H), 7.45-7.42 (m, 2H), 7.37-7.23 (m, 4H), 6.11-6.02 (m, 2H), 3.80-3.67 (m, 8H), 3.61-3.47 (m, 10H), 3.32 (dd, J=10.3, 7.5 Hz, 18H), 3.12 (d, J=8.8 Hz, 18H), 2.69-2.57 (m, 1H), 2.37-2.28 (m, 1H), 2.08-1.94 (m, 6H), 1.88-1.74 (m, 2H), 1.53-1.39 (m, 4H), 1.28 (d, J=6.6 Hz, 6H).

Example 174: 4-([[(1S,2S)-4,6-Dichloro-2-[(R)-3-methylpiperazin-1-yl]-2,3-dihydro-1H-inden-1-yl]oxy)-N—[(S)-1-(20-[(S)-3-([4-([(1S,2S)-4,6-dichloro-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide

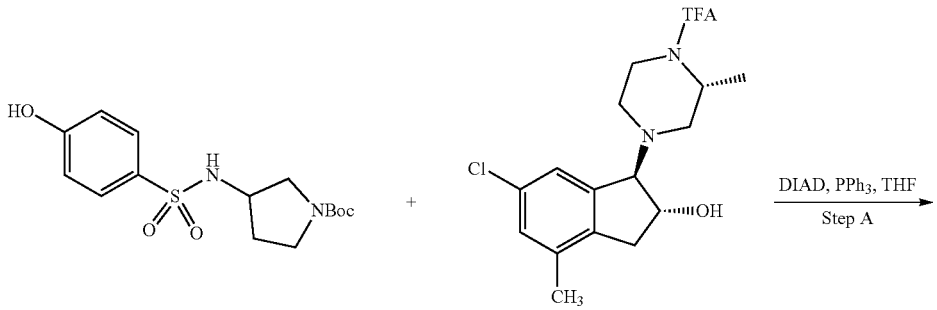

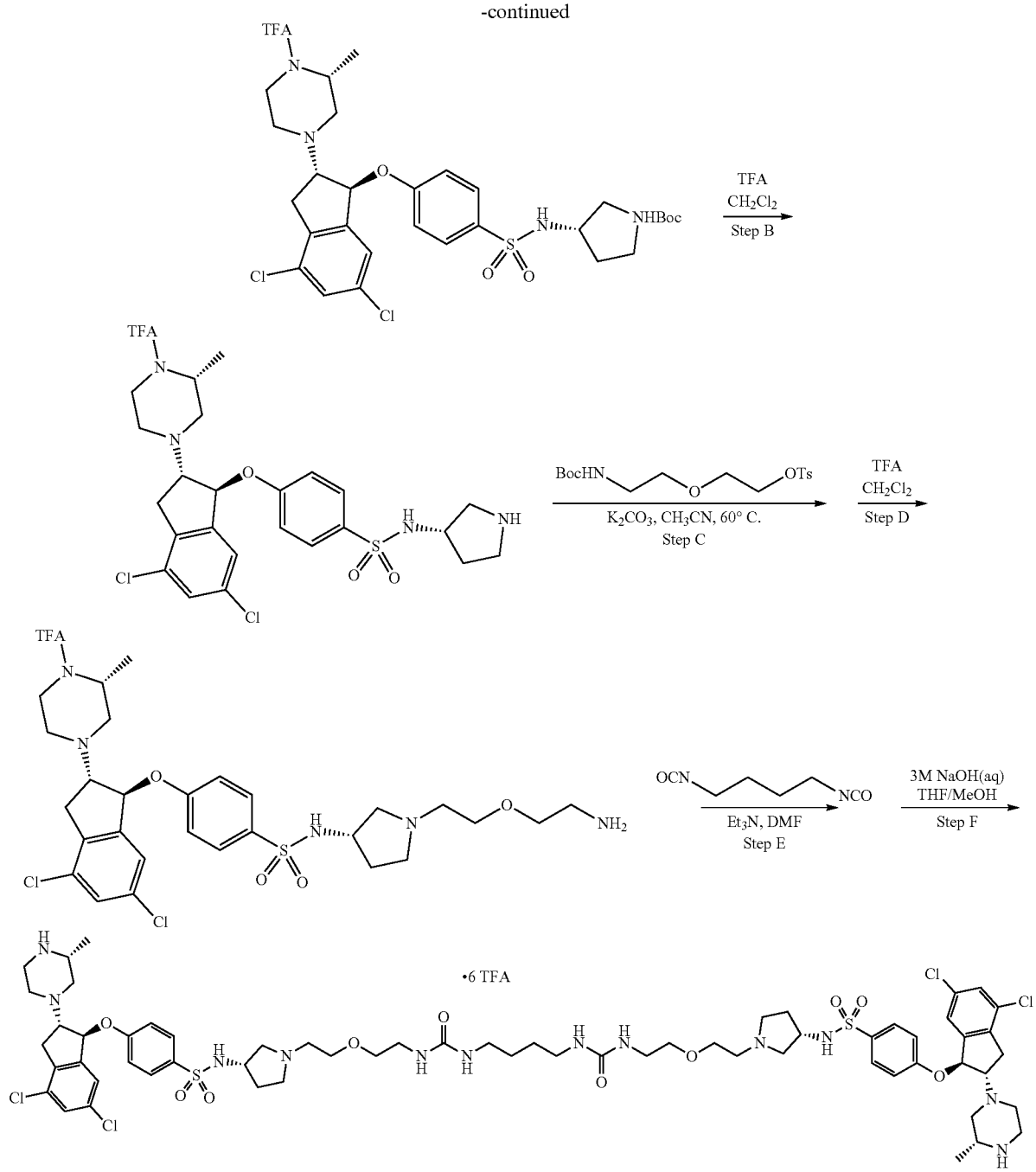

Example 172

Step A: (S)-tert-Butyl 3-(4-hydroxyphenylsulfonamido)pyrrolidine-1-carboxylate (0.47 g, 1.37 mmol, 1.1 eq), 1-((R)-4-((1R,2R)-4,6-dichloro-2-hydroxy-2,3-dihydro-1H-inden-1-yl)-2-methylpiperazin-1-yl)-2,2,2-trifluoroethanone (0.5 g, 1.25 mmol), and Ph₃P (0.49 g, 1.87 mmol, 1.5 eq) were dissolved in THF (3 mL), the mixture heated at 40° C. for 15 minutes under $N_2$, then a solution of diisopropyl azodicarboxylate (0.39 mL, 2.0 mmol, 1.6 eq) in THF (1.2 mL) was added dropwise within 15 minutes. The reaction mixture was stirred for 10 min (LCMS showed no starting aminoalcohol). The reaction mixture was concentrated under vacuum and purified by silica gel chromatography with hexane:EtOAc (0 to 60%) providing 840 mg (93%) of product as a white foam. LCMS: ret time 3.96 min. MS (m/z): [M+H]⁺ 721.1.

Step B: TFA (1.0 mL, 12.9 mmol, 11.7 eq) was added to a solution of (S)-tert-butyl 3-(4-(((1S,2S)-4,6-dichloro-1-((R)-3-methyl-4-(2,2,2-trifluoroacetyl)piperazin-1-yl)-2,3-dihydro-1H-inden-2-yl)oxy)phenylsulfonamido)pyrrolidine-1-carboxylate (800 mg, 1.1 mmol) in DCM (5.0 mL). The reaction mixture was stirred for 16 h, the DCM removed by evaporation, and the residue was purified by prep-HPLC with the following conditions: Column, Atlantis Prep T3 OBD, 50*250 mm, 10 um; mobile phase, water (0.1% TFA)

and CH$_3$CN (30.0% CH$_3$CN up to 70.0% in 50 min); Detector, UV 214 nm. Product eluted ~65% MeCN. Collected fractions were concentrated under vacuum, neutralized with solid NaHCO$_3$ (pH 9), and extracted with 9:1 CHCl$_3$:IPA (3×40 mL). Combined organics were washed with brine (40 mL), dried over Na$_2$SO$_4$, filtered, and concentrated to afford 500 mg (73%) of product as a white solid. LCMS: ret time 2.95 min. MS (m/z): [M+H]$^+$ 621.2.

Step C: 2-(2-(((tert-Butoxycarbonyl)amino)ethoxy)ethyl 4-methylbenzenesulfonate (126 mg, 0.35 mmol, 1.1 eq), 4-(((1S,2S)-4,6-dichloro-1-((R)-3-methyl-4-(2,2,2-trifluoroacetyl)piperazin-1-yl)-2,3-dihydro-1H-inden-2-yl)oxy)-N—((S)-pyrrolidin-3-yl)benzenesulfonamide (200 mg, 0.32 mmol) and K$_2$CO$_3$ (89 mg, 0.64 mmol, 2 eq) were mixed in MeCN (2.0 mL) and the mixture stirred at 55° C. for 16 h giving approx. 50% conversion (LCMS). DMF (0.5 mL) was added and the slurry was stirred for another 24 h at 60° C. giving complete conversion. The reaction mixture was filtered, the filtrates concentrated, and the residue purified by silica gel column with DCM:MeOH (0 to 10%). The product 144 mg (56%) was collected as a white foam. LCMS: ret time 3.3 min. MS (m/z): [M+H]$^+$ 808.25.

Step D: TFA (150 μL, 1.95 mmol 11 eq) was added to a solution of tert-butyl (2-(2-((S)-3-(4-(((1S,2S)-4,6-dichloro-1-((R)-3-methyl-4-(2,2,2-trifluoroacetyl)piperazin-1-yl)-2,3-dihydro-1H-inden-2-yl)oxy)phenylsulfonamido)pyrrolidin-1-yl)ethoxy)ethyl)carbamate (145 mg, 0.18 mmol) in DCM (2 mL). The reaction mixture was stirred for 15 h then concentrated under vacuum. The residue was dissolved in water (5 mL) and neutralized with solid NaHCO$_3$ (pH ~8). The aqueous layer was extracted with EtOAc (3×10 mL). The organic layer was dried over Na$_2$SO$_4$, filtered, and concentrated to afford 120 mg (95%) of desired product. LCMS: ret time 2.43 min. MS (m/z): [M+H]$^+$ 708.2.

Step E: A solution of 1,4-diisocyanatobutane (10 mg, 0.071 mmol, 0.42 eq) in DMF (0.1 mL) was added to a solution of N—((S)-1-(2-(2-aminoethoxy)ethyl)pyrrolidin-3-yl)-4-(((1S,2S)-4,6-dichloro-1-((R)-3-methyl-4-(2,2,2-trifluoroacetyl)piperazin-1-yl)-2,3-dihydro-1H-inden-2-yl)oxy)benzenesulfonamide (120 mg, 0.17 mmol) in DMF (0.4 mL). The reaction mixture was stirred at rt for 2 h, concentrated under vacuum, and the residue purified by silica gel column DCM:85DCM/15MeOH/5Et$_3$N (0 to 10%). Product eluted ~85% of polar solvent. 150 mg (theoretical 110 mg, not completely dry) of product was collected as a white foam. LCMS: ret time 3.56 min. MS (m/z): [M/2+H]$^+$ 778.3.

Step F: 3M aq NaOH (400 μL, 1.2 mmol, 17 eq) was added to a solution of (S,S,R)—N,N'-((3S,3'S)-1,1'-(7,14-dioxo-3,18-dioxa-6,8,13,15-tetraazaicosane-1,20-diyl)bis(pyrrolidine-3,1-diyl))bis(4-(((1S,2S)-4,6-dichloro-1-((R)-3-methyl-4-(2,2,2-trifluoroacetyl)piperazin-1-yl)-2,3-dihydro-1H-inden-2-yl)oxy)benzenesulfonamide) (110 mg, 0.071 mmol) in MeOH (1 mL):THF (0.5 mL). The addition was portionwise (130+130+240 μL) within 2 h, with LCMS monitoring of the reaction progress. After 2.5 h, the reaction was complete by LCMS. The reaction was quenched with 4 N HCl (pH ~2), the volatiles removed under vacuum, and the residue purified by prep-HPLC with the following conditions: Column, Atlantis Prep T3 OBD, 50*250 mm, 10 um; mobile phase, water (0.1% TFA) and CH$_3$CN (20.0% CH$_3$CN up to 60.0% in 50 min); Detector, UV 214 nm. 127.7 mg (88%) was collected as a white solid. 124.7 mg registered as NTX-0010630 tare: 4.9286. LCMS: ret time 1.89 min. MS (m/z): [M/2+H]$^+$ 682.3. $^1$H NMR (Methanol-d4, 400 MHz) δ 7.87 (s, 4H), 7.43-7.41 (m, 2H), 7.33 (d, J=9.0 Hz, 5H), 7.11-7.09 (m, 2H), 6.07-6.04 (m, 2H), 3.77-3.70 (m, 8H), 3.70-3.62 (m, 3H), 3.55-3.49 (m, 6H), 3.26-3.06 (m, 7H), 2.64 (s, 1H), 2.37-2.28 (m, 1H), 1.50-1.44 (m, 3H), 1.28 (d, J=6.6 Hz, 6H).

Example 175: N$^1$,N$^{14}$-Bis(2-[(S)-3-([4-([(1S,2S)-4,6-dichloro-2-[(R)-3-methylpiperazin-1-yl]-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide

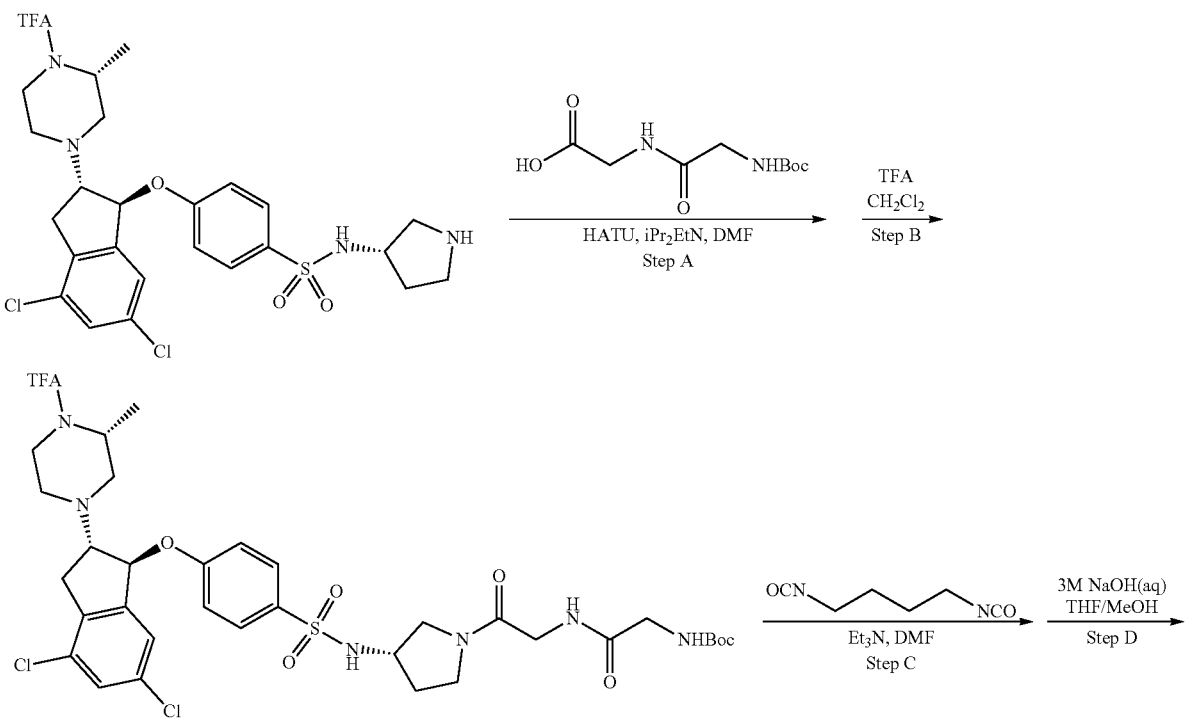

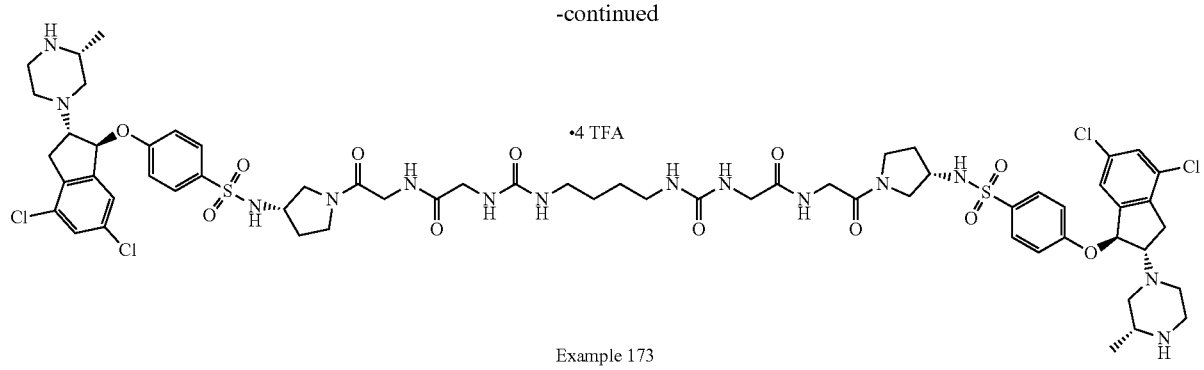

Example 173

Step A: 2-(2-((tert-Butoxycarbonyl)amino)acetamido)acetic acid (84 mg, 0.36 mmol, 1.5 eq), 4-(((1S,2S)-4,6-dichloro-1-((R)-3-methyl-4-(2,2,2-trifluoroacetyl)piperazin-1-yl)-2,3-dihydro-1H-inden-2-yl)oxy)-N—((S)-pyrrolidin-3-yl)benzenesulfonamide (150 mg, 0.24 mmol), and HATU (183 mg, 0.48 mmol, 2 eq) were mixed in DMF (1 mL). Diisopropylethylamine (170 μL, 0.96 mmol. 4 eq) was added and the mixture stirred for 15 minutes—complete by LCMS. The reaction mixture was concentrated under vacuum and the residue purified by silica gel column with DCM:MeOH (0 to 10%); 220 mg (>100%, not dry) of product was collected as a slightly yellowish solid. LCMS: ret time 3.50 min. MS (m/z): [M+H]+ 835.2.

Step B: TFA (300 μL, 3.9 mmol, 16 eq) was added to a solution of tert-butyl (2-((2-((S)-3-(4-(((1S,2S)-4,6-dichloro-1-((R)-3-methyl-4-(2,2,2-trifluoroacetyl)piperazin-1-yl)-2,3-dihydro-1H-inden-2-yl)oxy)phenylsulfonamido)pyrrolidin-1-yl)-2-oxoethyl)amino)-2-oxoethyl)carbamate (theoretical 200 mg, 0.24 mmol) in DCM (2 mL). The reaction mixture was stirred at rt for 1 h—complete by LCMS. The volatiles were removed by evaporation and the residue dissolved in water (20 mL) and neutralized with solid NaHCO$_3$ (pH 9). The solution was extracted with EtOAc (2×20 mL), then with 9:1 CHCl$_3$:IPA (2×20 mL) [compound mostly went to EtOAc]. The combined organic layers were dried over Na$_2$SO$_4$, filtered, and concentrated to afford 173 mg (98%) of product as a tan foam. LCMS: ret time 2.89. MS (m/z): [M+H]+ 735.2.

Step C: A solution of 1,4-diisocyanatobutane (14.5 mg, 0.10 mmol, 0.45 eq) in DMF (0.14 mL) was added to a solution of 2-amino-N-(2-((S)-3-(4-(((1S,2S)-4,6-dichloro-1-((R)-3-methyl-4-(2,2,2-trifluoroacetyl)piperazin-1-yl)-2,3-dihydro-1H-inden-2-yl)oxy)phenylsulfonamido)pyrrolidin-1-yl)-2-oxoethyl)acetamide (170 mg, 0.23 mmol) in DMF (0.5 mL). The reaction mixture was stirred for 0.5 h—complete by LCMS. The reaction mixture was concentrated under vacuum and the residue purified by silica gel chromatography with DCM:8.5DCM/1.5MeOH/0.5Et$_3$N (0 to 65%). The product eluted at 60% of polar solvent, 200 mg (theoretical 165 mg) collected as a white foam. LC/MS: ret time 3.28 minutes, MS (m/z): [M/2+H]+ 782.3.

Step D: 3 M aq NaOH (100 μL, 0.3 mmol, 3 eq) was added to a solution of N$^1$,N$^{14}$-bis(2-((S)-3-(4-(((1S,2S)-4,6-dichloro-1-((R)-3-methyl-4-(2,2,2-trifluoroacetyl)piperazin-1-yl)-2,3-dihydro-1H-inden-2-yl)oxy)phenylsulfonamido)pyrrolidin-1-yl)-2-oxoethyl)-4,11-dioxo-3,5,10,12-tetraazatetradecane-1,14-diamide (165 mg, 0.1 mmol) in THF:MeOH 0.6:0.07 mL. After 1 h, added additional NaOH (300 μL) and MeOH (200 μL) in two portions over the next 2 hours. After 1 h the reaction was complete. The reaction was quenched with 4 N HCl (pH ~2), the volatiles removed under vacuum, and the residue purified by prep-HPLC with the following conditions: Column, Atlantis Prep T3 OBD, 50*250 mm, 10 um; mobile phase, water (0.1% TFA) and CH$_3$CN (20.0% CH$_3$CN up to 60.0% in 50 min); Detector, UV 214 nm. 92 mg (48%) was collected as a white solid. 90.6 mg registered as NTX-0010628 tare: 4.9269. LCMS: ret time 2.5 min. MS (m/z): [M/2+H]+ 709.3. $^1$H NMR (Methanol-d4, 400 MHz) δ 7.91-7.80 (m, 4H), 7.43-7.37 (m, 2H), 7.30 (s, 4H), 7.16-7.10 (m, 2H), 6.07-6.00 (m, 2H), 3.94-3.89 (m, 3H), 3.79 (d, J=4.9 Hz, 5H), 3.59-3.50 (m, 4H), 3.13 (s, 14H), 1.53-1.45 (m, 4H), 1.25 (d, J=6.6 Hz, 6H).

Example 176: 4-([(1S,2S)-4-Cyano-6-methyl-2-(piperazin-1-yl)-2,3-dihydro-1H-inden-1-yl]oxy)-N-[26-([4-([(1S,2S)-4-cyano-6-methyl-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide

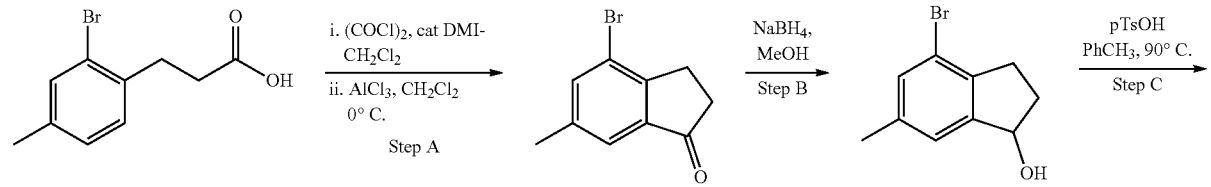

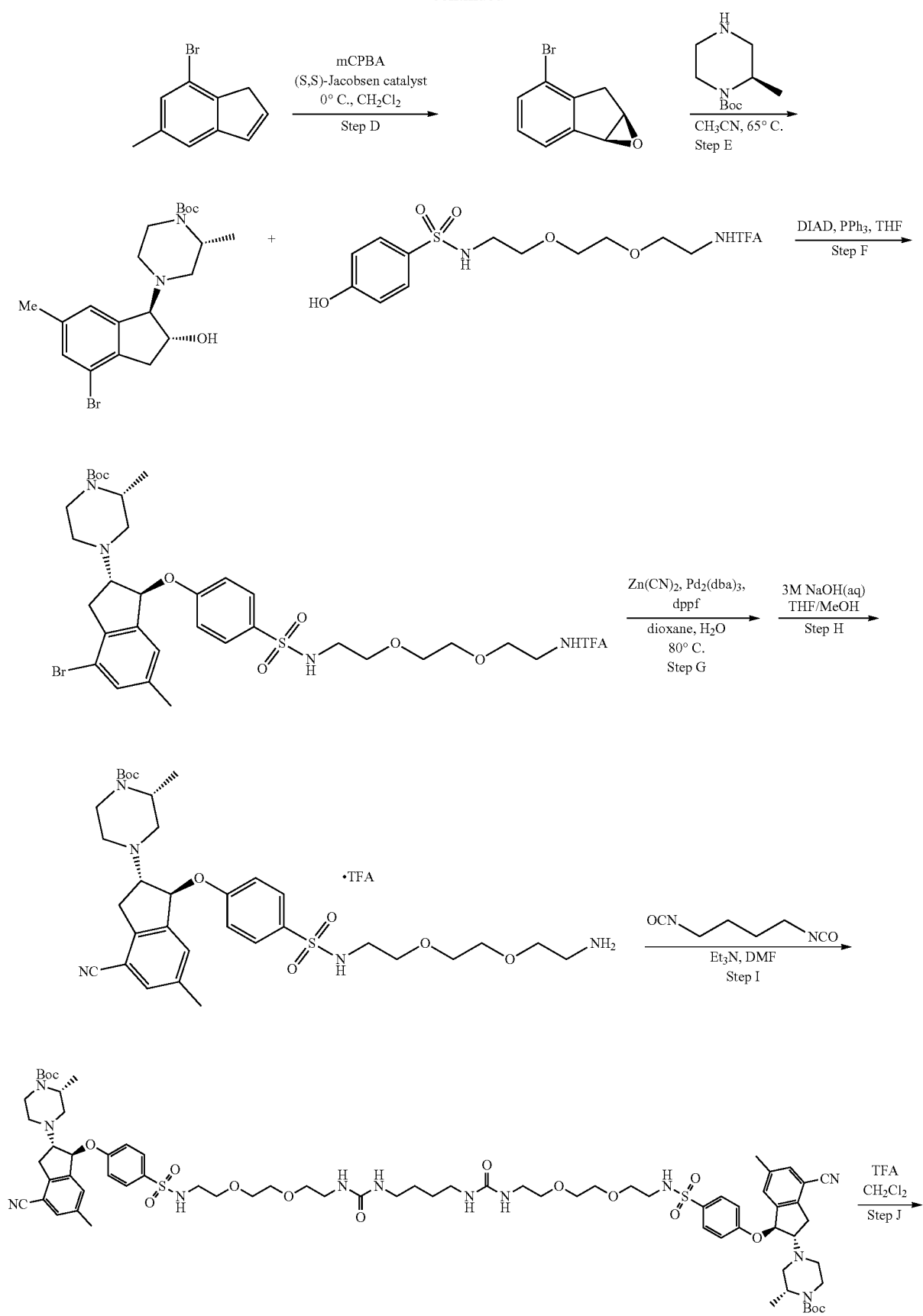

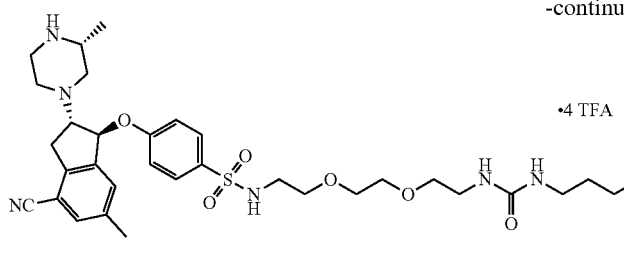
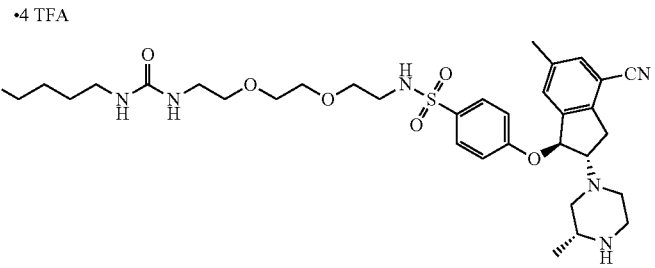

Example 157

Step A: 3-(2-Bromo-4-methylphenyl)propanoic acid (2.4 g, 9.9 mmol) was dissolved in DCM (12 mL) and DMF (0.1 mL, 1.3 mmol, 0.13 eq), Oxalyl chloride (1.7 mL, 19.7 mmol, 2 eq) was added dropwise over 7 minutes. The reaction mixture was stirred at rt under $N_2$ for 1.5 h (LCMS showed no starting material). The reaction mixture was concentrated under vacuum to ⅓ of original volume and added to a precooled suspension of $AlCl_3$ (1.7 g, 12.8 mmol, 1.3 eq) in DCM (10 mL) over 5 minutes, keeping internal temperature <5° C. The reaction mixture was stirred at 3-5° C. for 20 minutes before the ice bath was removed and mixture stirred for another 20 minutes—complete by LCMS. The reaction mixture was quenched by slow addition of cold 3 M aq HCl (20 mL) under cooling. The solution was extracted with DCM (3×25 mL). The combined organic layers were washed with brine (2×25 mL), dried over $Na_2SO_4$, filtered, and concentrated under vacuum. The residual solid was suspended in hexane and collected by filtration—product 2.0 g (90%), white solid; LCMS. NMR are good. The filtrates were purified by silica gel chromatography Hexane:EtOAc (0 to 15%) to afford 0.1 g of product. LCMS: ret time 2.75 minutes, MS (m/z): $[M+H]^{1+}$ 225.0.

Step B: To 4-bromo-6-methyl-2,3-dihydro-1H-inden-1-one (2.1 g, 9.3 mmol) in methanol (23 mL) was added $NaBH_4$ (320 mg, 8.45 mmol, 0.9 eq), becoming homogenous with addition. After 10 min, the reaction was complete (LCMS) and the solvent was evaporated. The residue was slurried in 40 mL of water and extracted with EtOAc (3×35 mL). The combined organic layers were washed with brine (2×30 mL), dried over $Na_2SO_4$, filtered, and concentrated to 2.1 g (99%) of white solid. LCMS and NMR are good. The crude was used directly in the next step. LCMS: ret. time 2.49 minutes. MS (m/z): $[M-H_2O+H]^+$ 209.0.

Step C: 4-Bromo-6-methyl-2,3-dihydro-1H-inden-1-ol (2.1 g, 9.2 mmol) suspended in toluene (10 mL), $pTsOH.H_2O$ (175 mg, 0.92 mmol, 0.1 eq) was added at room temperature and mixture heated to 90° C. (internal). The reaction mixture was stirred at 90° C. for 20 min—complete by LCMS. Upon cooling EtOAc (30 mL) was added and the resulting solution washed with brine (2×15 mL). The organic phase was dried over $Na_2SO_4$, filtered, and concentrated under vacuum to afford 1.8 g of crude product as a yellowish oil. NMR and LCMS showed mixture of 2 compounds which were separated by silica gel chromatography with hexane (2 long columns). Desired product—indene, eluted first, providing 600 mg (31%) as a colorless liquid. Ret time 3.6 minutes, no ionization, NMR confirmed structure.

Step D: 7-Bromo-5-methyl-1H-indene (0.6 g, 2.86 mmol) was dissolved in DCM (18 mL) and treated with a solution of pyridine 1-oxide (1.35 g, 14.3 mmol, 5 eq) in DCM (10 mL), followed by (S,S)-Jacobsen catalyst (Sigma-Aldrich 404454, CAS 135620-04-1). The mixture was cooled to 0° C. and stirred for 15 minutes. mCPBA (0.98 g, 5.72 mmol, 2 eq) was added in 3 portions over 10 minutes. The reaction mixture was stirred at 0° C. for another hour (complete by TLC). The reaction mixture was quenched with 3 M aq NaOH (8 mL), the organic layer separated, and the aqueous layer extracted with hexane (2×20 mL). The combined organic layers were washed with water (20 mL) and brine (20 mL), dried over $Na_2SO_4$, filtered, and concentrated under vacuum. The residue was purified by silica gel chromatography with hexane:DCM (0 to 40%) to afford 320 mg (50%) of scalemic epoxide, used for the next step without resolution.

Step E: 5-Bromo-3-methyl-6,6a-dihydro-1aH-indeno[1,2-b]oxirene (300 mg, 1.33 mmol) [scalemic material from epoxidation step] and (R)-tert-butyl 2-methylpiperazine-1-carboxylate (318 mg, 1.59 mmol, 1.2 eq) were mixed in MeCN (4 mL) and heated at 65° C. for 16 h. The reaction mixture was concentrated under vacuum and the residue purified by silica gel chromatography with hexane:EtOAc (0 to 40%): 260 mg (46%) of product was collected as a tan foam. NMR showed presence of other diastereomer (~10%). LCMS: ret time 2.36 min. MS (m/z): $[M+H]^+$ 425.1.

Step F: (R)-tert-Butyl 4-((1R,2R)-4-bromo-2-hydroxy-6-methyl-2,3-dihydro-1H-inden-1-yl)-2-methylpiperazine-1-carboxylate (0.2 g, 0.47 mmol). 2,2,2-trifluoro-N-(2-(2-(2-(4-hydroxyphenylsulfonamido)ethoxy)ethoxy)ethyl) acetamide (0.2 g, 0.51 mmol, 1.1 eq) and $Ph_3P$ (0.18 g, 0.7 mmol, 1.5 eq) were dissolved in THF (1.2 mL) and the mixture heated at 40° C. for 15 minutes under $N_2$. A solution of diisopropyl azodicarboxylate (0.15 mL, 0.75 mmol, 1.6 eq) in THF (0.4 mL) was added dropwise within 5 minutes. The reaction mixture was stirred for 20 more minutes—complete by LCMS. The reaction mixture was concentrated under vacuum and the residue was purified by silica gel chromatography with hexane:EtOAc (0 to 70%) to afford 0.35 g (92%) of product as a white foam. NMR and LCMS showed impurity of other diastereomer which came from the prev. step. LCMS major diastereomer: ret time 3.44 min. MS (m/z): $[M+H]^+$ 807.2.

Step C: (R)-tert-Butyl 4-((1S,2S)-4-bromo-6-methyl-1-(4-(N-(2-(2-(2-(2,2,2-trifluoroacetamido)ethoxy)ethoxy)ethyl)sulfamoyl)phenoxy)-2,3-dihydro-1H-inden-2-yl)-2-methylpiperazine-1-carboxylate (0.35 g, 0.43 mmol) and Zn(CN)$_2$ (30.4 mg, 0.26 mmol, 0.6 eq) were dissolved in NMP (1.5 mL), N$_2$ bubbled through solution, then (Ph$_3$P)$_4$Pd (50 mg, 0.04 mmol, 0.1 eq) was added. The reaction mixture was stirred under N$_2$ at 100° C. for 3 h. The reaction mixture was diluted in water (10 mL) and the suspension was extracted with EtOAc (3×15 mL). The combined organics were washed with brine (3×7 mL), dried with Na$_2$SO$_4$, concentrated wider vacuum, and the residue purified by silica gel chromatography with hexane:EtOAc (0 to 100%), 0.25 g (77%) of product was collected as a white foam. LCMS: major diastereomer 3.13 minutes. MS (m/z): [M+H]$^+$ 754.3.

Step H: 3 M aq NaOH (300 µL, 0.9 mmol, 2.7 eq) was added to a solution of (R)-tert-butyl 4-((1S,2S)-4-cyano-6-methyl-1-(4-(N-(2-(2-(2-(2,2,2-trifluoroacetamido)ethoxy)ethoxy)ethyl)sulfamoyl)phenoxy)-2,3-dihydro-1H-inden-2-yl)-2-methylpiperazine-1-carboxylate (250 mg, 0.33 mmol) in MeOH (1.2 mL):THF (0.3 mL). The reaction mixture was stirred for 1.5 h at rt—complete by LCMS. The reaction mixture was concentrated under vacuum and the residue dissolved in MeCN/H$_2$O and purified by prep-HPLC with the following conditions: Column, Atlantis Prep T3 OBD, 50*250 mm, 10 um; mobile phase, water (0.1% TFA) and CH$_3$CN isochratic for 10 min then up to 60.0% in 20 min); Detector, UV 214 nm. 245 mg (96%) was collected as a white solid. LCMS: ret time 2.43 min. MS (m/z): [M+H]$^+$ 658.3.

Step I: Triethylamine (100 µL, 0.72 mmol, 4.3 eq) was added to a solution of (R)-tert-butyl 4-((1S,2S)-1-(4-(N-(2-(2-(2-aminoethoxy)ethoxy)ethyl)sulfamoyl)phenoxy)-4-cyano-6-methyl-2,3-dihydro-1H-inden-2-yl)-2-methylpiperazine-1-carboxylate 2,2,2-trifluoroacetate (130 mg, 0.17 mmol, 1 eq) in DMF (0.5 mL). A solution of 1,4-diisocyanatobutane (9.5 mg, 0.067 mmol, 0.4 eq) in DMF (0.1 mL) was added. The reaction mixture was stirred for 20 min at rt—complete by LCMS. The reaction mixture was concentrated under vacuum and the residue purified by silica gel chromatography DCM:85DCM/15MeOH/5Et$_3$N (0 to 90%). 150 mg of product was collected (not completely dry) as a white solid. LCMS: ret time 3.64 minutes. MS (m/z): [M/2+H]$^+$ 728.4.

Step J: (2R,2'R)-di-tert-Butyl 4,4'-((1S,1'S,2S,2'S)-(((((26-(hydrosulfonylamino)-10,17-dioxo-3,6,21,24-tetraoxa-9,11,16,18-tetraazahexacosyl)amino)sulfonyl)bis(4,1-phenylene))bis(oxy))bis(6-cyano-4-methyl-2,3-dihydro-1H-indene-2,1-diyl))bis(2-methylpiperazine-1-carboxylate) (100 mg, 0.68 mmol) was dissolved in DCM (0.5 mL) then TFA (200µ, 2.61 mmol, 38 eq) was added. The reaction mixture was stirred for 2 h—complete by LCMS. The reaction mixture was concentrated and the residue purified by prep-HPLC with the following conditions: Column, Atlantis Prep T3 OBD, 50*250 mm, 10 um; mobile phase, water (0.1% TFA) and CH$_3$CN (20.0-60.0% CH$_3$CN); Detector, UV 214 nm. 84 mg (72%) was collected as a white solid. LCMS: ret time 2.36 min. MS (m/z): [M+H]$^+$ 628.3. $^1$H NMR (Methanol-d4, 400 MHz) δ 7.85 (d, J=9.0 Hz, 4H), 7.51 (s, 2H), 7.30 (t, J=5.9 Hz, 7H), 6.05-6.00 (m, 2H), 3.72-3.64 (m, 1H), 3.55 (dd, J=6.2, 1.6 Hz, 9H), 3.49 (td, J=5.5, 2.8 Hz, 9H), 3.39-3.30 (m, 5H), 3.20-3.00 (m, 19H), 2.68-2.58 (m, 1H), 2.31 (s, 9H), 1.45 (s, 4H), 1.28 (d, J=6.6 Hz, 6H).

Example 177: 3-(2-{2-[(3S)-3-(4-{[(1S,2S)-6-chloro-4-cyano-2-[(3R)-3-methylpiperazin-1-yl]-2,3-dihydro-1H-inden-1-yl]oxy}(2,3,5,6-$^2$H$_4$)benzenesulfonamido)pyrrolidin-1-yl]ethoxy}ethyl)-1-(4-{[(2-{2-[(3S)-3-(4-{[(1S,2S)-6-chloro-4-cyano-2-[(3R)-3-methylpiperazin-1-yl]-2,3-dihydro-1H-inden-1-yl]oxy}(2,3,5,6-$^2$H$_4$)benzenesulfonamido)pyrrolidin-1-yl]ethoxy}ethyl)carbamoyl]amino}(1,1,2,2,3,3,4,4-$^2$H$_8$)butyl)urea

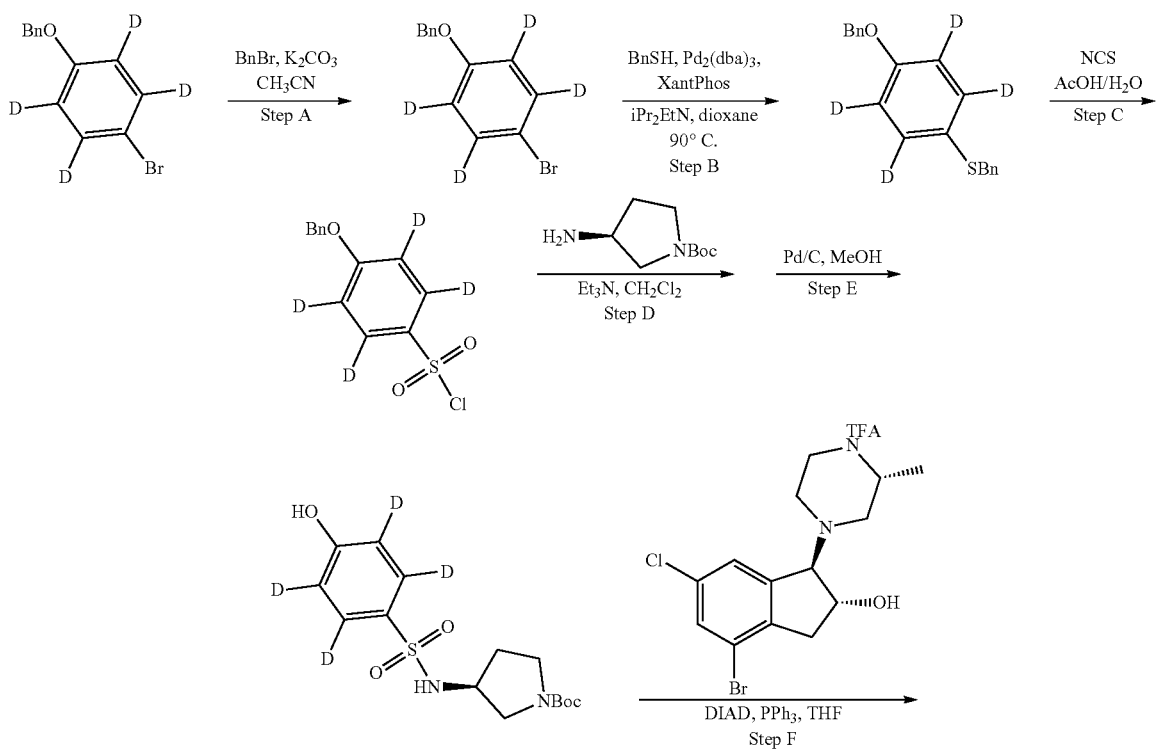

463 -continued 464
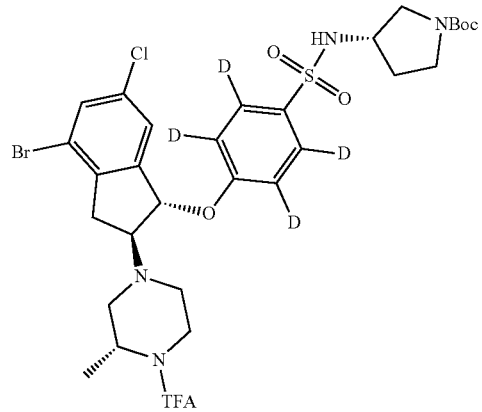
Zn(CN)₂, Pd₂(dba)₃, dppf,
dioxane, H₂O
80° C.
Step G
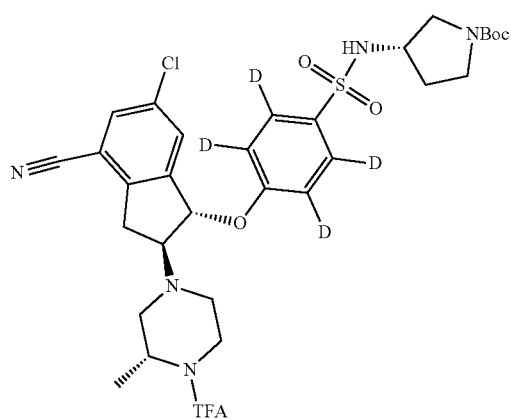
TFA, CH₂Cl₂
Step H
BocHN-CH₂CH₂-O-CH₂CH₂-OTs
K₂CO₃, CH₃CN, 50° C.
Step I
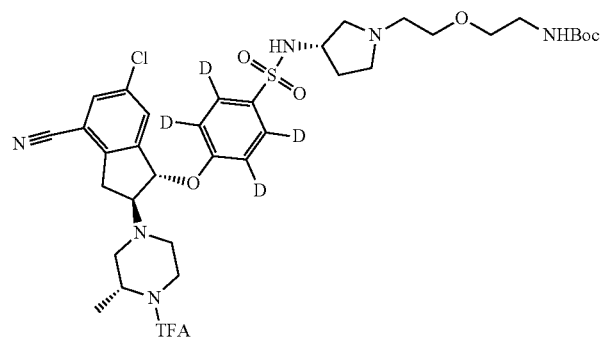
TFA, CH₂Cl₂
Step J
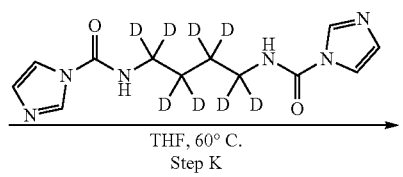
THF, 60° C.
Step K
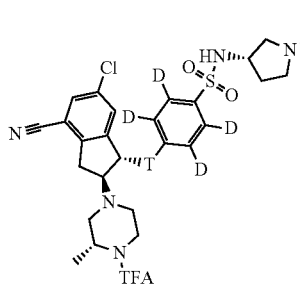
3M NaOH(aq)
THF/MeOH
Step L

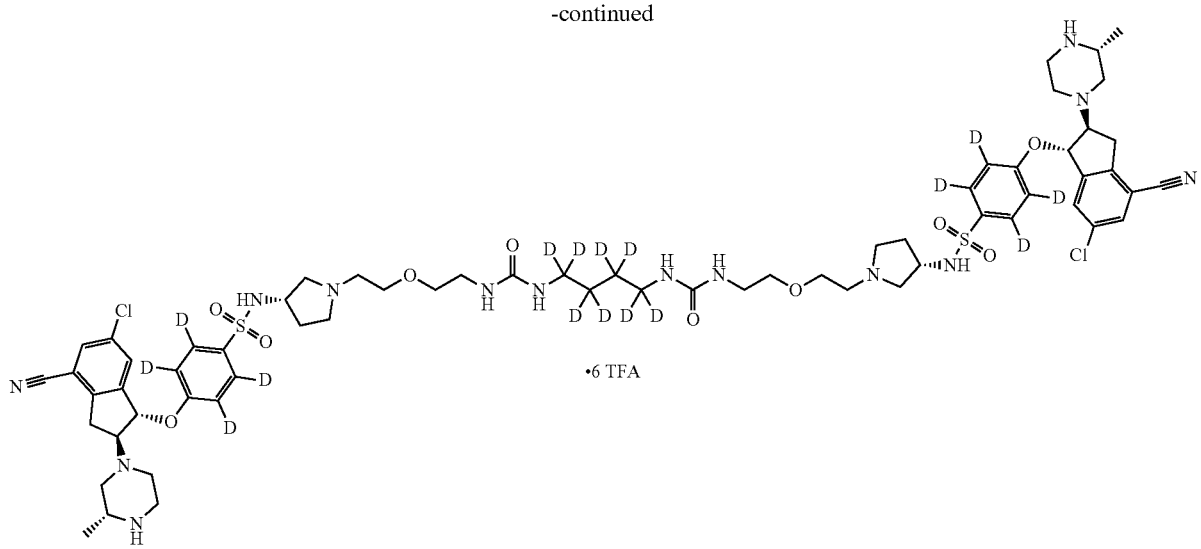

Step A: 4-Bromophenol-2,3,5,6-$d_4$ (300 mg, 1.69 mmol, 1 eq) was dissolved in acetonitrile (5 mL). Powdered potassium carbonate (0.39 g, 2.8 mmol, 1.6 eq) was added while stirring, followed by dropwise addition of benzyl bromide (0.24 mL, 2.0 mmol, 1.2 eq). The mixture was vigorously stirred under nitrogen over weekend (after 6 h ~90% conversion). The reaction mixture was filtered and filtrates concentrated under vacuum to afford crude product as a white solid, used for in next step without purification. LCMS: ret. time 3.52 min, no ionization.

Step B: Crude 1-(benzyloxy)-4-bromobenzene-2,3,5,6-$d_4$ (450 mg, 1.69 mmol, 1 eq), $Pd_2(dba)_3$ (38.4 mg, 0.042 mmol, 0.025 eq), and xantphos (48.6 mg, 0.084 mmol, 0.05 eq) were dissolved in dioxane (6.7 mL) and $iPr_2EtN$ (0.58 mL, 3.38 mmol, 2 eq). The solution was degassed with $N_2$, the vial sealed, and BnSH (0.2 mL, 1.69 mmol, 1 eq) added. The reaction mixture was stirred at 90° C. for 5 h, concentrated under vacuum, and the residue purified by silica gel column with hexane:EtOAc (0 to 10%) to afford 310 mg (60%) of product as a white solid. LCMS: ret time 3.84 min. MS (m/z): [M+H]$^+$ 311.5.

Step C: Benzyl(4-(benzyloxy)phenyl-2,3,5,6-$d_4$)sulfane (310 mg, 1 mmol, 1 eq) was suspended in AcOR/$H_2O$ (7.5:2.5 mL). NCS (399 mg, 3 mmol, 3 eq) was added and reaction mixture stirred at rt for 2 h—complete by LCMS. The reaction mixture was diluted in EtOAc (50 mL) and washed with sat NaHCO$_3$ (2×15 mL), brine (20 mL). The organic phase was dried over $Na_2SO_4$, filtered, and concentrated to afford crude product (286 mg, theoretical) as a white solid. The material was used for the next step without purification. LCMS ret time 3.34 min, no ionization.

Step D: To a solution of crude 4-(benzyloxy)benzenesulfonyl chloride-2,3,5,6-$d_4$ (theoretical 0.29 g, 1.0 mmol) in DCM (2 mL) was added solution of (S)-tert-butyl 3-aminopyrrolidine-1-carboxylate (0.23 g, 1.2 mmol, 1.2 equiv) in DCM (1 mL) then $Et_3N$ (0.17 mL, 1.2 mmol, 1.2 eq) was added. The reaction mixture was stirred at rt for 20 minutes—complete by LC/MS. The reaction mixture was concentrated under vacuum and the residue purified by silica gel chromatography with hexane:EtOAc (0 to 50%) to afford 320 mg (73%) of product as a white solid. LCMS: retention time 3.14 minutes. MS (m/z): [M+Na]$^+$ 459.1.

Step E: tert-Butyl (S)-3-((4-(benzyloxy)phenyl)sulfonamido-2,3,5,6-$d_4$)pyrrolidine-1-carboxylate (320 mg, 0.73 mmol) and Pd (10% on carbon, 50% wet, 100 mg, 0.05 mmol) were mixed in MeOH (3.7 mL). Vac/$H_2$ cycles were performed and the reaction slurry was stirred under $H_2$ at room temperature for 2.5 h—complete by LCMS. The reaction mixture was filtered through a pad of Celite 545, and eluted with EtOAc. The filtrate was concentrated to afford 250 mg (99%) of product as a white foam. LCMS: ret time 2.09 min. MS (m/z): [M+Na]$^+$ 369.1.

Step F: 1-((R)-4-((1R,2R)-4-Bromo-6-chloro-2-hydroxy-2,3-dihydro-1H-inden-1-yl)-2-methylpiperazin-1-yl)-2,2,2-trifluoroethanone (289 mg, 0.66 mmol, 1 eq), boc-(S)-3-((4-hydroxyphenyl)sulfonamido-2,3,5,6-$d_4$)pyrrolidine (250 mg, 0.72 mmol, 1.1 eq) and triphenylphosphine (257 mg. 0.98 mmol, 1.5 eq) were mixed in THF (2.0 mL) and stirred at 40° C. for 15 minutes under $N_2$. A solution of DIAD (0.2 mL, 1.07 mmol, 1.6 eq) in THF (0.7 mL) was added dropwise within 5 minutes. The reaction mixture was stirred for 10 min—complete by LCMS. The reaction mixture was concentrated under vacuum and the residue purified by silica gel chromatography with hexane:EtOAc (0 to 50%) affording 290 mg (58%) of product as a white foam. LCMS: ret time 4.05 min. MS (m/z): [M+H]$^+$ 769.15.

Step G: The bromide (270 mg, 0.35 mmol, 1 eq), $Zn(CN)_2$ (23 mg, 0.19 mmol, 0.55 eq), Zn (~4 mg), $Pd_2(dba)_3$ (96 mg, 0.1 mmol, 0.3 eq), and dppf (116 mg, 0.21 mmol, 0.6 eq) were dissolved in 3:1 dioxane:$H_2O$ (3.5 mL) and the reaction mixture stirred at 80° C. under $N_2$ for 2.5 h—complete by LCMS. The reaction mixture was diluted in EtOAc (40 mL) and washed with brine (15 mL). The organic phase was dried over $Na_2SO_4$, filtered, concentrated, and the residue purified by silica gel column with hexane:EtOAc (0 to 60%) affording 205 mg (82%) of product as an orange foam.

Step H: TFA (0.2 mL, 2.61 mmol, 9.3 equiv) was added to a solution of (S)-tert-butyl 3-(4-(((1S,2S)-4-chloro-6-cyano-1-((R)-3-methyl-4-(2,2,2-trifluoroacetyl)piperazin-1-yl)-2,3-dihydro-1H-inden-2-yl)oxy)phenyl-$d_4$-sulfonamido)pyrrolidine-1-carboxylate (0.2 g, 0.28 mmol) in DCM (1.4 mL). The reaction mixture was stirred at rt for 16 h—complete by LCMS. The reaction mixture was concentrated under vacuum and the residue purified by prep-HPLC with the following conditions: Column, Atlantis Prep T3 OBD, 50*250 mm, 10 um; mobile phase, water (0.1% TFA) and CH$_3$CN (30.0% CH$_3$CN up to 70.0% in 50 min); Detector, UV 214 nm. Product eluted 58% MeCN. MeCN removed under vacuum, the aq phase neutralized with solid NaHCO$_3$ and extracted with EtOAc (3×25 mL). Organic phases dried over Na$_2$SO$_4$, filtered and concentrated to afford 136 mg (80%) of product. LCMS: ret time 2.61 min. MS (m/z): [M+H]$^+$ 616.2.

Step I: 2-(2-((tert-Butoxycarbonyl)amino)ethoxy)ethyl 4-methylbenzenesulfonate (102 mg, 0.29 mmol, 1.3 eq), 4-(((1S,2S)-4-chloro-6-cyano-1-((R)-3-methyl-4-(2,2,2-trifluoroacetyl)piperazin-1-yl)-2,3-dihydro-1H-inden-2-yl)oxy)-N—((S)-pyrrolidin-3-yl)benzene-d$_4$-sulfonamide (136 mg, 0.22 mmol), and K$_2$CO$_3$ (61 mg, 0.44 mmol. 2 eq) were mixed in MeCN (1.7 mL) and stirred at 50° C. for 20 h—complete consumption of amine by LCMS. The reaction mixture was diluted with EtOAc, filtered, and concentrated under vacuum. The residue was purified by silica gel chromatography with hexane:EtOAc (50 to 80%) then with DCM:MeOH (0 to 6%) providing 128 mg (73%) of product as a white solid. LCMS: ret time 3.0 min, MS (m/z): [M+H]$^{30}$ 803.3.

Step TFA (100 μL, 1.27 mmol, 8 eq) was added to a solution of tert-butyl. (2-(2-((S)-3-((4-(((1S,2S)-6-chloro-4-cyano-2-((R)-3-methyl-4-(2,2,2-trifluoroacetyl)piperazin-1-yl)-2,3-dihydro-1H-inden-1-yl)oxy)phenyl)sulfonamido-2,3,5,6-d$_4$)pyrrolidin-1-yl)ethoxy)ethyl)carbamate (1.28 mg, 0.16 mmol) in DCM (1 mL). The reaction mixture was stirred at rt for 5 h—complete by LCMS. The reaction mixture was concentrated. The residue was dissolved in water (3 mL), neutralized with solid NaHCO$_3$, and extracted with 9:1 CHCl$_3$:IPA (3×5 mL). The combined organics were washed with brine, dried over Na$_2$SO$_4$, filtered, and concentrated under vacuum to afford 108 mg (97%) of product as a white foam. LCMS: retention time 2.27 minutes. MS (m z): [M+H]$^+$ 703.3.

Step K: Butane-1,4-diamine dihydrochloride (300 mg, 1.86 mmol) and CDI (930 mg, 5.7 mmol, 3 eq) were dissolved in MeCN (3.5 mL, 0.5M) and suspension was cooled to 0° C., then diisopropylethylamine (0.97 mL, 5.6 mmol, 3 eq) was added. The reaction mixture was allowed to warm to rt and stirred for 1.5 h. The reaction mixture was quenched with H$_2$O (2 mL) and filtered, the solids washed with 4:1 MeCN:H$_2$O (3 mL) then with MeCN (4×2 mL), dried under vacuum to provide 400 mg (78%) of product as a white solid.

N—((S)-1-(2-(2-aminoethoxy)ethyl)pyrrolidin-3-yl)-4-(((1S,2S)-6-chloro-4-cyano-2-((R)-3-methyl-4-(2,2,2-trifluoroacetyl)piperazin-1-yl)-2,3-dihydro-1H-inden-1-yl)oxy)benzene-d$_4$-sulfonamide (100 mg, 0.14 mmol, 2.2 eq) and N,N'-(butane-d$_8$-1,4-diyl)bis(1H-imidazole-1-carboxamide) (18.3 mg, 0.065 mmol) were mixed in THF (0.6 mL) and stirred at 60° C. for 1.5 h—complete by LCMS. The reaction mixture was concentrated under vacuum and the residue purified by silica gel column DCM: 85/15/5 DCM/MeOH/Et$_3$N (0 to 70%) to afford product as a tan foam. LCMS: ret time 3.13 min. MS (m/z): [M/2+H]$^+$ 777.3.

Step L: Sodium hydroxide (3 M NaOH(aq), 100 μL, 0.3 mmol, 4.7 eq) was added to a solution of protected dimer (100 mg, 0.065 mmol) in THF:MeOH (0.38:0.26 mL). The reaction mixture was stirred for 1 h (LCMS showed only sm). Additional 3M aq NaOH (200 μL, 0.6 mmol, 9.4 eq) was added to the reaction mixture in 2 portions within 1 hour at which point the reaction complete by LCMS. The reaction mixture was neutralized with 4 N HCl (0.3 mL, 1.2 mmol, 1.3 eq relative to NaOH), the volatiles removed under vacuum, and the residue purified by prep-HPLC with the following conditions: Column, Atlantis Prep T3 OBD, 50*250 mm, 10 um; mobile phase, water (0.1% TFA) and CH$_3$CN (25.0% CH$_3$CN up to 60.0% in 50 min); Detector, UV 214 nm. Lyophilization provided 64 mg (73%) of the title compound as a white solid. LCMS: ret time 1.95 min. MS (m/z): 681.3 [M/2+H]$^+$. $^1$H NMR (Methanol-d4, 400 MHz) δ 7.77 (d, J=1.9 Hz, 2H), 7.44 (d, J=0.9 Hz, 2H), 6.08 (d, J=5.9 Hz, 2H), 3.74 (t, J=4.9 Hz, 13H), 3.52 (t, J=5.4 Hz, 6H), 3.23-2.97 (m, 9H), 2.63 (t, J=12.0 Hz, 1H), 2.34 (t, J=9.8 Hz, 2H), 1.28 (d, J=6.6 Hz, 6H).

Example 178: 3-(2-{2-[(3S)-3-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]ethoxy}ethyl)-1-(4-{[(2-{2-[(3S)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]ethoxy}ethyl)carbamoyl]amino}(1,1,2,2,3,3,4,4-$^2$H$_8$)butyl)urea

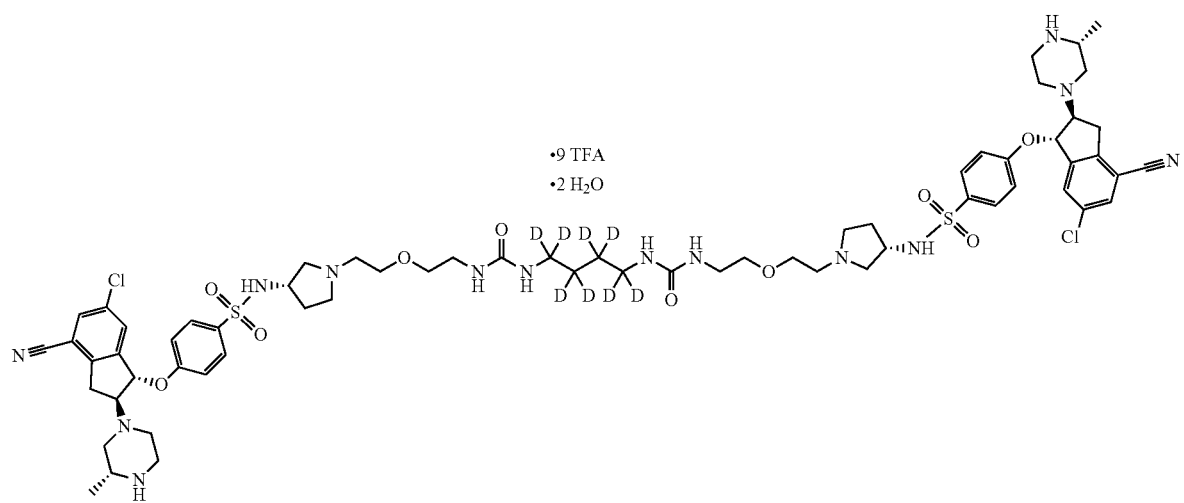 [SMILES: [2H]C([2H])(NC(=O)NCCOCCN1CC[C@H](NS(=O)(=O)c2ccc(O[C@H]3c4cc(Cl)cc(C#N)c4C[C@@H]3N3CCN[C@H](C)C3)cc2)C1)C([2H])([2H])C([2H])([2H])C([2H])([2H])NC(=O)NCCOCCN1CC[C@H](NS(=O)(=O)c2ccc(O[C@H]3c4cc(Cl)cc(C#N)c4C[C@@H]3N3CCN[C@H](C)C3)cc2)C1]

The title compound was prepared from INT-M5E utilizing the same procedures in Example 177. LCMS: ret time 1.9 min. MS (m/z) [M/3+H]$^+$ 452.1. $^1$H NMR (Methanol-d4, 400 MHz) δ 7.89 (d, J=8.9 Hz, 4H), 7.79-7.76 (m, 2H), 7.47-7.41 (m, 2H), 7.35 (d, J=9.0 Hz, 5H), 6.11-6.04 (m, 2H), 4.04-3.87 (m, 1H), 3.74 (d, J=4.9 Hz, 9H), 3.52 (s, 4H), 3.14 (s, 15H), 2.68-2.58 (m, 2H), 2.39-2.27 (m, 3H), 2.06-1.88 (m, 2H), 1.28 (d, J=6.6 Hz, 7H).

Example 179: (1S,2S)-1-(4-{[(3S)-1-[2-(2-{[(4-{[(2-{2-[(3S)-3-(4-{[(1S,2S)-4-carboxy-6-chloro-2-[(3R)-3-methylpiperazin-1-yl]-2,3-dihydro-1H-inden-1-yl]oxy}benzenesulfonamido)-1-hydroxy-1λ$^4$-pyrrolidin-1-yl]ethoxy}ethyl)carbamoyl]amino}butyl)carbamoyl]amino}ethoxy)ethyl]-1-hydroxy-1λ$^4$-pyrrolidin-3-yl]sulfamoyl}phenoxy)-6-chloro-2-[(3R)-3-methyl piperazin-1-yl]-2,3-dihydro-1H-indene-4-carboxylic acid

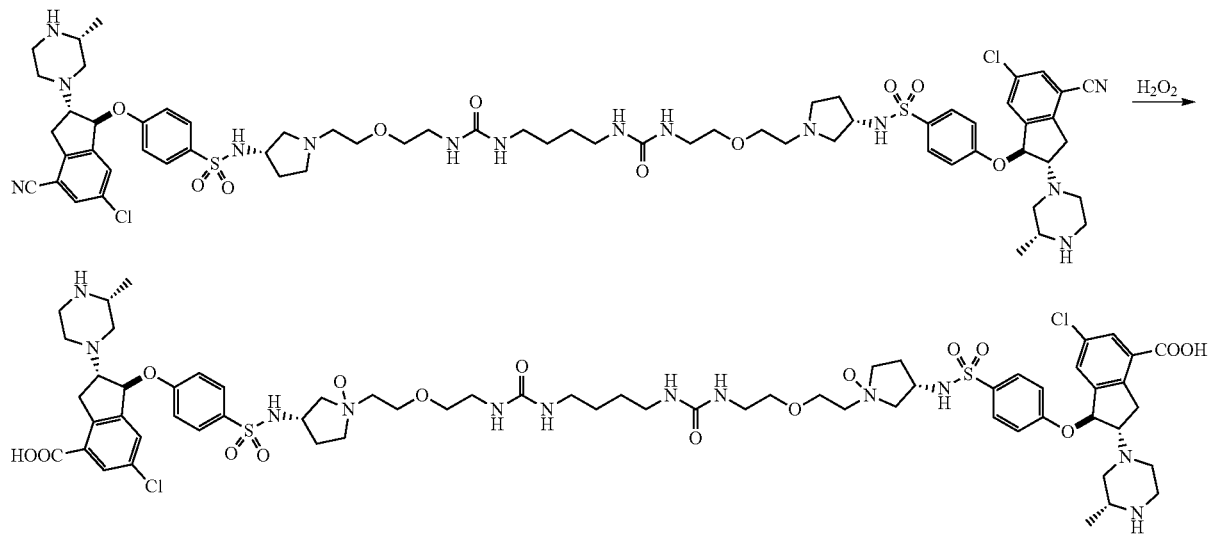

Hydrogen peroxide (3%, 0.1 mL, 87.9 mmol, 2.4 eq) was added to Example 132 (50 mg, 37.1 mmol), followed by water (0.2 mL). The suspension was sonicated for 1 hour. The reaction mixture diluted with 1 M HCl, filtered, and purified by prep-HPLC with the following conditions: Column, Atlantis Prep 13 OBD, 50*250 mm, 10 um; mobile phase, water (0.1% TFA) and CH$_3$CN (25.0% CH$_3$CN up to 50.0% in 50 min); Detector, UV 214 nm. Lyophilization provided the title diacid di-N-oxide (NMR, HPLC), MS (m/z): 708.2 [M/2+H]$^+$, 472.5 [M/3+H]$^+$. $^1$H NMR (Methanol-d4, 400 MHz) δ 7.87-7.72 (m, 3H), 7.59 (s, 2H), 7.25 (dd, J=14.4, 5.5 Hz, 6H), 5.93 (d, J=5.6 Hz, 2H), 4.16 (s, 1H), 4.00-3.75 (m, 14H), 3.02 (s, 12H), 2.54 (s, 1H), 2.40 (s, 1H), 2.23 (s, 1H), 1.39 (s, 3H), 1.25-1.13 (m, 6H).

Example 180: Cell-Based Assay of NHE-3 Activity (Pre-Incubation Inhibition)

Rat and human NHE-3-mediated Na$^+$-dependent H$^+$ antiport was measured using a modification of the pH sensitive dye method originally reported by Paradiso (*Proc. Natl. Acad. Sci. USA*. (1984) 81(23): 7436-7440). PS120 fibroblasts stably expressing human NHE3 and NHERF2 were obtained from Mark Donowitz (Baltimore, Md.). Opossum kidney (OK) cells were obtained from the ATCC and propagated per their instructions. The rat NHE-3 gene (GenBank M85300) was introduced into OK cells via electroporation, and cells were seeded into 96 well plates and grown overnight. Medium was aspirated from the wells then incubated for 30 min at 37° C. with NH$_4$Cl-HEPES buffer (20 mM NH$_4$Cl, 80 mM NaCl, 50 mM HEPES, 5 mM KCl, 2 mM CaCl$_2$, 1 mM MgCl$_2$, pH 7.4) containing 5 μM BCECF-AM. Cells were washed once with Ammonium free, Na$^+$-free HEPES (100 mM choline, 50 mM HEPES, 10 mM glucose, 5 mM KCl, 2 mM CaCl$_2$, 1 mM MgCl$_2$, pH 7.4) and incubated in the same buffer for 10 minutes at room temperature to lower intracellular pH with 0-30 μM test compound. After incubation, NHE-3-mediated recovery of neutral intracellular pH was initiated by addition of Na-HEPES buffer containing 0.4 μM ethyl isopropyl amiloride (EIPA, a selective antagonist of NHE-1 activity that does not inhibit NHE-3). Changes in intracellular pH were monitored using a FLIPR Tetra® (Molecular Devices, Sunnyvale, Calif.) by excitation at λ$_{ex}$ 439 to 505 nm, and measuring BCECF fluorescence at λ$_{em}$ 538 nm. The initial rate of the fluorescence ratio change was used as a measure of NHE-mediated Na$^+$/H$^+$ activity, and reported as the change in fluorescence ratio per minute. Initial rates were plotted as the average of 2 or more replicates, and pIC$_{50}$ values were estimated using GraphPad Prism.

TABLE 2

Data for example in human Preincubation assay:

| Result | pIC$_{50}$ Range | % inhibition range |
|---|---|---|
| A | NHE3 pIC$_{50}$ < 6 | NHE3 < 40% |
| B | NHE3 pIC$_{50}$ 6-7 | 40-70% |
| C | NHE3 pIC$_{50}$ > 7 | >70% |

| | human Preincubation | |
|---|---|---|
| Example | pIC50 | % Inhibition |
| 1 | C | C |
| 2 | C | C |
| 3 | C | C |
| 4 | C | B |

TABLE 2-continued

Data for example in human Preincubation assay:

| | | |
|---|---|---|
| 5 | C | B |
| 6 | A | A |
| 7 | C | C |
| 8 | A | A |
| 9 | C | A |
| 10 | C | B |
| 11 | C | C |
| 12 | C | A |
| 13 | A | A |
| 14 | A | B |
| 15 | B | C |
| 16 | C | B |
| 17 | C | C |
| 18 | C | B |
| 19 | A | A |
| 20 | A | A |
| 21 | C | A |
| 22 | C | C |
| 23 | C | C |
| 24 | C | C |
| 25 | C | C |
| 26 | C | C |
| 27 | C | C |
| 28 | C | C |
| 29 | C | C |
| 30 | C | C |
| 31 | C | C |
| 32 | C | C |
| 33 | C | C |
| 34 | C | C |
| 35 | C | C |
| 36 | C | C |
| 37 | C | B |
| 38 | A | A |
| 39 | C | A |
| 40 | A | A |
| 41 | C | C |
| 42 | C | C |
| 43 | C | C |
| 44 | C | C |
| 45 | C | C |
| 46 | C | C |
| 47 | C | C |
| 48 | B | B |
| 49 | B | C |
| 50 | C | B |
| 51 | C | B |
| 52 | C | C |
| 53 | C | C |
| 54 | C | C |
| 55 | C | C |
| 56 | C | C |
| 57 | C | C |
| 58 | C | C |
| 59 | C | C |
| 60 | C | C |
| 61 | C | C |
| 62 | C | C |
| 63 | C | B |
| 64 | A | A |
| 65 | A | A |
| 66 | A | A |
| 67 | B | C |
| 68 | C | C |
| 69 | C | C |
| 70 | C | C |
| 71 | A | B |
| 72 | C | C |
| 73 | B | C |
| 74 | A | C |
| 75 | B | B |
| 76 | C | C |
| 77 | A | C |
| 78 | C | C |
| 79 | C | C |
| 80 | B | B |
| 81 | C | C |
| 82 | C | B |
| 83 | C | C |
| 84 | C | C |
| 85 | C | C |
| 86 | C | C |
| 87 | C | C |
| 88 | C | C |
| 89 | C | C |
| 90 | C | C |
| 91 | C | C |
| 92 | C | C |
| 93 | C | C |
| 94 | C | C |
| 95 | C | C |
| 96 | C | C |
| 97 | C | C |
| 98 | C | C |
| 99 | C | C |
| 100 | C | C |
| 101 | C | C |
| 102 | C | C |
| 103 | C | C |
| 104 | C | C |
| 105 | C | C |
| 106 | C | C |
| 107 | C | C |
| 108 | C | C |
| 109 | C | C |
| 110 | C | C |
| 111 | C | C |
| 112 | C | C |
| 113 | C | C |
| 114 | C | C |
| 115 | C | C |
| 120 | C | C |
| 121 | C | B |
| 122 | C | C |
| 123 | C | C |
| 124 | C | C |
| 126 | C | C |
| 127 | C | C |
| 128 | A | A |
| 129 | A | A |
| 130 | C | B |
| 131 | C | C |
| 132 | C | C |
| 133 | C | C |
| 134 | C | C |
| 135 | C | C |
| 136 | C | C |
| 137 | C | C |
| 142 | C | C |
| 143 | C | C |
| 146 | C | C |
| 154 | C | C |

Example 181: Cell-Based Assay of NHE-3 Activity
(Persistent Inhibition)

The ability of compounds to inhibit human and rat NHE-3-mediated $Na^+$ dependent $H^+$ antiport after application and washout was measured using a modification of the pH sensitive dye method described above. PS120 fibroblasts stably expressing human NHE3 and NHERF2 were obtained from Mark Donowitz (Baltimore, Md.). Opossum kidney (OK) cells were obtained from the ATCC and propagated per their instructions. The rat NHE-3 gene was introduced into OK cells via electroporation, and cells were seeded into 96 well plates and grown overnight. Medium was aspirated from the wells, cells were washed once with NaCl-HEPES buffer (100 mM NaCl, 50 mM HEPES, 10 mM glucose, 5 mM KCl, 2 mM $CaCl_2$, 1 mM $MgCl_2$, pH 7.4), then overlayed with NaCl-HEPES buffer containing 0-30 µM test compound. After a 60 min incubation at room temperature, the test drug containing buffer was aspirated from the cells. Following aspiration, cells were washed once with NaCl-HEPES buffer without drug, then incubated for 30 min at 37° C. with NH$_4$Cl-HEPES buffer (20 mM NH$_4$Cl, 80 mM NaCl, 50 mM HEPES, 5 mM KCl, 2 mM CaCl$_2$, 1 mM MgCl$_2$, pH 7.4) containing 5 μM BCECF-AM. Cells were washed once with Ammonium free, Na$^+$-free HEPES (100 mM choline, 50 mM HEPES, 10 mM glucose, 5 mM KCl, 2 mM CaCl$_2$, 1 mM MgCl$_2$, pH 7.4) and incubated in the same buffer for 10 minutes at room temperature to lower intracellular pH. NHE-3-mediated recovery of neutral intracellular pH was initiated (10 min after compound washout) by addition of Na-HEPES buffer. For the rat NHE3 assay, the Na-HEPES buffer contained 0.4 ethyl isopropyl amiloride (EIPA, a selective antagonist of NHE-1 activity that does not inhibit NHE-3). Changes in intracellular pH were monitored using a FLIPR Tetra® (Molecular Devices, Sunnyvale, Calif.) by excitation at $\lambda_{ex}$ 439 to 505 nm, and measuring BCECF fluorescence at $\lambda_{em}$ 538 nm. The initial rate of the fluorescence ratio change was used as a measure of NHE-mediated Na$^+$/H$^+$ activity, and reported as the change in fluorescence ratio per minute. Initial rates were plotted as the average of 2 or more replicates, and pIC$_{50}$ values were estimated using GraphPad Prism.

TABLE 3

Data for example in human Persistence assay:

| Result | pIC$_{50}$ Range | % inhibition range |
|---|---|---|
| A | NHE3 pIC$_{50}$ < 6 | NHE3 < 40% |
| B | NHE3 pIC$_{50}$ 6-7 | 40-70% |
| C | NHE3 pIC$_{50}$ > 7 | >70% |

| | human Persistence | |
|---|---|---|
| Example | pIC50 | % inhibition |
| 1 | C | B |
| 2 | C | C |
| 3 | C | C |
| 4 | C | B |
| 5 | C | C |
| 6 | A | A |
| 7 | C | C |
| 8 | A | A |
| 9 | B | B |
| 10 | C | C |
| 11 | C | C |
| 12 | B | B |
| 13 | A | A |
| 14 | A | A |
| 15 | A | A |
| 16 | C | B |
| 17 | C | C |
| 18 | C | B |
| 19 | A | A |
| 20 | A | A |
| 21 | A | C |
| 22 | C | C |
| 23 | C | C |
| 24 | C | C |
| 25 | C | C |
| 26 | C | C |
| 27 | C | C |
| 28 | C | C |
| 29 | C | C |
| 30 | C | C |
| 31 | C | C |
| 32 | C | C |
| 33 | C | C |
| 34 | C | C |
| 35 | C | C |
| 36 | C | C |
| 37 | C | B |
| 38 | A | A |
| 39 | C | A |
| 40 | A | A |
| 41 | C | C |
| 42 | C | C |
| 43 | C | C |
| 44 | B | C |
| 45 | C | C |
| 46 | C | C |
| 47 | C | C |
| 48 | B | C |
| 49 | C | C |
| 50 | C | B |
| 51 | C | B |
| 52 | C | C |
| 53 | C | C |
| 54 | C | B |
| 55 | C | C |
| 56 | C | C |
| 57 | C | C |
| 58 | C | C |
| 59 | C | C |
| 60 | C | C |
| 61 | C | C |
| 62 | A | A |
| 63 | B | B |
| 64 | A | A |
| 65 | A | A |
| 66 | A | A |
| 67 | B | B |
| 68 | C | C |
| 69 | B | C |
| 70 | C | C |
| 71 | A | B |
| 72 | B | C |
| 73 | A | B |
| 74 | A | A |
| 75 | A | A |
| 76 | A | A |
| 77 | A | A |
| 78 | C | C |
| 79 | B | C |
| 80 | B | B |
| 81 | B | C |
| 82 | B | C |
| 83 | B | C |
| 84 | C | C |
| 85 | C | C |
| 86 | C | C |
| 87 | C | C |
| 88 | C | C |
| 89 | C | C |
| 90 | B | C |
| 91 | C | C |
| 92 | C | C |
| 93 | C | C |
| 94 | C | C |
| 95 | C | C |
| 96 | C | C |
| 97 | C | C |
| 98 | C | C |
| 99 | B | C |
| 100 | C | C |
| 101 | C | B |
| 102 | C | C |
| 103 | C | C |
| 104 | C | C |
| 105 | C | C |
| 106 | C | C |
| 107 | C | C |
| 108 | C | C |
| 109 | C | C |
| 110 | C | C |
| 111 | C | C |
| 112 | C | C |
| 113 | C | C |

TABLE 3-continued

Data for example in human Persistence assay:

| | | |
|---|---|---|
| 114 | C | C |
| 115 | C | C |
| 120 | C | C |
| 121 | C | A |
| 122 | C | C |
| 123 | C | C |
| 124 | B | C |
| 126 | C | B |
| 127 | C | A |
| 128 | C | A |
| 129 | C | A |
| 130 | B | C |
| 131 | B | C |
| 132 | C | C |
| 133 | C | C |
| 134 | C | C |
| 135 | C | C |
| 136 | C | C |
| 137 | C | C |
| 142 | C | C |
| 143 | C | C |
| 146 | C | A |
| 154 | C | C |

Example 182: Sustained Inhibition of Apical Acid Secretion in Human Organoid Monolayer Cell Cultures Basal media (BM) consisted of advanced DMEM/F12 containing 10 mM HEPES Invitrogen, 15630-080), 1:100 Glutamax (Invitrogen, 35050-061), and 1:100 penicillin/streptomycin (Invitrogen, 15140-122). Supplemented basal media (SBM) contained 1:100 N2 (Invitrogen, 17502-048), 1:50 B27 (Invitrogen, 12587-010), 1 mM N-acetylcysteine (Sigma, A9165), and 10 nM [Leu15]-gastrin I (Sigma, G9145). Growth factors used included 50 ng per mL mouse EGF (Peprotech, 315-09), 100 ng per mL mouse noggin (Peprotech, 250-38), 500 ng per mL human R-spondin 1 (R&D, 4645-RS), 100 ng per mL mouse Wnt-3a (R&D, 1324-WN), 20 µM. Y-27632 (Tocris, 1254), 10 mM nicotinamide (Sigma, N0636), 500 nM A83-01 (Tocris, 2939), 10 µM SB202190 (Tocris, 1264). Transwells were 0.4 µm pore polyester membrane 24-well Transwell inserts (Corning). Cultures were incubated at 37° C. in 5% $CO_2$.

Human ileum organoids were cultured in WENRNAS (Wnt, EGF, noggin, R-spondin1, Nicotinamide, A83-01, SB202190) and typically grown for 7-12 days before being used to plate monolayer cultures. On day 0, organoid cultures embedded in Matrigel were treated with TrypLE Express to break organoids into small pieces and/or single cells. The cells were resuspended to $0.5 \times 10^6$ cells/mL in SBM containing WENRAY (Wnt, EGF, noggin, R-spondin1, A83-01, Y-27632). Following this step, 200 µL of cell suspension was plated into the apical side of a 24-well Transwell (100,000 cells/well) and 600 µL of SBM with WENRAY was added to the basolateral side. Ileum cells were differentiated with ENRA (EGF, noggin, R-spondin 1, A83-01) on day 3. The color of apical compartment turns from pink or orange to yellow due to the increase in NHE3 expression after differentiation.

Each human ileum monolayer culture well was washed twice with fresh SBM on the apical side on day 6 before compound dosing. All compound stocks were 10 mM dissolved in DMSO. Each compound stock was individually mixed with fresh SBM to reach final compound concentration 1 µM and dosed only on the apical side of the monolayer (total volume 200 µl). DMSO at the equivalent concentration was used as the vehicle control. Duplicate wells were dosed for each compound. On day 8, apical media pH was measured by pH electrode, to determine the ability of example compounds to produce sustained inhibition of NHE3 activity in a human monolayer culture system by preventing proton secretion into the apical compartment. Each of the duplicate apical pH values for each example compound was compared to the average of the DMSO wells and expressed as a percent inhibition of apical acid secretion.

TABLE 4

| Result | % Inhibition (GI Segment) |
|---|---|
| A | <50% |
| B | 50-70% |
| C | >70% |

| Example | % inhibition (ileum) | % inhibition (duodenum) |
|---|---|---|
| 17 | B | B |
| 23 | B | B |
| 24 | A | B |
| 26 | B | B |
| 28 | B | B |
| 29 | C | C |
| 31 | C | C |
| 32 | C | C |
| 33 | C | C |
| 34 | B | B |
| 35 | C | C |
| 36 | C | C |
| 41 | B | C |
| 42 | C | C |
| 43 | B | C |
| 45 | B | C |
| 49 | C | C |
| 52 | C | C |
| 55 | A | B |
| 78 | C | C |
| 91 | B | C |
| 105 | C | C |
| 106 | C | C |
| 107 | C | C |
| 109 | C | C |
| 110 | C | C |
| 115 | C | C |
| 122 | C | C |
| 123 | C | C |
| 126 | A | A |

Example 183: Increased Trans-Epithelial Resistance in Human Organoid Monolayer Cell Cultures Basal media (B consisted of advanced DMEM/F12 containing 10 mM HEPES (Invitrogen, 15630-080), 1:100 Glutamax (Invitrogen, 35050-061), and 1:100 penicillin/streptomycin (Invitrogen, 15140-122). Supplemented basal media (SBM) contained 1:100 N2 (Invitrogen, 17502-048), 1:50 B27 (Invitrogen, 12587-010), 1 mM N-acetylcysteine (Sigma, A9165), and 10 nM [Leu15]-gastrin I (Sigma, G9145). Growth factors used included 50 ng per mL mouse EGF (Peprotech, 315-09), 100 ng per mL mouse noggin (Peprotech, 250-38), 500 ng per mL human R-spondin 1 (R&D, 4645-RS), 100 ng per mL mouse Wnt-3a (R&D, 1324-WN), 20 µM Y-27632 (Tocris, 1254), 10 mM nicotinamide (Sigma, N0636), 500 nM A83-01 (Tocris, 2939), 10 µM SB202190 (Tocris, 1264). Transwells were 0.4 µm pore polyester membrane 24-well Transwell inserts (Corning). Cultures were incubated at 37° C. in 5% $CO_2$.

Human duodenum organoids were cultured in WENR-NAS (Wnt, EGF, noggin, R-spondin1, Nicotinamide, A83-01, SB202190) and typically grown for 7-12 days before being used to plate monolayer cultures. On day 0, organoid cultures embedded in Matrigel were treated with TrypLE Express to break organoids into small pieces and/or single cells. The cells were resuspended to $0.5 \times 10^6$ cells/mL in SBM containing WENRAY (Wnt, EGF, noggin, R-spondin1, A83-01, Y-27632). Following this step, 200 μL of cell suspension was plated into the apical side of a 24-well Transwell (100,000 cells/well) and 600 μL of SBM with WENRAY was added to the basolateral side. Duodenum cells were differentiated with ENA (EGF, noggin, A83-01) on day 3. The color of apical compartment turns from pink or orange to yellow due to the increase in NHE3 expression after differentiation.

Each human duodenum monolayer culture well was washed twice with fresh SBM on the apical side on day 6 or day 7 before dosing. All compound stocks were 10 mM dissolved DMSO. Each compound stock was individually mixed with fresh SBM to reach final compound concentration 1 μM and dosed only on the apical side of the monolayer (total volume 200 μl). DMSO at the equivalent concentration was used as the vehicle control. Duplicate wells were dosed for each compound. Transepithelial electrical resistance (TEER) was used as a quantitative technique to measure of tight junction permeability. TEER values were recorded (MERS00002, Millipore) before dosing and 30 mins and 1 hr after dosing for all wells. Each of the duplicate TEER values following treatment were corrected for the individual well baseline TEER. Baseline corrected TEER for each example compound was compared to the average of the DMSO wells and expressed as a percent TEER of vehicle control.

TABLE 5

| Result | TEER (% of vehicle) |
|---|---|
| A | <100% |
| B | 100-130% |
| C | >130% |

| Example | TEER at 30 minutes (% of Vehicle) | TEER at 60 minutes (% of Vehicle) |
|---|---|---|
| 17 | B | B |
| 24 | B | B |
| 30 | B | B |
| 31 | B | C |
| 32 | B | C |
| 33 | B | C |
| 41 | B | B |
| 42 | B | C |
| 43 | B | B |
| 91 | B | B |
| 105 | C | C |
| 106 | C | C |
| 107 | C | B |
| 110 | C | B |
| 115 | B | B |
| 126 | B | B |

Example 184: Inhibition of Intestinal Sodium Absorption in Mice

Urinary and fecal sodium excretions were measured to assess the ability of selected example compounds to inhibit the absorption of sodium from the intestinal lumen. In addition, an assessment of the absence or presence of diarrhea in response to compound treatment was made. Approximately eight-week old, male, CD-1 mice were purchased from Envigo (Livermore, Calif.), were housed 6 per cage and acclimated for at least 48 hours before study initiation. Animals were fed Harlan Teklad Global TD.160470 rodent chow (Madison, Wis.), standard laboratory rodent chow Harlan Teklad Global 2018 with the addition of 0.4% inorganic phosphorous. Animals had ad libitum access to food and water for the duration of the study and were maintained in a temperature and humidity controlled room on a standard light/dark cycle of 6 AM to 6 PM. To initiate the study, mice were weighed and then individually placed in metabolic cages. Following a 3-day acclimation period to the metabolic cage, a 24-hr baseline collection of urine and feces was performed. Mice (n=8/group) were then dosed by oral gavage with test compound (15 mg/kg) or vehicle (3 mM HCl, 0.01% Tween80) at a dose volume of 5 mL/kg, twice daily at 6 AM and 3 PM for 3 consecutive days. Each day, measurements of body weight. 24-hour food intake, water intake, urine volume and wet fecal weight were recorded, along with any observation of diarrhea. Fecal samples were dried using a lyophilizer for at least 3 days, following which dry weight was recorded and fecal fluid content was calculated based on the difference between the wet and dry stool weights. Fecal fluid content on day 3 of compound treatment was calculated as a change from the vehicle group mean. For urine samples, the volumes were determined gravimetrically. Feces and urine were analyzed for sodium content by microwave plasma-atomic emission spectroscopy or ion chromatography, respectively. Urine samples were analyzed on an ion chromatography system (Thermo Fisher ICS-3000 or ICS-5000+) coupled with conductivity detectors. Chromatographic separation of cations was performed using an IonPac CS12A (Thermo Fisher) 2×250 mm analytical column with an isocratic elution using 25 nM methanesulfonic acid. Concentrations were interpolated from a a standard curve (prepared in 10 mM HCl) for sodium ion based on retention time and peak area. Fecal sample analysis by Microwave Plasma Atomic Emission Spectrometry (MP-AES). Dry fecal samples were ground into a fine powder on a homogenizer and the ground samples (400-600 mg aliquots weighed) were digested with nitric acid by microwave method (Mars 6). These digested samples were diluted with 1% Nitric acid and analyzed on Agilent 4100 MP-AES. Concentrations were calculated relative to a standard curve (prepared in 1% Nitric acid) for sodium based on the signal intensity. Sodium was detected at a wavelength of 588.995 nm. Twenty-four-hour urinary sodium excretion (ma/24-hours) was calculated by multiplying urinary sodium concentration by 24-hour urine volume. Twenty-four-hour fecal sodium excretion (mg/24-hours) was calculated by multiplying fecal sodium concentration by 24-hour dry fecal weight. The urinary and fecal sodium excretion on day 3 of compound treatment were normalized to dietary sodium intake and expressed as a percentage of the vehicle mean.

TABLE 6

| Result | Urinary Na Excretion (% of vehicle) | Fecal Na Excretion (% of vehicle) | Fecal fluid content (□ from vehicle) | |
|---|---|---|---|---|
| A | >70% | <150% | <5 | |
| B | 50-70% | 150-200% | 5-10 | |
| C | <50% | >200% | >10 | |

| Example | Urinary Na Excretion (% of vehicle) | Fecal Na Excretion (% of vehicle) | Fecal fluid content (Δ from vehicle) | Diarrhea (±) |
|---|---|---|---|---|
| 17 | B | B | B | — |
| 23 | B | B | B | — |
| 24 | B | C | A | — |
| 26 | B | B | B | — |
| 27 | B | C | C | — |

TABLE 6-continued

| | | | | |
|---|---|---|---|---|
| 28 | A | B | B | — |
| 29 | B | B | A | — |
| 30 | B | C | C | — |
| 31 | B | C | B | — |
| 32 | B | B | A | — |
| 33 | C | C | C | — |
| 34 | B | B | B | — |
| 35 | A | B | A | — |
| 36 | B | B | B | — |
| 41 | C | C | B | — |
| 42 | C | B | B | — |
| 43 | C | C | C | — |
| 45 | A | A | A | — |
| 49 | A | A | A | — |
| 52 | B | C | B | — |
| 53 | A | A | B | — |
| 55 | A | B | B | — |
| 78 | A | A | A | — |
| 88 | B | B | B | — |

Example 185: Inhibition of Intestinal Sodium Absorption in Rats

Urinary sodium excretion and fecal form were measured to assess the ability of selected example compounds to inhibit the absorption of sodium from the intestinal lumen. Eight-week old, male, Sprague Dawley rats were purchased from Envigo (Livermore, Calif.), were housed 2 per cage and acclimated for at least 48 hours before study initiation. Animals were fed. Harlan Teklad Global TD.160470 rodent chow (Madison, Wis.), standard laboratory rodent chow Harlan Teklad Global 2018 with the addition of 0.4% inorganic phosphorous. Animals had ad libitum access to food and water for the duration of the study and were maintained in a temperature and humidity controlled room on a standard light/dark cycle of 6 AM to 6 PM. On the day of study initiation, rats (n=5/group) were dosed by oral gavage with test compound or vehicle (3 mM HCl, 0.01% Tween80) at a dose volume of 5 mg/kg. Immediately after dose administration animals were placed in individual metabolic cages. At 13-hours post-dose, urine samples were collected and fecal form was assessed. In addition, the weight of food consumed over the 13-hour period was measured and recorded. Fecal forms were scored according to a common scale associated with increasing fecal water to the wettest observation in the cage's collection funnel (1, normal pellet; 2, pellet adhering to sides of collection funnel due to moisture; 3, loss of normal pellet shape; 4, complete loss of shape with a blotting pattern; 5, liquid fecal streams evident). Fecal form score (FFS) was calculated for each group as the median of each individual rat's FFS within the group and reported in Table 7. Fecal samples were dried using a lyophilizer for at least 3 days, following which dry weight was recorded and fecal fluid content was calculated based on the difference between the wet and dry stool weights. Fecal fluid content was calculated as a change from the vehicle group mean. For urine samples, the volumes were determined gravimetrically. Urine samples were analyzed on an ion chromatography system (Thermo Fisher ICS-3000 or ICS-5000+) coupled with conductivity detectors. Chromatographic separation of cations was performed using an IonPac CS12A (Thermo Fisher) 2×250 mm analytical column with an isocratic elution using 25 mM methanesulfonic acid. Concentrations were interpolated from a standard curve (prepared in 10 mM HCl) for sodium based on retention time and peak area. Thirteen-s-hour urinary sodium excretion (mg/13-hours) was calculated by multiplying urinary sodium concentration by 13-hour urine volume. The urinary sodium excretion of compound treatment was normalized to dietary sodium intake and expressed as a percentage of the vehicle mean.

TABLE 7

| Result | Urinary Na (% of Vehicle, out/in) |
|---|---|
| A | >70% |
| B | 40-70% |
| C | <40% |

| Example | Dose (mg/kg) | Urinary Na (% of Vehicle, out/in) | FFS (1-5) |
|---|---|---|---|
| 41 | 0.003 | A | 2 |
| 41 | 0.01 | A | 2 |
| 41 | 0.03 | B | 2 |
| 41 | 0.1 | C | 5 |
| 115 | 0.003 | A | 1 |
| 115 | 0.01 | A | 2 |
| 115 | 0.03 | A | 2 |
| 115 | 0.1 | C | 2 |
| 107 | 0.03 | B | 3 |
| 107 | 0.1 | B | 3 |
| 107 | 0.3 | C | 3 |
| 120 | 0.03 | A | 2 |
| 120 | 0.1 | B | 3 |
| 120 | 0.3 | C | 4 |
| 132 | 0.03 | A | 3 |
| 132 | 0.1 | B | 3 |
| 132 | 0.3 | C | 3 |
| 123 | 0.03 | A | 3 |
| 123 | 0.1 | B | 3 |
| 123 | 0.3 | C | 3 |
| 122 | 0.03 | A | 2 |
| 122 | 0.1 | A | 2 |
| 122 | 0.3 | B | 3 |
| 133 | 0.03 | A | 3 |
| 133 | 0.1 | C | 3 |
| 133 | 0.3 | C | 3 |
| 143 | 0.03 | B | 3 |
| 143 | 0.1 | C | 3 |
| 143 | 0.3 | C | 4 |

Example 186: Inhibition of Intestinal Sodium and Phosphorous Absorption in the Rat Balance Model Urinary and fecal sodium excretion, along with urinary phosphorous excretion are measured to assess the ability of selected example compounds to inhibit the absorption of sodium and phosphorous from the intestinal lumen. In addition, an assessment of fecal form in response to compound treatment is made. Approximately eight-week old, male, Sprague Dawley rats are purchased from Envigo (Livermore, Calif.), housed 2 per cage and acclimated for at least 48 hours before study initiation. Animals are fed Harlan Teklad Global TD.160470 rodent chow (Madison, Wis.), standard laboratory rodent chow Harlan Teklad Global 2018 with the addition of 0.4% inorganic phosphorous. Animals have ad libitum access to food and water for the duration of the study and are maintained in a temperature and humidity controlled room on a reversed light/dark cycle of 6 PM to 6 AM. To initiate the study, rats are weighed and individually placed in metabolic cages. Following a 2-day acclimation period to the metabolic cage, a 24-hr baseline collection of urine and feces is performed. Rats (n=6/group) are then dosed by oral gavage with test compound or vehicle (3 mM HCl, 0.01% Tween80) at a dose volume of 5 mL/kg, twice daily at 6 AM and 3 PM for 3 consecutive days. Each day, measurements of body weight, 24-hour food intake, water intake, urine volume and wet fecal weight are recorded, along with any observation of diarrhea. Fecal samples are dried using a lyophilizer for at least 3 days, following which dry weight is recorded and fecal fluid content is calculated based on the difference between the wet and dry stool weights. Fecal fluid content on day 3 of compound treatment is calculated as a change from the vehicle group mean. For urine samples, the volumes are determined gravimetrically. Feces and urine are analyzed for sodium and phosphorous content by microwave plasma-atomic emission spectroscopy or ion chromatography, respectively. Urine samples are analyzed on an ion chromatography system (Thermo Fisher ICS-3000 or ICS-5000+) coupled with conductivity detectors. Chromatographic separation of cations is performed using an IonPac CS12A (Thermo Fisher) 2×250 mm analytical column with an isocratic elution using 25 mM methanesulfonic acid. Chromatographic separation of anions is performed using an IonPac AS18 (Thermo Fisher) 2×250 mm analytical column with an isocratic elution using 35 mM potassium hydroxide. Concentrations are interpolated from a standard curve (prepared in 10 mM HCl) for each ion based on retention time and peak area. Fecal sample analysis by Microwave Plasma Atomic Emission Spectrometry (MP-AES). Dry fecal samples are ground into a fine powder on a homogenizer and the ground samples (400-600 mg aliquots weighed) are digested with nitric acid by microwave method (Mars 6). These digested samples are diluted with 1% Nitric acid and analyzed on Agilent 4100 MP-AES. Concentrations are interpolated from a standard curve (prepared in 1% Nitric acid) for sodium based on the signal intensity. Sodium is detected at a wavelength of 588.995 nm. Twenty-four-hour urinary sodium and phosphorous excretion (mg/24-hours) is calculated by multiplying urinary sodium or phosphorous concentration, respectively, by 24-hour urine volume. Twenty-four-hour fecal sodium excretion (mg/24-hours) is calculated by multiplying fecal sodium concentration by 24-hour dry fecal weight. The urinary and fecal sodium excretion and urinary phosphorous excretion on day 3 of compound treatment are normalized to dietary sodium or phosphorous intake, respectively, and expressed as a percentage of the vehicle mean.

Example 187: Restoration of Gastrointestinal Motility in Opioid Induced Constipation Gastrointestinal transit is measured in mice treated with the peripherally acting μ-opioid agonist loperamide to assess the ability of selected example compounds to restore gastrointestinal motility in a model of opioid induced constipation. Approximately eight-week old, female, CD1 rats are purchased from Envigo (Livermore, Calif.), are housed 4 per cage and acclimated for at least 48 hours before study initiation. Animals are fed standard laboratory rodent chow Harlan Teklad Global 2018 (Madison, Wis.). Animals have ad libitum access to food and water for the duration of the acclimation period and are maintained in a temperature and humidity controlled room on a standard light/dark cycle of 6 AM to 6 PM. Following an overnight fast, with free access to water, animals are dosed by oral gavage with varying doses of test compound or vehicle (3 mM HCl, 0.01% Tween80), at a dose volume of 5 mL/kg. Approximately fifteen minutes following oral dosing of test compound or vehicle, animals are dosed by subcutaneous injection with loperamide (0.3 to 6 mg/kg) or vehicle (30:70 PG:0.9% NaCl) at a dose volume of 5 mL/kg. Fifteen minutes later, animals are dosed orally with Evans Blue Dye (6%) at a dose volume of 100 μL. 30 minutes later, animals are euthanized by carbon dioxide inhalation, and the length from the pylorus to cecum (whole length of the small intestine) and the length from the pylorus to the Evans Blue dye front are measured and recorded. For an individual animal, the length travels by the Evans Blue dye front is divided by the length of the whole small intestine, measured from the pylorus to the cecum, and multiplied by 100, to provide the distance of the small intestine travelled by the dye as a percentage. In animals dosed orally with vehicle and injected subcutaneously with vehicle (vehicle/vehicle), the Evans Blue dye front travels approximately 70% of the length of the small intestine in the 30-minute period. In animals dosed orally with vehicle and injected subcutaneously with loperamide (vehicle/loperamide), the Evans Blue dye front travels approximately only 25% of the length of the small intestine in the 30-minute period, indicating decreased gastrointestinal motility in response to loperamide. The effect of example compounds on GIT motility in the presence of loperamide is calculated as the ability to restore vehicle/vehicle transit distance from the vehicle/loperamide transit, expressed as a percentage.

TABLE 8

| Result | % Restoration of Transit |
|---|---|
| A | <20% |
| B | 20-40% |
| C | >40% |

| Example | Dose (mg/kg) | % Restoration of Transit |
|---|---|---|
| Standard | 15 | C |
| 41 | 15 | A |
| 115 | 15 | B |
| 132 | 15 | C |
| 123 | 15 | A |
| Standard | 15 | C |
| 43 | 15 | A |
| 43 | 1.5 | B |
| 43 | 5 | A |

Example 188: Restoration of Gastrointestinal Motility in Multiple Sclerosis

Gastrointestinal transit time is measured to assess the ability of selected example compounds to restore gastrointestinal motility in a model of multiple sclerosis. Multiple sclerosis (MS) patients often experience constipation and other gastrointestinal manifestations related to disturbed gastrointestinal motility. The Experimental Autoimmune Encephalomyelitis (EAE) mouse model is one of the most frequently used animal models for studying multiple sclerosis (MS), in which immunization against CNS-specific antigen results in central nervous system inflammation. This model results in a spectrum of acute, chronic, and relapsing disease that results in varying degrees of progressive paralysis and gastrointestinal dysmotility.

Animals are 8-16 weeks of age at study initiation, and are fed standard laboratory rodent chow Harlan Teklad Global 2018 (Madison, Wis.), Animals have ad libitum access to food and water for the duration of the study and are maintained in a temperature and humidity controlled room on a standard light/dark cycle of 6 AM to 6 PM. EAE is induced in female mice by injection of a combination of antigen (MOG35-55, S.C.) in complete Freund's adjuvant (CFA), and pertussis toxin (PTX, IP). After somatic motor symptoms develop, generally 10 or more days' post immunization, EAE mice are dosed by oral gavage with test compound at varying doses (0.01 to 30 mg/kg) or vehicle (3 mM HCl, 0.01% Tween80) at a dose volume of 5 mL/kg. Test compound is administered for a single dose or twice daily for multiple doses. Fecal output is monitored for a standardized period of time (1-24 hours) and recorded as fecal pellet number, fecal mass and fecal dry weight. Whole gastrointestinal transit time is determined by oral gavage of carmine red or Evans Blue and calculating the latency for dye to appear in the feces. Small intestinal transit is measured by dosing carmine red or Evans Blue by oral gavage and measuring the distance of the leading edge of the dye from compared to the whole length of the small intestine 15 minutes to two hours following oral dosing of the dye. Colonic motility is assessed by measuring time to extrusion of a single glass head inserted a standardized distance into the distal colon. The effect of example compounds on GIT motility in EAE mice is calculated as the ability to restore transit distance to those observed in control mice from those observed in EAE treated with vehicle, expressed as a percentage.

Example 189: Restoration of Gastrointestinal Motility in Parkinson's Disease

Gastrointestinal transit time is measured to assess the ability of selected example compounds to restore gastrointestinal motility in a model of Parkinson's disease. Parkinson's disease (PD) is a neurodegenerative disorder characterized by chronic and progressive motor impairment. PD patients also experience significant non-motor symptoms including constipation and other gastrointestinal manifestations related to disturbed gastrointestinal motility. The toxin, 1-methyl-4-phenyl-1,2,3,6-tetrahydropyridine (MPTP) has been widely used to develop animal models for testing new therapies in the PD. This model results in motor changes and pathology that resemble PD and has also been reported to manifest gastrointestinal dysmotility (*Scientific Reports*, 2016 6:30269)

Animals are 8-16 weeks of age at study initiation, and fed standard laboratory rodent chow Harlan Teklad Global 2018 (Madison, Wis.). Animals have ad libitum access to food and water for the duration of the study and are maintained in a temperature and humidity controlled room on a standard light/dark cycle of 6 AM to 6 PM. PD is induced in mice by multiple, generally four, intraperitoneal injections of MPTP. After MPTP is injected, generally 4 to 20 days' post injection, PD mice are dosed by oral gavage with test compound at varying doses (0.01 to 30 mg/kg) or vehicle (3 mM HCl, 0.01% Tween80) at a dose volume of 5 mL/kg. Test compound is administered once or twice daily for multiple doses. Fecal output is monitored for a standardized period of time (1-24 hours) and recorded as fecal pellet number, fecal mass and fecal dry weight. Whole gastrointestinal transit time is determined by oral gavage of carmine red or Evans Blue and calculating the latency for dye to appear in the feces. Small intestinal transit is measured by dosing carmine red or Evans Blue by oral gavage and measuring the distance of the leading edge of the dye from compared to the whole length of the small intestine 15 minutes to two hours following oral dosing of the dye. Colonic motility is assessed by measuring time to extrusion of a single glass bead inserted a standardized distance into the distal colon. The effect of example compounds on GIT motility in PD mice is calculated as the ability to restore transit distance to those observed in control mice from those observed in PD mice treated with vehicle, expressed as a percentage.

Example 190: Effect on Blood Pressure in a Models of Salt-Sensitive Hypertension Arterial blood pressure is measured to assess the ability of selected example compounds to attenuate hypertension in a model of salt-sensitive hypertension. Dahl Salt Sensitive (DSS) rats are a well characterized model of salt-sensitive hypertension and end-organ injury. Salt-sensitive hypertension is established in DSS rats by increasing the NaCl content of the diet from 0.49% up to 4% NaCl for a period of 1 to 4-weeks. DSS rats maintained on 0.49% NaCl are used as a control group. Animals are 6-10 weeks of age at study initiation, and have ad libitum access to food and water for the duration of the study and are maintained in a temperature and humidity controlled room on a 12-hr light/dark cycle. Rats (n=6-8/group) are dosed by oral gavage with test compound (0.01-30 mg/kg) or vehicle (3 mM HCl, 0.01% Tween80) at a dose volume of 5 mL/kg, twice daily for 1 to 3 weeks, while maintained on a 4% NaCl diet. Arterial blood pressure is measured weekly by tail cuff plethysmography. A 24-hr urine collection is also collected weekly by placing animals individually in metabolic cages.

Example 191: Effect on Cardiac Function in Models of Heart Failure

Serial echocardiography is used to measure cardiac function and morphology to assess the ability of selected example compounds to improve cardiac function, structure and neuro-humoral activation in a rat model of heart failure. Male Dahl Salt Sensitive (DSS) rats or male Lewis rats are used to induce heart failure by permanent left main coronary arterial ligation. Animals are 6-10 weeks of age at study initiation, and have ad libitum access to food and water for the duration of the study and are maintained in a temperature and humidity controlled room on a 12-hr light/dark cycle. Rats (n=6-10/group) are dosed by oral gavage with test compound (0.01 to 30 mg/kg) or vehicle (3 mM HCl, 0.01% Tween80) at a dose volume of 5 mL/kg, twice daily for 1 to 8 weeks. Serial echocardiography is performed weekly to assess time-dependent cardiac remodelling (HWI, LVI, chamber size), time-dependent cardiac performance (EF, dP/dt, LVEDP) changes and time-dependent cardiac morphometry (HWI, LVI, LVEDV, LVESV) indices. Terminal assessment of load-dependent and load-independent left ventricular function are made using pressure-volume loop analysis. Extracellular volume expansion is assessed by measuring volume sensitive hormones ANP and BNP.

Example 192: Pain Relief in IBS-C—Reduction of Visceral Hypersensitivity in Rats The ability of selected example compounds to reduce the hypersensitivity of the colon to balloon distension (CRD) in a rat model of visceral hypersensitivity is measured by grading the rat's abdominal withdrawal reflex (AWR) and by measuring electromyographic (EMG) responses. Visceral hypersensitivity is induced by injecting 10-day old male Sprague Dawley rat pups with a 0.2 mL infusion of 0.5% acetic acid solution in saline into the colon 2 cm from the anus. Control rats receive an equal volume of saline. Visceral hypersensitivity is then assessed in these rats as adults, between 8 and 12 weeks of age. Rats (n=4-10/group) are dosed by oral gavage with test compound (0.01 to 30 mg/kg) or vehicle (3 mM HCl, 0.01% Tween80) at a dose volume of 5 mL/kg, twice daily for up to 2 weeks prior to the assessment of visceral hypersensitivity. Visceral hypersensitivity is measured by grading the response to CRD. Under mild sedation with 1% methohexital sodium, a flexible balloon attached to Tygon tubing is inserted 8 cm into the descending colon and rectum via the anus and secured in place by taping the tube to the tail. Approximately 30 minutes later, CRD is performed by rapidly inflating the balloon to varying pressures (10 to 80 mmHg) measured by a sphygmomanometer connected to a pressure transducer for a 20 second period followed by a 2-minute rest period. Behavioral responses to CRD are measured by grading the AWR by blinded observer and assigning an AWR score as follows: 1, normal behavior without response; 2, contraction of abdominal muscles; 3, lifting of abdominal wall; 4, body arching and lifting of pelvic structures. EMG responses are measured continuously in response to CRD via two electrodes implanted at least one-week prior to in the external oblique muscle and calculated as the area under the curve of the EMG in response to CRD.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

The invention claimed is:
1. A compound of formula I:

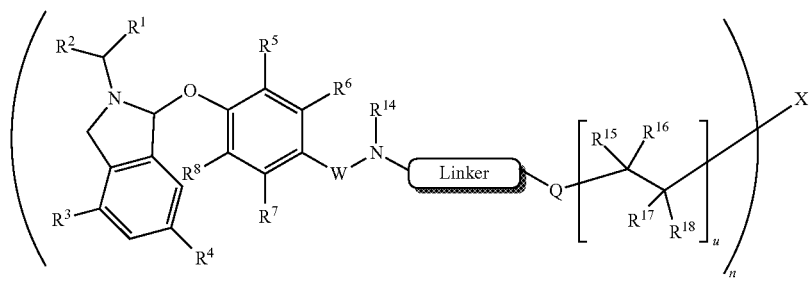

(I)

or a pharmaceutically acceptable salt thereof,
wherein:
Linker is —$R^{13}$—(CH$R^{13}$)$_p$—[Y—(CH$_2$)$_r$]$_s$—Z—$R^{13}$—(CH$_2$)$_t$—Z—;
X is a bond, H, N, O, C$R^{11}R^{12}$, C$R^{11}$, C, —NHC(O)NH—, —(CH$R^{13}$)$_p$- or $C_3$-$C_6$cyclolakyl;
W is independently, at each occurrence, S(O)$_2$, C(O), or —(CH$_2$)$_m$—;
Z is independently, at each occurrence, a bond, C(O), or —C(O)NH—;
Y is independently, at each occurrence, O, S, NH, N($C_1$-$C_3$alkyl), or —C(O)NH—;
Q is a bond, NH, —C(O)NH—, —NHC(O)NH—, —NHC(O)N(CH$_3$)—, or —NHC(O)NH—(CH$R^3$);
m is an integer from 1 to 2;
n is an integer from 1 to 4;
r and p are independently, at each occurrence, integers from 0 to 8;
s is an integer from 0 to 4;
t is an integer from 0 to 4;
u is an integer from 0 to 2;

$R^1$ and $R^2$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, wherein each alkyl, alkenyl, cycloalkenyl, alkynyl, cycloalkyl, heterocyclyl, aryl, or heteroaryl is optionally substituted with one or more halogen, OH, CN, —NO$_2$, oxo, —S$R^9$, —O$R^9$, —NH$R^9$, —N$R^9R^{10}$, —S(O)$_2$N($R^9$)$_2$—, —S(O)$_2R^9$, —C(O)$R^9$, —C(O)O$R^9$, —C(O)N$R^9R^{10}$, —N$R^9$S(O)$_2$$R^{10}$, —S(O)$R^9$, —S(O)N$R^9R^{10}$, —N$R^8$S(O)$R^9$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl; or
$R^1$ and $R^2$ together with the nitrogen to which they are attached can form a heterocyclyl or heteroaryl containing 1-5 heteroatoms selected from the group consisting of N, S, P and O, wherein the heterocyclyl or heteroaryl group is optionally substituted with one or more halogen, OH, CN, —NO$_2$, oxo, —S$R^9$, —O$R^9$, —NH$R^9$, —N$R^9R^{10}$, —S(O)$_2$N($R^9$)$_2$—, —S(O)$_2R^9$, —C(O)$R^9$, —C(O)O$R^9$, —C(O)N$R^9R^{10}$, —N$R^9$S(O)$_2R^{10}$, —S(O)$R^9$, —S(O)N$R^9R^{10}$, —NRS(O)$R^{10}$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl;
$R^3$ is CN and $R^4$ is halogen, OH, CN, $C_1$-$C_6$alkyl, $C_1$-$C_6$alkoxy, $C_1$-$C_6$haloalkyl, $C_1$-$C_6$haloalkoxy, or —C(O)N$R^9R^{10}$;
$R^5$, $R^6$, $R^7$, and Re are independently H, halogen, OH. CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —S$R^9$, —O$R^9$, —NH$R^9$, —N$R^9R^{10}$, —S(O)$_2$N ($R^9$)$_2$—, —S(O)$_2R^9$, —C(O)$R^9$, —C(O)O$R^9$, —N$R^9$S (O)$_2R^{10}$, —S(O)$R^9$, —S(O)N$R^9R^{10}$, —N$R^8$S(O)$R^9$;
$R^9$ and $R^{10}$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl containing 1-5 heteroatoms selected from the group consisting of N, S, P and O
$R^{11}$ and $R^{12}$ are independently H, $C_1$-$C_6$alkyl, OH, NH$_2$, CN, or NO$_2$;
$R^{13}$ is independently, at each occurrence, a bond, H, $C_1$-$C_6$alkyl, $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R^{19}$;
$R^{14}$ is independently, at each occurrence, H, $C_1$-$C_6$alkyl, or $C_1$-$C_6$haloalkyl; or R⁶ and R¹⁴ together with the atoms to which they are attached may combine to form, independently, at each occurrence, 5- to-6 membered heterocyclyl, wherein each $C_3$-$C_8$ cycloalkyl, or heterocyclyl is optionally substituted with one or more $R^{19}$; or R³ and R¹⁴ together with the atoms to which they are attached may combine to form independently, at each occurrence, $C_3$-$C_8$ cycloalkyl, heterocyclyl, aryl, or heteroaryl containing 1-5 heteroatoms selected from the group consisting of N, S, P and O, wherein each heterocyclyl or heteroaryl is optionally substituted with one or more $R^{19}$;

$R^{15}$, $R^{16}$, $R^{17}$, and $R^{18}$ are independently, at each occurrence, H, OH, $NH_2$, or $C_1$-$C_3$ alkyl, wherein the alkyl is optionally substituted with one or more $R^{19}$;

$R^{19}$ are independently, at each occurrence, H, OH, $NH_2$, oxo, $C_1$-$C_6$alkyl, $C_1$-$C_6$Hhaloalkyl, $C_1$-$C_6$alkoxy; and provided that:

(1) when X is H, n is 1;

(2) when X is a bond, O, or $CR^{11}R^{12}$, n is 2;

(3) when n is 3, X is $CR^{11}$ or N;

(4) when n is 4 X is C; and (5) only one of Q or X is —NHC(O)NH— at the time.

2. The compound of claim 1, wherein Linker is selected the group consisting of:

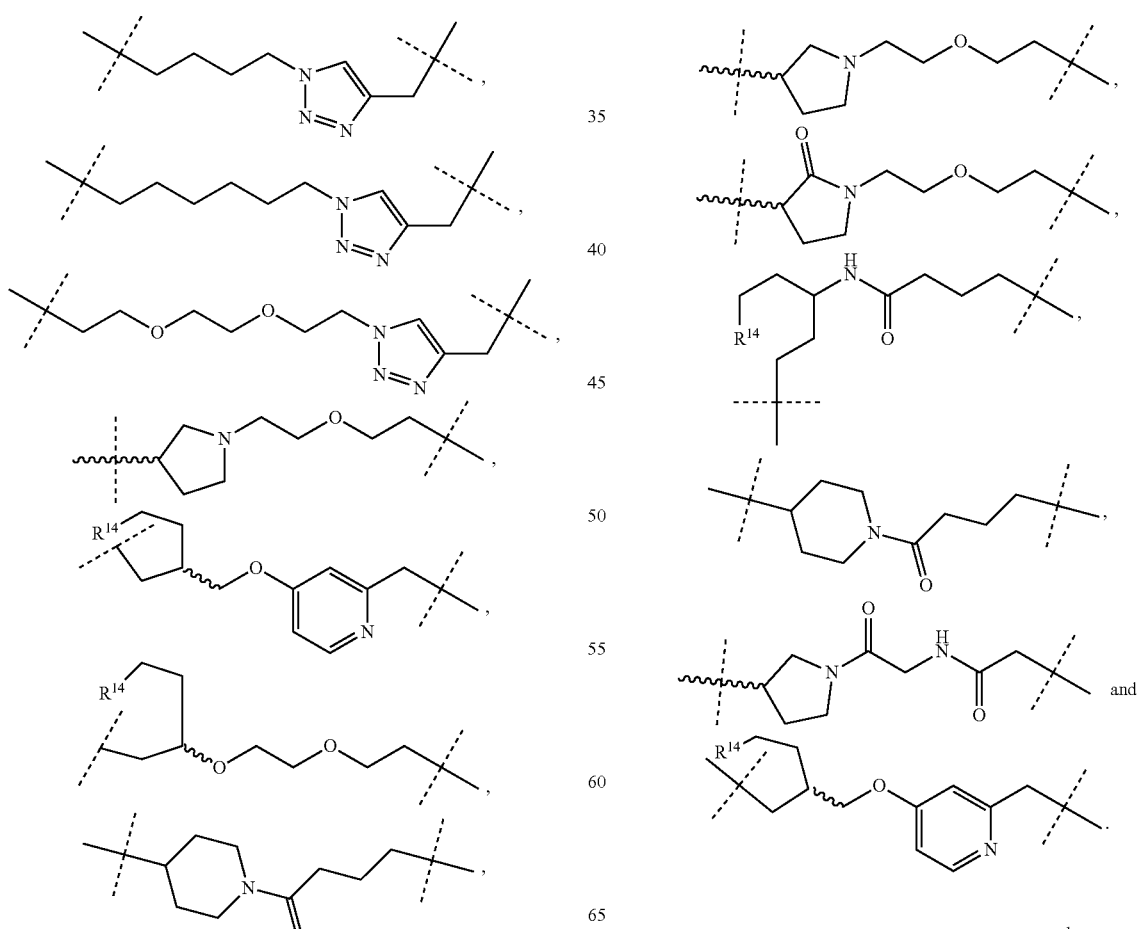

3. The compound of claim 1, wherein Linker is selected from the group consisting of:

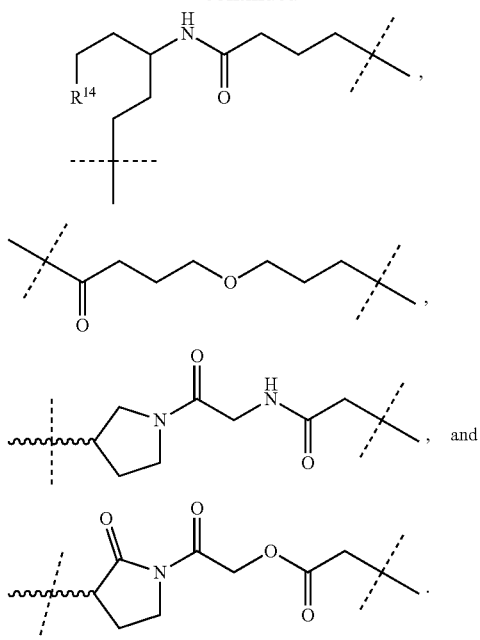

4. The compound of claim 1, wherein $R^1$ and $R^2$ are methyl.

5. The compound of claim 1, wherein $R^1$ and $R^2$ together with the nitrogen to which they are attached can form a heterocyclyl, wherein the heterocyclyl is optionally substituted with one or more oxo.

6. The compound of claim 1 having the formula Ia:

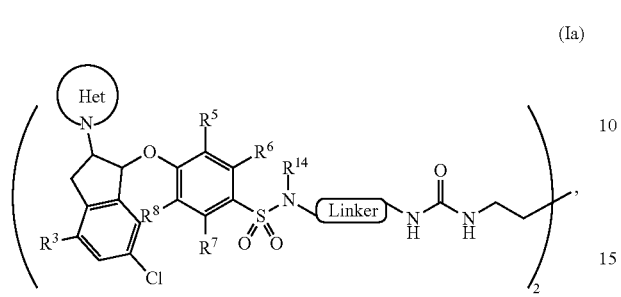

(Ia)

wherein the ring Het represents $R^1$ and $R^2$ together with the nitrogen to which they are attached can form a heterocyclyl or heteroaryl containing 1-5 heteroatoms selected from the group consisting of N, S, P and O, wherein the heterocyclyl or heteroaryl group is optionally substituted with one or more halogen, OH, CN, —$NO_2$, oxo, —$SR^9$, —$OR^9$, —$NHR^9$, —$NR^9R^{10}$, —$S(O)_2N(R^9)_2$—, —$S(O)_2R^9$, —$C(O)R^9$, —$C(O)OR^9$, —$C(O)NR^9R^{10}$, —$NR^9S(O)_2R^{10}$, —$S(O)R^9$, —$S(O)NR^9R^{10}$, —$NR^9S(O)R^{10}$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl.

7. The compound of claim 1 having the formula Ib:

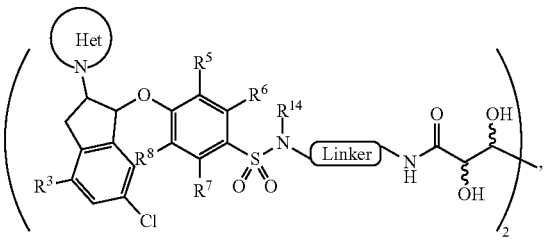

(Ib)

wherein the ring Het represents $R^1$ and $R^2$ together with the nitrogen to which they are attached can form a heterocyclyl or heteroaryl containing 1-5 heteroatoms selected from the group consisting of N, S, P and O, wherein the heterocyclyl or heteroaryl group is optionally substituted with one or more halogen, OH, CN, —$NO_2$, oxo, —$SR^9$, —$OR^9$, —$NHR^9$, —$NR^9R^{10}$, —$S(O)_2N(R^9)_2$—, —$S(O)_2R^9$, —$C(O)R^9$, —$C(O)OR^9$, —$C(O)NR^9R^{10}$, —$NR^9S(O)_2R^{10}$, —$S(O)R^9$, —$S(O)NR^9R^{10}$, —$NR^9S(O)R^{10}$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl.

8. The compound of claim 1 having the formula Ic:

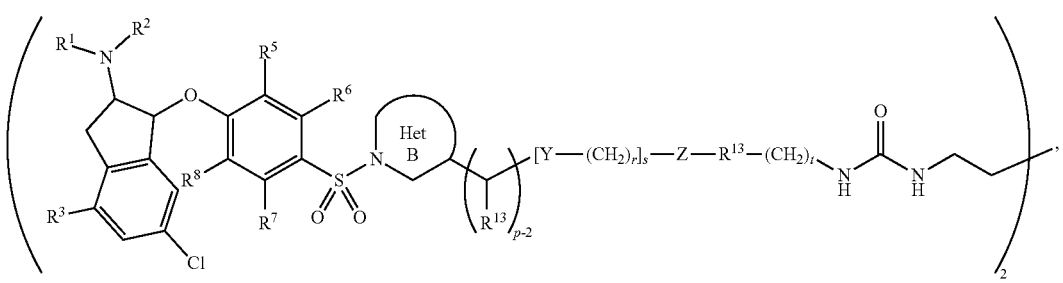

(Ic)

wherein Het B represents a $C_3$-$C_8$ cycloalkyl, heterocyclyl, aryl, or heteroaryl containing 1-5 heteroatoms selected from the group consisting of N, S, P and O, wherein each heterocyclyl or heteroaryl is optionally substituted with one or more $R^{19}$.

9. The compound of claim 1 having the formula Id:

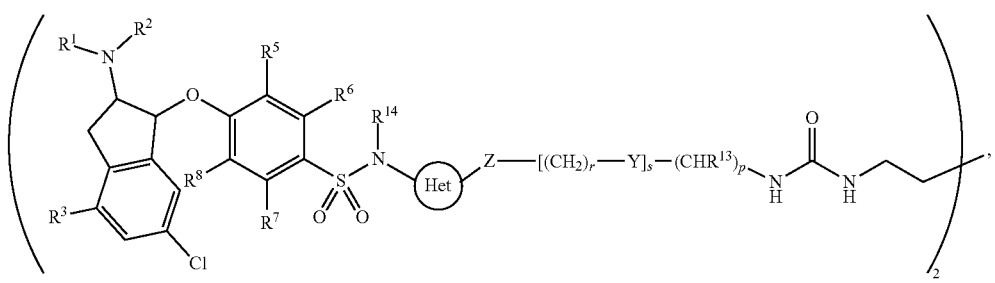

(Id)

wherein Het is $R^{13}$ which represents $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R^{19}$.

10. The compound of claim 1 having the formula Ie:

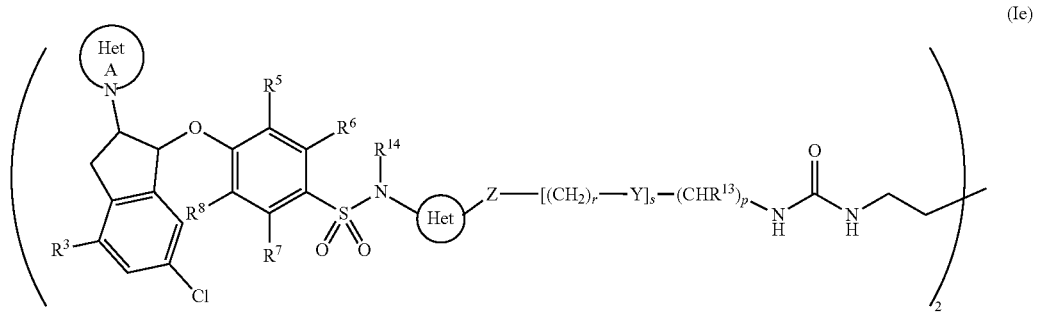

wherein the ring Het A represents $R^1$ and $R^2$ together with the nitrogen to which they are attached can form a heterocyclyl or heteroaryl containing 1-5 heteroatoms selected from the group consisting of N, S, P and O, wherein the heterocyclyl or heteroaryl group is optionally substituted with one or more halogen, OH, CN, $-NO_2$, oxo, $-SR^9$, $-OR^9$, $-NHR^9$, $-NR^9R^{10}$, $-S(O)_2N(R^9)_2-$, $-S(O)_2R^9$, $-C(O)R^9$, $-C(O)OR^9$, $-C(O)NR^9R^{10}$, $-NR^9S(O)_2R^{10}$, $-S(O)R^9$, $-S(O)NR^9R^{10}$, $-NR^9S(O)R^{10}$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, heterocycle, aryl, or heteroaryl; and Het is $R^{13}$ which represents $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R^{19}$.

11. The compound of claim 1 having the formula If:

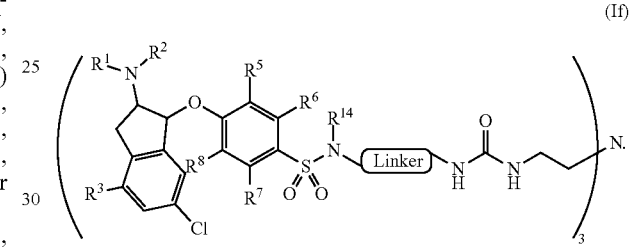

12. The compound of claim 1 having the formula If:

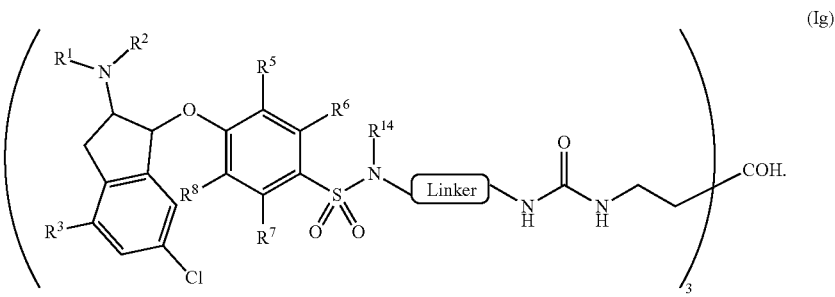

13. The compound of claim 1 having the formula Ig:

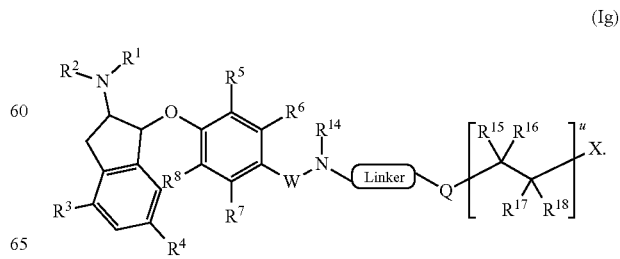

14. The compound of claim 1 having the formula Ih:

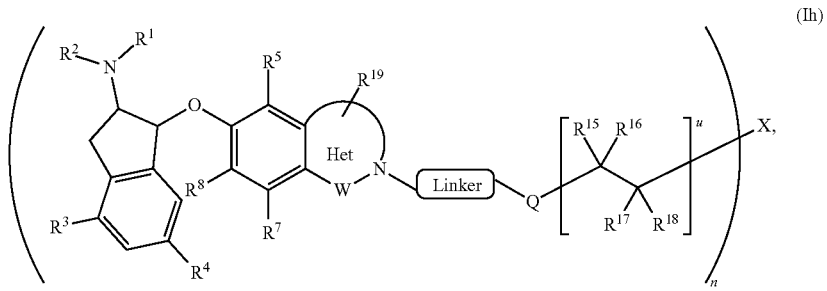

wherein:
Het represents $R^6$ and $R^{14}$ together with the atoms to which they are attached forming, independently, at each occurrence, a 5- to-6 membered heterocyclyl.

15. The compound of formula I having the formula Ii:

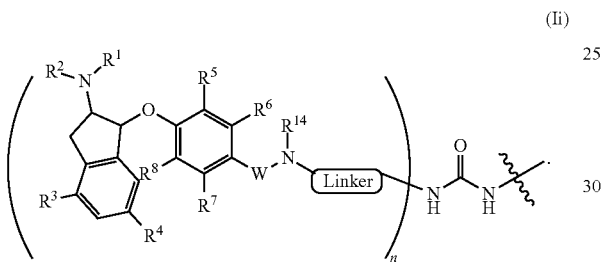

16. The compound of claim 1 selected from the group consisting of:

3-[2-(2-[2-[(4-[[(1S,2S)-2-[(3R)-3-Aminopiperidin-1-yl]-6-chloro-4-cyano-2,3-dihydro-1H-inden-1-yl]oxy]benzene)sulfonamido]ethoxy]ethoxy)ethyl]-1-[4-([[2-(2-[2-[(4-[[(1S,2S)-2-[(3R)-3-aminopiperidin-1-yl]-6-chloro-4-cyano-2,3-dihydro-1H-inden-1-yl]oxy]benzene) sulfonamido]ethoxy]ethoxy)ethyl]carbamoyl]amino)butyl]urea;

3-[2-(2-[2-[(4-[[(1S,2S)-2-[(3R)-3-Aminopiperidin-1-yl]-6-chloro-4-cyano-2,3-dihydro-1H-inden-1-yl]oxy]-3-methylbenzene)sulfonamido]ethoxy]ethoxy)ethyl]-1-[4-([[2-(2-[2-[(4-[[(1S,2S)-2-[(3R)-3-aminopiperidin-1-yl]-6-chloro-4-cyano-2,3-dihydro-1H-inden-1-yl]oxy]-3-methylbenzene) sulfonamido]ethoxy]ethoxy)ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]-3-methylbenzene)sulfonamido]ethoxy]ethoxy]ethyl]-1-[4-([[2-(2-[2-[(4-[[(1S,2S)-6-chloro-4-cyano-2-(dimethylamino)-2,3-dihydro-1H-inden-1-yl]oxy]-3-methylbenzene) sulfonamido]ethoxy]ethoxy) ethyl]carbamoyl]amino)butyl]urea;

3-[2-(2-[2-[(4-[[(1S,2S)-6-Chloro-4-cyano-2-(dimethylamino)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-(dimethylamino)-2,3-dihydro-1H-inden-1-yl]oxy]-3-fluorobenzene) sulfonamido]ethoxy]ethoxy)ethyl]carbamoyl]amino) butyl]urea;

3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-methylbenzene)sulfonamido]ethoxy]ethoxy) ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-methylbenzene) sulfonamido]ethoxy]ethoxy)ethyl]carbamoyl]amino) butyl]urea:

3-[2-(2-[2-[(4-[[(1S,2S)-6-Chloro-4-cyano-2-[(3R)-3-(dimethylamino)piperidin-1-yl]-2,3-dihydro-1H-inden-1-yl]oxy]-3-fluorobenzene)sulfonamido]ethoxy]ethoxy) ethyl]-1-[4-([[2-(2-[2-[(4-[[(1S,2S)-6-chloro-4-cyano-2-[(3R)-3-(dimethylamino)piperidin-1-yl]-2,3-dihydro-1H-inden-1-yl]oxy]-3-fluorobenzene)sulfon amido]ethoxy]ethoxy)ethyl]carbamoyl]amino)butyl] urea;

3-[2-(2-[2-[(4-[[(1S,2S)-6-Chloro-4-cyano-2-(piperazin-1-yl)-2,3-dihydro-1H-inden-1-yl]oxy]benzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]benzene)sulfonamido]ethoxy]ethoxy)ethyl]carbamoyl]amino)butyl]urea;

3-[2-(2-[2-[(4-[[(1S,2S)-6-Chloro-4-cyano-2-(piperazin-1-yl)-2,3-dihydro-1H-inden-1-yl]oxy]-3-methylbenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-methylbenzene)sulfonamido]ethoxy]ethoxy)ethyl]carbamoyl]amino) butyl]urea;

3-[2-(2-[2-[(4-[[(1S,2S)-6-Chloro-4-cyano-2-(piperazin-1-yl)-2,3-dihydro-1H-inden-1-yl]oxy]-3-fluorobenzene)sulfonamido]ethoxy]ethoxy)ethyl]-1-[4-([[2-(2-[2-[(4-[[(1S,2S)-6-chloro-4-cyano-2-(piperazin-1-yl)-2,3-dihydro-1H-inden-1-yl]oxy]-3-fluorobenzene) sulfonamido]ethoxy]ethoxy)ethyl]carbamoyl]amino) butyl]urea;

3-[2-(2-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy) ethyl]-1-[4-([[2-(2-[[(3S)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]ethoxy)ethyl]carbamoyl]amino)butyl]urea;

3-[2-(2-[[(3R)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]ethoxy) ethyl]-1-[4-([[2-(2-[[(3R)-1-[(4-[[(1S,2S)-6-chloro-4-cyano-2-(dimethylamino)-2,3-dihydro-1H-inden-1-yl]

oxy]-3-methylbenzene)sulfonyl]pyrrolidin-3-yl]
methoxy]ethoxy)ethyl]carbamoyl]amino)butyl]urea;

3-[(4-[[(3S)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-4-[3S-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-[(4-[[(3R)-1-[(4-[[(1S,2S)-6-Chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]-1-[4-([[(4-[[(3R)-1-[(4-[[(1S,2S)-6-chloro-4-cyano-2-(dimethylamino)-2,3-dihydro-1H-inden-1-yl]oxy]-3-methylbenzene)sulfonyl]pyrrolidin-3-yl]methoxy]pyridin-2-yl)methyl]carbamoyl]amino)butyl]urea;

3-(2-[2-[(3S)-3-[(4-[[(1S,2S)-6-Chloro-4-cyano-2-(dimethylamino)-2,3-dihydro-H-inden-1-yl]oxy]-3-methylbenzene)sulfonamido]pyrrolidin-1-yl]ethoxy]ethyl)-1-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea;

3-(2-[2-[(3R)-3-[(4-[[(1S,2S)-6-Chloro-4-cyano-2-(dimethylamino)-2,3-dihydro-1H-inden-1-yl]oxy]-3-methylbenzene)sulfonamido]pyrrolidin-1-yl]ethoxy]ethyl)-1-(4-[[(2-[2-[(3R)-3-[(4-[[(1S,2S)-6-chloro-4-cyano-2-(dimethylamino)-2,3-dihydro-1H-inden-1-yl]oxy]-3-methylbenzene)sulfonamido]pyrrolidin-1-yl]ethoxy]ethyl)carbamoyl]amino]butyl)urea;

1-(2-[2-[(3S)-3-[(4-[[(1S,2S)-6-Chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)-3-(4-[[(2-[2-[(3S)-3-[(4-[[(1S,2S)-6-chloro-4-cyano-2-(dimethylamino)-2,3-dihydro-1H-inden-1-yl]oxy]-3-methylbenzene)sulfonamido]-2-oxopyrrolidin-1-yl]ethoxy]ethyl)carbamoyl]amino]butyl)urea;

4-([[(1S,2S)-6-Chloro-4-cyano-2-(piperazin-1-yl)-2,3-dihydro-1H-inden-1-yl]oxy)-N—[(S)-1-(20-[(S)-3-([4-([[(1S,2S)-6-chloro-4-cyano-2-(piperazin-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; tetra(trifluoroacetate);

4-([[(1S,2S)-6-Chloro-4-cyano-2-(piperazin-1-yl)-2,3-dihydro-1H-inden-1-yl]oxy)-N—[(R)-1-(20-[(R)-3-([4-([[(1S,2S)-6-chloro-4-cyano-2-(piperazin-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide; tetra(trifluoroacetate);

4-([[(1S,2S)-6-Chloro-4-cyano-2-(piperazin-1-yl)-2,3-dihydro-1H-inden-1-yl]oxy)-N—[(R)-1-(20-[(R)-3-[(4-([[(1S,2S)-6-chloro-4-cyano-2-(piperazin-1-yl)-2,3-dihydro-1H-inden-1-yl]oxy)-3-fluorophenyl)sulfonamide)pyrrolidin-1-yl]-7,14-dioxo-3,18-dioxa-6,8,13,15-tetraazaicosyl)pyrrolidin-3-yl]-3-fluorobenzenesulfonamide; tetra(trifluoroacetate);

4-([[(1S,2S)-6-Chloro-4-cyano-2-(piperazin-1-yl)-2,3-dihydro-1H-inden-1-yl]oxy)-N—[(S)-1-(20-[(S)-3-([4-([[(1S,2S)-6-chloro-4-cyano-2-(piperazin-1-yl)-2,3-dihydro-1H-inden-1-yl]oxy)-3-fluorophenyl)sulfonamide)pyrrolidin-1-yl]-7,14-dioxo-3,18-dioxa-6,8,13,15-tetraazaicosyl)pyrrolidin-3-yl]-3-fluorobenzenesulfonamide; tetra(trifluoroacetate);

4-([(1S,2S)-6-Chloro-4-cyano-2-(piperazin-1-yl)-2,3-dihydro-1H-inden-1-yl]oxy)-N-[1-(18-[4-([[(1S,2S)-6-chloro-4-cyano-2-(piperazin-1-yl)-2,3-dihydro-1H-inden-1-yl]oxy)phenyl]sulfonamido)piperidin-1-yl]-6,13,18-trioxo-5,7,12,14-tetraazaoctadecanoyl)piperidin-4-yl]benzenesulfonamide;

4-([[(1S,2S)-6-Chloro-4-cyano-2-(piperazin-1-yl)-2,3-dihydro-1H-inden-1-yl]oxy)-N—[(S)-1-(14-[(S)-3-([4-([[(1S,2S)-6-chloro-4-cyano-2-(piperazin-1-yl)-2,3-dihydro-1H-inden-1-yl]oxy)phenyl]sulfonamido)pyrrolidin-1-yl]-4,11,14-trioxo-3,5,10,12-tetraazatetradecanoyl)pyrrolidin-3-yl]benzenesulfonamide;

4-([[(1S,2S)-6-Chloro-4-cyano-2-(piperazin-1-yl)-2,3-dihydro-1H-inden-1-yl]oxy)-N—[(S)-1-[(2S,13S)-14-[(S)-3-([4-([[(1S,2S)-6-chloro-4-cyano-2-(piperazin-1-yl)-2,3-dihydro-1H-inden-1-yl]oxy)phenyl]sulfonamido)pyrrolidin-1-yl]-2,13-dimethyl-4,11,14-trioxo-3,5,10,12-tetraazatetradecanoyl]pyrrolidin-3-yl]benzenesulfonamide;

$N^1,N^{14}$-bis(2-[(S)-3-([4-([[(1S,2S)-6-chloro-4-cyano-2-(piperazin-1-yl)-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide;

$N^1,N^{14}$-bis(2-[(R)-3-([4-([[(1S,2S)-6-chloro-4-cyano-2-(piperazin-1-yl)-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide;

$N^1,N^{18}$-Bis(1-([4-([[(1S,2S)-6-chloro-4-cyano-2-(piperazin-1-yl)-2,3-dihydro-1H-inden-1-yl]oxy)phenyl]sulfonyl)piperidin-4-yl)-6,13-dioxo-5,7,12,14-tetraazaoctadecanediamide;

4-([[(1S,2S)-6-Chloro-4-cyano-2-[(R)-3-(dimethylamino)piperidin-1-yl]-2,3-dihydro-1H-inden-1-yl]oxy)-N-[26-([4-([[(1S,2S)-6-chloro-4-cyano-2-[(R)-3-(dimethylamino)piperidin-1-yl]-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

-([(1S,2S)-6-Chloro-4-cyano-2-[(S)-3-(dimethylamino)piperidin-1-yl]-2,3-dihydro-1H-inden-1-yl]oxy)-N-[26-([4-([[(1S,2S)-6-chloro-4-cyano-2-[(S)-3-(dimethylamino)piperidin-1-yl]-2,3-dihydro-1H-inden-1-yl]oxy)phenyl]sulfonamido)-10,17-dioxo-3,6,21,24-tetraoxa-9,11,16,18-tetraazahexacosyl]benzenesulfonamide;

4-([[(1S,2S)-6-chloro-4-cyano-2-(piperazin-1-yl)-2,3-dihydro-1H-inden-1-yl]oxy)-N-[1-(20-[4-([[(1S,2S)-6-chloro-4-cyano-2-(piperazin-1-yl)-2,3-dihydro-1H-inden-1-yl]oxy)phenyl]sulfonamide]piperidin-1-yl]-7,14-dioxo-3,18-dioxa-6,8,13,15-tetraazaicosyl)piperidin-4-yl]benzenesulfonamide;

$N^1,N^{18}$-Bis([4-([[(1S,2S)-6-chloro-4-cyano-2-(piperazin-1-yl)-2,3-dihydro-1H-inden-1-yl]oxy)phenyl]sulfonyl)-6,13-dioxo-5,7,12,14-tetraazaoctadecanediamide;

N-([4-([[(1S,2S)-6-chloro-4-cyano-2-(piperazin-1-yl)-2,3-dihydro-1H-inden-1-yl]oxy)phenyl]sulfonyl)-1-[16-(4-[([4-([[(1S,2S)-6-chloro-4-cyano-2-(piperazin-1-yl)-2,3-dihydro-1H-inden-1-yl]oxy)phenyl]sulfonyl)carbamoyl]piperidin-1-yl]-5,12-dioxo-4,6,11,13-tetraazahexadecyl]piperidine-4-carboxamide;

4-([[(1S,2S)-6-chloro-4-cyano-2-(1,4-diazepan-1-yl)-2,3-dihydro-1H-inden-1-yl]oxy)-N—[(S)-1-(20-[(S)-3-([4-([[(1S,2S)-6-chloro-4-cyano-2-(1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-(1,4-diazepan-1-yl)-2,3-dihydro-1H-inden-1-yl]oxy)-N—[(R)-1-(20-[(R)-3-([4-([[(1S,2S)-6-chloro-4-cyano-2-(1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-(4-methyl-1,4-diazepan-1-yl)-2,3-dihydro-1H-inden-1-yl]oxy)-N-[(S)-1-(20-[(S)-3-([4-([[(1S,2S)-6-chloro-4-cyano-2-(4-methyl-1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-(4-methyl-1,4-diazepan-1-yl)-2,3-dihydro-1H-inden-1-yl]oxy)-N—[(R)-1-(20-[(R)-3-([4-([[(1S,2S)-6-chloro-4-cyano-2-(4-methyl-1,4-diazepan-1-yl)-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-2-[(1S,4S)-2,5-diazabicyclo[2.2.1]heptan-2-yl]-6-chloro-4-cyano-2,3-dihydro-1H-inden-1-yl]oxy)-N—[(S)-1-(20-[(S)-3-([4-([[(1S,2S)-2-[(1S,4S)-2,5-diazabicyclo[2.2.1]heptan-2-yl]-6-chloro-4-cyano-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-2-[(1S,4S)-2,5-diazabicyclo[2.2.1]heptan-2-yl]-6-chloro-4-cyano-2,3-dihydro-1H-inden-1-yl]oxy)-N—[(R)-1-(20-[(R)-3-([4-([[(1S,2S)-2-[(1S,4S)-2,5-diazabicyclo[2.2.1]heptan-2-yl]-6-chloro-4-cyano-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-[(R)-3-methylpiperazin-1-yl]-2,3-dihydro-1H-inden-1-yl]oxy)-N-[(S)-1-(20-[(S)-3-([4-([[(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-[(R)-3-methylpiperazin-1-yl]-2,3-dihydro-1H-inden-1-yl]oxy)-N—[(R)-1-(20-[(R)-3-([4-([[(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-[(S)-3-methylpiperazin-1-yl]-2,3-dihydro-1H-inden-1-yl]oxy)-N-[(S)-1-(20-[(S)-3-([4-([[(1S,2S)-6-chloro-4-cyano-2-[(S)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-[(S)-3-methylpiperazin-1-yl]-2,3-dihydro-1H-inden-1-yl]oxy)-N—[(R)-1-(20-[(R)-3-([4-([[(1S,2S)-6-chloro-4-cyano-2-[(S)-3-methylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-[(3S,5R)-3,5-dimethylpiperazin-1-yl]-2,3-dihydro-1H-inden-1-yl]oxy)-N—[(S)-1-(20-[(S)-3-([4-([[(1S,2S)-6-chloro-4-cyano-2-[(3S,5R)-3,5-dimethylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-[(3S,5R)-3,5-dimethylpiperazin-1-yl]-2,3-dihydro-1H-inden-1-yl]oxy)-N—[(R)-1-(20-[(R)-3-([4-([[(1S,2S)-6-chloro-4-cyano-2-[(3S,5R)-3,5-dimethylpiperazin-1-yl]-2,3-dihydro-1H-inden-1-yl]oxy)phenyl]sulfonamido)pyrrolidin-1-yl]-7,14-dioxo-3,18-dioxa-6,8,13,15-tetraazaicosyl)pyrrolidin-3-yl]benzenesulfonamide;

4-([[(1S,2S)-6-chloro-4-cyano-2-(piperazin-1-yl)-2,3-dihydro-1H-inden-1-yl]oxy)-N—[(S)-1-(20-[(S)-3-([4-([[(1S,2S)-6-chloro-4-cyano-2-(piperazin-1-yl)-2,3-dihydro-1H-inden-1-yl]oxy)phenyl]sulfonamido)-2-oxopiperidin-1-yl]-7,14-dioxo-3,18-dioxa-6,8,13,15-tetraazaicosyl)-2-oxopiperidin-3-yl]benzenesulfonamide;

4-([[(1S,2S)-6-Chloro-4-cyano-2-(piperazin-1-yl)-2,3-dihydro-1H-inden-1-yl]oxy)-N-[2-(2-[2-(3-[(1r,4r)-4-(3-[2-(2-[2-([4-([[(1S,2S)-6-chloro-4-cyano-2-(piperazin-1-yl)-2,3-dihydro-1H-inden-1-yl]oxy)phenyl]sulfonamido)ethoxy]ethoxy)ethyl]ureido)cyclohexyl]ureido)ethoxy]ethoxy)ethyl]benzenesulfonamide;

4-([[(1S,2S)-6-Chloro-4-cyano-2-(piperazin-1-yl)-2,3-dihydro-1H-inden-1-yl]oxy)-N—[(R)-1-(18-[(R)-3-([4-([[(1S,2S)-6-chloro-4-cyano-2-(piperazin-1-yl)-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl]benzenesulfonamide;

4-([[(1S,2S)-6-Chloro-4-cyano-2-(piperazin-1-yl)-2,3-dihydro-1H-inden-1-yl]oxy)benzenesulfonamide;

N-(2-[2-(2-Aminoethoxy)ethoxy]ethyl)-4-([[(1S,2S)-6-chloro-4-cyano-2-(piperazin-1-yl)-2,3-dihydro-1H-inden-1-yl]oxy)benzenesulfonamide;

N-[1-(4-Aminobutanoyl)piperidin-4-yl]-4-([[(1S,2S)-6-chloro-4-cyano-2-(piperazin-1-yl)-2,3-dihydro-1H-inden-1-yl]oxy)benzenesulfonamide;

4-([[(1S,2S)-6-Chloro-4-cyano-2-(piperazin-1-yl)-2,3-dihydro-1H-inden-1-yl]oxy)-N-(3-oxo-7,10-dioxa-2,4-diazadodecan-12-yl)benzenesulfonamide;

4-([[(1S,2S)-6-Chloro-4-cyano-2-(piperazin-1-yl)-2,3-dihydro-1H-inden-1-yl]oxy)-N-(1-[4-(3-methylureido)butanoyl]piperidin-4-yl)benzenesulfonamide;

4-([[(1S,2S)-6-Chloro-4-cyano-2-(piperazin-1-yl)-2,3-dihydro-1H-inden-1-yl]oxy)-N-[(2S,3R,4S,5R)-1,3,4,5,6-pentahydroxyhexan-2-yl]benzenesulfonamide;

4-([4-([[(1S,2S)-6-Chloro-4-cyano-2-(piperazin-1-yl)-2,3-dihydro-1H-inden-1-yl]oxy)phenyl]sulfonamido)-N-[(2S,3R,4S,5R)-1,3,4,5,6-pentahydroxyhexan-2-yl]piperidine-1-carboxamide;

4-(3-[4-([4-([[(1S,2S)-6-Chloro-4-cyano-2-(piperazin-1-yl)-2,3-dihydro-1H-inden-1-yl]oxy)phenyl]sulfonamido)-4-oxobutyl]ureido)-N-([4-([[(1S,2S)-6-chloro-4-cyano-2-(piperazin-1-yl)-2,3-dihydro-1H-inden-1-yl]oxy)phenyl]sulfonyl)butanamide;

4-([[(1S,2S)-6-Chloro-4-cyano-2-(piperazin-1-yl)-2,3-dihydro-1H-inden-1-yl]oxy)-N-[1-(4-[3-(4-[4-([[(1S,2S)-6-chloro-4-cyano-2-(piperazin-1-yl)-2,3-dihydro-1H-inden-1-yl]oxy)phenyl]sulfonamido)piperidin-1-yl]-4-oxobutyl)ureido]butanoyl)piperidin-4-yl]benzenesulfonamide;

4-([[(1S,2S)-6-Chloro-4-cyano-2-(piperazin-1-yl)-2,3-dihydro-1H-inden-1-yl]oxy)-N-[19-([4-([[(1S,2S)-6-chloro-4-cyano-2-(piperazin-1-yl)-2,3-dihydro-1H-inden-1-yl]oxy)phenyl]sulfonamido)-10-oxo-3,6,14,17-tetraoxa-9,11-diazanonadecyl]benzenesulfonamide;

4-([[(1S,2S)-4-Cyano-6-methyl-2-(piperazin-1-yl)-2,3-dihydro-1H-inden-1-yl]oxy)-N-[26-([4-([[(1S,2S)-4-cyano-6-methyl-2-(piperazin-1-yl)-2,3-dihydro-1H-inden-1-yl]oxy)phenyl]sulfonamido)-10,17-dioxo-3,6,21,24-tetraoxa-9,11,16,18-tetraazahexacosyl] benzenesulfonamide;

1,1'-(Butane-1,4-diyl)bis[3-(4-[6-([[(1S,2S)-6-chloro-4-cyano-2-(piperazin-1-yl)-2,3-dihydro-1H-inden-1-yl]oxy)-3,4-dihydroisoquinolin-2(1H)-yl]-4-oxobutyl) urea];

1,1'-(Butane-1,4-diyl)bis[3-(4-[7-([[(1S,2S)-6-chloro-4-cyano-2-(piperazin-1-yl)-2,3-dihydro-1H-inden-1-yl]oxy)-3,4-dihydroisoquinolin-2(1H)-yl]-4-oxobutyl) urea];

N,N'-(6,14-Dioxo-10-oxa-5,7,13,15-tetraazanonadecane-1,19-diyl)bis[6-([[(1S,2S)-6-chloro-4-cyano-2-(piperazin-1-yl)-2,3-dihydro-1H-inden-1-yl]oxy)-3,4-dihydroisoquinoline-2(1H)-carboxamide];

N,N'-(6,14-Dioxo-10-oxa-5,7,13,15-tetraazanonadecane-1,19-diyl)bis[7-([[(1S,2S)-6-chloro-4-cyano-2-(piperazin-1-yl)-2,3-dihydro-1H-inden-1-yl]oxy)-3,4-dihydroisoquinoline-2(1H)-carboxamide];

4-([[(1S,2S)-6-Chloro-4-cyano-2-[(R)-3-methylpiperazin-1-yl]-2,3-dihydro-1H-inden-1-yl]oxy)-N-[(S)-1-(18-[(S)-3-([4-([[(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl] benzenesulfonamide;

4-([[(1S,2S)-6-Chloro-4-cyano-2-[(R)-3-methylpiperazin-1-yl]-2,3-dihydro-1H-inden-1-yl]oxy)-N—[(R)-1-(18-[(R)-3-([4-([[(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-6,13,18-trioxo-5,7,12,14-tetraazaoctadecanoyl)pyrrolidin-3-yl] benzenesulfonamide;

4-([[(1S,2S)-6-Chloro-4-cyano-2-[(R)-3-methylpiperazin-1-yl]-2,3-dihydro-1H-inden-1-yl]oxy)-N-[1-(18-[4-(4-([[(1S,2S)-6-chloro-4-cyano-2-[(R)-3-methylpiperazin-1-yl]-2,3-dihydro-1H-inden-1-yl]oxy)phenyl] sulfonamido)piperidin-1-yl]-6,13,18-trioxo-5,7,12,14-tetraazaoctadecanoyl)piperidin-4-yl] benzenesulfonamide;

$N^1,N^{14}$-Bis(2-[(S)-3-([4-([[(1S,2S)-6-chloro-4-cyano-2-[(R)-3-methylpiperazin-1-yl]-2,3-dihydro-1H-inden-1-yl]oxy)phenyl]sulfonamido)pyrrolidin-1-yl]-2-oxoethyl)-4,11-dioxo-3,5,10,12-tetraazatetradecanediamide;

4-([[(1S,2S)-6-Chloro-4-cyano-2-[(R)-3-methylpiperazin-1-yl]-2,3-dihydro-1H-inden-1-yl]oxy)-N-[1-(20-[4-([4-([[(1S,2S)-6-chloro-4-cyano-2-[(R)-3-methylpiperazin-1-yl]-2,3-dihydro-1H-inden-1-yl]oxy)phenyl] sulfonamido)piperidin-1-yl]-7,14-dioxo-3,18-dioxa-6,8,13,15-tetraazaicosyl)piperidin-4-yl] benzenesulfonamide;

1,1'-(Butane-1,4-diyl)bis(3-[2-(2-[6-([[(S,2S)-6-chloro-4-cyano-2-(piperazin-1-yl)-2,3-dihydro-1H-inden-1-yl]oxy)-1-oxoisoindolin-2-yl]ethoxy]urea);

1,1'-(Butane-1,4-diyl)bis(3-[2-(2-[5-([[(1S,2S)-6-chloro-4-cyano-2-(piperazin-1-yl)-2,3-dihydro-1H-inden-1-yl]oxy)-1-oxoisoindolin-2-yl]ethoxy)ethyl]urea);

3-(2-{2-[(3S)-3-(4-{[(3S,2S)-6-chloro-4-cyano-2-[(3R)-3-methylpiperazin-1-yl]-2,3-dihydro-1H-inden-1-yl]oxy}(2,3,5,6-$^2H_4$)benzenesulfonamido)pyrrolidin-1-yl]ethoxy}ethyl)-1-(4-{[(2-{2-[(3S-3-(4-{[(1S,2S)-6-chloro-4-cyano-2-[(3R)-3-methylpiperazin-1-yl]-2,3-dihydro-1H-inden-1-yl]oxy)(2,3,5,6-%)

benzenesulfonamido)pyrrolidin-1-yl]ethoxy)ethyl) carbamoyl]amino}(1,1,2,2,3,3,4,4-$^2H_8$)butyl)urea:

3-(2-{2-[2-(4-{[(1S,2S)-4-cyano-6-methyl-2-[(3R)-3-methylpiperazin-1-yl]-2,3-dihydro-1H-inden-1-yl] oxy}benzenesulfonamido)ethoxy]ethoxy}ethyl)-1-(4-{[(2-{2-[2-(4-{[(1S,2S)-4-cyano-6-methyl-2-[(3R)-3-methylpiperazin-1-yl]-2,3-dihydro-1H-inden-1-yl] oxy}benzenesulfonamido)ethoxy]ethoxy)ethyl) carbamoyl]amino)butyl)urea;

3-(2-{2-[2-(4-{[(1 S,2S)-6-chloro-4-cyano-2-(piperazin-1-yl)-2,3-dihydro-1H-inden-1-yl] oxy}benzenesulfonamido)ethoxy]ethoxy}ethyl)-1-[(1s,4s)-4-{[(2-(2-[2-(4-{[(1S,2S)-6-chloro-4-cyano-2-(piperazin-1-yl)-2,3-dihydro-1H-inden-1-yl] oxy}benzenesulfonamido)ethoxy]ethoxy}ethoxy) carbamoyl]amino}cyclohexyl)urea;

1,3-bis(2-{2-[2-(4-{[(S,2S)-6-chloro-4-cyano-2-(piperazin-1-yl)-2,3-dihydro-1H-inden-1-yl] oxy}benzenesulfonamido)ethoxy]ethoxy}ethyl)urea;

4-([[(1S,2S)-6-Chloro-4-cyano-2-(piperazin-1-yl)-2,3-dihydro-1H-inden-1-yl]oxy)-N-[19-([4-([[(1S,2S)-6-chloro-4-cyano-2-(piperazin-1-yl)-2,3-dihydro-1H-inden-1-yl]oxy)phenyl]sulfonamido)-10-oxo-3,6,14,17-tetraoxa-9,11-diazanonadecyl]benzenesulfonamide;

3-(2-{2-[2-(4-{[(1S,2S)-6-chloro-4-cyano-2-(piperazin-1-yl)-2,3-dihydro-1H-inden-1-yl] oxy}benzenesulfonamido)ethoxy]ethoxy}ethyl)-1-[(1r,4r)-4-{[(2-{2-[2-(4-{[(1S,2S)-6-chloro-4-cyano-2-(piperazin-1-yl)-2,3-dihydro-1H-inden-1-yl] oxy}benzenesulfonamido)ethoxy}ethoxy)ethyl) carbamoyl]amino)cyclohexyl)urea:

3-(2-{2-[(3S)-3-(4-{[(1S,2S)-6-chloro-4-cyano-2-[(3R)-3-methylpiperazin-1-yl]-2,3-dihydro-1H-inden-1-yl] oxy}benzenesulfonamido)pyrrolidin-1-yl] ethoxy}ethyl)-1-(4-{[(2-{2-[(3S)-3-(4-{[(S,2S)-6-chloro-4-cyano-2-[(3R)-3-methylpiperazin-1-yl]-2,3-dihydro-1H-inden-1-yl]oxy}benzenesulfonamido) pyrrolidin-1-yl]ethoxy}ethyl)carbamoyl]amino}(1,1,2,2,3,3,4,4-$^2H_8$)butyl)urea;

3-{4-[(3S)-3-(4-{[(1S,2S)-6-chloro-4-cyano-2-[(3R)-3-methylpiperazin-1-yl]-2,3-dihydro-1H-inden-1-yl] oxy}benzenesulfonamido)pyrrolidin-1-yl]-4-oxobutyl}-1-{4-[({4-[(3S)-3-(4-{[(1S,2S)-6-chloro-4-cyano-2-[(3R)-3-methylpiperazin-1-yl]-2,3-dihydro-1H-inden-1-yl]oxy}benzenesulfonamido)pyrrolidin-1-yl]-4-oxobutyl}carbamoyl)amino]butyl}urea;

3-{4-[4-(4-{[(1S,2S)-6-chloro-4-cyano-2-[(3R)-3-methylpiperazin-1-yl]-2,3-dihydro-1H-inden-1-yl] oxy}benzenesulfonamido)piperidin-1-yl]-4-oxobutyl}-1-{4-[({4-[4-(4-{[(1S,2S)-6-chloro-4-cyano-2-[(3R)-3-methylpiperazin-1-yl]-2,3-dihydro-1H-inden-1-yl]oxy}benzenesulfonamido)piperidin-1-yl]-4-oxobutyl}carbamoyl)amino]butyl}urea;

N-{2-[(3R)-3-(4-{[(1S,2S)-6-chloro-4-cyano-2-(piperazin-1-yl)-2,3-dihydro-1H-inden-1-yl] oxy}benzenesulfonamido)pyrrolidin-1-yl]-2-oxoethyl}-2-({[4-({[({2-[(3R)-3-(4-{[(1S,2S)-6-chloro-4-cyano-2-(piperazin-1-yl)-2,3-dihydro-1H-inden-1-yl] oxy}benzenesulfonamido)pyrrolidin-1-yl]-2-oxoethyl}carbamoyl)methyl]carbamoyl}amino)butyl] carbamoyl}amino)acetamide;

3-(2-{2-[4-(4-{[(1S,2S)-6-chloro-4-cyano-2-[(3R)-3-methylpiperazin-1-yl]-2,3-dihydro-1H-inden-1-yl] oxy}benzenesulfonamido)piperidin-1-yl] ethoxy}ethyl)-1-(4-{[(2-{2-[4-(4-{[(1S,2S)-6-chloro-4-cyano-2-[(3R)-3-methylpiperazin-1-yl]-2,3-dihydro- 1H-inden-1-yl]oxy}benzenesulfonamido)piperidin-1-yl]ethoxy}ethyl)carbamoyl]amino}butyl)urea;

3-{2-[(3S)-3-(4-{[(1S,2S)-6-chloro-4-cyano-2-(piperazin-1-yl)-2,3-dihydro-1H-inden-1-yl]oxy}benzenesulfonamido)pyrrolidin-1-yl]-2-oxoethyl}-1-{4-[({2-[(3S)-3-(4-{[(S,2S)-6-chloro-4-cyano-2-(piperazin-1-yl)-2,3-dihydro-1H-inden-1-yl]oxy}benzenesulfonamido)pyrrolidin-1-yl]-2-oxoethyl}carbamoyl)amino]butyl}urea; and (3S)-N-(4-{[(1S,2S)-6-chloro-4-cyano-2-(piperazin-1-yl)-2,3-dihydro-1H-inden-1-yl]oxy}benzenesulfonyl)-1-[2-(2-{[(4-{[(2-{2-[(3S)-3-[(4-{[(1S,2S)-6-chloro-4-cyano-2-(piperazin-1-yl)-2,3-dihydro-1H-inden-1-yl]oxy}benzenesulfonyl)carbamoyl]pyrrolidin-1-yl]ethoxy)ethyl)carbamoyl]amino)butyl)carbamoyl]amino}ethoxy)ethyl]pyrrolidine-3-carboxamide.

17. A pharmaceutical composition comprising a compound of claim 1, and a pharmaceutically acceptable carrier.

18. A method for inhibiting NHE-mediated antiport of sodium and hydrogen ions, the method comprising administering to a mammal in need thereof a pharmaceutically effective amount of a compound of claim 1.

19. A method for treating a disorder associated with fluid retention or salt overload, the method comprising administering to a mammal in need thereof a pharmaceutically effective amount of a compound of claim 1.

20. The method of claim 19, wherein the disorder is selected from the group consisting of gastrointestinal motility disorder, irritable bowel syndrome, chronic constipation, chronic idiopathic constipation, chronic constipation occurring in cystic fibrosis, opioid-induced constipation, chronic intestinal pseudo-obstruction, colonic pseudo-obstruction, ulcerative colitis, inflammatory bowel disease, gastrointestinal tract disorder is associated with chronic kidney disease (stage 4 or 5), constipation induced by calcium supplement, constipation associated with the use of a therapeutic agent, constipation associated with a neuropathic disorder (Parkinson's disease, multiple sclerosis), post-surgical constipation (postoperative ileus), idiopathic constipation (functional constipation or slow transit constipation), constipation associated with neuropathic, metabolic or an endocrine disorder, constipation due the use of drugs selected from analgesics (e.g., opioids), antihypertensive, anticonvulsants, antidepressants, antispasmodics and antipsychotics, gastric ulcers, infectious diarrhea, leaky gut syndrome, cystic fibrosis gastrointestinal disease, microscopic colitis, necrotizing enterocolitis, atopy, food allergy, acute inflammation, chronic inflammation, obesity-induced metabolic diseases, kidney disease, chronic kidney disease, diabetic kidney disease, heart disease, heart failure, congestive heart failure, hypertension, essential hypertension, primary hypertension, salt-sensitive hypertension, liver disease, cirrhosis, nonalcoholic steatohepatitis, nonalcoholic fatty liver disease, steatosis, primary sclerosing cholangitis, primary biliary cholangitis, portal hypertension, Type 1 diabetes, celiac disease, multiple sclerosis, ankylosing spondylitis, rheumatoid arthritis, lupus, alopecia areata, polymyalgia rheumatica, multiple sclerosis, fibromyalgia, chronic fatigue syndrome, Sjogren's syndrome, vitiligo, thyroiditis, vasculitis, Crohn's disease, ulcerative colitis, urticaria (hives), Raynaud's syndrome, schizophrenia, autism spectrum disorders, multiple sclerosis, hepatic encephalopathy, small intestinal bacterial overgrowth, secondary hyperparathyroidism (PTH), celiac disease, hyperphosphatemia and chronic alcoholism.

\* \* \* \* \*

UNITED STATES PATENT AND TRADEMARK OFFICE
CERTIFICATE OF CORRECTION

PATENT NO. : 11,242,337 B2
APPLICATION NO. : 16/476836
DATED : February 8, 2022
INVENTOR(S) : Dragoli et al.

It is certified that error appears in the above-identified patent and that said Letters Patent is hereby corrected as shown below:

In the Claims

Column 485, Lines 33-47, Claim 1, please delete

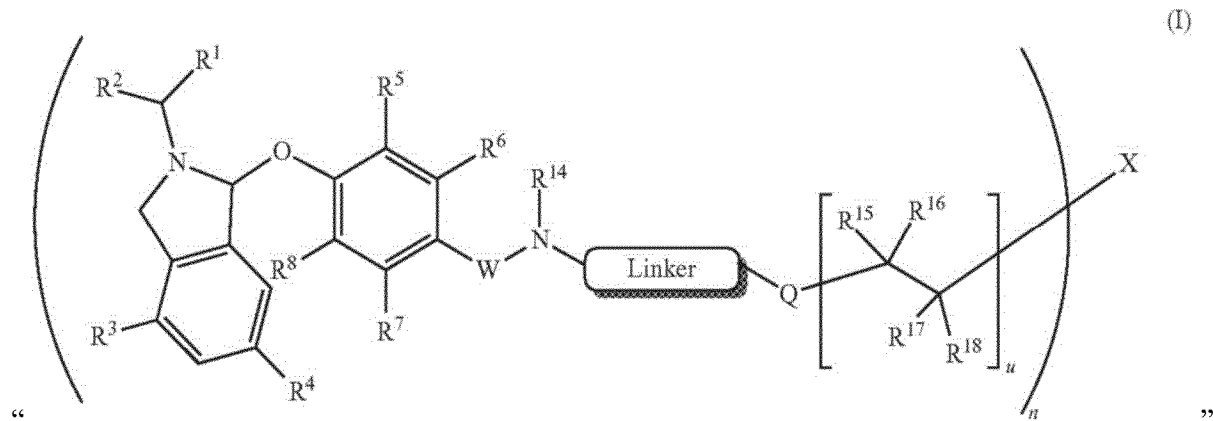

"

and insert

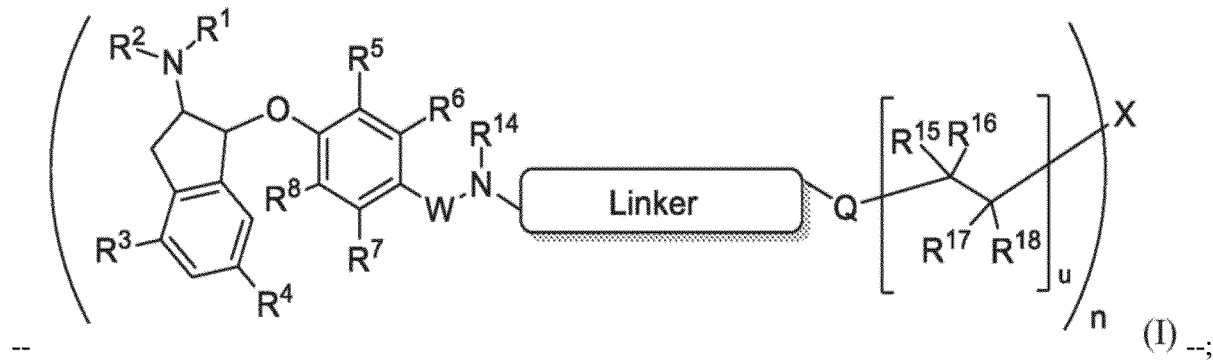

--

Signed and Sealed this
Sixth Day of September, 2022

Katherine Kelly Vidal
*Director of the United States Patent and Trademark Office*

CERTIFICATE OF CORRECTION (continued)
U.S. Pat. No. 11,242,337 B2

Column 486, Lines 23-24, Claim 1, please delete "—S(O)R⁹,   —S(O)NR⁹R¹⁰," and insert -- —S(O)R$^9$, —S(O)NR$^9$R$^{10}$,--;

Column 487, Line 4, Claim 1, please delete "each C$_3$-C$_8$ cycloalkyl" and insert --each C$_3$-C$_8$cycloalkyl--;

Column 487, Line 6, Claim 1, please delete "R$^3$ and R$^{13}$" and insert --R$^{13}$ and R$^{14}$--;

Column 487, Line 8, Claim 1, please delete "each C$_3$-C$_8$ cycloalkyl" and insert --each C$_3$-C$_8$cycloalkyl--;

Column 487, Line 15, Claim 1, please delete "C$_1$-C$_3$ alkyl" and insert --C$_1$-C$_3$alkyl--;

Column 488, Lines 20-25, Claim 2, please delete

"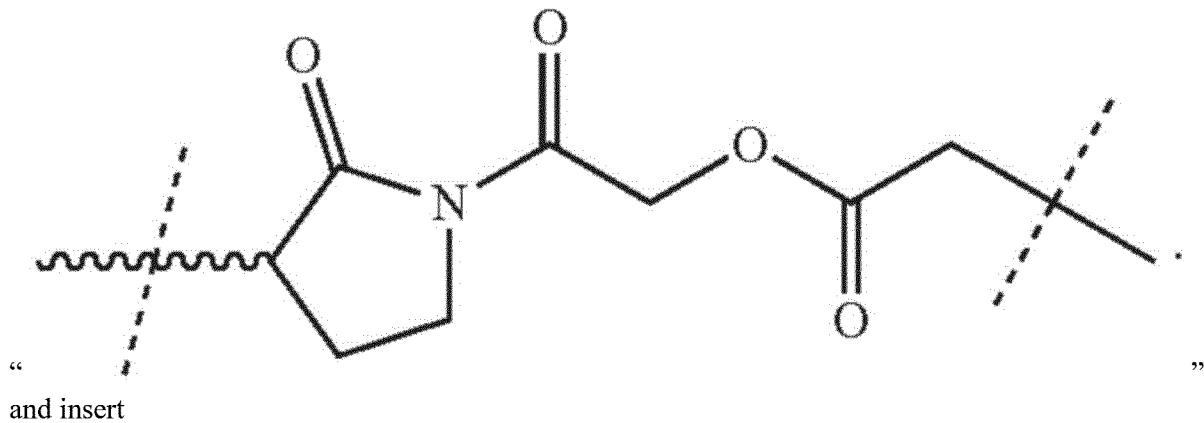"

and insert

--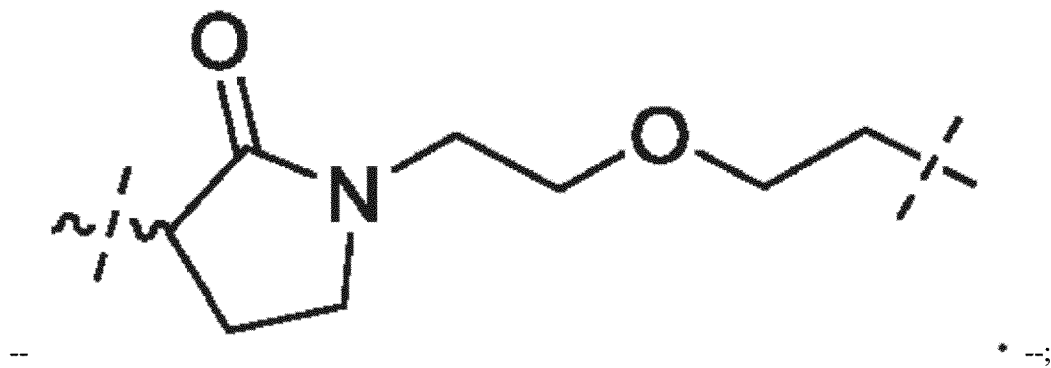 *--;

Column 490, Lines 44, Claim 8, please delete "C$_3$-C$_8$ cycloalkyl" and insert --C$_3$-C$_8$cycloalkyl--;

Column 493, Line 42, Claim 16, please delete "benzene) sulfonamido" and insert --benzene)sulfonamido--;

Column 493, Line 49, Claim 16, please delete "methylbenzene) sulfonamido" and insert --methylbenzene)sulfonamido--;

CERTIFICATE OF CORRECTION (continued)
U.S. Pat. No. 11,242,337 B2

Column 495, Line 6, Claim 16, please delete "methyl]-1-[4([[(4-4-[3S-1" and insert --methyl-1-4-([(4-[[(3S)-1--; and Column 499, Line 67, Claim 16, please delete "oxy)(2,3,5,6-%)" and insert --oxy}(2,3,5,6-$^2H_4$)--.